(12) United States Patent
Connor

(10) Patent No.: US 9,814,426 B2
(45) Date of Patent: Nov. 14, 2017

(54) MOBILE WEARABLE ELECTROMAGNETIC BRAIN ACTIVITY MONITOR

(71) Applicant: Robert A. Connor, Forest Lake, MN (US)

(72) Inventor: Robert A. Connor, Forest Lake, MN (US)

(73) Assignee: Medibotics LLC, St. Paul, MN (US)

( * ) Notice: Subject to any disclaimer, the term of this patent is extended or adjusted under 35 U.S.C. 154(b) by 397 days.

(21) Appl. No.: 14/599,522

(22) Filed: Jan. 18, 2015

(65) Prior Publication Data

US 2015/0313496 A1 Nov. 5, 2015

Related U.S. Application Data

(63) Continuation-in-part of application No. 14/562,719, filed on Dec. 7, 2014, which is a continuation-in-part
(Continued)

(51) Int. Cl.
*A61B 5/04* (2006.01)
*A61B 5/00* (2006.01)
(Continued)

(52) U.S. Cl.
CPC ........ *A61B 5/6814* (2013.01); *A61B 5/02055* (2013.01); *A61B 5/0476* (2013.01); *A61B 5/0478* (2013.01); *A61B 5/021* (2013.01); *A61B 5/02438* (2013.01); *A61B 5/0404* (2013.01); *A61B 5/0488* (2013.01); *A61B 5/0533* (2013.01); *A61B 5/0816* (2013.01); *A61B 5/1112* (2013.01); *A61B 5/1118* (2013.01);
(Continued)

(58) Field of Classification Search
CPC ... A61B 5/6814; A61B 5/0478; A61B 5/0476; A61B 5/02055; A61B 5/6803; A61B 2562/0209; A61B 5/1118; A61B 5/4866; A61B 2560/0468; A61B 5/1112; A61B 5/4205; A61B 5/021; A61B 5/02438; A61B 5/0404; A61B 5/0533; A61B 5/14551
See application file for complete search history.

(56) References Cited

U.S. PATENT DOCUMENTS

| | | |
|---|---|---|
| 3,760,796 A | 9/1973 | Baessler et al. |
| 3,998,213 A | 12/1976 | Price |
| (Continued) | | |

FOREIGN PATENT DOCUMENTS

| | | |
|---|---|---|
| EP | 2642914 | 10/2013 |
| WO | WO2006073384 | 12/2004 |
| (Continued) | | |

*Primary Examiner* — Tiffany Weston
*Assistant Examiner* — Tho Tran

(57) ABSTRACT

This invention is a mobile wearable electromagnetic brain activity monitor comprising a frame worn on a person's head, electromagnetic energy sensors which collect data concerning the person's electromagnetic brain activity, and a control unit. The electromagnetic energy sensors can be electroencephalogram (EEG) electrodes. In an example, the frame can be circular. In an example, the frame can loop around the person's head from one ear to the other ear. In an example, the frame can be an eyewear frame which also includes light-transmitting optical members.

4 Claims, 67 Drawing Sheets

Related U.S. Application Data of application No. 13/523,739, filed on Jun. 14, 2012, now Pat. No. 9,042,596.

(60) Provisional application No. 61/932,517, filed on Jan. 28, 2014, provisional application No. 61/939,244, filed on Feb. 12, 2014, provisional application No. 62/017,615, filed on Jun. 26, 2014, provisional application No. 62/089,696, filed on Dec. 9, 2014.

(51) Int. Cl.

| | | |
|---|---|---|
| *A61B 5/0476* | (2006.01) | |
| *A61B 5/0205* | (2006.01) | |
| *A61B 5/0478* | (2006.01) | |
| *A61B 5/021* | (2006.01) | |
| *A61B 5/024* | (2006.01) | |
| *A61B 5/0404* | (2006.01) | |
| *A61B 5/0488* | (2006.01) | |
| *A61B 5/053* | (2006.01) | |
| *A61B 5/08* | (2006.01) | |
| *A61B 5/11* | (2006.01) | |
| *A61B 5/1455* | (2006.01) | |

(52) U.S. Cl.
CPC ......... *A61B 5/14551* (2013.01); *A61B 5/4205* (2013.01); *A61B 5/4866* (2013.01); *A61B 5/6803* (2013.01); *A61B 2560/0468* (2013.01); *A61B 2562/0209* (2013.01)

(56) References Cited

U.S. PATENT DOCUMENTS

| | | |
|---|---|---|
| 4,537,198 A | 8/1985 | Corbett |
| 4,610,259 A | 9/1986 | Cohen et al. |
| 4,632,122 A | 12/1986 | Johansson |
| 4,683,892 A | 8/1987 | Johansson |
| 4,697,598 A | 10/1987 | Bernard et al. |
| 4,709,702 A | 12/1987 | Sherwin |
| 4,770,180 A | 9/1988 | Schmidt et al. |
| 4,800,888 A | 1/1989 | Itil et al. |
| 4,836,219 A | 6/1989 | Hobson et al. |
| 4,844,086 A | 7/1989 | Duffy |
| 4,910,804 A * | 3/1990 | Lidgren ............... A41D 20/00 2/181.8 |
| 4,967,038 A | 10/1990 | Gevins et al. |
| 4,974,602 A | 12/1990 | Abraham-Fuchs et al. |
| 5,038,782 A | 8/1991 | Gevins et al. |
| 5,154,180 A | 10/1992 | Blanchet et al. |
| 5,291,888 A | 3/1994 | Tucker |
| 5,293,867 A | 3/1994 | Oommen |
| 5,299,118 A | 3/1994 | Martens et al. |
| 5,309,095 A | 5/1994 | Ahonen et al. |
| 5,311,876 A | 5/1994 | Olsen et al. |
| 5,357,957 A | 10/1994 | Itil et al. |
| 5,447,166 A | 9/1995 | Gevins |
| 5,479,934 A | 1/1996 | Imran |
| 5,564,433 A | 10/1996 | Thornton |
| 5,655,534 A | 8/1997 | Ilmoniemi |
| 5,687,291 A | 11/1997 | Smyth |
| 5,724,987 A | 3/1998 | Gevins et al. |
| 5,740,812 A | 4/1998 | Cowan |
| 5,800,351 A | 9/1998 | Mann |
| 5,813,993 A | 9/1998 | Kaplan et al. |
| 5,840,040 A | 11/1998 | Altschuler et al. |
| 5,954,667 A | 9/1999 | Finkenzeller et al. |
| 5,983,129 A | 11/1999 | Cowan et al. |
| 5,999,846 A | 12/1999 | Pardey et al. |
| 6,001,065 A | 12/1999 | Devito |
| 6,014,582 A | 1/2000 | He |
| 6,032,065 A | 2/2000 | Brown |
| 6,066,084 A | 5/2000 | Edrich et al. |
| 6,066,163 A | 5/2000 | John |
| 6,067,464 A | 5/2000 | Musha |
| 6,067,467 A | 5/2000 | John |
| 6,154,669 A | 11/2000 | Hunter et al. |
| 6,161,030 A | 12/2000 | Levendowski et al. |
| 6,167,298 A | 12/2000 | Levin |
| 6,171,258 B1 | 1/2001 | Karakasoglu et al. |
| 6,175,753 B1 | 1/2001 | Menkes et al. |
| 6,201,982 B1 | 3/2001 | Menkes et al. |
| 6,254,536 B1 | 7/2001 | Devito |
| 6,256,531 B1 | 7/2001 | Ilmoniemi et al. |
| 6,272,378 B1 | 8/2001 | Baumgart-Schmitt |
| 6,301,493 B1 | 10/2001 | Marro et al. |
| 6,381,481 B1 | 4/2002 | Levendowski et al. |
| 6,488,617 B1 | 12/2002 | Katz |
| 6,496,724 B1 | 12/2002 | Levendowski et al. |
| 6,510,340 B1 | 1/2003 | Jordan |
| 6,544,170 B1 | 4/2003 | Kajihara et al. |
| 6,549,804 B1 | 4/2003 | Osorio et al. |
| 6,564,102 B1 | 5/2003 | Boveja |
| 6,572,542 B1 | 6/2003 | Houben et al. |
| 6,574,513 B1 | 6/2003 | Collura et al. |
| 6,625,485 B2 | 9/2003 | Levendowski et al. |
| 6,640,122 B2 | 10/2003 | Manoli et al. |
| 6,654,633 B2 | 11/2003 | Stengel et al. |
| 6,690,959 B2 | 2/2004 | Thompson |
| 6,694,180 B1 | 2/2004 | Boesen |
| 6,811,538 B2 | 11/2004 | Westbrook et al. |
| 6,832,110 B2 | 12/2004 | Sohmer et al. |
| 6,947,790 B2 | 9/2005 | Gevins et al. |
| 6,954,700 B2 | 10/2005 | Higashida et al. |
| 6,961,601 B2 | 11/2005 | Matthews et al. |
| 7,054,680 B1 | 5/2006 | Genger et al. |
| 7,058,445 B2 | 6/2006 | Kemere et al. |
| 7,127,283 B2 | 10/2006 | Kageyama |
| 7,141,987 B2 | 11/2006 | Hibbs et al. |
| 7,146,217 B2 | 12/2006 | Firlik et al. |
| 7,158,822 B2 | 1/2007 | Payne, Jr. |
| 7,173,437 B2 | 2/2007 | Hervieux et al. |
| 7,190,995 B2 | 3/2007 | Chervin et al. |
| 7,197,350 B2 | 3/2007 | Kopke |
| 7,204,250 B1 | 4/2007 | Burton |
| 7,206,625 B2 | 4/2007 | Kurtz et al. |
| 7,225,013 B2 | 5/2007 | Geva et al. |
| 7,228,169 B2 | 6/2007 | Viertio-Oja et al. |
| 7,231,723 B1 | 6/2007 | O'Neill et al. |
| 7,242,984 B2 | 7/2007 | DiLorenzo |
| 7,245,956 B2 | 7/2007 | Matthews et al. |
| 7,297,119 B2 | 11/2007 | Westbrook et al. |
| 7,299,088 B1 | 11/2007 | Thakor et al. |
| 7,344,244 B2 | 3/2008 | Goodall et al. |
| D565,735 S | 4/2008 | Washbon |
| 7,390,088 B2 | 6/2008 | Goodall et al. |
| 7,460,903 B2 | 12/2008 | Pineda et al. |
| 7,466,148 B2 | 12/2008 | Fridman et al. |
| 7,486,988 B2 | 2/2009 | Goodall et al. |
| 7,499,894 B2 | 3/2009 | Marom et al. |
| 7,546,158 B2 | 6/2009 | Allison et al. |
| 7,548,774 B2 | 6/2009 | Kurtz et al. |
| 7,551,952 B2 | 6/2009 | Gevins et al. |
| 7,575,005 B2 | 8/2009 | Mumford et al. |
| 7,580,742 B2 | 8/2009 | Tan et al. |
| 7,668,588 B2 | 2/2010 | Kovacs |
| 7,689,274 B2 | 3/2010 | Mullen et al. |
| 7,844,324 B2 | 11/2010 | Sarkela et al. |
| 7,885,706 B2 | 2/2011 | Ludvig et al. |
| 7,904,144 B2 | 3/2011 | Causevic et al. |
| 7,942,824 B1 | 5/2011 | Kayyali et al. |
| 7,974,696 B1 | 7/2011 | Dilorenzo |
| 7,992,560 B2 | 8/2011 | Burton et al. |
| 8,055,722 B2 | 11/2011 | Hille |
| 8,069,852 B2 | 12/2011 | Burton et al. |
| 8,103,328 B2 | 1/2012 | Turner et al. |
| 8,118,741 B2 | 2/2012 | Beck-Nielsen |
| 8,147,419 B2 | 4/2012 | Krauss et al. |
| 8,155,736 B2 | 4/2012 | Sullivan et al. |
| 8,157,730 B2 | 4/2012 | Leboeuf et al. |
| 8,170,637 B2 | 5/2012 | Lee et al. |
| 8,172,766 B1 | 5/2012 | Kayyali et al. |
| 8,190,248 B2 | 5/2012 | Besio et al. |
| 8,190,249 B1 | 5/2012 | Gharieb et al. |

(56) References Cited

U.S. PATENT DOCUMENTS

| | | |
|---|---|---|
| 8,193,821 B2 | 6/2012 | Mueller et al. |
| 8,209,004 B2 | 6/2012 | Freer et al. |
| 8,209,224 B2 | 6/2012 | Pradeep et al. |
| 8,224,433 B2 | 7/2012 | Suffin et al. |
| 8,204,786 B2 | 8/2012 | Leboeuf et al. |
| 8,244,342 B2 | 8/2012 | Goodall et al. |
| 8,271,075 B2 | 9/2012 | Chuang et al. |
| 8,277,385 B2 | 10/2012 | Berka et al. |
| 8,281,787 B2 | 10/2012 | Burton |
| 8,290,563 B2 | 10/2012 | Jin et al. |
| 8,298,140 B2 | 10/2012 | Beck-Nielsen et al. |
| 8,301,218 B2 | 10/2012 | Nguyen et al. |
| 8,335,715 B2 | 12/2012 | Pradeep et al. |
| 8,346,354 B2 | 1/2013 | Hyde et al. |
| 8,348,840 B2 | 1/2013 | Heit et al. |
| 8,350,804 B1 | 1/2013 | Moll |
| 8,355,769 B2 | 1/2013 | Levendowski et al. |
| 8,376,965 B2 | 2/2013 | Schuette et al. |
| 8,386,312 B2 | 2/2013 | Pradeep et al. |
| 8,386,313 B2 | 2/2013 | Pradeep et al. |
| 8,391,966 B2 | 3/2013 | Luo et al. |
| 8,391,967 B2 | 3/2013 | Freer et al. |
| 8,392,250 B2 | 3/2013 | Pradeep et al. |
| 8,392,251 B2 | 3/2013 | Pradeep et al. |
| 8,392,253 B2 | 3/2013 | Pradeep et al. |
| 8,392,254 B2 | 3/2013 | Pradeep et al. |
| 8,392,255 B2 | 3/2013 | Pradeep et al. |
| 8,396,529 B2 | 3/2013 | Lee et al. |
| 8,396,545 B2 | 3/2013 | Berridge et al. |
| 8,396,744 B2 | 3/2013 | Pradeep et al. |
| 8,428,682 B1 | 4/2013 | Rood et al. |
| 8,437,843 B1 | 5/2013 | Kayyali et al. |
| 8,442,626 B2 | 5/2013 | Zavoronkovs et al. |
| 8,457,709 B2 | 6/2013 | Matthews et al. |
| 8,463,354 B2 | 6/2013 | Fadem |
| 8,465,408 B2 | 6/2013 | Phillips et al. |
| 8,467,133 B2 | 6/2013 | Miller |
| 8,472,120 B2 | 6/2013 | Border et al. |
| 8,473,345 B2 | 6/2013 | Pradeep et al. |
| 8,475,354 B2 | 7/2013 | Phillips et al. |
| 8,477,425 B2 | 7/2013 | Border et al. |
| 8,482,859 B2 | 7/2013 | Border et al. |
| 8,484,081 B2 | 7/2013 | Pradeep et al. |
| 8,488,246 B2 | 7/2013 | Border et al. |
| 8,494,610 B2 | 7/2013 | Pradeep et al. |
| 8,494,905 B2 | 7/2013 | Pradeep et al. |
| 8,521,270 B2 | 8/2013 | Hunter et al. |
| 8,532,756 B2 | 9/2013 | Schalk et al. |
| 8,533,042 B2 | 9/2013 | Pradeep et al. |
| 8,543,219 B2 | 9/2013 | Tass |
| 8,548,555 B2 | 10/2013 | Jin et al. |
| 8,548,558 B2 | 10/2013 | Dunagan et al. |
| 8,548,852 B2 | 10/2013 | Pradeep et al. |
| 8,560,360 B2 | 10/2013 | Olsen et al. |
| 8,562,540 B2 | 10/2013 | Goodall et al. |
| 8,585,568 B2 | 11/2013 | Phillips et al. |
| 8,628,462 B2 | 1/2014 | Berka et al. |
| 8,628,472 B2 | 1/2014 | Beck-Nielsen |
| 8,634,892 B2 | 1/2014 | Lee et al. |
| 8,639,313 B2 | 1/2014 | Westbrook et al. |
| 8,640,698 B2 | 2/2014 | Darkin et al. |
| 8,655,428 B2 | 2/2014 | Pradeep et al. |
| 8,655,437 B2 | 2/2014 | Pradeep et al. |
| 8,676,230 B2 | 3/2014 | Alexander et al. |
| 8,688,209 B2 | 4/2014 | Verbitskiy |
| 8,700,142 B2 | 4/2014 | John et al. |
| 8,731,633 B2 | 5/2014 | Asjes et al. |
| 8,733,927 B1 | 5/2014 | Lewis |
| 8,733,928 B1 | 5/2014 | Lewis |
| 8,781,570 B2 | 7/2014 | Chuang et al. |
| 8,784,293 B2 | 7/2014 | Berka et al. |
| 8,798,736 B2 | 8/2014 | Sullivan et al. |
| 8,805,514 B2 | 8/2014 | Pless et al. |
| 8,812,075 B2 | 8/2014 | Nguyen et al. |
| 8,818,498 B2 | 8/2014 | Terada et al. |
| 8,818,515 B2 | 8/2014 | Bikson et al. |
| 8,868,216 B2 | 10/2014 | Dunagan |
| 8,903,494 B2 | 12/2014 | Goldwasser et al. |
| 2001/0044573 A1 | 11/2001 | Manoli et al. |
| 2001/0056225 A1 | 12/2001 | DeVito |
| 2002/0029005 A1 | 3/2002 | Levendowski et al. |
| 2002/0077534 A1 | 6/2002 | DuRousseau |
| 2002/0091335 A1 | 7/2002 | John et al. |
| 2002/0095099 A1 | 7/2002 | Quyen et al. |
| 2002/0165462 A1 | 11/2002 | Westbrook et al. |
| 2002/0183605 A1 | 12/2002 | Devlin et al. |
| 2002/0188216 A1* | 12/2002 | Kayyali ............... A61B 5/0464 600/518 |
| 2003/0018278 A1 | 1/2003 | Jordan |
| 2003/0055355 A1 | 3/2003 | Viertio-Oja |
| 2003/0073917 A1 | 4/2003 | Echauz et al. |
| 2003/0074033 A1 | 4/2003 | Pless et al. |
| 2003/0088161 A1 | 5/2003 | Stengel et al. |
| 2003/0195429 A1 | 10/2003 | Wilson |
| 2003/0225340 A1* | 12/2003 | Collura ............... A61B 5/0482 600/545 |
| 2003/0225342 A1 | 12/2003 | Hong et al. |
| 2004/0073129 A1 | 4/2004 | Caldwell et al. |
| 2004/0097824 A1 | 5/2004 | Kageyama |
| 2004/0138578 A1 | 7/2004 | Pineda et al. |
| 2004/0163648 A1 | 8/2004 | Burton |
| 2004/0193068 A1 | 9/2004 | Burton et al. |
| 2004/0249302 A1 | 12/2004 | Donoghue et al. |
| 2004/0254493 A1 | 12/2004 | Chervin et al. |
| 2004/0267152 A1 | 12/2004 | Pineda |
| 2005/0027207 A1 | 2/2005 | Westbrook et al. |
| 2005/0073322 A1 | 4/2005 | Hibbs et al. |
| 2005/0076908 A1 | 4/2005 | Lee et al. |
| 2005/0131288 A1 | 6/2005 | Turner et al. |
| 2005/0165323 A1 | 7/2005 | Montgomery et al. |
| 2005/0215916 A1 | 9/2005 | Fadem et al. |
| 2005/0268916 A1 | 12/2005 | Mumford et al. |
| 2005/0275416 A1 | 12/2005 | Hervieux et al. |
| 2005/0277821 A1 | 12/2005 | Payne |
| 2006/0015027 A1 | 1/2006 | Matthews et al. |
| 2006/0032504 A1 | 2/2006 | Burton et al. |
| 2006/0041196 A1 | 2/2006 | Matthews et al. |
| 2006/0094974 A1 | 5/2006 | Cain |
| 2006/0100538 A1 | 5/2006 | Genger et al. |
| 2006/0217781 A1 | 9/2006 | John |
| 2006/0252978 A1 | 11/2006 | Vesely et al. |
| 2006/0252979 A1 | 11/2006 | Vesely et al. |
| 2006/0258930 A1 | 11/2006 | Wu et al. |
| 2006/0293578 A1 | 12/2006 | Rennaker |
| 2007/0010757 A1 | 1/2007 | Goodall et al. |
| 2007/0019279 A1 | 1/2007 | Goodall et al. |
| 2007/0027367 A1 | 2/2007 | Oliver et al. |
| 2007/0066914 A1 | 3/2007 | Le et al. |
| 2007/0093706 A1 | 4/2007 | Gevins et al. |
| 2007/0106145 A1 | 5/2007 | Kim et al. |
| 2007/0106169 A1 | 5/2007 | Fadem |
| 2007/0112262 A1 | 5/2007 | Payne |
| 2007/0112277 A1 | 5/2007 | Fischer et al. |
| 2007/0135701 A1 | 6/2007 | Fridman et al. |
| 2007/0173705 A1 | 7/2007 | Teller et al. |
| 2007/0173733 A1 | 7/2007 | Le et al. |
| 2007/0185697 A1 | 8/2007 | Tan et al. |
| 2007/0191727 A1* | 8/2007 | Fadem ............... A61B 5/0002 600/544 |
| 2007/0225577 A1 | 9/2007 | Mathan |
| 2007/0225585 A1 | 9/2007 | Washbon et al. |
| 2007/0238945 A1 | 10/2007 | Delic et al. |
| 2007/0249952 A1 | 10/2007 | Rubin et al. |
| 2007/0255127 A1 | 11/2007 | Mintz et al. |
| 2007/0270678 A1 | 11/2007 | Fadem et al. |
| 2008/0082019 A1 | 4/2008 | Ludving et al. |
| 2008/0091118 A1 | 4/2008 | Georgopoulos |
| 2008/0146890 A1 | 6/2008 | LeBoeuf et al. |
| 2008/0146892 A1 | 6/2008 | LeBoeuf et al. |
| 2008/0161654 A1 | 7/2008 | Teller et al. |
| 2008/0161655 A1 | 7/2008 | Teller et al. |
| 2008/0161673 A1 | 7/2008 | Goodall et al. |
| 2008/0161707 A1 | 7/2008 | Farringdon et al. |
| 2008/0171943 A1 | 7/2008 | Farringdon et al. |

(56) References Cited

U.S. PATENT DOCUMENTS

| | | |
|---|---|---|
| 2008/0177193 A1 | 7/2008 | Farringdon et al. |
| 2008/0177197 A1 | 7/2008 | Lee et al. |
| 2008/0183082 A1 | 7/2008 | Farringdon et al. |
| 2008/0183090 A1 | 7/2008 | Farringdon et al. |
| 2008/0183097 A1 | 7/2008 | Leyde et al. |
| 2008/0208072 A1 | 8/2008 | Fadem et al. |
| 2008/0218472 A1 | 9/2008 | Breen et al. |
| 2008/0275359 A1 | 11/2008 | Mintz et al. |
| 2008/0281221 A1 | 11/2008 | Greco et al. |
| 2009/0024049 A1 | 1/2009 | Pradeep et al. |
| 2009/0024475 A1 | 1/2009 | Pradeep et al. |
| 2009/0030303 A1 | 1/2009 | Pradeep et al. |
| 2009/0030717 A1 | 1/2009 | Pradeep et al. |
| 2009/0030930 A1 | 1/2009 | Pradeep et al. |
| 2009/0062676 A1 | 3/2009 | Kruglikov et al. |
| 2009/0062679 A1 | 3/2009 | Tan et al. |
| 2009/0082643 A1 | 3/2009 | Pradeep et al. |
| 2009/0082690 A1 | 3/2009 | Phillips et al. |
| 2009/0088619 A1* | 4/2009 | Turner ............ A61B 5/0478 600/383 |
| 2009/0105576 A1 | 4/2009 | Do et al. |
| 2009/0105577 A1 | 4/2009 | Wu et al. |
| 2009/0112080 A1 | 4/2009 | Matthews |
| 2009/0137924 A1 | 5/2009 | Kapoor et al. |
| 2009/0281446 A2 | 11/2009 | Ludvig et al. |
| 2009/0287107 A1 | 11/2009 | Beck-Nielsen et al. |
| 2009/0292180 A1 | 11/2009 | Mirow |
| 2009/0292221 A1 | 11/2009 | Viirre et al. |
| 2009/0312624 A1 | 12/2009 | Berridge et al. |
| 2009/0312808 A1 | 12/2009 | Tyler et al. |
| 2009/0318825 A1 | 12/2009 | Kilborn |
| 2009/0327068 A1 | 12/2009 | Pradeep et al. |
| 2009/0328089 A1 | 12/2009 | Pradeep et al. |
| 2010/0016751 A1 | 1/2010 | Hunter et al. |
| 2010/0042011 A1 | 2/2010 | Doidge et al. |
| 2010/0049008 A1 | 2/2010 | Doherty et al. |
| 2010/0060300 A1 | 3/2010 | Muller et al. |
| 2010/0087701 A1 | 4/2010 | Berka et al. |
| 2010/0099954 A1 | 4/2010 | Dickinson et al. |
| 2010/0125190 A1* | 5/2010 | Fadem ............ A61B 5/0478 600/383 |
| 2010/0145215 A1 | 6/2010 | Pradeep et al. |
| 2010/0145217 A1 | 6/2010 | Otto et al. |
| 2010/0147304 A1 | 6/2010 | Burton |
| 2010/0214318 A1 | 8/2010 | Pradeep et al. |
| 2010/0217099 A1 | 8/2010 | LeBoeuf et al. |
| 2010/0217100 A1* | 8/2010 | LeBoeuf ............ A61B 5/00 600/301 |
| 2010/0234752 A1 | 9/2010 | Sullivan et al. |
| 2010/0240982 A1 | 9/2010 | Westbrook et al. |
| 2010/0249538 A1 | 9/2010 | Pradeep et al. |
| 2010/0268096 A1 | 10/2010 | Berka et al. |
| 2010/0286532 A1 | 11/2010 | Farringdon et al. |
| 2010/0317955 A1 | 12/2010 | Madsen et al. |
| 2011/0015503 A1* | 1/2011 | Joffe ............ A61B 5/04004 600/301 |
| 2011/0028798 A1 | 2/2011 | Hyde et al. |
| 2011/0029038 A1 | 2/2011 | Hyde et al. |
| 2011/0029044 A1 | 2/2011 | Hyde et al. |
| 2011/0034822 A1 | 2/2011 | Phillips et al. |
| 2011/0040202 A1 | 2/2011 | Luo et al. |
| 2011/0046473 A1 | 2/2011 | Pradeep et al. |
| 2011/0046502 A1 | 2/2011 | Pradeep et al. |
| 2011/0046504 A1 | 2/2011 | Pradeep et al. |
| 2011/0071416 A1 | 3/2011 | Terada et al. |
| 2011/0098112 A1 | 4/2011 | LeBoeuf et al. |
| 2011/0098593 A1 | 4/2011 | Low et al. |
| 2011/0106621 A1 | 5/2011 | Pradeep et al. |
| 2011/0106627 A1 | 5/2011 | LeBoeuf et al. |
| 2011/0112427 A1 | 5/2011 | Phillips et al. |
| 2011/0118536 A1 | 5/2011 | Phillips et al. |
| 2011/0172503 A1 | 7/2011 | Knepper et al. |
| 2011/0208015 A1 | 8/2011 | Welch et al. |
| 2011/0221656 A1 | 9/2011 | Haddick et al. |
| 2011/0221669 A1 | 9/2011 | Shams et al. |
| 2011/0221672 A1 | 9/2011 | Osterhout et al. |
| 2011/0222745 A1 | 9/2011 | Osterhout et al. |
| 2011/0227820 A1 | 9/2011 | Haddick et al. |
| 2011/0237971 A1 | 9/2011 | Pradeep et al. |
| 2011/0245633 A1 | 10/2011 | Goldberg et al. |
| 2011/0248729 A2 | 10/2011 | Mueller et al. |
| 2011/0270117 A1 | 11/2011 | Warwick et al. |
| 2011/0282231 A1 | 11/2011 | Pradeep et al. |
| 2011/0282232 A1 | 11/2011 | Pradeep et al. |
| 2011/0295083 A1 | 12/2011 | Doelling et al. |
| 2011/0298706 A1 | 12/2011 | Mann |
| 2011/0301488 A1 | 12/2011 | Schuette et al. |
| 2011/0313308 A1 | 12/2011 | Zavoronkovs et al. |
| 2012/0029379 A1 | 2/2012 | Sivadas |
| 2012/0041331 A1 | 2/2012 | Burton et al. |
| 2012/0041498 A1 | 2/2012 | Gliner et al. |
| 2012/0059273 A1 | 3/2012 | Meggiolaro et al. |
| 2012/0062445 A1 | 3/2012 | Haddick et al. |
| 2012/0072289 A1 | 3/2012 | Pradeep et al. |
| 2012/0075168 A1 | 3/2012 | Osterhout et al. |
| 2012/0083673 A1 | 4/2012 | Al-Ali et al. |
| 2012/0123290 A1 | 5/2012 | Kidmose et al. |
| 2012/0136273 A1 | 5/2012 | Michelson, Jr. |
| 2012/0150545 A1 | 6/2012 | Simon |
| 2012/0165695 A1 | 6/2012 | Kidmose et al. |
| 2012/0176302 A1 | 7/2012 | Mangoubi et al. |
| 2012/0177233 A1 | 7/2012 | Kidmose et al. |
| 2012/0179061 A1 | 7/2012 | Ramanan et al. |
| 2012/0203079 A1 | 8/2012 | McLaughlin |
| 2012/0203081 A1 | 8/2012 | Leboeuf et al. |
| 2012/0209101 A1 | 8/2012 | Kidmose et al. |
| 2012/0209133 A1 | 8/2012 | Beck-Nielsen |
| 2012/0209346 A1 | 8/2012 | Bikson et al. |
| 2012/0212398 A1 | 8/2012 | Border et al. |
| 2012/0212400 A1 | 8/2012 | Border et al. |
| 2012/0218172 A1 | 8/2012 | Border et al. |
| 2012/0218301 A1 | 8/2012 | Miller |
| 2012/0220889 A1 | 8/2012 | Sullivan et al. |
| 2012/0226127 A1 | 9/2012 | Asjes et al. |
| 2012/0235820 A1 | 9/2012 | Kidmose |
| 2012/0235883 A1 | 9/2012 | Border et al. |
| 2012/0235886 A1 | 9/2012 | Border et al. |
| 2012/0235887 A1 | 9/2012 | Border et al. |
| 2012/0235900 A1 | 9/2012 | Border et al. |
| 2012/0236030 A1 | 9/2012 | Border et al. |
| 2012/0238856 A1 | 9/2012 | Kidmose et al. |
| 2012/0242678 A1 | 9/2012 | Border et al. |
| 2012/0242698 A1 | 9/2012 | Haddick et al. |
| 2012/0245450 A1 | 9/2012 | Lee et al. |
| 2012/0245653 A1 | 9/2012 | Bikson et al. |
| 2012/0253921 A1 | 10/2012 | Pradeep et al. |
| 2012/0265261 A1 | 10/2012 | Bikson et al. |
| 2012/0289869 A1 | 11/2012 | Tyler |
| 2012/0290521 A1 | 11/2012 | Frank et al. |
| 2012/0295589 A1 | 11/2012 | Alexander et al. |
| 2012/0296476 A1 | 11/2012 | Cale et al. |
| 2012/0302858 A1 | 11/2012 | Kidmose et al. |
| 2012/0316418 A1 | 12/2012 | Kilsgaard et al. |
| 2013/0035578 A1 | 2/2013 | Chiu et al. |
| 2013/0046151 A1 | 2/2013 | Bsoul et al. |
| 2013/0046206 A1 | 2/2013 | Preminger |
| 2013/0056010 A1 | 3/2013 | Walker et al. |
| 2013/0060097 A1 | 3/2013 | Rubin |
| 2013/0073396 A1 | 3/2013 | Pradeep et al. |
| 2013/0079659 A1 | 3/2013 | Akhadov et al. |
| 2013/0096363 A1 | 4/2013 | Schneider et al. |
| 2013/0120246 A1 | 5/2013 | Schuette et al. |
| 2013/0127708 A1 | 5/2013 | Jung et al. |
| 2013/0127980 A1 | 5/2013 | Haddick et al. |
| 2013/0130799 A1 | 5/2013 | Van Hulle et al. |
| 2013/0131464 A1 | 5/2013 | Westbrook et al. |
| 2013/0131537 A1 | 5/2013 | Tam |
| 2013/0144106 A1 | 6/2013 | Phillips et al. |
| 2013/0144107 A1 | 6/2013 | Phillips et al. |
| 2013/0144108 A1 | 6/2013 | Phillips et al. |
| 2013/0150650 A1 | 6/2013 | Phillips et al. |
| 2013/0150651 A1 | 6/2013 | Phillips et al. |
| 2013/0177883 A1 | 7/2013 | Barnehama et al. |
| 2013/0179087 A1 | 7/2013 | Garripoli |

(56) References Cited

U.S. PATENT DOCUMENTS

| | | |
|---|---|---|
| 2013/0184552 A1 | 7/2013 | Westermann et al. |
| 2013/0184779 A1 | 7/2013 | Bikson et al. |
| 2013/0185144 A1 | 7/2013 | Pradeep et al. |
| 2013/0211226 A1 | 8/2013 | Lee et al. |
| 2013/0211276 A1 | 8/2013 | Luo et al. |
| 2013/0242262 A1 | 9/2013 | Lewis |
| 2013/0253334 A1 | 9/2013 | Al-Ali et al. |
| 2013/0268038 A1 | 10/2013 | Bikson et al. |
| 2013/0274580 A1 | 10/2013 | Madsen et al. |
| 2013/0281759 A1 | 10/2013 | Hagedorn et al. |
| 2013/0295016 A1 | 11/2013 | Gerber et al. |
| 2013/0296731 A1 | 11/2013 | Kidmose et al. |
| 2013/0303837 A1 | 11/2013 | Berka et al. |
| 2013/0310676 A1 | 11/2013 | Jung |
| 2013/0314243 A1 | 11/2013 | Le |
| 2013/0314303 A1 | 11/2013 | Osterhout et al. |
| 2013/0317382 A1 | 11/2013 | Le |
| 2013/0317384 A1 | 11/2013 | Le |
| 2013/0332259 A1 | 12/2013 | Pradeep et al. |
| 2013/0338446 A1 | 12/2013 | Van Vugt et al. |
| 2013/0338738 A1 | 12/2013 | Molina et al. |
| 2014/0023999 A1 | 1/2014 | Greder |
| 2014/0051044 A1 | 2/2014 | Badower et al. |
| 2014/0051961 A1 | 2/2014 | Badower et al. |
| 2014/0058189 A1 | 2/2014 | Stubbeman |
| 2014/0107520 A1 | 4/2014 | Hang et al. |
| 2014/0135644 A1 | 5/2014 | Kim |
| 2014/0148657 A1 | 5/2014 | Hendler et al. |
| 2014/0148872 A1 | 5/2014 | Goldwasser et al. |
| 2014/0160250 A1 | 6/2014 | Pomerantz et al. |
| 2014/0160424 A1 | 6/2014 | Benko et al. |
| 2014/0163408 A1 | 6/2014 | Kocher |
| 2014/0164056 A1 | 6/2014 | Johnson et al. |
| 2014/0171775 A1 | 6/2014 | Kilsgaard et al. |
| 2014/0171820 A1 | 6/2014 | Causevic |
| 2014/0180158 A1 | 6/2014 | Cheng et al. |
| 2014/0200432 A1 | 7/2014 | Banerji et al. |
| 2014/0206323 A1 | 7/2014 | Scorcioni |
| 2014/0206975 A1 | 7/2014 | Lang |
| 2014/0211593 A1 | 7/2014 | Tyler et al. |
| 2014/0213874 A1 | 7/2014 | Tong et al. |
| 2014/0221779 A1 | 8/2014 | Schoonover et al. |
| 2014/0223462 A1 | 8/2014 | Aimone et al. |
| 2014/0228652 A1 | 8/2014 | Terada et al. |
| 2014/0267005 A1 | 9/2014 | Urbach |
| 2014/0267401 A1 | 9/2014 | Urbach |
| 2014/0275875 A1 | 9/2014 | Su et al. |
| 2014/0276183 A1 | 9/2014 | Badower |
| 2014/0277582 A1 | 9/2014 | Leuthardt et al. |
| 2014/0288614 A1 | 9/2014 | Hagedorn et al. |
| 2014/0303450 A1 | 10/2014 | Caponi |
| 2014/0316230 A1 | 10/2014 | Denison et al. |
| 2014/0323900 A1 | 10/2014 | Bibian et al. |
| 2014/0333529 A1 | 11/2014 | Kim et al. |
| 2014/0336473 A1 | 11/2014 | Greco |
| 2014/0347265 A1* | 11/2014 | Aimone .............. G09G 3/003 345/156 |
| 2014/0354534 A1 | 12/2014 | Mullins |
| 2014/0369537 A1 | 12/2014 | Pontoppidan et al. |
| 2014/0375545 A1 | 12/2014 | Ackerman et al. |
| 2015/0005840 A1 | 1/2015 | Pal et al. |
| 2015/0005841 A1 | 1/2015 | Pal et al. |
| 2015/0018705 A1 | 1/2015 | Barlow et al. |
| 2015/0019135 A1 | 1/2015 | Kacyvenski et al. |
| 2016/0015289 A1* | 1/2016 | Simon .............. A61B 5/04842 600/301 |

FOREIGN PATENT DOCUMENTS

| | | |
|---|---|---|
| WO | WO2007143663 | 6/2007 |
| WO | WO2007144307 | 12/2007 |
| WO | WO2012069549 | 5/2012 |
| WO | WO2013008011 | 11/2012 |
| WO | WO2013026481 | 2/2013 |

* cited by examiner

Step 1: Food Consumption and Brain Activity Linked

Step 2: Linked Data Used to Modify Food Consumption

Step 1: Food Consumption and Brain Activity Linked

Step 2: Linked Data Used to Modify Food Consumption

Step 1: Food Consumption and Brain Activity Linked

Step 2: Linked Data Used to Modify Food Consumption

*EM data from a selected recording place (relative to a reference place) and selected time. In an example, this can comprise an EEG channel.*

Fig. 69

$Stat[E_{p1,t...}]$

*A statistical method for EM data from a selected place over time. In an example, this method can provide a summary statistic or classification for an EEG channel which is related to food consumption.*

Fig. 70

$Stat[E_{p...,t...}]$

*A statistical method for EM data from multiple places over time. In an example, this method can provide a summary statistic or classification for a montage of EEG channels which is related to food consumption.*

Fig. 71

$Stat[E_{p,t...} = E_{p,t...+(f1 \to f2)}]$

*A statistical method for EM data from one or more places that repeats over time with a frequency within a selected frequency range. In an example, this method can provide a summary statistic or classification for a wave frequency band which is related to food consumption.*

Fig. 72

$Stat\{Stat[E_{p,t...} = E_{p,t...+(f1 \to f2)}], Stat[E_{p,t...} = E_{p,t...+(f... \to f...)}]\}$

*A statistical method for statistical results for each of multiple frequency ranges -- for EM data that repeats over time with a frequency within a frequency range. In an example, this method can provide a summary statistic or classification for a relationship among multiple bands which is related to food consumption.*

Fig. 73

$Stat \left\{ \begin{array}{l} Stat[E_{p,t...} = E_{p,t...+(f1 \to f2)}], Stat[E_{p,t...} = E_{p,t...+(f... \to f...)}], \\ Stat[E_{p...,t...} = E_{p...,t...+(f1 \to f2)}], Stat[E_{p...,t...} = E_{p...,t...+(f... \to f...)}] \end{array} \right\}$

*A statistical method for statistical results for each of multiple frequency ranges and each of multiple places -- for EM data that repeats over time with a frequency within a frequency range. In an example, this method can provide a summary statistic or classification for a relationship among multiple bands and places which is related to food consumption.*

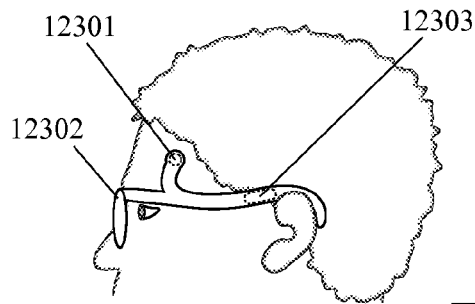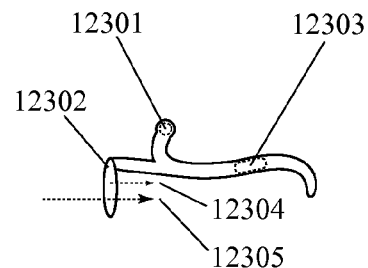
Fig. 123
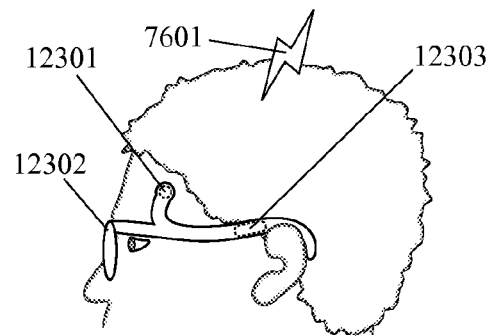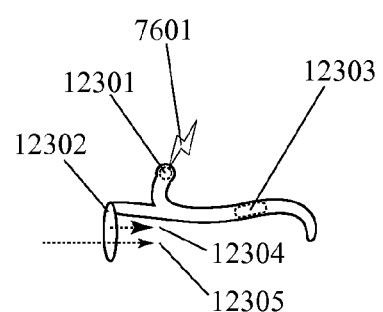
Fig. 124
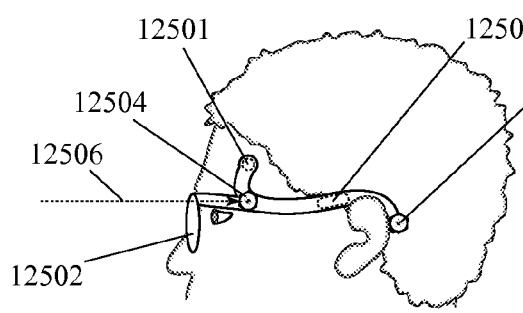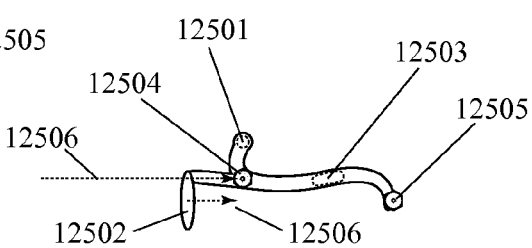
Fig. 125
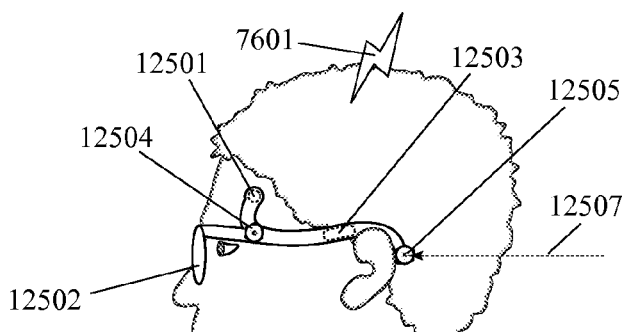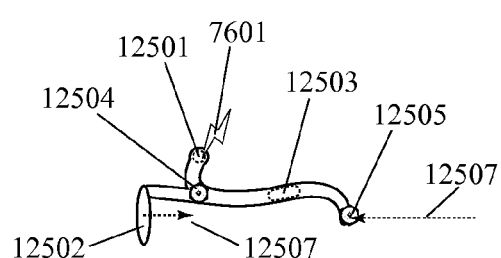
Fig. 126

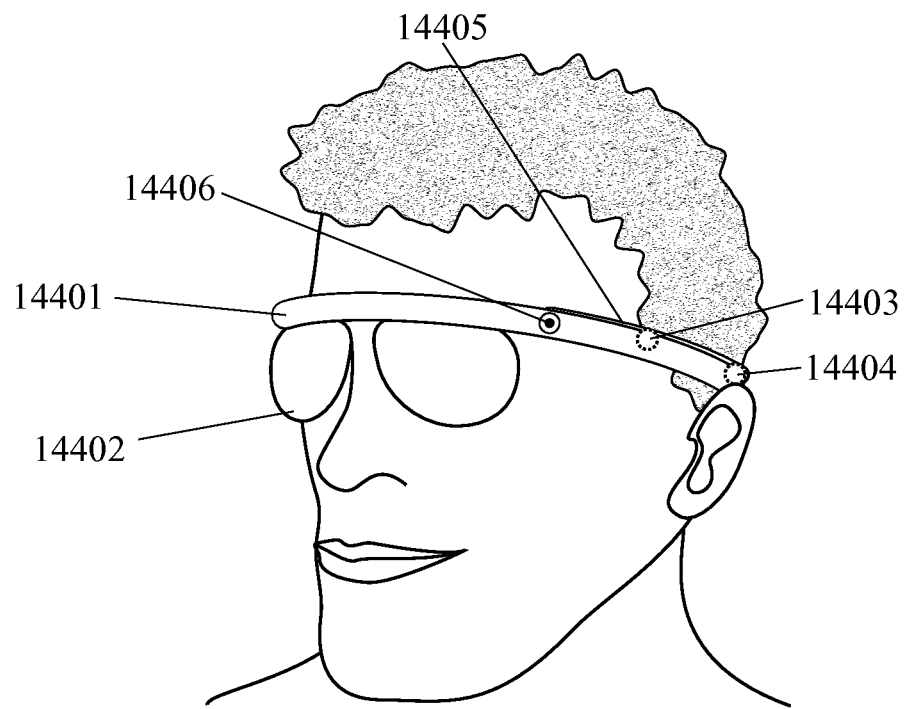
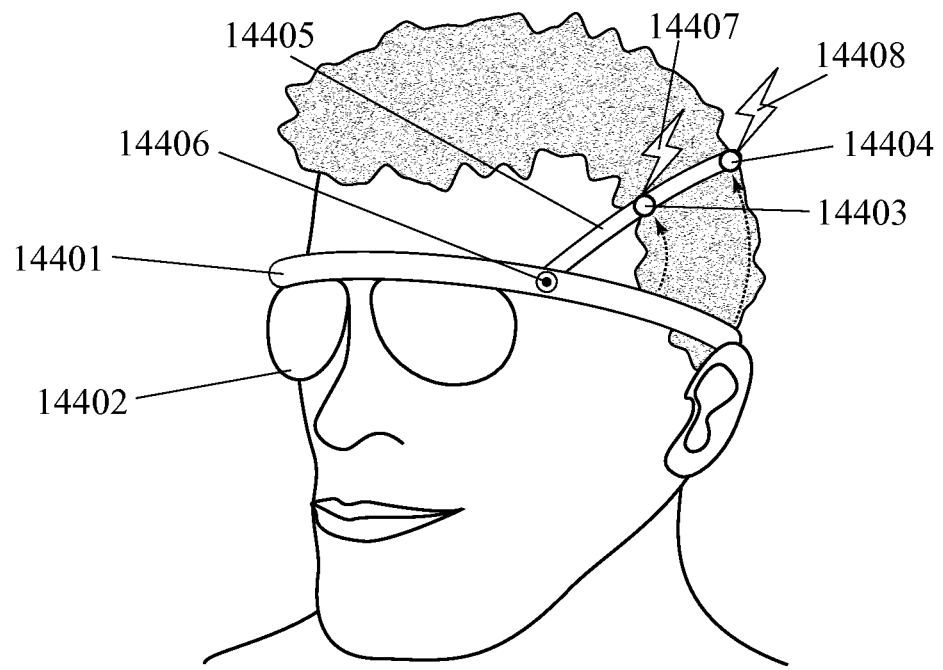
Fig. 144

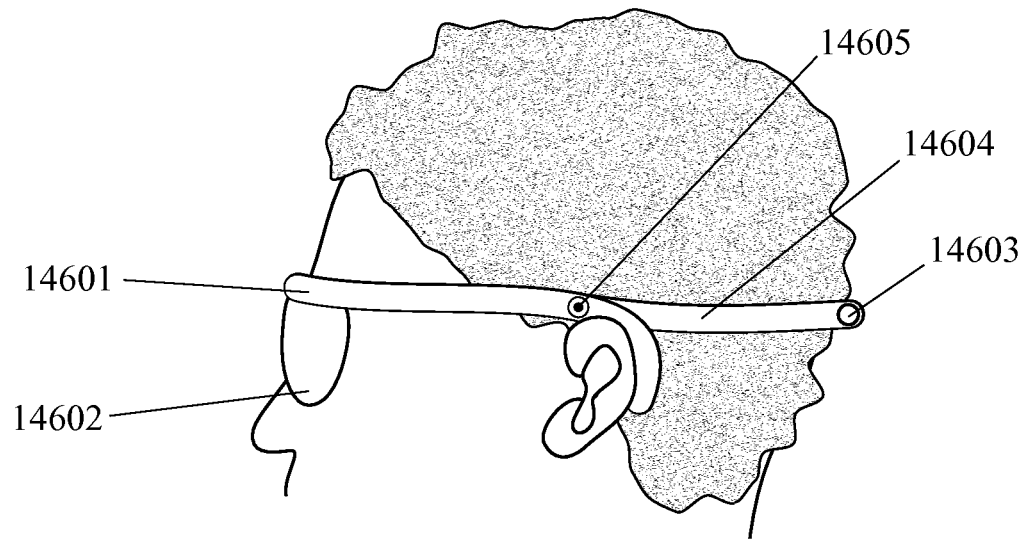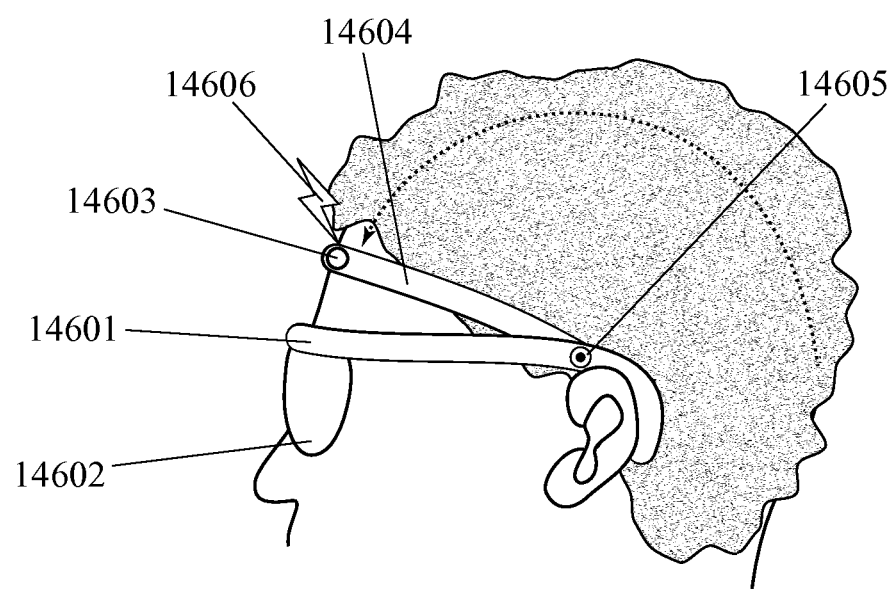
Fig. 146

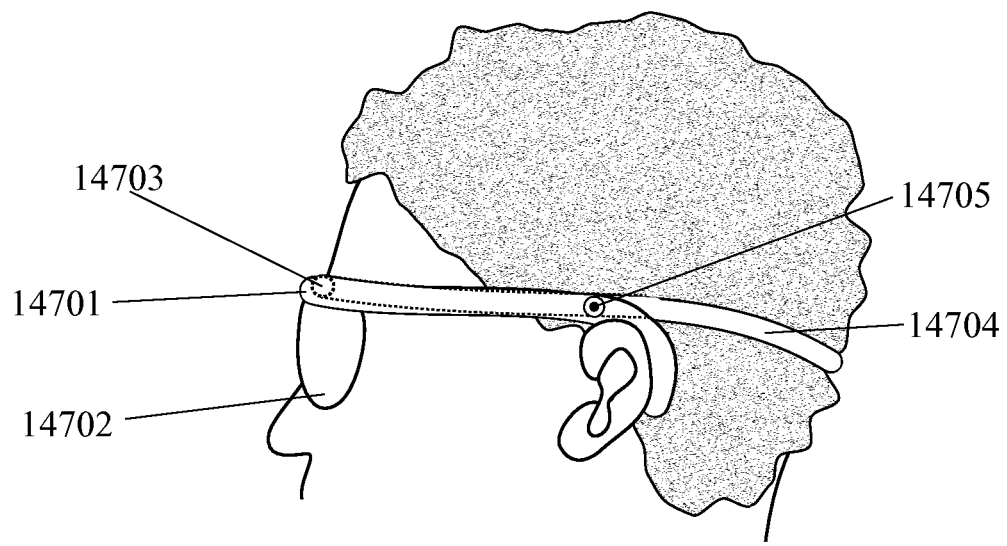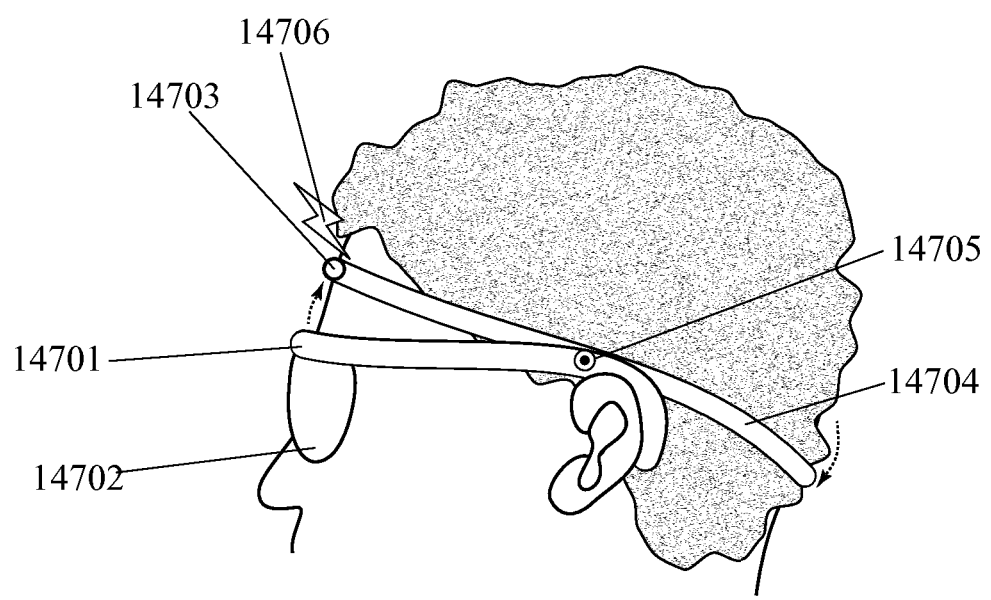
Fig. 147

MOBILE WEARABLE ELECTROMAGNETIC BRAIN ACTIVITY MONITOR

CROSS-REFERENCE TO RELATED APPLICATIONS

This patent application is: (1) is a continuation-in-part of U.S. patent application Ser. No. 14/562,719 entitled "Willpower Glasses™—A Wearable Food Consumption Monitor" by Robert A. Connor with a filing date of Dec. 7, 2014 which was a continuation-in-part of U.S. patent application Ser. No. 13/523,739 entitled "The Willpower Watch™: A Wearable Food Consumption Monitor" by Robert A. Connor with a filing date of Jun. 14, 2012 and also claimed the priority benefit of U.S. Provisional Patent Application No. 61/932,517 entitled "Nutrode™: Wearable EEG Monitor for Modifying Food Consumption" by Robert A. Connor with a filing date of Jan. 28, 2014; (2) claims the priority benefit of U.S. Provisional Patent Application No. 61/932,517 entitled "Nutrode™: Wearable EEG Monitor for Modifying Food Consumption" by Robert A. Connor with a filing date of Jan. 28, 2014; (3) claims the priority benefit of U.S. Provisional Patent Application No. 61/939,244 entitled "Brainwave-Controlled Eyewear" by Robert A. Connor with a filing date of Feb. 12, 2014; (4) claims the priority benefit of U.S. Provisional Patent Application No. 62/017,615 entitled "Nervision™ Integrated Eyewear and EEG Monitor" by Robert A. Connor with a filing date of Jun. 26, 2014; and (5) claims the priority benefit of U.S. Provisional Patent Application No. 62/089,696 entitled "Electroencephalographic Eyewear" by Robert A. Connor with a filing date of Dec. 9, 2014. The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to devices and methods for monitoring electromagnetic brain activity.

INTRODUCTION

This invention relates to mobile wearable devices, systems, and methods for measuring electromagnetic energy from a person's brain. The ability to measure electromagnetic brain activity (such as electroencephalographic EEG activity) with a mobile wearable device allows such measurement while a person is ambulatory. With a mobile and wearable device, a person is free to do their normal activities. This provides useful information which is not possible with EEG monitoring devices which require that the person stay in fixed location (such as a hospital or medical office) with wires sprouting from their head like a modern-day Medusa.

The invention disclosed herein is not the first one to tackle this problem. Many talented folks have created designs for mobile wearable devices, systems, and methods for measuring electromagnetic energy from a person's brain. However, this present invention does offer some innovative device designs and application methods which do not appear to be anticipated by the prior art. This present invention offers some wearable EEG monitor designs that are less intrusive than those in the prior art, including discrete integration of a wearable EEG monitor with eyewear. This present invention also offers some innovative applications and methods, including using a wearable EEG monitor to modify food consumption or to control electronically-functional eyewear.

The mobile wearable electromagnetic brain activity monitor and methods disclosed herein can be very useful. In an example, the mobile wearable electromagnetic brain activity monitor and methods disclosed herein can be used to monitor, measure, and modify a person's food consumption. In an example, the mobile wearable electromagnetic brain activity monitor and methods disclosed herein can be used to control eyewear with light-transmitting members whose light absorption, light reflection, light refraction, light spectrum transformation, focal direction, focal distance, light polarization, or parallax view are controlled by the wearer's brain activity. In an example, the mobile wearable electromagnetic brain activity monitor and methods disclosed herein can be generally used as a Human-to-Computer Interface (HCI).

I apologize to the reader for the length of this disclosure. It incorporates the work from four provisional patent applications which all relate to this invention. Hopefully the "Introduction to the Figures" section will help to guide the reader with respect to the structure of the disclosure and to find sections which may be of particular interest.

REVIEW AND CATEGORIZATION OF THE RELEVANT ART

It can be challenging trying to classify relevant art in this field into discrete categories. However, classification of relevant art into categories, even if imperfect, can be an invaluable tool for reviewing the relevant art. Towards this end, I herein identify 21 categories of relevant art and provide examples of relevant art in each category (including patent or patent application number, inventor, publication date, and title). Some examples of relevant art disclose multiple concepts and thus appear in more than one category.

The 21 categories of relevant art which are used for this review are as follows: (1) device like a skull cap with EEG/brainwave sensors; (2) device like a baseball cap with EEG/brainwave sensors; (3) device with [multiple] front-to-back arcuate members and EEG/brainwave sensors; (4) device with [multiple] side-to-side arcuate members and EEG/brainwave sensors; (5) device with multiple cross-crossing arcuate members and EEG/brainwave sensors; (6) device with multiple arms radially-extending from side and EEG/brainwave sensors; (7) device with multiple arms radially-downward from top and EEG/brainwave sensors; (8) device with multiple arms radially-forward from rear and EEG/brainwave sensors; (9) device with multiple arms radially-backward from front and EEG/brainwave sensors; (10) device with circular horizontal loop (e.g. headband style) and EEG/brainwave sensors; (11) device with top semicircular loop (e.g. headphone style) and EEG/brainwave sensors; (12) device with rear semicircular loop and EEG/brainwave sensors; (13) device with frontal semicircular loop and EEG/brainwave sensors; (14) device like eyeglasses or other eyewear with EEG/brainwave sensors; (15) device like a hearing aid or other earwear with EEG/brainwave sensors; (16) device like a breathing mask with EEG/brainwave sensors; (17) specific type of EEG/brainwave sensor; (18) adhesive EEG/brainwave sensors; (19) method for EEG/brainwave analysis; (20) device that actively emits brain-stimulating energy; and (21) miscellaneous.

I have labeled this section as a review of the relevant art, instead of a review of the prior art, for two reasons. First, some of the art included in this review has a priority date after the priority date of this disclosure, so I do not wish to call all of this art "prior." Second, some of the examples in this present disclosure can be classified into one or more of these categories but are nonetheless novel, so I do not wish to imply that all of the art in these categories is "prior". These caveats notwithstanding, I hope that the reader finds this review and categorization of the relevant art to be useful.

1. Device Like a Skull Cap with EEG/Brainwave Sensor(s)

Devices in this category hold electromagnetic brain activity sensors in contact with (or proximity to) a person's head using a sensor-holding member configured like a skull cap. A "skull cap" is defined herein as a wearable cap-like or hat-like member that covers most of the hair-covered portion of a person's head and flexibly conforms to the contours of the head. A skull cap is generally held snugly against the surface of the head by straps and/or elastic bands. Due to the high percentage of the surface area of the top of a person's head which is covered by such a device, such a device can be used to hold a relatively large number of electromagnetic brain activity sensors in a variety of positions across a person's head. Most of the devices in this category are relatively obtrusive and would be awkward to wear outside a medical setting. They are generally not appropriate for wearing during the activities of daily life.

Prior art which appears to be within this category includes U.S. Pat. No. 4,537,198 (Corbett, Aug. 27, 1985, "Electrode Cap"), U.S. Pat. No. 4,632,122 (Johansson, Dec. 30, 1986, "Method and Apparatus for Conducting Brain Function Diagnostic Test"), U.S. Pat. No. 4,683,892 (Johansson, Aug. 4, 1987, "Method and Apparatus for Conducting Brain Function Diagnostic Test"), U.S. Pat. No. 4,709,702 (Sherwin, Dec. 1, 1987, "Electroencephalographic Cap"), U.S. Pat. No. 4,800,888 (Itil et al., Jan. 31, 1989, "Enhanced Electrode Headset"), U.S. Pat. No. 5,038,782 (Gevins et al., Aug. 13, 1991, "Electrode System for Brain Wave Detection"), U.S. Pat. No. 5,724,987 (Gevins et al., Mar. 10, 1998, "Neurocognitive Adaptive Computer-Aided Training Method and System"), U.S. Pat. No. 6,067,464 (Musha, May 23, 200, "Electrode"), U.S. Pat. No. 8,155,736 (Sullivan et al., Apr. 10, 2012, "EEG Control of Devices Using Sensory Evoked Potentials"), and U.S. Pat. No. 8,391,966 (Luo et al., Mar. 5, 2013, "Sensory-Evoked Potential (SEP) Classification/Detection in the Time Domain").

Prior art which appears to be within this category also includes U.S. patent applications: 20070225577 (Mathan, Sep. 27, 2007, "System and Method for Providing Sensor Based Human Factors Protocol Analysis"), 20070225585 (Washbon and Delic, Sep. 27, 2007, "Headset for Electrodes"), 20070238945 (Delic et al., Oct. 11, 2007, "Electrode Headset"), 20070255127 (Mintz et al., Nov. 1, 2007, "Mobile Electroencephalograph Data Collection and Diagnosis System"), 20080275359 (Mintz et al., Nov. 6, 2008, "Mobile in Vivo Brain Scan and Analysis System"), 20100234752 (Sullivan et al., Sep. 16, 2010, "EEG Control of Devices Using Sensory Evoked Potentials"), 20110040202 (Luo et al., Feb. 17, 2011, "Sensory-Evoked Potential (SEP) Classification/Detection in the Time Domain"), 20110298706 (Mann, Dec. 8, 2011, "Brainwave Actuated Apparatus"), and 20120059273 (Meggiolaro et al., Mar. 8, 2012, "Process and Device for Brain Computer Interface").

Prior art which appears to be within this category also includes U.S. patent applications: 20120136273 (Michelson Jr., May 31, 2012, "Apparatus and Method for Monitoring and Analyzing Brainwaves"), 20120220889 (Sullivan et al., Aug. 30, 2012, "EEG Control of Devices Using Sensory Evoked Potentials"), 20120289869 (Tyler, Nov. 15, 2012, "Devices and Methods for Modulating Brain Activity"), 20130211276 (Luo et al., Aug. 15, 2013, "Sensory-Evoked Potential (SEP) Classification/Detection in the Time Domain"), 20130281759 (Hagedorn et al., Oct. 24, 2013, "Transcranial Stimulation Device and Method Based on Electrophysiological Testing"), 20140163408 (Kocher, Jun. 12, 2014, "System for Analyzing Mental and Behavioral Correlations"), and 20140288614 (Hagedorn et al., Sep. 25, 2014, "Electrophysiology Measurement and Training and Remote Databased and Data Analysis Measurement Method and System").

2. Device Like a Baseball Cap with EEG/Brainwave Sensor(s)

Devices in this category hold electromagnetic brain activity sensors in contact with (or proximity to) a person's head using a sensor-holding member configured like a baseball cap. A "baseball cap" is defined herein as a wearable member with a generally-hemispherical portion which fits over the top of a person's head and an attached visor which extends outward from the person's forehead. Sometimes arcuate bands are embedded in the cap in circular-around-the-head, side-to-side-over-the-top, and/or front-to-back-over-the-top configurations. Devices in this category generally do not cover as much of the surface of the head and may not fit as tightly against the surface of the head as skull cap devices. On the plus side, devices in this category are generally less obtrusive than skull cap devices. However, there are still many circumstances and settings wherein wearing a baseball cap is inappropriate.

Prior art which appears to be within this category includes U.S. Pat. No. 4,697,598 (Bernard et al., Oct. 6, 1987, "Evoked Potential Autorefractometry System"), U.S. Pat. No. 4,709,702 (Sherwin, Dec. 1, 1987, "Electroencephalographic Cap"), U.S. Pat. No. 6,161,030 (Levendowski et al., Dec. 12, 2000, "Portable EEG Electrode Locator Headgear"), U.S. Pat. No. 6,381,481 (Levendowski et al., Apr. 30, 2002, "Portable EEG Electrode Locator Headgear"), U.S. Pat. No. 6,574,513 (Collura et al., Jun. 3, 2003, "EEG Electrode Assemblies"), U.S. Pat. No. 6,640,122 (Manoli et al., Oct. 28, 2003, "EEG Electrode and EEG Electrode Locator Assembly"), and U.S. Pat. No. 7,204,250 (Burton, Apr. 17, 2007, "Bio-Mask"), U.S. Pat. No. 8,281,787 (Burton, Oct. 9, 2012, "Bio-Mask with Integral Sensors").

Prior art which appears to be within this category also includes U.S. patent applications: 20020029005 (Levendowski et al., Mar. 7, 2002, "Portable EEG Electrode Locator Headgear"), 20040073129 (Caldwell et al., Apr. 15, 2004, "EEG System for Time-Scaling Presentations"), 20040163648 (Burton, Aug. 26, 2004, "Bio-Mask with Integral Sensors"), 20100147304 (Burton, Jun. 17, 2010, "Bio-Mask with Integral Sensors"), 20110015503 (Joffe et al., Jan. 20, 2011, "Medical Apparatus for Collecting Patient Electroencephalogram (EEG) Data"), 20110046502 (Pradeep et al., Feb. 24, 2011, "Distributed Neuro-Response Data Collection and Analysis"), 20110046504 (Pradeep et al., Feb. 24, 2011, "Distributed Neuro-Response Data Collection and Analysis"), and 20110270117 (Warwick et al., Nov. 3, 2011, "Remote Continuous Seizure Monitor and Alarm").

3. Device with [Multiple] Front-to-Back Arcuate Member(s) and EEG/Brainwave Sensor(s)

Devices in this category hold electromagnetic brain activity sensors in contact with (or proximity to) a person's head using (multiple) arcing member(s) which span a person's head from front-to-back (or vice versa). Devices in this category can look similar to some types of bicycle helmets with front-to-back arcuate members. In an example, the front-to-back arcing members can converge at the forehead and at the rear of the head. In an example, a device in this category can comprise: a first arcuate member which encircles a person's head: a second arcuate member which loops front-to-back over the top of the head; and third and fourth arcuate members which loop front-to-back over the sides of the head between the first and second members. Devices in this category can hold a relatively large number of electromagnetic brain activity sensors along arcuate front-to-rear lines on a person's head. However, such devices tend to be too obtrusive to wear during the activities of daily life.

Prior art which appears to be within this category includes U.S. Pat. No. 3,998,213 (Price, Dec. 21, 1976, "Self-Adjustable Holder for Automatically Positioning Electroencephalographic Electrodes"), U.S. Pat. No. 8,355,769 (Levendowski et al., Jan. 15, 2013, "System for the Assessment of Sleep Quality in Adults and Children"), U.S. Pat. No. 8,463,354 (Fadem, Jun. 11, 2013, "Electrode System with Rigid-Flex Circuit"), U.S. Pat. No. 8,639,313 (Westbrook et al, Jan. 28, 2014, "System for the Assessment of Sleep Quality in Adults and Children"); and U.S. patent applications 20100125190 (Fadem, May 20, 2010, "Electrode System"), 20100240982 (Westbrook et al., Sep. 23, 2010, "System for the Assessment of Sleep Quality in Adults and Children"), and 20130131464 (Westbrook et al., May 23, 2013, "System for the Assessment of Sleep Quality in Adults and Children").

4. Device with [Multiple] Side-to-Side Arcuate Member(s) and EEG/Brainwave Sensor(s)

Devices in this category hold electromagnetic brain activity sensors in contact with (or proximity to) a person's head using (multiple) arcing member(s) which span a person's head from side to side. In an example, side-to-side arcing members can converge near, or over, the person's ears. In an example, devices in this category can be similar to those in the previous category, except having been rotated 90 degrees so that the arcuate members converge on the sides of the person's head rather than the front and rear of the person's head. Devices in this category can hold a relatively large number of electromagnetic brain activity sensors along arcuate side-to-side lines on a person's head. However, such devices tend to be too obtrusive to wear during the activities of daily life.

Prior art which appears to be within this category includes U.S. Pat. No. 4,836,219 (Hobson et al., Jun. 6, 1989, "Electronic Sleep Monitor Headgear"), U.S. Pat. No. 5,800, 351 (Mann, Sep. 1, 1998, "Electrode Supporting Head Set"), U.S. Pat. No. 6,574,513 (Collura et al., Jun. 3, 2003, "EEG Electrode Assemblies"), U.S. Pat. No. 7,158,822 (Payne Jr., Jan. 2, 2007, "Electrode Holder, Headwear, and Wire Jacket Adapted for Use in Sleep Apnea Testing"), and U.S. Pat. No. 7,885,706 (Ludvig et al., Feb. 8, 2011, "System and Device for Seizure Detection").

Prior art which appears to be within this category also includes U.S. patent applications: 20030018278 (Jordan, Jan. 23, 2003, "Electroencephalogram Acquisition Unit and System"), 20050277821 (Payne, Dec. 15, 2005, "Electrode Holder, Headwear, and Wire Jacket Adapted for Use in Sleep Apnea Testing"), 20070112262 (Payne, May 17, 2007, "Electrode Holder, Headwear, and Wire Jacket Adapted for Use in Sleep Apnea Testing"), 20080082019 (Ludving et al., Apr. 3, 2008, "System and Device for Seizure Detection"), 20090281446 (Ludvig et al., Nov. 12, 2009, "System and Device for Seizure Detection"), 20110015503 (Joffe et al., Jan. 20, 2011, "Medical Apparatus for Collecting Patient Electroencephalogram (EEG) Data"), and 20110270117 (Warwick et al., Nov. 3, 2011, "Remote Continuous Seizure Monitor and Alarm").

5. Device with Multiple Cross-Crossing Arcuate Members and EEG/Brainwave Sensor(s)

Devices in this category hold electromagnetic brain activity sensors in contact with (or proximity to) a person's head using multiple arcing members which span a person's head from front-to-rear and also multiple arcing members which span a person's head from side-to-side. In an example, the front-to-rear arcuate members and the side-to-side arcuate members can form a criss-cross pattern on the person's head. Devices in this category can hold a relatively large number of electromagnetic brain activity sensors on a person's head. However, such devices tend to be too obtrusive to wear during the activities of daily life.

Prior art which appears to be within this category includes U.S. Pat. No. 3,998,213 (Price, Dec. 21, 1976, "Self-Adjustable Holder for Automatically Positioning Electroencephalographic Electrodes"), U.S. Pat. No. 5,293,867 (Oommen, Mar. 15, 1994, "Method and Apparatus for Marking Electrode Locations for Electroencephalographic Procedure"), U.S. Pat. No. 5,479,934 (Imran, Jan. 2, 1996, "EEG Headpiece with Disposable Electrodes and Apparatus and System and Method for Use Therewith"), U.S. Pat. No. 6,488,617 (Katz, Dec. 3, 2002, "Method and Device for Producing a Desired Brain State"), U.S. Pat. No. 8,463,354 (Fadem, Jun. 11, 2013, "Electrode System with Rigid-Flex Circuit"); and U.S. patent applications 20030018278 (Jordan, Jan. 23, 2003, "Electroencephalogram Acquisition Unit and System"), and 20100125190 (Fadem, May 20, 2010, "Electrode System").

6. Device with Multiple Arms Radially-Extending from Side and EEG/Brainwave Sensor(s)

Devices in this category hold electromagnetic brain activity sensors in contact with (or proximity to) a person's head using multiple sensor-holding protrusions, fingers, or arms which extend radially outward from a central position on one side (or from central positions on both sides) of a person's head. In an example, such devices can include bilateral clusters (one on each side of the head) of radially-extending protrusions, fingers, or arms. In an example, radially-extending protrusions, fingers, or arms can curve around the head toward the front, top, and/or rear portions of the head. To use colorful language, some such devices can look like a wearer has one or two starfish (or even octopi) clinging to the sides of their head. Such devices can be less obtrusive than those in the preceding categories (especially when they do not span the forehead or the top of the head), but can still attract attention if worn during the activities of daily life.

Prior art which appears to be within this category includes U.S. Pat. No. 5,954,667 (Finkenzeller et al., Sep. 21, 1999, "Device for Deriving Acoustically Evoked Brain Potentials"), U.S. Pat. No. 8,271,075 (Chuang et al., Sep. 18, 2012, "Audio Headset with Bio-Signal Sensors"), U.S. Pat. No. 8,392,250 (Pradeep et al., Mar. 5, 2013, "Neuro-Response Evaluated Stimulus in Virtual Reality Environments"), U.S. Pat. No. 8,392,251 (Pradeep et al., Mar. 5, 2013, "Location Aware Presentation of Stimulus Material"), U.S. Pat. No. 8,396,744 (Pradeep et al., Mar. 12, 2013, "Effective Virtual Reality Environments for Presentation of Marketing Materials"), U.S. Pat. No. 8,548,852 (Pradeep et al., Oct. 1, 2013, "Effective Virtual Reality Environments for Presentation of Marketing Materials"), and U.S. Pat. No. 8,655,428 (Pradeep et al., Feb. 18, 2014, "Neuro-Response Data Synchronization").

Prior art which appears to be within this category also includes U.S. patent applications: 20070106169 (Fadem, May 10, 2007, "Method and System for an Automated E.E.G. System for Auditory Evoked Responses"), 20070191727 (Fadem, Aug. 16, 2007, "Evoked Response Testing System for Neurological Disorders"), 20070225585 (Washbon and Delic, Sep. 27, 2007, "Headset for Electrodes"), 20070238945 (Delic et al., Oct. 11, 2007, "Electrode Headset"), 20080208072 (Fadem et al., Aug. 28, 2008, "Biopotential Waveform Data Fusion Analysis and Classification Method"), 20110237971 (Pradeep et al., Sep. 29, 2011, "Discrete Choice Modeling Using Neuro-Response Data"), and 20110282231 (Pradeep et al., Nov. 17, 2011, "Mechanisms for Collecting Electroencephalography Data").

Prior art which appears to be within this category also includes U.S. patent applications: 20110282232 (Pradeep et al., Nov. 17, 2011, "Neuro-Response Data Synchronization"), 20120072289 (Pradeep et al., Mar. 22, 2012, "Biometric Aware Content Presentation"), 20130131537 (Tam, May 23, 2013, "Tong Ren Brainwave Entrainment"), 20130185144 (Pradeep et al., Jul. 18, 2013, "Systems and Methods for Analyzing Neuro-Reponse Data and Virtual Reality Environments"), 20130314243 (Le, Nov. 28, 2013, "System and Method for Enabling Collaborative Analysis of a Biosignal"), 20130317382 (Le, Nov. 28, 2013, "System and Method for Providing and Aggregating Biosignals and Action Data"), and 20130317384 (Le, Nov. 28, 2013, "System and Method for Instructing a Behavior Change in a User").

7. Device with Multiple Arms Radially-Downward from Top and EEG/Brainwave Sensor(s)

Devices in this category hold electromagnetic brain activity sensors in contact with (or proximity to) a person's head using multiple sensor-holding protrusions, fingers, or arms which extend radially downward from a position on the top of a person's head. In an example, radially-extending protrusions, fingers, or arms can curve around the head toward the front, sides, and/or rear portions of the head. To use the colorful language from the previous category, now a figurative starfish (or octopus) is clinging to the top of the person's head. Such devices can be less obtrusive than some of those in the preceding categories, but can still attract attention if worn during the activities of daily life.

Prior art which appears to be within this category includes U.S. Pat. No. 6,067,464 (Musha, May 23, 200, "Electrode"), U.S. Pat. No. 6,154,669 (Hunter et al., Nov. 28, 2000, "Headset for EEG Measurements"), U.S. Pat. No. 6,161,030 (Levendowski et al., Dec. 12, 2000, "Portable EEG Electrode Locator Headgear"), U.S. Pat. No. 6,381,481 (Levendowski et al., Apr. 30, 2002, "Portable EEG Electrode Locator Headgear"), U.S. Pat. No. 7,551,952 (Gevins et al., Jun. 23, 2009, "EEG Electrode Headset"), U.S. Pat. No. 8,103,328 (Turner et al., Jan. 24, 2012, "Self-Locating Sensor Mounting Apparatus"), U.S. Pat. No. 8,392,250 (Pradeep et al., Mar. 5, 2013, "Neuro-Response Evaluated Stimulus in Virtual Reality Environments"), U.S. Pat. No. 8,392,251 (Pradeep et al., Mar. 5, 2013, "Location Aware Presentation of Stimulus Material"), U.S. Pat. No. 8,396,744 (Pradeep et al., Mar. 12, 2013, "Effective Virtual Reality Environments for Presentation of Marketing Materials"), U.S. Pat. No. 8,548,852 (Pradeep et al., Oct. 1, 2013, "Effective Virtual Reality Environments for Presentation of Marketing Materials"), and U.S. Pat. No. 8,655,428 (Pradeep et al., Feb. 18, 2014, "Neuro-Response Data Synchronization").

Prior art which appears to be within this category also includes U.S. patent applications: 20020029005 (Levendowski et al., Mar. 7, 2002, "Portable EEG Electrode Locator Headgear"), 20070093706 (Gevins et al., Apr. 26, 2007, "EEG Electrode Headset"), 20090088619 (Turner et al., Apr. 2, 2009, "Self-Locating Sensor Mounting Apparatus"), 20110098593 (Low et al., Apr. 28, 2011, "Head Harness & Wireless EEG Monitoring System"), 20110237971 (Pradeep et al., Sep. 29, 2011, "Discrete Choice Modeling Using Neuro-Response Data"), 20110282231 (Pradeep et al., Nov. 17, 2011, "Mechanisms for Collecting Electroencephalography Data"), 20110282232 (Pradeep et al., Nov. 17, 2011, "Neuro-Response Data Synchronization"), 20120072289 (Pradeep et al., Mar. 22, 2012, "Biometric Aware Content Presentation"), and 20130185144 (Pradeep et al., Jul. 18, 2013, "Systems and Methods for Analyzing Neuro-Reponse Data and Virtual Reality Environments").

8. Device with Multiple Arms Radially-Forward from Rear and EEG/Brainwave Sensor(s)

Devices in this category hold electromagnetic brain activity sensors in contact with (or proximity to) a person's head using multiple sensor-holding protrusions, fingers, or arms which extend radially forward from a central position at the rear of a person's head. In an example, radially-extending protrusions, fingers, or arms can curve around the head toward the top and sides of the head. To use the colorful language from the previous category, now a figurative starfish (or octopus) is clinging to the back of the person's head. Such devices can be less obtrusive than some of those in the preceding categories, but can still attract attention if worn during the activities of daily life.

Prior art which appears to be within this category includes U.S. Pat. No. 4,770,180 (Schmidt et al., Sep. 13, 1988, "Electroencephalographic Head Set with a Disposable Monitor"), U.S. Pat. No. 4,967,038 (Gevins et al., Oct. 30, 1990, "Dry Electrode Brain Wave Recording System"), U.S. Pat. No. 5,038,782 (Gevins et al., Aug. 13, 1991, "Electrode System for Brain Wave Detection"), and D565735 (Washbon, Apr. 1, 2008, "Electrode Headset"); and U.S. patent applications 20070225585 (Washbon and Delic, Sep. 27, 2007, "Headset for Electrodes"), 20070238945 (Delic et al., Oct. 11, 2007, "Electrode Headset"), 20090105576 (Do et al., Apr. 23, 2009, "Electrode Conductive Element"), 20120029379 (Sivadas, Feb. 2, 2012, "Mind Strength Trainer"), and 20130046206 (Preminger, Feb. 21, 2013, "System and Method for Neurocognitive Training and/or Neuropsychological Assessment").

9. Device with Multiple Arms Radially-Backward from Front and EEG/Brainwave Sensor(s)

Devices in this category hold electromagnetic brain activity sensors in contact with (or proximity to) a person's head using multiple sensor-holding protrusions, fingers, or arms which extend radially backward from a position on the front of a person's head (such as the forehead). In an example, radially-extending protrusions, fingers, or arms can curve around the head toward the top and sides of the head. Such devices can be obtrusive and attract attention, especially if worn to a showing of the movie "Aliens". Prior art which appears to be within this category includes U.S. patent application 20020188216 (Kayyali et al., Dec. 12, 2002, "Head Mounted Medical Device").

10. Device with Circular Horizontal Loop (e.g. Headband Style) and EEG/Brainwave Sensor(s)

Devices in this category hold electromagnetic brain activity sensors in contact with (or proximity to) a person's head using a sensor-holding member which is configured like a headband, ring, or other generally-circular member which encircles a person's head in (or close to) a horizontal plane when the person is upright. In an example, such a device can span a portion of a person's forehead as it encircles the person's head. Since devices in this category can span a portion of the forehead, such devices can be used with sensors which require contact with (or proximity to) portions of the head which do not have hair. Such devices can be appropriate for wearing while running or doing other types of exercise, but there are still many settings wherein wearing a headband or head-encircling ring is generally not appropriate.

Prior art which appears to be within this category includes U.S. Pat. No. 6,001,065 (Devito, Dec. 14, 1999, "Method and Apparatus for Measuring and Analyzing Physiological Signals for Active or Passive Control of Physical and Virtual Spaces and the Contents Therein"), U.S. Pat. No. 6,171,258 (Karakasoglu et al., Jan. 9, 2001, "Multi-Channel Self-Contained Apparatus and Method for Diagnosis of Sleep Disorders"), U.S. Pat. No. 6,254,536 (Devito, Jul. 3, 2001, "Method and Apparatus for Measuring and Analyzing Physiological Signals for Active or Passive Control of Physical and Virtual Spaces and the Contents Therein"), U.S. Pat. No. 6,811,538 (Westbrook et al., Nov. 2, 2004, "Sleep Apnea Risk Evaluation"), U.S. Pat. No. 7,297,119 (Westbrook et al., Nov. 20, 2007, "Sleep Apnea Risk Evaluation"), and U.S. Pat. No. 7,885,706 (Ludvig et al., Feb. 8, 2011, "System and Device for Seizure Detection").

Prior art which appears to be within this category also includes U.S. patent applications: 20010056225 (DeVito, Dec. 27, 2001, "Method and Apparatus for Measuring and Analyzing Physiological Signals for Active or Passive Control of Physical and Virtual Spaces and the Contents Therein"), 20020165462 (Westbrook et al., Nov. 7, 2002, "Sleep Apnea Risk Evaluation"), 20020188216 (Kayyali et al., Dec. 12, 2002, "Head Mounted Medical Device"), 20040267152 (Pineda, Dec. 20, 2004, "Method and System for Predicting and Preventing Seizures"), 20050027207 (Westbrook et al., Feb. 3, 2005, "Sleep Apnea Risk Evaluation"), and 20070249952 (Rubin et al., Oct. 25, 2007, "Systems and Methods for Sleep Monitoring").

Prior art which appears to be within this category also includes U.S. patent applications: 20080082019 (Ludving et al., Apr. 3, 2008, "System and Device for Seizure Detection"), 20090281446 (Ludvig et al., Nov. 12, 2009, "System and Device for Seizure Detection"), 20100099954 (Dickinson et al., Apr. 22, 2010, "Data-Driven Sleep Coaching System"), 20120150545 (Simon, Jun. 14, 2012, "Brain-Computer Interface Test Battery for the Physiological Assessment of Nervous System Health"), 20130060097 (Rubin, Mar. 7, 2013, "Multi-Modal Sleep System"), 20130127708 (Jung et al., May 23, 2013, "Cell-Phone Based Wireless and Mobile Brain-Machine Interface"), and 20130338446 (Van Vugt et al., Dec. 19, 2013, "Sleep Disturbance Monitoring Apparatus").

11. Device with Top Semicircular Loop (e.g. Headphone Style) and EEG/Brainwave Sensor(s)

Devices in this category hold electromagnetic brain activity sensors in contact with (or proximity to) a person's head using a (semicircular) arcuate member which looks like a set of headphones, hair band, or tiara. In an example, such a device can loop over the top of a person's head, from one side to the other side. In an example, such a device can loop over the top of a person's head from one ear to the other ear. In example, such a device can not only look like a set of headphones, but can actually be a set of headphones, wherein these headphones also include one or more electromagnetic brain activity sensors. Wearing a set of headphones or a hair band is more common (and thus may attract less attention) than wearing most of the devices discussed in preceding categories, but there are still many settings wherein wearing such a device would attract attention and be inappropriate.

Prior art which appears to be within this category includes U.S. Pat. No. 4,697,598 (Bernard et al., Oct. 6, 1987, "Evoked Potential Autorefractometry System"), U.S. Pat. No. 4,709,702 (Sherwin, Dec. 1, 1987, "Electroencephalographic Cap"), U.S. Pat. No. 5,740,812 (Cowan, Apr. 21, 1998, "Apparatus for and Method of Providing Brainwave Biofeedback"), U.S. Pat. No. 6,154,669 (Hunter et al., Nov. 28, 2000, "Headset for EEG Measurements"), U.S. Pat. No. 6,167,298 (Levin, Dec. 26, 2000, "Devices and Methods for Maintaining an Alert State of Consciousness Through Brain Wave Monitoring"), U.S. Pat. No. 7,689,274 (Mullen et al., Mar. 30, 2010, "Brain-Wave Aware Sleep Management"), U.S. Pat. No. 8,271,075 (Chuang et al., Sep. 18, 2012, "Audio Headset with Bio-Signal Sensors"), and U.S. Pat. No. 8,301,218 (Nguyen et al., Oct. 30, 2012, "Contoured Electrode"), U.S. Pat. No. 8,812,075 (Nguyen et al., Aug. 19, 2014, "Contoured Electrode").

Prior art which appears to be within this category also includes U.S. patent applications: 20120029379 (Sivadas, Feb. 2, 2012, "Mind Strength Trainer"), 20120226127 (Asjes et al., Sep. 6, 2012, "Device for Positioning Electrodes on a User's Scalp"), 20130177883 (Barnehama et al., Jul. 11, 2013, "Systems and Methods for Directing Brain Activity"), and 20130310676 (Jung, Nov. 21, 2013, "EEG Hair Band").

12. Device with Rear Semicircular Loop and EEG/Brainwave Sensor(s)

Devices in this category hold electromagnetic brain activity sensors in contact with (or proximity to) a person's head using a (semicircular) arcuate member which loops around the rear portion of a person's head, from one side to the other side. In an example, such a device can loop around the rear portion of a person's head from one ear to the other ear. Such a device can be less obtrusive than many of the devices in preceding categories because it does not span the top of the head or face, but it is not well-suited for use with sensors which require contact with skin without hair. Prior art which appears to be within this category includes U.S. patent application 20140316230 (Denison et al., Oct. 23, 2014, "Methods and Devices for Brain Activity Monitoring Supporting Mental State Development and Training").

13. Device with Frontal Semicircular Loop and EEG/Brainwave Sensor(s)

Devices in this category hold electromagnetic brain activity sensors in contact with (or proximity to) a person's head using a (semicircular) arcuate member which loops around the front of a person's head, from one side to the other side. In an example, such a device can loop around the front of a person's head from one ear to the other ear. In an example, such a device can span a person's forehead. Such a device can be well-suited for use with sensors which require contact with skin without hair, but can be somewhat obtrusive since it spans a portion of a person's face. Prior art which appears to be within this category includes U.S. patent application 20080177197 (Lee et al., Jul. 24, 2008, "Method and Apparatus for Quantitatively Evaluating Mental States Based on Brain Wave Signal Processing System").

14. Device Like Eyeglasses or Other Eyewear with EEG/Brainwave Sensor(s)

Devices in this category hold electromagnetic brain activity sensors in contact with (or proximity to) a person's head using a sensor-holding member which looks like a pair of eyeglasses, goggles, or other eyewear. In an example, such a device can span from one ear, to the face, across the face (over the bridge of the nose), and then to the other ear. In example, such a device can not only look like a pair of eyeglasses, but can actually be a pair of eyeglasses, wherein these eyeglasses include one or more electromagnetic brain activity sensors. Some of the art in this category predominantly focuses on the optical aspects of a pair of eyeglasses, with only tangential mention of a possible EEG sensor, but such art is included in this category for the sake of completeness. Wearing a pair of eyeglasses is very common and thus attracts less attention than virtually all of the devices discussed in preceding categories. However, conventional eyeglass frames (especially those with straight side pieces) do not contact a person's temple or forehead. Accordingly, conventional eyeglass frame configurations are not ideally-suited for holding one or more electromagnetic brain activity sensors in contact with a person's temple and/or forehead.

Prior art which appears to be within this category includes U.S. Pat. No. 7,344,244 (Goodall et al., Mar. 18, 2008, "Adjustable Lens System with Neural-Based Control"), U.S. Pat. No. 7,390,088 (Goodall et al., Jun. 24, 2008, "Adjustable Lens System with Neural-Based Control"), U.S. Pat. No. 7,486,988 (Goodall et al., Feb. 3, 2009, "Method and System for Adaptive Vision Modification"), U.S. Pat. No. 8,244,342 (Goodall et al., Aug. 14, 2012, "Method and System for Adaptive Vision Modification"), U.S. Pat. No. 8,346,354 (Hyde et al., Jan. 1, 2013, "Determining a Neuromodulation Treatment Regimen in Response to Contactlessly Acquired Information"), U.S. Pat. No. 8,467,133 (Miller, Jun. 18, 2013, "See-Through Display with an Optical Assembly Including a Wedge-Shaped Illumination System"), U.S. Pat. No. 8,472,120 (Border et al., Jun. 25, 2013, "See-Through Near-Eye Display Glasses with a Small Scale Image Source"), U.S. Pat. No. 8,477,425 (Border et al., Jul. 2, 2013, "See-Through Near-Eye Display Glasses Including a Partially Reflective, Partially Transmitting Optical Element"), U.S. Pat. No. 8,482,859 (Border et al., Jul. 9, 2013, "See-Through Near-Eye Display Glasses Wherein Image Light Is Transmitted to and Reflected From an Optically Flat Film"), U.S. Pat. No. 8,488,246 (Border et al., Jul. 16, 2013, "See-Through Near-Eye Display Glasses Including a Curved Polarizing Film in the Image Source, a Partially Reflective, Partially Transmitting Optical Element and an Optically Flat Film"), and U.S. Pat. No. 8,562,540 (Goodall et al., Oct. 22, 2013, "Method and System for Adaptive Vision Modification").

Prior art which appears to be within this category also includes U.S. patent applications: 20060252978 (Vesely et al., Nov. 9, 2006, "Biofeedback Eyewear System"), 20060252979 (Vesely et al., Nov. 9, 2006, "Biofeedback Eyewear System"), 20070010757 (Goodall et al., Jan. 11, 2007, "Method and System for Adaptive Vision Modification"), 20070019279 (Goodall et al., Jan. 25, 2007, "Adjustable Lens System with Neural-Based Control"), 20070106145 (Kim et al., May 10, 2007, "Accessories for Remote Monitoring"), 20080161673 (Goodall et al., Jul. 3, 2008, "Method and System for Adaptive Vision Modification"), 20110028798 (Hyde et al., Feb. 3, 2011, "Electronically Initiating an Administration of a Neuromodulation Treatment Regimen Chosen in Response to Contactlessly Acquired Information"), 20110029038 (Hyde et al., Feb. 3, 2011, "Determining a Neuromodulation Treatment Regimen in Response to Contactlessly Acquired Information"), 20110029044 (Hyde et al., Feb. 3, 2011, "Stimulating a Nervous System Component of a Mammal in Response to Contactlessly Acquired Information"), 20110221656 (Haddick et al., Sep. 15, 2011, "Displayed Content Vision Correction with Electrically Adjustable Lens"), and 20110221669 (Shams et al., Sep. 15, 2011, "Gesture Control in an Augmented Reality Eyepiece").

Prior art which appears to be within this category also includes U.S. patent applications: 20110221672 (Osterhout et al., Sep. 15, 2011, "Hand-Worn Control Device in an Augmented Reality Eyepiece"), 20110222745 (Osterhout et al., Sep. 15, 2011, "Method and Apparatus for Biometric Data Capture"), 20110227820 (Haddick et al., Sep. 22, 2011, "Lock Virtual Keyboard Position in an Augmented Reality Eyepiece"), 20120062445 (Haddick et al., Mar. 15, 2012, "Adjustable Wrap Around Extendable Arm for a Head-Mounted Display"), 20120075168 (Osterhout et al., Mar. 29, 2012, "Eyepiece with Uniformly Illuminated Reflective Display"), 20120150545 (Simon, Jun. 14, 2012, "Brain-Computer Interface Test Battery for the Physiological Assessment of Nervous System Health"), 20120212398 (Border et al., 823/2012, "See-Through Near-Eye Display Glasses Including a Partially Reflective, Partially Transmitting Optical Element"), and 20120212400 (Border et al., Aug. 23, 2012, "See-Through Near-Eye Display Glasses Including a Curved Polarizing Film in the Image Source, a Partially Reflective, Partially Transmitting Optical Element and an Optically Flat Film").

Prior art which appears to be within this category also includes U.S. patent applications: 20120218172 (Border et al., Aug. 30, 2012, "See-Through Near-Eye Display Glasses with a Small Scale Image Source"), 20120218301 (Miller, Aug. 30, 2012, "See-Through Display with an Optical Assembly Including a Wedge-Shaped Illumination System"), 20120235883 (Border et al., Sep. 20, 2012, "See-Through Near-Eye Display Glasses with a Light Transmissive Wedge Shaped Illumination System"), 20120235886 (Border et al., Sep. 20, 2012, "See-Through Near-Eye Display Glasses with a Small Scale Image Source"), 20120235887 (Border et al., Sep. 20, 2012, "See-Through Near-Eye Display Glasses Including a Partially Reflective, Partially Transmitting Optical Element and an Optically Flat Film"), and 20120235900 (Border et al., Sep. 20, 2012, "See-Through Near-Eye Display Glasses with a Fast Response Photochromic Film System for Quick Transition From Dark to Clear").

Prior art which appears to be within this category also includes U.S. patent applications: 20120236030 (Border et al., Sep. 20, 2012, "See-Through Near-Eye Display Glasses Including a Modular Image Source"), 20120242678 (Border et al., Sep. 27, 2012, "See-Through Near-Eye Display Glasses Including an Auto-Brightness Control for the Display Brightness Based on the Brightness in the Environment"), 20120242698 (Haddick et al., Sep. 27, 2012, "See-Through Near-Eye Display Glasses with a Multi-Segment Processor-Controlled Optical Layer"), 20130056010 (Walker et al., Mar. 7, 2013, "Autonomous Positive Airway Pressure System"), 20130127980 (Haddick et al., May 23, 2013, "Video Display Modification Based on Sensor Input for a See-Through Near-to-Eye Display"), and 20130242262 (Lewis, Sep. 19, 2013, "Enhanced Optical and Perceptual Digital Eyewear").

Prior art which appears to be within this category also includes U.S. patent applications: 20130303837 (Berka et al., Nov. 14, 2013, "Systems and Methods for Optimization of Sleep and Post-Sleep Performance"), 20130314303 (Osterhout et al., Nov. 28, 2013, "AR Glasses with User Action Control of and Between Internal and External Applications with Feedback"), 20140023999 (Greder, Jan. 23, 2014, "Detection and Feedback of Information Associated with Executive Function"), 20140267005 (Urbach, Sep. 18, 2014, "Piece for Augmented and Virtual Reality"), 20140267401 (Urbach, Sep. 18, 2014, "Visual Cortex Thought Detector Interface"), 20140347265 (Aimone et al., Nov. 27, 2014, "Wearable Computing Apparatus and Method"), and 20140375545 (Ackerman et al., Dec. 25, 2014, "Adaptive Event Recognition").

15. Device Like a Hearing Aid or Other Earwear with EEG/Brainwave Sensor(s)

Devices in this category hold electromagnetic brain activity sensors in contact with (or proximity to) a person's head using a sensor-holding member which looks like a hearing aid, ear bud, ear set, or other earwear. In an example, such a device can be inserted into an ear or encircle a portion of an ear. Wearing a hearing aid or pair of ear buds is relatively common and thus can attract less attention than many of the devices discussed in preceding categories. However, conventional hearing aid and ear bud designs do not generally contact a person's forehead and thus are not well-suited to hold one or more electromagnetic brain activity sensors in contact with a person's forehead when that is a desired location for collecting brain activity data.

Prior art which appears to be within this category includes U.S. Pat. No. 6,694,180 (Boesen, Feb. 17, 2004, "Wireless Biopotential Sensing Device and Method with Capability of Short-Range Radio Frequency Transmission and Reception"), U.S. Pat. No. 8,157,730 (Leboeuf et al., Apr. 17, 2012, "Physiological and Environmental Monitoring Systems and Methods"), U.S. Pat. No. 8,204,786 (LeBoeuf et al., Jun. 19, 2012, "Physiological and Environmental Monitoring Systems and Methods"), 20060094974 (Cain, May 4, 2006, "Systems and Methods for Detecting Brain Waves"), 20070112277 (Fischer et al., May 17, 2007, "Apparatus and Method for the Measurement and Monitoring of Bioelectric Signal Patterns"), 20080146890 (LeBoeuf et al., Jun. 19, 2008, "Telemetric Apparatus for Health and Environmental Monitoring"), and 20080146892 (LeBoeuf et al., Jun. 19, 2008, "Physiological and Environmental Monitoring Systems and Methods").

Prior art which appears to be within this category also includes U.S. patent applications: 20090112080 (Matthews, Apr. 30, 2009, "System for Measuring Electric Signals"), 20100217099 (LeBoeuf et al., Aug. 26, 2010, "Methods and Apparatus for Assessing Physiological Conditions"), 20100217100 (LeBoeuf et al., Aug. 26, 2010, "Methods and Apparatus for Measuring Physiological Conditions"), 20110098112 (LeBoeuf et al., Apr. 28, 2011, "Physiological and Environmental Monitoring Systems and Methods"), 20110106627 (LeBoeuf et al., May 5, 2011, "Physiological and Environmental Monitoring Systems and Methods"), 20120123290 (Kidmose et al., May 17, 2012, "EEG Monitoring System and Method of Monitoring an EEG"), 20120165695 (Kidmose et al., Jun. 28, 2012, "EEG Monitoring Apparatus and Method for Presenting Messages Therein"), and 20120177233 (Kidmose et al., Jul. 12, 2012, "Hearing Aid Adapted for Detecting Brain Waves and a Method for Adapting Such a Hearing Aid").

Prior art which appears to be within this category also includes U.S. patent applications: 20120203081 (Leboeuf et al., Aug. 9, 2012, "Physiological and Environmental Monitoring Apparatus and Systems"), 20120209101 (Kidmose et al., Aug. 16, 2012, "Ear Plug with Surface Electrodes"), 20120235820 (Kidmose, Sep. 20, 2012, "Method and Apparatus for Alerting a Person Carrying an EEG Assembly"), 20120238856 (Kidmose et al., Sep. 20, 2012, "Portable Monitoring Device with Hearing Aid and EEG Monitor"), 20120302858 (Kidmose et al., Nov. 29, 2012, "Portable EEG Monitor System with Wireless Communication"), 20120316418 (Kilsgaard et al., Dec. 13, 2012, "Two Part EEG Monitor with Databus and Method of Communicating Between the Parts"), and 20130035578 (Chiu et al., Feb. 7, 2013, "Portable Brain Activity Monitor and Method").

Prior art which appears to be within this category also includes U.S. patent applications: 20130184552 (Westermann et al., Jul. 18, 2013, "Bi-Hemispheric Brain Wave System and Method of Performing Bi-Hemispherical Brain Wave Measurements"), 20130296731 (Kidmose et al., Nov. 7, 2013, "Personal EEG Monitoring Device with Electrode Validation"), 20140171775 (Kilsgaard et al., Jun. 19, 2014, "EEG Monitor with Capacitive Electrodes and a Method of Monitoring Brain Waves"), 20140316230 (Denison et al., Oct. 23, 2014, "Methods and Devices for Brain Activity Monitoring Supporting Mental State Development and Training"), 20140369537 (Pontoppidan et al., Dec. 18, 2014, "Hearing Assistance Device with Brain Computer Interface"), 20140369537 (Pontoppidan et al., Dec. 18, 2014, "Hearing Assistance Device with Brain Computer Interface"), and WO2013026481 (Kilsgaard et al., Feb. 28, 2013, "EEG Monitor with Capacitive Electrodes and Method of Monitoring Brain Waves").

16. Device Like a Breathing Mask with EEG/Brainwave Sensor(s)

Devices in this category hold electromagnetic brain activity sensors in contact with (or proximity to) a person's head using a sensor-holding member which looks like a respiratory mask. In an example, such a mask can be a CPAP mask or other positive airway pressure mask which is generally worn by a person when they are sleeping. In an example, such devices can include members which span a portion of a person's forehead to position sensors there. Such devices can provide useful EEG data during sleep if a person wears a breathing mask while they sleep, but are not well-suited for use during the day.

Prior art which appears to be within this category includes U.S. Pat. No. 6,171,258 (Karakasoglu et al., Jan. 9, 2001, "Multi-Channel Self-Contained Apparatus and Method for Diagnosis of Sleep Disorders"), U.S. Pat. No. 6,811,538 (Westbrook et al., Nov. 2, 2004, "Sleep Apnea Risk Evaluation"), U.S. Pat. No. 7,054,680 (Genger et al., May 30, 2006, "Device for Detecting Electrical Potentials in the Forehead-Area of a Patient"), U.S. Pat. No. 7,204,250 (Burton, Apr. 17, 2007, "Bio-Mask"), U.S. Pat. No. 7,297,119 (Westbrook et al., Nov. 20, 2007, "Sleep Apnea Risk Evaluation"), U.S. Pat. No. 7,575,005 (Mumford et al., Aug. 18, 2009, "Mask Assembly with Integrated Sensors"), U.S. Pat. No. 7,942,824 (Kayyali et al., May 17, 2011, "Integrated Sleep Diagnostic and Therapeutic System and Method"), U.S. Pat. No. 7,992,560 (Burton et al., Aug. 9, 2011, "Adaptable Breathing Mask"), U.S. Pat. No. 8,069,852 (Burton et al., Dec. 6, 2011, "Method and Apparatus for Maintaining and Monitoring Sleep Quality During Therapeutic Treatments"), U.S. Pat. No. 8,147,419 (Krauss et al., Apr. 3, 2012, "Automated Interpretive Medical Care System and Methodology"), U.S. Pat. No. 8,172,766 (Kayyali et al., May 8, 2012, "Integrated Sleep Diagnosis and Treatment Device and Method"), U.S. Pat. No. 8,281,787 (Burton, Oct. 9, 2012, "Bio-Mask with Integral Sensors"), U.S. Pat. No. 8,355,769 (Levendowski et al., Jan. 15, 2013, "System for the Assessment of Sleep Quality in Adults and Children"), U.S. Pat. No. 8,639,313 (Westbrook et al, Jan. 28, 2014, "System for the Assessment of Sleep Quality in Adults and Children"), and U.S. Pat. No. 8,640,698 (Darkin et al., Feb. 4, 2014, "Method and Apparatus for Monitoring the Condition of a Patient with Diabetes").

Prior art which appears to be within this category also includes U.S. patent applications: 20020165462 (Westbrook et al., Nov. 7, 2002, "Sleep Apnea Risk Evaluation"), 20040163648 (Burton, Aug. 26, 2004, "Bio-Mask with Integral Sensors"), 20050027207 (Westbrook et al., Feb. 3, 2005, "Sleep Apnea Risk Evaluation"), 20050268916 (Mumford et al., Dec. 8, 2005, "Mask Assembly with Integrated Sensors"), 20060032504 (Burton et al., Feb. 16, 2006, "Adaptable Breathing Mask"), 20060100538 (Genger et al., May 11, 2006, "Device for Detecting Electrical Potentials of the Forehead Region of a Patent"), 20100147304 (Burton, Jun. 17, 2010, "Bio-Mask with Integral Sensors"), 20100240982 (Westbrook et al., Sep. 23, 2010, "System for the Assessment of Sleep Quality in Adults and Children"), 20110295083 (Doelling et al., Dec. 1, 2011, "Devices, Systems, and Methods for Monitoring, Analyzing, and/or Adjusting Sleep Conditions"), 20120041331 (Burton et al., Feb. 16, 2013, "Adaptable Breathing Mask"), 20130056010 (Walker et al., Mar. 7, 2013, "Autonomous Positive Airway Pressure System"), and 20130131464 (Westbrook et al., May 23, 2013, "System for the Assessment of Sleep Quality in Adults and Children").

17. Specific Type of EEG/Brainwave Sensor

Devices in this category focus on a specific type and/or design of EEG or other electromagnetic brain activity sensor rather than a device to hold such sensors in place on a person's head or a specific configuration of such sensors on a person's head. Some prior art discloses both a novel type of sensor and a device to hold one or more such sensors on a person's head. Art that discloses both a specific type of sensor and a specific type of device to hold it on a person's head is included twice in this review—once in a category of device to hold the sensors and once in this category for a type of sensor. Since the emphasis of this disclosure is not on a specific type of sensor, prior art included in this category is not exhaustive.

Prior art which appears to be within this category includes U.S. Pat. No. 4,632,122 (Johansson, Dec. 30, 1986, "Method and Apparatus for Conducting Brain Function Diagnostic Test"), U.S. Pat. No. 4,683,892 (Johansson, Aug. 4, 1987, "Method and Apparatus for Conducting Brain Function Diagnostic Test"), U.S. Pat. No. 5,309,095 (Ahonen et al., May 3, 1994, "Compact Magnetometer Probe and an Array of Them Covering the Whole Human Skull for Measurement of Magnetic Fields Arising from the Activity of the Brain"), U.S. Pat. No. 5,357,957 (Itil et al., Oct. 25, 1994, "Electrode Assembly for EEG Headset"), U.S. Pat. No. 6,066,084 (Edrich et al., May 23, 2000, "Method and Apparatus for Focused Neuromagnetic Stimulation and Detection"), U.S. Pat. No. 6,175,753 (Menkes et al., Jan. 16, 2001, "Methods and Mechanisms for Quick-Placement Electroencephalogram (EEG) Electrodes"), U.S. Pat. No. 6,201,982 (Menkes et al., Mar. 13, 2001, "Quick-Placement Electroencephalogram (EEG) Electrode"), U.S. Pat. No. 6,690,959 (Thompson, Feb. 10, 2004, "Skin-Mounted Electrodes with Nano Spikes"), and U.S. Pat. No. 6,961,601 (Matthews et al., Nov. 1, 2005, "Sensor System for Measuring Biopotentials").

Prior art which appears to be within this category also includes U.S. Pat. No. 7,141,987 (Hibbs et al., Nov. 28, 2006, "Sensor System for Measurement of One or More Vector Components of an Electric Field"), U.S. Pat. No. 7,158,822 (Payne Jr., Jan. 2, 2007, "Electrode Holder, Headwear, and Wire Jacket Adapted for Use in Sleep Apnea Testing"), U.S. Pat. No. 7,206,625 (Kurtz et al., Apr. 17, 2007, "Method and Apparatus for the Collection of Physiological Electrical Potentials"), U.S. Pat. No. 7,466,148 (Fridman et al., Dec. 16, 2008, "Sensor System for Measuring an Electric Potential Signal of an Object"), U.S. Pat. No. 7,548,774 (Kurtz et al., Jun. 16, 2009, "Method and Apparatus for the Collection of Physiological Electrical Potentials"), U.S. Pat. No. 8,170,637 (Lee et al., May 1, 2012, "Dry Electrode Device and Method of Assembly"), and U.S. Pat. No. 8,190,248 (Besio et al., May 29, 2012, "Medical Devices for the Detection, Prevention and/or Treatment of Neurological Disorders, and Methods Related Thereto").

Prior art which appears to be within this category also includes U.S. Pat. No. 8,193,821 (Mueller et al., Jun. 5, 2012, "Sensor System and Methods for the Capacitive Measurement of Electromagnetic Signals Having a Biological Origin"), U.S. Pat. No. 8,290,563 (Jin et al., Oct. 16, 2012, "Active Dry Sensor Module for Measurement of Bioelectricity"), U.S. Pat. No. 8,301,218 (Nguyen et al., Oct. 30, 2012, "Contoured Electrode"), U.S. Pat. No. 8,396,529 (Lee et al., Mar. 12, 2013, "Dry Electrode Device and Method of Assembly"), U.S. Pat. No. 8,457,709 (Matthews et al., Jun. 4, 2013, "Sensor Mounting System"), U.S. Pat. No. 8,548,555 (Jin et al., Oct. 1, 2013, "Active Dry Sensor Module for Measurement of Bioelectricity"), U.S. Pat. No. 8,548,558 (Dunagan et al., Oct. 1, 2013, "Electrode Capable of Attachment to a Garment, System, and Methods of Manufacturing"), U.S. Pat. No. 8,634,892 (Lee et al., Jan. 21, 2014, "Dry Electrode Device and Method of Assembly"), U.S. Pat. No. 8,812,075 (Nguyen et al., Aug. 19, 2014, "Contoured Electrode"), and U.S. Pat. No. 8,868,216 (Dunagan, Oct. 21, 2014, "Electrode Garment").

Prior art which appears to be within this category also includes U.S. patent applications: 20050073322 (Hibbs et al., Apr. 7, 2005, "Sensor System for Measurement of One or More Vector Components of an Electric Field"), 20050215916 (Fadem et al., Sep. 29, 2005, "Active, Multiplexed Digital Electrodes for EEG, ECG and EMG applications"), 20050277821 (Payne, Dec. 15, 2005, "Electrode Holder, Headwear, and Wire Jacket Adapted for Use in Sleep Apnea Testing"), 20070112262 (Payne, May 17, 2007, "Electrode Holder, Headwear, and Wire Jacket Adapted for Use in Sleep Apnea Testing"), 20070135701 (Fridman et al., Jun. 14, 2007, "Sensor System for Measuring an Electric Potential Signal of an Object"), 20070270678 (Fadem et al., Nov. 22, 2007, "Wireless Electrode for Biopotential Measurement"), 20090105576 (Do et al., Apr. 23, 2009, "Electrode Conductive Element"), 20100060300 (Muller et al., Mar. 11, 2010, "Sensor System and Methods for the Capacitive Measurement of Electromagnetic Signals Having a Biological Origin"), 20110248729 (Mueller et al., Oct. 13, 2011, "Sensor System and Methods for the Capacitive Measurement of Electromagnetic Signals Having a Biological Origin"), 20120245450 (Lee et al., Sep. 27, 2012, "Dry Electrode Device and Method of Assembly"), 20130211226 (Lee et al., Aug. 15, 2013, "Dry Electrode Device and Method of Assembly"), and 20130268038 (Bikson et al., Oct. 10, 2013, "Electrode Assembly").

18. Adhesive EEG/Brainwave Sensor(s)

This category involves holding electromagnetic brain activity sensors in contact with (or proximity to) a person's head using (multiple) adhesive members. Prior art included in this category is not exhaustive. Prior art which appears to be within this category includes U.S. Pat. No. 6,032,065 (Brown, Feb. 29, 2000, "Sensor Mask and Method of Making Same"), U.S. Pat. No. 6,272,378 (Baumgart-Schmitt, Aug. 7, 2001, "Device and Method for Determining Sleep Profiles"), U.S. Pat. No. 6,301,493 (Marro et al., Oct. 9, 2001, "Reservoir Electrodes for Electroencephalograph Headgear Appliance"), U.S. Pat. No. 7,299,088 (Thakor et al., Nov. 20, 2007, "Apparatus and Methods for Brain Rhythm Analysis"), and U.S. Pat. No. 8,428,682 (Rood et al., Apr. 23, 2013, "Wet or Dry Electrode, Other Sensors, Actuators, or Markers with a Novel Adhesive Collar").

Prior art which appears to be within this category also includes U.S. patent applications: 20020183605 (Devlin, Dec. 5, 2002, "Electrode Array System for Measuring Electrophysiological Signals"), 20020188216 (Kayyali et al., Dec. 12, 2002, "Head Mounted Medical Device"), 20060258930 (Wu et al., Nov. 16, 2006, "Device for Use in Sleep Stage Determination Using Frontal Electrodes"), 20090105577 (Wu et al., Apr. 23, 2009, "Device for Detecting Electrical Potentials Using Frontal Electrodes"), 20110172503 (Knepper et al., Jul. 14, 2011, "Physiological Data Collection System"), 20110208015 (Welch et al., Aug. 25, 2011, "Wireless Patient Monitoring System"), and 20120083673 (Al-Ali et al., Apr. 5, 2012, "Depth of Consciousness Monitor Including Oximeter").

Prior art which appears to be within this category also includes U.S. patent applications: 20130253334 (Al-Ali et al., Sep. 26, 2013, "Wireless Patient Monitoring Device"), 20140275875 (Su et al., Sep. 18, 2014, "System and Method for Positioning a Sensor"), 20150005840 (Pal et al., Jan. 1, 2015, "Transdermal Electrical Stimulation Methods for Modifying or Inducing Cognitive State"), 20150005841 (Pal et al., Jan. 1, 2015, "Transdermal Electrical Stimulation Devices for Modifying or Inducing Cognitive State"), and 20150019135 (Kacyvenski et al., Jan. 15, 2015, "Motion Sensor and Analysis").

19. Method for EEG/Brainwave Analysis

This category includes selected art which primarily focuses on methods for collection and analysis of data concerning electromagnetic brain activity. There is a large body of prior art on such methods. Art included in this category is not exhaustive. Prior art which appears to be within this category includes U.S. Pat. No. 3,760,796 (Baessler et al., Sep. 25, 1973, "Method and Apparatus for Automatic Analysis of Brain Wave Signals"), U.S. Pat. No. 4,610,259 (Cohen et al., Sep. 9, 1986, "EEG Signal Analysis System"), U.S. Pat. No. 4,697,598 (Bernard et al., Oct. 6, 1987, "Evoked Potential Autorefractometry System"), U.S. Pat. No. 4,844,086 (Duffy, Jul. 4, 1989, "Cross Correlation Analysis in Brain Electrical Activity Mapping"), U.S. Pat. No. 4,974,602 (Abraham-Fuchs et al., Dec. 4, 1990, "Arrangement for Analyzing Local Bioelectric Currents in Biological Tissue Complexes"), U.S. Pat. No. 5,154,180 (Blanchet et al., Oct. 13, 1992, "Method and Device for Determining a Subject's Sleep State by Processing an Electroencephalographic Signal"), U.S. Pat. No. 5,299,118 (Martens et al., Mar. 29, 1994, "Method and System for Analysis of Long Term Physiological Polygraphic Recordings"), U.S. Pat. No. 5,311,876 (Olsen et al., May 17, 1994, "Automatic Detection of Seizures Using Electroencephalographic Signals"), and U.S. Pat. No. 5,447,166 (Gevins, Sep. 5, 1995, "Neurocognitive Adaptive Computer Interface Method and System Based on On-Line Measurement of the User's Mental Effort").

Prior art which appears to be within this category also includes U.S. Pat. No. 5,655,534 (Ilmoniemi, Aug. 12, 1997, "Method and Apparatus for Separating the Different Components of Evoked Response and Spontaneous Activity Brain Signals as Well as of Signals Measured from the Heart"), U.S. Pat. No. 5,687,291 (Smyth, Nov. 11, 1997, "Method and Apparatus for Estimating a Cognitive Decision Made in Response to a Known Stimulus from the Corresponding Single-Event Evoked Cerebral Potential"), U.S. Pat. No. 5,724,987 (Gevins et al., Mar. 10, 1998, "Neurocognitive Adaptive Computer-Aided Training Method and System"), U.S. Pat. No. 5,813,993 (Kaplan et al., Sep. 29, 1998, "Alertness and Drowsiness Detection and Tracking System"), U.S. Pat. No. 5,840,040 (Altschuler et al., Nov. 24, 1998, "Encephalolexianalyzer"), U.S. Pat. No. 5,983,129 (Cowan et al., Nov. 9, 1999, "Method for Determining an Individual's Intensity of Focused Attention and Integrating Same into Computer Program"), U.S. Pat. No. 5,999,846 (Pardey et al., Dec. 7, 1999, "Physiological Monitoring"), U.S. Pat. No. 6,001,065 (Devito, Dec. 14, 1999, "Method and Apparatus for Measuring and Analyzing Physiological Signals for Active or Passive Control of Physical and Virtual Spaces and the Contents Therein"), and U.S. Pat. No. 6,014,582 (He, Jan. 11, 2000, "Method and Apparatus of Biosignal Spatial Analysis").

Prior art which appears to be within this category also includes U.S. Pat. No. 6,067,467 (John, May 23, 2000, "EEG Operative and Post-Operative Patient Monitoring Method"), U.S. Pat. No. 6,254,536 (Devito, Jul. 3, 2001, "Method and Apparatus for Measuring and Analyzing Physiological Signals for Active or Passive Control of Physical and Virtual Spaces and the Contents Therein"), U.S. Pat. No. 6,272,378 (Baumgart-Schmitt, Aug. 7, 2001, "Device and Method for Determining Sleep Profiles"), U.S. Pat. No. 6,496,724 (Levendowski et al., Dec. 17, 2002, "Method for the Quantification of Human Alertness"), U.S. Pat. No. 6,544,170 (Kajihara et al., Apr. 8, 2003, "Biosignal Measuring Method and Apparatus"), U.S. Pat. No. 6,549,804 (Osorio et al., Apr. 15, 2003, "System for the Prediction, Rapid Detection, Warning, Prevention or Control of Changes in Activity States in the Brain of a Subject"), U.S. Pat. No. 6,572,542 (Houben et al., Jun. 3, 2003, "System and Method for Monitoring and Controlling the Glycemic State of a Patient"), U.S. Pat. No. 6,625,485 (Levendowski et al., Sep. 23, 2003, "Method for the Quantification of Human Alertness"), U.S. Pat. No. 6,654,633 (Stengel et al., Nov. 25, 2003, "Mobile Neurological Signal Data Acquisition System and Method"), and U.S. Pat. No. 6,832,110 (Sohmer et al., Dec. 14, 2004, "Method for Analysis of Ongoing and Evoked Neuro-Electrical Activity").

Prior art which appears to be within this category also includes U.S. Pat. No. 6,947,790 (Gevins et al., Sep. 20, 2005, "Neurocognitive Function EEG Measurement Method and System"), U.S. Pat. No. 6,954,700 (Higashida et al., Oct. 11, 2005, "Efficacy of Biological State and Action Affecting Biological State, Judging Apparatus, Judging System, Judging Program and Recording Medium Holding the Program"), U.S. Pat. No. 7,058,445 (Kemere et al., Jun. 6, 2006, "Decoding of Neural Signals for Movement Control"), U.S. Pat. No. 7,127,283 (Kageyama, Oct. 24, 2006, "Control Apparatus Using Brain Wave Signal"), U.S. Pat. No. 7,190,995 (Chervin et al., Mar. 13, 2007, "System and Method for Analysis of Respiratory Cycle-Related EEG Changes in Sleep-Disordered Breathing"), U.S. Pat. No.

7,225,013 (Geva et al., May 29, 2007, "Adaptive Prediction of Changes of Physiological/Pathological States Using Processing of Biomedical Signals"), U.S. Pat. No. 7,228,169 (Viertio-Oja et al., Jun. 5, 2007, "Method and Apparatus for Determining the Cerebral State of a Patient with Fast Response"), U.S. Pat. No. 7,299,088 (Thakor et al., Nov. 20, 2007, "Apparatus and Methods for Brain Rhythm Analysis"), and U.S. Pat. No. 7,460,903 (Pineda et al., Dec. 2, 2008, "Method and System for a Real Time Adaptive System for Effecting Changes in Cognitive-Emotive Profiles").

Prior art which appears to be within this category also includes U.S. Pat. No. 7,499,894 (Marom et al., Mar. 3, 2009, "Cerebral Programming"), U.S. Pat. No. 7,546,158 (Allison et al., Jun. 9, 2009, "Communication Methods Based on Brain Computer Interfaces"), U.S. Pat. No. 7,580,742 (Tan et al., Aug. 25, 2009, "Using Electroencephalograph Signals for Task Classification and Activity Recognition"), U.S. Pat. No. 7,844,324 (Sarkela et al., Nov. 30, 2010, "Measurement of EEG Reactivity"), U.S. Pat. No. 7,904,144 (Causevic et al., Mar. 8, 2011, "Method for Assessing Brain Function and Portable Automatic Brain Function Assessment Apparatus"), U.S. Pat. No. 8,055,722 (Hille, Nov. 8, 2011, "Notification Control Through Brain Monitoring of End User Concentration"), U.S. Pat. No. 8,118,741 (Beck-Nielsen, Feb. 21, 2012, "Method and Apparatus for Prediction and Warning of Hypoglycaemic Attack"), U.S. Pat. No. 8,147,419 (Krauss et al., Apr. 3, 2012, "Automated Interpretive Medical Care System and Methodology"), U.S. Pat. No. 8,157,730 (Leboeuf et al., Apr. 17, 2012, "Physiological and Environmental Monitoring Systems and Methods"), U.S. Pat. No. 8,190,249 (Gharieb et al., May 29, 2012, "Multi-Parametric Quantitative Analysis of Bioelectrical Signals"), and U.S. Pat. No. 8,204,786 (LeBoeuf et al., Jun. 19, 2012, "Physiological and Environmental Monitoring Systems and Methods").

Prior art which appears to be within this category also includes U.S. Pat. No. 8,209,224 (Pradeep et al., Jun. 26, 2012, "Intracluster Content Management Using Neuro-Response Priming Data"), U.S. Pat. No. 8,224,433 (Suffin et al., Jul. 17, 2012, "Electroencephalography Based Systems and Methods for Selecting Therapies and Predicting Outcomes"), U.S. Pat. No. 8,277,385 (Berka et al., Oct. 2, 2012, "Method and Apparatus for Non-Invasive Assessment of Hemodynamic and Functional State of the Brain"), U.S. Pat. No. 8,298,140 (Beck-Nielsen et al., Oct. 30, 2012, "Analysis of EEG Signals to Detect Hypoglycaemia"), U.S. Pat. No. 8,335,715 (Pradeep et al., Dec. 18, 2012, "Advertisement Exchange Using Neuro-Response Data"), U.S. Pat. No. 8,346,354 (Hyde et al., Jan. 1, 2013, "Determining a Neuromodulation Treatment Regimen in Response to Contactlessly Acquired Information"), U.S. Pat. No. 8,348,840 (Heit et al., Jan. 8, 2013, "Device and Method to Monitor, Assess and Improve Quality of Sleep"), U.S. Pat. No. 8,355,769 (Levendowski et al., Jan. 15, 2013, "System for the Assessment of Sleep Quality in Adults and Children"), U.S. Pat. No. 8,376,965 (Schuette et al., Feb. 19, 2013, "Method and Apparatus for Using Biopotentials for Simultaneous Multiple Control Functions in Computer Systems"), and U.S. Pat. No. 8,386,312 (Pradeep et al., Feb. 26, 2013, "Neuro-Informatics Repository System").

Prior art which appears to be within this category also includes U.S. Pat. No. 8,386,313 (Pradeep et al., Feb. 26, 2013, "Stimulus Placement System Using Subject Neuro-Response Measurements"), U.S. Pat. No. 8,391,966 (Luo et al., Mar. 5, 2013, "Sensory-Evoked Potential (SEP) Classification/Detection in the Time Domain"), U.S. Pat. No. 8,392,250 (Pradeep et al., Mar. 5, 2013, "Neuro-Response Evaluated Stimulus in Virtual Reality Environments"), U.S. Pat. No. 8,392,251 (Pradeep et al., Mar. 5, 2013, "Location Aware Presentation of Stimulus Material"), U.S. Pat. No. 8,392,253 (Pradeep et al., Mar. 5, 2013, "Neuro-Physiology and Neuro-Behavioral Based Stimulus Targeting System"), U.S. Pat. No. 8,392,254 (Pradeep et al., Mar. 5, 2013, "Consumer Experience Assessment System"), U.S. Pat. No. 8,392,255 (Pradeep et al., Mar. 5, 2013, "Content Based Selection and Meta Tagging of Advertisement Breaks"), U.S. Pat. No. 8,396,545 (Berridge et al., Mar. 12, 2013, "Electrophysiological Screens for Cognitive Modulators"), U.S. Pat. No. 8,396,744 (Pradeep et al., Mar. 12, 2013, "Effective Virtual Reality Environments for Presentation of Marketing Materials"), U.S. Pat. No. 8,442,626 (Zavoronkovs et al., May 14, 2013, "Systems and Methods for Communicating with a Computer Using Brain Activity Patterns"), U.S. Pat. No. 8,473,345 (Pradeep et al., Jun. 25, 2013, "Protocol Generator and Presenter Device for Analysis of Marketing and Entertainment Effectiveness"), and U.S. Pat. No. 8,484,081 (Pradeep et al., Jul. 9, 2013, "Analysis of Marketing and Entertainment Effectiveness Using Central Nervous System, Autonomic Nervous System, and Effector Data").

Prior art which appears to be within this category also includes U.S. Pat. No. 8,494,610 (Pradeep et al., Jul. 23, 2013, "Analysis of Marketing and Entertainment Effectiveness Using Magnetoencephalography"), U.S. Pat. No. 8,494,905 (Pradeep et al., Jul. 23, 2013, "Audience Response Analysis Using Simultaneous Electroencephalography (EEG) and Functional Magnetic Resonance Imaging (fMRI)"), U.S. Pat. No. 8,521,270 (Hunter et al., Aug. 27, 2013, "Quantitative EEG Method to Identify Individuals at Risk for Adverse Antidepressant Effects"), U.S. Pat. No. 8,532,756 (Schalk et al., Sep. 10, 2013, "Method for Analyzing Function of the Brain and Other Complex Systems"), U.S. Pat. No. 8,533,042 (Pradeep et al., Sep. 10, 2013, "Neuro-Response Stimulus and Stimulus Attribute Resonance Estimator"), U.S. Pat. No. 8,548,852 (Pradeep et al., Oct. 1, 2013, "Effective Virtual Reality Environments for Presentation of Marketing Materials"), U.S. Pat. No. 8,560,360 (Olsen et al., Oct. 15, 2013, "Method, System and Computer Program for Automated Interpretation of Measurements in Response to Stimuli"), U.S. Pat. No. 8,628,462 (Berka et al., Jan. 14, 2014, "Systems and Methods for Optimization of Sleep and Post-Sleep Performance"), U.S. Pat. No. 8,628,472 (Beck-Nielsen, Jan. 14, 2014, "Method and Apparatus for Prediction and Warning of Hypoglycaemic Attack"), U.S. Pat. No. 8,655,428 (Pradeep et al., Feb. 18, 2014, "Neuro-Response Data Synchronization"), and U.S. Pat. No. 8,655,437 (Pradeep et al., Feb. 18, 2014, "Analysis of the Mirror Neuron System for Evaluation of Stimulus").

Prior art which appears to be within this category also includes U.S. patent applications: 20010056225 (DeVito, Dec. 27, 2001, "Method and Apparatus for Measuring and Analyzing Physiological Signals for Active or Passive Control of Physical and Virtual Spaces and the Contents Therein"), 20020095099 (Quyen et al., Jul. 18, 2002, "Method and Device for the Medical Monitoring in Real Time of a Patient From the Analysis of Electro-Encephalograms, Application of This Method to Characterize and to Differentiate Between Physiological or Pathologial Conditions, and a Method for Anticipating Epileptic Seizures in Real Time"), 20030055355 (Viertio-Oja, Mar. 20, 2003, "Method and Apparatus for Determining the Cerebral State of a Patient with Fast Response"), 20030088161 (Stengel et al., May 8, 2003, "Mobile Neurological Signal Data Acquisition System and Method"), 20030195429 (Wilson, Oct. 16, 2003, "Method and System for Detecting Seizures Using Electroencephalograms"), 20030225342 (Hong et al., Dec. 4, 2003, "Brain Response Monitoring Apparatus and Method"), 20040097824 (Kageyama, May 20, 2004, "Control Apparatus Using Brain Wave Signal"), 20040138578 (Pineda et al., Jul. 15, 2004, "Method and System for a Real Time Adaptive System for Effecting Changes in Cognitive-Emotive Profiles"), and 20040193068 (Burton et al., Sep. 30, 2004, "Methods and Apparatus for Monitoring Consciousness").

Prior art which appears to be within this category also includes U.S. patent applications: 20040249302 (Donoghue et al., Dec. 9, 2004, "Methods and Systems for Processing of Brain Signals"), 20040254493 (Chervin et al., Dec. 16, 2004, "System and Method for Analysis of Respiratory Cycle-Related EEG Changes in Sleep-Disordered Breathing"), 20040267152 (Pineda, Dec. 20, 2004, "Method and System for Predicting and Preventing Seizures"), 20050076908 (Lee et al., Apr. 14, 2005, "Autonomic Arousal Detection System and Method"), 20070066914 (Le et al., Mar. 22, 2007, "Method and System for Detecting and Classifying Mental States"), 20070112277 (Fischer et al., May 17, 2007, "Apparatus and Method for the Measurement and Monitoring of Bioelectric Signal Patterns"), 20070173733 (Le et al., Jul. 26, 2007, "Detection of and Interaction Using Mental States"), 20070185697 (Tan et al., Aug. 9, 2007, "Using Electroencephalograph Signals for Task Classification and Activity Recognition"), 20070191727 (Fadem, Aug. 16, 2007, "Evoked Response Testing System for Neurological Disorders"), and 20070225577 (Mathan, Sep. 27, 2007, "System and Method for Providing Sensor Based Human Factors Protocol Analysis").

Prior art which appears to be within this category also includes U.S. patent applications: 20080091118 (Georgopoulos, Apr. 17, 2008, "Analysis of Brain Patterns Using Temporal Measures"), 20080146890 (LeBoeuf et al., Jun. 19, 2008, "Telemetric Apparatus for Health and Environmental Monitoring"), 20080146892 (LeBoeuf et al., Jun. 19, 2008, "Physiological and Environmental Monitoring Systems and Methods"), 20080183097 (Leyde et al., Jul. 31, 2008, "Methods and Systems for Measuring a Subject's Susceptibility to a Seizure"), 20080208072 (Fadem et al., Aug. 28, 2008, "Biopotential Waveform Data Fusion Analysis and Classification Method"), 20080218472 (Breen et al., Sep. 11, 2008, "Interface to Convert Mental States and Facial Expressions to Application Input"), 20090024049 (Pradeep et al., Jan. 22, 2009, "Cross-Modality Synthesis of Central Nervous System, Autonomic Nervous System, and Effector Data"), 20090024475 (Pradeep et al., Jan. 22, 2009, "Neuro-Feedback Based Stimulus Compression Device"), and 20090030303 (Pradeep et al., Jan. 29, 2009, "Audience Response Analysis Using Simultaneous Electroencephalography (EEG) and Functional Magnetic Resonance Imaging (fMRI)").

Prior art which appears to be within this category also includes U.S. patent applications: 20090030717 (Pradeep et al., Jan. 29, 2009, "Intra-Modality Synthesis of Central Nervous System, Autonomic Nervous System, and Effector Data"), 20090030930 (Pradeep et al., Jan. 29, 2009, "Neuro-Informatics Repository System"), 20090062676 (Kruglikov et al., Mar. 5, 2009, "Phase and State Dependent EEG and Brain Imaging"), 20090062679 (Tan et al., Mar. 5, 2009, "Categorizing Perceptual Stimuli by Detecting Subconcious Responses"), 20090082643 (Pradeep et al., Mar. 26, 2009, "Analysis of Marketing and Entertainment Effectiveness Using Magnetoencephalography"), 20090287107 (Beck-Nielsen et al., Nov. 19, 2009, "Analysis of EEG Signals to Detect Hypoglycaemia"), 20090292180 (Mirow, Nov. 26, 2009, "Method and Apparatus for Analysis of Psychiatric and Physical Conditions"), 20090292221 (Viirre et al., Nov. 26, 2009, "EEG Feedback Controlled Sound Therapy for Tinnitus"), 20090312624 (Berridge et al., Dec. 17, 2009, "Electrophysiological Screens for Cognitive Modulators"), 20090312808 (Tyler et al., Dec. 7, 2009, "Systems and Methods for Altering Brain and Body Functions and for Treating Conditions and Diseases of the Same"), 20090318825 (Kilborn, Dec. 24, 2009, "Investigating Neurological Function"), and 20090327068 (Pradeep et al., Dec. 31, 2009, "Neuro-Physiology and Neuro-Behavioral Based Stimulus Targeting System").

Prior art which appears to be within this category also includes U.S. patent applications: 20090328089 (Pradeep et al., Dec. 31, 2009, "Audience Response Measurement and Tracking System"), 20100016751 (Hunter et al., Jan. 21, 2010, "Quantitative EEG Method to Identify Individuals at Risk for Adverse Antidepressant Effects"), 20100042011 (Doidge et al., Feb. 18, 2010, "Three-Dimensional Localization, Display, Recording, and Analysis of Electrical Activity in the Cerebral Cortex"), 20100049008 (Doherty et al., Feb. 25, 2010, "Method and Apparatus for Assessing Sleep Quality"), 20100087701 (Berka et al., Apr. 8, 2010, "Systems and Methods for Optimization of Sleep and Post-Sleep Performance"), 20100099954 (Dickinson et al., Apr. 22, 2010, "Data-Driven Sleep Coaching System"), 20100145215 (Pradeep et al., Jun. 10, 2010, "Brain Pattern Analyzer Using Neuro-Response Data"), 20100214318 (Pradeep et al., Aug. 26, 2010, "Neurologically Informed Morphing"), 20100217099 (LeBoeuf et al., Aug. 26, 2010, "Methods and Apparatus for Assessing Physiological Conditions"), 20100217100 (LeBoeuf et al., Aug. 26, 2010, "Methods and Apparatus for Measuring Physiological Conditions"), and 20100249538 (Pradeep et al., Sep. 30, 2010, "Presentation Measure Using Neurographics").

Prior art which appears to be within this category also includes U.S. patent applications: 20100268096 (Berka et al., Oct. 21, 2010, "Method and Apparatus for Non-Invasive Assessment of Hemodynamic and Functional State of the Brain"), 20110028798 (Hyde et al., Feb. 3, 2011, "Electronically Initiating an Administration of a Neuromodulation Treatment Regimen Chosen in Response to Contactlessly Acquired Information"), 20110029038 (Hyde et al., Feb. 3, 2011, "Determining a Neuromodulation Treatment Regimen in Response to Contactlessly Acquired Information"), 20110029044 (Hyde et al., Feb. 3, 2011, "Stimulating a Nervous System Component of a Mammal in Response to Contactlessly Acquired Information"), 20110040202 (Luo et al., Feb. 17, 2011, "Sensory-Evoked Potential (SEP) Classification/Detection in the Time Domain"), 20110046473 (Pradeep et al., Feb. 24, 2011, "EEG Triggered fMRI Signal Acquisition"), 20110046502 (Pradeep et al., Feb. 24, 2011, "Distributed Neuro-Response Data Collection and Analysis"), 20110046504 (Pradeep et al., Feb. 24, 2011, "Distributed Neuro-Response Data Collection and Analysis"), and 20110098112 (LeBoeuf et al., Apr. 28, 2011, "Physiological and Environmental Monitoring Systems and Methods").

Prior art which appears to be within this category also includes U.S. patent applications: 20110106621 (Pradeep et al., May 5, 2011, "Intracluster Content Management Using Neuro-Response Priming Data"), 20110106627 (LeBoeuf et al., May 5, 2011, "Physiological and Environmental Monitoring Systems and Methods"), 20110237971 (Pradeep et al., Sep. 29, 2011, "Discrete Choice Modeling Using Neuro- Response Data"), 20110245633 (Goldberg et al., Oct. 6, 2011, "Devices and Methods for Treating Psychological Disorders"), 20110282231 (Pradeep et al., Nov. 17, 2011, "Mechanisms for Collecting Electroencephalography Data"), 20110282232 (Pradeep et al., Nov. 17, 2011, "Neuro-Response Data Synchronization"), 20110298706 (Maim, Dec. 8, 2011, "Brainwave Actuated Apparatus"), 20110301488 (Schuette et al., Dec. 8, 2011, "Method and Apparatus for Using Biopotentials for Simultaneous Multiple Control Functions In Computer Systems"), 20110301488 (Schuette et al., Dec. 8, 2011, "Method and Apparatus for Using Biopotentials for Simultaneous Multiple Control Functions in Computer Systems"), and 20110313308 (Zavoronkovs et al., Dec. 22, 2011, "Systems and Methods for Communicating with a Computer Using Brain Activity Patterns").

Prior art which appears to be within this category also includes U.S. patent applications: 20120072289 (Pradeep et al., Mar. 22, 2012, "Biometric Aware Content Presentation"), 20120136273 (Michelson Jr., May 31, 2012, "Apparatus and Method for Monitoring and Analyzing Brainwaves"), 20120165695 (Kidmose et al., Jun. 28, 2012, "EEG Monitoring Apparatus and Method for Presenting Messages Therein"), 20120203081 (Leboeuf et al., Aug. 9, 2012, "Physiological and Environmental Monitoring Apparatus and Systems"), 20120209133 (Beck-Nielsen, Aug. 16, 2012, "Method and Apparatus for Prediction and Warning of Hypoglycaemic Attack"), 20120235820 (Kidmose, Sep. 20, 2012, "Method and Apparatus for Alerting a Person Carrying an EEG Assembly"), 20120238856 (Kidmose et al., Sep. 20, 2012, "Portable Monitoring Device with Hearing Aid and EEG Monitor"), 20120245653 (Bikson et al., Sep. 27, 2012, "Neurocranial Electrostimulation Models, Systems, Devices and Methods"), 20120253921 (Pradeep et al., Oct. 4, 2012, "Intracluster Content Management Using Neuro-Response Priming Data"), 20120265261 (Bikson et al., Oct. 18, 2012, "Neurocranial Electrostimulation Models, Systems, Devices, and Methods"), 20120290521 (Frank et al., Nov. 15, 2012, "Discovering and Classifying Situations that Influence Affective Response"), and 20120295589 (Alexander et al., Nov. 22, 2012, "Bio Signal Based Mobile Device Applications").

Prior art which appears to be within this category also includes U.S. patent applications: 20120296476 (Cale et al., Nov. 22, 2012, "Environmental Control Method and System"), 20120302858 (Kidmose et al., Nov. 29, 2012, "Portable EEG Monitor System with Wireless Communication"), 20130046151 (Bsoul et al., Feb. 21, 2013, "System and Method for Real-Time Measurement of Sleep Quality"), 20130046206 (Preminger, Feb. 21, 2013, "System and Method for Neurocognitive Training and/or Neuropsychological Assessment"), 20130073396 (Pradeep et al., Mar. 21, 2013, "Advertisement Exchange Using Neuro-Response Data"), 20130079659 (Akhadov et al., Mar. 28, 2013, "Integration of Electroencephalography (EEG) and Transcranial Direct Current Stimulation (tDCS) with High-Speed Operation, Electrode, Re-Use, Automated tDCS Electrode Configuration, and Multiple Independent tDCS Curent Sources"), 20130096363 (Schneider et al., Apr. 18, 2013, "Neuromodulation of Deep-Brain Targets by Transcranial Magnetic Stimulation Enhanced by Transcranial Direct Current Stimulation"), and 20130120246 (Schuette et al., May 16, 2013, "Method and Apparatus for Using Biopotentials for Simultaneous Multiple Control Functions in Computer Systems").

Prior art which appears to be within this category also includes U.S. patent applications: 20130130799 (Van Hulle et al., May 23, 2013, "Brain-Computer Interfaces and Use Thereof"), 20130130799 (Van Hulle et al., May 23, 2013, "Brain-Computer Interfaces and Use Thereof"), 20130131537 (Tam, May 23, 2013, "Tong Ren Brainwave Entrainment"), 20130177883 (Barnehama et al., Jul. 11, 2013, "Systems and Methods for Directing Brain Activity"), 20130179087 (Garripoli, Jul. 11, 2013, "Methods and Systems for Determining, Monitoring, and Analyzing Personalized Response Variables Using Brain Wave Frequency Data and Interactive Multimedia Display"), 20130185144 (Pradeep et al., Jul. 18, 2013, "Systems and Methods for Analyzing Neuro-Reponse Data and Virtual Reality Environments"), 20130211276 (Luo et al., Aug. 15, 2013, "Sensory-Evoked Potential (SEP) Classification/Detection in the Time Domain"), 20130274580 (Madsen et al., Oct. 17, 2013, "Analysis of EEG Signals to Detect Hypoglycaemia"), 20130295016 (Gerber et al., Nov. 7, 2013, "Signatures of Electroencephalographic Oscillations"), 20130314243 (Le, Nov. 28, 2013, "System and Method for Enabling Collaborative Analysis of a Biosignal"), and 20130317382 (Le, Nov. 28, 2013, "System and Method for Providing and Aggregating Biosignals and Action Data").

Prior art which appears to be within this category also includes U.S. patent applications: 20130317384 (Le, Nov. 28, 2013, "System and Method for Instructing a Behavior Change in a User"), 20130332259 (Pradeep et al., Dec. 12, 2013, "Neuro-Response Stimulus and Stimulus Attribute Resonance Estimator"), 20140163408 (Kocher, Jun. 12, 2014, "System for Analyzing Mental and Behavioral Correlations"), 20140164056 (Johnson et al., Jun. 12, 2014, "Biosensitive Response Evaluation for Design and Research"), 20140223462 (Aimone et al., Aug. 7, 2014, "System and Method for Enhancing Content Using Brain-State Data"), 20140277582 (Leuthardt et al., Sep. 18, 2014, "Brain-Controlled Body Movement Assistance Devices and Methods"), 20140288614 (Hagedorn et al., Sep. 25, 2014, "Electrophysiology Measurement and Training and Remote Databased and Data Analysis Measurement Method and System"), and 20140303450 (Caponi, Oct. 9, 2014, "System and Method for Stimulus Optimization Through Closed Loop Iterative Biological Sensor Feedback").

Prior art which appears to be within this category also includes U.S. patent applications: 20140316230 (Denison et al., Oct. 23, 2014, "Methods and Devices for Brain Activity Monitoring Supporting Mental State Development and Training"), 20140323900 (Bibian et al., Oct. 30, 2014, "Multi-Channel Brain or Cortical Activity Monitoring and Method"), 20140347265 (Aimone et al., Nov. 27, 2014, "Wearable Computing Apparatus and Method"), and 20150018705 (Barlow et al., Jan. 15, 2015, "Neural Analysis and Treatment System"); and non-U.S. patents EP2642914 (Madsen et al., Oct. 2, 2013, "Analysis of EEG signals to Detect Hypoglycaemia"), WO2006073384 (Gevins et al., Dec. 30, 2004, "Neurocognitive Function EEG Measurement Method and System"), WO2007143663 (Hunter et al., Jun. 5, 2007, "Quantitative EEG Method to Identify Individuals at Risk for Adverse Antidepressant Effects"), WO2007144307 (Beck-Nielsen et al., Dec. 21, 2007, "Analysis of EEG Signals to Detect Hypoglycaemia"), WO2012069549 (Jensen and Madsen, May 31, 2012, "Analysis of EEG Signals to Detect Hypoglycaemia"), and WO2013008011 (Gandhi, Nov. 7, 2012, "Predicting the Levels of Substances such as Cortisol from EEG Analysis").

20. Device that Actively Emits Brain-Stimulating Energy

This category includes selected devices and methods for actively emitting energy to affect brain activity. In an example, this energy can be electromagnetic energy. In an example, this energy can be sound energy or light energy. There is a large body of prior art on such devices and methods. Art included in this category is not exhaustive. Prior art which appears to be within this category includes U.S. Pat. No. 6,066,084 (Edrich et al., May 23, 2000, "Method and Apparatus for Focused Neuromagnetic Stimulation and Detection"), U.S. Pat. No. 6,066,163 (John, May 23, 2000, "Adaptive Brain Stimulation Method and System"), U.S. Pat. No. 6,256,531 (Ilmoniemi et al., Jul. 3, 2001, "Method and Apparatus for Mapping Cortical Connections"), U.S. Pat. No. 6,488,617 (Katz, Dec. 3, 2002, "Method and Device for Producing a Desired Brain State"), U.S. Pat. No. 6,564,102 (Boveja, May 13, 2003, "Apparatus and Method for Adjunct (Add-On) Treatment of Coma and Traumatic Brain Injury with Neuromodulation using an External Stimulator"), U.S. Pat. No. 7,146,217 (Firlik et al., Dec. 5, 2006, "Methods and Apparatus for Effectuating a Change in a Neural-Function of a Patient"), and U.S. Pat. No. 7,197,350 (Kopke, Mar. 27, 2007, "Device for Determining Acoustically Evoked Brainstem Potentials").

Prior art which appears to be within this category also includes U.S. Pat. No. 7,242,984 (DiLorenzo, Jul. 10, 2007, "Apparatus and Method for Closed-Loop Intracranial Stimulation for Optimal Control of Neurological Disease"), U.S. Pat. No. 7,460,903 (Pineda et al., Dec. 2, 2008, "Method and System for a Real Time Adaptive System for Effecting Changes in Cognitive-Emotive Profiles"), U.S. Pat. No. 8,155,736 (Sullivan et al., Apr. 10, 2012, "EEG Control of Devices Using Sensory Evoked Potentials"), U.S. Pat. No. 8,543,219 (Tass, Sep. 24, 2013, "Device for Modulation of Neuronal Activity in the Brain by Means of Sensory Stimulation and Detection of Brain Activity"), U.S. Pat. No. 8,818,515 (Bikson et al., Aug. 26, 2014, "Voltage Limited Neurostimulation"), U.S. Pat. No. 8,903,494 (Goldwasser et al., Dec. 2, 2014, "Wearable Transdermal Electrical Stimulation Devices and Methods of Using Them"), and 20040138578 (Pineda et al., Jul. 15, 2004, "Method and System for a Real Time Adaptive System for Effecting Changes in Cognitive-Emotive Profiles").

Prior art which appears to be within this category also includes U.S. patent applications: 20060217781 (John, Sep. 28, 2006, "Systems and Methods for Treating Disorders of the Central Nervous System by Modulation of Brain Networks"), 20070112277 (Fischer et al., May 17, 2007, "Apparatus and Method for the Measurement and Monitoring of Bioelectric Signal Patterns"), 20100234752 (Sullivan et al., Sep. 16, 2010, "EEG Control of Devices Using Sensory Evoked Potentials"), 20110029044 (Hyde et al., Feb. 3, 2011, "Stimulating a Nervous System Component of a Mammal in Response to Contactlessly Acquired Information"), 20120041498 (Gliner et al., Feb. 16, 2012, "Systems and Methods for Enhancing or Affecting Neural Stimulation Efficiency and/or Efficacy"), 20120209346 (Bikson et al., Aug. 16, 2012, "Transcranial Stimulation"), 20120220889 (Sullivan et al., Aug. 30, 2012, "EEG Control of Devices Using Sensory Evoked Potentials"), and 20120245653 (Bikson et al., Sep. 27, 2012, "Neurocranial Electrostimulation Models, Systems, Devices and Methods").

Prior art which appears to be within this category also includes U.S. patent applications: 20120265261 (Bikson et al., Oct. 18, 2012, "Neurocranial Electrostimulation Models, Systems, Devices, and Methods"), 20120289869 (Tyler, Nov. 15, 2012, "Devices and Methods for Modulating Brain Activity"), 20130079659 (Akhadov et al., Mar. 28, 2013, "Integration of Electroencephalography (EEG) and Transcranial Direct Current Stimulation (tDCS) with High-Speed Operation, Electrode, Re-Use, Automated tDCS Electrode Configuration, and Multiple Independent tDCS Curent Sources"), 20130096363 (Schneider et al., Apr. 18, 2013, "Neuromodulation of Deep-Brain Targets by Transcranial Magnetic Stimulation Enhanced by Transcranial Direct Current Stimulation"), 20130184779 (Bikson et al., Jul. 18, 2013, "Voltage Limited Neurostimulation"), 20130268038 (Bikson et al., Oct. 10, 2013, "Electrode Assembly"), and 20130281759 (Hagedorn et al., Oct. 24, 2013, "Transcranial Stimulation Device and Method Based on Electrophysiological Testing").

Prior art which appears to be within this category also includes U.S. patent applications: 20130296731 (Kidmose et al., Nov. 7, 2013, "Personal EEG Monitoring Device with Electrode Validation"), 20130338738 (Molina et al., Dec. 19, 2013, "Device and Method for Cognitive Enhancement of a User"), 20140058189 (Stubbeman, Feb. 27, 2014, "Systems and Methods Using Brain Stimulation for Treating Disorders"), 20140148872 (Goldwasser et al., May 29, 2014, "Wearable Transdermal Electrical Stimulation Devices and Methods of Using Them"), 20140211593 (Tyler et al., Jul. 31, 2014, "Method and System for Direct Communication"), 20150005840 (Pal et al., Jan. 1, 2015, "Transdermal Electrical Stimulation Methods for Modifying or Inducing Cognitive State"), and 20150005841 (Pal et al., Jan. 1, 2015, "Transdermal Electrical Stimulation Devices for Modifying or Inducing Cognitive State").

21. Miscellaneous

This category includes devices with sensors to measure electromagnetic brain activity sensors which do not fit well into one of the above categories, but are nonetheless relevant to this disclosure. Art included in this category is not exhaustive. Prior art which appears to be within this category includes U.S. Pat. No. 5,291,888 (Tucker, Mar. 8, 1994, "Head Sensor Positioning Network"), U.S. Pat. No. 6,510,340 (Jordan, Jan. 21, 2003, "Method and Apparatus for Electroencephalography"), U.S. Pat. No. 7,173,437 (Hervieux et al, Feb. 6, 2007, "Garment Incorporating Embedded Physiological Sensors"), U.S. Pat. No. 7,231,723 (O'Neill et al., Jun. 19, 2007, "Device for Neural Sensor Placement and Reference System Measurements"), U.S. Pat. No. 7,245,956 (Matthews et al., Jul. 17, 2007, "Unobtrusive Measurement System for Bioelectric Signals"), U.S. Pat. No. 7,245,956 (Matthews et al., Jul. 17, 2007, "Unobtrusive Measurement System for Bioelectric Signals"), U.S. Pat. No. 7,668,588 (Kovacs, Feb. 23, 2010, "Dual-Mode Physiologic Monitoring Systems and Methods"), U.S. Pat. No. 7,974,696 (Dilorenzo, Jul. 5, 2011, "Closed-Loop Autonomic Neuromodulation for Optimal Control of Neurological and Metabolic Disease"), U.S. Pat. No. 8,118,741 (Beck-Nielsen, Feb. 21, 2012, "Method and Apparatus for Prediction and Warning of Hypoglycaemic Attack"), and U.S. Pat. No. 8,209,004 (Freer et al., Jun. 26, 2012, "Body-Based Monitoring of Brain Electrical Activity").

Prior art which appears to be within this category also includes U.S. Pat. No. 8,298,140 (Beck-Nielsen et al., Oct. 30, 2012, "Analysis of EEG Signals to Detect Hypoglycaemia"), U.S. Pat. No. 8,391,967 (Freer et al., Mar. 5, 2013, "Body-Based Monitoring of Brain Electrical Activity"), U.S. Pat. No. 8,437,843 (Kayyali et al., May 7, 2013, "EEG Data Acquisition System with Novel Features"), U.S. Pat. No. 8,465,408 (Phillips et al., Jun. 18, 2013, "Systems and Methods for Modulating the Electrical Activity of a Brain Using Neuro-EEG Synchronization Therapy"), U.S. Pat. No. 8,475,354 (Phillips et al., Jul. 2, 2013, "Systems and Methods for Neuro-EEG Synchronization Therapy"), U.S. Pat. No. 8,585,568 (Phillips et al., Nov. 19, 2013, "Systems and Methods for Neuro-EEG Synchronization Therapy"), and U.S. Pat. No. 8,628,472 (Beck-Nielsen, Jan. 14, 2014, "Method and Apparatus for Prediction and Warning of Hypoglycaemic Attack").

Prior art which appears to be within this category also includes U.S. patent applications: 20020091335 (John et al., Jul. 11, 2002, "Brain Function Scan System"), 20050131288 (Turner et al., Jun. 16, 2005, "Flexible, Patient-Worn, Integrated, Self-Contained Sensor Systems for the Acquisition and Monitoring of Physiologic Data"), 20050165323 (Montgomery et al., Jul. 28, 2005, "Physiological Signal Monitoring Apparatus and Method"), 20050275416 (Hervieux et al., Dec. 5, 2005, "Garment Incorporating Embedded Physiological Sensors"), 20060015027 (Matthews et al., Jan. 19, 2006, "Unobtrusive Measurement System for Bioelectric Signals"), 20060041196 (Matthews et al., Feb. 23, 2006, "Unobtrusive Measurement System for Bioelectric Signals"), 20060293578 (Rennaker, Dec. 28, 2006, "Brian Machine Interface Device"), 20070027367 (Oliver et al., Feb. 1, 2007, "Mobile, Personal, and Non-Intrusive Health Monitoring and Analysis System"), 20070173705 (Teller et al., Jul. 26, 2007, "Apparatus for Monitoring Health, Wellness and Fitness"), 20080161654 (Teller et al., Jul. 3, 2008, "Method and Apparatus for Auto Journaling of Body States and Providing Derived Physiological States Utilizing Physiological and/or Contextual Parameter"), and 20080161655 (Teller et al., Jul. 3, 2008, "Method and Apparatus for Auto Journaling of Body States and Providing Derived Physiological States Utilizing Physiological and/or Contextual Parameter").

Prior art which appears to be within this category also includes U.S. patent applications: 20080161707 (Farringdon et al., Jul. 3, 2008, "Method and Apparatus for Measuring Heart-Related Parameters and Deriving Human Status Parameters From Sensed Physiological and Contextual Parameters"), 20080171943 (Farringdon et al., Jul. 17, 2008, "Method and Apparatus for Measuring Heart-Related Parameters and Deriving Human Status Parameters From Sensed Physiological and Contextual Parameters"), 20080177193 (Farringdon et al., Jul. 24, 2008, "Method and Apparatus for Measuring Heart-Related Parameters and Deriving Human Status Parameters From Sensed Physiological and Contextual Parameters"), 20080183082 (Farringdon et al., Jul. 31, 2008, "Method and Apparatus for Measuring Heart-Related Parameters and Deriving Human Status Parameters From Sensed Physiological and Contextual Parameters"), 20080183090 (Farringdon et al., Jul. 31, 2008, "Method and Apparatus for Measuring Heart-Related Parameters and Deriving Human Status Parameters From Sensed Physiological and Contextual Parameters"), and 20090082690 (Phillips et al., Mar. 26, 2009, "Systems and Methods for Neuro-EEG Synchronization Therapy").

Prior art which appears to be within this category also includes U.S. patent applications: 20090105577 (Wu et al., Apr. 23, 2009, "Device for Detecting Electrical Potentials Using Frontal Electrodes"), 20090287107 (Beck-Nielsen et al., Nov. 19, 2009, "Analysis of EEG Signals to Detect Hypoglycaemia"), 20100042011 (Doidge et al., Feb. 18, 2010, "Three-Dimensional Localization, Display, Recording, and Analysis of Electrical Activity in the Cerebral Cortex"), 20100145217 (Otto et al., Jun. 10, 2010, "Scalp Potential Measuring Method and Apparatus"), 20100286532 (Farringdon et al., Nov. 11, 2010, "Wearable Apparatus for Measuring Heart-Related Parameters and Deriving Human Status Parameters From Sensed Physiological and Contextual Parameters"), 20100317955 (Madsen et al., Dec. 16, 2010, "Implantable Electronic Devices for Detecting Hypoglycaemia Using EEG Signals"), and 20110034822 (Phillips et al., Feb. 10, 2011, "Systems and Methods for Modulating the Electrical Activity of a Brain Using Neuro-EEG Synchronization Therapy").

Prior art which appears to be within this category also includes U.S. patent applications: 20110112427 (Phillips et al., May 12, 2011, "Systems and Methods for Neuro-EEG Synchronization Therapy"), 20110118536 (Phillips et al., May 19, 2011, "Systems and Methods for Neuro-EEG Synchronization Therapy"), 20110245633 (Goldberg et al., Oct. 6, 2011, "Devices and Methods for Treating Psychological Disorders"), 20120203079 (McLaughlin, Aug. 9, 2012, "Wireless, Implantable Electro-Encephalography System"), 20120209133 (Beck-Nielsen, Aug. 16, 2012, "Method and Apparatus for Prediction and Warning of Hypoglycaemic Attack"), 20130144106 (Phillips et al., Jun. 6, 2013, "Systems and Methods for Neuro-EEG Synchronization Therapy"), 20130144107 (Phillips et al., Jun. 6, 2013, "Systems and Methods for Neuro-EEG Synchronization Therapy RAPY"), 20130144108 (Phillips et al., Jun. 6, 2013, "Systems and Methods for Neuro-EEG Synchronization Therapy"), and 20130150650 (Phillips et al., Jun. 13, 2013, "Systems and Methods for Neuro-EEG Synchronization Therapy").

Prior art which appears to be within this category also includes U.S. patent applications: 20130150651 (Phillips et al., Jun. 13, 2013, "Systems and Methods for Neuro-EEG Synchronization Therapy"), 20130274580 (Madsen et al., Oct. 17, 2013, "Analysis of EEG Signals to Detect Hypoglycaemia"), 20140200432 (Banerji et al., Jul. 17, 2014, "Systems, Apparatuses, Devices, and Processes for Synergistic Neuro-Physiological Rehabilitation and/or Functional Development"), 20140277582 (Leuthardt et al., Sep. 18, 2014, "Brain-Controlled Body Movement Assistance Devices and Methods"); and non-U.S. patents EP2642914 (Madsen et al., Oct. 2, 2013, "Analysis of EEG signals to Detect Hypoglycaemia"), WO2007144307 (Beck-Nielsen et al., Dec. 21, 2007, "Analysis of EEG Signals to Detect Hypoglycaemia"), and WO2012069549 (Jensen and Madsen, May 31, 2012, "Analysis of EEG Signals to Detect Hypoglycaemia").

SUMMARY OF THE INVENTION

This invention is a mobile wearable electromagnetic brain activity monitor comprising: a wearable frame worn on a person's head; a plurality of electromagnetic energy sensors which collect data concerning the person's electromagnetic brain activity; and a control unit. In an example, the plurality of electromagnetic energy sensors are electroencephalogram (EEG) electrodes. In an example, the wearable frame can be substantially circular (or elliptical), spanning the person's forehead and the rear of the person's head. In an example, the wearable frame can loop around the person's head from one ear to the other. In an example, the wearable frame can be an eyeglasses and/or eyewear frame, including one or more light-transmitting optical members.

This mobile wearable electromagnetic brain activity monitor can be used for a variety of purposes. In an example, this mobile wearable electromagnetic brain activity monitor can be used to monitor, measure, and modify the person's food consumption. In an example, this mobile wearable electromagnetic brain activity monitor can be used to control eyewear with light-transmitting members whose light absorption, light reflection, light refraction, light spectrum transformation, focal direction, focal distance, light polarization, or parallax view can be controlled by the wearer's brain activity. In an example, this mobile wearable electromagnetic brain activity monitor can be generally used as a Human-to-Computer Interface (HCI).

INTRODUCTION TO THE FIGURES

FIGS. 1 through 155 show examples of how this invention can be embodied in a mobile wearable electromagnetic brain activity monitor, but they do not limit the full generalizability of the claims. FIGS. 1 through 74 highlight how such a monitor can be used to measure and modify a person's food consumption. FIGS. 75 through 134 highlight how such a monitor can be used to control electronically-functional eyewear. FIGS. 135 through 155 highlight how such a monitor can comprise eyewear. We now introduce these figures individually.

FIGS. 68, 69, 70, 71, 72, and 73 show statistical methods to identify patterns of brain activity.

Figure 74:
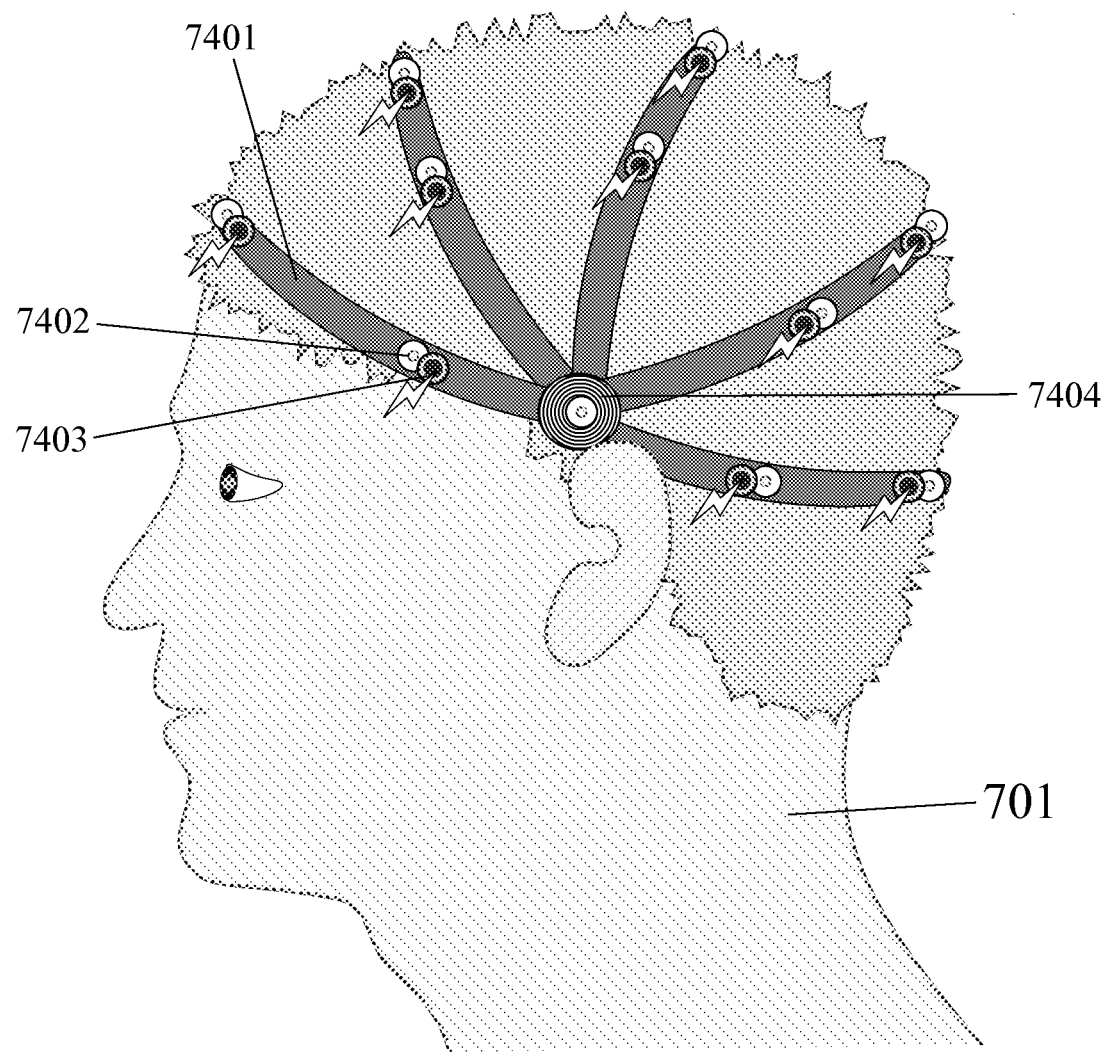

FIG. 74 shows a device which actively alters brain activity to modify a person's food consumption.

Figure 75:
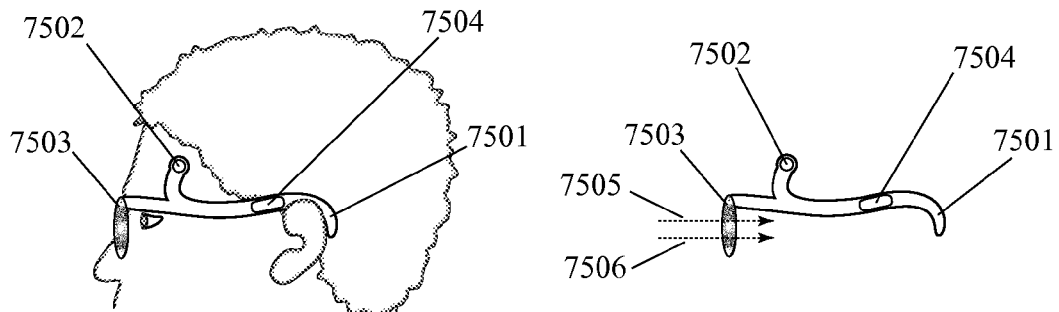
Figure 76:
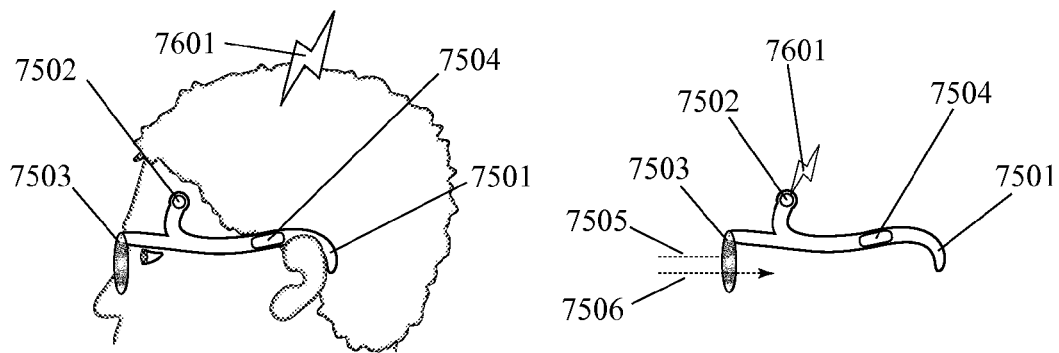

FIGS. 75 and 76 show EEG monitoring eyewear that reduces light transmission based on brain activity.

Figure 77:
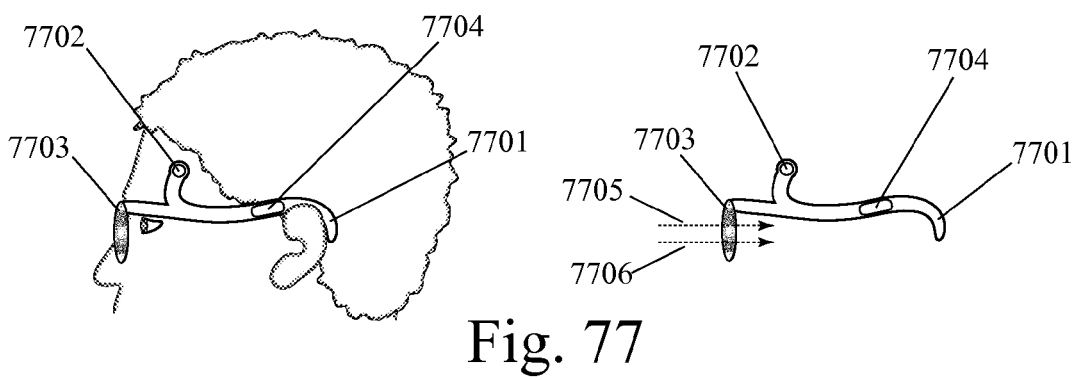
Figure 78:
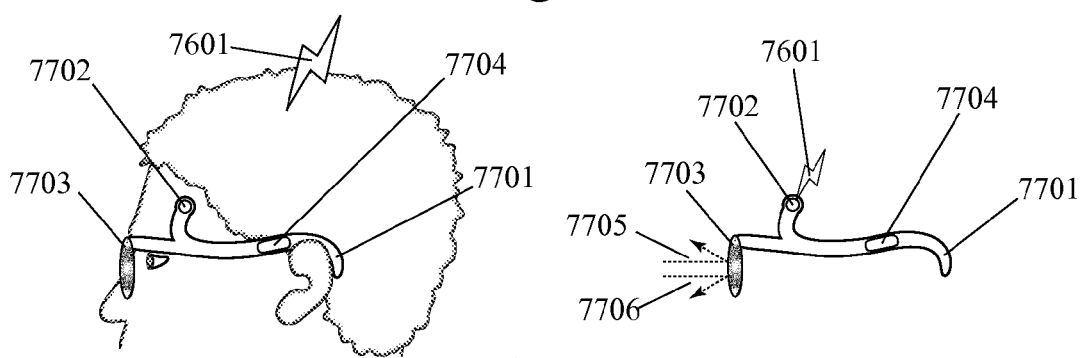

FIGS. 77 and 78 show EEG monitoring eyewear that reflects light based on brain activity.

Figure 79:
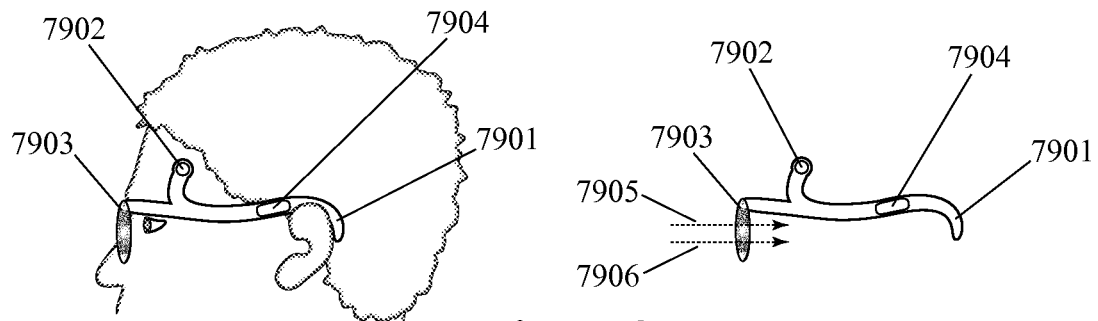
Figure 80:
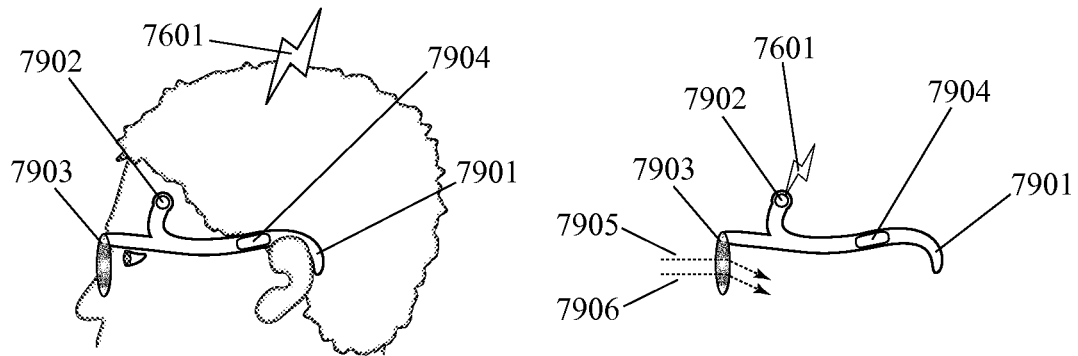

FIGS. 79 and 80 show EEG monitoring eyewear that refracts inbound light based on brain activity.

Figure 81:
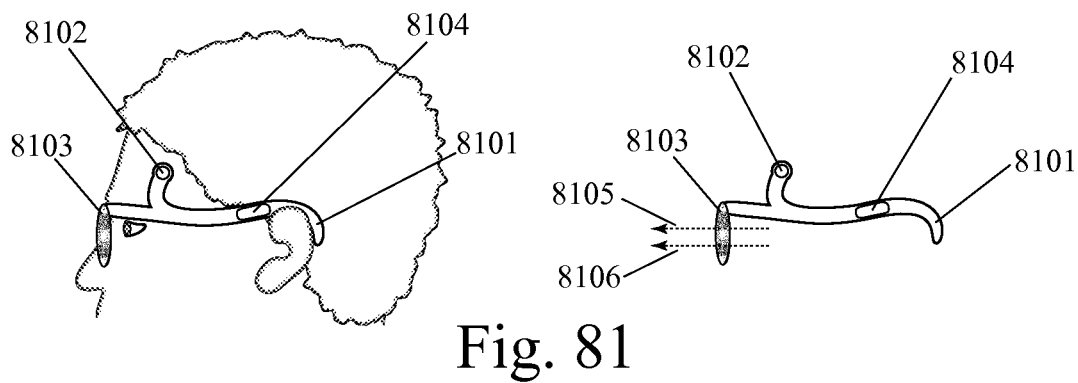
Figure 82:
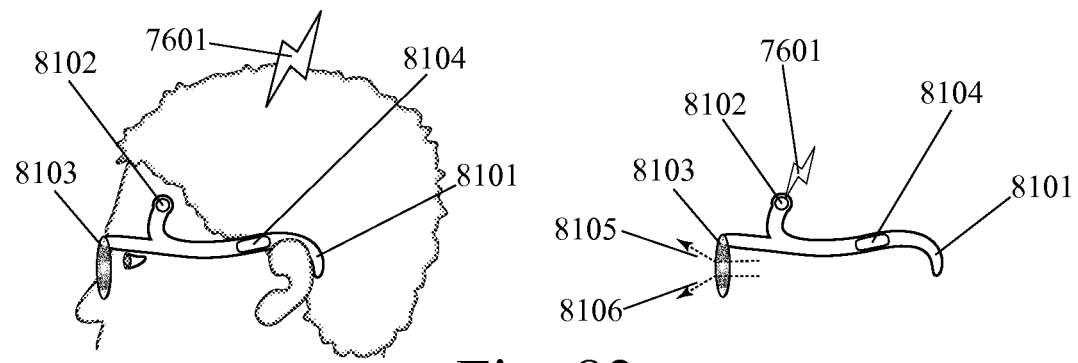

FIGS. 81 and 82 show EEG monitoring eyewear that refracts outbound light based on brain activity.

Figure 83:
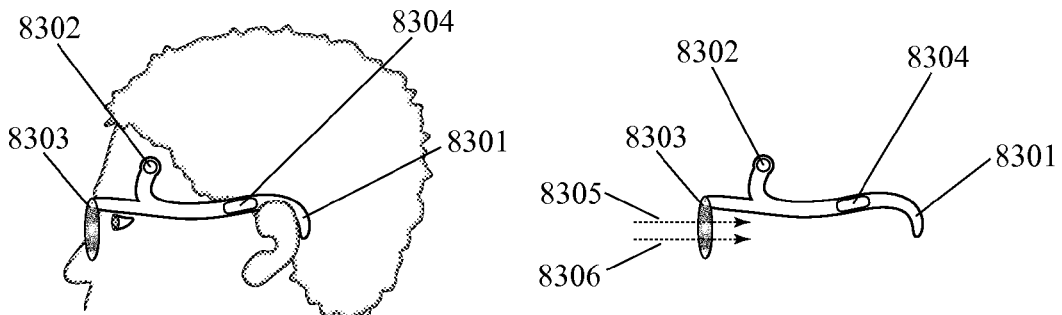
Figure 84:
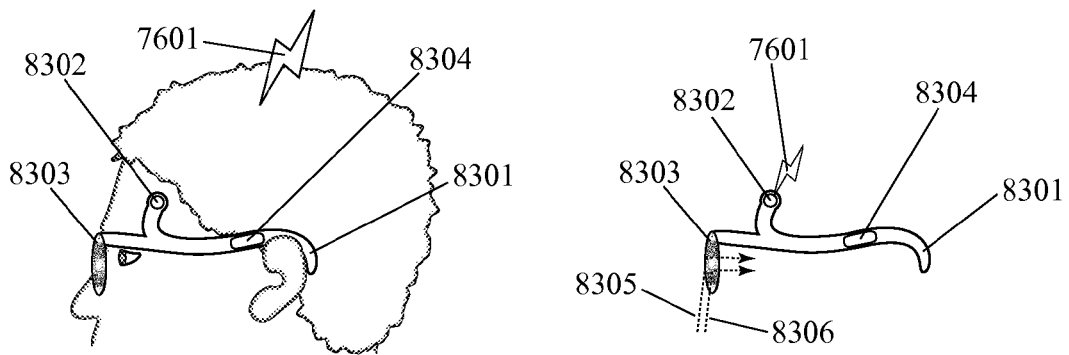

FIGS. 83 and 84 show EEG monitoring eyewear that redirects inbound light based on brain activity.

Figure 85:
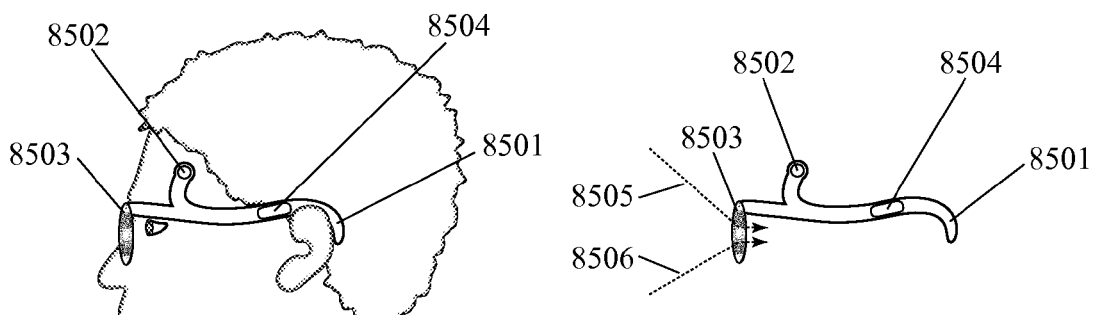
Figure 86:
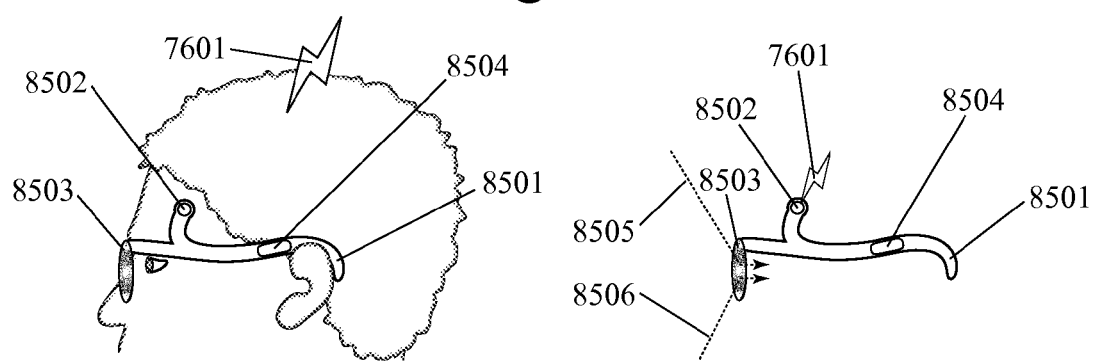

FIGS. 85 and 86 show EEG monitoring eyewear that changes field of view based on brain activity.

Figure 87:
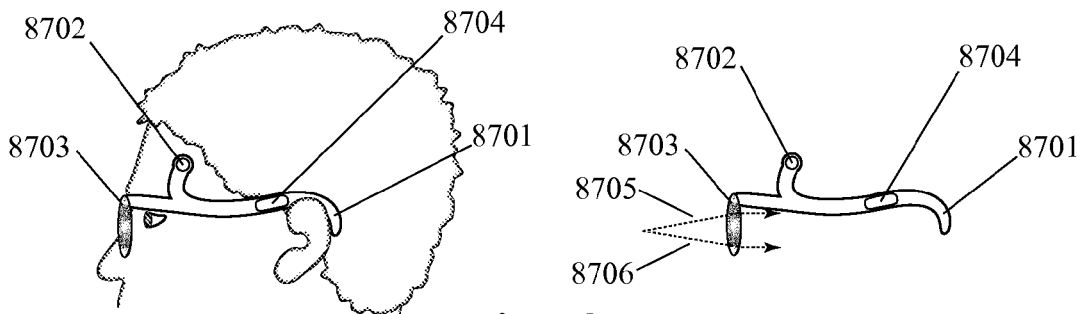
Figure 88:
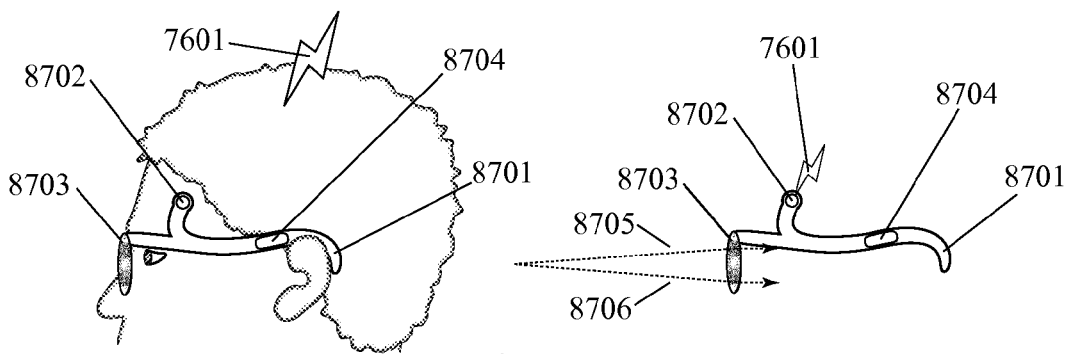

FIGS. 87 and 88 show EEG monitoring eyewear that changes focal length based on brain activity.

Figure 89:
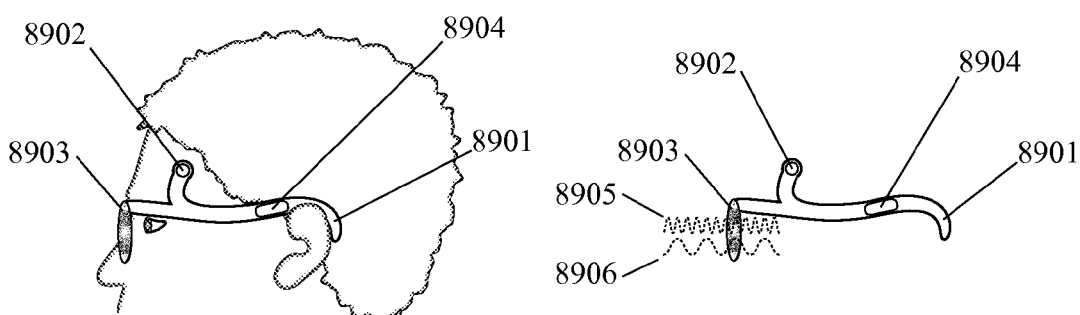
Figure 90:
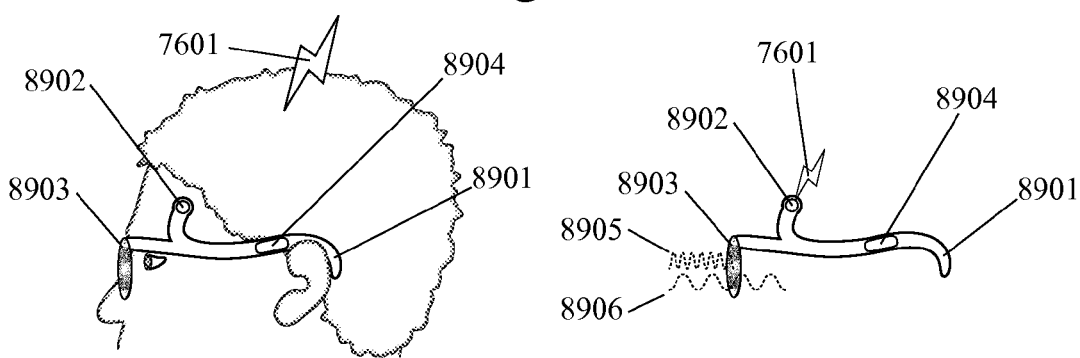

FIGS. 89 and 90 show EEG monitoring eyewear that filters light based on brain activity.

Figure 91:
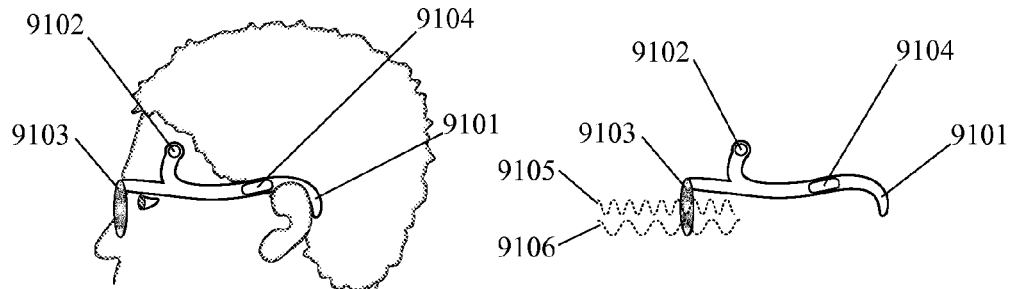
Figure 92:
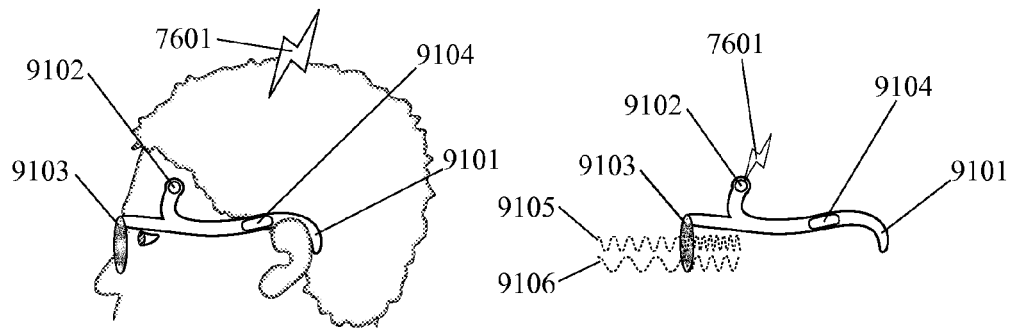

FIGS. 91 and 92 show EEG monitoring eyewear that shifts light wavelength based on brain activity.

Figure 93:
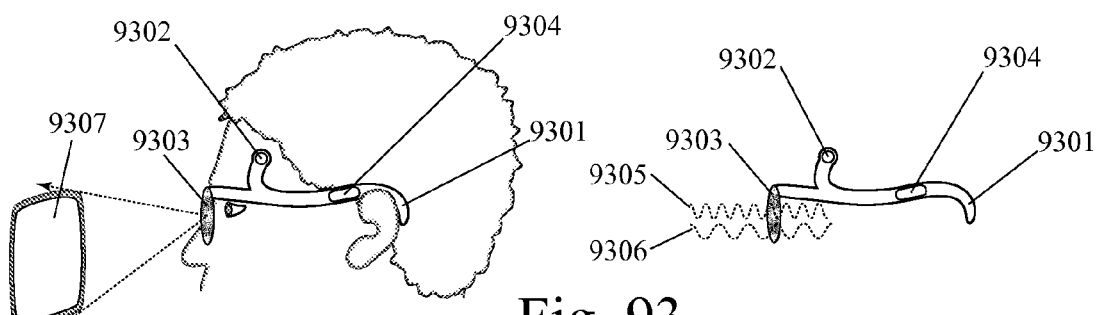
Figure 94:
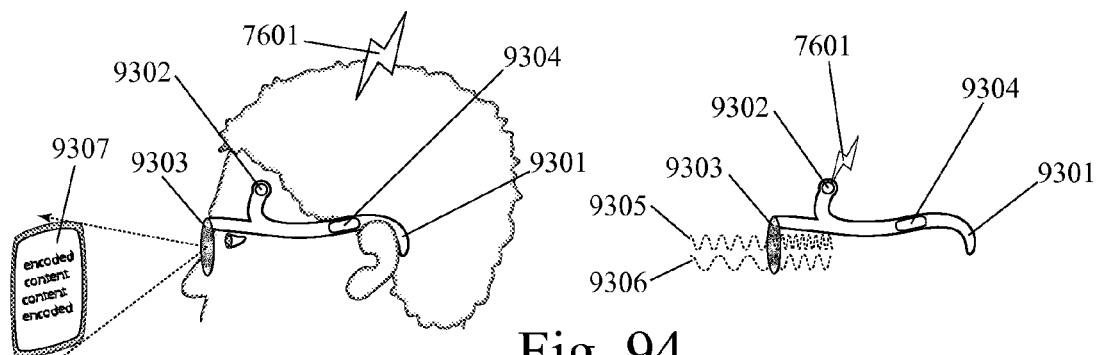

FIGS. 93 and 94 show EEG monitoring eyewear for reading hidden content based on brain activity.

Figure 95:
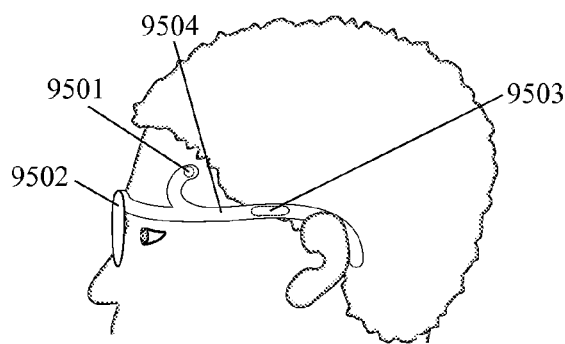
Figure 96:
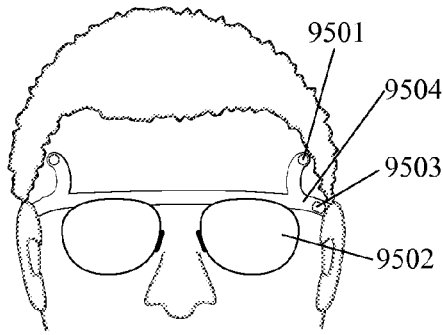

FIGS. 95 and 96 show EEG monitoring eyewear with an upward protrusion to a person's temple.

Figure 97:
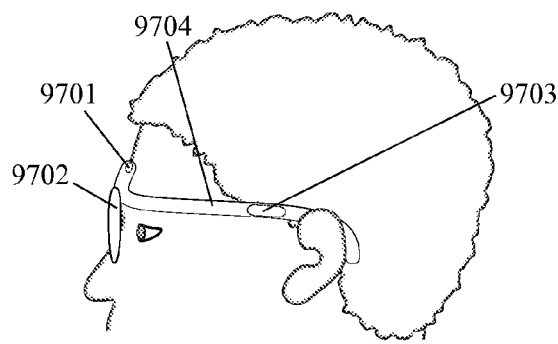
Figure 98:
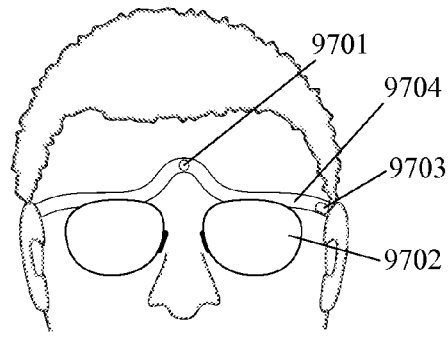

FIGS. 97 and 98 show a first example of EEG monitoring eyewear that spans a portion of the forehead.

Figure 99:
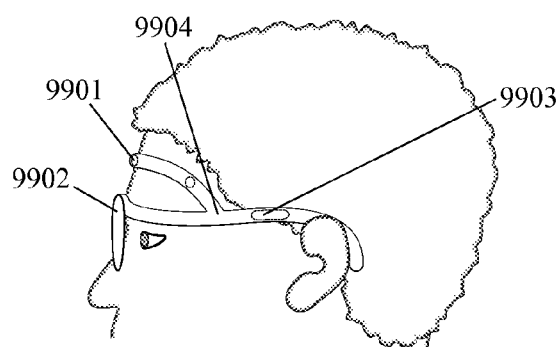
Figure 100:
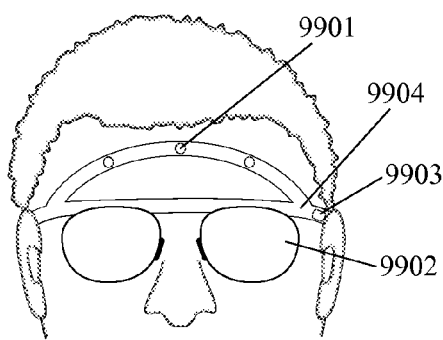

FIGS. 99 and 100 show a second example of EEG monitoring eyewear that spans a portion of the forehead.

Figure 101:
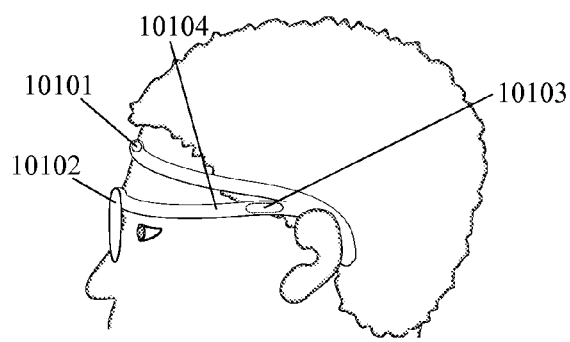
Figure 102:
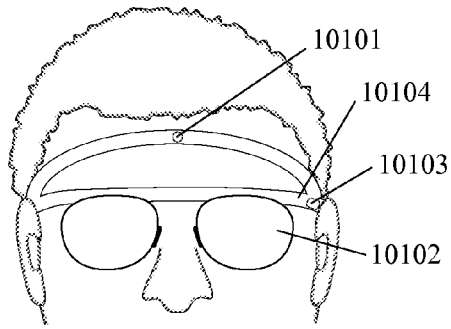

FIGS. 101 and 102 show a third example of EEG monitoring eyewear that spans a portion of the forehead.

Figure 103:
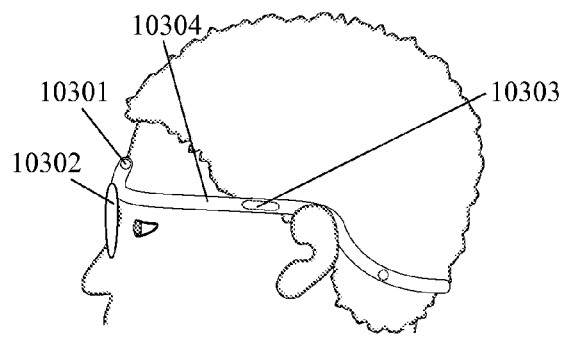
Figure 104:
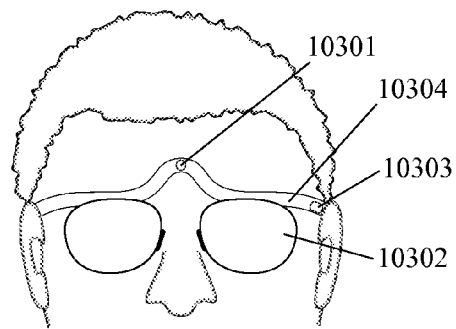

FIGS. 103 and 104 show a first example of EEG monitoring eyewear that encircles the head.

Figure 105:
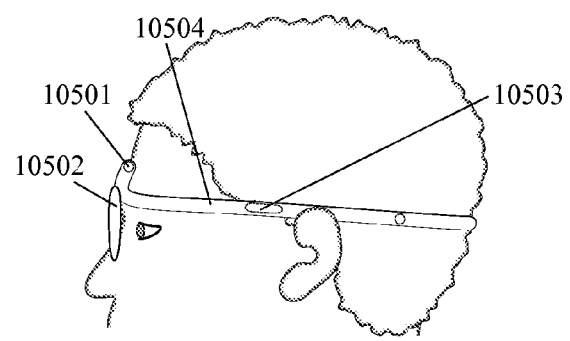
Figure 106:
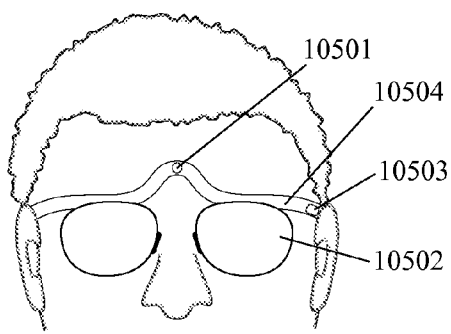

FIGS. 105 and 106 show a second example of EEG monitoring eyewear that encircles the head.

Figure 107:
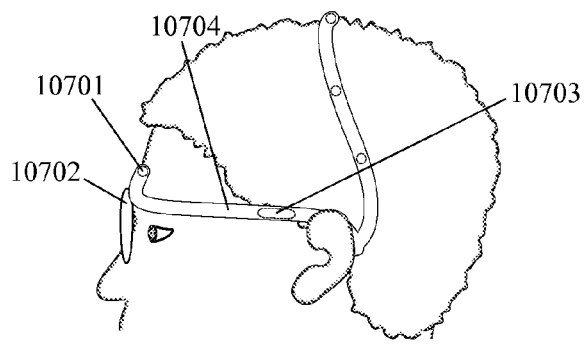
Figure 108:
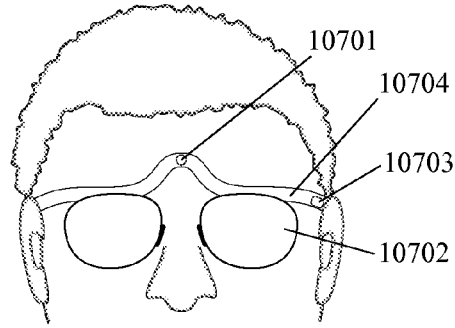

FIGS. 107 and 108 show EEG monitoring eyewear that curves up over the top of the head.

Figure 109:
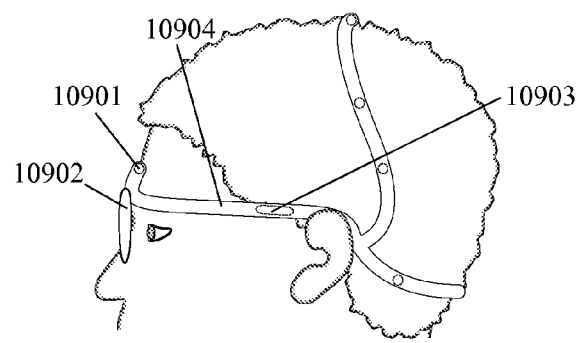
Figure 110:
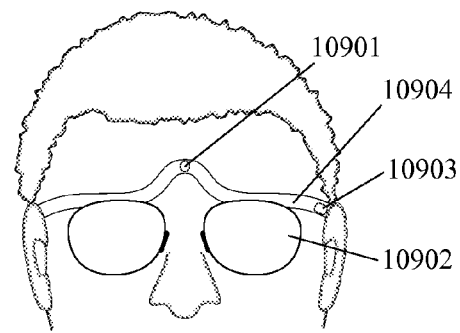

FIGS. 109 and 110 show EEG monitoring eyewear that loops over the top and around the back of the head.

Figure 111:
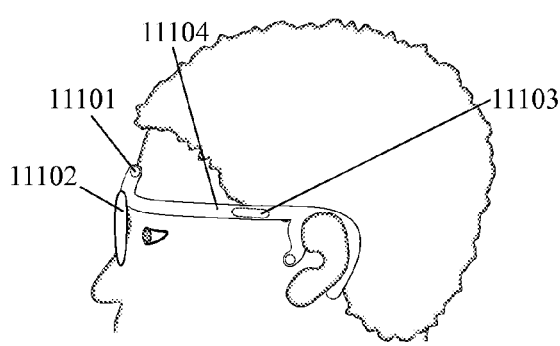
Figure 112:
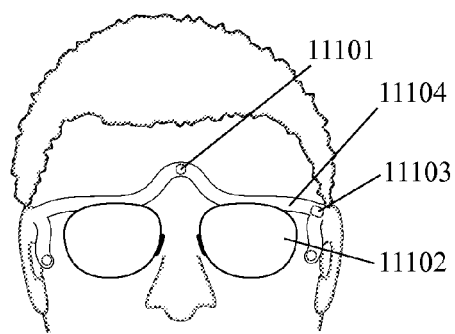

FIGS. 111 and 112 show EEG monitoring eyewear with a downward protrusion in front of the ear.

Figure 113:
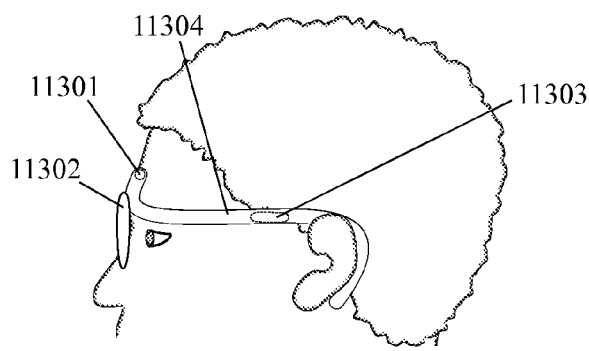
Figure 114:
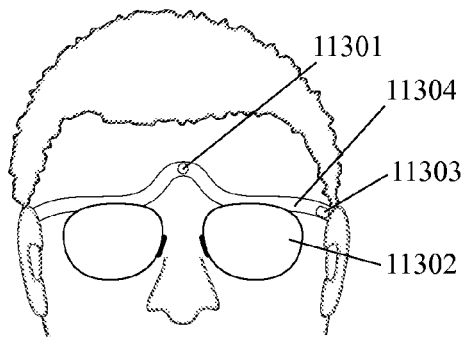

FIGS. 113 and 114 show EEG monitoring eyewear that loops around the back of the ear.

Figure 115:
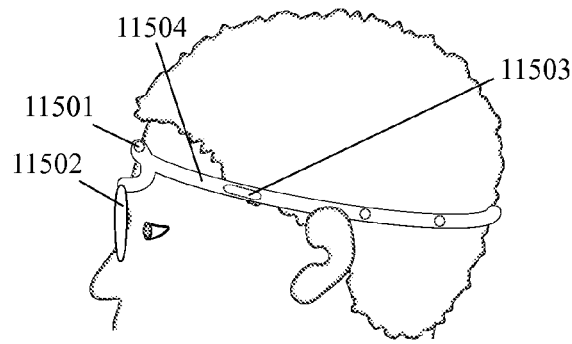
Figure 116:
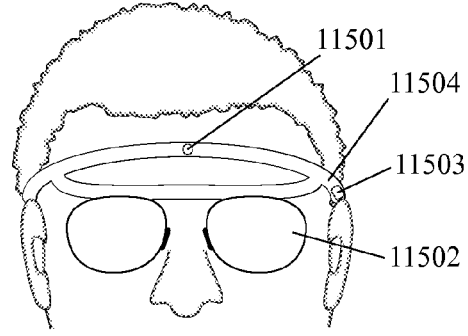

FIGS. 115 and 116 show a fourth example of EEG monitoring eyewear that spans a portion of the forehead.

Figure 117:
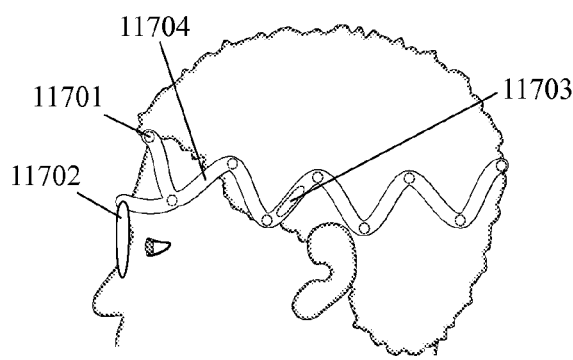
Figure 118:
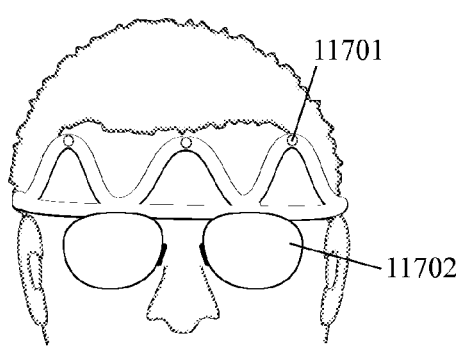

FIGS. 117 and 118 show EEG monitoring eyewear that sinusoidally encircles the head.

Figure 119:
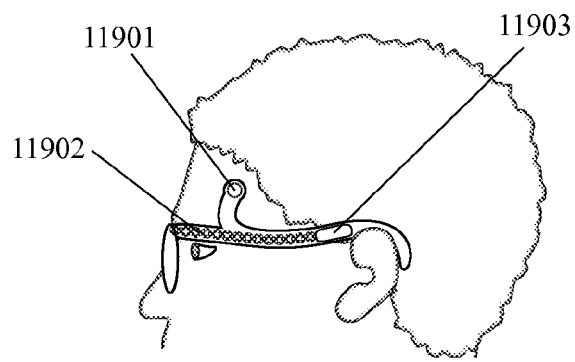
Figure 120:
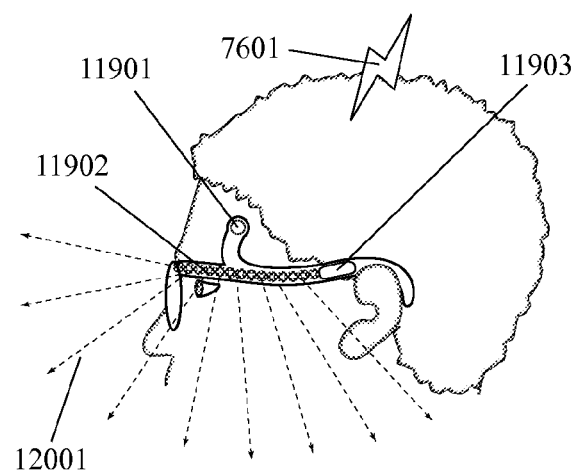

FIGS. 119 and 120 show a first example of EEG monitoring eyewear with changing lights based on brain activity.

Figure 121:
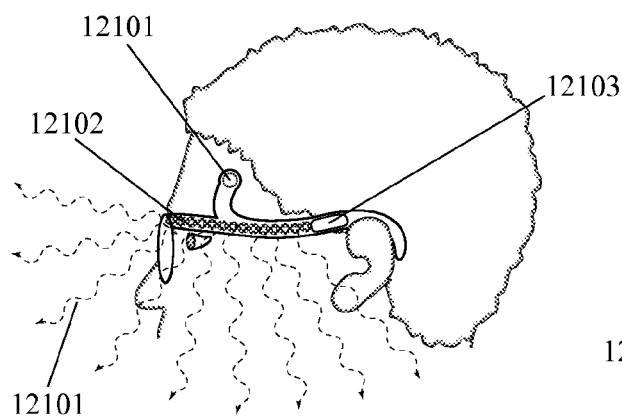
Figure 122:
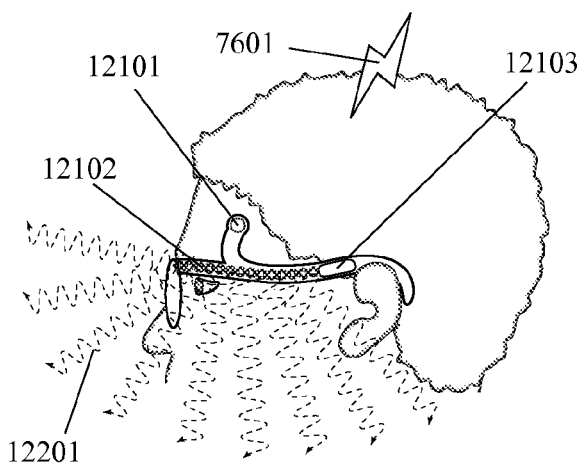

FIGS. 121 and 122 show a second example of EEG monitoring eyewear with changing lights based on brain activity.

FIGS. 123 and 124 show EEG monitoring eyewear that shows augmented reality images based on brain activity.

FIGS. 125 and 126 show EEG monitoring eyewear that shows rear view images based on brain activity.

Figure 127:
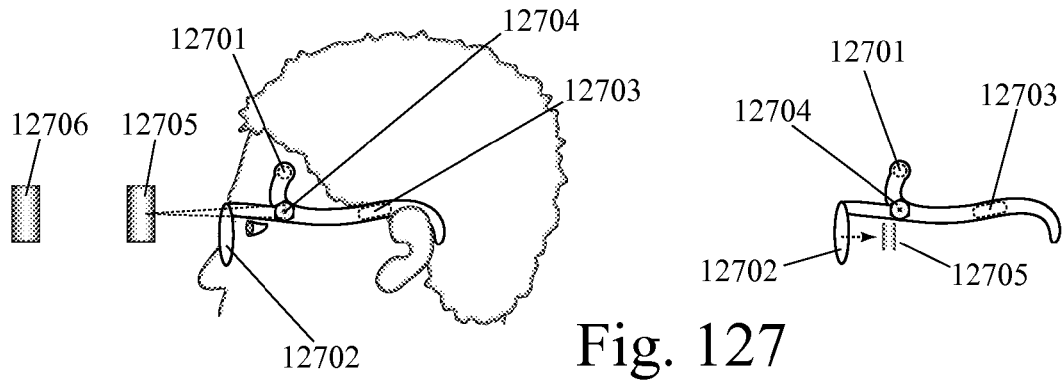
Figure 128:
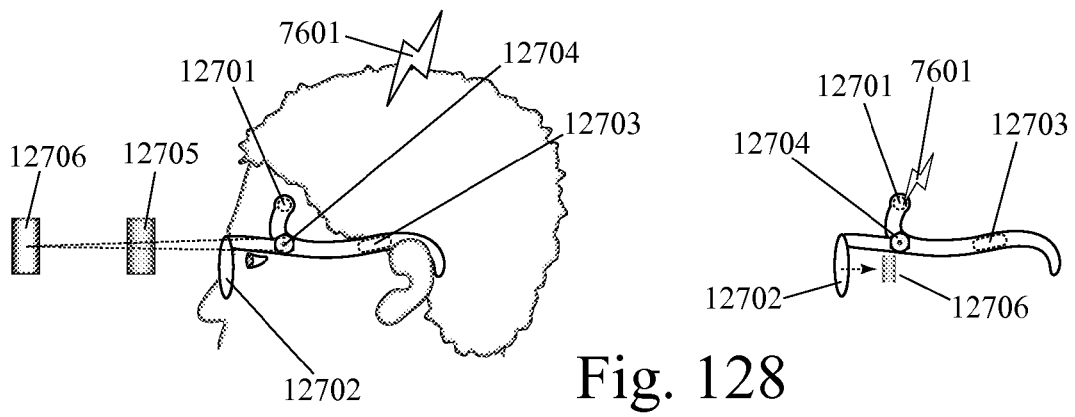

FIGS. 127 and 128 show EEG monitoring eyewear that changes focal distance based on brain activity.

Figure 129:
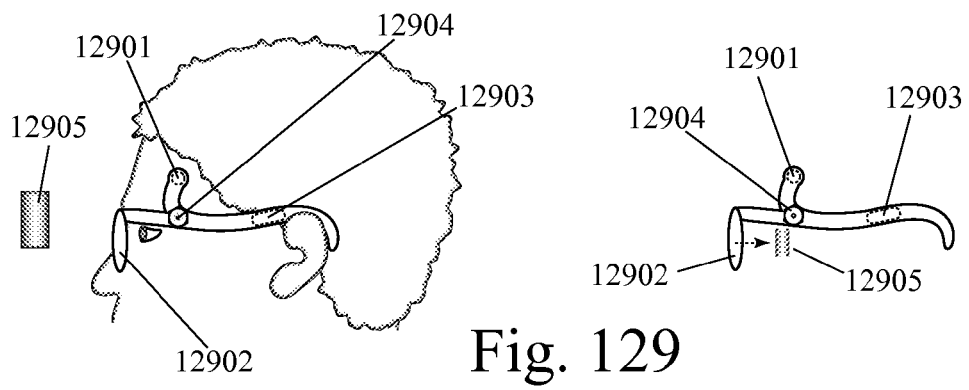
Figure 130:
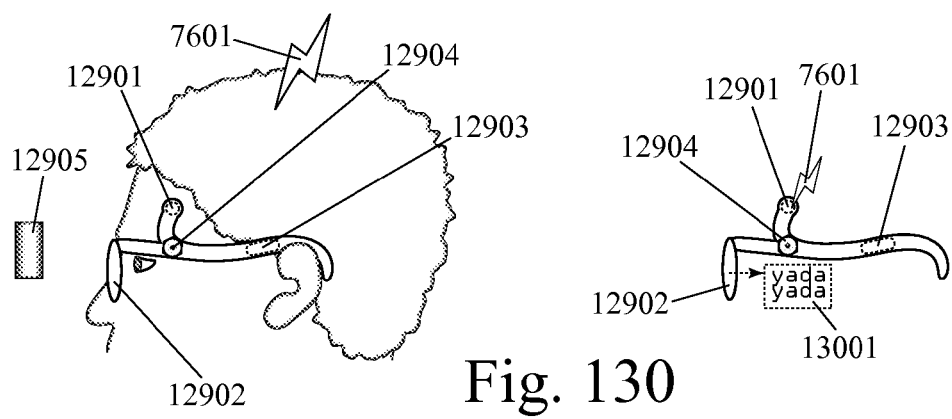

FIGS. 129 and 130 show EEG monitoring eyewear that displays environmental or virtual images based on brain activity.

Figure 131:
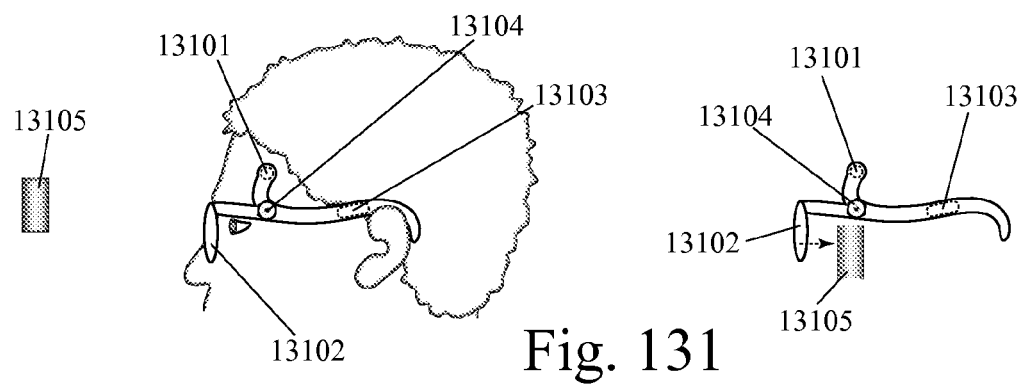
Figure 132:
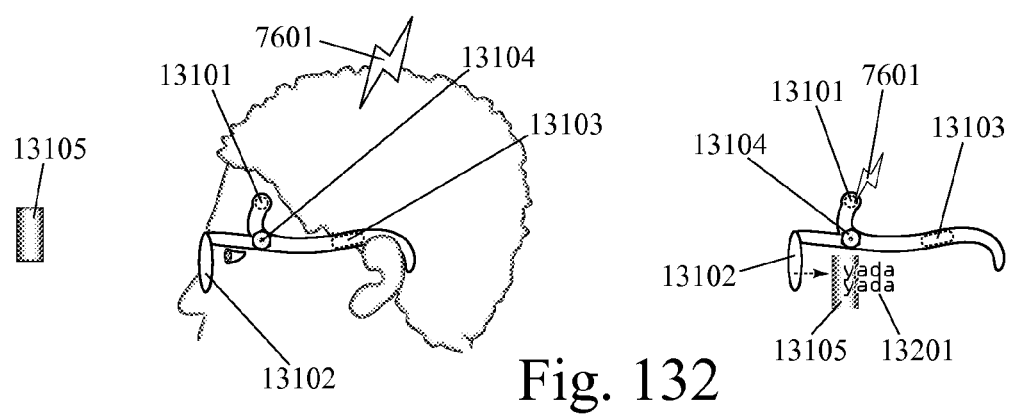

FIGS. 131 and 132 show EEG monitoring eyewear that displays environmental and virtual images based on brain activity.

Figures 133, 134:
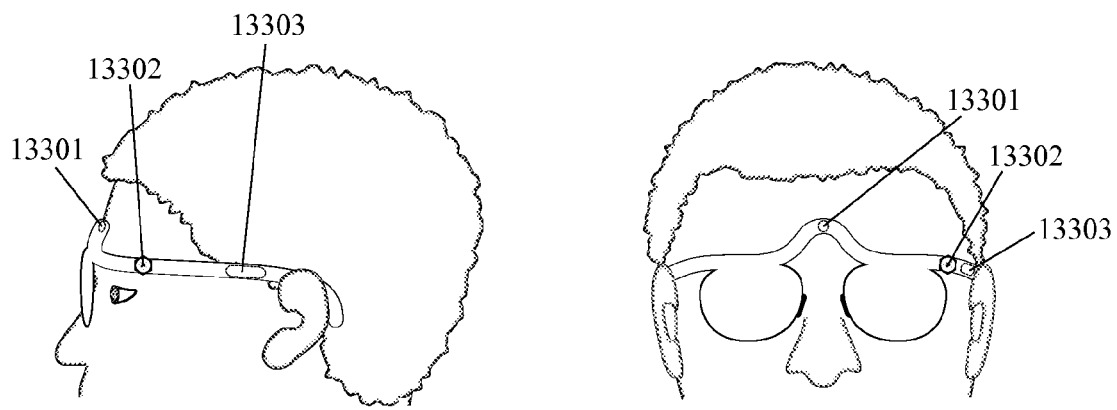

FIGS. 133 and 134 show EEG monitoring eyewear with a camera.

Figure 135:
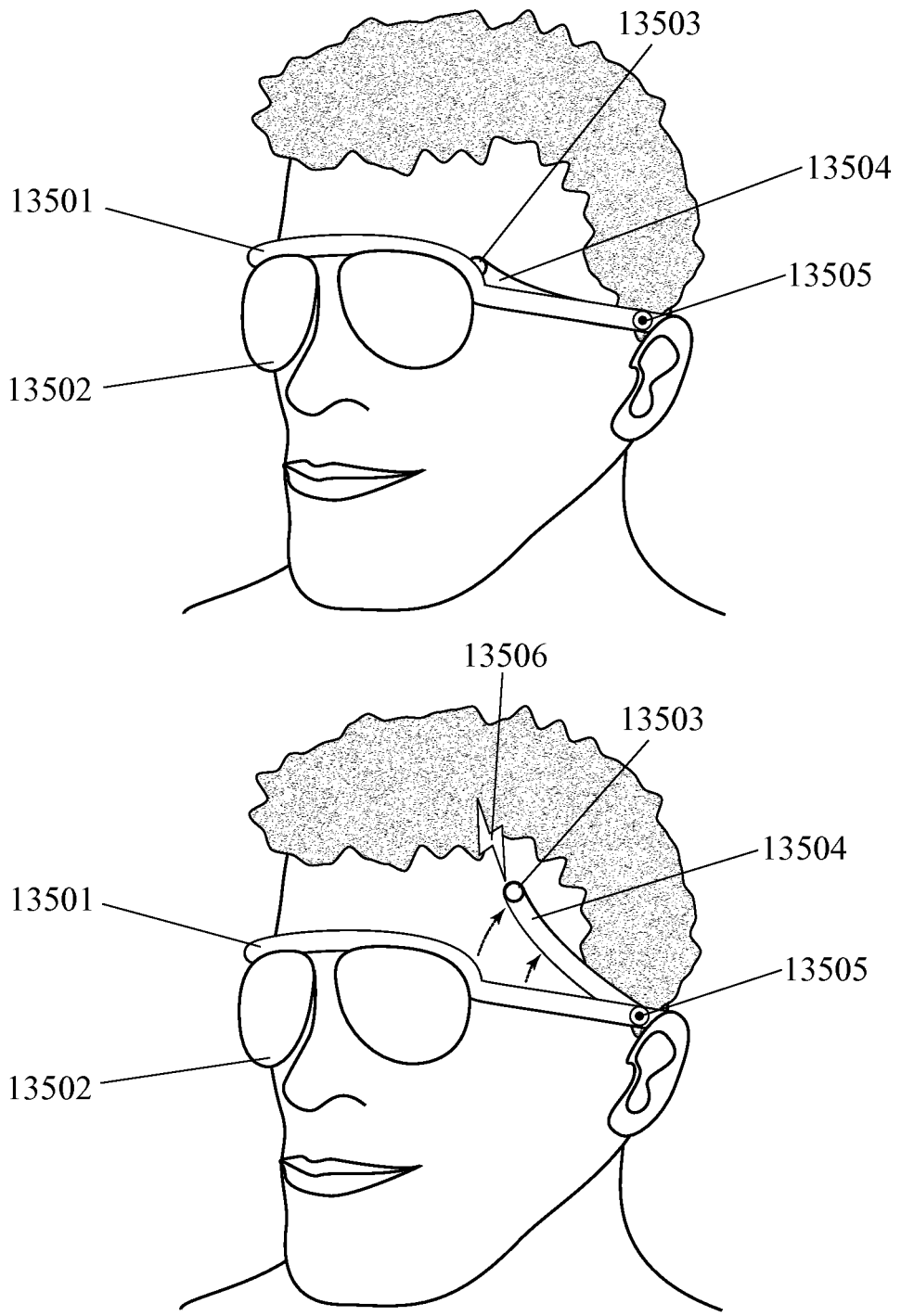

FIG. 135 shows a first example of EEG monitoring eyewear with a retractable sensor-holding arm.

Figure 136:
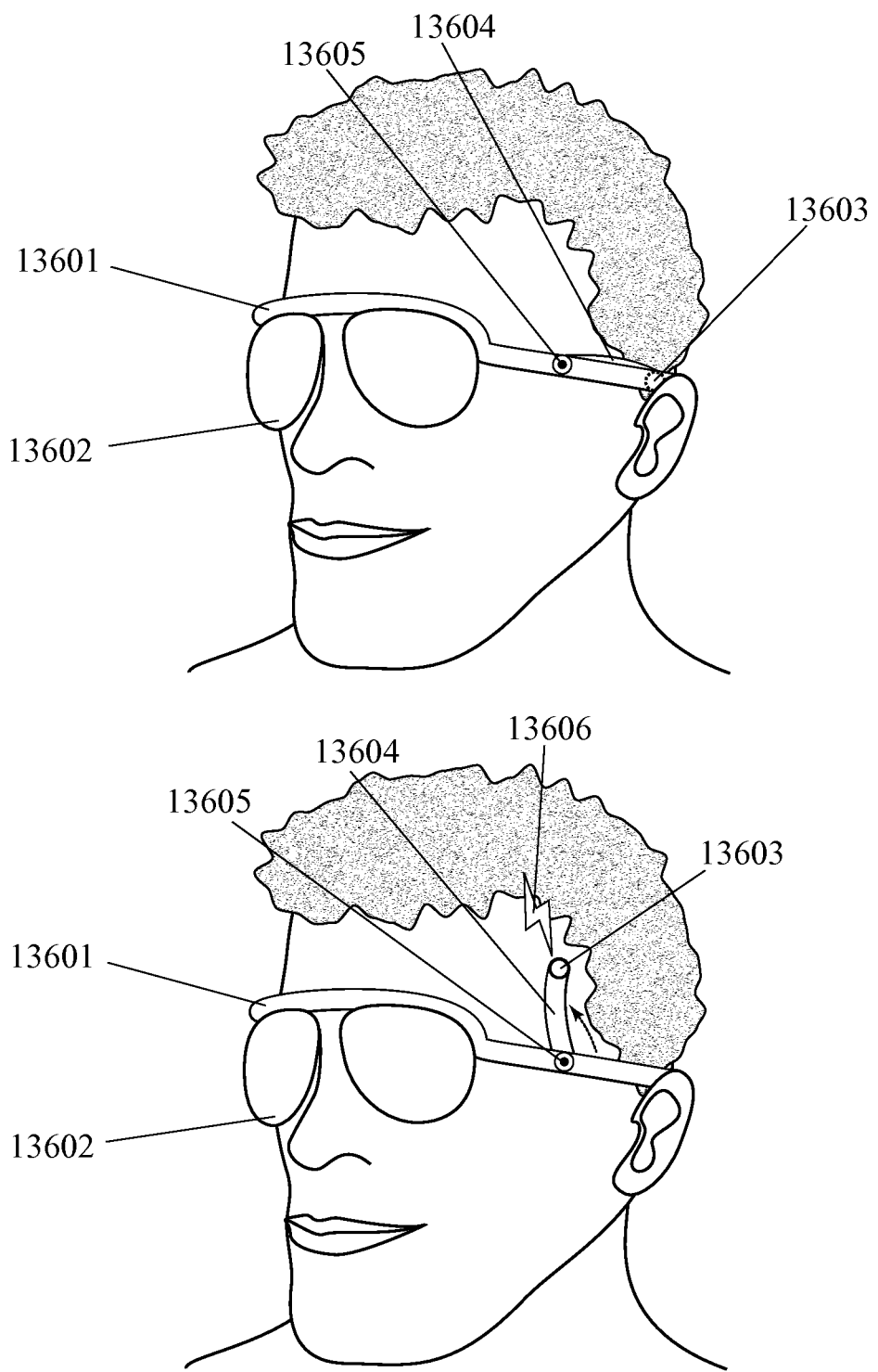

FIG. 136 shows a second example of EEG monitoring eyewear with a retractable sensor-holding arm.

Figure 137:
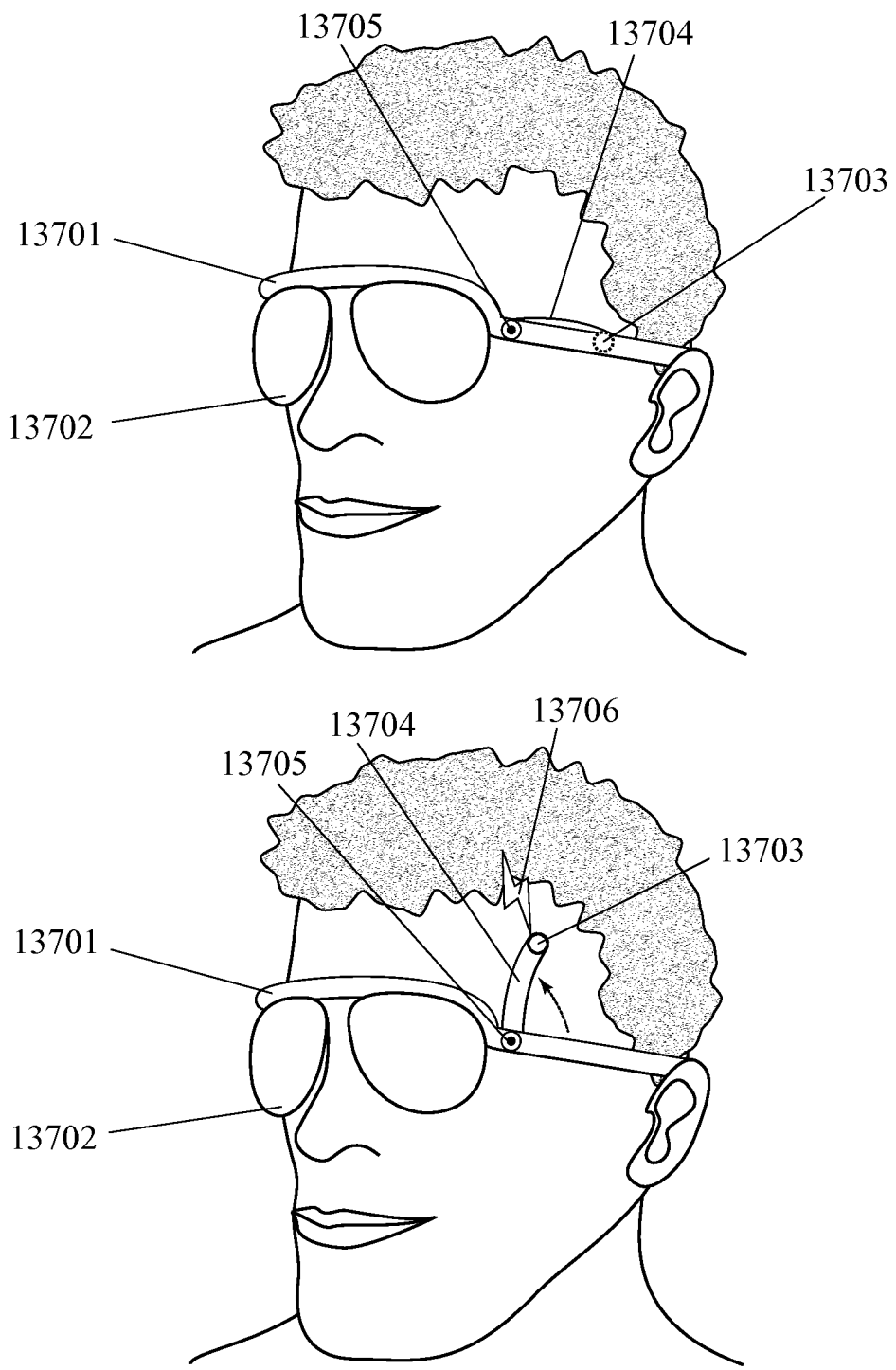

FIG. 137 shows a third example of EEG monitoring eyewear with a retractable sensor-holding arm.

Figure 138:
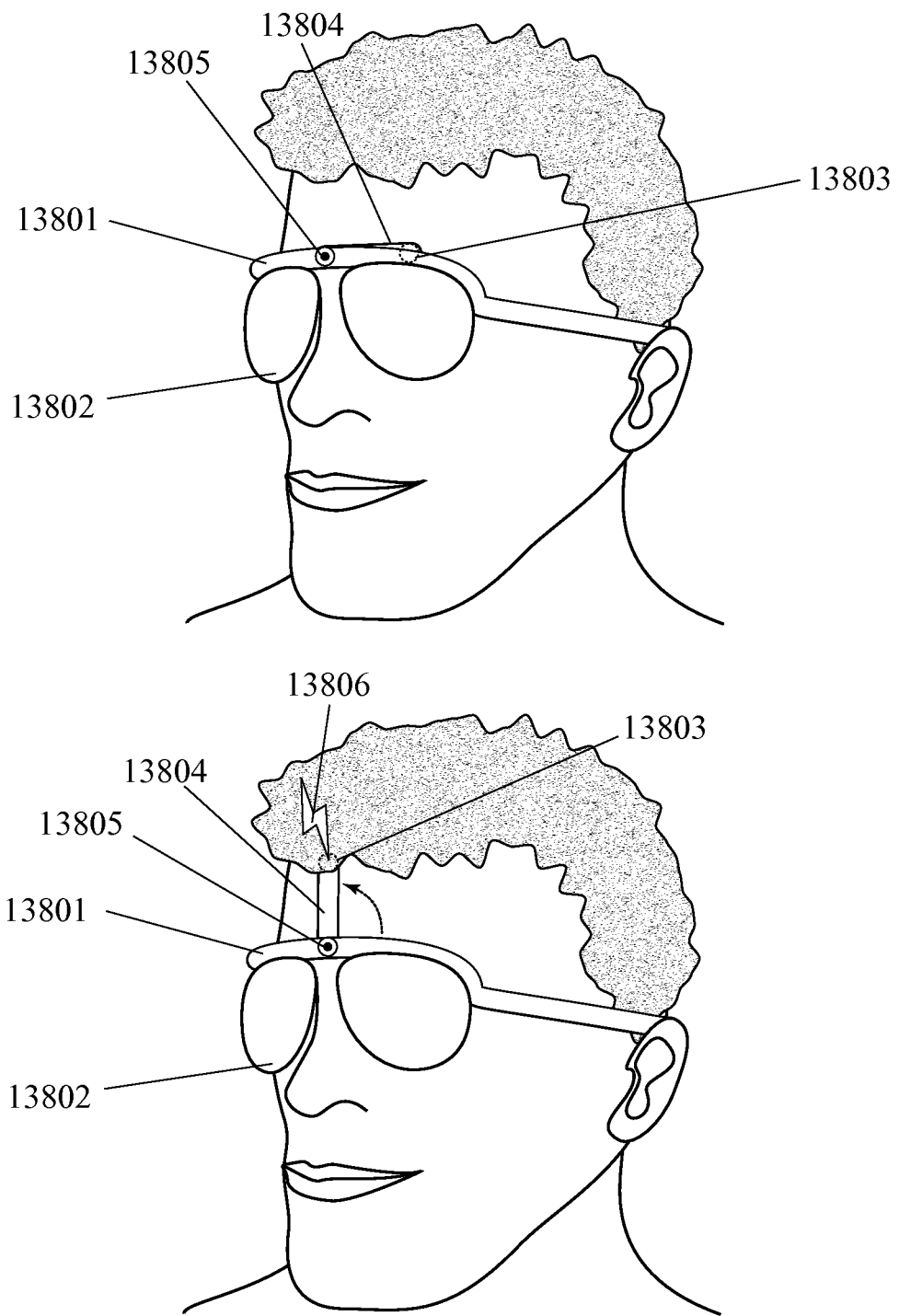

FIG. 138 shows a fourth example of EEG monitoring eyewear with a retractable sensor-holding arm.

Figure 139:
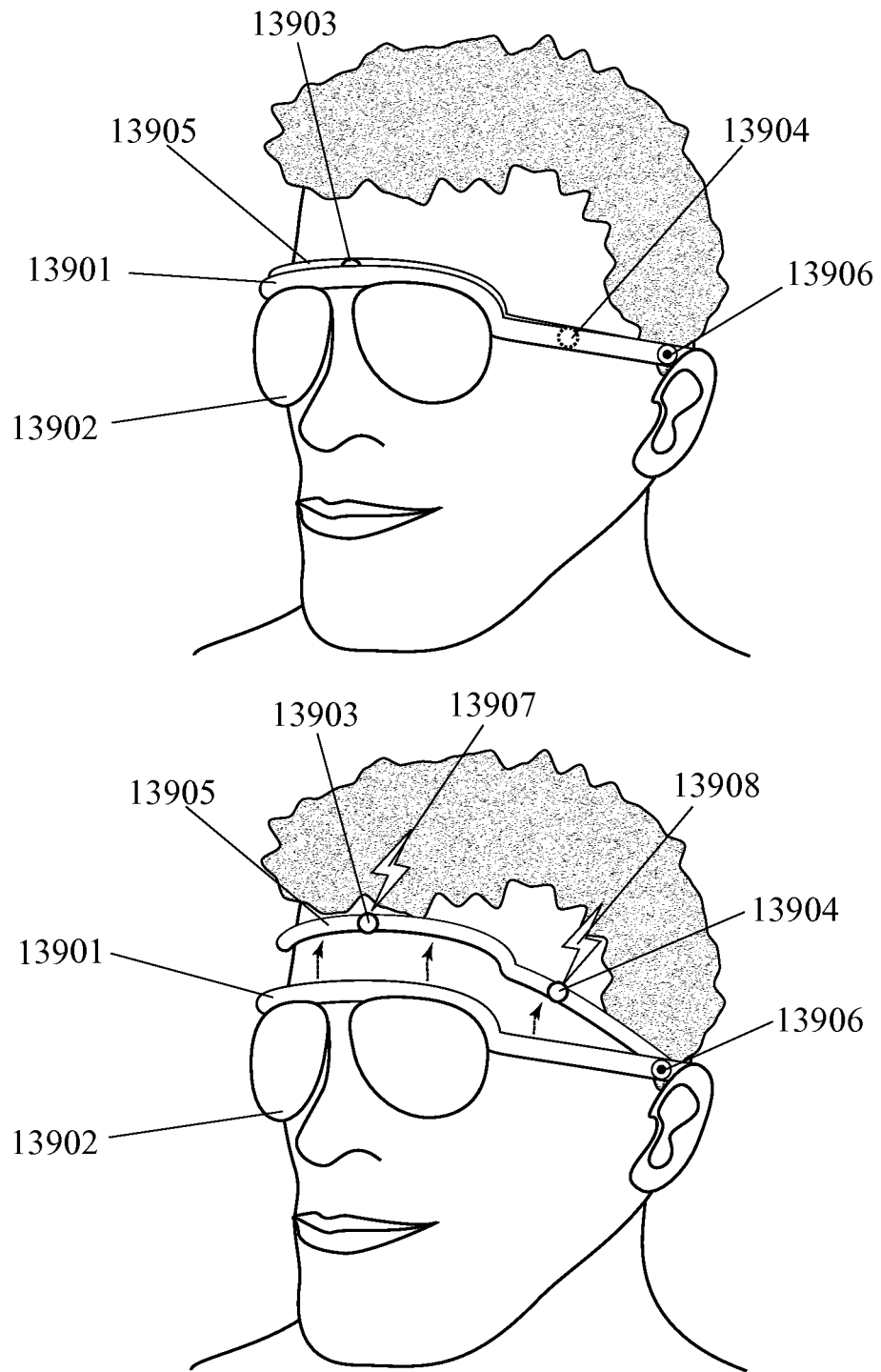

FIG. 139 shows a first example of EEG monitoring eyewear with a retractable sensor-holding band.

Figure 140:
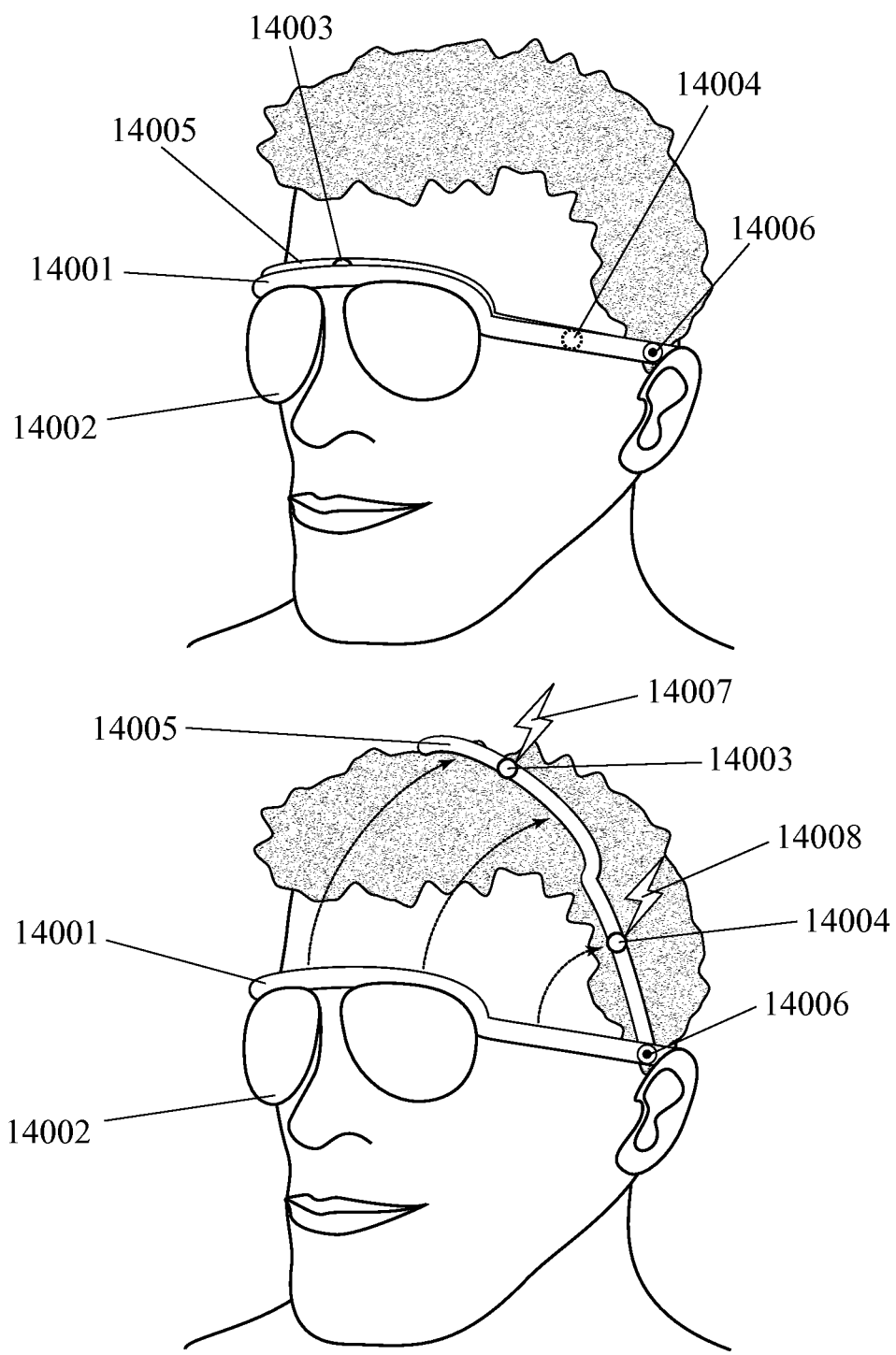

FIG. 140 shows a second example of EEG monitoring eyewear with a retractable sensor-holding band.

Figure 141:
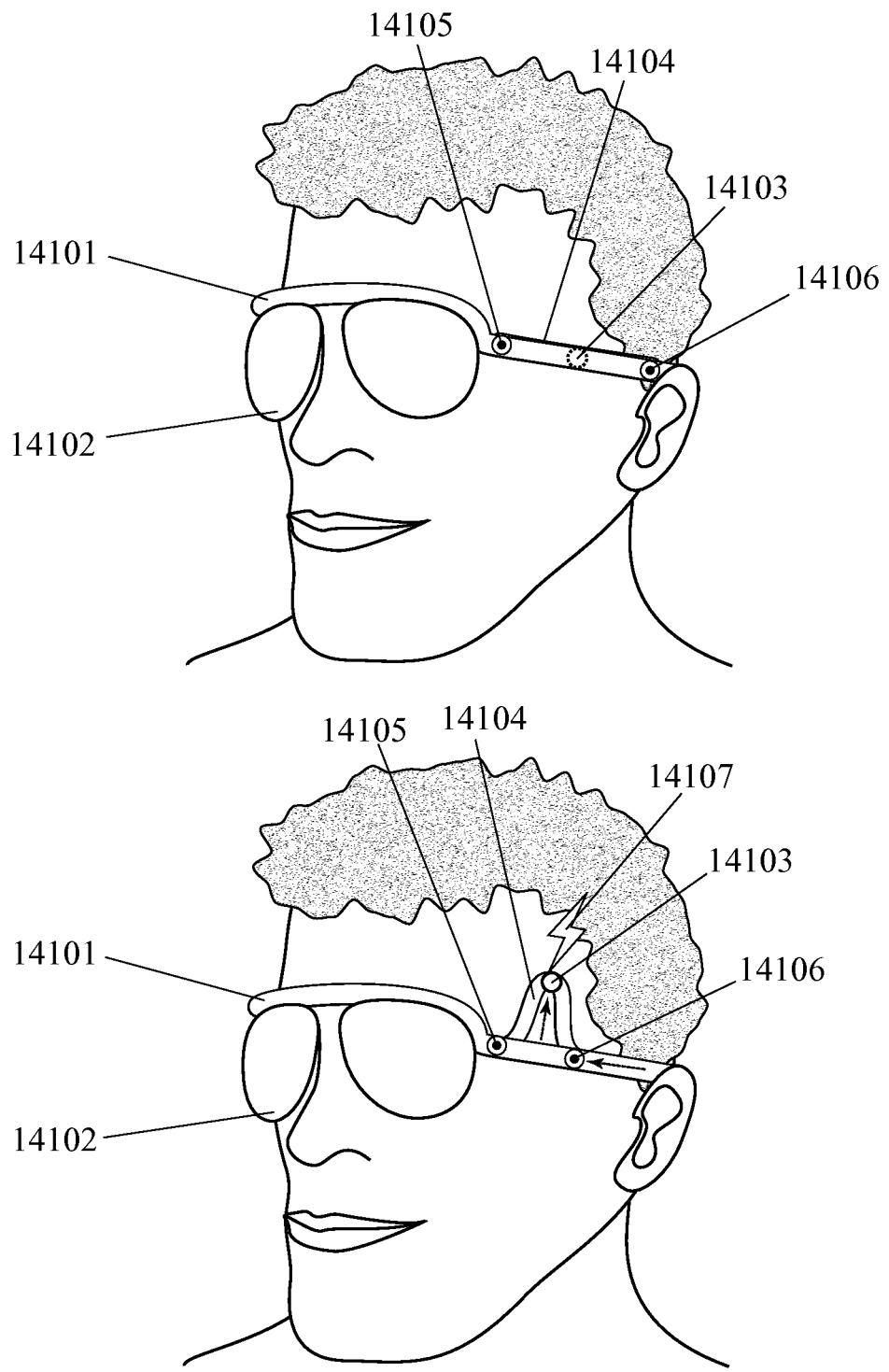

FIG. 141 shows a first example of EEG monitoring eyewear with a retractable sensor-holding loop.

Figure 142:
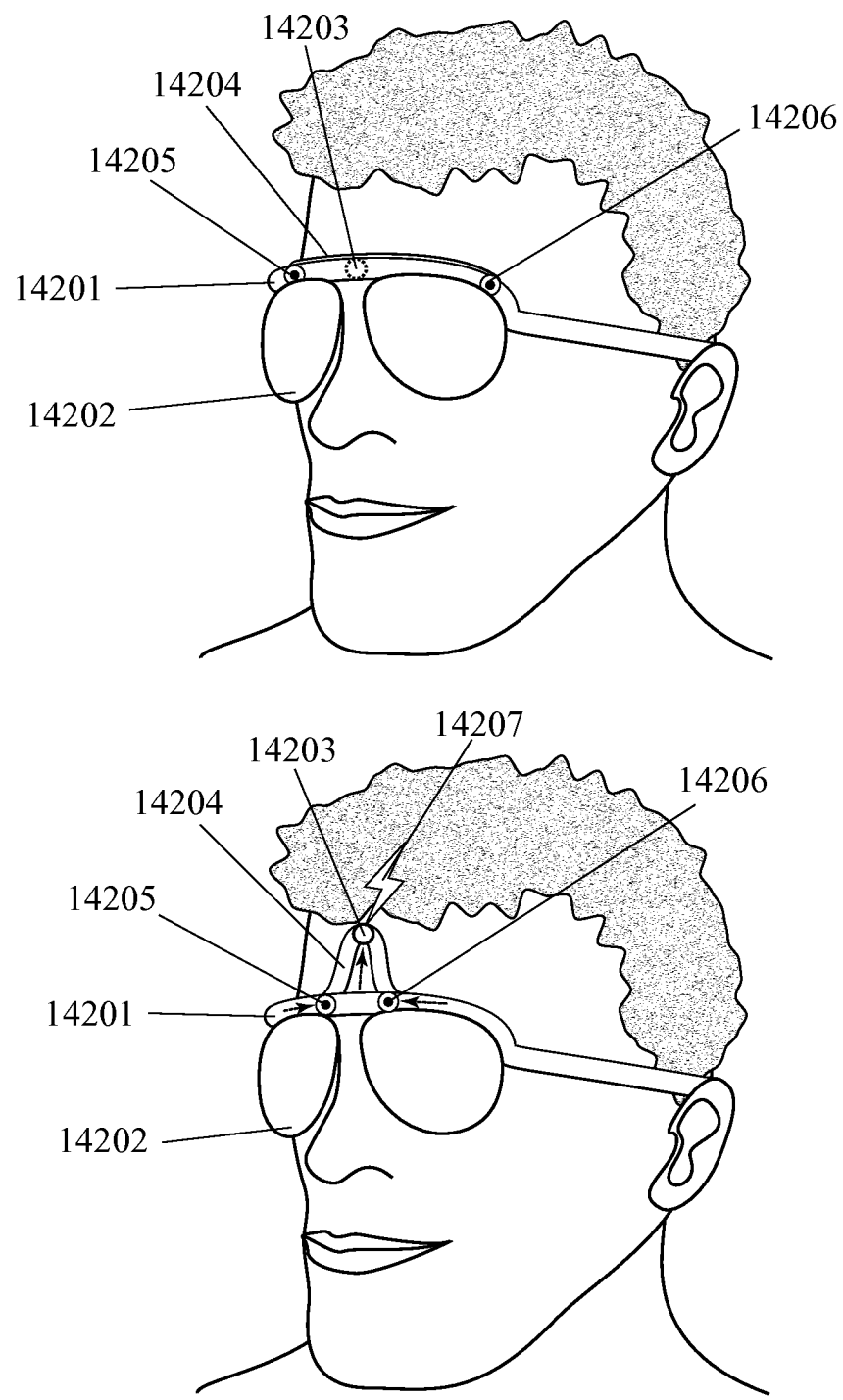

FIG. 142 shows a second example of EEG monitoring eyewear with a retractable sensor-holding loop.

Figure 143:
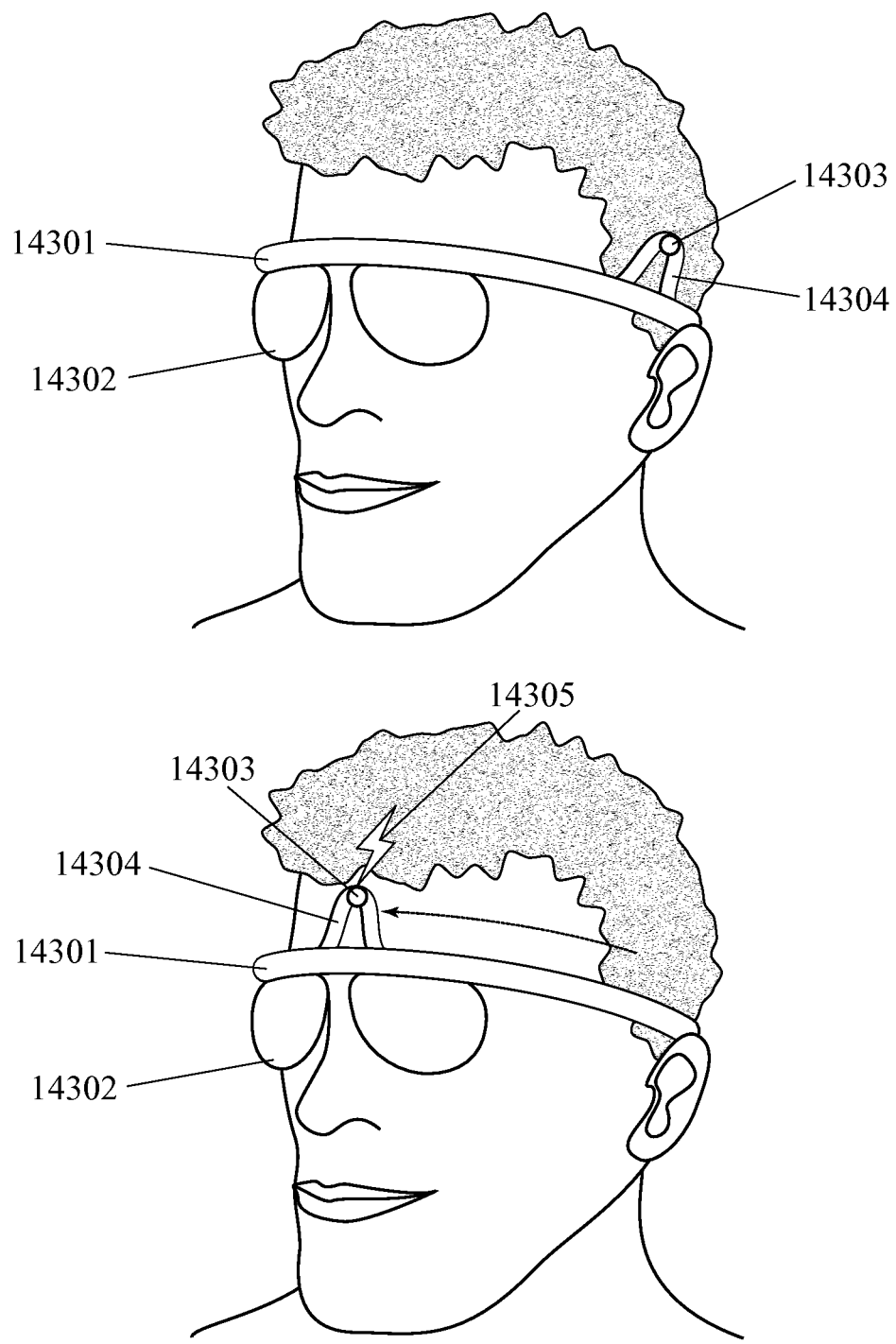

FIG. 143 shows EEG monitoring eyewear with a sliding sensor-holding loop.

FIG. 144 shows a third example of EEG monitoring eyewear with a retractable sensor-holding band.

Figure 145:
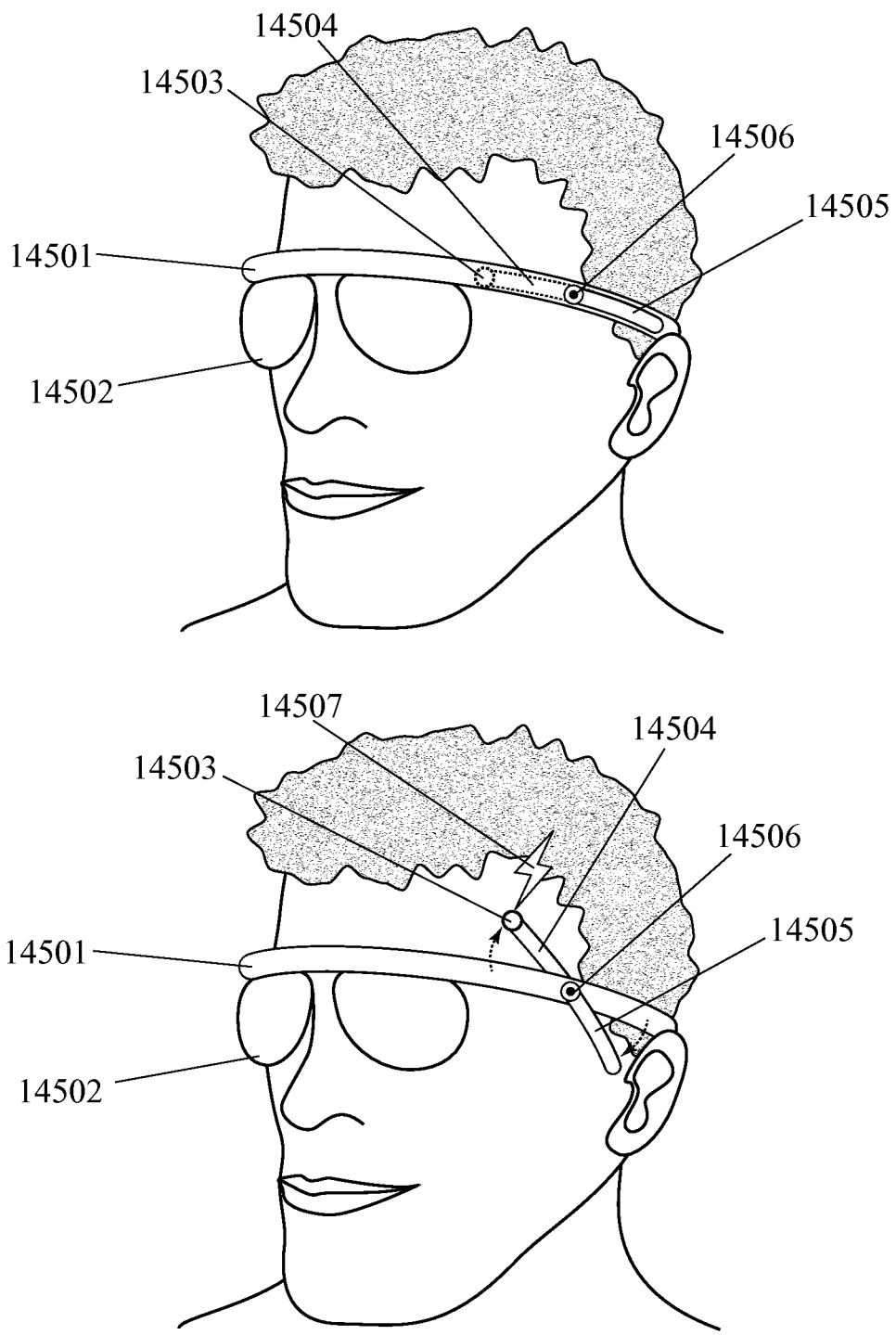

FIG. 145 shows EEG monitoring eyewear with a rotating sensor-holding arm.

FIG. 146 shows a first example of EEG monitoring eyewear with a rotating sensor-holding band.

FIG. 147 shows a second example of EEG monitoring eyewear with a rotating sensor-holding band.

Figure 148:
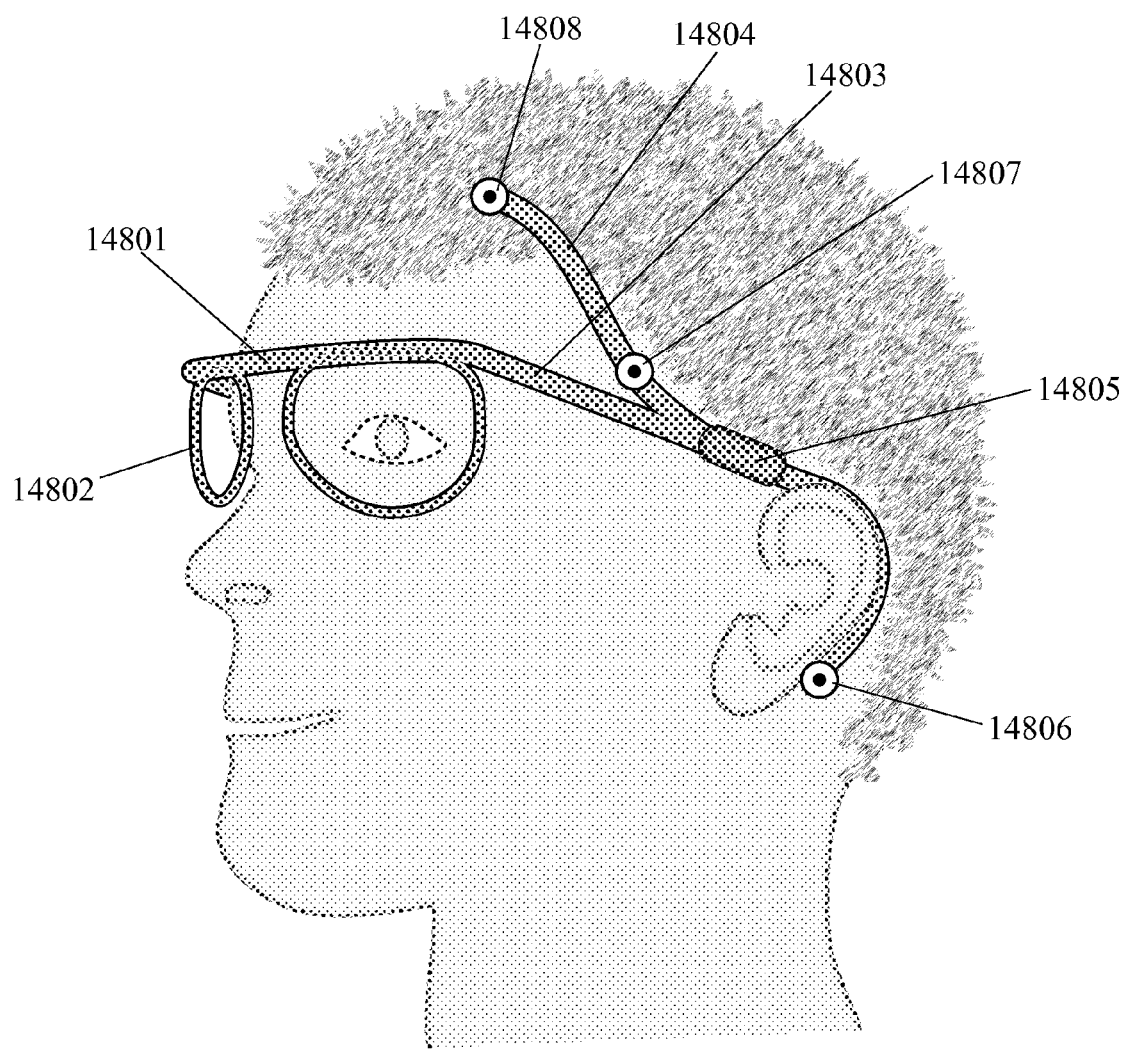

FIG. 148 shows EEG monitoring eyewear with a forehead-ascending sensor-holding arm.

Figure 149:
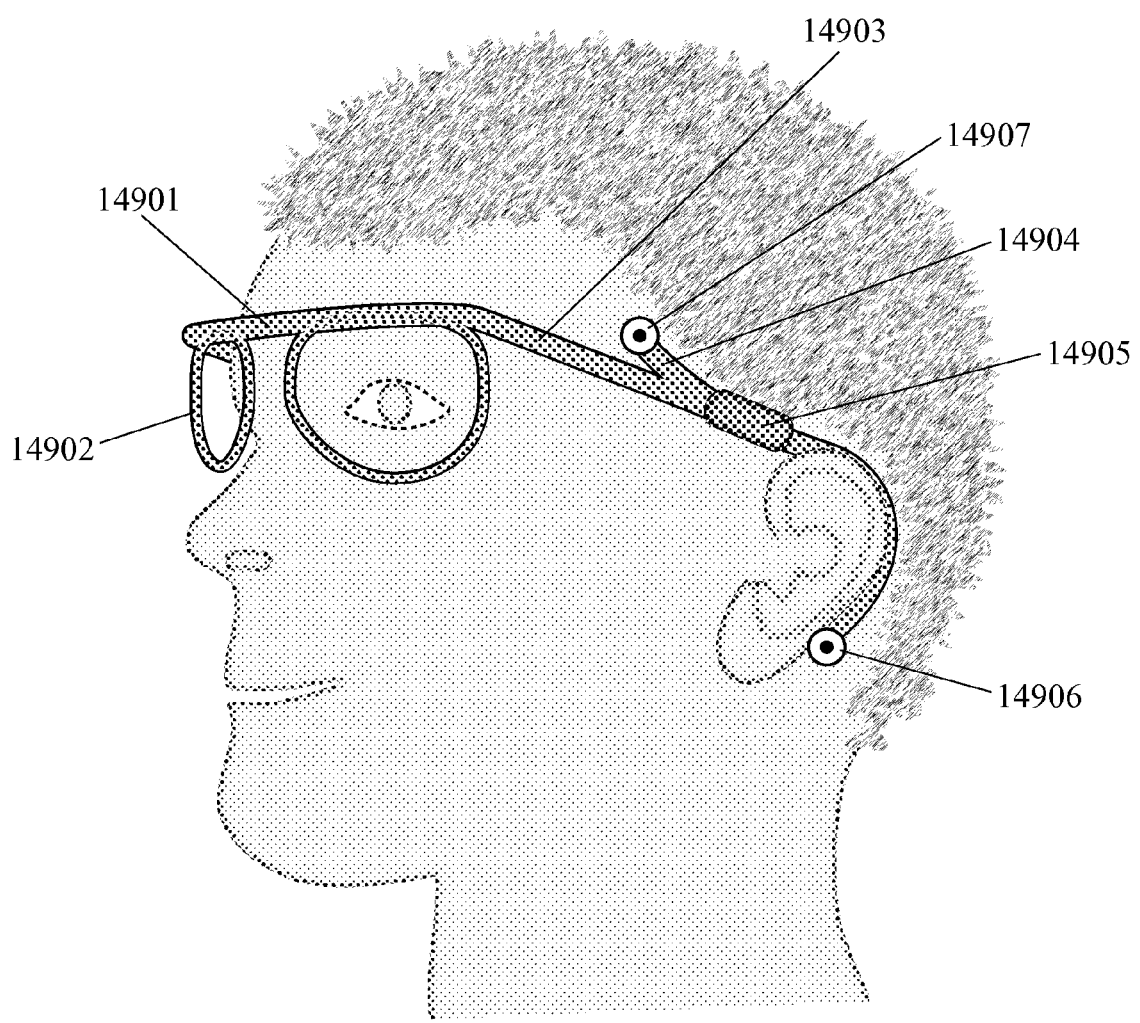

FIG. 149 shows EEG monitoring eyewear with a temple-ascending sensor-holding arm.

Figure 150:
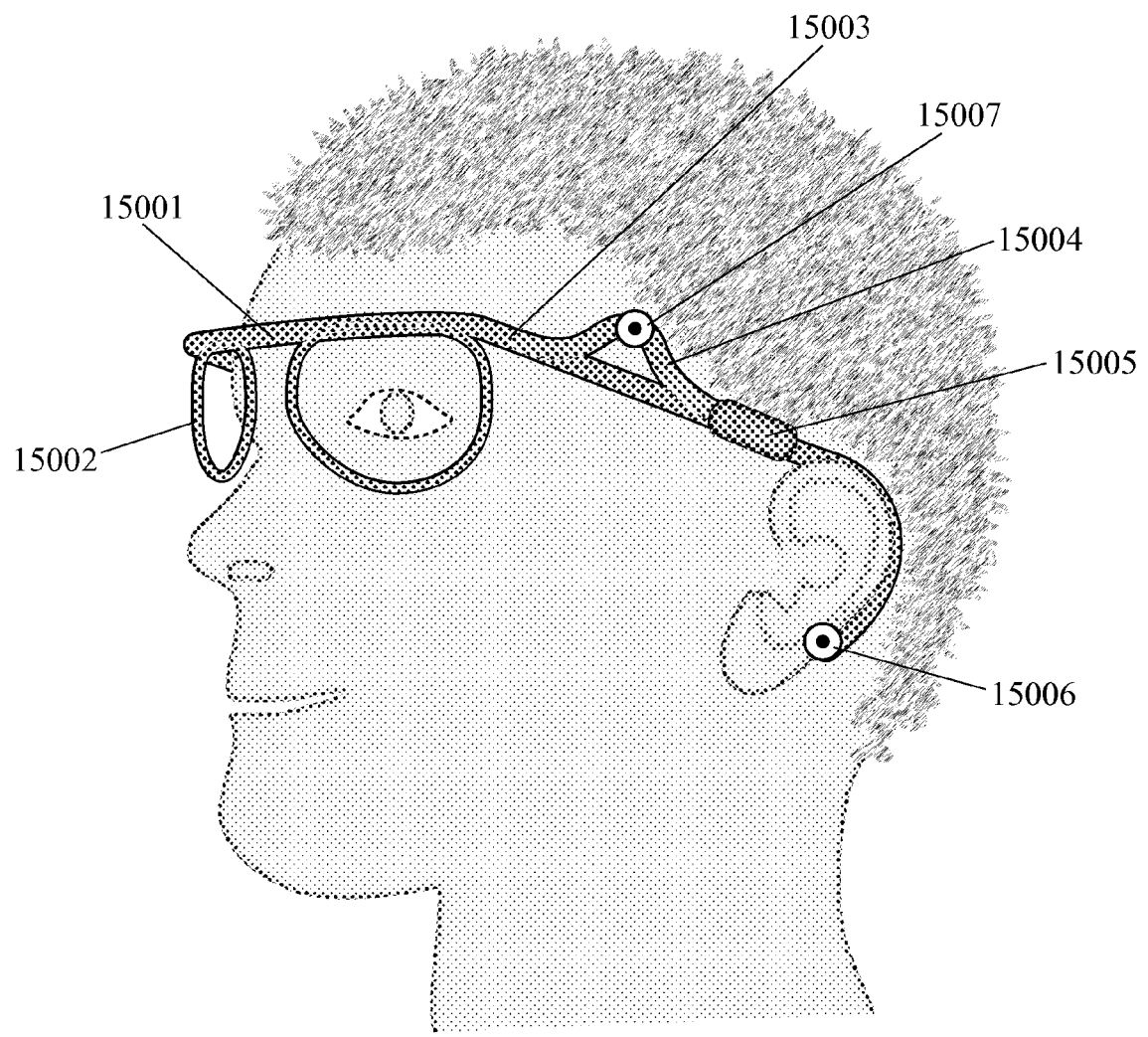

FIG. 150 shows a first example of EEG monitoring eyewear with a temple-ascending sensor-holding loop.

Figure 151:
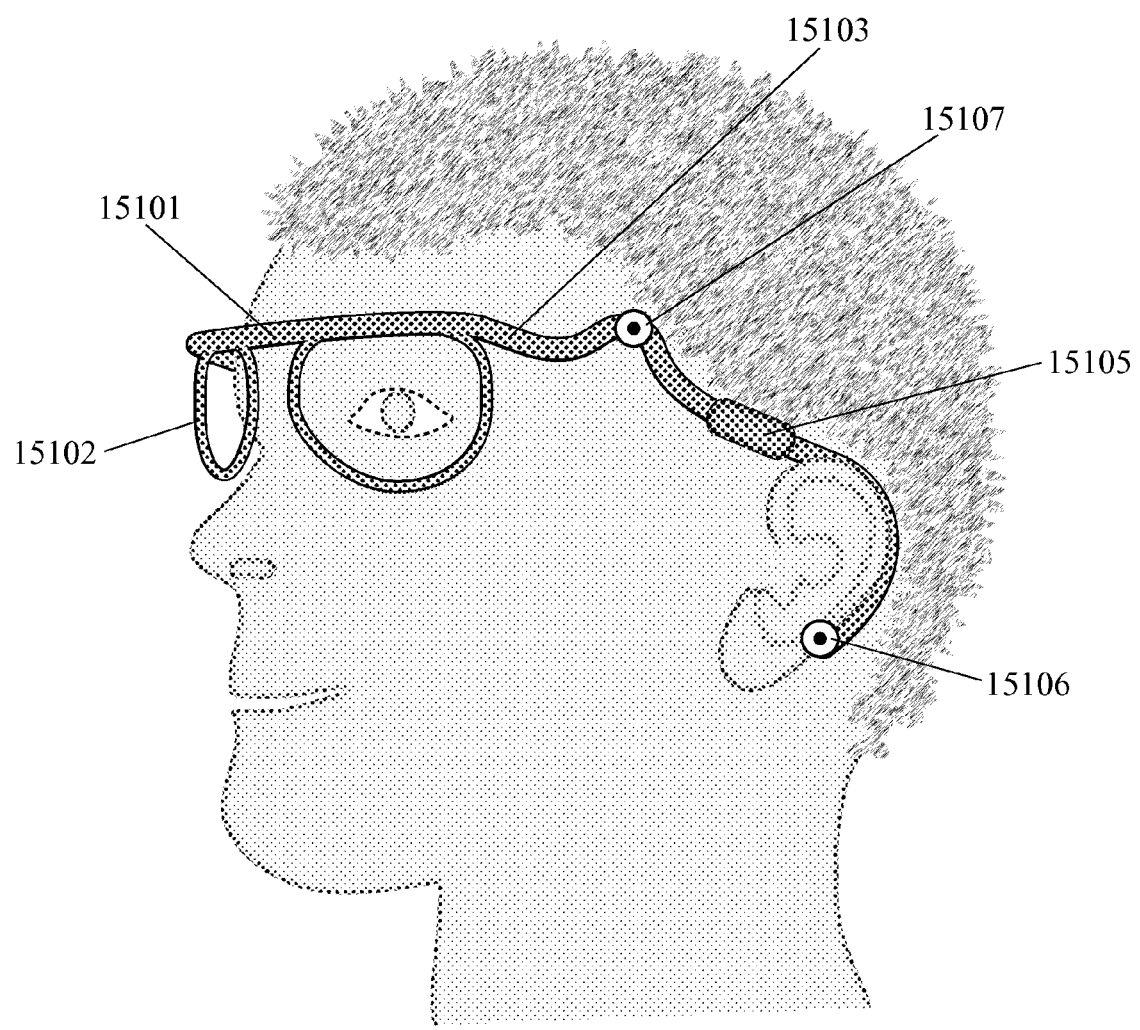

FIG. 151 shows a second example of EEG monitoring eyewear with a temple-ascending sensor-holding loop.

Figure 152:
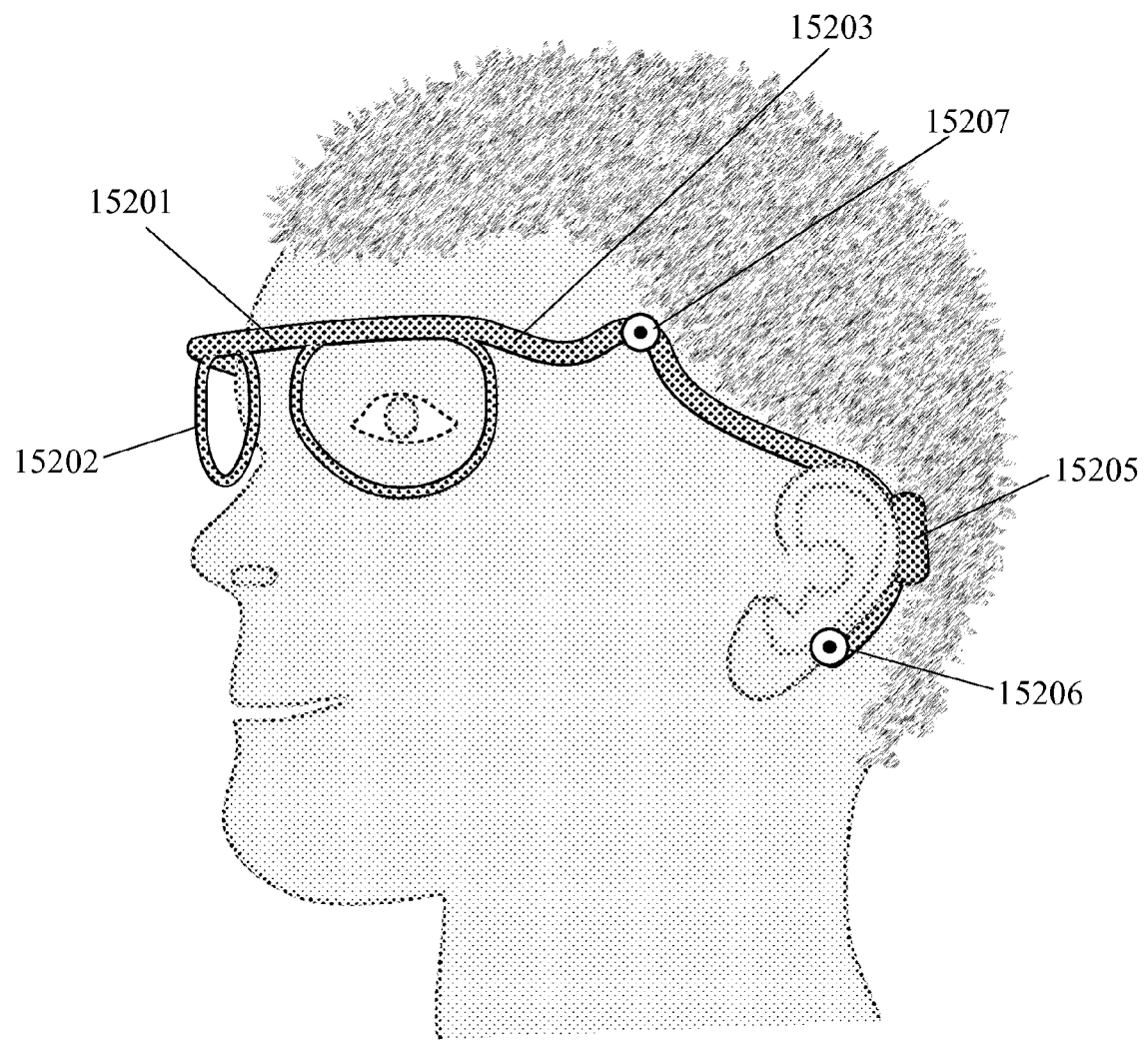

FIG. 152 shows a third example of EEG monitoring eyewear with a temple-ascending sensor-holding loop.

Figure 153:
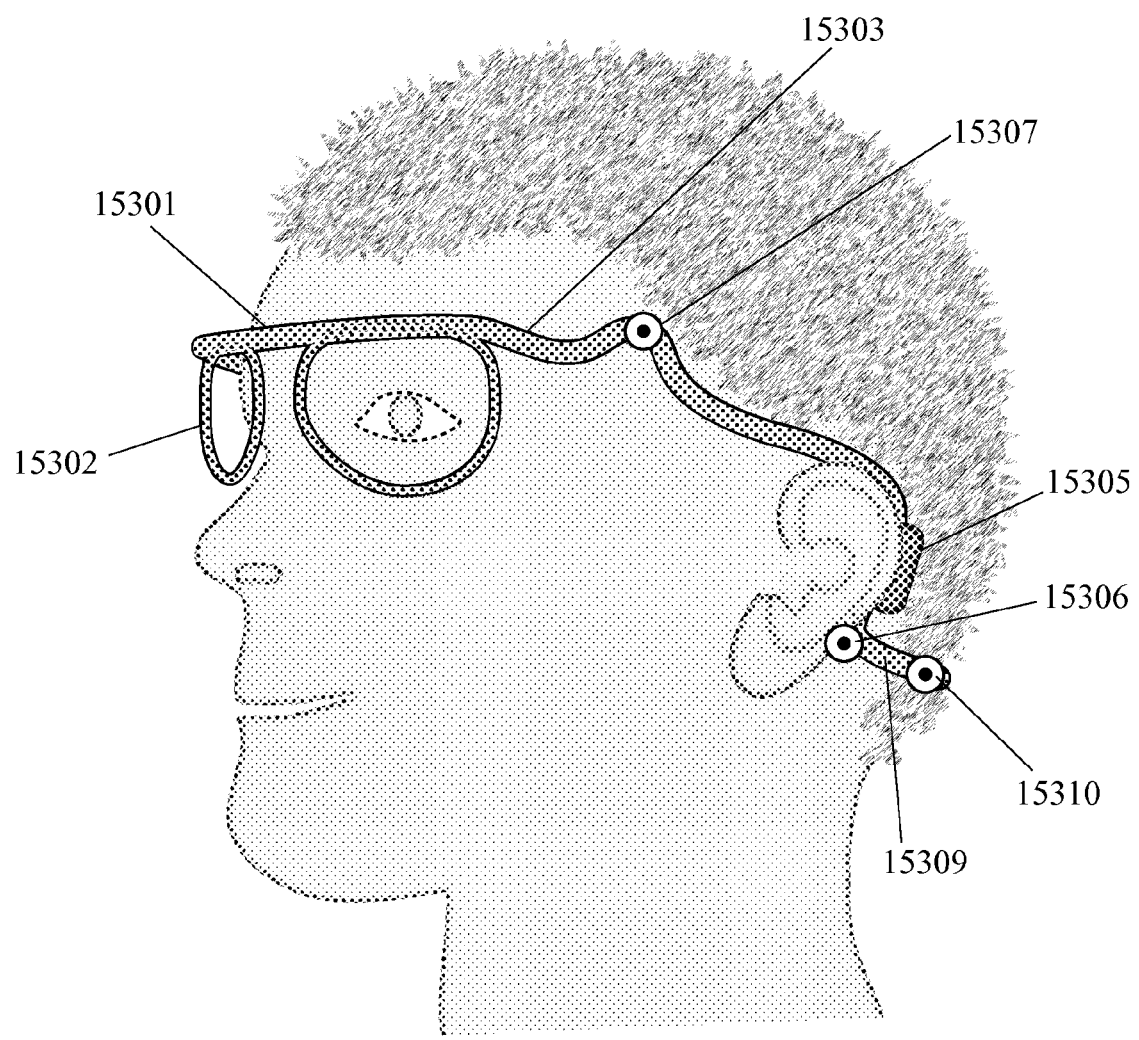

FIG. 153 shows EEG monitoring eyewear with a temple-ascending loop and a loop around the rear of the head.

Figure 154:
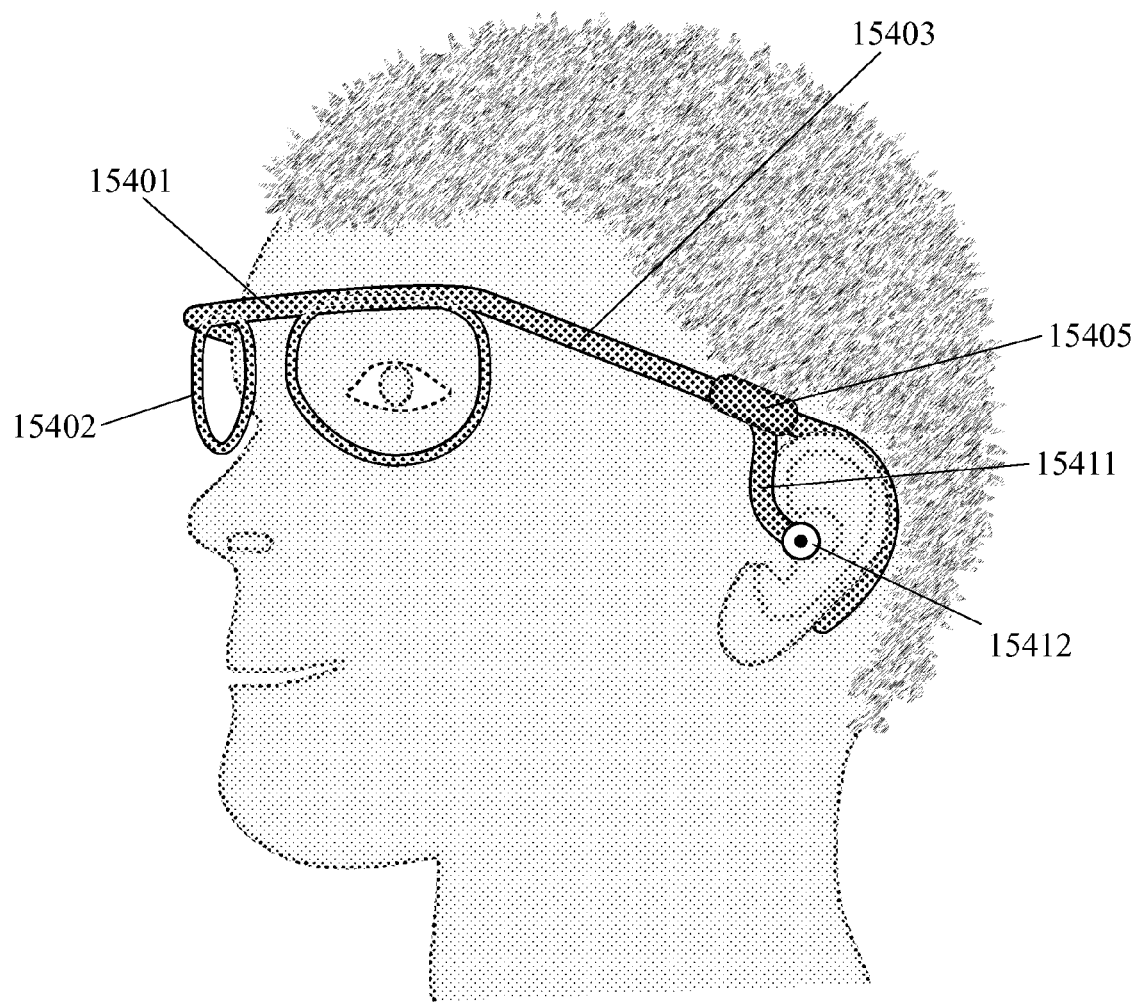

FIG. 154 shows EEG monitoring eyewear with downward sensor-holding protrusion in front of the ear.

Figure 155:
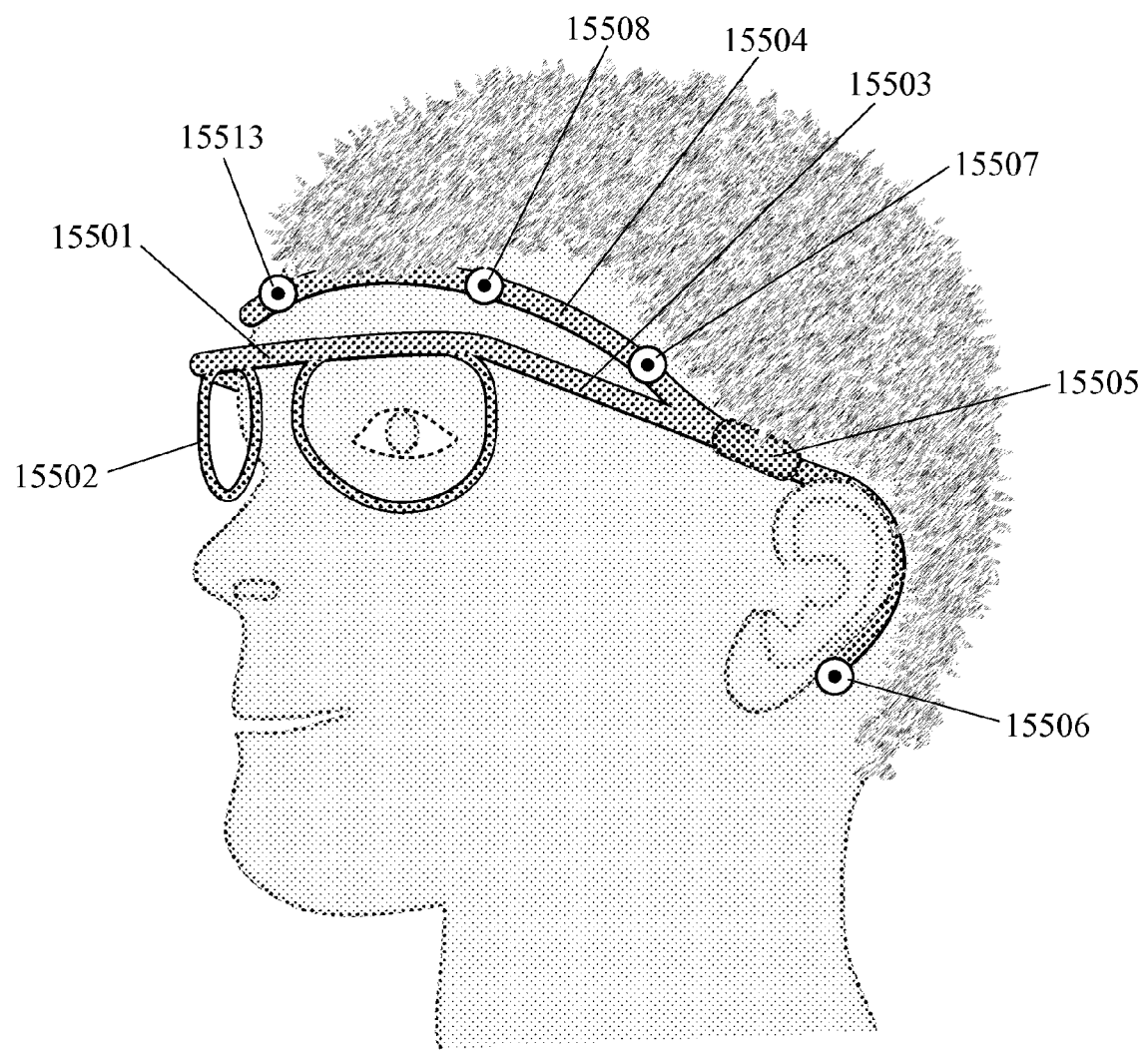

FIG. 155 shows EEG monitoring eyewear with a forehead-spanning sensor-holding band.

DETAILED DESCRIPTION OF THE FIGURES

Figure 1:
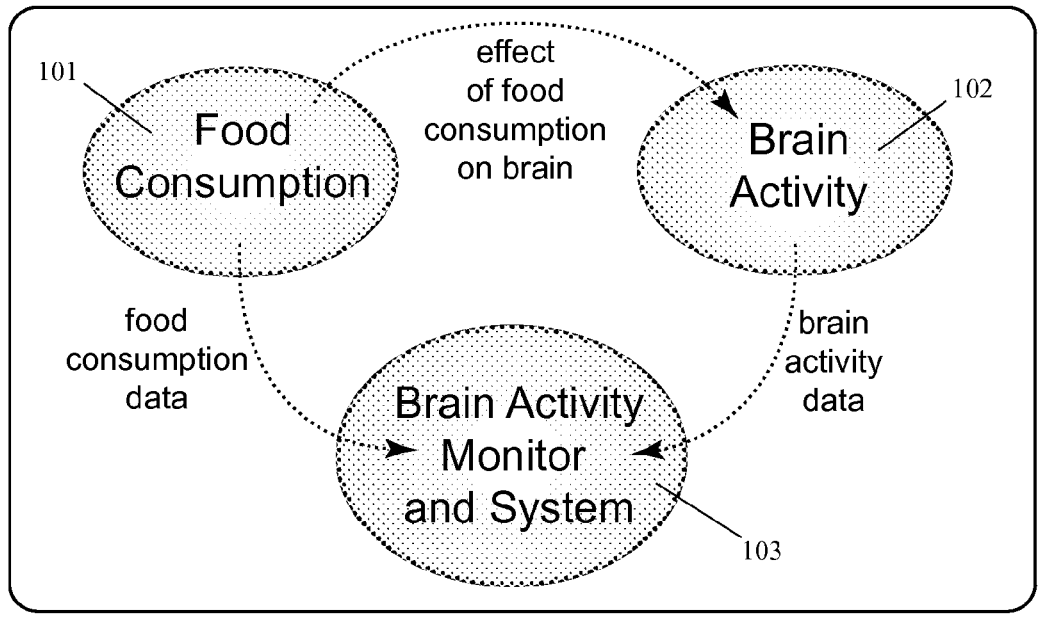
FIG. 1 shows a first (calibration) step of a first method for modifying food consumption using an EEG monitor.

FIGS. 1 through 155 show examples of how this invention can be embodied a mobile wearable electromagnetic brain activity monitor comprising: a wearable frame worn on a person's head; a plurality of electromagnetic energy sensors which collect data concerning the person's electromagnetic brain activity; and a control unit. However, these examples do not limit the full generalizability of the claims. In an example, the electromagnetic energy sensors can be electroencephalogram (EEG) electrodes. In an example, the wearable frame can be substantially circular (or elliptical), spanning the person's forehead and the rear of the person's head. In an example, the wearable frame can loop around the person's head from one ear to the other.

This mobile wearable electromagnetic brain activity monitor can be used for a variety of purposes. As highlighted by FIGS. 1 through 74, this mobile wearable electromagnetic brain activity monitor can be used to monitor, measure, and modify the person's food consumption. As highlighted by FIGS. 75 through 134, this mobile wearable electromagnetic brain activity monitor can be used to control eyewear with light-transmitting members whose light absorption, light reflection, light refraction, light spectrum transformation, focal direction, focal distance, light polarization, or parallax view can be controlled by the wearer's brain activity. As highlighted by FIGS. 135 through 155, this mobile wearable electromagnetic brain activity monitor can also comprise eyeglasses and/or other eyewear.

FIGS. 1 through 6 provide a conceptual introduction to a method, device, and system to measure and/or modify a person's food consumption using a wearable electroencephalogram (EEG) monitor. As shown in FIG. 1, a person's food consumption 101 has an effect on their electromagnetic brain activity 102. Data concerning the person's food consumption 101 and data concerning their electromagnetic brain activity 102 can be collected in a chronologically-linked manner. These two data streams (concerning food consumption and brain activity) can then be jointly analyzed by a brain activity monitor and system 103 in order to identify significant relationships between patterns of food consumption and patterns of brain activity. In an example, this analysis can include a (short) time lag between food consumption and brain activity. In an example, a food-brainwave database can be created, wherein this database links patterns of food consumption 101 with patterns of electromagnetic brain activity 102.

FIG. 1 shows the operation of a method for measuring and/or modifying food consumption during a first time period (which can be called a "calibration" period or an "association-creating" period) in which data concerning food consumption 101 and data concerning electromagnetic brain activity 102 are independently collected and jointly analyzed in order to identify significant associations between them. In an example, during a first (calibration) time period, data concerning food consumption can be manually entered via a human-to-computer interface which is part of a wearable EEG monitor. In an example, during a first (calibration) time period, data concerning food consumption can be manually entered into a physically-separate device or a remote computer as part of an overall system of wirelessly-linked devices.

Figure 2:
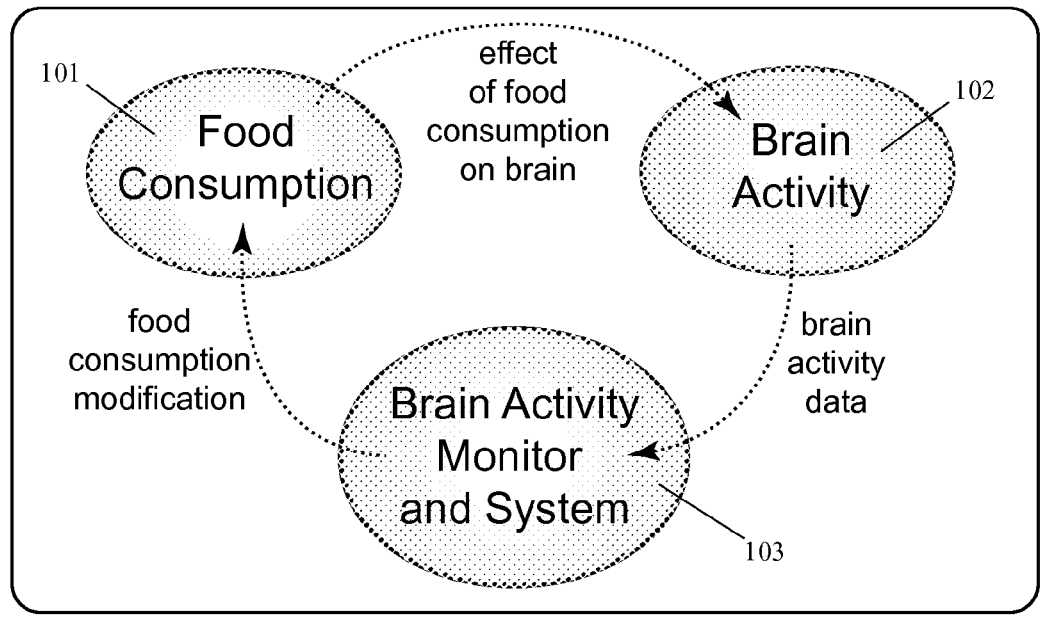
FIG. 2 shows the second step of this first method for modifying food consumption using an EEG monitor.

FIG. 2 shows the operation of this method during a second time period (after calibration) during which the previously-identified associations are used to estimate a person's food consumption based on their brain activity. In particular, during the second time period (shown in FIG. 2), the person's electromagnetic brain activity 102 is monitored and data concerning their brain activity is collected. Combining this brain activity data 102 with the associations between food consumption and brain activity which were identified in the first (calibration) period, the person's food consumption 101 is estimated from the person's brain activity 102. In an example, data concerning food consumption and brain activity can be analyzed within a data processor which is part of a wearable EEG monitor. In an example, data concerning food consumption and brain activity can be wirelessly transmitted to a physically-separate device or a remote computer and analyzed in that separate device or remote computer as part of an overall system of wirelessly-linked devices.

In an example, a food-brainwave database which links food consumption patterns to brain activity patterns can be created de novo for a specific person. In an example, a previously-created food-brainwave database, which links food consumption patterns to brain activity patterns, can be used and a first (calibration) period can be shortened or skipped entirely. In an example, a general population food-brainwave database which links food consumption patterns to brain activity patterns can be created for a general population and then tailored, customized, or adapted for use for a specific person. In an example, a general population food-brainwave database can be tailored, customized, or adapted for use for a specific person based on demographic, physiologic, behavioral, health status, geographic and/or environmental parameters for that person. In an example, a general population food-brainwave database can be tailored, customized, or adapted for use for a specific person based on the person's baseline brainwave information. In an example, such tailoring, customization, or adaptation can include Bayesian statistical methods, an artificial neural network, evolving algorithms, and/or machine learning.

In an example, food consumption can comprise total consumption of food of any type, including beverages as well as solid food. In an example, tracking and estimation of food consumption can be much more detailed and specific. In an example, food consumption can comprise consumption of specific types and amounts of foods, ingredients, and/or nutrients. In an example, a type of food, ingredient, or nutrient can be selected from the group consisting of: a specific type of carbohydrate, a class of carbohydrates, or all carbohydrates; a specific type of sugar, a class of sugars, or all sugars; a specific type of fat, a class of fats, or all fats; a specific type of cholesterol, a class of cholesterols, or all cholesterols; a specific type of protein, a class of proteins, or all proteins; a specific type of fiber, a class of fiber, or all fiber; a specific sodium compound, a class of sodium compounds, and all sodium compounds; high-carbohydrate food, high-sugar food, high-fat food, fried food, high-cholesterol food, high-protein food, high-fiber food, and high-sodium food.

In an example, food consumption can be directly measured during a first (calibration) time period (in FIG. 1) by active entry of food information by a person via a human-to-computer interface such as a touchscreen, speech recognition interface, gesture recognition interface, EMG recognition interface, eye movement recognition interface, keypad, buttons, or knobs. In an example, a person can enter information concerning food that they eat via a software application on a portable electronic device using a menu-driven interface with pictures and descriptions of common foods and portions. In an example, food consumption can be directly measured during a first (calibration) time period in FIG. 1 by automatic tracking of food consumption via a wearable or handheld imaging device. In an example, a person can take pictures of food from different angles for 3D modeling of food volume as well as automatic food identification. In an example, electronically-functional eyewear with imaging capability can automatically track and identify food consumption using pattern recognition and/or gesture recognition. In an example, a person can use a spectroscopic food probe, scanner, or utensil to also collect information concerning the chemical composition of food. In an example, food consumption can also be independently measured by an intraoral chemical-composition sensor.

As shown in FIG. 2, this invention can be embodied in a method that is able to not only track a person's food consumption, but also to help the person to modify their food consumption to improve their nutrition, weight management, and overall health. In addition to estimating the person's food consumption based on their brain activity, a brain activity monitor and system 103 can also provide feedback to the person in order to prompt the person to modify their food consumption.

In an example, a brain activity monitor and system 103 can provide feedback to a person via a visual, auditory, or tactile computer-to-human interface in order to inform the person of their estimated food consumption and/or to prompt the person to modify their food consumption. In an example, this feedback can be based on the person's cumulative amount of food consumption. In an example, this feedback can be based on the person's consumption of a specific type or amount of food, ingredient, or nutrient. In an example, this feedback can be conveyed through a physically-separate device such as a smart phone, smart watch, smart wrist band, electronically-functional eyewear and/or contact lenses, wearable camera, other wearable device, tablet, desktop, or other remote computer.

In an example, feedback can be conveyed to a person in the form of a written or spoken message that is delivered through a computer-to-human interface. In an example, feedback can be a text message. In an example, an interface for providing feedback can be part of a wearable EEG monitor itself. In an example, feedback can be delivered via a smart watch, a smart phone, or electronically-functional eyewear. In an example, feedback can be in the form of a visual, auditory, or tactile stimulus. In an example, feedback can be a gentle vibration or quiet tone. In an example, feedback can convey information concerning what type and/or amount of food consumption triggered the feedback and provide suggestions concerning how to modify food consumption to ensure proper nutrition.

In an example, feedback can be triggered by a person's consumption of selected types or amounts of foods, nutrients, and/or ingredients as estimated by brain activity data collected by a wearable EEG monitor. In an example, this feedback can be triggered by the person's cumulative consumption of food and/or calories during a selected period of time. In an example, this feedback can encourage the person to modify their food consumption patterns to achieve better nutrition, proper energy balance, and/or predefined health goals. In an example, this feedback can be part of an overall system for proper nutrition, weight management, and improved health.

In an example, electromagnetic brain activity can be measured by a plurality of electrodes in a mobile electroencephalogram (EEG) monitor which the person wears on their head in an ongoing manner. In an example, electrodes used can be dry electrodes. In an example, a person's brain activity can be measured from one or multiple selected recording sites using a mobile wearable EEG monitor. In an example, measurement of brain activity can comprise measuring electromagnetic data concerning impedance, voltage difference, and/or energy transfer between two sites on a person's head—a selected recording site and a reference site. In an example, electromagnetic brain activity data can be measured by an electrode or other brain activity sensor at a selected recording place. In an example, electromagnetic brain activity data from a selected recording place (relative to a reference place) can be called a "channel." In an example, electromagnetic brain activity data from multiple recording places can be called a "montage."

In various examples, one or multiple recording places can be selected from the group of EEG placement sites consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2. In an example, one or more reference places can be selected from the group of sites consisting of A1 and A2. In an example, brain activity data can be recorded at a rate in the range of 100 to 300 samples per second.

In an example, there can be different regions of brain activity for neural processing of the color, shape, texture, odor, taste, and feel of food. In an example, identification of food types and estimates of food quantity can be based on multivariate analysis of the activities of different brain regions associated with visual processing, image recognition, olfactory processing, taste processing, texture processing, and sensorymotor processing (such as chewing and swallowing).

In an example, there can be a progressive or phased effect of food consumption on brain activity. In an example, a first phase can occur when a person sees and smells food prior to eating it. In an example, a second phase can occur as a person tastes, smells, and feels food as they eat it. In an example, a third phase can occur as food is digested within a person's gastrointestinal tract and nutrients from food enter the person's blood stream. In an example, statistical analysis of brain activity can comprise analysis of the separate, sequential, or cumulative effects of these three phases of food consumption.

In an example, this invention can be embodied in a mobile wearable EEG monitor. A person can wear a mobile wearable EEG monitor on an ongoing and ambulatory basis. This EEG monitor can measure their brain activity, via one or more EM data channels, during different activities including eating. In an example, this invention can also comprise the use of one or more statistical methods to identify associations between: (a) the occurrence of hunger, satiation, a pleasant taste or odor in general, an unpleasant taste or odor in general, a specific taste, a specific odor, food consumption in general, consumption of a specific type of food, consumption of a specific type of nutrient, or consumption of a specific type of ingredient; and (b) the occurrence of a specific pattern of brain activity which is measured from one or more data channels on a mobile wearable EEG monitor.

In an example, these associations can be used to create a food-brainwave database (or library) which links consumption of specific types and/or amounts of foods, nutrients, or ingredients with particular patterns of brain activity. In an example, this database of links between types of food consumption and types of brain activity can be generally applicable for all people. In an example, this database of links between types of food consumption and types of brain activity can be specifically-developed and/or customized for a particular person. In an example, a first database can link consumption of specific types and amounts of food to specific patterns of brain activity and a second database can link specific types and amounts of food to specific types and amounts of nutrients. In an example, sequential use of both databases can provide information on the types and amounts of nutrients which a person consumes based on information concerning their brain activity. In an alternative example, a single database can directly link specific patterns of brain activity and specific types and amounts of nutrients.

In an example, these identified associations between food consumption and brain activity can be used to track a person's consumption of foods, nutrients, and/or ingredients. In an example, these associations between food consumption and brain activity can be used to provide feedback to the person concerning their consumption of foods, nutrients, and/or ingredients. In an example, these associations between food consumption and brain activity can be used to provide feedback to the person concerning their brain activity related to consumption of foods, nutrients, and/or ingredients. In an example, these associations between food consumption and brain activity can be used to modify the person's consumption of foods, nutrients, and/or ingredients.

In an example, brain activity can be associated with food consumption during a first (calibration and/or database-creation) time period. In an example, during this calibration period, a database or data library can be created in which statistical models and parameters for linking brain activity to food consumption are estimated. These statistical models and parameters can be estimated for a general population or can be specific to a particular person. In an example, statistical models or parameters can be first estimated for the general population and then customized or adapted to a specific person, optionally through the use of Bayesian statistical methods. In an example, a general database, model, or model parameter can be customized, adjusted, modified, tailored, or adapted for a specific person. In an example, application of a database, model, or model parameter can control for variables selected from the group consisting of: a person's age, a person's gender, a person's health status, the time of day, level of recent physical activity, geographic location, and environmental variables. In an example, a database, model, and model parameters can be estimated de novo for a specific person.

During a calibration period, data concerning food consumption and data concerning brain activity can be collected in a chronologically-linked manner. Data from these two sources can then be jointly analyzed using statistical methods in order to identify significant associations between specific patterns of food consumption and specific patterns of brain activity. In an example, these data streams can be analyzed within the data processor of a wearable EEG monitor. In an example, these data streams can be transmitted wirelessly to a separate device or remote location wherein the data is analyzed. In an example, a calibration or database-creation process can be an iterative one—employing Bayesian statistics, adaptive algorithms, and/or an artificial neural network. In an example, a general database or statistical method that links food consumption and brain activity patterns can be created for the general population and then customized for a specific person. In an example, a database or statistical method that links food consumption and brain activity patterns can be created de novo for a specific person.

In an example, estimation of models and parameters for associating specific patterns of brain activity with specific types of food consumption can be an iterative or evolving process employing machine learning and/or an artificial neural network. In an example, a database can link consumption of specific foods, ingredients, or nutrients with specific patterns of EM brain activity. In an example, this linkage can be dependent on, or control for, a variety of control parameters including: person's age and gender, time of day, activity level, location, etc. In an example, such a database can include brainwave patterns associated with common foods, portion sizes which are commonly associated with these foods, ingredients which are commonly associated with these foods, nutrients which are commonly associated with these foods, and calories which are commonly associated with these foods.

In an example, information concerning food consumption can be collected by a means other than collection of information on brain activity during a first (calibration and/or database-creation) period. In an example, during a calibration and/or database-creation period, information concerning food consumption can be manually entered and/or collected by the person wearing the EEG monitor. In an example, during a calibration and/or database-creation period, information concerning food consumption can be automatically collected by a mechanism and/or device other than measurement of brain activity by the wearable EEG monitor. In an example, during a calibration and/or database creation period, information concerning food consumption can be collected by an interactive combination of automatic data collection and manual data entry.

In an example, during a first (calibration) time period, a person can manually enter information concerning food consumption via a hand-held mobile device such as a smart phone, electronic pad, or electronic tablet. In an example, a person can manually enter information concerning food consumption via a wearable device such as a smart watch, smart bracelet, or electronically-functional eyewear. In an example, a person can manually enter information concerning food consumption via a laptop, desktop, or other relatively fixed-location computer. In an example, a person can manually enter information concerning food consumption via a touchscreen, keyboard, keypad, touch buttons, or gesture recognition interface. In an example, food consumption information can be entered and/or collected via an eye movement detector or EMG sensor. In an example, software for entry of food consumption information can include pictures and descriptions of common food items. In an example, a person can manually enter information concerning food consumption via a speech recognition interface.

In an example, during a first (calibration) time period, a person can actively collect information concerning food consumption by taking one or more pictures of food. In an example, such picture taking can be done with a handheld device which must be manually aimed toward food and manually triggered to take pictures. In an example, images of food can be automatically collected by an automatic imaging device which the person wears. In an example, images of food consumed can be automatically collected via a wearable camera or by eyewear with automatic imaging functionality. In an example, manually or automatically obtained pictures of food from different angles can be analyzed using three-dimensional modeling to estimate the volume of food consumed. In an example, a camera or other imaging device can take simultaneous pictures of food from different angles. In an example, a camera or other imaging device can take sequential pictures of food from different angles due to movement of the device, movement of the food, or both such movements. In an example, food consumption can be estimated by a wearable camera or electronically-functional eyewear based on gesture recognition as the person's hands interact with food and their mouth.

In an example, food type can be identified from a picture of food using one or more methods selected from the group consisting of: analysis of food color, shape, and texture; packaging logo and/or label recognition or identification;

and bar code recognition or identification. In an example, information concerning food consumed can be collected by scanning a bar code or other digital code associated with a food product sold in a store or menu item in a restaurant. In an example, location as detected by a GPS unit can be a factor in food identification, especially if the location is a restaurant that serves standardized servings and/or sells standardized packages of food.

In an example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; and a GPS unit. In an example, a control unit can comprise a data processor.

In an example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; a GPS unit; and a database which includes associations between specific patterns of food consumption and specific patterns of electromagnetic brain activity, which translates specific types and amounts of food into specific types and amounts of nutrients, or which does both.

In an example, information concerning the types and amounts of food consumed can be collected from a smart food utensil, food probe, or food scanner that analyses the composition and volume of food consumed. In an example, food composition can be automatically analyzed via spectroscopy. In an example, information concerning specific types and amounts of food consumed can be collected during a calibration and/or database-creation period and this information can then be automatically linked to specific types and amounts of nutrients and/or ingredients using a database of common foods, their ingredients, and their nutritional composition. In an example, a hand-held or wearable spectroscopy device can be used to provide independent data concerning the types and amounts of nutrients and/or ingredients in specific types and amounts of food. In an example, a spectroscopy device can analyze the spectrum of light reflected from the surface of food or passing through a layer of food.

In an example, electromagnetic data concerning brain activity can be filtered to remove artifacts before the application of primary statistical methods. In an example, electromagnetic signals from eye blinks, eye flutters, or other eye movements can be removed prior to the application of primary statistical methods. In an example, a notch filter can be used as well to remove 60 Hz artifacts caused by AC electrical lines. In various examples, one or more data filters can be selected from the group consisting of: a high-pass filter, a band-pass filter, a loss-pass filter, an electromyographic activity filter, a 0.5-1 Hz filter, and a 35-70 Hz filter. In an example, a specific pattern of brain activity can follow a specific pattern of food consumption after a time lag. In an example, this time lag can be in the range of 20-100 milliseconds.

In an example, a specific pattern of brain activity associated with a specific pattern of food consumption can be analyzed as an Event Related Potential (ERP). In an example, a specific pattern of food consumption can be associated with a transient pattern of brain activity which does not repeat over time. In an example, a specific pattern of food consumption can be associated with a rhythmic pattern of brain activity which does repeat over time. In an example, statistical methods used to associate specific brainwave patterns with the consumption of specific types and/or amounts of food, ingredients, or nutrients can include analysis of wave frequency, wave frequency band, wave amplitude, wave phase, and wave form or morphology. In an example, wave form or morphology can be identified from the group consisting of: simple sinusoidal wave, composite sinusoidal wave, simple saw-tooth wave, composite saw-tooth wave, biphasic wave, tri-phasic wave, and spike.

During a first (calibration and/or database creation) time period, one or more primary statistical methods can be used to identify significant associations between patterns of food consumption and patterns of brain activity. In an example, a statistical method can comprise finding the mean or average value of data from one or more brain activity channels during a period of time. In an example, a statistical method can comprise identifying a significant change in the mean or average value of data from one or more brain activity channels during or after food consumption. In an example, a statistical method can comprise finding the median value of data from one or more brain activity channels during a period of time. In an example, a statistical method can comprise identifying a significant change in the median value of data from one or more brain activity channels during or after food consumption. In an example, a statistical method can comprise identifying significant changes in the relative mean or median data values among multiple brain activity channels during or after food consumption. In an example, a statistical method can comprise identifying significant changes in mean data values from a first set of electrode locations relative to mean data values from a second set of electrode locations during or after food consumption. In an example, a statistical method can comprise identifying significant changes in mean data recorded from a first region of the brain relative to mean data recorded from a second region of the brain during or after food consumption.

In an example, a statistical method can comprise finding the minimum or maximum value of data from one or more brain activity channels during a period of time. In an example, a statistical method can comprise identifying a significant change in the minimum or maximum value of data from one or more brain activity channels during or after food consumption. In an example, a statistical method can comprise identifying significant changes in the relative minimum or maximum data values among multiple brain activity channels during or after food consumption. In an example, a statistical method can comprise identifying significant changes in minimum or maximum data values from a first set of electrode locations relative to minimum or maximum data values from a second set of electrode locations during or after food consumption. In an example, a statistical method can comprise identifying significant changes in minimum or maximum data values recorded from a first region of the brain relative to minimum or maximum data values recorded from a second region of the brain during or after food consumption.

In an example, a statistical method can comprise finding the variance or the standard deviation of data from one or more brain activity channels during a period of time. In an example, a statistical method can comprise identifying a significant change in the variance or the standard deviation of data from one or more brain activity channels during or after food consumption. In an example, a statistical method can comprise identifying significant changes in the covariation and/or correlation among data from multiple brain activity channels during or after food consumption. In an example, a statistical method can comprise identifying significant changes in the covariation or correlation between data from a first set of electrode locations relative and data from a second set of electrode locations during or after food consumption. In an example, a statistical method can comprise identifying significant changes in the covariation or correlation of data values recorded from a first region of the brain and a second region of the brain during or after food consumption.

In an example, a statistical method can comprise finding the mean amplitude of waveform data from one or more channels during a period of time. In an example, a statistical method can comprise identifying a significant change in the mean amplitude of waveform data from one or more channels during or after food consumption. In an example, a statistical method can comprise identifying significant changes in the relative means of wave amplitudes from one or more channels during or after food consumption. In an example, a statistical method can comprise identifying significant changes in the amplitude of EM signals recorded from a first region of the brain relative to the amplitude of EM signals recorded from a second region of the brain during or after food consumption.

In an example, a statistical method can comprise finding the power of waveform brain activity data from one or more channels during a period of time. In an example, a statistical method can comprise identifying a significant change in the power of waveform data from one or more channels during or after food consumption. In an example, a statistical method can comprise identifying significant changes in the relative power levels of one or more channels during or after food consumption. In an example, a statistical method can comprise identifying significant changes in the power of EM signals recorded from a first region of the brain relative to the power of EM signals recorded from a second region of the brain during or after food consumption.

In an example, a statistical method can comprise finding a frequency or frequency band of waveform and/or rhythmic brain activity data from one or more channels which repeats over time. In an example, Fourier Transform methods can be used to find a frequency or frequency band of waveform and/or rhythmic data which repeats over time. In an example, a statistical method can comprise decomposing a complex waveform into a combination of simpler waveforms which each repeat at a different frequency or within a different frequency band. In an example, Fourier Transform methods can be used to decomposing a complex waveform into a combination of simpler waveforms which each repeat at a different frequency or within a different frequency band.

In an example, a statistical method can comprise identifying significant changes in the amplitude, power level, phase, frequency, and/or oscillation of waveform data from one or more channels during or after food consumption. In an example, a statistical method can comprise identifying significant changes in the amplitude, power level, phase, frequency, and/or oscillation of waveform data within a selected frequency band during or after food consumption. In an example, a statistical method can comprise identifying significant changes in the relative amplitudes, power levels, phases, frequencies, and/or oscillations of waveform data among different frequency bands during or after food consumption. In various examples, these significant changes can be identified using Fourier Transform methods.

In an example, brainwaves (or other rhythmic, cyclical, and/or repeating electromagnetic signals associated with brain activity) can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using five common clinical frequency bands—Delta, Theta, Alpha, Beta, and Gamma. In an example, changes in brainwaves in a single frequency band, changes in brainwaves in multiple frequency bands, or changes in brainwaves in a first frequency band relative to those in a second frequency band can be associated with changes in food consumption. These associations can be used, in turn, to track and modify food consumption.

In an example, Delta brainwaves can be measured and analyzed within a selected frequency band. In an example, Delta brainwaves can be measured and analyzed within the frequency band of 1 to 4 Hz. In various examples, Delta brainwaves (or other rhythmic, cyclical, and/or repeating electromagnetic signals associated with brain activity) can be measured and analyzed within a frequency band selected from the group consisting of: 0.5-3.5 Hz, 0.5-4 Hz, 1-3 Hz, 1-4 Hz, and 2-4 Hz. In an example, changes in Delta brainwaves can be identified and associated with changes in food consumption in order to track and/or modify food consumption. In an example, specific patterns or trends in brainwaves in the Delta frequency band can be statistically associated with consumption of specific amounts and types of foods, ingredients, and/or nutrients. These statistical associations can be used to track an individual's cumulative consumption of specific amounts of these of foods, ingredients, and/or nutrients during a period of time. These statistical associations can also be used to provide feedback to an individual in order to modify their consumption of these foods, ingredients, and/or nutrients.

In an example, hunger or satiety can be associated with a change in the power of brainwaves in the Delta frequency band. In an example, hunger can be associated with a decrease in the relative power of brainwaves in the Delta band. In an example, satiety can be associated with an increase in the relative power of brainwaves in the Delta band. In an example, hunger or satiety can be associated with a frequency shift within the Delta frequency band. In an example, hunger can be associated with an upward shift in the frequency of brainwaves within the Delta band. In an example, satiety can be associated with a downward shift in the frequency of brainwaves within the Delta band.

In an example, hunger or satiety can be associated with a change in wave shape for brainwaves in the Delta frequency band. In an example, hunger or satiety can be associated with a change in which brain regions originate or modify brainwaves within the Delta frequency band. In an example, hunger or satiety can be associated with a change in brainwave activity within the Delta band from the anterior vs. posterior a person's brain. In an example, hunger or satiety can be associated with a change in brainwave activity within the Delta band for a particular brain lobe or organelle. In an example, hunger or satiety can be associated with a change in brainwave activity within the Delta band as measured from a specific electrode site, a specific electrode channel, and/or a specific montage of channels.

In an example, there can be changes in the power of brainwaves in the Delta frequency band during food consumption in general. In an example, food consumption can be associated with a change in the relative power of brainwaves in the Delta band. In an example, food consumption can be associated with a frequency shift in brainwaves within the Delta frequency band. In an example, food consumption can be associated with a change in wave shape for brainwaves in the Delta frequency band. In an example, food consumption can be associated with a change in which brain regions originate or modify brainwaves within the Delta frequency band. In an example, food consumption can be associated with a change in brainwave activity within the Delta band as measured from a specific electrode site, a specific electrode channel, and/or a specific montage of channels.

In an example, pleasant or unpleasant tastes and/or odors can be associated with changes in the power of brainwaves in the Delta frequency band. In an example, pleasant tastes and/or odors can be associated with increases in the relative power of brainwaves in the Delta band. In an example, unpleasant tastes and/or odors can be associated with decreases in the relative power of brainwaves in the Delta band. In an example, pleasant or unpleasant tastes and/or odors can be associated with shifts in the frequency of brainwaves within the Delta frequency band. In an example, pleasant tastes and/or odors can cause an upward shift in brainwave frequency within the Delta band. In an example, unpleasant tastes and/or odors can cause a downward shift in brainwave frequency within the Delta band. In an example, pleasant or unpleasant tastes or odors can be associated with changes in wave shape for brainwaves in the Delta frequency band. In an example, pleasant or unpleasant tastes or odors can be associated with changes in which brain regions originate or modify brainwaves within the Delta frequency band. In an example, pleasant or unpleasant tastes or odors can be associated with changes in brainwave activity within the Delta band as measured from a specific electrode site, a specific electrode channel, and/or a specific montage of channels.

In an example, specific tastes and/or odors can cause specific changes in the power, frequency, oscillation, wave shape, coherence, and/or brain region origins of brainwaves in the Delta frequency band. In an example, consumption of specific types of food, nutrients, and/or ingredients can cause specific changes in the power, frequency, oscillation, wave shape, coherence, and/or brain region origins of brainwaves in the Delta frequency band. In an example, changes in the power, frequency, oscillation, wave shape, coherence, and/or brain region origins of brainwaves in the Delta band can be caused by a person's consumption of foods, ingredients, and/or nutrients selected from the group consisting of: a selected type of carbohydrate, a class of carbohydrates, or all carbohydrates; a selected type of sugar, a class of sugars, or all sugars; a selected type of fat, a class of fats, or all fats; a selected type of cholesterol, a class of cholesterols, or all cholesterols; a selected type of protein, a class of proteins, or all proteins; a selected type of fiber, a class of fiber, or all fibers; a specific sodium compound, a class of sodium compounds, or all sodium compounds; high-carbohydrate food, high-sugar food, high-fat food, fried food, high-cholesterol food, high-protein food, high-fiber food, and/or high-sodium food.

In an example, Theta brainwaves can be measured and analyzed within a selected frequency band. In an example, Theta brainwaves can be measured and analyzed within the frequency band of 4 to 8 Hz. In various examples, Theta brainwaves or other rhythmic, cyclical, and/or repeating electromagnetic signals associated with brain activity can be measured and analyzed within a frequency band selected from the group consisting of: 3.5-7 Hz, 3-7 Hz, 4-7 Hz, 4-7.5 Hz, 4-8 Hz, and 5-7 Hz. In an example, changes in Theta brainwaves can be identified and associated with changes in food consumption in order to track and/or modify food consumption. In an example, specific patterns or trends in brainwaves in the Theta frequency band can be statistically associated with consumption of specific amounts and types of foods, ingredients, and/or nutrients. These statistical associations can be used to track an individual's cumulative consumption of specific amounts of these of foods, ingredients, and/or nutrients during a period of time. These statistical associations can also be used to provide feedback to an individual in order to modify their consumption of these foods, ingredients, and/or nutrients.

In an example, hunger or satiety can be associated with a change in the power of brainwaves in the Theta frequency band. In an example, hunger can be associated with an increase in the relative power of brainwaves in the Theta band. In an example, hunger can be associated with a frequency shift within the Theta frequency band. In an example, hunger or satiety can be associated with changes in wave shape for brainwaves in the Theta frequency band. In an example, hunger or satiety can be associated with a change in which brain regions originate or modify brainwaves within the Theta frequency band. In an example, hunger or satiety can be associated with a change in brainwave activity within the Theta band as measured from a specific electrode site, a specific electrode channel, and/or a specific montage of channels.

In an example, there can be changes in the power of brainwaves in the Theta frequency band during food consumption in general. In an example, food consumption can be associated with a change in the relative power of brainwaves in the Theta band. In an example, food consumption can be associated with a frequency shift in brainwaves within the Theta frequency band. In an example, food consumption can be associated with a change in wave shape for brainwaves in the Theta frequency band. In an example, food consumption can be associated with a change in which brain regions originate or modify brainwaves within the Theta frequency band. In an example, food consumption can be associated with a change in brainwave activity within the Theta band as measured from a specific electrode site, a specific electrode channel, and/or a specific montage of channels.

In an example, pleasant or unpleasant tastes and/or odors can be associated with changes in the power of brainwaves in the Theta frequency band. In an example, pleasant tastes and/or odors can be associated with a decrease in the relative power of brainwaves in the Theta band. In an example, pleasant or unpleasant tastes and/or odors can be associated with shifts in the frequency of brainwaves within the Theta frequency band. In an example, pleasant or unpleasant tastes or odors can be associated with changes in wave shape for brainwaves in the Theta frequency band. In an example, pleasant or unpleasant tastes or odors can be associated with changes in which brain regions originate or modify brainwaves within the Theta frequency band. In an example, pleasant or unpleasant tastes or odors can be associated with changes in brainwave activity within the Theta band as measured from a specific electrode site, a specific electrode channel, and/or a specific montage of channels.

In an example, specific tastes and/or odors can cause specific changes in the power, frequency, oscillation, wave shape, coherence, and/or brain region origins of brainwaves in the Theta frequency band. In an example, consumption of specific types of food, nutrients, and/or ingredients can cause specific changes in the power, frequency, oscillation, wave shape, coherence, and/or brain region origins of brainwaves in the Theta frequency band. In an example, changes in the power, frequency, oscillation, wave shape, coherence, and/or brain region origins of brainwaves in the Theta band can be caused by a person's consumption of foods, ingredients, and/or nutrients selected from the group consisting of: a selected type of carbohydrate, a class of carbohydrates, or all carbohydrates; a selected type of sugar, a class of sugars, or all sugars; a selected type of fat, a class of fats, or all fats; a selected type of cholesterol, a class of cholesterols, or all cholesterols; a selected type of protein, a class of proteins, or all proteins; a selected type of fiber, a class of fiber, or all fibers; a specific sodium compound, a class of sodium compounds, or all sodium compounds; high-carbohydrate food, high-sugar food, high-fat food, fried food, high-cholesterol food, high-protein food, high-fiber food, and/or high-sodium food.

In an example, Alpha brainwaves can be measured and analyzed within a selected frequency band. In an example, Alpha brainwaves can be measured and analyzed within the frequency band of 7 to 14 Hz. In various examples, Alpha brainwaves or other rhythmic, cyclical, and/or repeating electromagnetic signals associated with brain activity can be measured and analyzed within a frequency band selected from the group consisting of: 7-13 Hz, 7-14 Hz, 8-12 Hz, 8-13 Hz, 7-11 Hz, 8-10 Hz, and 8-10 Hz. In an example, changes in Alpha brainwaves can be identified and associated with changes in food consumption in order to track and/or modify food consumption In an example, specific patterns or trends in brainwaves in the Alpha frequency band can be statistically associated with consumption of specific amounts and types of foods, ingredients, and/or nutrients. These statistical associations can be used to track an individual's cumulative consumption of specific amounts of these of foods, ingredients, and/or nutrients during a period of time. These statistical associations can also be used to provide feedback to an individual in order to modify their consumption of these foods, ingredients, and/or nutrients.

In an example, hunger or satiety can be associated with a change in the power of brainwaves in the Alpha frequency band. In an example, hunger can be associated with an increase in the relative power of brainwaves in the Alpha band. In an example, satiety can be associated with a decrease in the relative power of brainwaves in the Alpha band. In an example, hunger or satiety can be associated with a frequency shift within the Alpha frequency band. In an example, hunger can be associated with a downward shift in the frequency of brainwaves within the Alpha band. In an example, satiety can be associated with an upward shift in the frequency of brainwaves within the Alpha band. In an example, hunger or satiety can be associated with a change in wave shape for brainwaves in the Alpha frequency band. In an example, hunger or satiety can be associated with a change in which brain regions originate or modify brainwaves within the Alpha frequency band. In an example, hunger or satiety can be associated with a change in brainwave activity within the Alpha band on one side of a person's brain relative to the other side. In an example, hunger or satiety can be associated with a change in brainwave activity within the Alpha band in a particular brain lobe or organelle. In an example, hunger or satiety can be associated with a change in brainwave activity within the Alpha band as measured from a specific electrode site, a specific electrode channel, and/or a specific montage of channels.

In an example, there can be changes in the power of brainwaves in the Alpha frequency band during food consumption in general. In an example, food consumption can be associated with a change in the relative power of brainwaves in the Alpha band. In an example, food consumption can be associated with a frequency shift in brainwaves within the Alpha frequency band. In an example, food consumption can be associated with a change in wave shape for brainwaves in the Alpha frequency band. In an example, food consumption can be associated with a change in which brain regions originate or modify brainwaves within the Alpha frequency band. In an example, food consumption can be associated with a change in brainwave activity within the Alpha band as measured from a specific electrode site, a specific electrode channel, and/or a specific montage of channels.

In an example, pleasant or unpleasant tastes and/or odors can be associated with changes in the power of brainwaves in the Alpha frequency band. In an example, pleasant tastes and/or odors can be associated with increases in the relative power of brainwaves in the Alpha band. In an example, unpleasant tastes and/or odors can be associated with decreases in the relative power of brainwaves in the Alpha band. In an example, pleasant or unpleasant tastes and/or odors can be associated with shifts in the frequency of brainwaves within the Alpha frequency band. In an example, pleasant tastes and/or odors can cause an upward shift in brainwave frequency within the Alpha band. In an example, unpleasant tastes and/or odors can cause a downward shift in brainwave frequency within the Alpha band. In an example, pleasant or unpleasant tastes or odors can be associated with changes in wave shape for brainwaves in the Alpha frequency band. In an example, pleasant or unpleasant tastes or odors can be associated with changes in which brain regions originate or modify brainwaves within the Alpha frequency band. In an example, pleasant or unpleasant tastes or odors can be associated with changes in brainwave activity within the Alpha band as measured from a specific electrode site, a specific electrode channel, and/or a specific montage of channels.

In an example, specific tastes and/or odors can cause specific changes in the power, frequency, oscillation, wave shape, coherence, and/or brain region origins of brainwaves in the Alpha frequency band. In an example, consumption of specific types of food, nutrients, and/or ingredients can cause specific changes in the power, frequency, oscillation, wave shape, coherence, and/or brain region origins of brainwaves in the Alpha frequency band. In an example, changes in the power, frequency, oscillation, wave shape, coherence, and/or brain region origins of brainwaves in the Alpha band can be caused by a person's consumption of foods, ingredients, and/or nutrients selected from the group consisting of: a selected type of carbohydrate, a class of carbohydrates, or all carbohydrates; a selected type of sugar, a class of sugars, or all sugars; a selected type of fat, a class of fats, or all fats; a selected type of cholesterol, a class of cholesterols, or all cholesterols; a selected type of protein, a class of proteins, or all proteins; a selected type of fiber, a class of fiber, or all fibers; a specific sodium compound, a class of sodium compounds, or all sodium compounds; high-carbohydrate food, high-sugar food, high-fat food, fried food, high-cholesterol food, high-protein food, high-fiber food, and/or high-sodium food.

In an example, Beta brainwaves can be measured and analyzed within a selected frequency band. In an example, Beta brainwaves can be measured and analyzed within the frequency band of 12 to 30 Hz. In various examples, Beta brainwaves or other rhythmic, cyclical, and/or repeating electromagnetic signals associated with brain activity can be measured and analyzed within a frequency band selected from the group consisting of: 11-30 Hz, 12-30 Hz, 13-18 Hz, 13-22 Hz, 13-26 Hz, 13-26 Hz, 13-30 Hz, 13-32 Hz, 14-24 Hz, 14-30 Hz, and 14-40 Hz. In an example, changes in Beta brainwaves can be identified and associated with changes in food consumption in order to track and/or modify food consumption. In an example, specific patterns or trends in brainwaves in the Beta frequency band can be statistically associated with consumption of specific amounts and types of foods, ingredients, and/or nutrients. These statistical associations can be used to track an individual's cumulative consumption of specific amounts of these of foods, ingredients, and/or nutrients during a period of time. These statistical associations can also be used to provide feedback to an individual in order to modify their consumption of these foods, ingredients, and/or nutrients.

In an example, Gamma brainwaves can be measured and analyzed within a selected frequency band. In an example, Gamma brainwaves can be measured and analyzed within the frequency band of 30 to 100 Hz. In various examples, Gamma brainwaves or other rhythmic, cyclical, and/or repeating electromagnetic signals associated with brain activity can be measured and analyzed within a frequency band selected from the group consisting of: 30-100 Hz, 35-100 Hz, 40-100 Hz, and greater than 30 Hz. In an example, changes in Gamma brainwaves can be identified and associated with changes in food consumption in order to track and/or modify food consumption. In an example, specific patterns or trends in brainwaves in the Gamma frequency band can be statistically associated with consumption of specific amounts and types of foods, ingredients, and/or nutrients. These statistical associations can be used to track an individual's cumulative consumption of specific amounts of these of foods, ingredients, and/or nutrients during a period of time. These statistical associations can also be used to provide feedback to an individual in order to modify their consumption of these foods, ingredients, and/or nutrients.

In an example, multivariate analysis of brainwave activity in the Delta, Theta, and Alpha frequency bands can identify patterns which are associated with: hunger, satiety, food consumption in general, pleasant tastes or odors in general, unpleasant tastes or odors in general, specific tastes or odors, and/or consumption of specific types of foods, nutrients, or ingredients. These statistical associations can be used to track an individual's cumulative consumption of amounts and types of foods, ingredients, and/or nutrients. These statistical associations can also be used to provide feedback to an individual in order to modify their consumption of these foods, ingredients, and/or nutrients.

In various examples, multivariate analysis of brainwave activity in two or more frequency bands selected from the group consisting of Delta, Theta, Alpha, Beta, and Gamma can identify patterns which are associated with: hunger, satiety, food consumption in general, pleasant tastes or odors in general, unpleasant tastes or odors in general, specific tastes or odors, and/or consumption of specific types of foods, nutrients, or ingredients. In an example, correlation and/or covariance analysis of brainwave activity in two or more of frequency bands selected from the group consisting of Delta, Theta, Alpha, Beta, and Gamma can identify patterns which are associated with: hunger, satiety, food consumption in general, pleasant tastes or odors in general, unpleasant tastes or odors in general, specific tastes or odors, and/or consumption of specific types of foods, nutrients, or ingredients. In an example, multivariate discriminant analysis of brainwave activity in two or more of frequency bands selected from the group consisting of Delta, Theta, Alpha, Beta, and Gamma can identify patterns which are associated with: hunger, satiety, food consumption in general, pleasant tastes or odors in general, unpleasant tastes or odors in general, specific tastes or odors, and/or consumption of specific types of foods, nutrients, or ingredients. These statistical associations can be used to track an individual's cumulative consumption of amounts and types of foods, ingredients, and/or nutrients. These statistical associations can also be used to provide feedback to an individual in order to modify their consumption of these foods, ingredients, and/or nutrients.

In various examples, specific patterns of brain activity can be associated with consumption of specific types and/or amounts of food, ingredients, and/or nutrients using one or more statistical methods selected from the group consisting of: ANOVA or MANOVA; artificial neural network; auto-regression; Bonferroni analysis; centroid analysis; chi-squared analysis; cluster analysis and grouping; decision tree or random forest analysis; Discrete Fourier transform (DFT), Fast Fourier Transform (FFT), or other Fourier Transform methods; factor analysis; feature vector analysis; fuzzy logic model; Gaussian model; hidden Markov model, input-output hidden Markov model, or other Markov model; inter-band mean; inter-band ratio; inter-channel mean; inter-channel ratio; inter-montage mean; inter-montage ratio; Kalman filter; kernel estimation; linear discriminant analysis; linear transform; logit model; machine learning; mean power; mean; median; multi-band covariance analysis; multi-channel covariance analysis; multivariate linear regression or multivariate least squares estimation; multivariate logit or other multivariate parametric classifiers; naïve Bayes classifier, trained Bayes classifier, dynamic Bayesian network, or other Bayesian methods; non-linear programming; pattern recognition; power spectral density or other power spectrum analysis; principal components analysis; probit model; support vector machine; time-series model; T-test; variance, covariance, or correlation; waveform identification; multi-resolution wavelet analysis or other wavelet analysis; whole band power; and Z-scores or other data normalization method.

As shown in FIG. 2, after a first (calibration) time period is completed, this invention can be used to track a person's food consumption by measuring and analyzing their brain activity using a wearable EEG monitor. In an example, food consumption can be automatically detected by measurement and analysis of brain activity. In an example, consumption of specific types of foods, ingredients, and nutrients can be automatically monitored, detected, and measured by a wearable EEG monitor using selected statistical methods, model parameters, and/or databases linking food consumption patterns to brain activity patterns. In an example, such a database can include brainwave patterns associated with common foods, portion sizes which are commonly associated with these foods, ingredients which are commonly associated with those foods, nutrients which are commonly associated with these foods, and calories which are commonly associated with these foods.

In an example, automatic monitoring of food consumption based on brain activity can make use of statistical methods, model parameters, and/or databases which were identified and created during an earlier calibration period. In an example, a person's consumption of selected foods, ingredients, and/or nutrients can also be modified through feedback based on these statistical methods, model parameters, and/or databases. In an example, feedback can help a person to eat less unhealthy food and/or eat more healthy food. In an example, feedback can help a person to better balance their caloric intake and caloric expenditure to better manage their weight. In an example, automatic monitoring and measurement of food consumption via a wearable EEG monitor can be supplemented or refined by other methods of monitoring and measuring food consumption.

In an example, this invention can using a wearable EEG monitor to track brain activity which, in turn, is used to estimate the wearer's consumption of selected types and amounts of foods, ingredients, and nutrients. In an example, this tracking of food consumption is based on identification of brain activity patterns which have been previously-associated with consumption of specific types and amounts of foods, ingredients, and nutrients. In an example, food consumption can be broadly defined to include consumption of liquid beverages and gelatinous food as well as solid food.

In an example, a type of food, ingredient, or nutrient can be selected from the group consisting of: a specific type of carbohydrate, a class of carbohydrates, or all carbohydrates; a specific type of sugar, a class of sugars, or all sugars; a specific type of fat, a class of fats, or all fats; a specific type of cholesterol, a class of cholesterols, or all cholesterols; a specific type of protein, a class of proteins, or all proteins; a specific type of fiber, a class of fiber, or all fiber; a specific sodium compound, a class of sodium compounds, and all sodium compounds; high-carbohydrate food, high-sugar food, high-fat food, fried food, high-cholesterol food, high-protein food, high-fiber food, and high-sodium food.

In an example, a type of nutrient can be selected from the group consisting of: amino acid or protein (a selected type or general class), carbohydrate (a selected type or general class, such as single carbohydrates or complex carbohydrates), cholesterol (a selected type or class, such as HDL or LDL), dairy products (a selected type or general class), fat (a selected type or general class, such as unsaturated fat, saturated fat, or trans fat), fiber (a selected type or class, such as insoluble fiber or soluble fiber), mineral (a selected type), vitamin (a selected type), nuts (a selected type or general class, such as peanuts), sodium compounds (a selected type or general class), sugar (a selected type or general class, such as glucose), and water. In an example, food can be classified into general categories such as fruits, vegetables, or meat.

In a broad range of examples, a type of food, ingredient, or nutrient can be selected from the group consisting of: a selected food, ingredient, or nutrient that has been designated as unhealthy by a health care professional organization or by a specific health care provider for a specific person; a selected substance that has been identified as an allergen for a specific person; peanuts, shellfish, or dairy products; a selected substance that has been identified as being addictive for a specific person; alcohol; a vitamin or mineral; vitamin A, vitamin B1, thiamin, vitamin B12, cyanocobalamin, vitamin B2, riboflavin, vitamin C, ascorbic acid, vitamin D, vitamin E, calcium, copper, iodine, iron, magnesium, manganese, niacin, pantothenic acid, phosphorus, potassium, riboflavin, thiamin, and zinc; a selected type of carbohydrate, class of carbohydrates, or all carbohydrates; a selected type of sugar, class of sugars, or all sugars; simple carbohydrates, complex carbohydrates; simple sugars, complex sugars, monosaccharides, glucose, fructose, oligosaccharides, polysaccharides, starch, glycogen, disaccharides, sucrose, lactose, starch, sugar, dextrose, disaccharide, fructose, galactose, glucose, lactose, maltose, monosaccharide, processed sugars, raw sugars, and sucrose; a selected type of fat, class of fats, or all fats; fatty acids, monounsaturated fat, polyunsaturated fat, saturated fat, trans fat, and unsaturated fat; a selected type of cholesterol, a class of cholesterols, or all cholesterols; Low Density Lipoprotein (LDL), High Density Lipoprotein (HDL), Very Low Density Lipoprotein (VLDL), and triglycerides; a selected type of protein, a class of proteins, or all proteins; dairy protein, egg protein, fish protein, fruit protein, grain protein, legume protein, lipoprotein, meat protein, nut protein, poultry protein, tofu protein, vegetable protein, complete protein, incomplete protein, or other amino acids; a selected type of fiber, a class of fiber, or all fiber; dietary fiber, insoluble fiber, soluble fiber, and cellulose; a specific sodium compound, a class of sodium compounds, and all sodium compounds; salt; a selected type of meat, a class of meats, and all meats; a selected type of vegetable, a class of vegetables, and all vegetables; a selected type of fruit, a class of fruits, and all fruits; a selected type of grain, a class of grains, and all grains; high-carbohydrate food, high-sugar food, high-fat food, fried food, high-cholesterol food, high-protein food, high-fiber food, and high-sodium food.

In an example, this invention can be embodied in a method for identifying associations between a person's food consumption and their electromagnetic brain activity comprising: (a) receiving data concerning a person's food consumption from a selected time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the selected time period from one or more electrodes or other brain activity sensors which are configured to be less than one inch from the surface of the person's head; and (c) identifying associations between patterns of food consumption and patterns of electromagnetic brain activity by analyzing data concerning the person's food consumption and data concerning the person's electromagnetic brain activity from the selected time period.

In an example, this invention can be embodied in a method for creating a food-brainwave database of associations between a person's food consumption and their electromagnetic brain activity comprising: (a) receiving data concerning a person's food consumption from a selected time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the selected time period from one or more electrodes or other brain activity sensors which are configured to be less than one inch from the surface of the person's head; and (c) creating a food-brainwave database, wherein this database links patterns of food consumption to patterns of electromagnetic brain activity, by analyzing data concerning the person's food consumption and data concerning the person's electromagnetic brain activity from the selected time period.

In an example, this invention can be embodied in a method for measuring a person's food consumption comprising: (a) receiving data concerning a person's food consumption from a first time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the first time period from one or more electrodes or other brain activity sensors which are configured to be less than one inch from the surface of the person's head; (c) identifying associations between patterns of food consumption and patterns of electromagnetic brain activity by analyzing data concerning the person's food consumption and data concerning the person's electromagnetic brain activity from the first time period; (d) receiving data concerning the person's electromagnetic brain activity from a second time period from one or more electrodes or other brain activity sensors which are configured to be less than one inch from the surface of the person's head; and (e) using associations between patterns of food consumption and patterns of electromagnetic brain activity in order to estimate the person's food consumption during the second time period from data concerning the person's electromagnetic brain activity from the second time period, wherein food consumption can comprise consumption of food overall or consumption of one or more selected amounts and/or types of foods, ingredients, or nutrients.

In an example, this invention can be embodied in a method for measuring a person's food consumption comprising: (a) receiving data concerning a person's electromagnetic brain activity from a selected time period from one or more electrodes or other brain activity sensors which are configured to be less than one inch from the surface of the person's head; and (b) using associations between patterns of food consumption and patterns of electromagnetic brain activity in order to estimate the person's food consumption during the selected time period from data concerning the person's electromagnetic brain activity from the selected time period, wherein food consumption can comprise consumption of food overall or consumption of one or more selected amounts and/or types of foods, ingredients, or nutrients.

In an example, this invention can be embodied in a method for measuring a person's food consumption comprising: (a) receiving data concerning a person's food consumption from a first time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the first time period from one or more electrodes or other brain activity sensors which are configured to be less than one inch from the surface of the person's head; (c) creating a food-brainwave database, wherein this database links patterns of food consumption to patterns of electromagnetic brain activity, by analyzing data concerning the person's food consumption and data concerning the person's electromagnetic brain activity from the first time period; (d) receiving data concerning the person's electromagnetic brain activity from a second time period from one or more electrodes or other brain activity sensors which are configured to be less than one inch from the surface of the person's head; and (e) using the food-brainwave database, wherein this database links patterns of food consumption to patterns of electromagnetic brain activity, in order to estimate the person's food consumption during the second time period from data concerning the person's electromagnetic brain activity from the second time period, wherein food consumption can comprise consumption of food overall or consumption of one or more selected amounts and/or types of foods, ingredients, or nutrients.

In an example, this invention can be embodied in a method for measuring a person's food consumption comprising: (a) receiving data concerning a person's electromagnetic brain activity from a selected period from one or more electrodes or other brain activity sensors which are configured to be less than one inch from the surface of the person's head; and (b) using a food-brainwave database, wherein this database links patterns of food consumption to patterns of electromagnetic brain activity, in order to estimate the person's food consumption during the selected time period from data concerning the person's electromagnetic brain activity from the selected time period, wherein food consumption can comprise consumption of food overall or consumption of one or more selected amounts and/or types of foods, ingredients, or nutrients.

In an example, this invention can be embodied in a method for modifying a person's food consumption comprising: (a) receiving data concerning a person's food consumption from a first time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the first time period from one or more electrodes or other brain activity sensors which are configured to be less than one inch from the surface of the person's head; (c) identifying associations between patterns of food consumption and patterns of electromagnetic brain activity by analyzing data concerning the person's food consumption and data concerning the person's electromagnetic brain activity from the first time period; (d) receiving data concerning the person's electromagnetic brain activity from a second time period from one or more electrodes or other brain activity sensors which are configured to be less than one inch from the surface of the person's head; (e) using associations between patterns of food consumption and patterns of electromagnetic brain activity in order to estimate the person's food consumption during the second time period from data concerning the person's electromagnetic brain activity from the second time period, wherein food consumption can comprise consumption of food overall or consumption of one or more selected amounts and/or types of foods, ingredients, or nutrients; and (f) providing feedback to the person concerning their estimated food consumption during the second time period in order to prompt the person to modify their food consumption.

In an example, this invention can be embodied in a method for modifying a person's food consumption comprising: (a) receiving data concerning a person's electromagnetic brain activity from a selected time period from one or more electrodes or other brain activity sensors which are configured to be less than one inch from the surface of the person's head; (b) using associations between patterns of food consumption and patterns of electromagnetic brain activity in order to estimate the person's food consumption during the selected time period from data concerning the person's electromagnetic brain activity from the selected time period, wherein food consumption can comprise consumption of food overall or consumption of one or more selected amounts and/or types of foods, ingredients, or nutrients; and (c) providing feedback to the person concerning their estimated food consumption during the selected time period in order to prompt the person to modify their food consumption.

In an example, this invention can be embodied in a method for modifying a person's food consumption comprising: (a) receiving data concerning a person's food consumption from a first time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the first time period from one or more electrodes or other brain activity sensors which are configured to be less than one inch from the surface of the person's head; (c) creating a food-brainwave database, wherein this database links patterns of food consumption to patterns of electromagnetic brain activity, by analyzing data concerning the person's food consumption and data concerning the person's electromagnetic brain activity from the first time period; (d) receiving data concerning the person's electromagnetic brain activity from a second time period from one or more electrodes or other brain activity sensors which are configured to be less than one inch from the surface of the person's head; (e) using the food-brainwave database, wherein this database links patterns of food consumption to patterns of electromagnetic brain activity, in order to estimate the person's food consumption during the second time period from data concerning the person's electromagnetic brain activity from the second time period, wherein food consumption can comprise consumption of food overall or consumption of one or more selected amounts and/or types of foods, ingredients, or nutrients; and (f) providing feedback to the person concerning their estimated food consumption during the second time period in order to prompt the person to modify their food consumption.

In an example, this invention can be embodied in a method for modifying a person's food consumption comprising: (a) receiving data concerning a person's electromagnetic brain activity from a selected time period from one or more electrodes or other brain activity sensors which are configured to be less than one inch from the surface of the person's head; (b) using a food-brainwave database, wherein this database links patterns of food consumption to patterns of electromagnetic brain activity, in order to estimate the person's food consumption during the selected time period from data concerning the person's electromagnetic brain activity from the selected time period, wherein food consumption can comprise consumption of food overall or consumption of one or more selected amounts and/or types of foods, ingredients, or nutrients; and (c) providing feedback to the person concerning their estimated food consumption during the selected time period in order to prompt the person to modify their food consumption.

Figure 3:
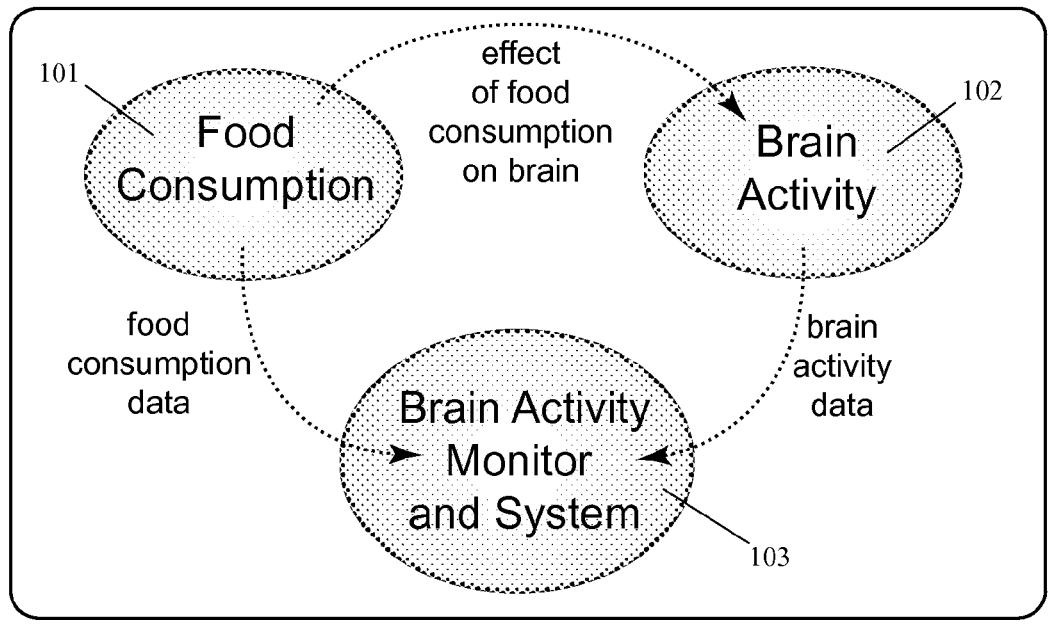
FIG. 3 shows a first (calibration) step of a second method for modifying food consumption using an EEG monitor.
Figure 4:
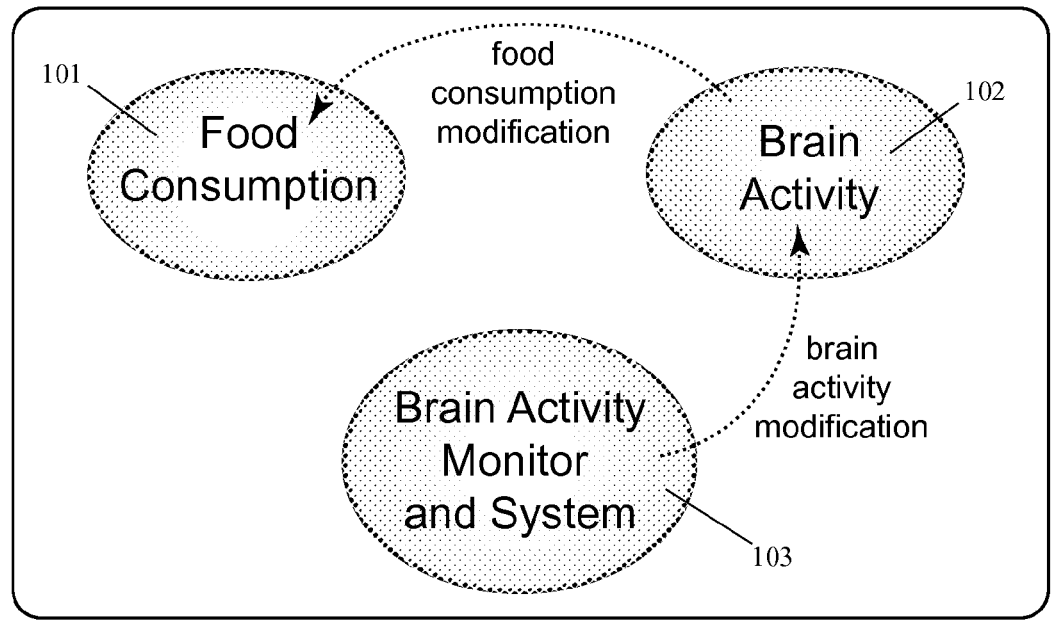
FIG. 4 shows the second step of this second method for modifying food consumption using an EEG monitor.

FIGS. 3 and 4 provide a conceptual introduction to how this invention can be embodied in a method, device, or system to measure and/or modify a person's food consumption using a wearable electroencephalogram (EEG) monitor wherein modification of food consumed is achieved by self-modification of brain activity by the person wearing the monitor. In this example, the operation of a brain activity monitor and system during a first (calibration) time period shown in FIG. 3 is the same as was shown in FIG. 1.

However, the type of feedback that is used to modify food consumption in FIG. 4 is different than the type of feedback that was used to modify food consumption in FIG. 2. In the example in FIG. 4, the person wearing the EEG monitor receives feedback concerning their brain activity. In an example, this feedback can be biofeedback. In an example, a visual, auditory, or tactile computer interface provides the person with feedback concerning their brain activity patterns and helps the person to self-modify these brain activity patterns as a means of modifying their food consumption. In an example, the feedback provided in FIG. 4 helps the person to self-modify their brain activity patterns in order to self-modify their desire for selected types or amounts of food.

In the example shown in FIG. 4, modification of food consumption is mediated through self-modification of a person's brain activity. In an example, interactive feedback concerning brain activity patterns can help a person to modify their brain activity patterns into brain activity patterns that are associated with feelings of satiety. In an example, self-modification of brain activity patterns into patterns that are associated with feelings of satiety can help a person to reduce their food consumption. In an example, interactive feedback concerning brain activity patterns can help a person to modify their brain activity patterns into brain activity patterns that are associated with consumption of food that they like. In an example, self-modification of brain activity patterns into patterns that are associated with consumption of food that they like can help a person to increase their consumption of healthy food that they normally dislike. In an example, such feedback can also be useful in helping a person to exercise self-control with respect to addictive behavior.

In an example, a computer interface which helps a person to self-modify their brain activity can comprise an interactive graphical display on a computer screen. In an example, this interactive graphical display can change from a first display configuration to a second display configuration as the person's brain activity changes from a first EM pattern to a second EM pattern. In an example, the second EM pattern of brain activity can be associated with a feeling of satiety. In an example, this second pattern of brain activity can be associated with consumption of a food that the person likes. In an example, the person can change their brain activity (to modify their food consumption) by concentrating on shifting the interactive graphic display from a first display configuration to a second display configuration. In an example, an interactive graphical display can be a changing geometric pattern, color pattern, moving bar, or moving dial. In an example, an interactive graphical display can be a face with a changing expression.

In an example, a computer interface which helps a person to self-modify their brain activity can comprise an interactive audio signal. In an example, this interactive audio signal can change from a first sound pattern to a second sound pattern as the person's brain activity changes from a first EM pattern to a second EM pattern. In an example, the second EM pattern of brain activity can be associated with a feeling of satiety. In an example, this second pattern of brain activity can be associated with consumption of a food that the person likes. In an example, the person can change their brain activity (to modify their food consumption) by concentrating on shifting the interactive audio signal from a first sound pattern to a second sound pattern. In an example, an interactive audio signal can be a changing tone or a changing blend of tones. In an example, an interactive audio signal can be music with changing parameters.

In an example, this invention can be embodied in a method for modifying a person's food consumption comprising: (a) receiving data concerning a person's food consumption from a first time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the first time period from one or more electrodes or other brain activity sensors which are configured to be less than one inch from the surface of the person's head; (c) identifying associations between patterns of food consumption and patterns of electromagnetic brain activity by analyzing data concerning the person's food consumption and data concerning the person's electromagnetic brain activity from the first time period; (d) receiving data concerning the person's electromagnetic brain activity from a second time period from one or more electrodes or other brain activity sensors which are configured to be less than one inch from the surface of the person's head; (e) using associations between patterns of food consumption and patterns of electromagnetic brain activity in order to estimate the person's food consumption during the second time period from data concerning the person's electromagnetic brain activity from the second time period, wherein food consumption can comprise consumption of food overall or consumption of one or more selected amounts and/or types of foods, ingredients, or nutrients; and (f) providing feedback to the person concerning their estimated food consumption and their electromagnetic brain activity from the second time period in order to prompt the person to modify their food consumption by self-modifying their electromagnetic brain activity.

In an example, this invention can be embodied in a method for modifying a person's food consumption comprising: (a) receiving data concerning a person's electromagnetic brain activity from a selected time period from one or more electrodes or other brain activity sensors which are configured to be less than one inch from the surface of the person's head; (b) using associations between patterns of food consumption and patterns of electromagnetic brain activity in order to estimate the person's food consumption during the selected time period from data concerning the person's electromagnetic brain activity from the selected time period, wherein food consumption can comprise consumption of food overall or consumption of one or more selected amounts and/or types of foods, ingredients, or nutrients; and (c) providing feedback to the person concerning their estimated food consumption and their electromagnetic brain activity from the selected time period in order to prompt the person to modify their food consumption by self-modifying their electromagnetic brain activity.

In an example, this invention can be embodied in a method for modifying a person's food consumption comprising: (a) receiving data concerning a person's food consumption from a first time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the first time period from one or more electrodes or other brain activity sensors which are configured to be less than one inch from the surface of the person's head; (c) creating a food-brainwave database, wherein this database links patterns of food consumption to patterns of electromagnetic brain activity, by analyzing data concerning the person's food consumption and data concerning the person's electromagnetic brain activity from the first time period; (d) receiving data concerning the person's electromagnetic brain activity from a second time period from one or more electrodes or other brain activity sensors which are configured to be less than one inch from the surface of the person's head; (e) using the food-brainwave database, wherein this database links patterns of food consumption to patterns of electromagnetic brain activity, in order to estimate the person's food consumption during the second time period from data concerning the person's electromagnetic brain activity from the second time period, wherein food consumption can comprise consumption of food overall or consumption of one or more selected amounts and/or types of foods, ingredients, or nutrients; and (f) providing feedback to the person concerning their estimated food consumption and their electromagnetic brain activity from the second time period in order to prompt the person to modify their food consumption by self-modifying their electromagnetic brain activity.

In an example, this invention can be embodied in a method for modifying a person's food consumption comprising: (a) receiving data concerning a person's electromagnetic brain activity from a selected time period from one or more electrodes or other brain activity sensors which are configured to be less than one inch from the surface of the person's head; (b) using a food-brainwave database, wherein this database links patterns of food consumption to patterns of electromagnetic brain activity, in order to estimate the person's food consumption during the selected time period from data concerning the person's electromagnetic brain activity from the selected time period, wherein food consumption can comprise consumption of food overall or consumption of one or more selected amounts and/or types of foods, ingredients, or nutrients; and (c) providing feedback to the person concerning their estimated food consumption and their electromagnetic brain activity from the selected time period in order to prompt the person to modify their food consumption by self-modifying their electromagnetic brain activity.

In an example, this invention can be embodied in a method for modifying a person's food consumption comprising: (a) receiving data concerning a person's food consumption from a first time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the first time period from one or more electrodes or other brain activity sensors which are configured to be less than one inch from the surface of the person's head; (c) identifying associations between patterns of food consumption and patterns of electromagnetic brain activity by analyzing data concerning the person's food consumption and data concerning the person's electromagnetic brain activity from the first time period; (d) receiving data concerning the person's electromagnetic brain activity from a second time period from one or more electrodes or other brain activity sensors which are configured to be less than one inch from the surface of the person's head; and (e) providing feedback to the person concerning their electromagnetic brain activity from the second time period in order to prompt the person to modify their food consumption by self-modifying their electromagnetic brain activity.

In an example, this invention can be embodied in a method for modifying a person's food consumption comprising: (a) receiving data concerning a person's electromagnetic brain activity from a selected time period from one or more electrodes or other brain activity sensors which are configured to be less than one inch from the surface of the person's head; and (b) providing feedback to the person concerning their electromagnetic brain activity from the selected time period in order to prompt the person to modify their food consumption by self-modifying their electromagnetic brain activity.

In an example, this invention can be embodied in a method for modifying a person's food consumption comprising: (a) receiving data concerning a person's food consumption from a first time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the first time period from one or more electrodes or other brain activity sensors which are configured to be less than one inch from the surface of the person's head; (c) creating a food-brainwave database, wherein this database links patterns of food consumption to patterns of electromagnetic brain activity, by analyzing data concerning the person's food consumption and data concerning the person's electromagnetic brain activity from the first time period; (d) receiving data concerning the person's electromagnetic brain activity from a second time period from one or more electrodes or other brain activity sensors which are configured to be less than one inch from the surface of the person's head; and (e) providing feedback to the person concerning their electromagnetic brain activity from the second time period in order to prompt the person to modify their food consumption by self-modifying their electromagnetic brain activity.

In an example, this invention can be embodied in a method for modifying a person's food consumption comprising: (a) receiving data concerning a person's electromagnetic brain activity from a selected time period from one or more electrodes or other brain activity sensors which are configured to be less than one inch from the surface of the person's head; and (b) providing feedback to the person concerning their electromagnetic brain activity from the selected time period in order to prompt the person to modify their food consumption by self-modifying their electromagnetic brain activity.

Figure 5:
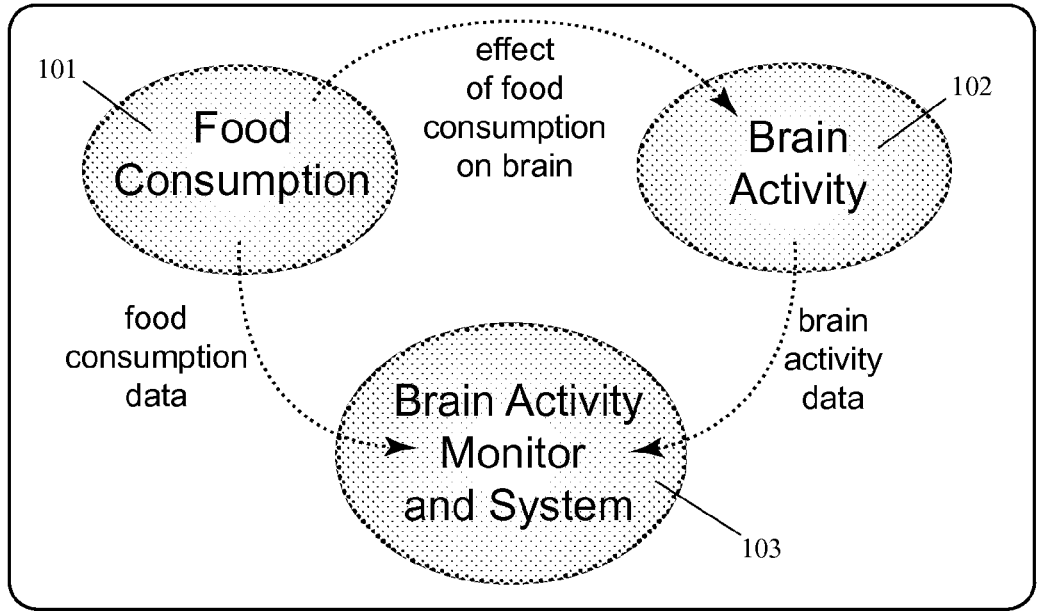
FIG. 5 shows a first (calibration) step of a third method for modifying food consumption using an EEG monitor.
Figure 6:
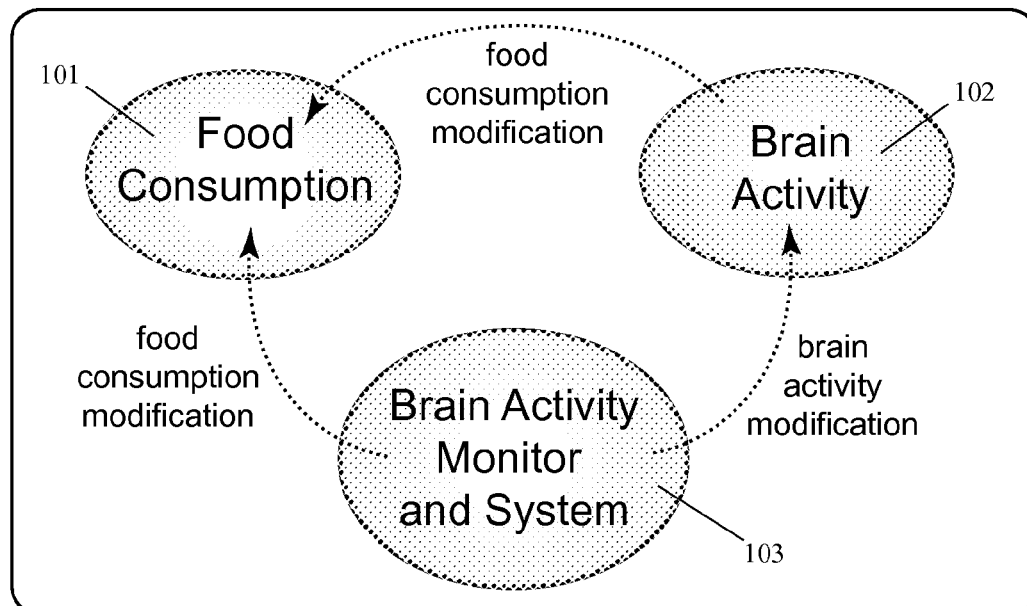
FIG. 6 shows the second step of this third method for modifying food consumption using an EEG monitor.

FIGS. 5 and 6 show an example of how this invention can be embodied in a method, device, or system to measure and/or modify a person's food consumption that uses both: (a) direct visual, auditory, and/or tactile feedback which prompts the person to modify their food consumption; and (b) interactive indirect feedback concerning the person's electromagnetic brain activity which prompts the person to self-modify their brain activity in order to modify their food consumption. In this example, FIG. 5 is the same as FIG. 1, but FIG. 6 includes both the direct feedback that was introduced in FIG. 2 and the indirect biofeedback that was introduced in FIG. 4.

As shown in FIGS. 4 and 6, an embodiment of this invention can provide feedback concerning brain activity to a person wearing a mobile EEG monitor and this feedback can help the person to modify their food consumption. In an example, such feedback can enable the person to modify their brain activity which, in turn, modifies their food consumption. In an example, such feedback can be triggered by the person's consumption of selected types or amounts of foods, nutrients, and/or ingredients as measured by brain activity data collected by the mobile EEG monitor. This tracking of food consumption based on brain activity patterns can be based on previously-identified associations between specific types of food consumption and specific patterns of brain activity. In an alternative example, this feedback can be self-initiated by the person in a proactive manner when the person craves an amount or type of food which is unhealthy to consume.

As shown in FIGS. 4 and 6, modification of food consumption can be caused by biofeedback and self-modification of brain activity. In an example, this invention can provide a computer-user interface which conveys information concerning brain activity patterns to a person wearing a mobile EEG monitor and helps the person to self-modify these brain activity patterns in order to change their desire for, and consumption of, a selected type or amount of food. In an example, a computer-user interface can help the person to self-modify their brain activity pattern toward a pattern that has been shown to be associated with satiety. In an example, this computer-user interface can provide interactive visual, auditory, and/or tactile cues to help the person self-modify their brain activity pattern. In an example, this computer-user interface can provide interactive graphical, avatar, or musical cues to help the person self-modify their brain activity. In an example, this computer-user interface can help the person to modify their brain activity pattern from a first pattern that is associated with hunger to a second pattern that is associated with satiety. In an example, self-modification of brain activity toward satiety can help the person to limit overeating.

In an example, a computer-user interface can help a person to self-modify their brain activity pattern toward a pattern that has been shown to be associated with a good-tasting food. In an example, this computer-user interface can employ visual, auditory, and/or tactile cues to help the person self-modify their brain activity pattern toward an activity pattern that is associated with good-tasting food. In an example, this computer-user interface can help the person to modify their brain activity pattern from a first pattern that is associated with a first type or amount of food to a second pattern that is associated with a second type or amount of food. In an example, self-modification of brain activity toward a pattern that is associated with consuming a less-healthy (but more-appealing) type of food can help the person to instead consume a more-healthy (but less-appealing) type of food. In an example, with practice and help from this invention, a person may be able to train their brain to respond more favorably to healthy food and less favorably to unhealthy food. In an example, this invention can help a person to exercise "mind over platter".

In an example, this invention can be embodied in a device (or in a system of wirelessly-linked devices) which comprises hardware for the operation of the above-discussed methods of food consumption measurement and modification. In an example, this invention can be embodied in a device or system for measuring and/or modifying a person's food consumption which includes a mobile wearable EEG monitor. In an example, a wearable EEG monitor can comprise one or more components selected from the group consisting of: one or more electrodes or other brain activity sensors; one or more accelerometers; one or more cameras; a computer-to-human interface such as a display screen, one or more lights, one or more speakers, and/or one or more tactile actuators; a human-to-computer interface such as a touch screen, one or more touch-activated buttons, microphone and speech-recognition capability, and/or gesture recognition capability; a data memory component; a data processor; a GPS component; a heart rate monitor; a power source and/or power-transducing component; and a wireless data transmission and data reception component.

In an example, a wearable EEG monitor can comprise a plurality of electrodes and a control unit. In an example, a control unit can comprise one or more components selected from the group consisting of: a power source and/or power-transducing component; a wireless data transmission and data reception component; a data memory component; and a data processor. In an example, a control unit can further comprise one or more components selected from the group consisting of: a computer-to-human interface such as a display screen, one or more lights, one or more speakers, and/or one or more tactile actuators; a human-to-computer interface such as a touch screen, one or more touch-activated buttons, microphone and speech-recognition capability, and/or gesture recognition capability; one or more accelerometers; one or more cameras; and a GPS component.

In various examples, in addition to electrodes which measure brain activity, a wearable EEG monitor can further comprise one or more sensors selected from the group consisting of: accelerometer, inclinometer, gyroscope, strain gauge, or other motion or position sensor; microphone or other sound sensor; thermometer or other temperature sensor; camera or other imaging sensor; optical sensor or optoelectronic sensor; blood pressure sensor; ECG/EKG sensor, heart rate monitor, and/or heart rate sensor; EMG sensor or other muscle activity sensor; GPS sensor, other location sensor, magnetometer, or compass; spectroscopy sensor or other spectral analysis sensor; electrochemical sensor; blood oximetry sensor; piezoelectric sensor; chewing sensor or swallowing sensor; respiration sensor; pressure sensor; galvanic skin response sensor; and taste or odor sensor.

In an example, a power source for a wearable EEG monitor can be selected from the group consisting of: power from a power source that is internal to the device during regular operation (such as an internal battery, capacitor, energy-storing microchip, or wound coil or spring); power that is obtained, harvested, or transduced from a power source other than the person's body that is external to the device (such as a rechargeable battery, electromagnetic inductance from external source, solar energy, indoor lighting energy, wired connection to an external power source, ambient or localized radiofrequency energy, or ambient thermal energy); and power that is obtained, harvested, or transduced from the person's body (such as kinetic or mechanical energy from body motion, electromagnetic energy from the person's body, blood flow or other internal fluid flow, glucose metabolism, or thermal energy from the person's body.

In an example, a wearable EEG monitor can be in data communication with a separate electronic device comprising one or more components selected from the group consisting of: one or more accelerometers; one or more cameras; a computer-to-human interface such as a display screen, one or more lights, one or more speakers, and/or one or more tactile actuators; a human-to-computer interface such as a touch screen, one or more touch-activated buttons, microphone and speech-recognition capability, and/or gesture recognition capability; a data memory component; a data processor; a GPS component; a power source and/or power-transducing component; and a wireless data transmission and data reception component. In an example the combination of a wearable EEG monitor and a separate electronic device can together comprise a system for using brain activity to measure and modify food consumption.

In an example, the operation of this invention can occur within a self-contained wearable EEG monitor. In an example, the operation of this invention can occur within a distributed system of which a wearable device, such as a mobile wearable EEG monitor, is one component, and wherein the mobile wearable EEG monitor is in (wireless) communication with a remote computing device which is part of the overall system for using brain activity to measure and modify food consumption. In an example, all aspects of human-to-computer interaction and computer-to-human interaction can occur via one or more interfaces which are physical components of a wearable EEG monitor. In an example, some or all aspects of human-to-computer interaction and/or computer-to-human interaction can occur via one or more interfaces in one or more physically-separate remote devices with which a wearable EEG monitor is in wireless data communication. In an example, a person can use a physically-separate device to enter information concerning food consumption during a calibration period. In an example, a person can use a physically-separate device to enter information concerning food consumption when promoted by analysis of brain activity data collected by the wearable EEG monitor.

In an example, a separate computing device with which a wearable EEG monitor communicates can also be worn by the person. In an example, the EEG monitor together with a separate computing device can comprises a system for measuring and/or modifying a person's food consumption. In an example, a separate computing device with which an EEG monitor is in data communication can worn on a person's wrist, hand, finger, arm, waist, torso, legs, neck, ear(s), and/or head. In an example, a separate computing device with which an EEG monitor is in data communication can be attached to a person's clothing by a means selected from the group consisting of: band, strap, clip, clamp, snap, pin, hook and eye fastener, magnet, and adhesive.

In various example, a separate wearable computing device with which a wearable EEG monitor is in data communication can be selected from the group consisting of: a wristwatch, smart watch, fitness watch, watch phone, bracelet phone, smart bracelet, fitness bracelet, smart wrist band, electronically-functional wrist band, other wrist-worn electronic device, or smart armband; smart glasses, smart eyewear, augmented reality eyewear, virtual reality eyewear, an electronically-functional visor, electronically-functional contact lens, or other electronically-functional eyewear; a smart button, electronically-functional button, pin, brooch, pendant, beads, neck chain, necklace, dog tags, locket, or medallion; a smart finger ring, electronically-functional finger ring, electronically-functional earring, nose ring, or ear bud or clip; a wearable camera; an article of smart clothing, an electronically-functional shirt, electronically-functional pants, or a smart belt; electronically-functional headband, hair pin, headphones, or ear phones; electronically-functional dental appliance, dental attachment, palatal vault attachment, or other electronically-functional intraoral device.

In an example, a separate computing device with which the EEG monitor communicates can also be held and/or carried by the person. In an example, a separate hand-held or carried computing device with which an EEG monitor is in data communication can be selected from the group consisting of: smart phone, mobile phone, or cellular phone; PDA; electronic tablet; electronic pad; smart food utensil; and other electronically-functional handheld device. In an example, a separate computing device with which the EEG monitor communicates can in a relatively-fixed remote location. In an example, a separate computing device with which an EEG monitor is in data communication can be selected from the group consisting of: laptop computer, desktop computer, internet terminal, smart appliance, or other fixed-location electronic communication device.

In an example, the locations of electrodes (or other brain activity sensors) on a wearable EEG monitor can be identified according to the International 10-20 System and/or the Modified Combinatorial Nomenclature (MCN). In an example, with the possible exception of reference sites such as A1 and A2, the brain activity monitoring component of this invention can comprise a wearable array of 19 electrodes or other brain activity sensors. In an example, this array can be located substantially at the following placement sites: FP1, FP2, F7, F3, Fz, F4, F8, T3/T7, C3, C4, Cz, T4/T8, T5/P7, P3, Pz, P4, T6/P8, O1, and O2. In an example, with the possible exception of reference sites such as A1 and A2, the brain activity monitoring component of this invention can comprise a wearable array of 17 electrodes or other brain activity sensors. In an example, this array can be located substantially at the following placement sites: F3, F4, F7, F8, Fz, T3, T4, T5, T6, P3, P4, Pz, O1, O2, C3, C4, and Cz. In an example, with the possible exception of reference sites, this invention can comprise a wearable array of 16 electrodes or other brain activity sensors. In an example, a wearable array of brain activity sensors can be located substantially at the following placement sites: F3, Fz, F4, T3/T7, C3, C4, Cz, T4/T8, T5/P7, P3, Pz, P4, T6/P8, PO7, PO8, and Oz. In an example, this array can be placed substantially at the following placement sites: F3, Fz, F4, C3, C1, Cz, C2, C5, T4/T8, CPz, P3, Pz, P4, and POz.

In an example, with the possible exception of reference sites, the brain activity monitoring component of this invention can comprise a wearable array of 13 brain activity sensors. In an example, this array can be located substantially at the following placement sites: F3, Fz, F4, T3/T7, C3, C4, Cz, T4/T8, P3, P4, O1, and O2. In an example, with the possible exception of reference sites, this invention can comprise a wearable array of ten brain activity sensors. In an example, this array can be located substantially at the following placement sites: FP1, FP2, F3, F4, T3/T7, T4/T8, P3, P4, O1, and O2.

In an example, this invention can comprise a wearable array of eight brain activity sensors. In an example, this array can be placed substantially at the following placement sites: F3, F4, T3/T7, Cz, T4/T8, P3, Pz, and P4. In another example, this array can be located substantially at the following placement sites: F3, F4, C3, C4, Cz, Pz, O1, and O2. In another example, this array can be located substantially at the following placement sites: Fz, Cz, T5/P7, P3, Pz, P4, T6/P8, and Oz. In an example, this invention can comprise a wearable array of seven brain activity sensors. In an example, a wearable array of brain activity sensors can be placed substantially at the following placement sites: FP1, FP2, Fz, C3, C4, Cz, and Pz. In another example, this array can be located substantially at the following placement sites: F3, F4, Cz, P3, P4, O1, and O2.

In an example, with the possible exception of reference sites, the brain activity monitoring component of this invention can comprise a wearable array of six electrodes or other brain activity sensors. In an example, a wearable array of six brain activity sensors can be located substantially at the following placement sites: FP1, FP2, F7, F8, T3/T7, and T4/T8. In another example, this array can be placed substantially at: F3, F4, P3, P4, O1, and O2. In another example, a wearable array of brain activity sensors can be located substantially at the following placement sites: F3, F4, Cz, P2, O1, and O2. In another example, a wearable array of brain activity sensors can be located substantially at the following sites: F3, F8, T3/T7, T4/T8, T5/P7, and T6/P8. In another example, this array can be placed substantially at the following placement sites: FC3, T3/T7, C3, C4, Cz, and P3. In another example, this array can be located substantially at: T3/T7, T4/T8, T5/P7, T6/P8, O1, and O2. In an example, with the possible exception of reference sites, this invention can comprise a wearable array of five brain activity sensors. In an example, this array can be located substantially at the following placement sites: AFz, F3, F4, CP5, and CP6. In another example, this array can be placed substantially at the following sites: F3, F4, Cz, P3, and P4. In another example, this array can be located substantially at the following placement sites: T3/T7, Cz, T4/T8, CP3, and CP4.

In an example, with the possible exception of reference sites, the brain activity monitoring component of this invention can comprise a wearable array of four electrodes or other brain activity sensors. In an example, a wearable array of four brain activity sensors can be located substantially at: FP1, FP2, F7, and F8. In another example, this array can be placed substantially at the following placement sites: AF7, AF8, T3/T7, and T4/T8. In another example, this array can be located substantially at the following sites: F7, F3, F4, and F8. In another example, this array can be located substantially at the following placement sites: F7, F8, T3/T7, and T4/T8.

In an example, this array can be placed substantially at: F3, F4, P3, and P4. In another example, this array can be located substantially at the following placement sites: F3, Cz, P3, and O1. In another example, this array can be located substantially at the following sites: Fz, Cz, P3, and P4. In another example, this array can be placed substantially at the following placement sites: T3/T7, T4/T8, TP7, T5/P7, and T6/P8. In another example, this array can be located substantially at: T3/T7, T4/T8, PO7, and PO8. In another example, this array can be located substantially at the following placement sites: P3, P4, O1, and O2. In another example, this array can be placed substantially at the following sites: Cz, P3, Pz, and P4.

Figure 7:
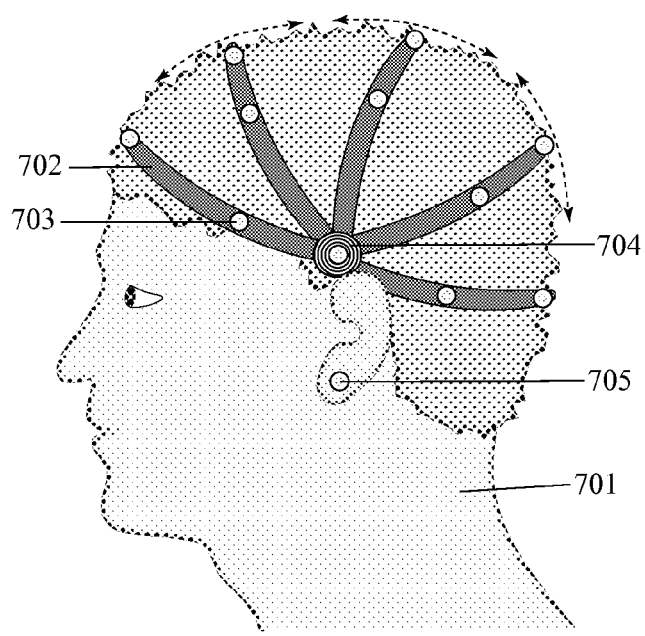
FIG. 7 shows a wearable EEG monitor with five adjustable arcuate bands worn around a person's head.

Starting with FIG. 7, we now transition to discussing some specific-hardware device and system embodiments of this invention. FIG. 7 shows an example of how this invention can be embodied in a wearable EEG monitor (702) for measuring and/or modifying a person's (701) food consumption comprising a plurality of electrodes or other brain activity sensors (including 703) which are configured to be worn less than one inch from the surface of the person's head and a control unit (704). In an example, control unit 704 can comprise a mobile power source and/or power transducer (wherein a power transducer harvests power from human physiological activity and/or environmental energy sources), a data processor; and a data transmitter.

FIG. 7 shows a left-side view of a person 701 wearing EEG monitor 702 with a plurality of electrodes or other brain activity sensors (including 703) and control unit 704. In this example, the electrodes or other brain activity sensors (including 703) are located at the following EEG electrode sites: frontal polar sites Fp1 and Fp2; frontal sites F7, F3, Fz, F4 and F8; temporal sites T3 (T7 in the MCN), T4 (T8 in the MCN), T5 (P7 in the MCN) and T6 (P8 in the MCN); central sites C3, C4 and Cz; parietal sites P3, P4 and Pz; and occipital sites O1 and O2; and earlobe reference sites A1 (705) and A2.

FIG. 7 shows only the left side and top line of the person's head. In this example, the configuration of electrodes or other brain activity sensors is assumed to be symmetric with respect to the left and right sides of the person's head. FIG. 7 shows electrodes or other brain activity sensors at the following left-side and top sites: frontal polar site Fp1; frontal sites F7, F3 and Fz; temporal sites T3 and T5; central sites C3 and Cz; parietal sites P3 and Pz; and occipital site O1. Since symmetry is assumed, electrodes or other brain activity sensors are also assumed to be at the following right-side sites which are not shown here: frontal polar site Fp2; frontal sites F4 and F8; temporal sites T4 and T6; central site C4; parietal site P4; and occipital site O2. FIG. 7 also shows optional earlobe reference site A1 (705). Symmetric reference sites include earlobe site A1 on the left side and earlobe site A2 (not shown) on the right side.

In this example, the electrodes or other brain activity sensors (including 703) are visible from an external side view of the EEG monitor. In an example, these sensors might not be visible from an external side perspective. They may only be visible on the inside of the bands. In an example, electrodes or other brain activity may be imbedded within the bands and may not be visible from any view.

In FIG. 7, wearable EEG monitor (702) is further comprised of five arcuate bands (or straps). In this example, each of these five bands arcs around an approximately-hemispherical portion of the person's head. In this example, these five bands converge at a pivoting location near the person's ear. In an example, a wearable EEG monitor can comprise three or four bands (or straps), each of which arcs around an approximately-hemispherical portion of the person's head. In various examples, these bands can be rigid, semi-rigid, flexible, or elastic. In this example, a bottom frontal band and a bottom posterior band together comprise a slightly-curved, roughly-circular loop that goes around the person's head. In this example, this circular loop is tilted at an acute angle with respect to the horizontal plane (when the person's head is upright), wherein this acute angle is in the range of 20 to 60 degrees.

In an example, the relative locations of a subset of bands can adjusted to customize the locations of electrodes or other brain activity sensors to the anatomy of a specific person. In an example, a subset of arcuate bands can be radially-adjusted by pivoting them around the point of band convergence. In the example shown in FIG. 7, the upper three bands can be radially-adjusted. Potential adjustment is indicated in FIG. 7 by three curved dotted-line arrows, at the distal arcs of these bands, each of which spans a small portion of the perimeter of the top of the person's head. In an example, a smaller or larger subset of bands can be radially-adjustable by pivoting. In an example, all five bands can be radially-adjustable by pivoting.

In an example, radial-adjustment of bands can be done until the pattern of brain activity which is measured by the electrodes or other brain activity sensors best matches a standard or otherwise-expected pattern under selected conditions. In an example, such adjustment can be done in an iterative manner during a fitting period. In an example, radial-adjustment of one or more bands can be done by hand. In an example, radial-adjustment or one or more bands can be done automatically by one or more actuators. In an example, control unit 704 can include one or more actuators.

In an example, individual electrodes or other brain activity sensors (including 703) can have fixed locations along the lengths of the bands. In an example, the location of one or more individual electrodes or other brain activity sensors can be moved along the lengths of bands, such as by movement along a track which spans a portion of the length of a band. In an example, this movement can be done by hand. In an example, this movement can be done automatically by one or more actuators. In example, this movement can help to customize the location of electrodes or other brain activity sensors to the anatomy of a specific person.

In an example, individual electrodes or other brain activity sensors (including 703) can have fixed locations with respect to contact between the surface of a band and the surface of a person's head. In an example, individual electrodes or other brain activity sensors can be spring-loaded to maintain a desired level of contact or pressure with the surface of a person's head. In an example, the location, degree of contact, and/or level of pressure between one or more individual electrodes and the surface of a person's head can be adjusted. In an example, adjustment of the degree of contact and/or level of pressure between electrodes or other brain activity sensors and the surface of a person's head can help to customize an EEG monitor to the anatomy of a specific person. In an example, such contact or pressure adjustment can be done by hand. In an example, such contact or pressure adjustment can be done automatically by one or more actuators. In an example, such contact or pressure can be adjusted automatically by an actuator if proper contact or EM signal measurement is reduced or lost while the person is wearing the device.

In the example shown in FIG. 7, all of the electrodes or other brain activity sensors which are physically present in the EEG monitor are actively used to monitor the person's brain activity. In an alternative example, an EEG monitor can comprise a large array of electrodes or other brain activity sensors and only a subset of them may be used to monitor a specific person's brain activity. In an example, the selection of a subset of electrodes or brain activity sensors to be actively used can serve to customize electrode or brain activity sensor configuration to the anatomy of a specific person. In an example, selection of a subset of a larger array of electrodes for active use can serve to customize electrode placement for a specific person without having to physically move electrode locations.

In an example, an EEG monitor can comprise a large array of potential connection locations for electrodes or other brain activity sensors, but not all of these potential connection locations are used for electrodes or other brain activity sensors for a specific person. In an example, the selection of which connection locations to which electrodes or other brain activity sensors are actually connected can serve to customize the configuration of electrodes or brain activity sensor for a specific person. In an example, the selection of which connection locations are used for electrodes or brain activity sensors can customize an EEG monitor to the anatomy of a specific person. In an example, individual electrodes or brain activity sensors can be selectively inserted by hand into a subset of a large array of connection locations in order to customize the placement of electrodes or other brain activity sensors for use for a specific person. In an example, this can allow customization of electrode or sensor placement for a specific person without having the expense of electrodes or sensors which are not used.

In the example shown in FIG. 7, control unit 704 is located where the bands converge. In an alternative example, a control unit can be located at a different location, such as along the length of one of the bands. In an example a control unit can be located at a position in front of a person's ear. In an example, a control unit can be incorporated into an eyewear frame which is physically-integrated into an EEG monitor as part of the same device or is wirelessly-integrated with an EEG monitor as part of an overall system for measuring and/or modifying a person's food consumption.

In an example, wearable EEG monitor 702 and/or control unit 704 can further comprise one or more components selected from the group consisting of: a power source and/or power-transducing component; a wireless data transmission and data reception component; a data memory component; and a data processor. In an example, wearable EEG monitor 702 and/or control unit 704 can further comprise one or more components selected from the group consisting of: a computer-to-human interface such as a display screen, one or more lights, one or more speakers, and/or one or more tactile actuators; a human-to-computer interface such as a touch screen, one or more touch-activated buttons, microphone and speech-recognition capability, and/or gesture recognition capability; one or more accelerometers; one or more cameras; and a GPS component.

In an example, wearable EEG monitor 702 and/or control unit 704 can further include one or more sensors selected from the group consisting of: accelerometer, inclinometer, gyroscope, strain gauge, or other motion or position sensor; microphone or other sound sensor; thermometer or other temperature sensor; camera or other imaging sensor; optical sensor or optoelectronic sensor; blood pressure sensor; ECG/EKG sensor, heart rate monitor, and/or heart rate sensor; EMG sensor or other muscle activity sensor; GPS sensor, other location sensor, magnetometer, or compass; spectroscopy sensor or other spectral analysis sensor; electrochemical sensor; blood oximetry sensor; piezoelectric sensor; chewing sensor or swallowing sensor; respiration sensor; pressure sensor; galvanic skin response sensor; and taste or odor sensor.

In this example, it is assumed that there are wires or other conductive connections between control unit 704 and electrodes or other brain activity sensors (including 703). Wires and other conductive connections are well known in the prior art and their exact configuration is not central to this invention. Accordingly, a wire configuration is not shown here. In an alternative example, electrodes or other brain activity sensors can be in wireless communication with a control unit.

In an example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; and a data transmitting member.

In an example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; and a database which includes associations between specific patterns of food consumption and specific patterns of electromagnetic brain activity, which translates specific types and amounts of food into specific types and amounts of nutrients, or which does both.

Figure 8:
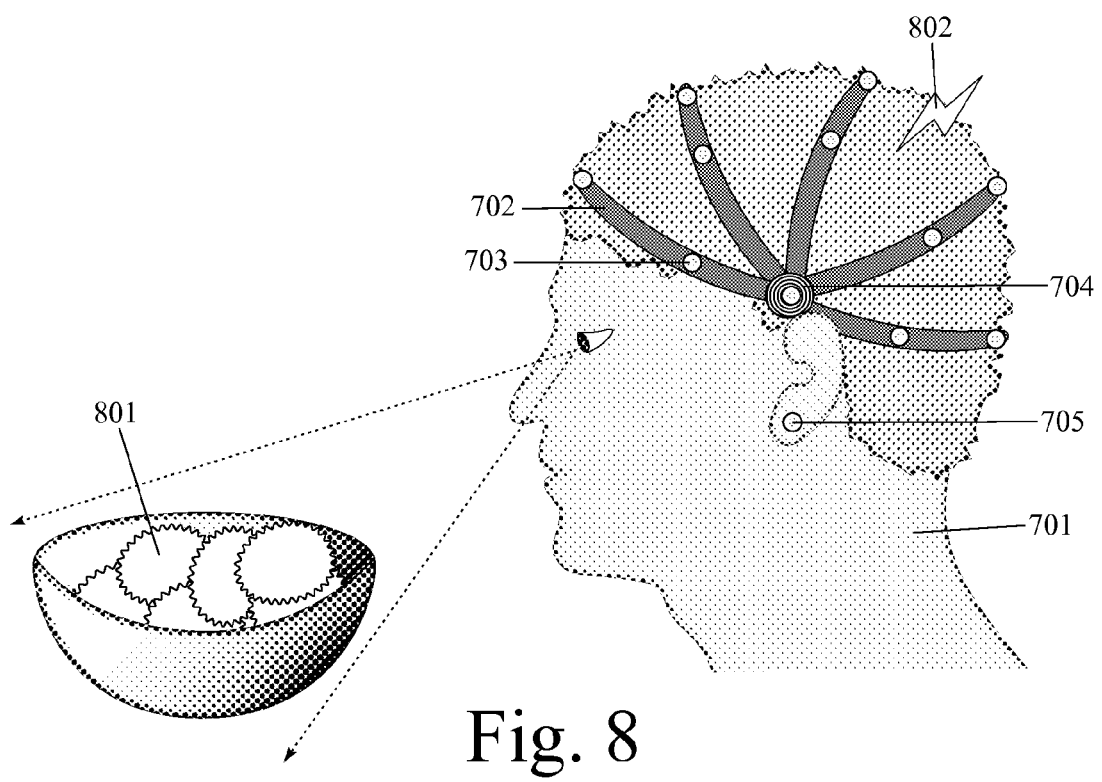
FIG. 8 shows a calibration period wherein a person views food, which evokes a response in their brain.
Figure 9:
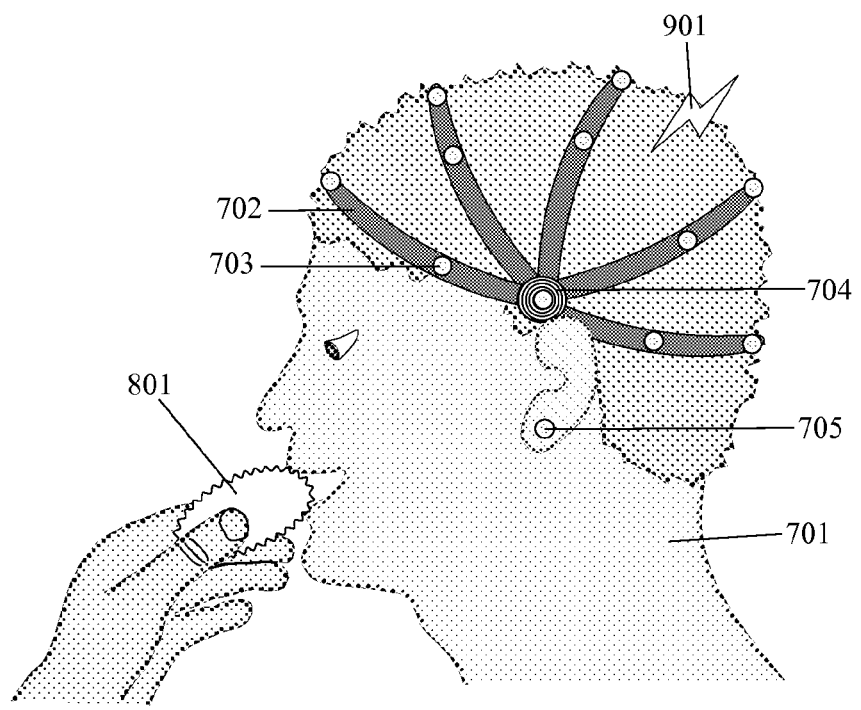
FIG. 9 shows a calibration period wherein a person eats food, which evokes a response in their brain.
Figure 10:
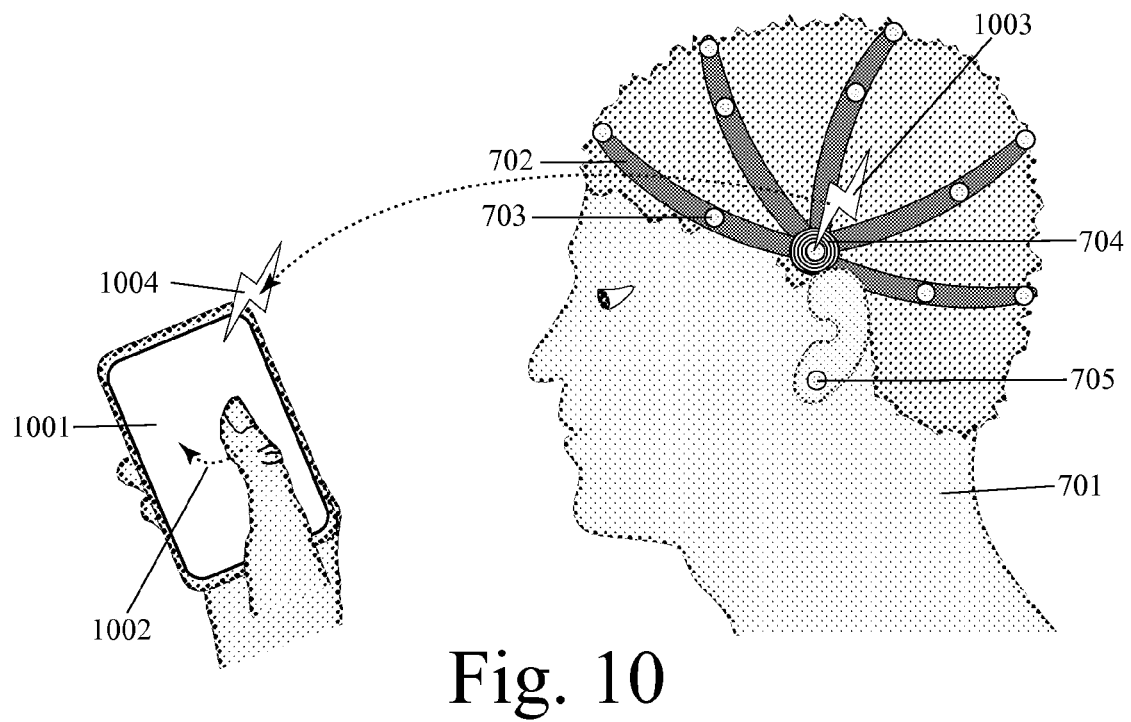
FIG. 10 shows a calibration period wherein a person enters information about the food.

FIGS. 8 through 14 comprise a chronological sequence which shows how wearable EEG monitor 702 can be used to measure and/or modify a person's food consumption. In an example, FIGS. 8 through 14 show how hardware can be used to implement the methods that were disclosed in FIGS. 1 and 2. FIGS. 8 through 10 show the operation of this hardware during a first (calibration) time period in which data concerning food consumption and data concerning brain activity are independently collected and significant associations are identified between patterns of food consumption and patterns of brain activity. FIGS. 11 through 14 show the operation of this hardware during a second (post-calibration) time period in which these associations are then used in combination with subsequent brain activity data in order to measure and/or modify the person's food consumption. Collectively, FIGS. 8 through 14 show a device and system for measuring and/or modifying a person's food consumption using a wearable EEG monitor.

FIG. 8 begins a first (calibration) time period sequence by showing person 701 (who is wearing EEG monitor 702) as this person views food 801. In this example, even the sight of food 801 evokes a response in the person's brain and a change 802 in the person's electromagnetic brain activity. In this example, change 802 in the person's electromagnetic brain activity is represented by a "lightning bolt" symbol due to its invisible (to the human eye) electromagnetic nature. This change 802 in brain activity can be called a first-phase of brain activity response to food because it is caused by the sight (and/or smell) of food before the person eats the food. Change 802 in electromagnetic brain activity is measured and/or recorded by the plurality of electrodes or other brain activity sensors (including 703) in EEG monitor 702.

FIG. 9 continues the first (calibration) time period sequence by showing person 701 eating food 801. In this example, the taste, smell, and tactile sensations of eating food evoke a second and/or continued response in the person's brain and a second and/or continued change 901 in the person's electromagnetic brain activity. In this example, change 901 is also represented by a "lightning bolt" symbol. Change 901 in the person's brain activity can be called a second-phase of brain activity response to food because it is triggered when the person actually starts eating food. Change 901 in electromagnetic brain activity is measured and/or recorded by the plurality of electrodes or other brain activity sensors (including 703) in EEG monitor 702.

FIG. 10 continues the first (calibration) time period sequence by showing person 701 manually entering information concerning food 801 into a handheld electronic device 1001. In this example, manual entry of data is done using a touch screen. This is represented in FIG. 10 by a dotted-line arrow (1002) next to the person's thumb. In this example, manual entry of information concerning food consumed occurs during a first (calibration) time period. In various examples, a person can manually enter data concerning the types and amounts of food which they eat into a smart phone, electronic tablet, laptop, smart watch, smart wrist band, electronically-functional eyewear, or other electronic device. In various examples, a person can enter food consumption data via a touchscreen, speech recognition interface, gesture recognition interface, EMG recognition interface, eye movement recognition interface, keypad, buttons, or knobs.

As shown in FIG. 10, handheld electronic device 1001 and wearable EEG monitor 702 are in wireless communication with each other. This wireless communication is represented by lightning bolt symbols 1003 and 1004 and the dotted-line arrow between them. In this example, wearable EEG monitor 702 and handheld electronic device 1001 together comprise a system for measuring and/or modifying a person's food consumption. Wireless communication between EEG monitor 702 and electronic device 1001 enables data concerning food consumption (having been entered into device 1001) and data concerning brain activity (having been recorded by monitor 702) to be chronologically linked and analyzed to identify associations between patterns of food consumption and patterns of electromagnetic brain activity.

In an example, the data processing that is required to analyze this data and identify these associations can occur in control unit 704 of wearable EEG monitor 702, in a data processor within handheld device 1001, or in a remote computer with which either the EEG monitor or the handheld device is in wireless communication. In an example, data concerning food consumption and brain activity can be analyzed to create a food-brainwave database which links specific patterns of food consumption with specific patterns of brain activity.

In an example, manual entry of food consumption information can be facilitated by an application on the handheld electronic device which provides a menu of common food items, including their images and descriptions. In an example, food consumption data can be collected and/or supplemented by having the person manually take pictures of food before a meal and a picture of any unconsumed food that remains after the meal. In an example, food consumption data can be collected and/or supplemented by analysis of images which are automatically taken by electronically-functional eyewear or a wearable camera. In an example, the amount of food eaten can be estimated by the difference in food volume between a before-meal food image and an after-meal food image.

In an example, food consumption data can be collected and/or supplemented by the use of a smart food utensil, mobile food probe, or mobile food scanner. In an example, a smart food utensil, mobile food probe, or mobile food scanner can include a spectroscopic sensor for analyzing the chemical composition of food. In an example, food consumption data can be collected and/or supplemented by scanning a bar code or other unique content on food packaging or a restaurant menu.

During a first (calibration) time period shown in FIGS. 8 through 10, data concerning the person's food consumption, including consumption of food 801, is collected by a means other than analysis of electromagnetic brain activity. Also, during the first (calibration) time period shown in FIGS. 8 through 10, data concerning the person's electromagnetic brain activity, including changes 802 and 901, is collected using wearable EEG monitor 702. Data concerning food consumption and brain activity are then jointly analyzed to identify significant associations between food consumption patterns and brain activity patterns.

In various examples, first-phase change 802 and second-phase change 901 in the person's electromagnetic brain activity can be measured and analyzed separately, sequentially, or jointly in order to link patterns of food consumption to patterns of brain activity. In this example, two phases of food consumption (before eating and during eating) are measured and analyzed. In an alternative example, only one phase of food consumption may be measured and analyzed. In an alternative example, three phases of food consumption (before eating, during eating, and after digestion) may be measured and analyzed. In an example, changes 802 and 901 can be linked to food consumption in general, without identifying a specific type of food. In an example, changes 802 and 901 can be linked to the consumption of specific types and amounts of food, ingredients, and/or nutrients, such as the specific types and amounts of ingredients in food 801.

FIGS. 11 through 14 show the operation of this hardware during a second (post-calibration) time period in which associations between food consumption and brain activity are used, in combination with monitored brain activity data, to measure and/or modify the person's food consumption. In an example, these associations can be embodied in a food-brainwave database. In an example, these associations can be embodied in a statistical model with estimated parameters.

In an example, associations and/or a food-brainwave database can have been created de novo for person 701 during a first (calibration) time period for person 701. In an alternative example, associations and/or a food-brainwave database can have been created for a general population and adapted for use for person 701. In an example, use of population-based associations and/or a population-based food-brainwave database can reduce or entirely eliminate the need for a first (calibration) time period for person 701.

Figure 11:
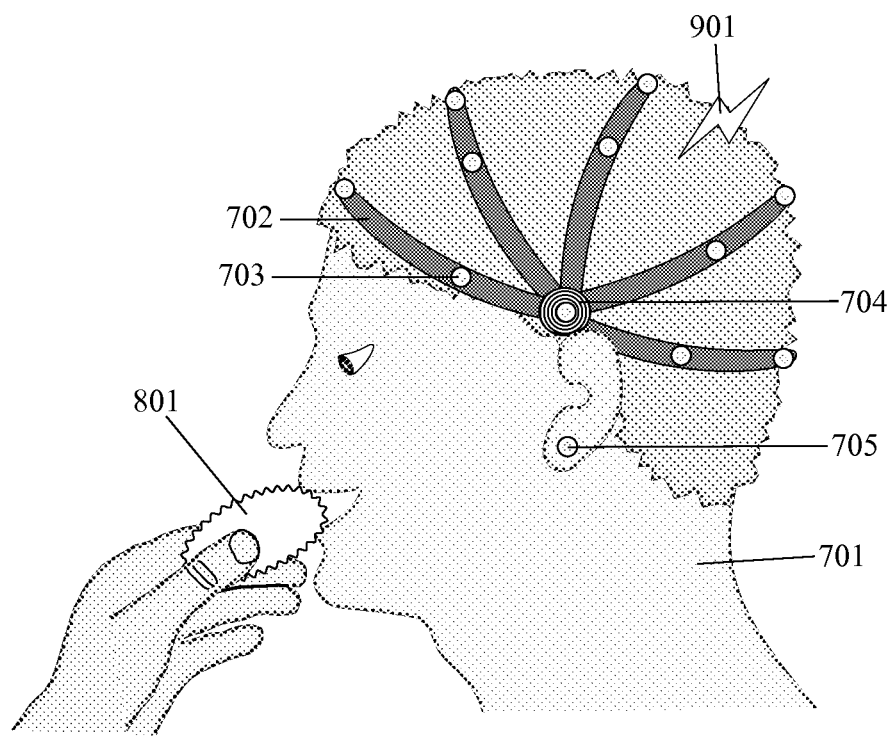
FIG. 11 shows a person eating food after a calibration time period.

FIG. 11 shows person 701 eating food 801 in a second (post calibration) time period. In this example, there is no independent entry of food consumption information during this second (post calibration) time period. During this second (post calibration) time period, food consumption is estimated based on the person's electromagnetic brain activity. In FIG. 11, the person's consumption of food 801 triggers a change (901) in the person's electromagnetic brain activity. Change 901 in brain activity is measured by wearable EEG monitor 702.

Figure 12:
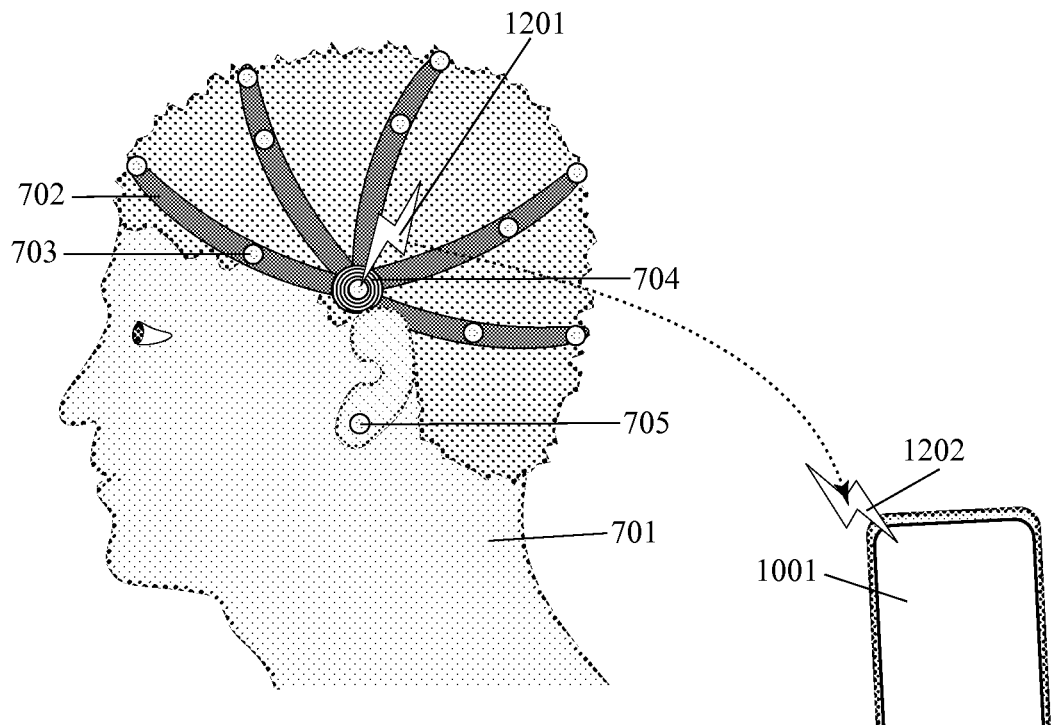
FIG. 12 shows transmission of brain activity data from a wearable EEG monitor to a handheld electronic device.

In FIG. 12, data concerning the person's brain activity, including change 901 in response to consumption of food 801, is wirelessly transmitted from control unit 704 of wearable EEG monitor 702 to handheld electronic device 1001. This wireless transmission is represented by lightning bolt symbols 1201 and 1202. In an example, data concerning the person's brain activity during an extended period of time can be measured and recorded. In an example, this extended period of time can be several hours or an entire day. In an example, this extended period of time can include multiple food consumption events, of which eating food 801 is only one event. In an example, brain activity data can be wirelessly transmitted from wearable EEG monitor 702 to handheld electronic device 1001 at regular time intervals during an extended period of time, after each food consumption event, or at the end of the extended period of time.

In an example, data concerning changes in a person's brain activity for an extended period of time can be used to estimate the person's cumulative food consumption during this period of time. In this manner, a log of the person's food consumption can be automatically created for this period of time. In an example, this automatic log of food consumption can be at the level of overall food consumption and/or total calories. In an example, this automatic log of food consumption can be at the level of specific types and amounts of foods, ingredients, and/or nutrients.

Figure 13:
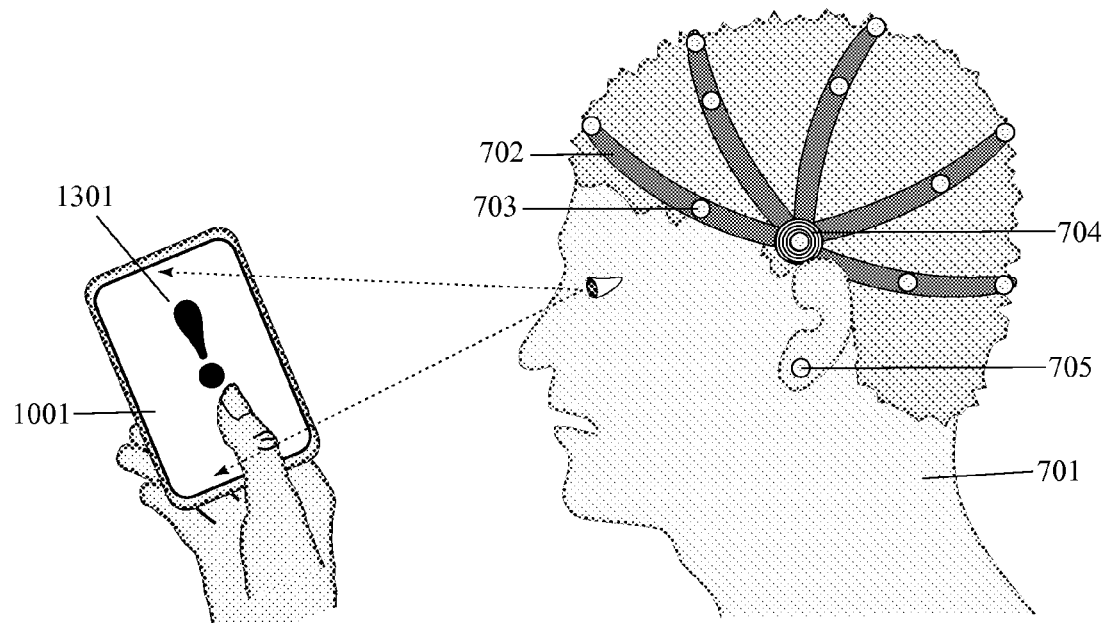
FIG. 13 shows a person receiving feedback concerning food consumption.

FIG. 13 shows an example of how a system or device can convey feedback to a person in order to modify their food consumption. In FIG. 13, person 701 is shown receiving visual feedback 1301 (represented here by an exclamation point) concerning their food consumption from handheld electronic device 1001. In an example, feedback 1301 can be a warning that the person has consumed an unhealthy type or amount of food. In an example, feedback 1301 can be a warning that the person has not consumed a selected healthy food. In an example, feedback 1301 can indicate that the person has eaten too many calories overall compared to their caloric expenditure during a selected period of time. In an example, feedback 1301 can indicate that the person has eaten an unhealthy ingredient and/or an ingredient to which they are allergic.

In an example, feedback 1301 can be a text message. In an example, feedback 1301 can comprise a negative expression on an animated face or avatar. In example, feedback 1301 can include positive suggestions for how the person can modify their food consumption in a healthier manner in order to achieve their health goals. In other examples, feedback to modify a person's food consumption can be conveyed to the person through a different visual, auditory, or tactile interface.

Figure 14:
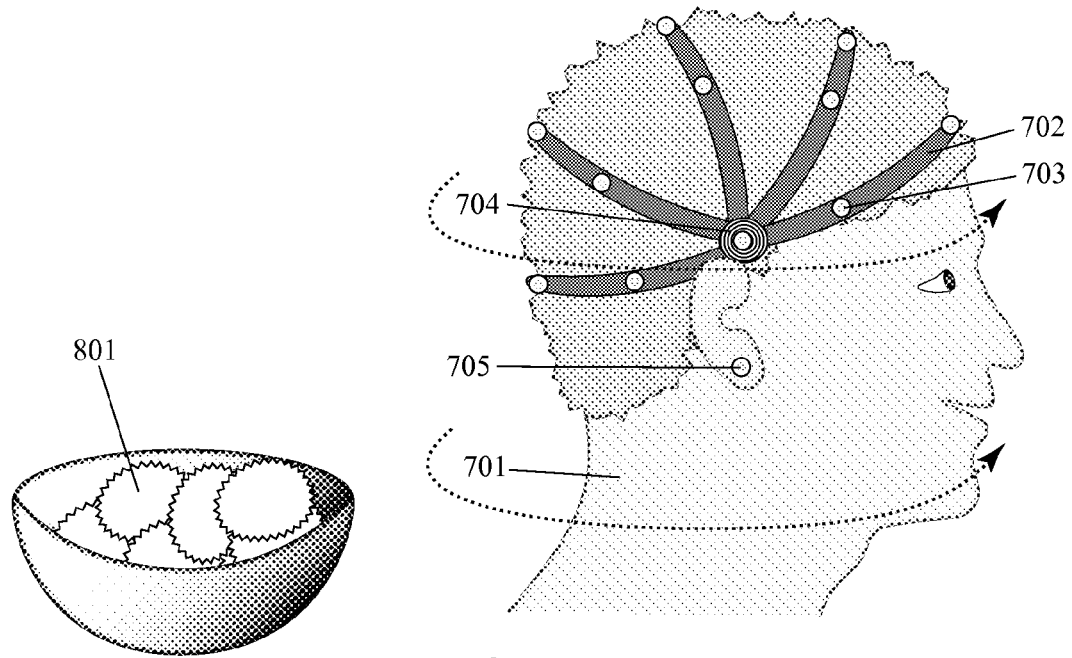
FIG. 14 shows a person's behavior affected by feedback concerning food consumption.

The behavior of person 701 in FIG. 14 indicates that feedback 1301 has been successful in modifying the person's food consumption. In FIG. 14, the person has seen food 801 in a bowl, but the person turns away from the food rather than eating it because of feedback 1301 which the person received in FIG. 13. In an example, feedback 1301 may have indicated that the person has eaten too many fatty snacks today and should avoid eating more fatty snacks. In an example, the person is turning away from a bowl of fatty snacks in FIG. 14 after having received such feedback. In an example, a device and system for modifying a person's food consumption using a wearable EEG monitor can help to strengthen a person's willpower to avoid over-consumption of unhealthy types or amounts of food.

In an example, this invention can be embodied in a system for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; and a smart phone, tablet, or other electronically-functional handheld device.

In an example, this invention can be embodied in a system for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; a smart phone, tablet, or other electronically-functional handheld device; and a database which includes associations between specific patterns of food consumption and specific patterns of electromagnetic brain activity, which translates specific types and amounts of food into specific types and amounts of nutrients, or which does both.

In an example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; and a visual interface for computer-to-human communication.

In an example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a visual interface for computer-to-human communication; and a database which includes associations between specific patterns of food consumption and specific patterns of electromagnetic brain activity, which translates specific types and amounts of food into specific types and amounts of nutrients, or which does both.

Figure 15:
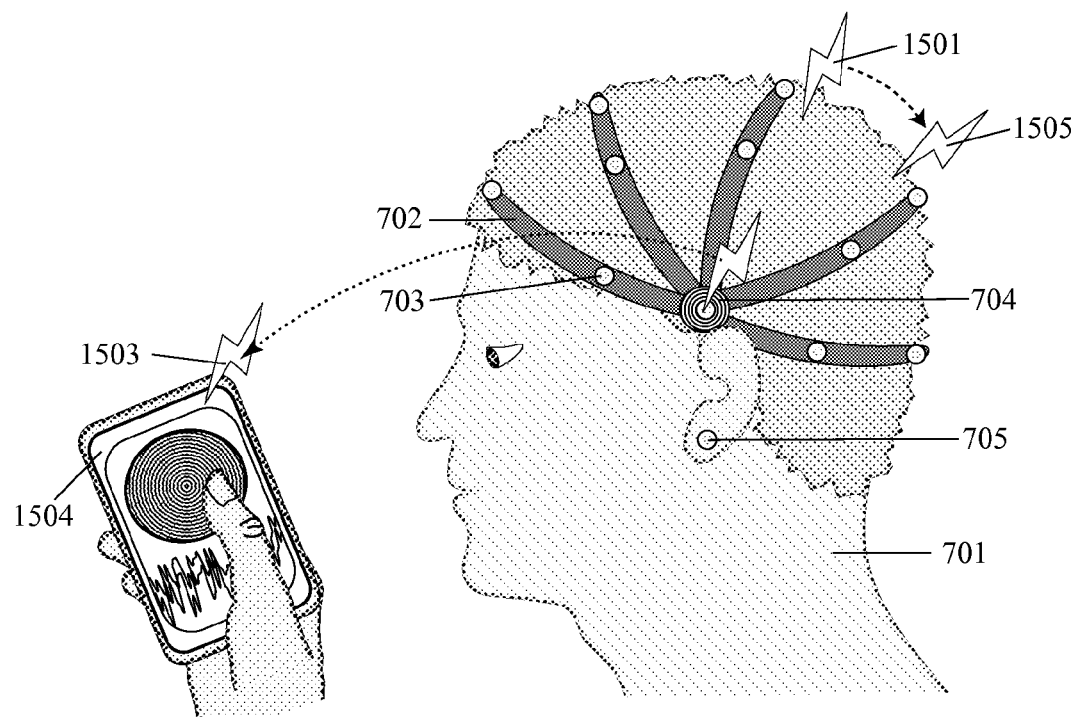
FIG. 15 shows a handheld device in wireless communication with a wearable EEG monitor.
Figure 16:
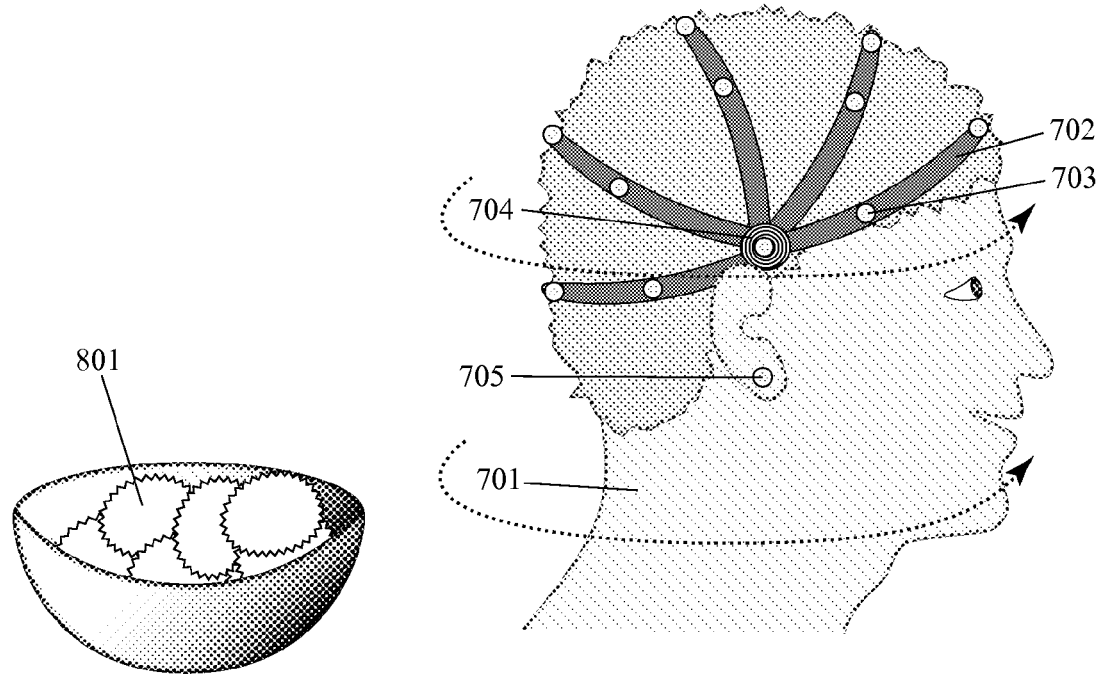
FIG. 16 shows a person having modified their brain activity to modify their food consumption.

FIGS. 15 and 16 show another example of how wearable EEG monitor 702 can be used to modify a person's food consumption. This example involves interactive feedback concerning the person's electromagnetic brain activity patterns. In this example, person 701 modifies their food consumption by self-modifying their electromagnetic brain activity patterns. FIGS. 15 through 16 show an example of hardware that can be used to implement the biofeedback methods that were disclosed in FIGS. 4 and 6.

FIG. 15 shows person 701 interacting with handheld electronic device 1504 which, in turn, is in wireless communication with wearable EEG monitor 702. This wireless communication is represented by lightning bolt symbol 1503 and the dotted-line arrow between handheld electronic device 1504 and wearable EEG monitor 702. FIG. 15 also shows a self-modified change in the person's electromagnetic brain activity from a first pattern 1501 to a second pattern 1505. In an example, first pattern 1501 can be an electromagnetic brain activity pattern which is generally associated with hunger and second pattern 1505 can be an electromagnetic brain activity pattern which is generally associated with satiety.

In an example, person 701 can receive interactive feedback concerning their electromagnetic brain activity pattern as measured by wearable EEG monitor 702, wirelessly transmitted to handheld electronic device 1504, and visually displayed on the screen of electronic device 1504. In an example, the visual display on electronic device 1504 can change as the person's brain activity pattern changes. In an example, changes in the visual display can help person 701 to self-modify their brain activity pattern in a way which modifies their food consumption. In an example, when the visual display is changed to a selected configuration, this indicates that the person's brain activity has changed from first pattern 1501 to second pattern 1505. In an example, when the person has modified the visual display to a selected configuration, then this indicates that the person has modified their brain activity pattern to one which is generally associated with satiety.

FIG. 16 shows that the person's self-modification of their electromagnetic brain activity has successfully modified their food consumption behavior. In this example, the person has seen food 801 in a bowl, but is turning away from food 801 rather than eating it. In this example, the person has been enabled to turn away from food 801 because they have self-modified their electromagnetic brain activity to a pattern 1505 which is generally associated with satiety. In an example, this is a case of "mind over platter."

In this example, the interactive feedback by which the person self-modifies their brain activity is visual feedback via a handheld electronic device. In another example, interactive feedback can be embodied in audio feedback—such as a series or tones or music whose parameters are changed by changes in measured brain activity. In another example, interactive feedback can be embodied in tactile feedback—such as a series of vibrations or pressure points applied to the person's skin by a wearable electronic device.

Figure 17:
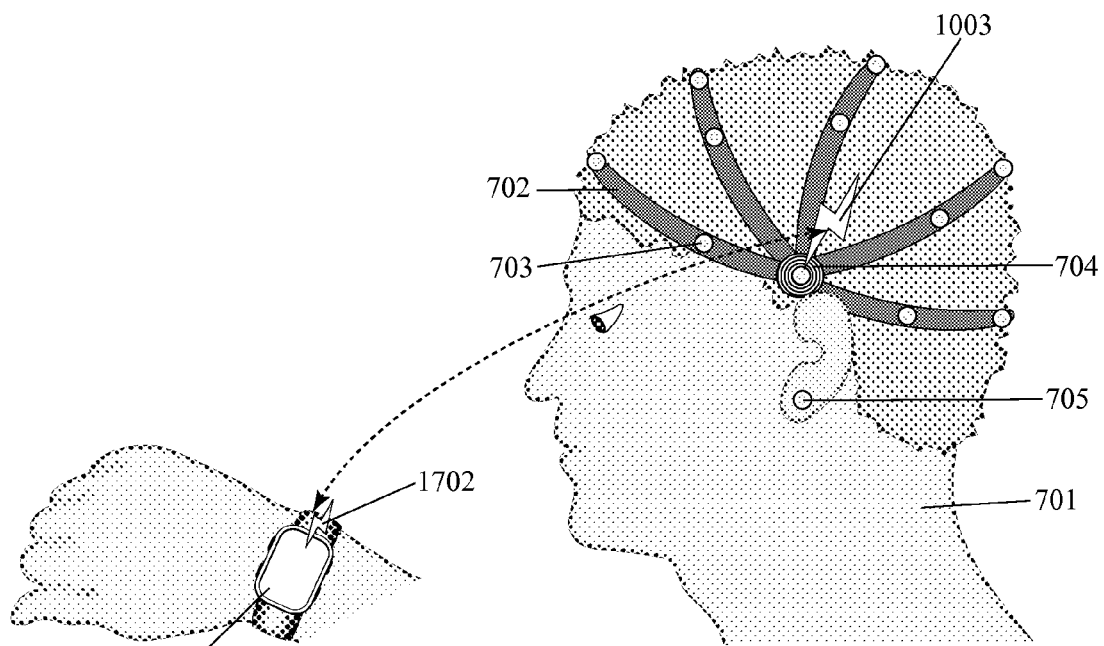
FIG. 17 shows a system comprising a wearable EEG monitor and a smart watch.

FIGS. 17 through 20 show some additional examples of systems of wirelessly-connected devices including a wearable EEG monitor which are used to measure and/or modify a person's food consumption. FIG. 17 shows a system comprising wearable EEG monitor 702 and smart watch (or other electronically-functional wrist band) 1701 which are in wireless communication with each other. In this example, wearable EEG monitor 702 and smart watch (or wrist band) 1701 together comprise a wirelessly-linked system for measuring and/or modifying a person's food consumption. Wireless communication between wearable EEG monitor 702 and smart watch (or wrist band) 1701 is represented by lightning bolt symbols 1702 and 1003 and the dotted-line bidirectional arrow between them.

In an example, smart watch (or wrist band) 1701 can comprise a convenient user interface for this system. In an example, smart watch (or wrist band) 1701 can comprise a human-to-computer interface for the system for entering information concerning food consumption during a first (calibration) period. In an example, smart watch (or wrist band) 1701 can house key data processing and/or transmitting components for this system. In an example, smart watch (or wrist band) 1701 can comprise a computer-to-human interface for providing feedback to the person from the system in order to modify the person's food consumption.

In an example, this invention can be embodied in a system for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; and a smart watch and/or electronically-functional band which is configured to be worn on a person's wrist.

In an example, this invention can be embodied in a system for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; a smart watch and/or electronically-functional band which is configured to be worn on a person's wrist; and a database which includes associations between specific patterns of food consumption and specific patterns of electromagnetic brain activity, which translates specific types and amounts of food into specific types and amounts of nutrients, or which does both.

Figure 18:
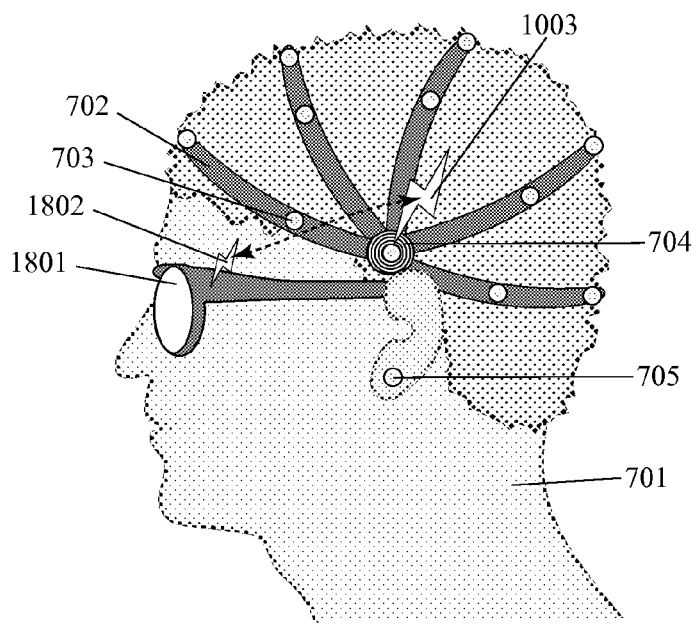
FIG. 18 shows a system comprising a wearable EEG monitor and electronically-functional eyewear.

FIG. 18 shows a system comprising wearable EEG monitor 702 and electronically-functional eyewear 1801 which are in wireless communication with each other. In this example, wearable EEG monitor and eyewear 1801 together comprise a wirelessly-linked system for measuring and/or modifying a person's food consumption. Wireless communication between wearable EEG monitor 702 and electronically-functional eyewear 1801 is represented by lightning bolt symbols 1802 and 1003 and the dotted-line arrow between them.

In an example, electronically-functional eyewear 1801 can comprise a convenient user interface for this system. In an example, electronically-functional eyewear 1801 can comprise a wearable camera whose images are analyzed to provide information concerning food consumption during a first (calibration) period. In an example, electronically-functional eyewear 1801 can house key data processing and/or transmitting components for this system. In an example, electronically-functional eyewear 1801 can comprise a computer-to-human interface for providing augmented reality visual feedback to modify the person's food consumption.

In an example, this invention can be embodied in a system for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; and a pair of smart glasses and/or electronically-functional eyewear which is configured to be worn on a person's head.

In an example, this invention can be embodied in a system for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; a pair of smart glasses and/or electronically-functional eyewear which is configured to be worn on a person's head; and a database which includes associations between specific patterns of food consumption and specific patterns of electromagnetic brain activity, which translates specific types and amounts of food into specific types and amounts of nutrients, or which does both.

Figure 19:
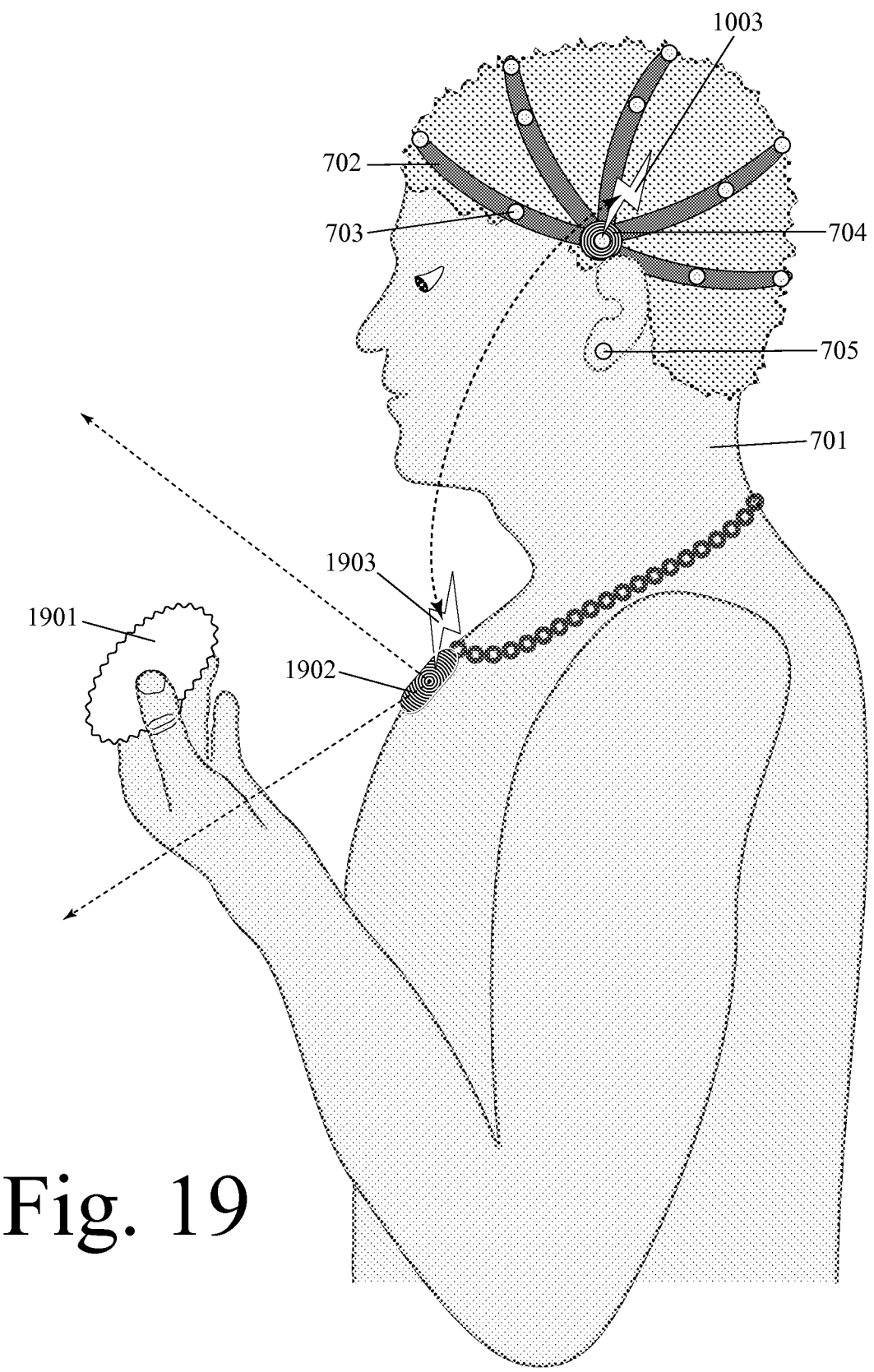
FIG. 19 shows a system comprising a wearable EEG monitor and an electronically-functional necklace.

FIG. 19 shows a system comprising wearable EEG monitor 702 and a neck-worn device 1902 which are in wireless communication with each other. In this example, wearable EEG monitor 702 and neck-worn device 1902 together comprise a wirelessly-linked system for measuring and/or modifying a person's food consumption. Wireless communication between wearable EEG monitor 702 and neck-worn device 1902 is represented by lightning bolt symbols 1903 and 1003 and the dotted-line arrow between them.

In an example, neck-worn device 1902 can comprise an electronically-functional necklace and/or a wearable camera. In an example, a neck-worn device comprising a wearable camera can take pictures of food 1901 as a person eats. Analysis of such food images can provide food consumption tracking during a first (calibration) time period. In an example, neck-worn device 1902 can further comprise a microphone. In an example, to help preserve visual privacy, a wearable camera may only be activated to take pictures when a microphone detects chewing and/or swallowing sounds which indicate that the person is probably eating. In an example, neck-worn device 1902 can further comprise a convenient user interface for this system and/or house key data processing components for this system.

In an example, this invention can be embodied in a system for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; and a smart necklace and/or electronically-functional device which is configured to worn on a person's neck.

In an example, this invention can be embodied in a system for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; a smart necklace and/or electronically-functional device which is configured to worn on a person's neck; and a database which includes associations between specific patterns of food consumption and specific patterns of electromagnetic brain activity, which translates specific types and amounts of food into specific types and amounts of nutrients, or which does both.

Figure 20:
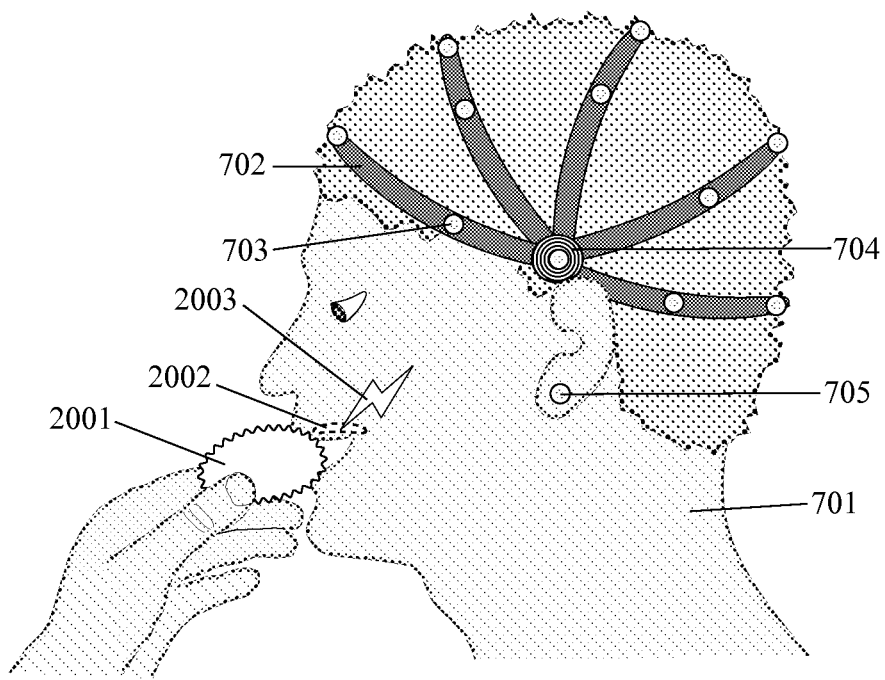
FIG. 20 shows a system comprising a wearable EEG monitor and an intraoral food sensor.

FIG. 20 shows a system comprising a wearable EEG monitor 702 and an intraoral food sensor 2002. These two components of the system are in wireless communication with each other. Together, wearable EEG monitor 702 and intraoral food sensor 2002 comprise a wirelessly-linked system for measuring and/or modifying a person's food consumption. In an example, intraoral food sensor 2002 can be attached to, or implanted within, the palatal vault of the person's mouth. In an example, intraoral food sensor can be attached to the person's teeth, gums, or jaw. In an example, intraoral food sensor can be attached to, or implanted within, the person's tongue. In an example, intraoral food sensor can be in fluid communication with saliva and other intraoral fluids and materials.

In an example, intraoral food sensor 2002 can analyze micro-samples of intraoral fluids in order to determine their chemical composition. In an example, for better operational efficiency, intraoral food sensor 2002 may only analyze micro-samples of intraoral fluids when other sensors (such as chewing sensors or swallow sensors) suggest that the person is eating something.

In an example, this invention can be embodied in a system for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; and a device which is configured to be in fluid communication with a person's mouth or other portion of the person's gastrointestinal tract.

In an example, this invention can be embodied in a system for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; a device which is configured to be in fluid communication with a person's mouth or other portion of the person's gastrointestinal tract; and a database which includes associations between specific patterns of food consumption and specific patterns of electromagnetic brain activity, which translates specific types and amounts of food into specific types and amounts of nutrients, or which does both.

Figure 21:
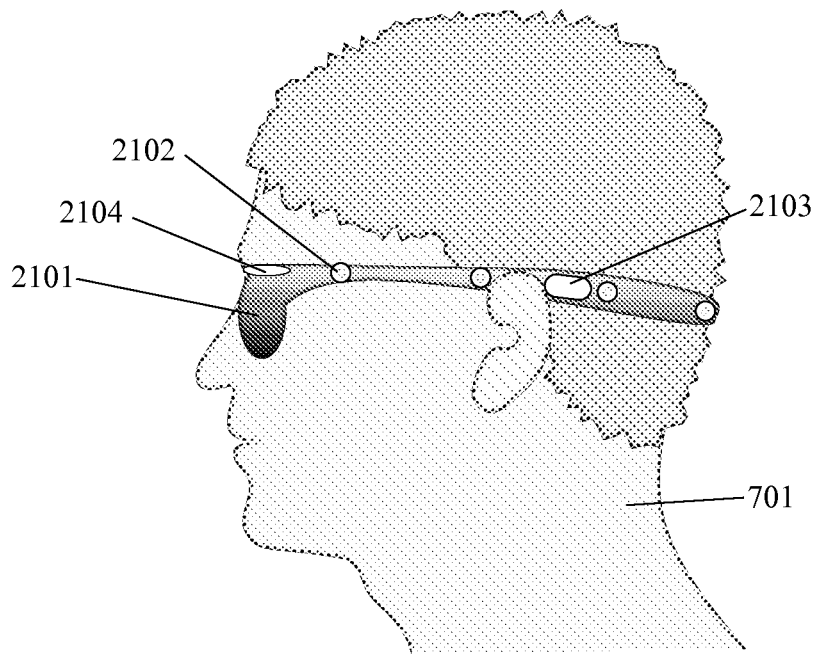
FIG. 21 shows a wearable EEG monitor comprising eyewear.

FIG. 21 shows a left-side view of another example of how this invention can be embodied in a wearable EEG monitor that is used to measure and/or modify a person's food consumption. In this example, this invention is embodied as a hybrid wearable EEG monitor with an integrated eyewear frame. In this example, wearable EEG monitor 2101 serves as both a brain activity monitor and electronically-functional eyewear. In this example, wearable EEG monitor 2101 comprises: a plurality of electrodes or other brain activity sensors (including 2102); a control unit 2103; and a wearable camera 2104. In an example, control unit 2103 further comprises a power source, a data processor, and a wireless data transmitter.

In this example, the anterior portion of wearable EEG monitor 2101 serves as an eyewear frame and the posterior portion of wearable EEG monitor 2101 loops completely around the back of the person's head. In this example, the front of this device rests on the bridge of the person's nose and the sides of this device rest on the person's ears. In this example, the anterior and posterior portions of this device form a continuous arcing band which encircles the person's head at a relatively-constant level which is just above the person's nose and ears.

In this example, the eyewear portion of this device has lenses, but no display screen. In another example, the eyewear portion of this device may have a display screen, but no lenses. In another example, the eyewear portion of this device may have both a display screen and lenses. In an example, the eyewear portion of this device can serve as an augmented reality interface. In an example, the eyewear portion of this device can serve as an in-your-face interface.

In an example, this invention can be embodied in a device for measuring and/or modifying a person's food consumption comprising: eyewear which is configured to be worn on a person's head; one or more electrodes or other brain activity sensors which are configured by the eyewear to be less than one inch from the surface of the person's head; a mobile power source and/or power transducer, wherein a power transducer harvests power from human physiological activity and/or environmental energy sources; a data processor; and a data transmitting member.

In an example, this invention can be embodied in a device for measuring and/or modifying a person's food consumption comprising: eyewear which is configured to be worn on a person's head; one or more electrodes or other brain activity sensors which are configured by the eyewear to be less than one inch from the surface of the person's head; a mobile power source and/or power transducer, wherein a power transducer harvests power from human physiological activity and/or environmental energy sources; a data processor; a data transmitter; and a database which includes associations between specific patterns of food consumption and specific patterns of electromagnetic brain activity, which translates specific types and amounts of food into specific types and amounts of nutrients, or which does both.

Figure 22:
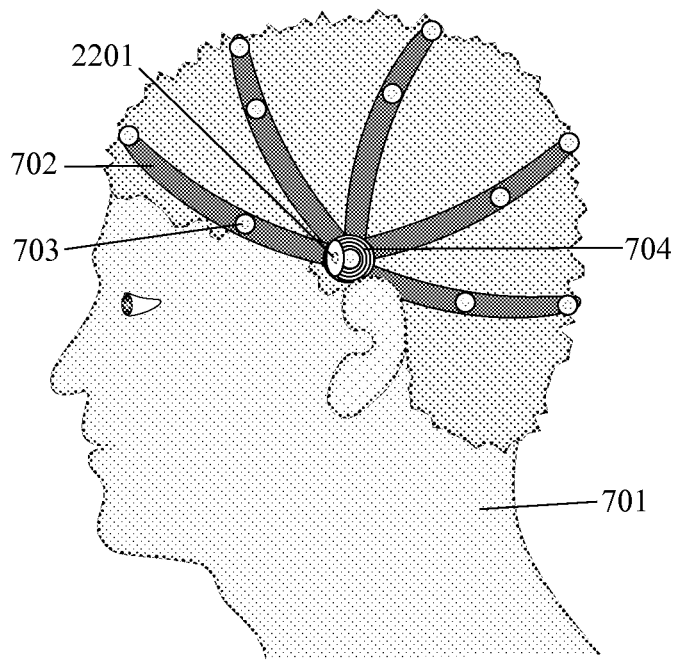
FIG. 22 shows a wearable EEG monitor with a camera.

FIG. 22 shows a wearable EEG monitor for measuring and/or modifying a person's food consumption that is that same as the one disclosed in FIG. 7, except that it now includes one or more wearable cameras 2201. In this example, a wearable camera 2201 is positioned on the side of a person's head near the point where multiple bands converge. In an example, two wearable cameras positioned on the left and right sides of the person's head can provide stereoscopic images of food during a first (calibration) time period. These images can be analyzed to estimate food consumption during the calibration period. In an example, visual pattern recognition can be used to determine food types. In an example, 3D modeling of stereoscopic images can be used to estimate food amounts.

In an example, wearable camera 2201 can take video pictures continually. In an example, in order to help maintain visual privacy, wearable camera 2201 may only be activated to take video pictures when data from other sources (such as motion sensors or sound sensors) suggests that the person is probably eating. In an example, in order to help maintain visual privacy, wearable camera 2201 may have a short focal length.

In an example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; and a wearable camera which is configured to record images of food consumption by a person.

In an example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; a wearable camera which is configured to record images of food consumption by a person; and a database which includes associations between specific patterns of food consumption and specific patterns of electromagnetic brain activity, which translates specific types and amounts of food into specific types and amounts of nutrients, or which does both.

In an example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; and a wearable camera which is configured to record images of food consumption by a person, wherein this camera is activated to take pictures when the person's electromagnetic brain activity pattern indicates probable food consumption.

In an example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; a wearable camera which is configured to record images of food consumption by a person, wherein this camera is activated to take pictures when the person's electromagnetic brain activity pattern indicates probable food consumption; and a database which includes associations between specific patterns of food consumption and specific patterns of electromagnetic brain activity, which translates specific types and amounts of food into specific types and amounts of nutrients, or which does both.

Figure 23:
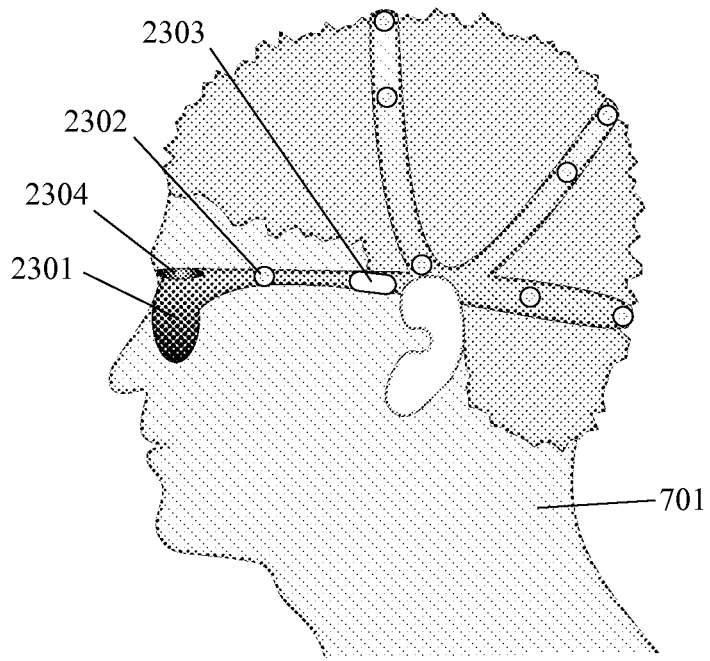
FIG. 23 shows a wearable EEG monitor comprising eyewear with two loops over the top of the head.

FIG. 23 shows a wearable EEG monitor that includes integrated eyewear, like the one disclosed in FIG. 21, but which also includes two upper arcuate members which loop over the top of the person's head. The addition of these two upper arcuate members increases the range of electrodes or other brain activity members covering the person's head. The addition of these two upper arcuate members provides electromagnetic recording coverage of the person's parietal lobe and upper occipital lobe. This can provide improved measurement of brain activity related to hunger and auditory sensation. In this example, control unit 2303 is located in front of the person's ears. In an example, control unit 2303 can further comprise a power source, a data processor, a data transmitter, and a user interface.

In this example, the bottom portions of the two upper arcuate members converge at locations just above the person's ears. In this example, the upper portions of the two upper arcuate members diverge, at an angle in the range of 20 to 80 degrees, as they leave a convergence location and loop around the top of the person's head. In various examples, these two upper arcuate members can be rigid, semi-rigid, flexible, or elastic. In various examples, these two upper arcuate members can be made of metal, plastic, or fabric.

Figure 24:
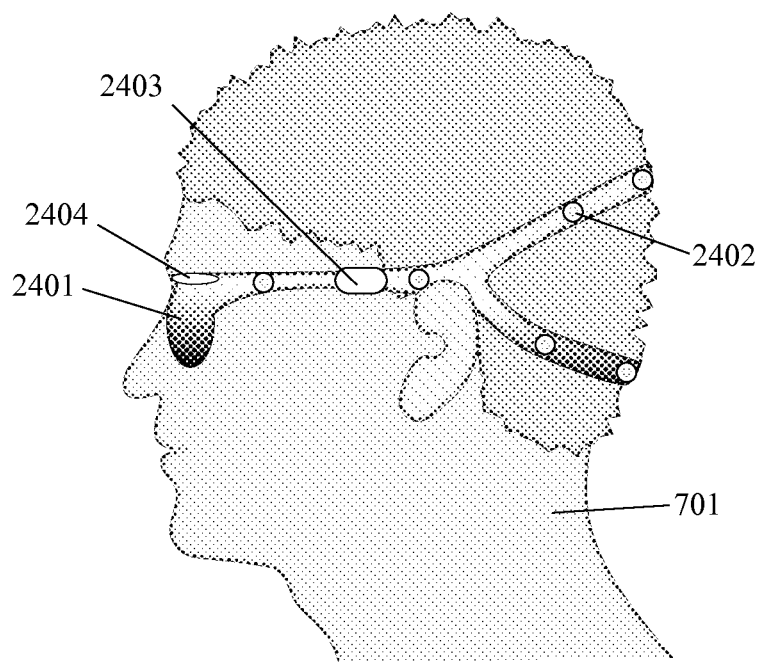
FIG. 24 shows a wearable EEG monitor comprising eyewear with two loops around the back of the head.

FIG. 24 shows another example of how this invention can be embodied in a wearable EEG monitor for measuring and/or modifying a person's food consumption, wherein this EEG monitor also serves as electronically-functional eyewear. In this example, the anterior portion of wearable EEG monitor 2401 comprises an eyewear frame. In this example, the posterior portion of wearable EEG monitor 2401 comprises two rear arcuate members which diverge from locations near the person's ears to loop around the back of the person's head. In this example, these two rear arcuate members diverge at an angle in the range of 20 to 80 degrees as they loop around the back of the person's head.

In the example shown in FIG. 24, a wearable EEG monitor 2401 for measuring and/or modifying a person's food consumption comprises: a plurality of electrodes or other brain activity sensors (including 2402); a control unit 2403; and a wearable camera 2404. In an example, control unit 2403 can further comprise a power source, data processor, a data transmitter, and a user interface. In various examples, these two rear arcuate members can be rigid, semi-rigid, flexible, or elastic. In various examples, these two rear arcuate members can be made of metal, plastic, or fabric.

Figure 25:
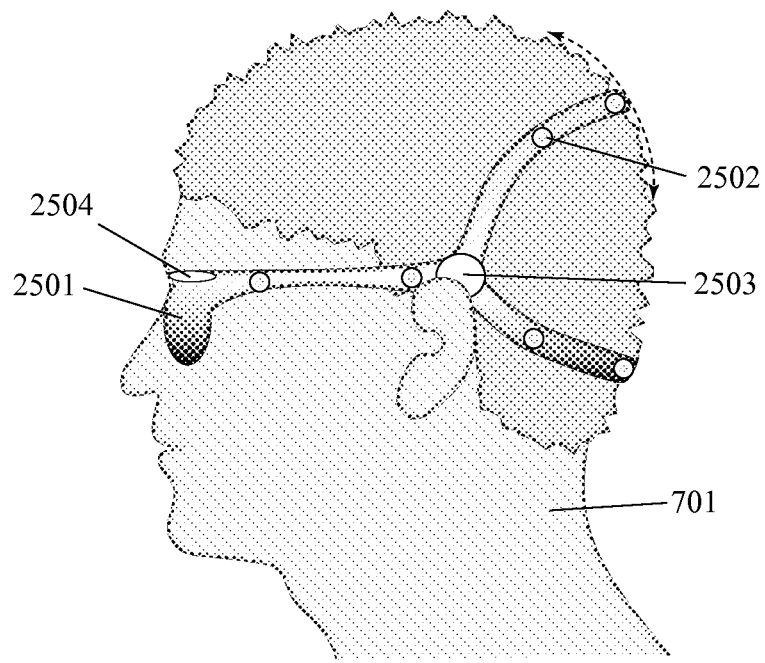
FIG. 25 shows a wearable EEG monitor comprising eyewear with a pivoting loop around the back of the head.

FIG. 25 shows an example of a wearable EEG monitor (2501) for measuring and/or modifying a person's food consumption that is similar to the one disclosed in FIG. 24, except that at least one of the two rear arcuate members can be radially-pivoted around their convergence point (where control unit 2503 is located, in this example). This pivoting action is represented in FIG. 25 by an arcuate dotted-line arrow above the upper rear arcuate member. This pivoting action changes the angle at which the two rear arcuate members diverge as they loop around the back of the person's head. This pivoting action enables customization and/or adjustment of the locations of electrodes or other brain activity sensors (including 2502) which span the person's occipital lobe and/or parietal lobe. In an example, this device can also comprise a control unit which further comprises a power source, a data processor, and a data transmitter.

Figure 26:
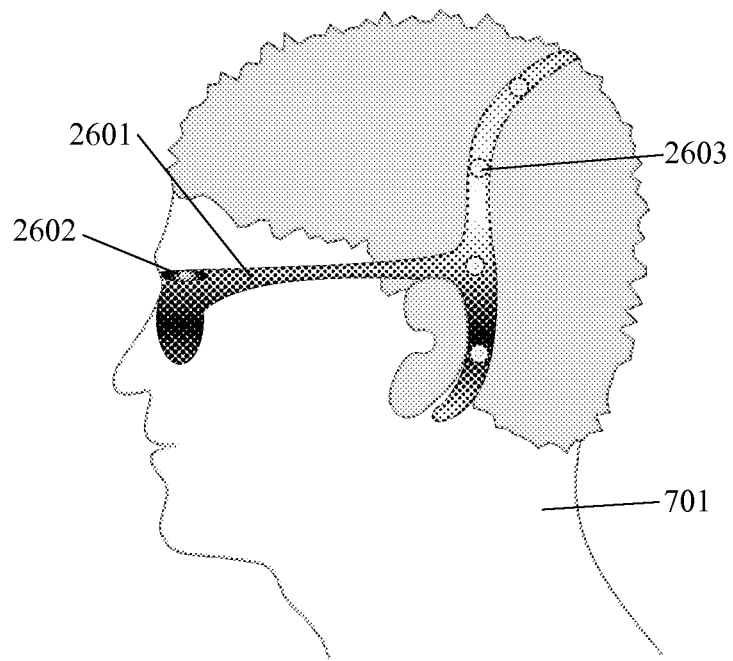
FIG. 26 shows a wearable EEG monitor comprising eyewear with a loop over the back of the head.

FIG. 26 shows another example of a wearable EEG monitor (2601) with an integrated eyewear frame which measures and/or modifies a person's food consumption. In this example, wearable EEG monitor 2601 comprises a plurality of electrodes or other brain activity sensors (including 2603) and a wearable camera 2602. In an example, this device can also comprise a control unit which further comprises a power source, a data processor, and a data transmitter. In this example, the anterior portion of wearable EEG monitor 2601 is an eyewear frame. In this example, the posterior portion of wearable EEG monitor 2601: starts near the bottom of the left ear, curves up around the rear of the left ear, loops over the top of the person's head, curves down around the rear of the right ear, and then ends near the bottom of the right ear. In this example, the anterior portion of the device rests on the bridge of the person's nose and the posterior portions of the device rest on the tops of the person's ears.

Figure 27:
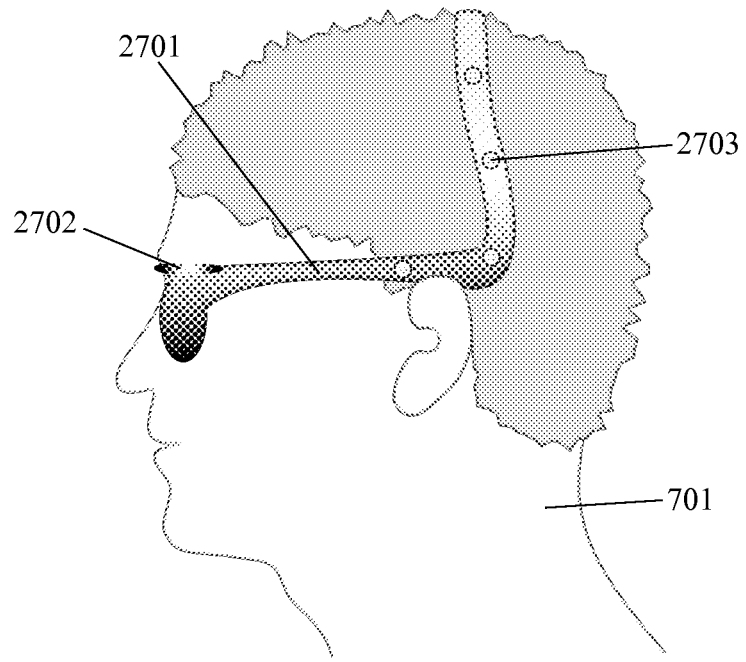
FIG. 27 shows a wearable EEG monitor comprising eyewear that curves up over the head.

FIG. 27 shows another example of a wearable EEG monitor (2701) with an integrated eyewear frame which measures and/or modifies a person's food consumption. In this example, wearable EEG monitor 2701 comprises a plurality of electrodes or other brain activity sensors (including 2703) and a wearable camera 2702. In an example, this device can also comprise a control unit which further comprises a power source, a data processor, and a data transmitter. In this example, the anterior portion of wearable EEG monitor 2701 is an eyewear frame. In this example, the device: spans backward from the bridge of the person's nose to a position atop the person's left ear; then curves up and over the top of the person's head; then curves down to a position atop the person's right ear; and then spans forward to the bridge of the person's nose. In this example, the anterior portion of this device rests on the bridge of the person's nose and the side portions of this device rest on the tops of the person's ears.

Figure 28:
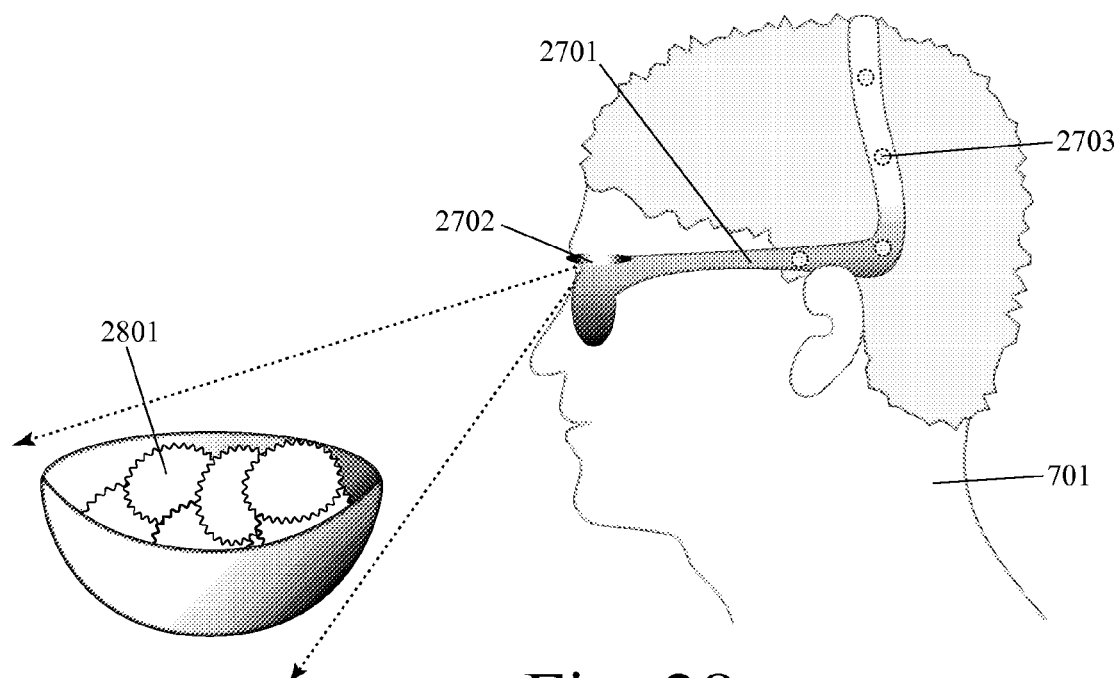
FIG. 28 shows a calibration period wherein a person views food, which evokes a response in their brain.
Figure 29:
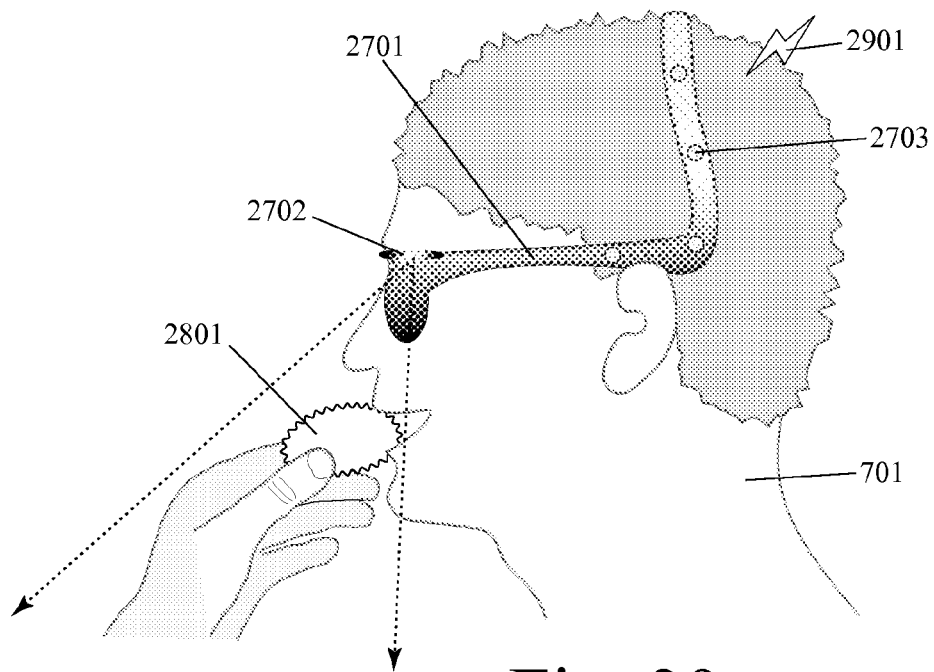
FIG. 29 shows a calibration period as a person eats the food, including automatic imaging of the food.

The sequence in FIGS. 28 through 32 shows an example of how the wearable EEG monitor that was introduced in FIG. 27 can be used to measure and modify a person's food consumption. In FIG. 28, person 701 sees (and smells) food 2801, but has not yet started to eat it. In FIG. 29, person 701 eats food 2801, which triggers a change 2901 in the electromagnetic brain activity which is recorded by the electrodes (including 2703) on wearable EEG monitor 2701. In an example, camera 2702 can take pictures of food 2801. In an example, the system can use previously-identified associations between food consumption and brain activity to identify the type and amount of food consumed, including food 2801, during a period of time. In an example, the system can automatically create a log of food consumption during this period of time.

Figure 30:
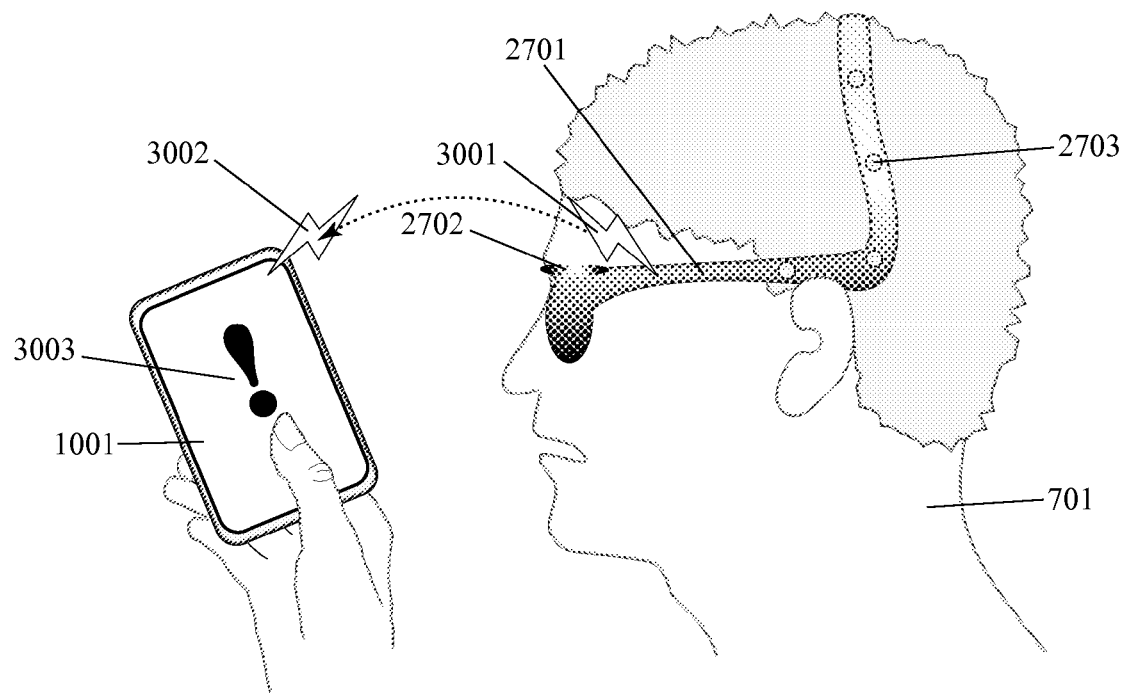
FIG. 30 shows a person receiving feedback concerning food consumption.

In FIG. 30, person 701 receives feedback 3003 from the system via a handheld electronic device 1001 in order to modify their food consumption. In this example, wearable EEG monitor 2701 and handheld electronic device 1001 are in wireless communication, as represented by lightning bolt symbols 3001 and 3002. In an example, an automatically-created food log based on brain activity patterns can indicate that the person has eaten an unhealthy type and/or amount of food during a period of time. In an example, feedback based on this log may suggest that the person should modify their food consumption to improve their nutrition, manage their energy balance, and/or meet health goals.

Figure 31:
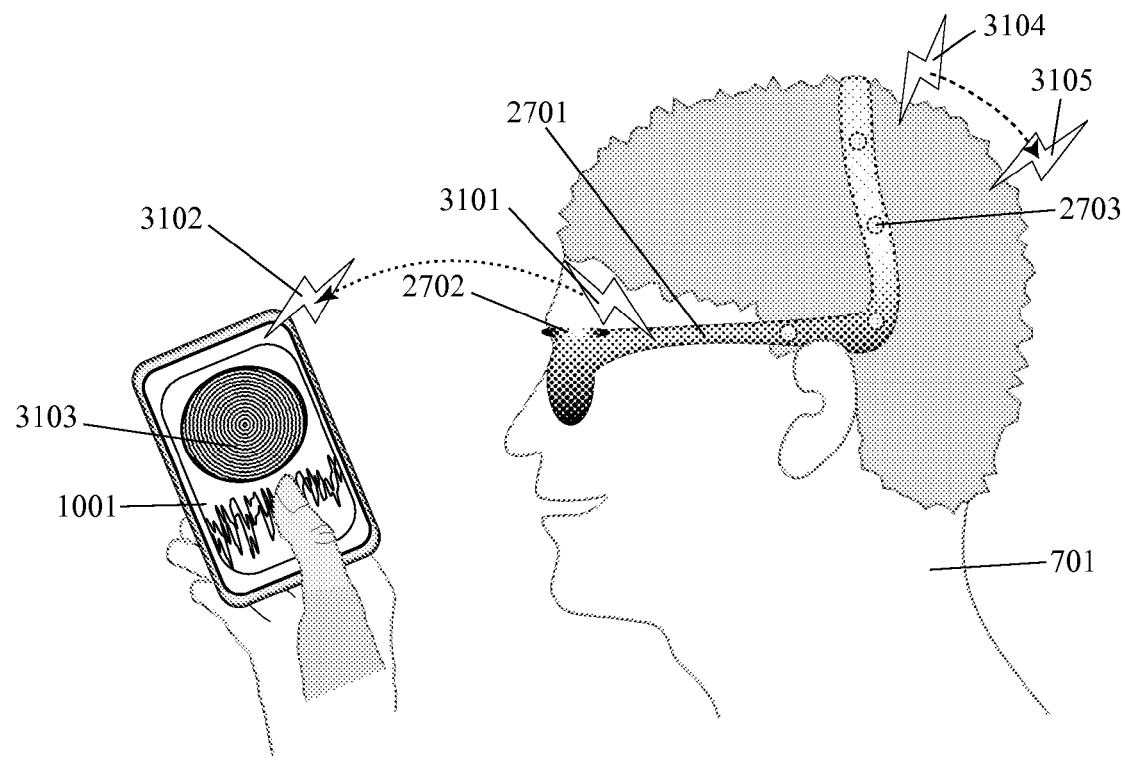
FIG. 31 shows a person modifying their brain activity using interactive biofeedback.

In an example, a person can directly modify their food consumption based on feedback 3003. In another example, as shown in FIG. 31, person 701 can indirectly modify their food consumption via self-modification of brain activity. In this latter example, shown in FIG. 31, person 701 uses an interactive biofeedback interface 3103 to self-modify their brain activity pattern which, in turn, modifies their food consumption. In various examples, an interactive biofeedback interface can be visual, auditory, and/or tactile. In this example, wearable EEG monitor 2701 and handheld electronic device 1001 share interactive wireless communication, as represented by lightning bolt symbols 3101 and 3102.

In an example, person 701 can use interactive biofeedback interface 3103 to self-modify their brain activity pattern from a first pattern 3104 which is generally associated with hunger to a second pattern 3105 which is generally associated with satiety. In an example, when the person is able to self-modify their brain activity to a pattern associated with satiety, they can better avoid eating an unhealthy amount or type of food. In an example, person 701 can initiate use of biofeedback interface 3103 based on feedback 3003. In an example, the person can initiate use of this biofeedback interface 3103 on their own, without prompting by feedback from a system.

Figure 32:
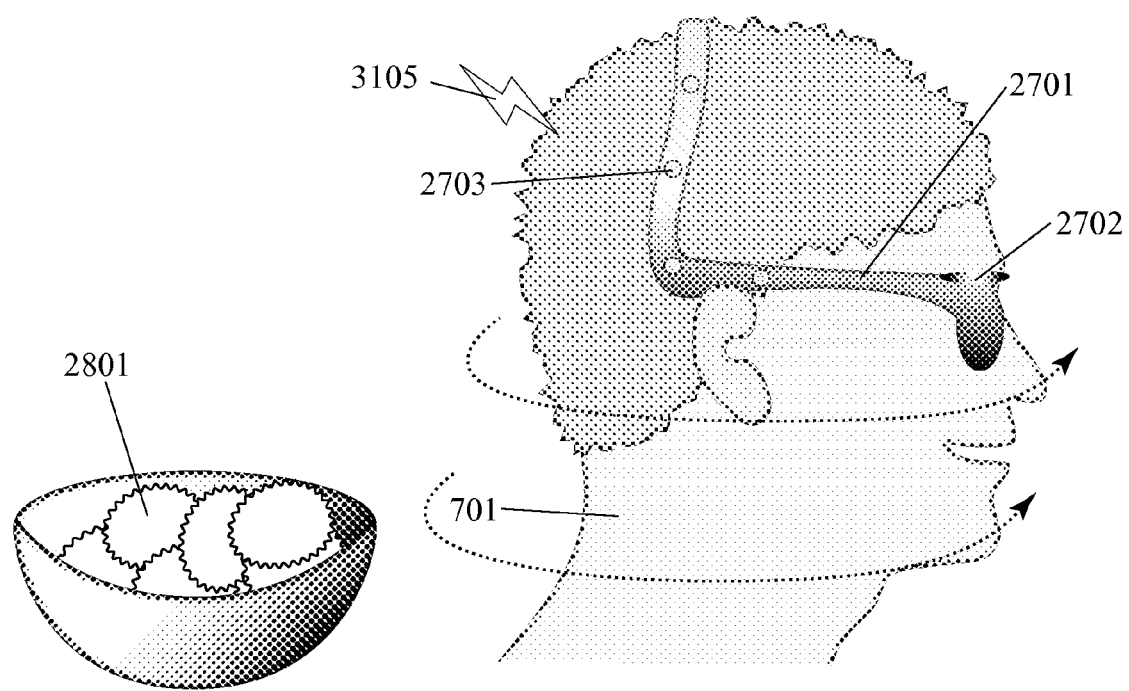
FIG. 32 shows a person's behavior affected by interactive feedback.

FIG. 32 shows person 701 turning away from a bowl of food 2801 instead of eating it. In an example, this modification of food consumption can be a direct result of feedback 3003 that was shown in FIG. 30. In an example, this modification of food consumption can be an indirect result of self-modification of brain activity patterns with the help of interactive biofeedback interface 3103, as shown in FIG. 31. In an example, this modification of food consumption can be the combined result of direct feedback and interactive biofeedback.

Figure 33:
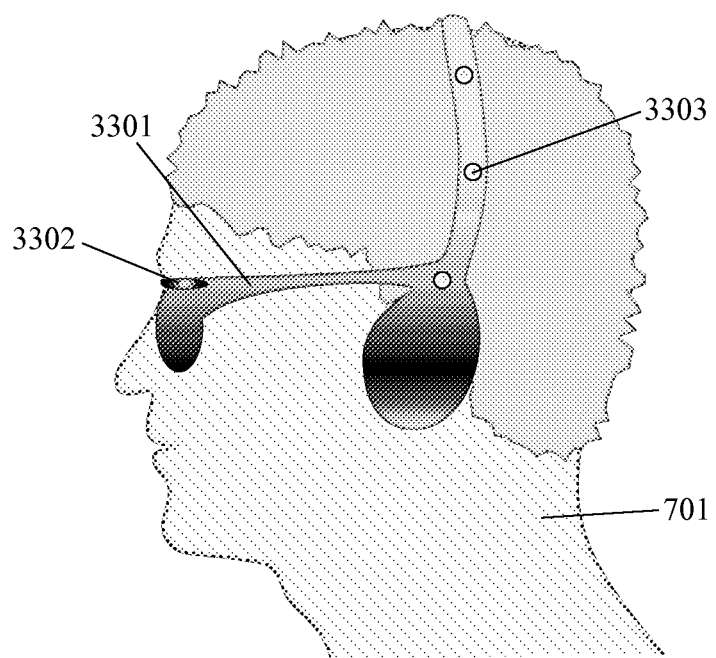
FIG. 33 shows a wearable EEG monitor comprising a combination of eyewear and headphones.

FIG. 33 shows an example of a wearable EEG monitor 3301 for measuring and/or modifying a person's food consumption which integrates both eyewear and headphone components. Wearable EEG monitor 3301 comprises a plurality of electrodes or other brain activity sensors (including 3303) and wearable camera 3302. In an example, this monitor can further comprise a control unit which, in turn, can comprise a power source, a data processor, and a data transmitter. In this example, the anterior portion of wearable EEG monitor comprises eyewear frames. In this example, the posterior portion of wearable EEG monitor comprises a set of headphones which cover the person's ears and loop over the top of the person's head. In this example, the eyewear frame and headphones are integrated into a single device.

Figure 34:
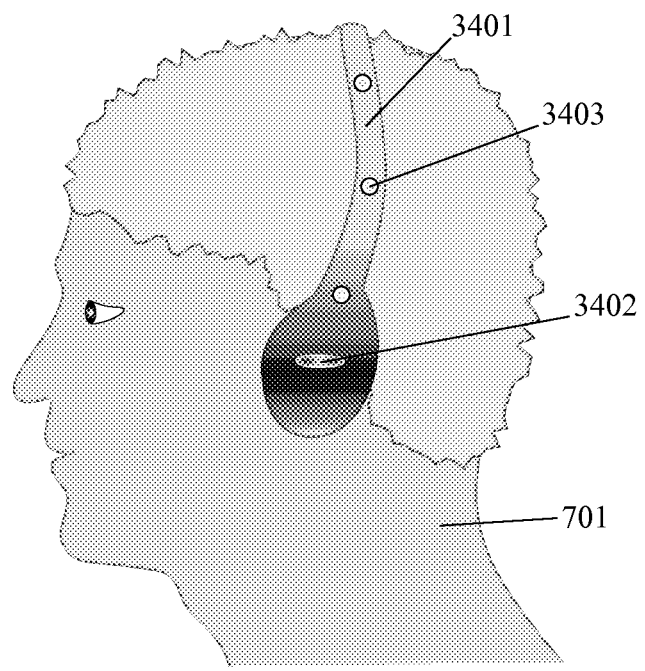
FIG. 34 shows a wearable EEG monitor comprising headphones alone.

FIG. 34 shows an example of a wearable EEG monitor 3401 for measuring and/or modifying a person's food consumption which is shaped like headphones which cover a person's ears and loop over the top of their head. Wearable EEG monitor 3401 comprises a plurality of electrodes or other brain activity sensors (including 3403) and one or more wearable cameras (including 3402). In an example, this monitor can further comprise a control unit which, in turn, can comprise a power source, a data processor, and a data transmitter.

Figure 35:
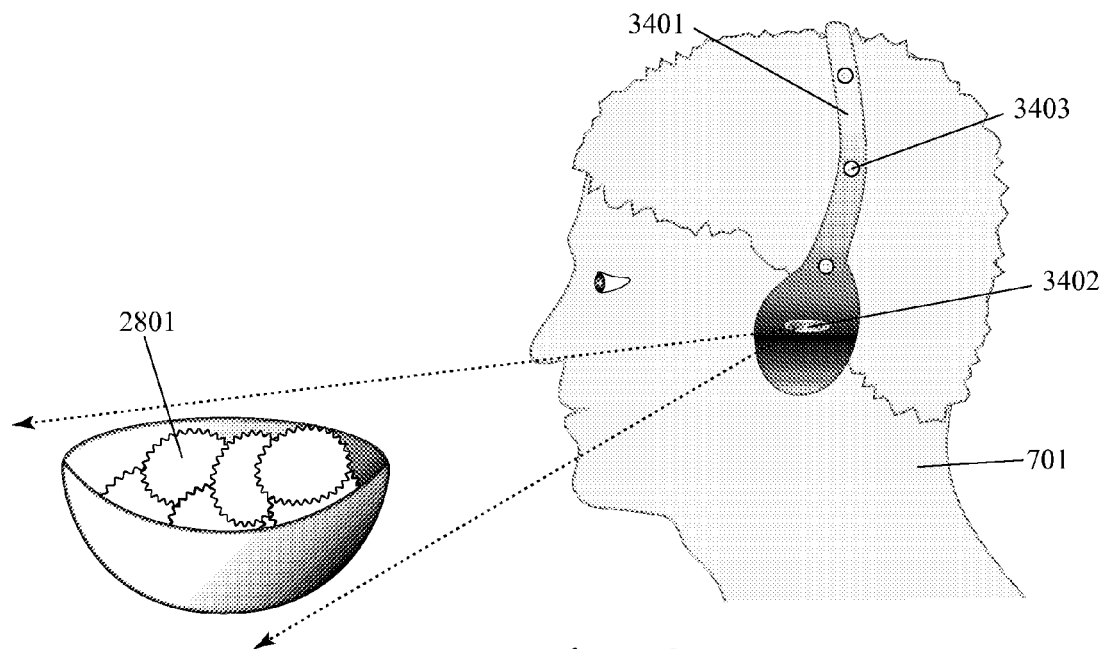
FIG. 35 shows a wearable EEG monitor with a camera that takes pictures of food before it is eaten.
Figure 36:
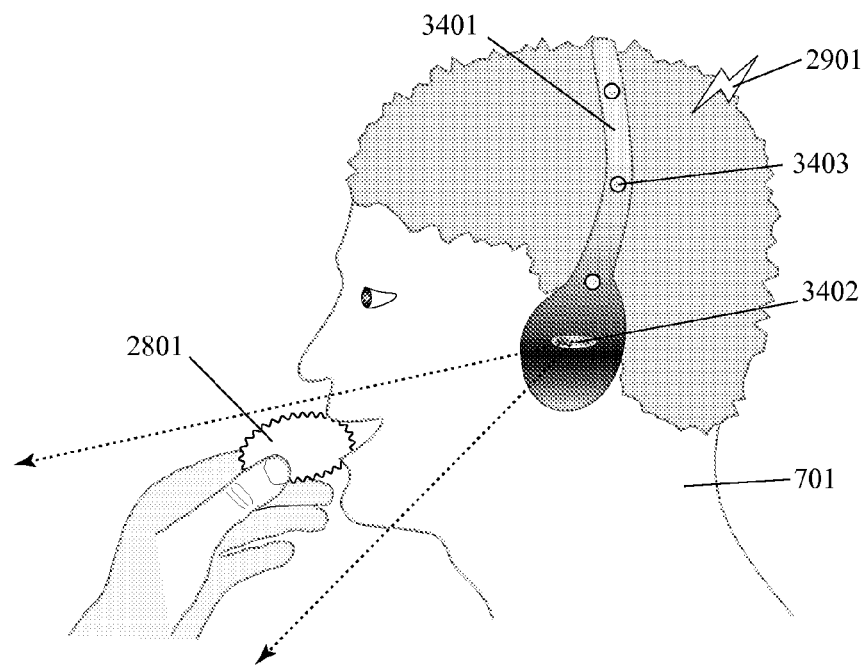
FIG. 36 shows a wearable EEG monitor with a camera that takes pictures of food and measures brain activity.

FIGS. 35 through 41 show examples of how wearable EEG monitor 3401 can be used to measure and/or modify a person's food consumption. FIG. 35 shows how one or more wearable cameras (including 3402) can take pictures of food 2801 before it is eaten. FIG. 36 shows how one or more wearable cameras (including 3402) can take pictures of food while it is being eaten. FIG. 36 also shows how electrodes or other brain activity sensors (including 3403) can record a change 2901 in electromagnetic brain activity which is caused by the consumption of food 2801.

Figure 37:
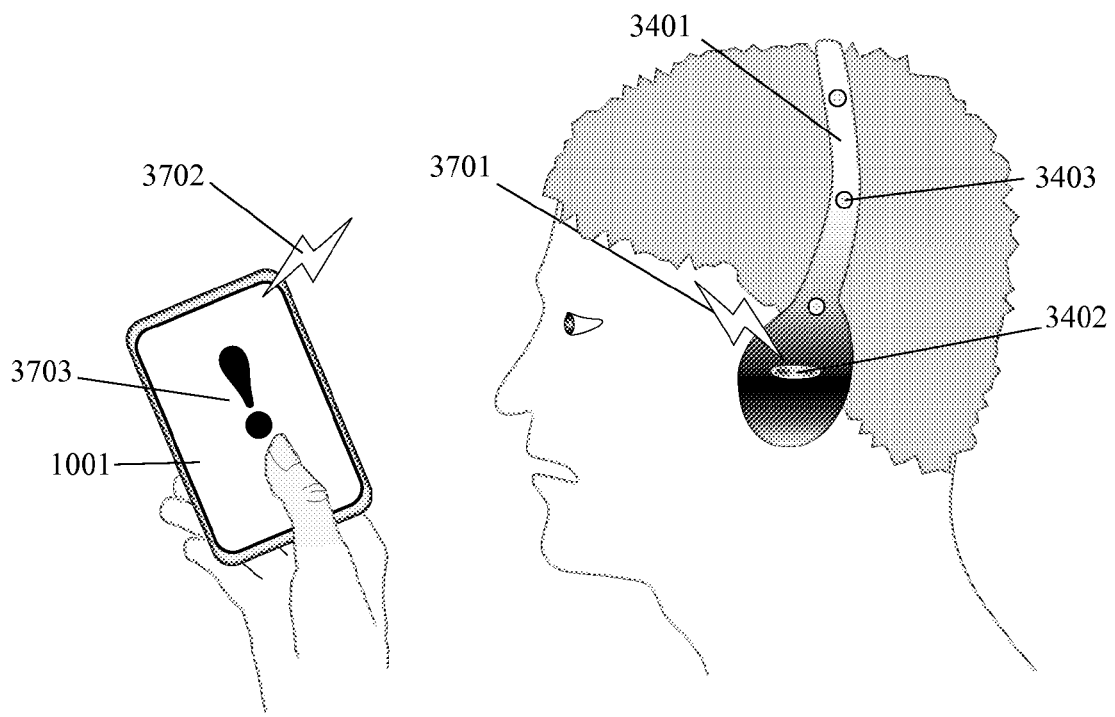
FIG. 37 shows a wearable EEG monitor conveying feedback about food consumption.
Figure 38:
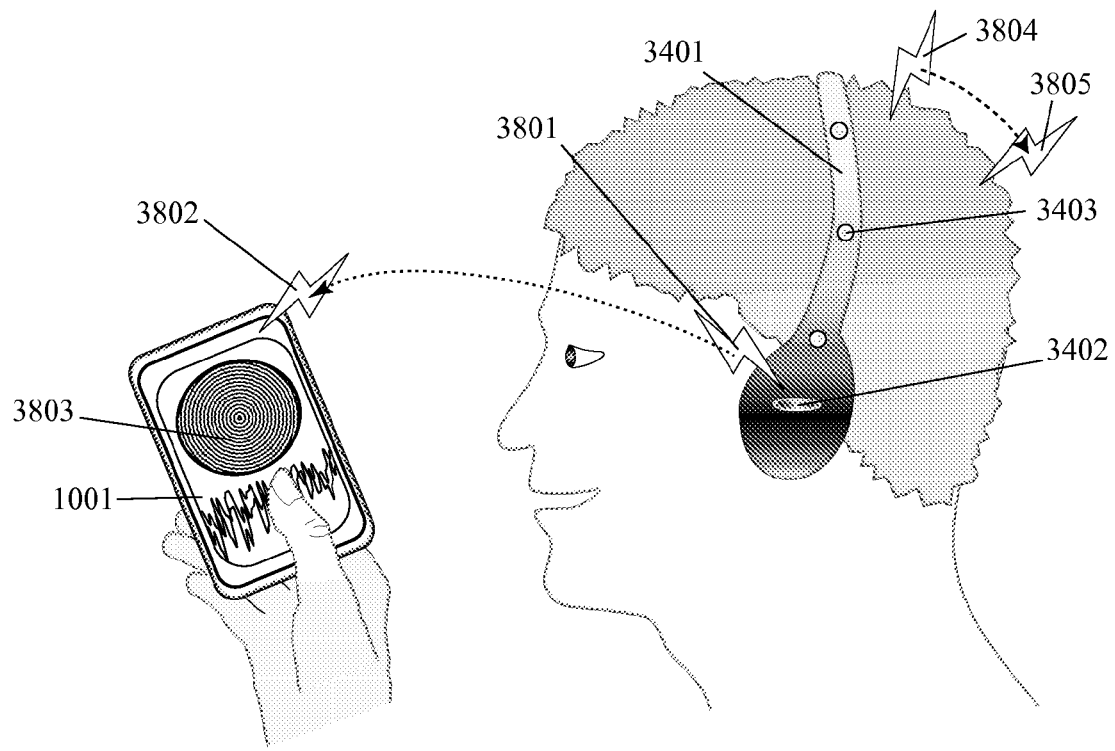
FIG. 38 shows a person modifying their brain activity using interactive biofeedback.
Figure 39:
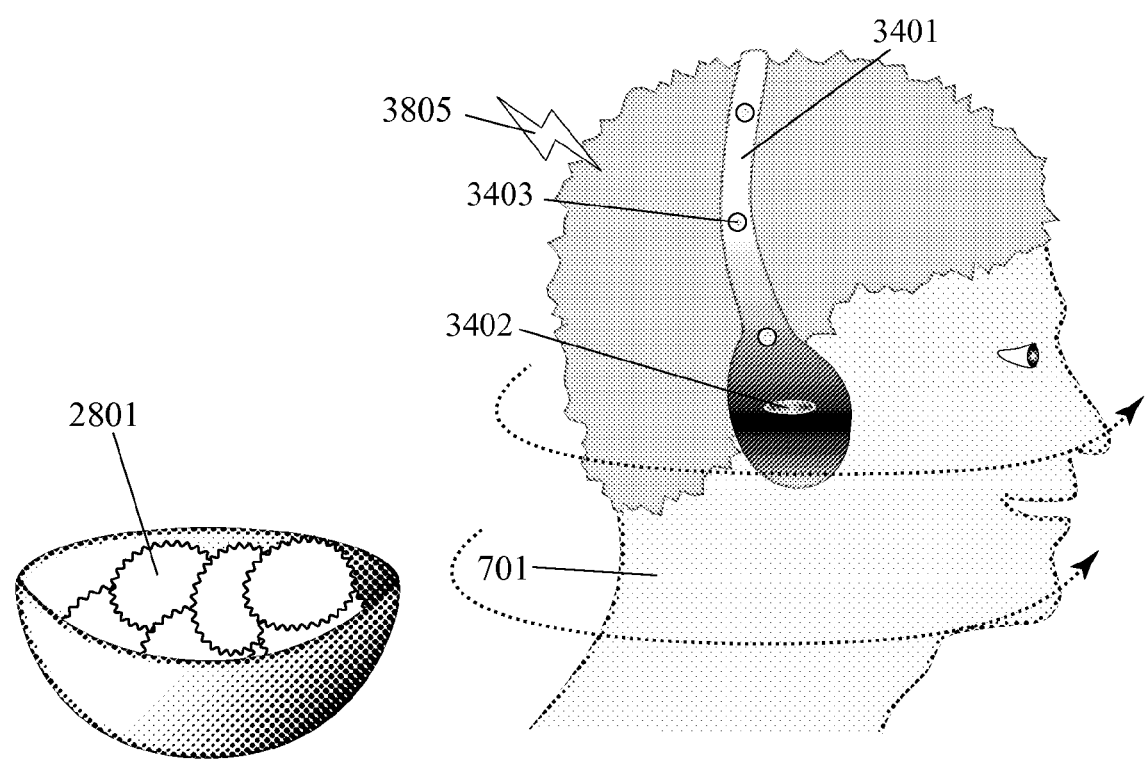
FIG. 39 shows a person's behavior affected by interactive feedback.

FIG. 37 shows wearable EEG monitor 3401 being in wireless communication with handheld electronic device 1001 and conveying feedback 3703 concerning food consumption to the person. FIG. 38 shows wearable EEG monitor 3401 being in wireless communication with handheld electronic device 1001 and helping the person to self-modify their brain activity using interactive biofeedback interface 3803. In an example, this biofeedback helps the person to self-modify their brain activity from a first pattern 3804 that is associated with hunger to a second pattern 3805 that is associated with satiety. FIG. 39 shows that the person turns away from food 2801 due to feedback 3703, self-modification of brain activity to a satiety pattern 3805, or both.

In an example, this invention can be embodied in a device for measuring and/or modifying a person's food consumption comprising: a set of headphones or hair band which is configured to be worn over the top of a person's head; one or more electrodes or other brain activity sensors which are configured by the set of headphones or hair band to be less than one inch from the surface of the person's head; a mobile power source and/or power transducer, wherein a power transducer harvests power from human physiological activity and/or environmental energy sources; a data processor; and a data transmitting member.

In an example, this invention can be embodied in a device for measuring and/or modifying a person's food consumption comprising: a set of headphones or hair band which is configured to be worn over the top of a person's head; one or more electrodes or other brain activity sensors which are configured by the set of headphones or hair band to be less than one inch from the surface of the person's head; a mobile power source and/or power transducer, wherein a power transducer harvests power from human physiological activity and/or environmental energy sources; a data processor; a data transmitter; and a database which includes associations between specific patterns of food consumption and specific patterns of electromagnetic brain activity, which translates specific types and amounts of food into specific types and amounts of nutrients, or which does both.

Figure 40:
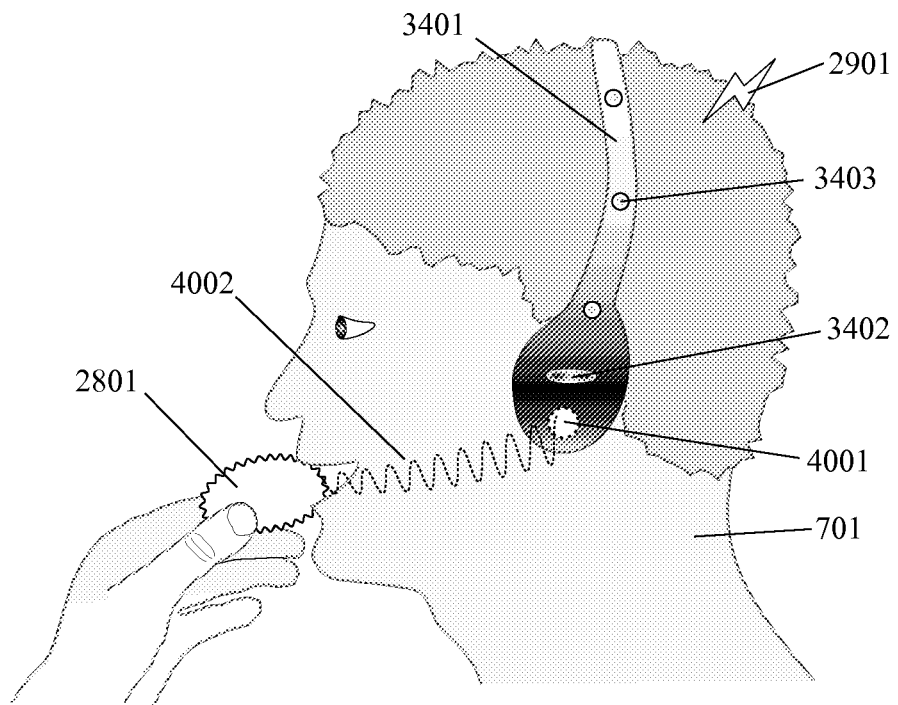
FIG. 40 shows a wearable EEG monitor comprising a headphone set with a microphone.
Figure 41:
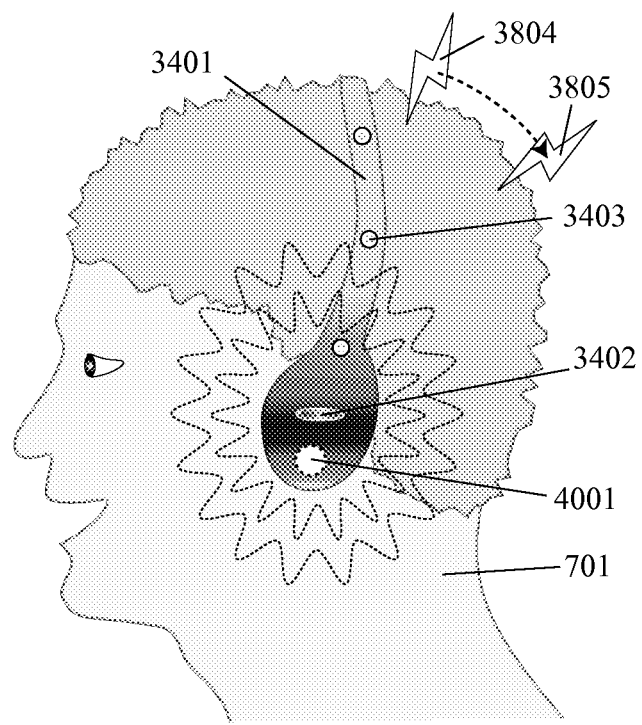
FIG. 41 shows a wearable EEG monitor with auditory biofeedback.

FIG. 40 shows a variation on a headphone-style wearable EEG monitor which also includes a microphone 4001. In this example, the wearable EEG monitor can also detect eating by detecting chewing and/or swallowing sounds. FIG. 41 shows a variation on the headphone-style wearable EEG monitor in which an interactive biofeedback interface is auditory in nature. In this example, changes in sound tones and/or musical parameters help person 701 to self-modify their brain activity pattern from a first pattern 3804 to a second pattern 3805. This change in brain activity pattern, in turn, modifies their food consumption.

In an example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; and a microphone.

In an example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; a microphone; and a database which includes associations between specific patterns of food consumption and specific patterns of electromagnetic brain activity, which translates specific types and amounts of food into specific types and amounts of nutrients, or which does both.

In an example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; and an auditory interface for computer-to-human communication.

In an example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; an auditory interface for computer-to-human communication; and a database which includes associations between specific patterns of food consumption and specific patterns of electromagnetic brain activity, which translates specific types and amounts of food into specific types and amounts of nutrients, or which does both.

Figure 42:
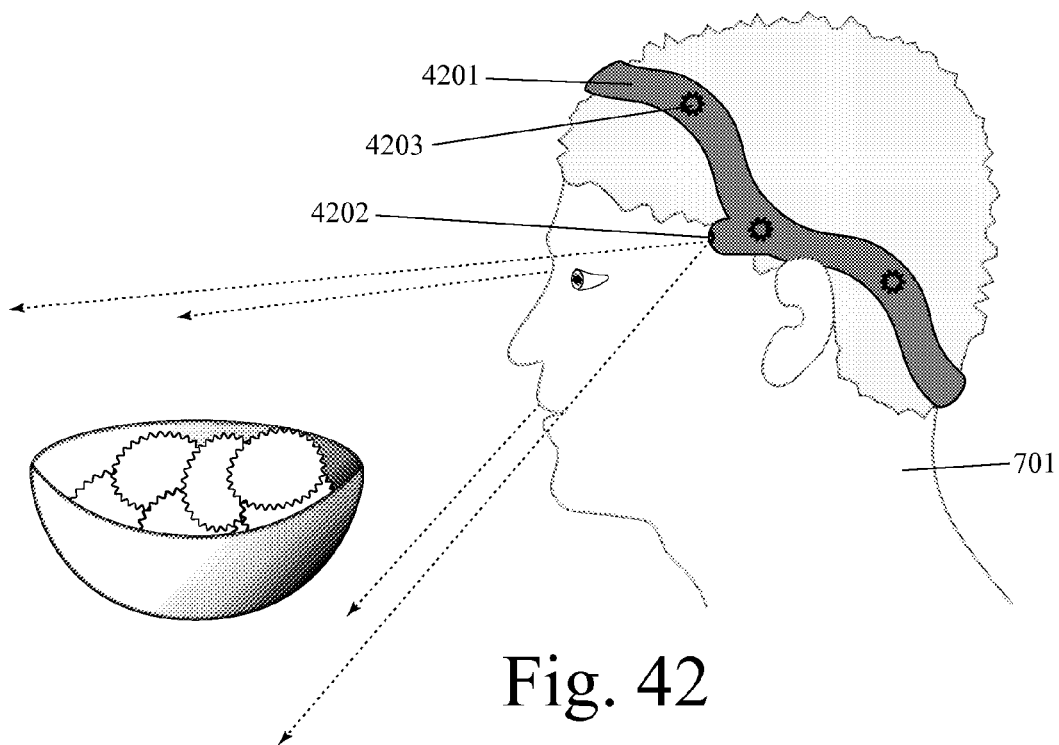
FIG. 42 shows a wearable EEG monitor which encircles the head in a sinusoidal manner.
Figure 43:
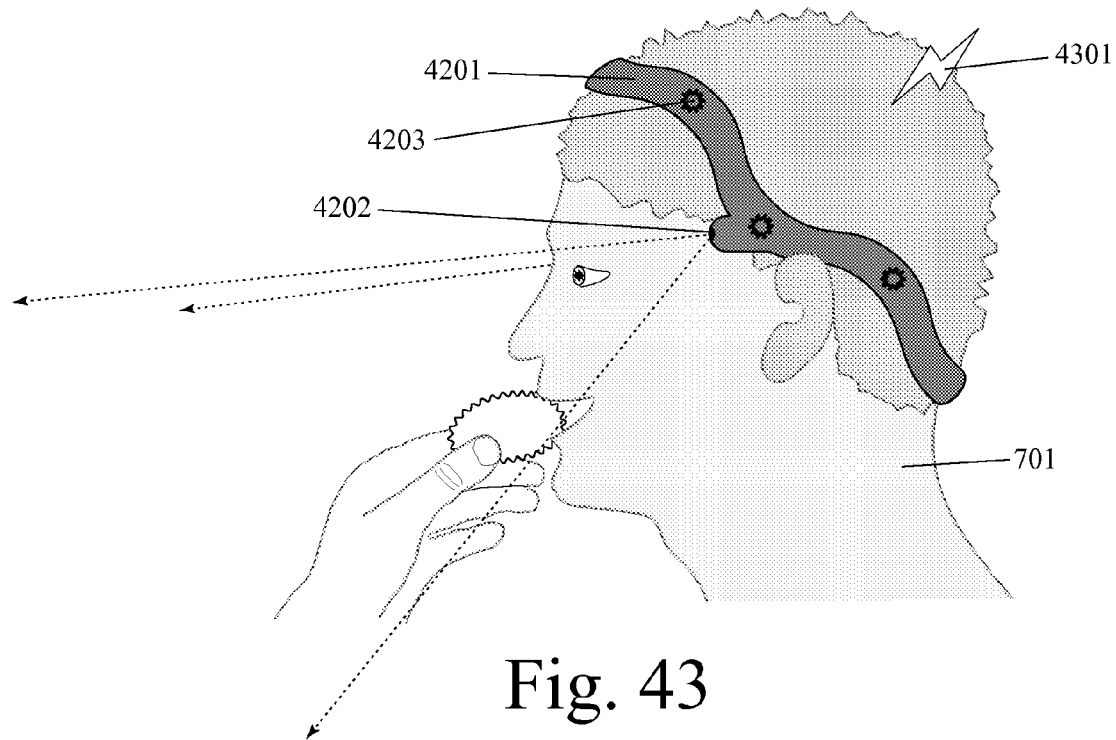
FIG. 43 shows food consumption triggering a change in brain activity.

FIGS. 42 and 43 show another example of a wearable EEG monitor (4201) which can be used to measure and/or modify a person's food consumption. Wearable EEG monitor 4201 comprises: a plurality of electrodes or other brain activity sensors (including 4203); and one or more wearable cameras (including 4202). In an example, wearable EEG monitor 4201 can further comprise a control unit. In an example, a control unit can further comprise a power source, a data processor, and a data transmitter. In this example, wearable EEG monitor 4201 encircles the person's head in a sinusoidal manner and rests on the tops of the person's ears. In the example shown in FIGS. 42 and 43, wearable EEG monitor 4201 comprises two wearable cameras, on the left and right sides of the person's head, in order to take stereoscopic pictures of food. Stereoscopic pictures of food can be useful for 3D modeling to better estimate food volume and the amount of food consumed by the person. FIG. 43 shows how consumption of food triggers a change 4301 in the person's electromagnetic brain activity. This change 4301 can be measured by the plurality of electrodes or other brain activity sensors (including 4203).

In an example, this invention can be embodied in a device for measuring and/or modifying a person's food consumption comprising: a headband which is configured to be worn around a person's head; one or more electrodes or other brain activity sensors which are configured by the headband to be less than one inch from the surface of the person's head; a mobile power source and/or power transducer, wherein a power transducer harvests power from human physiological activity and/or environmental energy sources; a data processor; and a data transmitting member.

In an example, this invention can be embodied in a device for measuring and/or modifying a person's food consumption comprising: a headband which is configured to be worn around a person's head; one or more electrodes or other brain activity sensors which are configured by the headband to be less than one inch from the surface of the person's head; a mobile power source and/or power transducer, wherein a power transducer harvests power from human physiological activity and/or environmental energy sources; a data processor; a data transmitter; and a database which includes associations between specific patterns of food consumption and specific patterns of electromagnetic brain activity, which translates specific types and amounts of food into specific types and amounts of nutrients, or which does both.

In an example, this invention can be embodied in a device for measuring and/or modifying a person's food consumption comprising: a headband which is configured to be worn around a person's head; one or more electrodes or other brain activity sensors which are configured by the headband to be less than one inch from the surface of the person's head; a mobile power source and/or power transducer, wherein a power transducer harvests power from human physiological activity and/or environmental energy sources; a data processor; a data transmitter; and a plurality of electromagnetic signal transmitters which are configured to be less than one inch from the surface of a person's head, wherein these electromagnetic signal transmitters collectively modify an electromagnetic field in order to reproduce a pattern of brain activity which is associated with satiety and/or consumption of a specific type of food, ingredient, or nutrient.

In an example, this invention can be embodied in a device for measuring and/or modifying a person's food consumption comprising: a headband which is configured to be worn around a person's head; one or more electrodes or other brain activity sensors which are configured by the headband to be less than one inch from the surface of the person's head; a mobile power source and/or power transducer, wherein a power transducer harvests power from human physiological activity and/or environmental energy sources; a data processor; a data transmitter; a plurality of electromagnetic signal transmitters which are configured to be less than one inch from the surface of a person's head, wherein these electromagnetic signal transmitters collectively modify an electromagnetic field in order to reproduce a pattern of brain activity which is associated with satiety and/or consumption of a specific type of food, ingredient, or nutrient; and a database which includes associations between specific patterns of food consumption and specific patterns of electromagnetic brain activity, which translates specific types and amounts of food into specific types and amounts of nutrients, or which does both.

Figure 44:
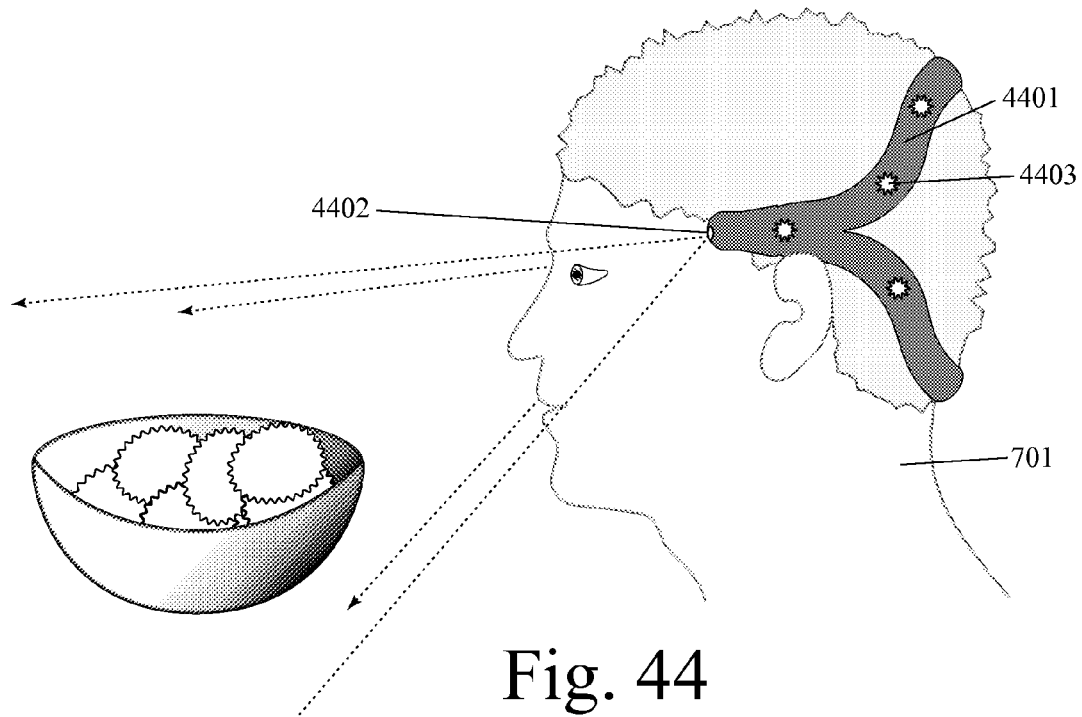
FIG. 44 shows a wearable EEG monitor shaped like a whale tail imaging food before it is eaten.
Figure 45:
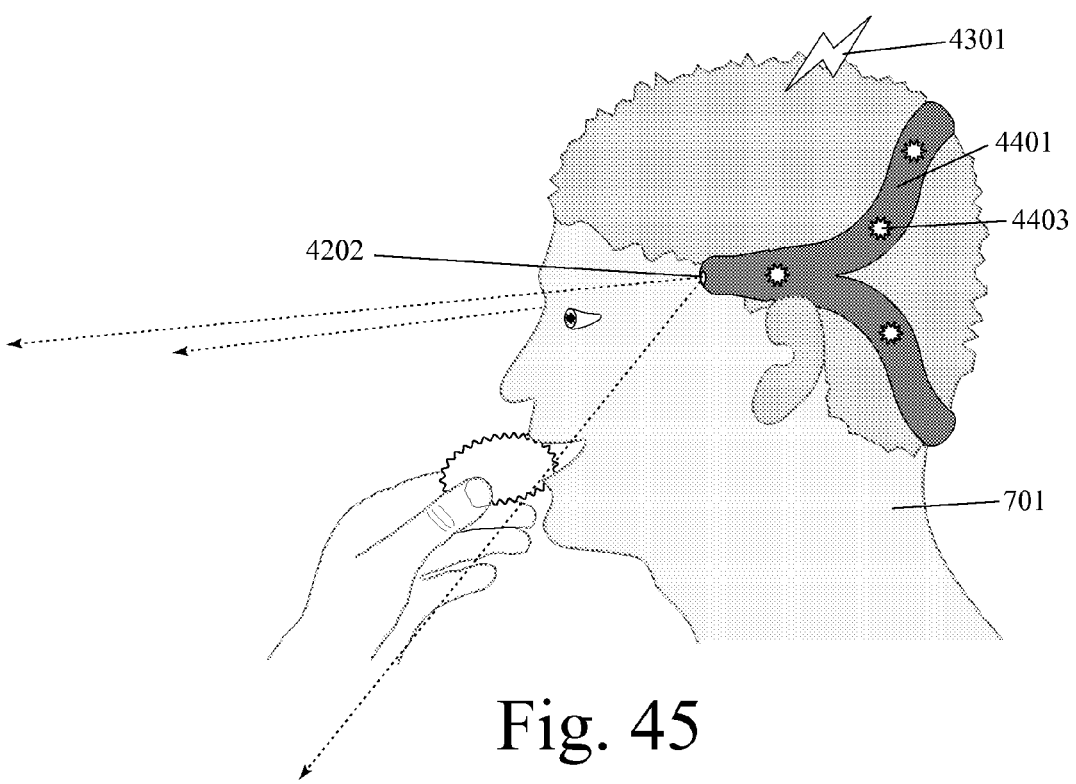
FIG. 45 shows a wearable EEG monitor shaped like a whale tail imaging food and measuring brain activity.

FIGS. 44 and 45 show another example of a wearable EEG monitor (4401) which can be used to measure and/or modify a person's food consumption. Wearable EEG monitor 4401 comprises: a plurality of electrodes or other brain activity sensors (including 4403); and one or more wearable cameras (including 4402). In an example, wearable EEG monitor 4401 can further comprise a control unit. In an example, a control unit can further comprise a power source, a data processor, and a data transmitter. In this example, wearable EEG monitor 4401 is comprised of an upper band which loops around the upper back of a person's head at a level above the person's ears and a lower band which loops around the lower back of the person's head at a level equal to, or lower than, the person's ears, wherein the ends of these two bands converge at locations above the person's ears and rest on the tops of the person's ears. In the example shown in FIGS. 44 and 45, wearable EEG monitor 4401 comprises two wearable cameras, on the left and right sides of the person's head, in order to take stereoscopic pictures of food. FIG. 45 also shows how consumption of food triggers a change 4301 in the person's electromagnetic brain activity. This change 4301 is measured by the plurality of electrodes or other brain activity sensors (including 4403).

Figure 46:
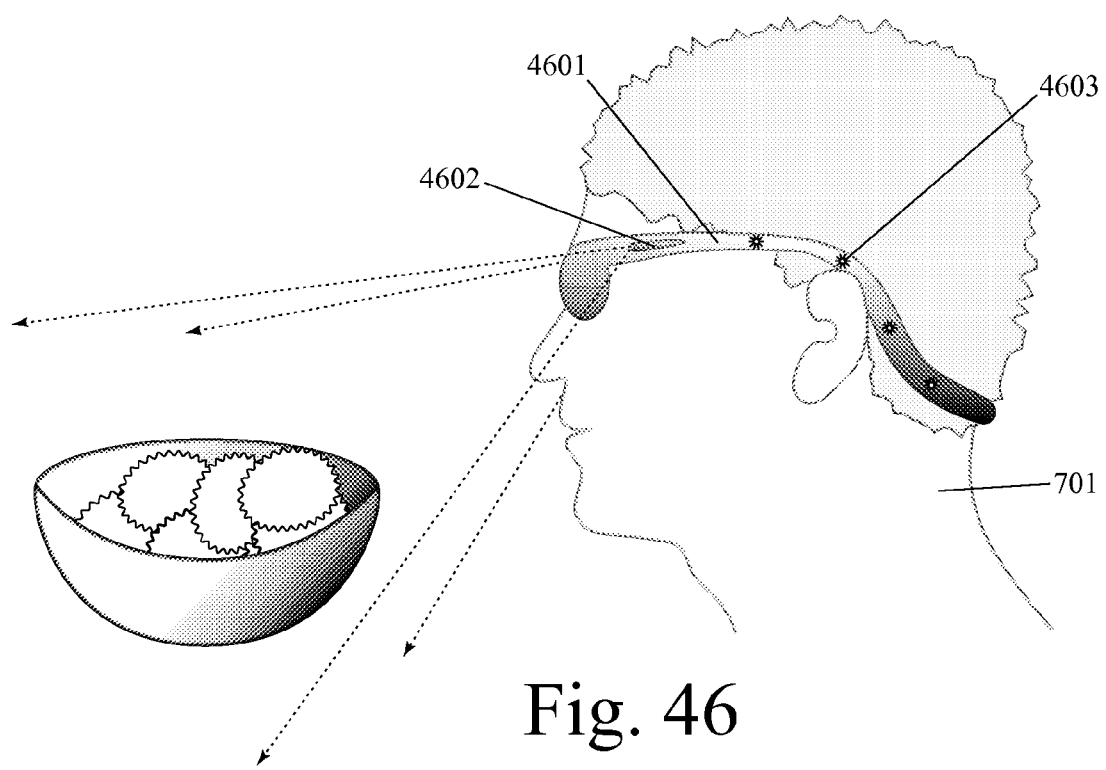
FIG. 46 shows a wearable EEG monitor comprising eyewear with cameras imaging food before it is eaten.
Figure 47:
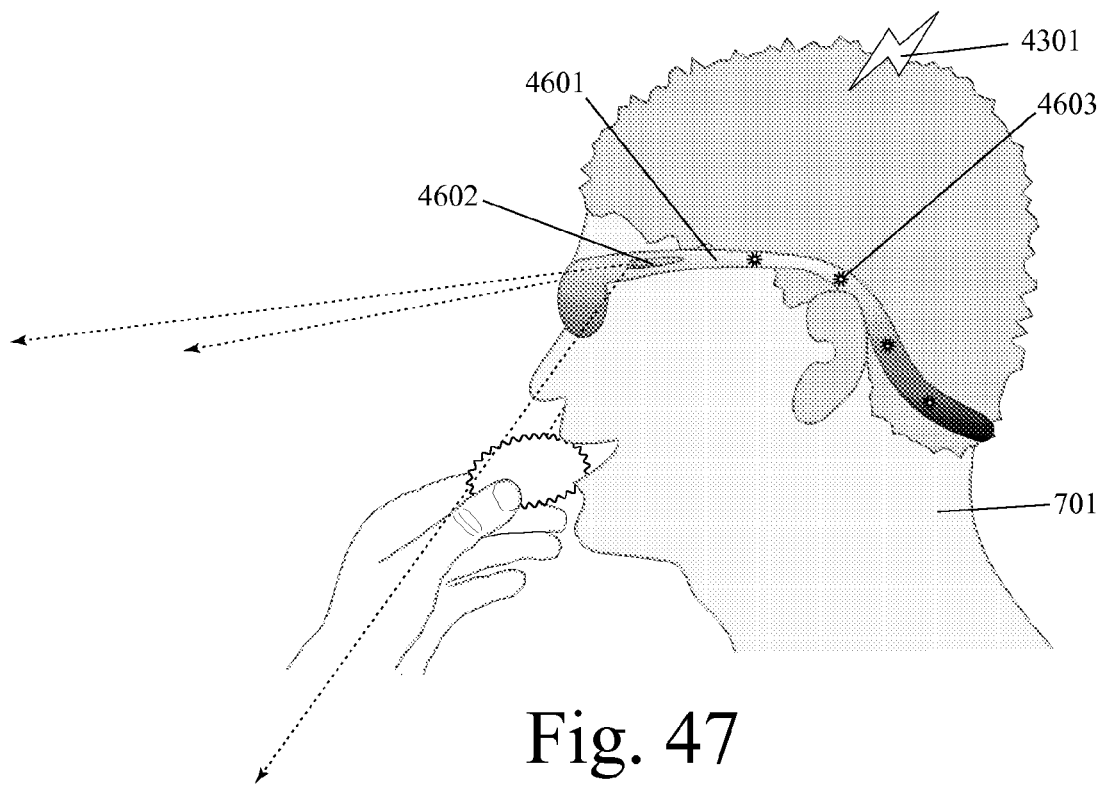
FIG. 47 shows a wearable EEG monitor comprising eyewear with cameras imaging food during eating.

FIGS. 46 and 47 show an example of a wearable EEG monitor that doubles as eyewear and can be used to measure and/or modify a person's food consumption. In this example, wearable EEG monitor 4601 comprises a plurality of electrodes or other brain activity sensors (including 4603) and two wearable cameras (including 4602 shown on the left side). In this example, this device is assumed to be left-right symmetric, so a second camera is assumed to be on the right side of the person's head. In an example, wearable EEG monitor 4601 can further comprise a control unit. In an example, this control unit can comprise a power source, data processor, and data transmitter.

As shown in FIGS. 46 and 47, the anterior portion of wearable EEG monitor 4601 comprises an eyewear frame. In this example, this eyewear frame includes lenses. In an example, this eyewear frame can include a display surface instead of lenses. In an example, lenses can function as a display surface. In an example, this eyewear frame can be rigid, semi-rigid, or flexible.

As shown in FIGS. 46 and 47, the posterior portion of wearable EEG monitor 4601 comprises an arcuate member which loops around the lower-rear portion of the back of the person's head at a level which is equal to, or lower than, the person's ears. The sides of this device rest on top of the person's ears. In an example, this posterior arcuate portion of this device can have the same degree of rigidity, flexibility, and/or elasticity as the anterior eyewear frame portion of this device. In an example, this posterior arcuate portion of this device can have a higher degree of flexibility and/or elasticity than the anterior eyewear frame portion of this device. In an example, the anterior eyewear frame portion of this device can be made of metal and/or plastic and the posterior arcuate portion of this device can be made of fabric.

As shown in FIGS. 46 and 47, the two wearable cameras (including 4602 on the left side) of this device can take stereoscopic pictures of food when the person is looking at food (see FIG. 46) and when the person is eating food (see FIG. 47). In an example, having images of food both before and during consumption can enable more accurate identification of food type and more accurate measure of food quantity consumed. Also, stereoscopic imaging of food can enable 3D and volumetric modeling to better estimate the quantity of food consumed.

FIG. 47 shows a change 4301 in electromagnetic brain activity that is triggered when the person eats food. This change 4301 in electromagnetic brain activity is measured by wearable EEG monitor 4601. This change 4301 in brain activity based on food consumption is then linked to previously-identified patterns of food consumption and used to estimate the type and quantity of food consumed.

Figure 48:
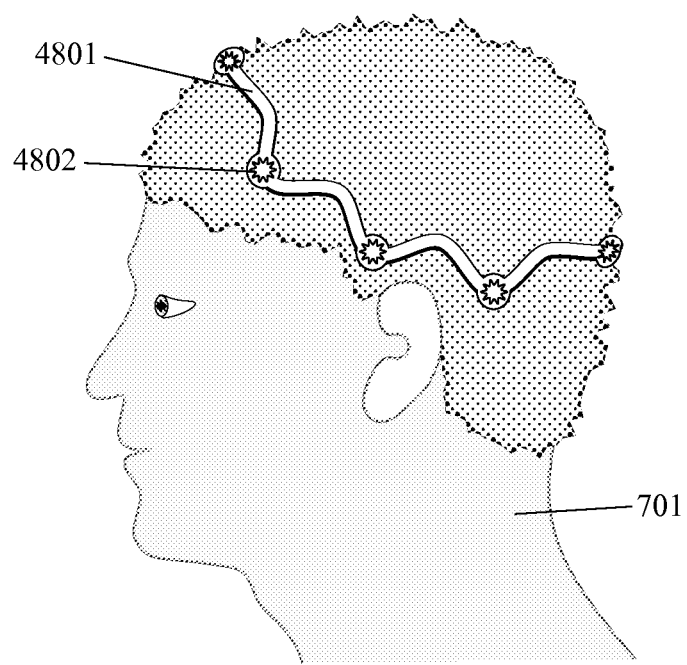
FIG. 48 shows a wearable EEG monitor comprising a sinusoidal headband.
Figure 49:
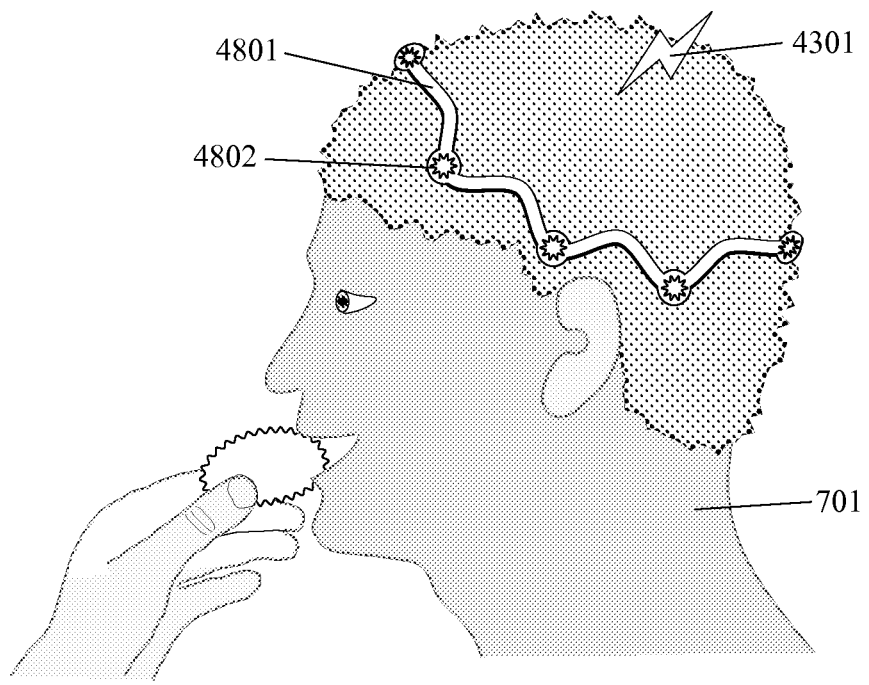
FIG. 49 shows food consumption triggering a change in brain activity.

FIGS. 48 and 49 show a wearable EEG monitor 4801 which comprises a crown-like sinusoidal headband (which encircles a person's head) with plurality of electrodes or other brain activity sensors (including 4802). FIG. 49 shows how eating food triggers a change 4301 in the person's electromagnetic brain activity, wherein this change can be measured by the plurality of electrodes or other brain activity sensors (including 4802).

Figure 50:
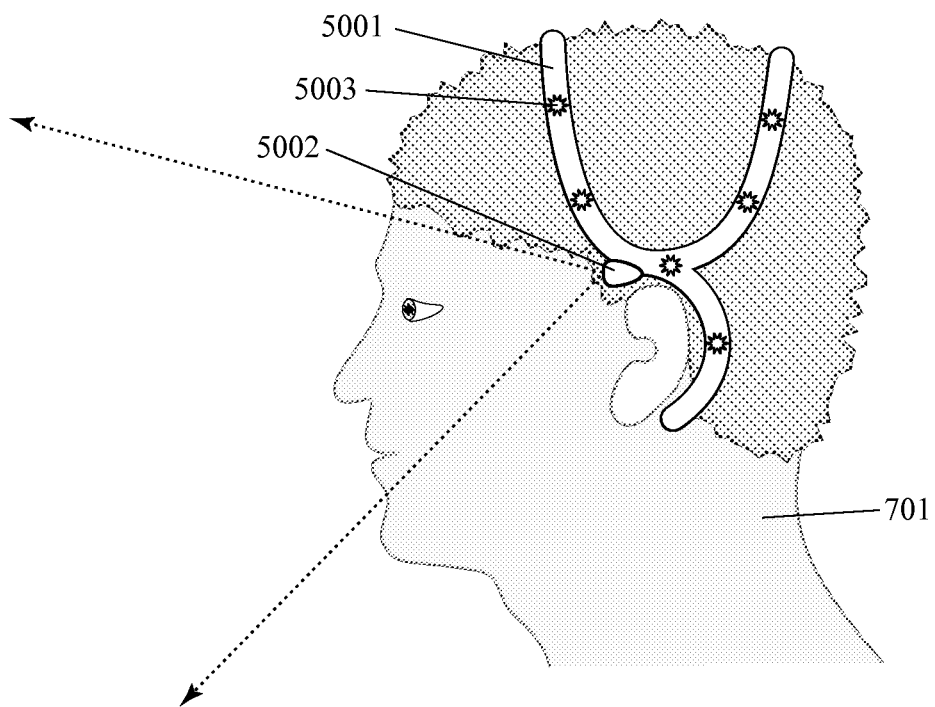
FIG. 50 shows a wearable EEG monitor with a saddle-shaped section which loops over the top of the head.
Figure 51:
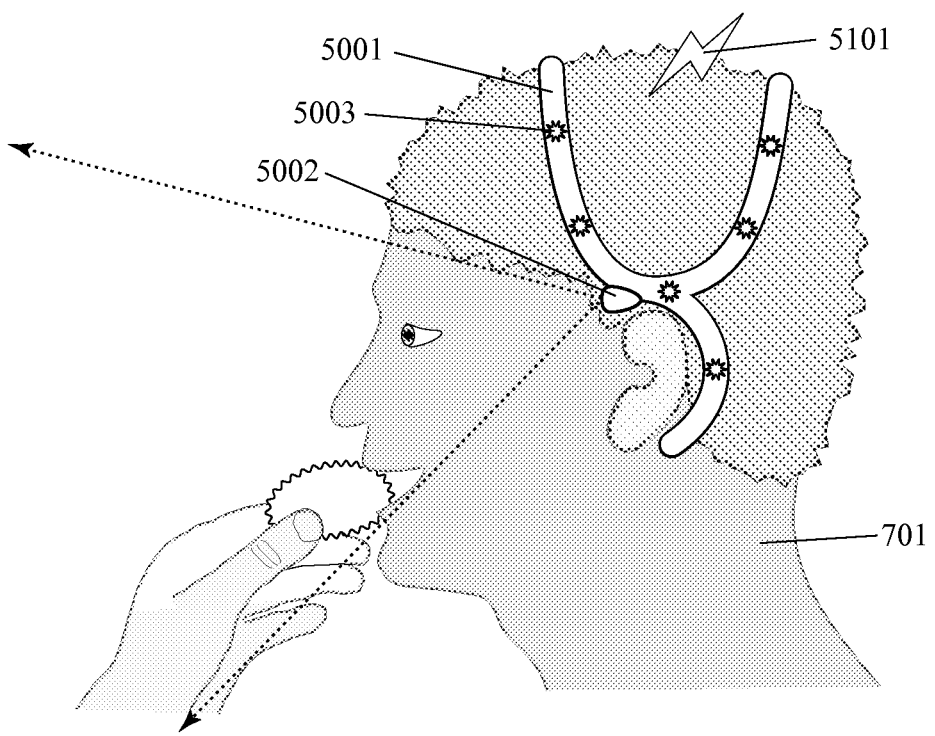
FIG. 51 shows food consumption triggering a change in brain activity.

FIGS. 50 and 51 show a wearable EEG monitor 5001 which comprises: a saddle-shaped section which loops over the top of the person's head (figuratively appearing as if a central oval or elliptical loop has been "melted" on the top of the person's head and "droops down" the sides of the person's head); and two arcs which extend from the bottom portions of the saddle-shaped section to curve down around the rear portions of the person's ears. This monitor has a plurality of electrodes or other brain activity sensors (including 5003) and one or more wearable cameras (including 5002). FIG. 51 shows how eating food triggers a change 5101 in the person's electromagnetic brain activity, wherein this change can be measured by the plurality of electrodes or other brain activity sensors (including 5003).

Figure 52:
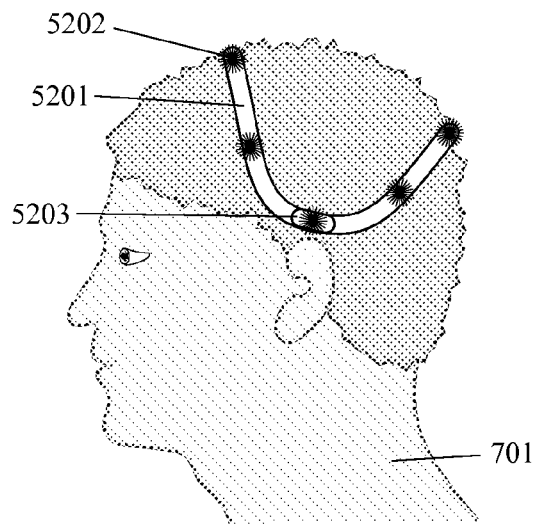
FIG. 52 shows a wearable EEG monitor shaped like the rim of a cap.

FIG. 52 shows a left-side view of an example of a wearable brain activity monitor comprising a head-worn sensor-positioning member 5201 which is configured to position a plurality of electrodes or other brain activity sensors, including 5202, at selected locations on the wearer's head. In this example, sensor-positioning member 5201 is assumed to be substantially symmetric with respect to the left side (shown) and the right side (not shown) of the wearer's head. This monitor further comprises control unit 5203, which need not be replicated on the right side.

In the example shown in FIG. 52, sensor-positioning member 5201 is configured to loop over the top portion of the wearer's head in a manner similar to the rim of a (skull) cap in which the right and left sides have been elongated. In this example, the right and left sides come down to locations just above the wearer's ears. In various examples, sensor-holding member 5201 can be shaped like a two-dimensional circle, oval, ellipse, oblong shape, egg shape, or conic section which has been curved in three-dimensional space in order to conform to the top portion of the wearer's head.

In an example, a portion of sensor-positioning member 5201 that is anterior to the wearer's ears spans an upper portion of the wearer's temporal lobe, a lower portion of their central sulcus, and a posterior portion of their cerebral cortex. In an example, electrodes or other brain activity sensors on sensor-positioning member 5201 collect data on brain activity concerning short term memory, emotion, smell, hunger, and/or taste. This brain activity data can be associated with selected quantities and types of food consumption and/or can be used to identify quantities and types of food consumed.

In an example, a portion of the sensor-positioning member 5201 that is posterior to the wearer's ears spans an upper portion of the wearer's temporal lobe and a posterior portion of their occipital lobe. In an example, electrodes or other brain activity sensors on sensor-positioning member 5201 collect data on brain activity concerning the sight, image recognition, and/or speech. This brain activity data can be associated with selected quantities and types of food consumption and/or can be used to identify quantities and types of food consumed.

In an example, a wearable brain activity monitor can comprise an array of eighteen electrodes or other brain activity sensors which are located substantially at the following set of placement sites—FC1, FC2, FC3, FC4, FC5, FC6, FCz, P1, P2, P3, P4, P5, P6, Pz, T7, T8, TP7 and TP8—or which comprise a subset of six or more sites from this set of placement sites.

In an example, control unit 5203 can further comprise: a data processing component and a power source (or transducer). In an example, control unit 5203 can further comprise: a data processing component; a power source (or transducer); and a data transmitting (and receiving) component. In an example, control unit 5203 can be in wireless communication with an external (or remote) device and/or with another component of an overall system for monitoring brain activity. In an example, control unit 5203 can further comprise: a data processing component; a power source (or transducer); a data transmitting (and receiving) component; and a user interface. In an example, control unit 5203 can be physically connected to the array of electrodes (or other brain activity sensors) by wires or other electromagnetically-conductive pathways. In an example, control unit 5203 can be in wireless electromagnetic communication with the array of electrodes (or other brain activity sensors).

Figure 53:
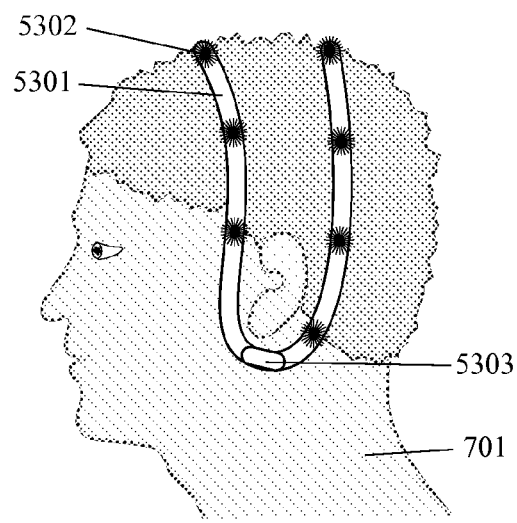
FIG. 53 shows a wearable EEG monitor with two arcs which loop over the top the head.

FIG. 53 shows a left-side view of an example of a wearable brain activity monitor comprising a head-worn sensor-positioning member 5301 which is configured to position a plurality of electrodes or other brain activity sensors, including 5302, at selected locations on the wearer's head. In this example, sensor-positioning member 5301 is assumed to be substantially symmetric with respect to the left side (shown) and the right side (not shown) of the wearer's head. This monitor further comprises control unit 5303, which need not be replicated on the right side.

In this example, sensor-positioning member 5301 is configured to have two (substantially-parallel) arcs which loop over the top portion of the wearer's head. In this example, these two loops are slightly concave with the concavity facing in an anterior direction. In another example, these two loops can be concave with the concavity facing in a posterior direction. In an alternative example, these two loops can be relatively straight. In this example, the ends of these two loops connect to each other below the wearer's ears, on the right and left sides of the wearer's head, respectively.

In various examples, sensor-holding member 5301 can be shaped like a two-dimensional oblong shape which has been curved in three-dimensional space in order to conform to the top portion of the wearer's head. In other, sensor-holding member 5201 can be shaped like a two-dimensional conic section which has been curved in three-dimensional space to conform to the top portion of the wearer's head.

In this example, the anterior loop of sensor-positioning member 5301 spans a laterally-central portion of the wearer's temporal lobe, a portion of their central sulcus, and a posterior portion of their cerebral cortex. In an example, electrodes or other brain activity sensors on sensor-positioning member 5301 collect data on brain activity concerning short term memory, emotion, smell, taste, and/or hunger. This brain activity data can be associated with selected quantities and types of food consumption and/or can be used to identify quantities and types of food consumed.

In this example, the posterior loop of sensor-positioning member 5301 spans a portion of the wearer's cerebellum, a posterior portion of their temporal lobe, a laterally-central portion of their occipital lobe, and the upper tip of their parietal lobe. In an example, electrodes or other brain activity sensors on sensor-positioning member 5301 collect data on brain activity concerning hearing, sight, image recognition, speech, object weight, object texture, and/or object temperature. This brain activity data can be associated with selected quantities and types of food consumption and/or can be used to identify quantities and types of food consumed.

In an example, a wearable brain activity monitor can comprise an array of eighteen electrodes or other brain activity sensors which are located substantially at the following set of placement sites—CP1, CP2, CP3, CP4, CP5, CP6, CPz, FC1, FC2, FC3, FC4, FC5, FC6, FCz, P7, P8, T7 and T8—or which comprise a subset of ten or more sites from this set of placement sites.

In an example, control unit 5303 can further comprise: a data processing component and a power source (or transducer). In an example, control unit 5303 can further comprise: a data processing component; a power source (or transducer); and a data transmitting (and receiving) component. In an example, control unit 5303 can be in wireless communication with an external (or remote) device and/or with another component of an overall system for monitoring brain activity. In an example, control unit 5303 can further comprise: a data processing component; a power source (or transducer); a data transmitting (and receiving) component; and a user interface. In an example, control unit 5303 can be physically connected to the array of electrodes (or other brain activity sensors) by wires or other electromagnetically-conductive pathways. In an example, control unit 5303 can be in wireless electromagnetic communication with the array of electrodes (or other brain activity sensors).

Figure 54:
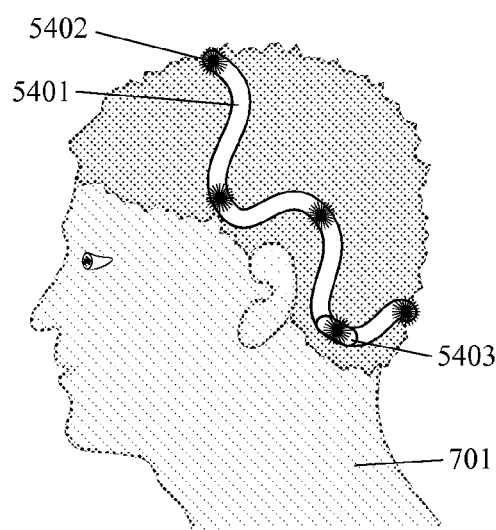
FIG. 54 shows a wearable EEG monitor which encircles the head in a tilted and sinusoidal manner.

FIG. 54 shows a left-side view of an example of a wearable brain activity monitor comprising a head-worn sensor-positioning member 5401 which is configured to position a plurality of electrodes or other brain activity sensors, including 5402, at selected locations on the wearer's head. In this example, the sensor-positioning member is assumed to substantially symmetric with respect to the left side (shown) and the right side (not shown) of the wearer's head. This monitor further comprises control unit 5403, which need not be replicated on the right side.

In this example, sensor-positioning member 5401 is configured to encircle an upper portion of the wearer's head in a tilted and sinusoidal manner. In various examples, a sensor-positioning member can encircle an upper portion of a wearer's head at an angle with respect to a horizontal plane when the wearer is standing upright which is within the range of 30 to 60 degrees. In this example, this angle is approximately 45 degrees. In various examples, a sensor-positioning member can have between 2 and 8 full-phase sinusoidal oscillations as it encircles the wearer's head. In this example, this member has four sinusoidal oscillations.

In this example, a portion of a sensor-positioning member which is anterior to the wearer's ears spans an upper portion of the wearer's temporal lobe, a central portion of their central sulcus, and a posterior portion of their cerebral cortex. In an example, electrodes or other brain activity sensors on a sensor-positioning member can collect data on brain activity concerning short term memory, emotion, smell, taste, and/or hunger. This brain activity data can be associated with selected quantities and types of food consumption and/or can be used to identify quantities and types of food consumed.

In this example, a portion of the sensor-positioning member which is anterior to the wearer's ears spans a lower portion of the wearer's occipital lobe, a posterior portion of their temporal lobe, and a laterally-central portion of their cerebellum. In an example, electrodes or other brain activity sensors on a sensor-positioning member can collect data on brain activity concerning speech, sight, image recognition, and/or hearing. This brain activity data can be associated with selected quantities and types of food consumption and/or can be used to identify quantities and types of food consumed.

In an example, a wearable brain activity monitor can comprise an array of seventeen electrodes or other brain activity sensors which are located substantially at the following set of placement sites—CP5, CP6, FC1, FC2, FC3, FC4, FC5, FC6, FCz, FT7, FT8, P5, P6, P7, P8, T7, T8—or which comprise a subset of six or more sites from this set of placement sites.

In an example, control unit 5403 can further comprise: a data processing component and a power source (or transducer). In an example, control unit 5403 can further comprise: a data processing component; a power source (or transducer); and a data transmitting (and receiving) component. In an example, control unit 5403 can be in wireless communication with an external (or remote) device and/or with another component of an overall system for monitoring brain activity. In an example, control unit 5403 can further comprise: a data processing component; a power source (or transducer); a data transmitting (and receiving) component; and a user interface. In an example, control unit 5403 can be physically connected to the array of electrodes (or other brain activity sensors) by wires or other electromagnetically-conductive pathways. In an example, control unit 5403 can be in wireless electromagnetic communication with the array of electrodes (or other brain activity sensors).

Figure 55:
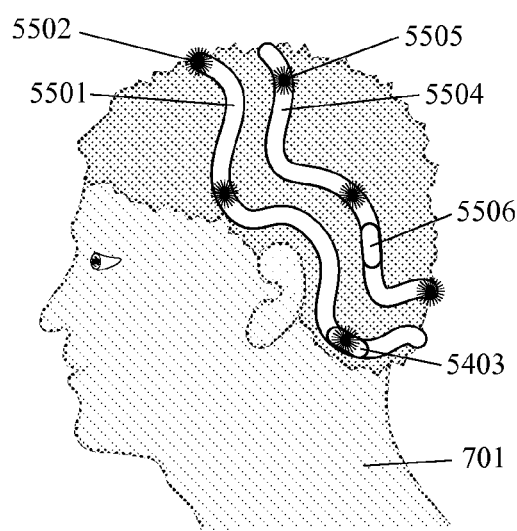
FIG. 55 shows a wearable EEG monitor with two members encircling the head in a tilted and sinusoidal manner.

FIG. 55 shows a left-side view of an example of a wearable brain activity monitor comprising two (wirelessly) linked head-worn sensor-positioning members, 5501 and 5504, which are configured to position a plurality of electrodes or other brain activity sensors, including 5502 and 5505, at selected locations on the wearer's head. In this example, sensor-positioning member 5504 is located above sensor-positioning member 5501. In this example, these two sensor-positioning members are assumed to be substantially symmetric with respect to the left side (shown) and the right side (not shown) of the wearer's head. This monitor further comprises control units 5503 and 5506, which need not be replicated on the right side.

In this example, sensor-positioning members 5501 and 5504 are each configured to encircle an upper portion of the wearer's head in a tilted and sinusoidal manner. In an example, each of these sensor-positioning members encircles an upper portion of a wearer's head at an angle with respect to the horizontal plane (when the wearer is standing upright) in the range of 30-60 degrees. In an example, each of these sensor-positioning members has a number of sinusoidal oscillations as it encircles the wearer's head in the range of 3-7 oscillations.

In this example, the portion of sensor-positioning member 5501 which is anterior to the wearer's ears spans an upper portion of the wearer's temporal lobe, a central portion of their central sulcus, and an upper portion of their cerebral cortex. In this example, the portion of sensor-positioning member 5501 which is posterior to the wearer's ears spans an upper portion of the wearer's temporal lobe and a portion of their cerebellum.

In this example, the portion of sensor-positioning member 5504 which is anterior to the wearer's ears spans a central portion of the wearer's occipital lobe and a portion of their parietal lobe. In this example, the portion of sensor-positioning member 5504 which is posterior to the wearer's ears spans a lower portion of the wearer's occipital lobe and a posterior portion of the wearer's cerebellum.

In an example, electrodes or other brain activity sensors on sensor-positioning members can collect data on brain activity concerning short term memory, smell, taste, emotion, hunger, speech, skin sensation, sight, image recognition, and/or hearing. This brain activity data can be associated with selected quantities and types of food consumption and/or can be used to identify quantities and types of food consumed.

In an example, a wearable brain activity monitor can comprise an array of 26 electrodes or other brain activity sensors which are located substantially at the following set of placement sites—C1, C2, C3, C4, C5, C6, CP5, CP6, Cz, FC1, FC2, FC3, FC4, FC5, FC6, FCz, FT7, FT8, P5, P6, PO7, PO8, T7, T8, TP7 and TP8—or which comprise a subset of eight or more sites from this set of placement sites.

In an example, control unit 5503 can further comprise: a data processing component and a power source (or transducer). In an example, control unit 5503 can further comprise: a data processing component; a power source (or transducer); and a data transmitting (and receiving) component. In an example, control unit 5503 can be in wireless communication with an external (or remote) device and/or with another component of an overall system for monitoring brain activity. In an example, control unit 5503 can further comprise: a data processing component; a power source (or transducer); a data transmitting (and receiving) component; and a user interface. In an example, control unit 5503 can be physically connected to the array of electrodes (or other brain activity sensors) by wires or other electromagnetically-conductive pathways. In an example, control unit 5503 can be in wireless electromagnetic communication with the array of electrodes (or other brain activity sensors).

Figure 56:
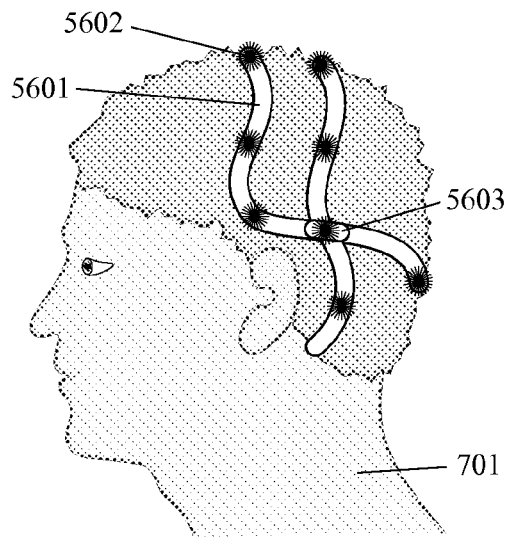
FIG. 56 shows a wearable EEG monitor with two upward elements and two downward elements.

FIG. 56 shows a left-side view of an example of a wearable brain activity monitor comprising a head-worn sensor-positioning member 5601 which is configured to position a plurality of electrodes or other brain activity sensors, including 5602, at selected locations on the wearer's head. In this example, the sensor-positioning member is assumed to be substantially symmetric with respect to the left side (shown) and the right side (not shown) of the wearer's head. This monitor further comprises control unit 5603, which need not be replicated on the right side.

In this example, sensor-positioning member 5601 comprises: (a) two arcuate elements which loop in a substantially-parallel manner over the top of the wearer's head; (b) an arcuate element which loops around the back of the wearer's head; and (c) two downward-protruding arcuate elements, one on the left side and one on the right side (not shown but assumed in symmetry) of the wearer's head which terminate in the areas behind the wearer's left and right ears, respectively.

In an example, the anterior element of the two which loop over the wearer's head spans an upper portion of the wearer's temporal lobe, a central portion of their parietal lobe, and an upper-posterior tip of their cerebral cortex. In an example, the posterior element of the two which loop over the wearer's head spans a laterally-central portion of the wearer's occipital lobe and the upper tip of their parietal lobe. In an example, the element which loops around the back of the wearer's head spans a posterior portion of the wearer's temporal lobe and a posterior portion of their cerebellum. In an example, each of the downward protruding elements spans a posterior portion of the wearer's temporal lobe and a central portion of their cerebellum.

In an example, electrodes or other brain activity sensors collect data on brain activity concerning: short term memory, smell, taste, emotion, hunger, skin sensation, speech, hearing, object weight, object texture, object temperature, and/or sight, image recognition. This brain activity data can be associated with selected quantities and types of food consumption and/or can be used to identify quantities and types of food consumed. In an example, a wearable brain activity monitor can comprise an array of 25 electrodes or other brain activity sensors which are located substantially at the following set of placement sites—C1, C2, C3, C4, C5, C6, CP1, CP2, CP3, CP4, CP5, CP6, CPz, Cz, O1, O2, Oz, P7, P8, PO7, PO8, T7, T8, TP7 and TP8—or which comprise a subset of ten or more sites from this set of placement sites.

In an example, control unit 5603 can further comprise: a data processing component and a power source (or transducer). In an example, control unit 5603 can further comprise: a data processing component; a power source (or transducer); and a data transmitting (and receiving) component. In an example, control unit 5603 can be in wireless communication with an external (or remote) device and/or with another component of an overall system for monitoring brain activity. In an example, control unit 5603 can further comprise: a data processing component; a power source (or transducer); a data transmitting (and receiving) component; and a user interface. In an example, control unit 5603 can be physically connected to the array of electrodes (or other brain activity sensors) by wires or other electromagnetically-conductive pathways. In an example, control unit 5603 can be in wireless electromagnetic communication with the array of electrodes (or other brain activity sensors).

Figure 57:
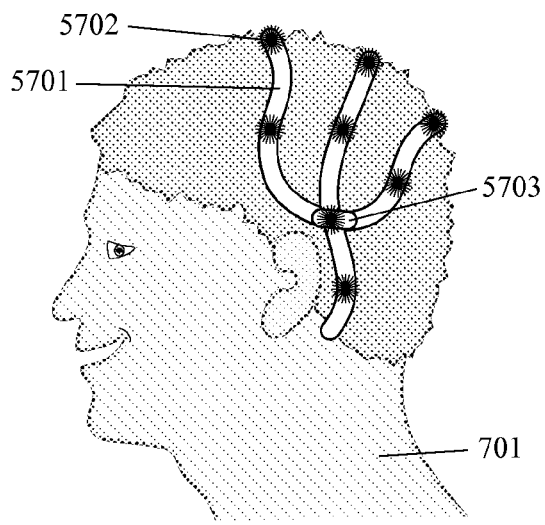
FIG. 57 shows a wearable EEG monitor shaped like the Greek letter Psi.

FIG. 57 shows a left-side view of an example of a wearable brain activity monitor comprising a head-worn sensor-positioning member 5701 which is configured to position a plurality of electrodes or other brain activity sensors including 5702 at selected locations on the wearer's head. In this example, the sensor-positioning member is assumed to be substantially symmetric with respect to the left side (shown) and the right side (not shown) of the wearer's head. This monitor further comprises control unit 5703, which need not be replicated on the right side.

In this example, sensor-positioning member 5701 comprises: (a) three arcuate elements which loop over the top of the wearer's head; and (b) two downward protruding elements, one on the left side and one on the right side (not shown but assumed in symmetry) of the wearer's head, which terminate in the areas behind the wearer's left and right ears, respectively. In this example, the left-side view of the shape of sensor-positioning member 5701 looks like the Greek letter Psi—which is appropriate for a brain monitor and the reason why the wearer is smiling in this figure.

In this example, the anterior one of the three elements which loops over the wearer's head spans an upper portion of the wearer's temporal lobe, a central portion of their parietal lobe, and a posterior-upper tip of their cerebral cortex. In an example, the central one of the three elements which loops over the wearer's head spans a laterally-central portion of the wearer's occipital lobe, including the somatosensory area. In an example, the posterior one of the three elements which loops over the wearer's head spans a posterior portion of the wearer's occipital lobe, including the visual processing area. In an example, each of the downward protruding elements spans a posterior portion of the wearer's temporal lobe and a portion of their cerebellum.

In an example, electrodes or other brain activity sensors collect data on brain activity concerning: short term memory, smell, taste, emotion, hunger, skin sensation, speech, hearing, object weight, object texture, object temperature, and/or sight, image recognition. This brain activity data can be associated with selected quantities and types of food consumption and/or can be used to identify quantities and types of food consumed. In an example, a wearable brain activity monitor can comprise an array of 27 electrodes or other brain activity sensors which are located substantially at the following set of placement sites—C1, C2, C3, C4, C5, C6, CP1, CP2, CP3, CP4, CP5, CP6, CPz, Cz, P1, P2, P3, P4, P5, P6, P7, P8, Pz, T7, T8, TP7 and TP8—or which comprise a subset of twelve or more sites from this set of placement sites.

In an example, control unit 5703 can further comprise: a data processing component and a power source (or transducer). In an example, control unit 5703 can further comprise: a data processing component; a power source (or transducer); and a data transmitting (and receiving) component. In an example, control unit 5703 can be in wireless communication with an external (or remote) device and/or with another component of an overall system for monitoring brain activity. In an example, control unit 5703 can further comprise: a data processing component; a power source (or transducer); a data transmitting (and receiving) component; and a user interface. In an example, control unit 5703 can be physically connected to the array of electrodes (or other brain activity sensors) by wires or other electromagnetically-conductive pathways. In an example, control unit 5703 can be in wireless electromagnetic communication with the array of electrodes (or other brain activity sensors).

Figure 58:
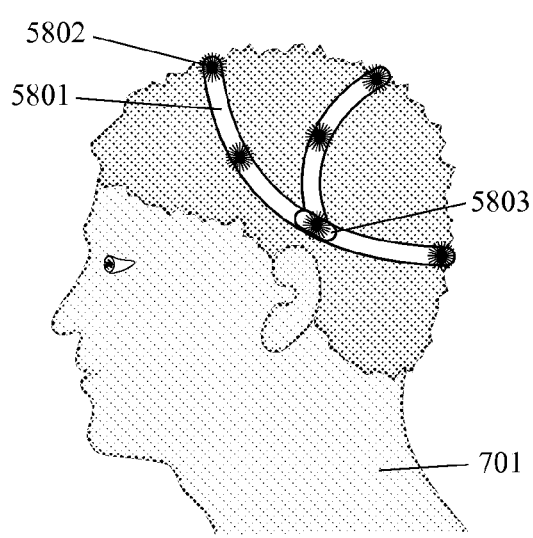
FIG. 58 shows a wearable EEG monitor with a ring element and a loop element over the top of the head.

FIG. 58 shows a left-side view of an example of a wearable brain activity monitor comprising a head-worn sensor-positioning member 5801 which is configured to position a plurality of electrodes or other brain activity sensors including 5802 at selected locations on the wearer's head. In this example, sensor-positioning member 5801 is assumed to be substantially symmetric with respect to the left side (shown) and the right side (not shown) of the wearer's head. This monitor further comprises control unit 5803, which need not be replicated on the right side.

In this example, sensor-positioning member 5801 comprises: (a) a ring element which encircles the top of the wearer's head in a manner like the rim of a (skull) cap; and (b) an arc element which loops over the top of the wearer's head in a manner like the upper portion of a pair of headphones. In this example, these two elements are joined on the left side and right side at locations just over the wearer's left ear and right ear, respectively. In an example, the portion of the ring element which is anterior to the wearer's ear spans an upper portion of the wearer's temporal lobe, a lower portion of their parietal lobe, a lower portion of their central sulcus, and a laterally-central portion of their cerebral cortex. In an example, electrodes or other brain activity sensors collect data on brain activity concerning short term memory, smell, taste, hunger, speech, and/or eye movement.

In an example, the portion of the ring element which is posterior to the wearer's ear spans an upper portion of the wearer's temporal lobe and an upper-posterior portion of their cerebellum. In an example, electrodes or other brain activity sensors collect data on brain activity concerning short term memory and/or hearing. In an example, the arc element spans a laterally-central portion of the occipital lobe, including the somatosensory area. In an example, electrodes or other brain activity sensors collect data on brain activity concerning language, hearing, object weight, object texture, object temperature, sight, and/or image recognition.

Brain activity data from the above electrodes or other brain activity sensors can be associated with selected quantities and types of food consumption and/or can be used to identify quantities and types of food consumed. In an example, a wearable brain activity monitor can comprise an array of 23 electrodes or other brain activity sensors which are located substantially at the following set of placement sites—CP1, CP2, CP3, CP4, CP5, CP6, CPz, FC1, FC2, FC3, FC4, FC5, FC6, FCz, O1, O2, Oz, P7, P8, PO7, PO8, TP7 and TP8—or which comprise a subset of eight or more sites from this set of placement sites.

In an example, control unit 5803 can further comprise: a data processing component and a power source (or transducer). In an example, control unit 5803 can further comprise: a data processing component; a power source (or transducer); and a data transmitting (and receiving) component. In an example, control unit 5803 can be in wireless communication with an external (or remote) device and/or with another component of an overall system for monitoring brain activity. In an example, control unit 5803 can further comprise: a data processing component; a power source (or transducer); a data transmitting (and receiving) component; and a user interface. In an example, control unit 5803 can be physically connected to the array of electrodes (or other brain activity sensors) by wires or other electromagnetically-conductive pathways. In an example, control unit 5803 can be in wireless electromagnetic communication with the array of electrodes (or other brain activity sensors).

Figure 59:
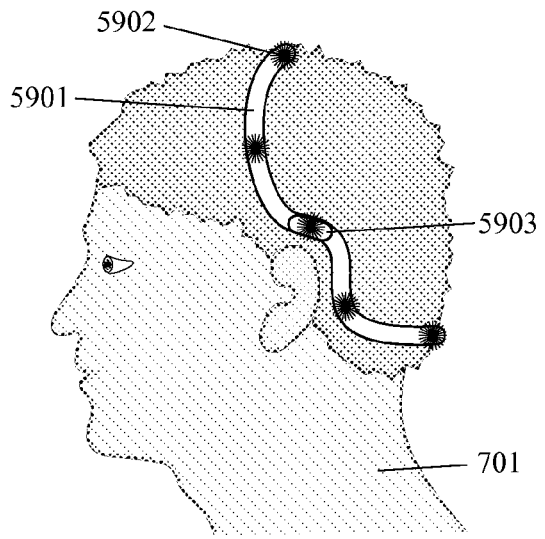
FIG. 59 shows a wearable EEG monitor with an anterior portion curving over the top of the wearer's head.

FIG. 59 shows a left-side view of an example of a wearable brain activity monitor comprising a head-worn sensor-positioning member 5901 which is configured to position a plurality of electrodes or other brain activity sensors including 5902 at selected locations on the wearer's head. In this example, the sensor-positioning member is assumed to be substantially symmetric with respect to the left side (shown) and the right side (not shown) of the wearer's head. This monitor further comprises control unit 5903, which need not be replicated on the right side.

In this example, sensor-positioning member 5901 comprises an arcuate loop which encircles the upper-posterior portion of the wearer's head. In this example, this sensor-positioning member comprises: an anterior portion that curves over the top of the wearer's head in a manner similar to the upper portion of headphones; a laterally-central portion that partially reflects the curves of the upper and posterior perimeters of the wearer's ears; and a posterior portion that loops around the rear of the wearer's head at substantially the same height as the wearer's ears.

In an example, the anterior portion of this loop spans an upper portion of the wearer's temporal lobe, a lower portion of their parietal lobe, a portion of their central sulcus, and a posterior portion of their cerebral cortex. In an example, electrodes or other brain activity sensors collect data on brain activity concerning short term memory, smell, taste, hunger, speech, and/or eye movement. In an example, the posterior portion of this loop spans an upper portion of the wearer's temporal lobe and a central portion of their cerebellum. In an example, electrodes or other brain activity sensors collect data on brain activity concerning short term memory and/or hearing. This brain activity data can be associated with selected quantities and types of food consumption and/or can be used to identify quantities and types of food consumed.

In an example, a wearable brain activity monitor can comprise an array of thirteen electrodes or other brain activity sensors which are located substantially at the following set of placement sites—C1, C2, C3, C4, C5, C6, Cz, P7, P8, T7, T8, TP7 and TP8—or which comprise a subset of six or more sites from this set of placement sites.

In an example, control unit 5903 can further comprise: a data processing component and a power source (or transducer). In an example, control unit 5903 can further comprise: a data processing component; a power source (or transducer); and a data transmitting (and receiving) component. In an example, control unit 5903 can be in wireless communication with an external (or remote) device and/or with another component of an overall system for monitoring brain activity. In an example, control unit 5903 can further comprise: a data processing component; a power source (or transducer); a data transmitting (and receiving) component; and a user interface. In an example, control unit 5903 can be physically connected to the array of electrodes (or other brain activity sensors) by wires or other electromagnetically-conductive pathways. In an example, control unit 5903 can be in wireless electromagnetic communication with the array of electrodes (or other brain activity sensors).

In an example, this invention can be embodied in a device for measuring and/or modifying a person's food consumption comprising: a top-and-back loop member which is configured to be worn on a person's head, wherein this top-and-back loop member further comprises a first loop which loops over the top of the person's head and a second loop which loops around the back of the person's head; one or more electrodes or other brain activity sensors which are configured by the top-and-back loop member to be less than one inch from the surface of the person's head; a mobile power source and/or power transducer, wherein a power transducer harvests power from human physiological activity and/or environmental energy sources; a data processor; and a data transmitting member.

In an example, this invention can be embodied in a device for measuring and/or modifying a person's food consumption comprising: a top-and-back loop member which is configured to be worn on a person's head, wherein this top-and-back loop member further comprises a first loop which loops over the top of the person's head and a second loop which loops around the back of the person's head; one or more electrodes or other brain activity sensors which are configured by the top-and-back loop member to be less than one inch from the surface of the person's head; a mobile power source and/or power transducer, wherein a power transducer harvests power from human physiological activity and/or environmental energy sources; a data processor; a data transmitter; and a database which includes associations between specific patterns of food consumption and specific patterns of electromagnetic brain activity, which translates specific types and amounts of food into specific types and amounts of nutrients, or which does both.

Figure 60:
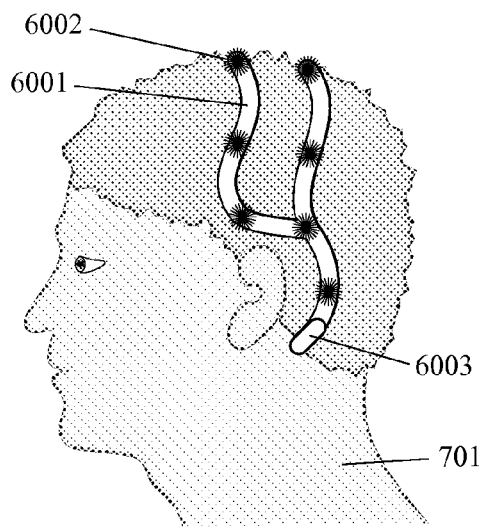
FIG. 60 shows a wearable EEG monitor shaped like a lower-case letter "Y".

FIG. 60 shows a left-side view of an example of a wearable brain activity monitor comprising a head-worn sensor-positioning member 6001 which is configured to position a plurality of electrodes or other brain activity sensors, including 6002, at selected locations on the wearer's head. In this example, the sensor-positioning member is assumed to be substantially symmetric with respect to the left side (shown) and the right side (not shown) of the wearer's head. This monitor further comprises control unit 6003, which need not be replicated on the right side.

In this example, sensor-positioning member 6001 comprises: (a) two arcuate elements which loop, from side to side, over the central upper portion of the wearer's head and (b) two (left and right side) downward-protruding arcuate elements which terminate in areas behind the wearer's left and right ears, respectively. In this example, the left-side view of the shape of sensor-positioning member 6001 looks similar to a lower-case letter "y".

In an example, the anterior element of the two elements which loop over the wearer's head spans an upper portion of the wearer's temporal lobe, a portion of their parietal lobe, and an upper-posterior portion of their cerebral cortex. In an example, electrodes or other brain activity sensors collect data on brain activity concerning short term memory, smell, taste, hunger, speech, and/or eye movement.

In an example, the posterior element of the two elements which loop over the wearer's head spans a laterally-central portion of the wearer's occipital lobe, including the somatosensory area. In an example, the down-ward protruding members span a posterior portion of the wearer's temporal lobe and a laterally-central portion of their cerebellum. In an example, electrodes or other brain activity sensors collect data on brain activity concerning sight, image recognition, speech, object weight, object texture, object temperature, and/or hearing.

This brain activity data can be associated with selected quantities and types of food consumption and/or can be used to identify quantities and types of food consumed.

In an example, a wearable brain activity monitor can comprise an array of twenty electrodes or other brain activity sensors which are located substantially at the following set of placement sites—C1, C2, C3, C4, C5, C6, CP1, CP2, CP3, CP4, CP5, CP6, CPz, Cz, P7, P8, T7, T8, TP7 and TP8—or which comprise a subset of ten or more sites from this set of placement sites.

In an example, control unit 6003 can further comprise: a data processing component and a power source (or transducer). In an example, control unit 6003 can further comprise: a data processing component; a power source (or transducer); and a data transmitting (and receiving) component. In an example, control unit 6003 can be in wireless communication with an external (or remote) device and/or with another component of an overall system for monitoring brain activity. In an example, control unit 6003 can further comprise: a data processing component; a power source (or transducer); a data transmitting (and receiving) component; and a user interface. In an example, control unit 6003 can be physically connected to the array of electrodes (or other brain activity sensors) by wires or other electromagnetically-conductive pathways. In an example, control unit 6003 can be in wireless electromagnetic communication with the array of electrodes (or other brain activity sensors).

Figure 61:
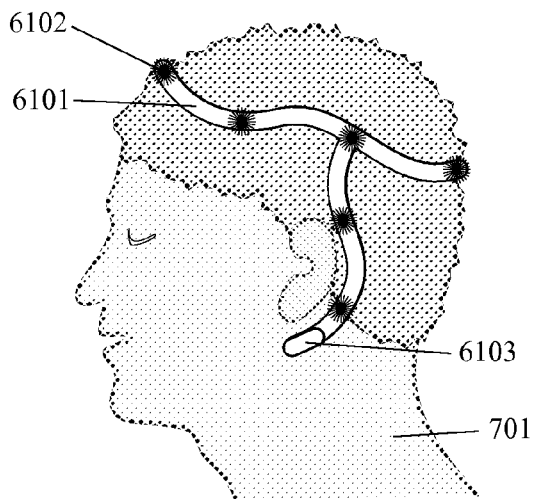
FIG. 61 shows a wearable EEG monitor with a ring and downward-protruding arcuate elements.

FIG. 61 shows a left-side view of an example of a wearable brain activity monitor comprising a head-worn sensor-positioning member 6101 which is configured to position a plurality of electrodes or other brain activity sensors, including 6102, at selected locations on the wearer's head. In this example, the sensor-positioning member is assumed to be substantially symmetric with respect to the left side (shown) and the right side (not shown) of the wearer's head. This monitor further comprises control unit 6103, which need not be replicated on the right side.

In this example, sensor-positioning member 6101 comprises: (a) an arcuate ring which encircles the upper portion of the wearer's head; and (b) two (left and right side) downward-protruding arcuate elements which terminate in areas just beneath or just behind the wearer's left and right ears, respectively. In an example, the left-side view of the shape of sensor-positioning member 6101 looks similar to a script lower-case Greek letter "Tau" which has been reflected around its vertical axis. In an example, the arcuate ring can tilted at an angle with respect to a horizontal plane wherein this angle is in the range of 10 to 40 degrees. In an example, the arcuate ring can be parallel with a horizontal plane as opposed to being tilted. In an example, the arcuate ring can have 3 to 8 sinusoidal oscillations. In an example, the arcuate ring can be a conic section without oscillations. In an example, the downward-protruding elements can curve around the posterior perimeter of the wearer's ears.

In an example, the arcuate ring spans a vertically-central portion of the wearer's occipital lobe, a vertically-central portion of their parietal lobe, their central sulcus, and a portion of their frontal lobe including their cerebral cortex. In an example, electrodes or other brain activity sensors collect data on brain activity concerning sight, image recognition, hearing and speech, skin sensations, emotions, hunger, and/or higher mental functions. In an example, the downward-protruding arcuate elements span a laterally-central portion of the wearer's occipital lobe, a posterior portion of their temporal lobe, and an anterior portion of their cerebellum. In an example, electrodes or other brain activity sensors collect data on brain activity concerning speech, short term memory, and/or hearing. This brain activity data can be associated with selected quantities and types of food consumption and/or can be used to identify quantities and types of food consumed.

In an example, a wearable brain activity monitor can comprise an array of eighteen electrodes or other brain activity sensors which are located substantially at the following set of placement sites—AF3, AF4, AFz, C5, C6, CP5, CP6, F5, F6, FC5, FC6, P5, P6, PO3, PO4, POz, TP7 and TP8—or which comprise a subset of eight or more sites from this set of placement sites.

In an example, control unit 6103 can further comprise: a data processing component and a power source (or transducer). In an example, control unit 6103 can further comprise: a data processing component; a power source (or transducer); and a data transmitting (and receiving) component. In an example, control unit 6103 can be in wireless communication with an external (or remote) device and/or with another component of an overall system for monitoring brain activity. In an example, control unit 6103 can further comprise: a data processing component; a power source (or transducer); a data transmitting (and receiving) component; and a user interface. In an example, control unit 6103 can be physically connected to the array of electrodes (or other brain activity sensors) by wires or other electromagnetically-conductive pathways. In an example, control unit 6103 can be in wireless electromagnetic communication with the array of electrodes (or other brain activity sensors).

Figure 62:
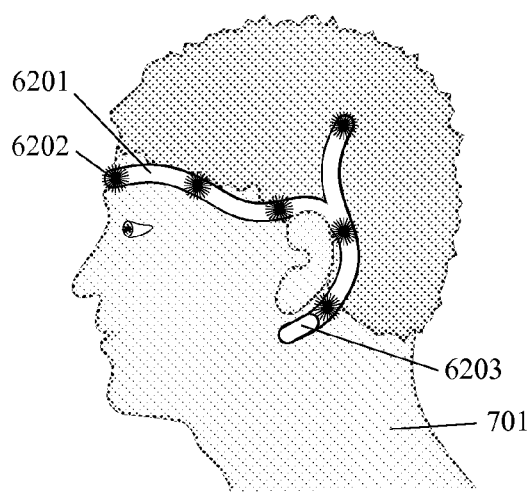
FIG. 62 shows a wearable EEG monitor with a loop from one ear to the other around the front of the head.

FIG. 62 shows a left-side view of an example of a wearable brain activity monitor comprising a head-worn sensor-positioning member 6201 which is configured to position a plurality of electrodes or other brain activity sensors, including 6202, at selected locations on the wearer's head. In this example, the sensor-positioning member is assumed to be substantially symmetric with respect to the left side (shown) and the right side (not shown) of the wearer's head. This monitor further comprises control unit 6203, which need not be replicated on the right side.

In this example, sensor-positioning member 6201 comprises: (a) an arcuate element which loops, from the top of one ear to the top of the other ear, around the front-central portion of the wearer's head; (b) two upward-protruding arcuate elements, which rise up from an area behind the wearer's ears and terminate on the right and left sides of their head, respectively, over their occipital lobe; and (c) two downward-protruding arcuate elements, which drop down from an area behind the wearer's ears and terminate in areas below their ears, respectively. In an example, this sensor-positioning member is shaped similar to an eyeglasses frame with the addition of upward protrusions (above the ears) and extended hooking-elements (around the ears).

In an example, the arcuate element which loops around the front-central portion of the wearer's head spans a central portion of the wearer's temporal lobe and their frontal lobe. In an example, electrodes or other brain activity sensors collect data on brain activity concerning short term memory, smell, taste, and/or higher mental functions. In an example, the upward-protruding arcuate elements span a central portion of the wearer's occipital lobe. In an example, electrodes or other brain activity sensors collect data on brain activity concerning speech, hearing, and visual processing. In an example, the downward-protruding arcuate elements span the wearer's cerebellum. In an example, electrodes or other brain activity sensors collect data on brain activity concerning hearing. This brain activity data can be associated with selected quantities and types of food consumption and/or can be used to identify quantities and types of food consumed.

In an example, a wearable brain activity monitor can comprise an array of twelve electrodes or other brain activity sensors which are located substantially at the following set of placement sites—AF7, AF8, CP5, CP6, F7, F8, FT7, FT8, T7, T8, TP7 and TP8—or which comprise a subset of eight or more sites from this set of placement sites.

In an example, control unit 6203 can further comprise: a data processing component and a power source (or transducer). In an example, control unit 6203 can further comprise: a data processing component; a power source (or transducer); and a data transmitting (and receiving) component. In an example, control unit 6203 can be in wireless communication with an external (or remote) device and/or with another component of an overall system for monitoring brain activity. In an example, control unit 6203 can further comprise: a data processing component; a power source (or transducer); a data transmitting (and receiving) component; and a user interface. In an example, control unit 6203 can be physically connected to the array of electrodes (or other brain activity sensors) by wires or other electromagnetically-conductive pathways. In an example, control unit 6203 can be in wireless electromagnetic communication with the array of electrodes (or other brain activity sensors).

Figure 63:
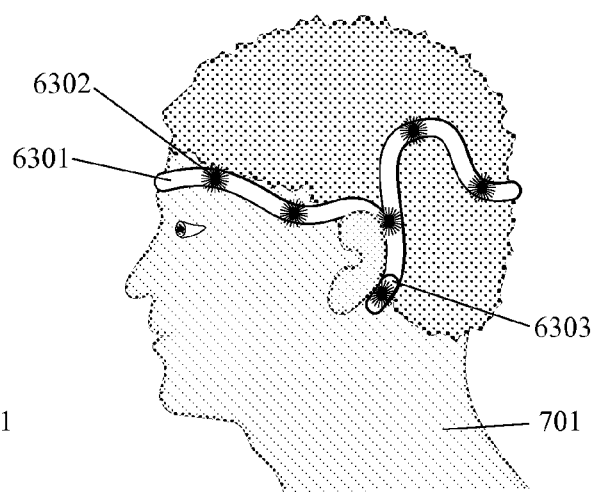
FIG. 63 shows a wearable EEG monitor with an anterior element from one ear to the other and also a rear loop.

FIG. 63 shows a left-side view of an example of a wearable brain activity monitor comprising a head-worn sensor-positioning member 6301 which is configured to position a plurality of electrodes or other brain activity sensors, including 6302, at selected locations on the wearer's head. In this example, the sensor-positioning member is assumed to be substantially symmetric with respect to the left side (shown) and the right side (not shown) of the wearer's head. This monitor further comprises control unit 6303, which need not be replicated on the right side.

In this example, sensor-positioning member 6301 comprises: (a) an anterior arcuate element which loops from one ear to the other ear, around the front-central portion of the wearer's head; (b) a posterior arcuate element which loops in a curvaceous manner from one ear to the other around the back-central portion of the wearer's head; and (c) two downward-protruding elements which curve around the backs of the wearer's ears and terminate in areas behind (or just below) the ears. In an example, the anterior and/or posterior arcuate elements are sinusoidal. In an example, the posterior arcuate element includes one or more two or more bends, curves, or loops which span above ear height.

In an example, the anterior arcuate element spans a central portion of the wearer's temporal lobe and a lower portion of their frontal lobe. In an example, electrodes or other brain activity sensors collect data on brain activity concerning short term memory, smell, taste, and/or higher mental functions. In an example, the posterior arcuate element spans a posterior portion of the wearer's temporal lobe, a central portion of their occipital lobe, and a posterior portion of their occipital lobe, including the visual processing area. In an example, electrodes or other brain activity sensors collect data on brain activity concerning speech, hearing, vision, and/or image recognition. In an example, the two downward-protruding elements span a posterior portion of the wearer's temporal lobe and an anterior portion of their cerebellum. In an example, electrodes or other brain activity sensors collect data on brain activity concerning hearing. This brain activity data can be associated with selected quantities and types of food consumption and/or can be used to identify quantities and types of food consumed.

In an example, a wearable brain activity monitor can comprise an array of sixteen electrodes or other brain activity sensors which are located substantially at the following set of placement sites—AF7, AF8, CP5, CP6, F7, F8, FT7, FT8, P5, P6, PO5, PO6, T7, T8, TP7 and TP8—or which comprise a subset of eight or more sites from this set of placement sites.

In an example, control unit 6303 can further comprise: a data processing component and a power source (or transducer). In an example, control unit 6303 can further comprise: a data processing component; a power source (or transducer); and a data transmitting (and receiving) component. In an example, control unit 6303 can be in wireless communication with an external (or remote) device and/or with another component of an overall system for monitoring brain activity. In an example, control unit 6303 can further comprise: a data processing component; a power source (or transducer); a data transmitting (and receiving) component; and a user interface. In an example, control unit 6303 can be physically connected to the array of electrodes (or other brain activity sensors) by wires or other electromagnetically-conductive pathways. In an example, control unit 6303 can be in wireless electromagnetic communication with the array of electrodes (or other brain activity sensors).

Figure 64:
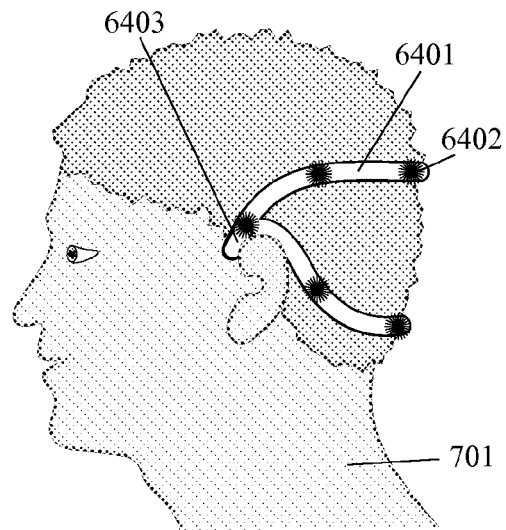
FIG. 64 shows a wearable EEG monitor with an upper loop and lower loop from one ear to the other.

FIG. 64 shows a left-side view of an example of a wearable brain activity monitor comprising a head-worn sensor-positioning member 6401 which is configured to position a plurality of electrodes or other brain activity sensors, including 6402, at selected locations on the wearer's head. In this example, the sensor-positioning member is assumed to be substantially symmetric with respect to the left side (shown) and the right side (not shown) of the wearer's head. This monitor further comprises control unit 6403, which need not be replicated on the right side.

In this example, sensor-positioning member 6401 comprises: (a) an upper loop from one ear to the other around the upper-posterior portion of the wearer's head; and (b) a lower loop from one ear to the other around the lower-posterior portion of the wearer's head. In an example, the upper and lower loops connect at areas just above the wearer's ears. In an example, the average height of the upper loop is above the average height of the wearer's ears. In an example, the average height of the lower loop is equal to, or lower than, the average height of the wearer's ears.

In an example, the upper loop spans a portion of the wearer's temporal lobe and a portion of their occipital lobe. In an example, electrodes or other brain activity sensors collect data on brain activity concerning short term memory, speech, hearing, visual processing, and/or image recognition. In an example, the lower loop spans a portion of the wearer's temporal lobe and a portion of their cerebellum. In an example, electrodes or other brain activity sensors collect data on brain activity concerning short term memory and hearing. This brain activity data can be associated with selected quantities and types of food consumption and/or can be used to identify quantities and types of food consumed.

In an example, a wearable brain activity monitor can comprise an array of thirteen electrodes or other brain activity sensors which are located substantially at the following set of placement sites—CP5, CP6, P3, P4, P5, P6, PO3, PO4, POz, T7, T8, TP7 and TP8—or which comprise a subset of six or more sites from this set of placement sites.

In an example, control unit 6403 can further comprise: a data processing component and a power source (or transducer). In an example, control unit 6403 can further comprise: a data processing component; a power source (or transducer); and a data transmitting (and receiving) component. In an example, control unit 6403 can be in wireless communication with an external (or remote) device and/or with another component of an overall system for monitoring brain activity. In an example, control unit 6403 can further comprise: a data processing component; a power source (or transducer); a data transmitting (and receiving) component; and a user interface. In an example, control unit 6403 can be physically connected to the array of electrodes (or other brain activity sensors) by wires or other electromagnetically-conductive pathways. In an example, control unit 6403 can be in wireless electromagnetic communication with the array of electrodes (or other brain activity sensors).

Figure 65:
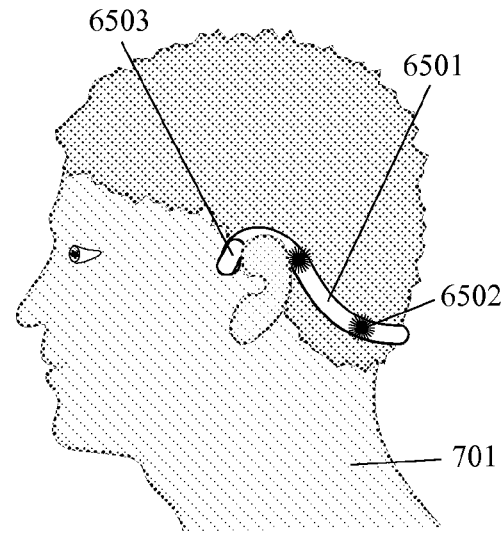
FIG. 65 shows a wearable EEG monitor with a loop from one ear to the other around the back of the head.

FIG. 65 shows a left-side view of an example of a wearable brain activity monitor comprising a head-worn sensor-positioning member 6501 which is configured to position a plurality of electrodes or other brain activity sensors, including 6502, at selected locations on the wearer's head. In this example, the sensor-positioning member is assumed to be substantially symmetric with respect to the left side (shown) and the right side (not shown) of the wearer's head. This monitor further comprises control unit 6503, which need not be replicated on the right side.

In this example, sensor-positioning member 6501 comprises a loop that spans from one ear to the other, looping around the lower-posterior portion of the wearer's head. In an example, the average height of this loop is equal to, or lower than, the average height of the wearer's ears. In this example, the left-side and right-side ends of the loop curve around and hook over the tops of the wearer's left and right ears, respectively, terminating in locations just forward of the upper portions of the ears. In this example, control unit 6503 is just forward of the upper portion of the upper portion of the left ear.

In this example, the loop spans a lower portion of the wearer's temporal lobe and a portion of their cerebellum. In an example, electrodes or other brain activity sensors collect data on brain activity concerning short term memory, smell, taste, vision and hearing. This brain activity data can be associated with selected quantities and types of food consumption and/or can be used to identify quantities and types of food consumed. In an example, a wearable brain activity monitor can comprise an array of four electrodes or other brain activity sensors which are located substantially at the following set of placement sites—T7, T8, TP7 and TP8—or which comprise a subset of two or more sites from this set of placement sites.

In an example, control unit 6503 can further comprise: a data processing component and a power source (or transducer). In an example, control unit 6503 can further comprise: a data processing component; a power source (or transducer); and a data transmitting (and receiving) component. In an example, control unit 6503 can be in wireless communication with an external (or remote) device and/or with another component of an overall system for monitoring brain activity. In an example, control unit 6503 can further comprise: a data processing component; a power source (or transducer); a data transmitting (and receiving) component; and a user interface. In an example, control unit 6503 can be physically connected to the array of electrodes (or other brain activity sensors) by wires or other electromagnetically-conductive pathways. In an example, control unit 6503 can be in wireless electromagnetic communication with the array of electrodes (or other brain activity sensors).

Figure 66:
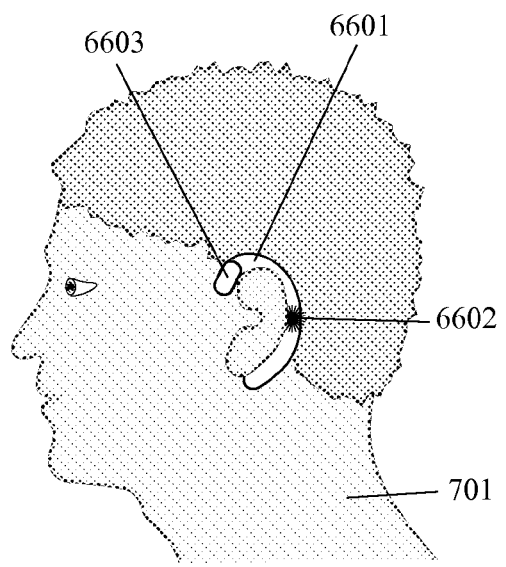
FIG. 66 shows a wearable EEG monitor that loops around a portion of the ear.

FIG. 66 shows a left-side view of an example of a wearable brain activity monitor comprising a head-worn sensor-positioning member 6601 which is configured to position a plurality of electrodes or other brain activity sensors, including 6602, at selected locations on the wearer's head. This monitor further comprises control unit 6603. In an example, the monitor can be symmetric, with a similarly-configured sensor-positioning member on the right side of the wearer's head. In an alternative example, the monitor can asymmetric, with no sensor-positioning member on the wearer's right side.

In this example, sensor-positioning member 6601 snuggly loops around a portion of the lateral perimeter of the wearer's ear. In this example, sensor-positioning member 6601 loops around approximately 70% of the lateral perimeter of the wearer's ear. In various examples, a sensor-positioning member can loop around a percentage of the lateral perimeter of the wearer's ear in the range of 50% to 80%. In an example, the polar coordinates of the lateral perimeter of the wearer's ear can be expressed in terms of positions on a clockface. In this example, sensor positioning member 6601 loops from approximately the 10 o'clock position to the 6 o'clock position. In various examples, a sensor-positioning member can loop around the ear within the range of 9 o'clock to 6 o'clock.

In this example, the loop spans a lower portion of the wearer's temporal lobe and a portion of their cerebellum. In an example, electrodes or other brain activity sensors collect data on brain activity concerning short term memory, smell, taste, vision and hearing. This brain activity data can be associated with selected quantities and types of food consumption and/or can be used to identify quantities and types of food consumed.

In an example, a wearable brain activity monitor can comprise an array of four electrodes or other brain activity sensors which are located substantially at the following set of placement sites—T7, T8, TP7 and TP8—or which comprise a subset of two or more sites from this set of placement sites.

In an example, control unit 6603 can further comprise: a data processing component and a power source (or transducer). In an example, control unit 6603 can further comprise: a data processing component; a power source (or transducer); and a data transmitting (and receiving) component. In an example, control unit 6603 can be in wireless communication with an external (or remote) device and/or with another component of an overall system for monitoring brain activity. In an example, control unit 6603 can further comprise: a data processing component; a power source (or transducer); a data transmitting (and receiving) component; and a user interface. In an example, control unit 6603 can be physically connected to the array of electrodes (or other brain activity sensors) by wires or other electromagnetically-conductive pathways. In an example, control unit 6603 can be in wireless electromagnetic communication with the array of electrodes (or other brain activity sensors).

In an example, this invention can be embodied in a device for measuring and/or modifying a person's food consumption comprising: a hearing aid or ear bud which is configured to be worn in, worn on, and/or worn around a person's ear; one or more electrodes or other brain activity sensors which are configured by the hearing aid or ear bud to be less than one inch from the surface of the person's head; a mobile power source and/or power transducer, wherein a power transducer harvests power from human physiological activity and/or environmental energy sources; a data processor; and a data transmitting member.

In an example, this invention can be embodied in a device for measuring and/or modifying a person's food consumption comprising: a hearing aid or ear bud which is configured to be worn in, worn on, and/or worn around a person's ear; one or more electrodes or other brain activity sensors which are configured by the hearing aid or ear bud to be less than one inch from the surface of the person's head; a mobile power source and/or power transducer, wherein a power transducer harvests power from human physiological activity and/or environmental energy sources; a data processor; a data transmitter; and a database which includes associations between specific patterns of food consumption and specific patterns of electromagnetic brain activity, which translates specific types and amounts of food into specific types and amounts of nutrients, or which does both.

Figure 67:
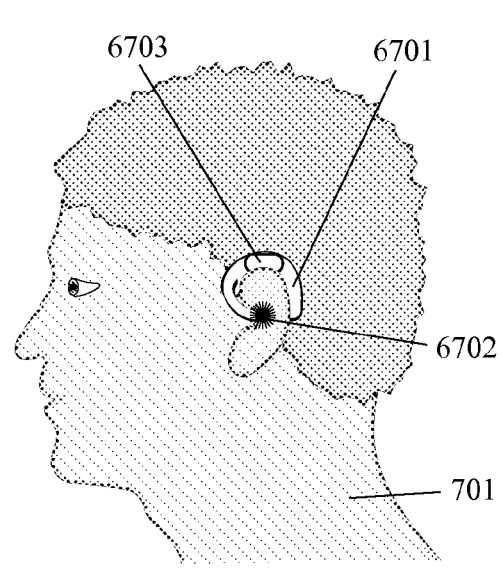
FIG. 67 shows a wearable EEG monitor that fits into the ear.

FIG. 67 shows a left-side view of an example of a wearable brain activity monitor comprising a head-worn sensor-positioning member 6701 which is configured to position a plurality of electrodes or other brain activity sensors, including 6702, at selected locations on the wearer's head. This monitor further comprises control unit 6703. In an example, the monitor can be symmetric, with a similarly-configured sensor-positioning member on the right side of the wearer's head. In an alternative example, the monitor can asymmetric, with no sensor-positioning member on the wearer's right side.

In this example, sensor-positioning member 6701 snuggly loops around a portion of the lateral perimeter of the wearer's ear and also fits into the wearer's ear canal. In an example, at least one electrode or other brain activity sensor is configured to be within the wearer's ear canal. In this example, sensor-positioning member 6701 loops around approximately 50% of the lateral perimeter of the wearer's ear. In various examples, a sensor-positioning member can loop around a percentage of the lateral perimeter of the wearer's ear in the range of 25% to 70%. In an example, the polar coordinates of the lateral perimeter of the wearer's ear can be expressed in terms of positions on a clockface. In this example, sensor positioning member 6701 loops from approximately the 9 o'clock position to the 3 o'clock position. In various examples, a sensor-positioning member can loop around the ear within the range of 9 o'clock to 5 o'clock.

In this example, the loop spans a lower portion of the wearer's temporal lobe and a portion of their cerebellum. In an example, electrodes or other brain activity sensors collect data on brain activity concerning short term memory, smell, taste, vision and hearing. This brain activity data can be associated with selected quantities and types of food consumption and/or can be used to identify quantities and types of food consumed. In an example, a wearable brain activity monitor can comprise an array of two electrodes or other brain activity sensors which are located substantially at the following set of placement sites—TP7 and TP8.

In an example, control unit 6703 can further comprise: a data processing component and a power source (or transducer). In an example, control unit 6703 can further comprise: a data processing component; a power source (or transducer); and a data transmitting (and receiving) component. In an example, control unit 6703 can be in wireless communication with an external (or remote) device and/or with another component of an overall system for monitoring brain activity. In an example, control unit 6703 can further comprise: a data processing component; a power source (or transducer); a data transmitting (and receiving) component; and a user interface. In an example, control unit 6703 can be physically connected to the array of electrodes (or other brain activity sensors) by wires or other electromagnetically-conductive pathways. In an example, control unit 6703 can be in wireless electromagnetic communication with the array of electrodes (or other brain activity sensors).

FIGS. 68 through 73 show examples of statistical methods which can be used to identify specific patterns of electromagnetic brain activity and to identify key associations between food consumption and electromagnetic brain activity as part of this invention. As shown in FIG. 68, electromagnetic data from a single EEG electrode at a selected recording place (relative to a reference electrode) can be called an EEG channel. FIG. 69 notes that a statistical method can create a summary statistic or classification for a pattern of data from an EEG channel during a period of time. In various examples, such a summary statistic or classification can be selected from the group consisting of: mean, median, variance, standard deviation, minimum, maximum, frequency, amplitude, and waveform. In various examples, such a summary statistic or classification can be selected from the group consisting of a change following food consumption in one or more of a mean, median, variance, standard deviation, minimum, maximum, frequency, amplitude, and waveform.

FIG. 70 notes that a statistical method can create a summary statistic or classification for data from multiple EEG channels in different recording places during a period of time. In various examples, such a summary statistic can selected from the group consisting of: the covariance and/or correlation matrix for data from multiple EEG channels; a difference, sum, ratio, product, or other arithmetic function of the mean values of data from multiple EEG channels; a discriminant function of data from multiple EEG channels; a linear function of data from multiple EEG channels; and a non-linear function of data from multiple EEG channels. In various examples, such a summary statistic can selected from the group consisting of change following food consumption in one or more of: the covariance and/or correlation matrix for data from multiple EEG channels; a difference, sum, ratio, product, or other arithmetic function of the mean values of data from multiple EEG channels; a discriminant function of data from multiple EEG channels; a linear function of data from multiple EEG channels; and a non-linear function of data from multiple EEG channels.

FIG. 71 notes that a statistical method can create a summary statistic or classification for electromagnetic data which repeats within a selected frequency range. In an example, Fourier Transformation can be used. In various examples, such a summary statistic or classification can be selected from the group consisting of: mean, median, variance, standard deviation, minimum, maximum, specific frequency, amplitude, power, and waveform. In various examples, such a summary statistic or classification can be selected from the group consisting of a change following food consumption in one or more of a mean, median, variance, standard deviation, minimum, maximum, specific frequency, amplitude, power, and waveform.

FIG. 72 notes that a statistical method can create a summary statistic or classification for electromagnetic data which repeats within each of multiple frequency ranges. In various examples, such a summary statistic can selected from the group consisting of: the covariance and/or correlation matrix for data from multiple frequency ranges; a difference, sum, ratio, product, or other arithmetic function of the mean values of data from multiple frequency ranges; a discriminant function of data from multiple frequency ranges; a linear function of data from multiple frequency ranges; and a non-linear function of data from multiple frequency ranges. In various examples, such a summary statistic can selected from the group consisting of change following food consumption in one or more of: the covariance and/or correlation matrix for data from multiple frequency ranges; a difference, sum, ratio, product, or other arithmetic function of the mean values of data from multiple frequency ranges; a discriminant function of data from multiple frequency ranges; a linear function of data from multiple frequency ranges; and a non-linear function of data from multiple frequency ranges.

FIG. 73 notes that a statistical method can create a summary statistic or classification for electromagnetic data which repeats within each of multiple frequency ranges and varies across multiple recording places. In various examples, such a summary statistic can selected from the group consisting of: the covariance and/or correlation matrix for data from multiple frequency ranges and multiple recording places; a difference, sum, ratio, product, or other arithmetic function of the mean values of data from multiple frequency ranges and multiple recording places; a discriminant function of data from multiple frequency ranges and multiple recording places; a linear function of data from multiple frequency ranges and multiple recording places; and a non-linear function of data from multiple frequency ranges and multiple recording places. In various examples, such a summary statistic can selected from the group consisting of change following food consumption in one or more of: the covariance and/or correlation matrix for data from multiple frequency ranges and multiple recording places; a difference, sum, ratio, product, or other arithmetic function of the mean values of data from multiple frequency ranges and multiple recording places; a discriminant function of data from multiple frequency ranges and multiple recording places; a linear function of data from multiple frequency ranges and multiple recording places; and a non-linear function of data from multiple frequency ranges and multiple recording places.

FIG. 74 shows another example of how a device or system comprising a wearable EEG monitor can be used to modify a person's food consumption. In this example, a device or system directly and actively modifies a person's electromagnetic brain activity in order to modify their food consumption. This method, device, or system modifies electromagnetic brain activity directly, rather than relying on the feedback or self-modification of brain activity discussed in earlier examples. In this example, a wearable EEG device not only measures electromagnetic brain activity, but also directly modifies electromagnetic brain activity.

Wearable EEG device 7401 shown in FIG. 74 comprises: a plurality of electrodes or other brain activity sensors (including 7402); a plurality of electromagnetic transmitters (including 7403); and a control unit 7404. In an example, control unit 7404 can further comprise a power source, a data processor, and a data transmitter. In this example, wearable EEG device 7401 comprises electromagnetic transmitters which are separate from electromagnetic sensors. In an example, a set of electrodes can sequentially function as electromagnetic sensors and electromagnetic transmitters. In an example, electromagnetic transmitters can be located at a subset of sites selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, O2, A1 and A2.

In an example, surface electromagnetic patterns (detected at selected locations on the surface of a person's head) can be analyzed to estimate the interior electromagnetic patterns (within particular brain regions) which caused these surface electromagnetic patterns. In an example, a three-dimensional model of the electromagnetic field which created a surface electromagnetic pattern can be created. In an example, this three-dimensional model of the electromagnetic field can then be used to infer the interior electromagnetic pattern which created the surface electromagnetic pattern. In an example, this three-dimensional model of the electromagnetic field can also be used, in reverse, to infer the surface electromagnetic pattern which would be required to recreate the interior electromagnetic pattern.

In an example, a surface electromagnetic pattern which is associated with satiety can be identified. In an example, the interior electromagnetic pattern which is associated with this surface electromagnetic pattern can be determined using a three-dimensional model of the brain's electromagnetic field. In an example, the surface electromagnetic pattern which would be required or recreate an interior electromagnetic pattern associated with satiety can be determined using the three-dimensional model in reverse. Finally, in an example, a person can be given a feeling of satiety by recreating this required surface electromagnetic pattern via an array of electromagnetic transmitters on the surface of their head. In an example, a wearable EEG device has such electromagnetic transmitters and thus have the capability to induce a feeling of satiety.

In an example, a surface electromagnetic pattern which is associated with consumption of good-tasting food can be identified. In an example, the interior electromagnetic pattern which is associated with this surface electromagnetic pattern can be determined using a three-dimensional model of the brain's electromagnetic field. In an example, the surface electromagnetic pattern which would be required to recreate an interior electromagnetic pattern associated with satiety can be determined using the three-dimensional model in reverse. Finally, in an example, a person can be given a eating good-tasting food by recreating this required surface electromagnetic pattern via an array of electromagnetic transmitters on the surface of their head. In an example, this can help a person to enjoy eating healthy food whose taste they would otherwise not enjoy.

In an example, this invention can be embodied in a method for modifying a person's food consumption comprising: (a) receiving data concerning a person's food consumption from a first time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the first time period from one or more electrodes or other brain activity sensors which are configured to be less than one inch from the surface of the person's head; (c) identifying associations between patterns of food consumption and patterns of electromagnetic brain activity by analyzing data concerning the person's food consumption and data concerning the person's electromagnetic brain activity from the first time period; (d) receiving data concerning the person's electromagnetic brain activity from a second time period from one or more electrodes or other brain activity sensors which are configured to be less than one inch from the surface of the person's head; (e) using associations between patterns of food consumption and patterns of electromagnetic brain activity in order to estimate the person's food consumption during the second time period from data concerning the person's electromagnetic brain activity from the second time period, wherein food consumption can comprise consumption of food overall or consumption of one or more selected amounts and/or types of foods, ingredients, or nutrients; and (f) providing feedback to the person concerning their estimated food consumption during the second time period in order to prompt the person to activate a plurality of electromagnetic transmitters which are less than one inch from the surface of the person's head, wherein activation of these electromagnetic transmitters modifies the person's electromagnetic brain activity to a pattern which is associated with satiety.

In an example, this invention can be embodied in a method for modifying a person's food consumption comprising: (a) receiving data concerning a person's electromagnetic brain activity from a selected time period from one or more electrodes or other brain activity sensors which are configured to be less than one inch from the surface of the person's head; (b) using associations between patterns of food consumption and patterns of electromagnetic brain activity in order to estimate the person's food consumption during the selected time period from data concerning the person's electromagnetic brain activity from the selected time period, wherein food consumption can comprise consumption of food overall or consumption of one or more selected amounts and/or types of foods, ingredients, or nutrients; and (c) providing feedback to the person concerning their estimated food consumption during the selected time period in order to prompt the person to activate a plurality of electromagnetic transmitters which are less than one inch from the surface of the person's head, wherein activation of these electromagnetic transmitters modifies the person's electromagnetic brain activity to a pattern which is associated with satiety.

In an example, this invention can be embodied in a method for modifying a person's food consumption comprising: (a) receiving data concerning a person's food consumption from a first time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the first time period from one or more electrodes or other brain activity sensors which are configured to be less than one inch from the surface of the person's head; (c) creating a food-brainwave database, wherein this database links patterns of food consumption to patterns of electromagnetic brain activity, by analyzing data concerning the person's food consumption and data concerning the person's electromagnetic brain activity from the first time period; (d) receiving data concerning the person's electromagnetic brain activity from a second time period from one or more electrodes or other brain activity sensors which are configured to be less than one inch from the surface of the person's head; (e) using the food-brainwave database, wherein this database links patterns of food consumption to patterns of electromagnetic brain activity, in order to estimate the person's food consumption during the second time period from data concerning the person's electromagnetic brain activity from the second time period, wherein food consumption can comprise consumption of food overall or consumption of one or more selected amounts and/or types of foods, ingredients, or nutrients; and (f) providing feedback to the person concerning their estimated food consumption during the second time period in order to prompt the person to activate a plurality of electromagnetic transmitters which are less than one inch from the surface of the person's head, wherein activation of these electromagnetic transmitters modifies the person's electromagnetic brain activity to a pattern which is associated with satiety.

In an example, this invention can be embodied in a method for modifying a person's food consumption comprising: (a) receiving data concerning a person's electromagnetic brain activity from a selected time period from one or more electrodes or other brain activity sensors which are configured to be less than one inch from the surface of the person's head; (b) using a food-brainwave database, wherein this database links patterns of food consumption to patterns of electromagnetic brain activity, in order to estimate the person's food consumption during the selected time period from data concerning the person's electromagnetic brain activity from the selected time period, wherein food consumption can comprise consumption of food overall or consumption of one or more selected amounts and/or types of foods, ingredients, or nutrients; and (c) providing feedback to the person concerning their estimated food consumption during the selected time period in order to prompt the person to activate a plurality of electromagnetic transmitters which are less than one inch from the surface of the person's head, wherein activation of these electromagnetic transmitters modifies the person's electromagnetic brain activity to a pattern which is associated with satiety.

In an example, this invention can be embodied in a method for modifying a person's food consumption comprising: (a) receiving data concerning a person's food consumption from a first time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the first time period from one or more electrodes or other brain activity sensors which are configured to be less than one inch from the surface of the person's head; (c) identifying associations between patterns of food consumption and patterns of electromagnetic brain activity by analyzing data concerning the person's food consumption and data concerning the person's electromagnetic brain activity from the first time period; (d) receiving data concerning the person's electromagnetic brain activity from a second time period from one or more electrodes or other brain activity sensors which are configured to be less than one inch from the surface of the person's head; (e) using associations between patterns of food consumption and patterns of electromagnetic brain activity in order to estimate the person's food consumption during the second time period from data concerning the person's electromagnetic brain activity from the second time period, wherein food consumption can comprise consumption of food overall or consumption of one or more selected amounts and/or types of foods, ingredients, or nutrients; and (f) automatically activating a plurality of electromagnetic transmitters which are less than one inch from the surface of the person's head in response to the person's food consumption from the second time period, wherein activation of these electromagnetic transmitters modifies the person's electromagnetic brain activity to a pattern which is associated with satiety.

In an example, this invention can be embodied in a method for modifying a person's food consumption comprising: (a) receiving data concerning a person's electromagnetic brain activity from a selected time period from one or more electrodes or other brain activity sensors which are configured to be less than one inch from the surface of the person's head; (b) using associations between patterns of food consumption and patterns of electromagnetic brain activity in order to estimate the person's food consumption during the selected time period from data concerning the person's electromagnetic brain activity from the selected time period, wherein food consumption can comprise consumption of food overall or consumption of one or more selected amounts and/or types of foods, ingredients, or nutrients; and (c) automatically activating a plurality of electromagnetic transmitters which are less than one inch from the surface of the person's head in response to the person's food consumption from the selected time period, wherein activation of these electromagnetic transmitters modifies the person's electromagnetic brain activity to a pattern which is associated with satiety.

In an example, this invention can be embodied in a method for modifying a person's food consumption comprising: (a) receiving data concerning a person's food consumption from a first time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the first time period from one or more electrodes or other brain activity sensors which are configured to be less than one inch from the surface of the person's head; (c) creating a food-brainwave database, wherein this database links patterns of food consumption to patterns of electromagnetic brain activity, by analyzing data concerning the person's food consumption and data concerning the person's electromagnetic brain activity from the first time period; (d) receiving data concerning the person's electromagnetic brain activity from a second time period from one or more electrodes or other brain activity sensors which are configured to be less than one inch from the surface of the person's head; (e) using the food-brainwave database, wherein this database links patterns of food consumption to patterns of electromagnetic brain activity, in order to estimate the person's food consumption during the second time period from data concerning the person's electromagnetic brain activity from the second time period, wherein food consumption can comprise consumption of food overall or consumption of one or more selected amounts and/or types of foods, ingredients, or nutrients; and (f) automatically activating a plurality of electromagnetic transmitters which are less than one inch from the surface of the person's head in response to the person's food consumption from the second time period, wherein activation of these electromagnetic transmitters modifies the person's electromagnetic brain activity to a pattern which is associated with satiety.

In an example, this invention can be embodied in a method for modifying a person's food consumption comprising: (a) receiving data concerning a person's electromagnetic brain activity from a selected time period from one or more electrodes or other brain activity sensors which are configured to be less than one inch from the surface of the person's head; (b) using a food-brainwave database, wherein this database links patterns of food consumption to patterns of electromagnetic brain activity, in order to estimate the person's food consumption during the selected time period from data concerning the person's electromagnetic brain activity from the selected time period, wherein food consumption can comprise consumption of food overall or consumption of one or more selected amounts and/or types of foods, ingredients, or nutrients; and (c) automatically activating a plurality of electromagnetic transmitters which are less than one inch from the surface of the person's head in response to the person's food consumption from the selected time period, wherein activation of these electromagnetic transmitters modifies the person's electromagnetic brain activity to a pattern which is associated with satiety.

In an example, this invention can be embodied in a method for modifying a person's food consumption comprising: (a) receiving data concerning a person's food consumption from a first time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the first time period from one or more electrodes or other brain activity sensors which are configured to be less than one inch from the surface of the person's head; (c) identifying associations between patterns of food consumption and patterns of electromagnetic brain activity by analyzing data concerning the person's food consumption and data concerning the person's electromagnetic brain activity from the first time period; (d) receiving data concerning the person's electromagnetic brain activity from a second time period from one or more electrodes or other brain activity sensors which are configured to be less than one inch from the surface of the person's head; and (e) providing feedback to the person concerning their estimated food consumption during the second time period in order to prompt the person to activate a plurality of electromagnetic transmitters which are less than one inch from the surface of the person's head, wherein activation of these electromagnetic transmitters modifies the person's electromagnetic brain activity to a pattern which is associated with satiety.

In an example, this invention can be embodied in a method for modifying a person's food consumption comprising: (a) receiving data concerning a person's electromagnetic brain activity from a selected time period from one or more electrodes or other brain activity sensors which are configured to be less than one inch from the surface of the person's head; and (b) providing feedback to the person concerning their estimated food consumption during the selected time period in order to prompt the person to activate a plurality of electromagnetic transmitters which are less than one inch from the surface of the person's head, wherein activation of these electromagnetic transmitters modifies the person's electromagnetic brain activity to a pattern which is associated with satiety.

In an example, this invention can be embodied in a method for modifying a person's food consumption comprising: (a) receiving data concerning a person's food consumption from a first time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the first time period from one or more electrodes or other brain activity sensors which are configured to be less than one inch from the surface of the person's head; (c) creating a food-brainwave database, wherein this database links patterns of food consumption to patterns of electromagnetic brain activity, by analyzing data concerning the person's food consumption and data concerning the person's electromagnetic brain activity from the first time period; (d) receiving data concerning the person's electromagnetic brain activity from a second time period from one or more electrodes or other brain activity sensors which are configured to be less than one inch from the surface of the person's head; and (e) providing feedback to the person concerning their estimated food consumption during the second time period in order to prompt the person to activate a plurality of electromagnetic transmitters which are less than one inch from the surface of the person's head, wherein activation of these electromagnetic transmitters modifies the person's electromagnetic brain activity to a pattern which is associated with satiety.

In an example, this invention can be embodied in a method for modifying a person's food consumption comprising: (a) receiving data concerning a person's electromagnetic brain activity from a selected time period from one or more electrodes or other brain activity sensors which are configured to be less than one inch from the surface of the person's head; and (b) providing feedback to the person concerning their estimated food consumption during the selected time period in order to prompt the person to activate a plurality of electromagnetic transmitters which are less than one inch from the surface of the person's head, wherein activation of these electromagnetic transmitters modifies the person's electromagnetic brain activity to a pattern which is associated with satiety.

In an example, this invention can be embodied in a method for modifying a person's food consumption comprising: (a) receiving data concerning a person's food consumption from a first time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the first time period from one or more electrodes or other brain activity sensors which are configured to be less than one inch from the surface of the person's head; (c) identifying associations between patterns of food consumption and patterns of electromagnetic brain activity by analyzing data concerning the person's food consumption and data concerning the person's electromagnetic brain activity from the first time period; (d) receiving data concerning the person's electromagnetic brain activity from a second time period from one or more electrodes or other brain activity sensors which are configured to be less than one inch from the surface of the person's head; and (e) automatically activating a plurality of electromagnetic transmitters which are less than one inch from the surface of the person's head in response to the person's food consumption from the second time period, wherein activation of these electromagnetic transmitters modifies the person's electromagnetic brain activity to a pattern which is associated with satiety.

In an example, this invention can be embodied in a method for modifying a person's food consumption comprising: (a) receiving data concerning a person's electromagnetic brain activity from a selected time period from one or more electrodes or other brain activity sensors which are configured to be less than one inch from the surface of the person's head; and (b) automatically activating a plurality of electromagnetic transmitters which are less than one inch from the surface of the person's head in response to the person's food consumption from the selected time period, wherein activation of these electromagnetic transmitters modifies the person's electromagnetic brain activity to a pattern which is associated with satiety.

In an example, this invention can be embodied in a method for modifying a person's food consumption comprising: (a) receiving data concerning a person's food consumption from a first time period: wherein this data is selected from the group consisting of: data communicated by the person via a touch screen interface, speech recognition interface, motion recognition interface, gesture recognition interface, eye movement interface, EMG recognition interface, or keyboard, keypad, or buttons, data from analysis of food images, food packaging, or food labels, data from a spectroscopic food probe, data from a smart food utensil, data from one or more wearable cameras, data from one or more motion sensors, data from one or more electromagnetic sensors in electromagnetic communication with the person's mouth, nose, tongue, esophagus, stomach, intestine or in electromagnetic communication with a nerve which innervates the person's mouth, nose, tongue, esophagus, stomach, or intestine, data from one or more optical sensors in optical communication with the person's mouth, nose, tongue, esophagus, stomach, intestine, or circulatory system, and data from one or more chemical sensors in fluid communication with the person's mouth, nose, tongue, esophagus, stomach, intestine, or circulatory system; and wherein food consumption can comprise consumption of food overall or consumption of one or more selected amounts and/or types of foods, ingredients, or nutrients; (b) receiving data concerning the person's electromagnetic brain activity from the first time period from one or more electrodes or other brain activity sensors which are configured to be less than one inch from the surface of the person's head; (c) creating a food-brainwave database, wherein this database links patterns of food consumption to patterns of electromagnetic brain activity, by analyzing data concerning the person's food consumption and data concerning the person's electromagnetic brain activity from the first time period; (d) receiving data concerning the person's electromagnetic brain activity from a second time period from one or more electrodes or other brain activity sensors which are configured to be less than one inch from the surface of the person's head; and (e) automatically activating a plurality of electromagnetic transmitters which are less than one inch from the surface of the person's head in response to the person's food consumption from the second time period, wherein activation of these electromagnetic transmitters modifies the person's electromagnetic brain activity to a pattern which is associated with satiety.

In another example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; and an accelerometer. In an example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; an accelerometer; and a database which includes associations between specific patterns of food consumption and specific patterns of electromagnetic brain activity, which translates specific types and amounts of food into specific types and amounts of nutrients, or which does both.

In another example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; and a blood chemistry sensor.

In another example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; a blood chemistry sensor; and a database which includes associations between specific patterns of food consumption and specific patterns of electromagnetic brain activity, which translates specific types and amounts of food into specific types and amounts of nutrients, or which does both.

In another example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; and a heart rate monitor. In an example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; a heart rate monitor; and a database which includes associations between specific patterns of food consumption and specific patterns of electromagnetic brain activity, which translates specific types and amounts of food into specific types and amounts of nutrients, or which does both.

In another example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; and a plurality of electromagnetic signal transmitters which are configured to be less than one inch from the surface of a person's head, wherein these electromagnetic signal transmitters collectively modify an electromagnetic field in order to reproduce a pattern of brain activity which is associated with satiety and/or consumption of a specific type of food, ingredient, or nutrient.

In another example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a data transmitter; a plurality of electromagnetic signal transmitters which are configured to be less than one inch from the surface of a person's head, wherein these electromagnetic signal transmitters collectively modify an electromagnetic field in order to reproduce a pattern of brain activity which is associated with satiety and/or consumption of a specific type of food, ingredient, or nutrient; and a database which includes associations between specific patterns of food consumption and specific patterns of electromagnetic brain activity, which translates specific types and amounts of food into specific types and amounts of nutrients, or which does both.

In another example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; and a tactile interface for computer-to-human communication.

In another example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; a tactile interface for computer-to-human communication; and a database which includes associations between specific patterns of food consumption and specific patterns of electromagnetic brain activity, which translates specific types and amounts of food into specific types and amounts of nutrients, or which does both.

In another example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; and an olfactory interface for computer-to-human communication.

In another example, this invention can be embodied in a device for measuring and/or modifying a person's food consumption comprising: a plurality of electrodes or other brain activity sensors which are configured to be worn less than one inch from the surface of a person's head; a mobile power source and/or power transducer, wherein a power transducer harvests power from human physiological activity and/or environmental energy sources; a data processor; an olfactory interface for computer-to-human communication; and a database which includes associations between specific patterns of food consumption and specific patterns of electromagnetic brain activity, which translates specific types and amounts of food into specific types and amounts of nutrients, or which does both.

In another example, this invention can be embodied in a device for measuring and/or modifying a person's food consumption comprising: a cap, beanie, hat, or helmet which is configured to be worn on a person's head; one or more electrodes or other brain activity sensors which are configured by the cap, beanie, hat, or helmet to be less than one inch from the surface of the person's head; a mobile power source and/or power transducer, wherein a power transducer harvests power from human physiological activity and/or environmental energy sources; a data processor; and a data transmitting member.

In another example, this invention can be embodied in a device for measuring and/or modifying a person's food consumption comprising: a cap, beanie, hat, or helmet which is configured to be worn on a person's head; one or more electrodes or other brain activity sensors which are configured by the cap, beanie, hat, or helmet to be less than one inch from the surface of the person's head; a mobile power source and/or power transducer, wherein a power transducer harvests power from human physiological activity and/or environmental energy sources; a data processor; a data transmitter; and a database which includes associations between specific patterns of food consumption and specific patterns of electromagnetic brain activity, which translates specific types and amounts of food into specific types and amounts of nutrients, or which does both.

In an example, this invention can be embodied in a method to modify a person's food consumption comprising: (a) receiving data concerning a person's food consumption and data concerning the person's brain activity from a first time period; (b) identifying associations between food consumption patterns and brain activity patterns based on data from the first time period; (c) receiving data concerning the person's brain activity from a second time period; (d) estimating the person's food consumption from the person's brain activity from the second time period using the associations which were previously identified.

In an example, this invention can be embodied in a wearable device to modify a person's food consumption comprising: (a) a plurality of electromagnetic sensors worn by a person on their head, wherein these electromagnetic sensors measure changes in the person's brain activity caused by food consumption, and wherein these changes in brain activity are then used to estimate the person's food consumption; (b) a power source; (c) a data processor; (d) a data transmitter; and (e) a user interface, wherein this interface provides feedback to the person concerning their estimated food consumption.

In an example, this invention can be embodied in a wearable device to modify a person's food consumption comprising: (a) a plurality of electromagnetic sensors worn by a person on their head, wherein these electromagnetic sensors measure changes in the person's brain activity caused by food consumption, and wherein these changes in brain activity are then used to estimate the person's food consumption; (b) a power source; (c) a data processor; (d) a data transmitter; and (e) a user interface, wherein this interface provides feedback to the person concerning their brain activity patterns to help the person self-modify their brain activity pattern to a pattern that is associated with satiety.

In an example, this invention can be embodied in a wearable device to modify a person's food consumption comprising: (a) a plurality of electromagnetic sensors worn by a person on their head, wherein these electromagnetic sensors measure changes in the person's brain activity caused by food consumption; (b) a plurality of electromagnetic transmitters worn by the person on their head, wherein these electromagnetic transmitters modify the person's brain activity pattern to a pattern associated with satiety; (c) a power source; (d) a data processor; and (e) a data transmitter.

In an example, this invention can be embodied in a system to modify a person's food consumption comprising: (a) a brain activity sensing device which is worn by a person on their head, wherein this device further comprises a plurality of electromagnetic sensors which measure changes in the person's brain activity caused by food consumption, wherein these changes are used to estimate the person's food consumption; a power source; a data processor; and a data transmitter; and (b) a user interface device with which the brain activity sensing device is in wireless communication, wherein this interface device provides feedback to the person concerning their estimated food consumption.

In an example, this invention can be embodied in a system to modify a person's food consumption comprising: (a) a brain activity sensing device which is worn by a person on their head, wherein this device further comprises a plurality of electromagnetic sensors which measure changes in the person's brain activity caused by food consumption, wherein these changes are used to estimate the person's food consumption; a power source; a data processor; and a data transmitter; and (b) a user interface device with which the brain activity sensing device is in wireless communication, wherein this interface device provides feedback to the person concerning their brain activity patterns to help the person self-modify their brain activity pattern to a pattern that is associated with satiety.

We now discuss FIGS. 75 through 134. These figures show examples of how this invention can be embodied in eyewear whose optical properties are controlled by changes in the wearer's electromagnetic brain activity. In an example, this eyewear can modify a person's view of their environment based on changes in their brain activity. This eyewear can enable a person to control characteristics of their visual perception of their environment by changing their brainwaves. In various examples, this eyewear can comprise lenses or other light-transmitting members whose light absorption, light reflection, light refraction, light spectrum transformation, focal direction, focal distance, light polarization, or parallax view can be controlled by the wearer's brain activity.

In an example, this invention can be embodied in eyewear with an integrated camera or other imaging component whose operation is controlled by changes in the wearer's electromagnetic brain activity. In a simple example, a camera can be turned on or off based on changes in the person's brain activity. In other examples, this eyewear can enable a person to control various parameters of how a camera records the environment. In an example, a camera's focal direction, focal distance, spectral filter, image retention, or image transmission can be controlled by a person via changes in their brain activity.

In an example, this invention can be embodied in eyewear that transmits and/or displays a combination of environmental objects and virtual objects. In an example, a person can modify and control the combination of environmental and virtual objects which they see by changing their brainwave patterns. In an example, a person can alter the relative proportion of environmental content vs. virtual content in an augmented reality system based on changes in their electromagnetic brain activity. In an example, a person can alter and control the type of virtual content which is combined with environmental content by changing their brain activity. In various examples, this invention can be embodied a type of eyewear selected from the group consisting of: non-prescription eyeglasses, prescription eyeglasses, sunglasses, goggles, contact lenses, visor, monocle, eyewear-based human-to-computer interface, eyeglasses with integrated camera, augmented reality (AR) glasses, and virtual reality (VR) glasses.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes; and (c) a data control unit. In an example, a data control unit can further comprise a power source, a data processor, and a data transmitter and/or receiver.

In an example, an electromagnetic energy sensor can be an electrode. In an example, an electromagnetic energy sensor can be an electroencephalogram (EEG) electrode. In an example, an electromagnetic energy sensor can be a dry electrode. In an example, an electromagnetic energy sensor can measure electromagnetic brain activity and/or brainwaves. In an example, an electromagnetic sensor can be located within an inch of the surface of a person's head. In an example, an electromagnetic sensor can be in direct contact with the surface of a person's head. In an example, electromagnetic energy data can be recorded at a rate in the range of 100 to 500 samples per second.

In an example, electromagnetic brain activity data from a single electromagnetic energy sensor (relative to a reference place) can be called a "channel." In an example, electromagnetic brain activity data from multiple electromagnetic energy sensors can be called a "montage." In various examples, one or more electromagnetic energy sensors can be configured at locations selected from the group of electrode sites consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2. In an example, one or more reference sites can be selected from the group of sites consisting of A1 and A2.

In an example, a light-transmitting optical member can be a lens. In an example, a lens can be one of two lenses in a pair of eyeglasses. In an example, a lens can be a contact lens. In an example, a lens can be located in goggles or a visor. In an example, a lens or other light-transmitting optical member can be made from a material whose optical attributes are changed by application of an electrical current. In an example, a lens can be a compound lens. In an example, a lens or other light-transmitting optical member can be made from multiple components whose combined optical attributes are changed by application of an electrical current. In an example, a lens or other light-transmitting optical member can have one or more optoelectronic or photoelectric components. In an example, a lens or other light-transmitting optical member can be a variable lens with a fluid component.

In an example, a light-transmitting optical member can be shaped such that its optical attributes are changed by its overall movement relative to a person's eye. In an example, a light-transmitting optical member can also comprise one or more actuators to move it or to move components within it. In an example, a light-transmitting optical member can have multiple components such that its optical attributes are changed by the movement of a first set of components relative to a second set of components. In an example, a lens or other light-transmitting optical member can comprise an array of micro-lenses or micro-mirrors. In an example, the absorption, reflection, refraction, polarization, or collimation of light through a light-transmitting optical member can be changed by application of electrical current to the member. In an example, the absorption, reflection, refraction, polarization, or collimation of light through a light-transmitting optical member can be changed by the overall movement of the member or by movement of a first set of components in an optical member relative to a second set of components in the optical member. In an example, a light-transmitting optical member or multiple components within such a member can be moved by a mechanism selected from the group consisting of: electric motor, piezoelectric actuator, Micro Electro Mechanical System (MEMS), and micro motor.

In an example, a light-transmitting optical member can be further comprised of one or more components selected from the group consisting of: simple lens, concave lens, concentric lenses, convex lens, diverging lens, asymmetric lens, compound lens, fly's eye lens, Fresnel lens, light-transducing element, microlens array, microspheres, optoelectronic lens, parabolic lens, wedge-shaped lens, liquid crystal, liquid lens, Digital Micromirror Device (DMD), Digital Light Processor (DLP), Electromagnetically Induced Transparency (EIT) structure, Liquid Crystal Display (LCD), MEMS-based lens array, MEMS-based mirror array, birefringent material, carbon nanotube, light-guiding metamaterial structure, light-guiding metamaterial structure, light-guiding tubes, metamaterial light channel, microscale glass beads, nanorods, nanoscale gratings, nanotubes, etched waveguide, nanoimprint lithography pathways, resonant grating filter, Split Ring Resonators (SRRs), thermoplastic nanoimprint pathways, crystal, crystal array, crystalline structures, photonic metamaterial, photonic crystal, fiber optics, optical fiber, polarizing filter, cylindrical prism, prism, wedge prism, acrylic mirror, concentric reflective surfaces, dielectric mirror, parabolic mirror, reflector array, and retroreflective structure.

In an example, a data control unit can comprise: a power source or transducer; and a data processor. In an example, a power source can be a battery. In various examples, a data control unit can further comprise one or more components selected from the group consisting of: a wireless data transmitter; a wireless data reception component; a data memory component; a computer-to-human interface; and a human-to-computer interface. In an example, a power source or transducer can further comprise: power from a source that is internal to the device during regular operation (such as an internal battery, capacitor, energy-storing microchip, wound coil or spring); power that is obtained, harvested, or transduced from a source other than the person's body that is external to the device (such as a rechargeable battery, electromagnetic inductance from external source, solar energy, indoor lighting energy, wired connection to an external power source, ambient or localized radiofrequency energy, or ambient thermal energy); and power that is obtained, harvested, or transduced from the person's body (such as kinetic or mechanical energy from body motion, electromagnetic energy from the person's body, or thermal energy from the person's body).

In an example, a data control unit can be in direct electrical communication with one or more electromagnetic energy sensors by wires or other electrically-conductive pathways. In an example, a data control unit can be in wireless communication with one or more electromagnetic energy sensors. In an example, a data control unit can be in direct electrical communication with one or more light-transmitting members by wires or other electrically-conductive pathways. In an example, a data control unit can be in wireless communication with one or more light-transmitting members.

In an example, a data control unit can be in wireless communication with a separate wearable device selected from the group consisting of: a wristwatch, smart watch, fitness watch, watch phone, bracelet phone, smart bracelet, fitness bracelet, smart wrist band, electronically-functional wrist band, other wrist-worn electronic device, or smart armband; a smart button, electronically-functional button, pin, brooch, pendant, beads, neck chain, necklace, dog tags, locket, or medallion; a smart finger ring, electronically-functional finger ring, electronically-functional earring, nose ring, or ear bud or clip; a wearable camera; an article of smart clothing, an electronically-functional shirt, electronically-functional pants, or a smart belt.

In an example, a data control unit can be in wireless communication with a separate mobile device selected from the group consisting of: smart phone, mobile phone, holophone, or cellular phone; PDA; electronic tablet; electronic pad; and other electronically-functional handheld device. In an example, a data control unit can be in wireless communication with a relatively fixed-location device selected from the group consisting of: laptop computer, desktop computer, internet terminal, smart appliance, home control system, and other fixed-location electronic communication device.

In an example, this invention can be embodied in eyewear that modifies visual perception based on electromagnetic energy measured from a person's head, comprising: (a) one or more electrodes configured to be within three inches of the surface of a person's head which measure electromagnetic energy from the person's head; (b) one or more lenses configured to be within three inches of the surface of the person's head and configured to transmit light into one or both of the person's eyes; (c) a power source or transducer; and (d) a data processor or transmitter.

In an example, electromagnetic energy data from one or more electromagnetic energy sensors can be statistically analyzed in order to identify significant patterns and/or changes in a person's electromagnetic brain activity. These significant patterns and/or changes in brain activity can then be used to control the transmission of light through one or more light-transmitting optical members in eyewear. In an example, this invention can comprise eyewear whose optical transmission attributes are modified by changes in a person's brainwaves. In various examples, the absorption, reflection, refraction, polarization, or parallax view of light through one or more light-transmitting optical members can be modified by a person's electromagnetic brain activity. In various examples, the focal distance, view direction, and/or view scope of images transmitted through one or more light-transmitting optical members can be modified by a person's electromagnetic brain activity. In various examples, the spectrum of light absorbed, transmitted, or shifted through the one or more light-transmitting optical members can be modified by a person's brain activity.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein one or more of the light-transmitting optical members has a first configuration which modifies transmitted light in a first manner and a second configuration which modifies transmitted light in a second manner, and wherein one or more light-transmitting optical members are changed from the first configuration to the second configuration, or vice versa, based on data from one or more of the electromagnetic energy sensors; and (c) a data control unit that further comprises a power source and a data processor.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein transmitted light is modified based on a change in data from the one or more of the electromagnetic energy sensors; and (c) a data control unit that further comprises a power source and a data processor.

In various examples, one or more primary statistical methods can be used to identify specific patterns in a person's electromagnetic brain activity and/or specific changes in the person's electromagnetic brain activity. In an example, data from one or more electromagnetic sensors can be filtered to remove artifacts before the application of a primary statistical method. In an example, a filter can be used to remove electromagnetic signals from eye blinks, eye flutters, or other eye movements before the application of a primary statistical method. In an example, a notch filter can be used as well to remove 60 Hz artifacts caused by AC electrical current. In various examples, one or more filters can be selected from the group consisting of: a high-pass filter, a band-pass filter, a loss-pass filter, an electromyographic activity filter, a 0.5-1 Hz filter, and a 35-70 Hz filter.

In an example, a pattern and/or change in electromagnetic brain activity can be a one-time pattern. In another example, a pattern of electromagnetic brain activity can repeat over time in a rhythmic manner. In an example, a primary statistical method can analyze repeating electromagnetic patterns by analyzing their frequency of repetition, their frequency band or range of repetition, their recurring amplitude, their wave phase, and/or their waveform. In an example repeating patterns and/or waveforms can be analyzed using Fourier Transform methods.

In an example, a primary statistical method for identifying patterns and/or changes in electromagnetic brain activity can comprise finding the mean or average value of data from one or more brain activity channels during a period of time. In an example, a statistical method can comprise identifying a significant change in the mean or average value of data from one or more brain activity channels. In an example, a statistical method can comprise finding the median value of data from one or more brain activity channels during a period of time. In an example, a statistical method can comprise identifying a significant change in the median value of data from one or more brain activity channels. In an example, a statistical method can comprise identifying significant changes in the relative mean or median data values among multiple brain activity channels. In an example, a statistical method can comprise identifying significant changes in mean data values from a first set of electrode locations relative to mean data values from a second set of electrode locations. In an example, a statistical method can comprise identifying significant changes in mean data recorded from a first region of the brain relative to mean data recorded from a second region of the brain.

In an example, a primary statistical method for identifying patterns and/or changes in electromagnetic brain activity can comprise finding the minimum or maximum value of data from one or more brain activity channels during a period of time. In an example, a statistical method can comprise identifying a significant change in the minimum or maximum value of data from one or more brain activity channels. In an example, a statistical method can comprise identifying significant changes in the relative minimum or maximum data values among multiple brain activity channels. In an example, a statistical method can comprise identifying significant changes in minimum or maximum data values from a first set of electrode locations relative to minimum or maximum data values from a second set of electrode locations. In an example, a statistical method can comprise identifying significant changes in minimum or maximum data values recorded from a first region of the brain relative to minimum or maximum data values recorded from a second region of the brain.

In an example, a primary statistical method for identifying patterns and/or changes in electromagnetic brain activity can comprise finding the variance or the standard deviation of data from one or more brain activity channels during a period of time. In an example, a statistical method can comprise identifying a significant change in the variance or the standard deviation of data from one or more brain activity channels. In an example, a statistical method can comprise identifying significant changes in the covariation and/or correlation among data from multiple brain activity channels. In an example, a statistical method can comprise identifying significant changes in the covariation or correlation between data from a first set of electrode locations relative and data from a second set of electrode locations. In an example, a statistical method can comprise identifying significant changes in the covariation or correlation of data values recorded from a first region of the brain and a second region of the brain.

In an example, a primary statistical method for identifying patterns and/or changes in electromagnetic brain activity can comprise finding the amplitude of waveform data from one or more channels during a period of time. In an example, a statistical method can comprise identifying a significant change in the amplitude of waveform data from one or more channels. In an example, a statistical method can comprise identifying significant changes in the relative wave amplitudes from one or more channels. In an example, a statistical method can comprise identifying significant changes in the amplitude of electromagnetic signals recorded from a first region of the brain relative to the amplitude of electromagnetic signals recorded from a second region of the brain.

In an example, a primary statistical method for identifying patterns and/or changes in electromagnetic brain activity can comprise finding the power of waveform brain activity data from one or more channels during a period of time. In an example, a statistical method can comprise identifying a significant change in the power of waveform data from one or more channels. In an example, a statistical method can comprise identifying significant changes in the relative power levels of one or more channels. In an example, a statistical method can comprise identifying significant changes in the power of electromagnetic signals recorded from a first region of the brain relative to the power of electromagnetic signals recorded from a second region of the brain.

In an example, a primary statistical method for identifying patterns and/or changes in electromagnetic brain activity can comprise finding a frequency or a frequency band of waveform and/or rhythmic brain activity data from one or more channels which repeats over time. In an example, Fourier Transform methods can be used to find a frequency or a frequency band of waveform and/or rhythmic data which repeats over time. In an example, a statistical method can comprise decomposing a complex waveform into a combination of simpler waveforms which each repeat at a different frequency or within a different frequency band. In an example, Fourier Transform methods can be used to decomposing a complex waveform into a combination of simpler waveforms which each repeat at a different frequency or within a different frequency band.

In an example, a primary statistical method for identifying patterns and/or changes in electromagnetic brain activity can comprise identifying significant changes in the amplitude, power level, phase, frequency, covariation, entropy, and/or oscillation of waveform data from one or more channels. In an example, a statistical method can comprise identifying significant changes in the amplitude, power level, phase, frequency, covariation, entropy, and/or oscillation of waveform data within a selected frequency band. In an example, a statistical method can comprise identifying significant changes in the relative amplitudes, power levels, phases, frequencies, covariations, entropies, and/or oscillations of waveform data among different frequency bands. In various examples, these significant changes can be identified using Fourier Transform methods.

In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a method can analyze changes in brainwaves in a single frequency band, changes in brainwaves in multiple frequency bands, or changes in brainwaves in a first frequency band relative to those in a second frequency band.

In an example, Delta brainwaves can be measured and analyzed within a frequency band of 1 to 4 Hz. In various examples, Delta brainwaves or other rhythmic, cyclical, and/or repeating electromagnetic signals associated with brain activity can be measured and analyzed within a frequency band selected from the group consisting of: 0.5-3.5 Hz, 0.5-4 Hz, 1-3 Hz, 1-4 Hz, and 2-4 Hz. In an example, a method can track a decrease or increase in the relative power of brainwaves in the Delta band. In an example, a method can track a frequency shift within the Delta frequency band. In an example, a method can track a change in wave shape for brainwaves in the Delta frequency band. In an example, a method can track a change in which brain regions originate or modify brainwaves within the Delta frequency band. In an example, a method can track a change in brainwave activity within the Delta band from the anterior vs. posterior areas of a person's brain. In an example, a method can track a change in brainwave activity within the Delta band for a particular brain lobe or organelle. In an example, a method can track a change in brainwave activity within the Delta band as measured from a specific electrode site, a specific electrode channel, and/or a specific montage of channels.

In an example, Theta brainwaves can be measured and analyzed within a frequency band of 4 to 8 Hz. In various examples, Theta brainwaves or other rhythmic, cyclical, and/or repeating electromagnetic signals associated with brain activity can be measured and analyzed within a frequency band selected from the group consisting of: 3.5-7 Hz, 3-7 Hz, 4-7 Hz, 4-7.5 Hz, 4-8 Hz, and 5-7 Hz. In an example, a method can track changes in the power of brainwaves in the Theta band. In an example, a method can track a frequency shift within the Theta band. In an example, a method can track changes in wave shape for brainwaves in the Theta band. In an example, a method can track a change in which brain regions originate or modify brainwaves within the Theta band. In an example, a method can track a change in brainwave activity within the Theta band as measured from a specific electrode site, a specific electrode channel, and/or a specific montage of channels.

In an example, Alpha brainwaves can be measured and analyzed within a frequency band of 7 to 14 Hz. In various examples, Alpha brainwaves or other rhythmic, cyclical, and/or repeating electromagnetic signals associated with brain activity can be measured and analyzed within a frequency band selected from the group consisting of: 7-13 Hz, 7-14 Hz, 8-12 Hz, 8-13 Hz, 7-11 Hz, 8-10 Hz, and 8-10 Hz. In an example, a method can track an increase or decrease in the relative power of brainwaves in the Alpha band. In an example, a method can track a downward or upward shift in the frequency of brainwaves within the Alpha band. In an example, a method can track a change in wave shape for brainwaves in the Alpha frequency band. In an example, a method can track a change in which brain regions originate or modify brainwaves within the Alpha frequency band. In an example, a method can track a change in brainwave activity within the Alpha band on one side of a person's brain relative to the other side. In an example, a method can track a change in brainwave activity within the Alpha band in a particular brain lobe or organelle. In an example, a method can track a change in brainwave activity within the Alpha band as measured from a specific electrode site, a specific electrode channel, and/or a specific montage of channels.

In an example, Beta brainwaves can be measured and analyzed within a frequency band of 12 to 30 Hz. In various examples, Beta brainwaves or other rhythmic, cyclical, and/or repeating electromagnetic signals associated with brain activity can be measured and analyzed within a frequency band selected from the group consisting of: 11-30 Hz, 12-30 Hz, 13-18 Hz, 13-22 Hz, 13-26 Hz, 13-26 Hz, 13-30 Hz, 13-32 Hz, 14-24 Hz, 14-30 Hz, and 14-40 Hz. In an example, specific patterns or trends in brainwaves in the Beta frequency band can be statistically identified.

In an example, Gamma brainwaves can be measured and analyzed within a frequency band of 30 to 100 Hz. In various examples, Gamma brainwaves or other rhythmic, cyclical, and/or repeating electromagnetic signals associated with brain activity can be measured and analyzed within a frequency band selected from the group consisting of: 30-100 Hz, 35-100 Hz, 40-100 Hz, and greater than 30 Hz. In an example, specific patterns or trends in brainwaves in the Gamma frequency band can be statistically identified. In an example, a person can be identified as having the "World's Best Gamma" and receive an appropriately-labeled coffee mug.

In an example, a primary statistical method can employ multivariate analysis of electromagnetic brainwave activity in the Delta, Theta, and Alpha frequency bands to identify patterns. In an example, a primary statistical method can comprise calculating an arithmetic function, or a change in an arithmetic function, of the different power levels in multiple frequency bands. In an example, a primary statistical method can comprise a difference, or a change in a difference, between power levels in different frequency bands. In an example, a primary statistical method can comprise a ratio, or a change in a ratio, of power levels in different frequency bands. In an example, a primary statistical method can comprise a sum, or a change in a sum, of power levels in different frequency bands. In an example, a primary statistical method can comprise a product, or a change in a product, of power levels in different frequency bands.

In various examples, specific patterns of electromagnetic brain activity can be analyzed and identified using one or more statistical methods selected from the group consisting of: ANOVA or MANOVA; artificial neural network; autoregression; Bonferroni analysis; centroid analysis; chi-squared analysis; cluster analysis and grouping; decision tree or random forest analysis; Discrete Fourier transform (DFT), Fast Fourier Transform (FFT), or other Fourier Transform methods; factor analysis; feature vector analysis; fuzzy logic model; Gaussian model; hidden Markov model, input-output hidden Markov model, or other Markov model; inter-band mean; inter-band ratio; inter-channel mean; inter-channel ratio; inter-montage mean; inter-montage ratio; Kalman filter; kernel estimation; linear discriminant analysis; linear transform; logit model; machine learning; mean power; mean; median; multi-band covariance analysis; multi-channel covariance analysis; multivariate linear regression or multivariate least squares estimation; multivariate logit or other multivariate parametric classifiers; naïve Bayes classifier, trained Bayes classifier, dynamic Bayesian network, or other Bayesian methods; non-linear programming; pattern recognition; power spectral density or other power spectrum analysis; principal components analysis; probit model; support vector machine; time-series model; T-test; variance, covariance, or correlation; waveform identification; multi-resolution wavelet analysis or other wavelet analysis; whole band power; and Z-scores or other data normalization method.

In an example, one or more electromagnetic energy sensors can measure electromagnetic activity concerning eye movements and/or muscle activity. In an example, an electromagnetic energy sensor can be an electrooculography (EOG) sensor or an electromyography (EMG) sensor. In an example, the optical attributes of electronically-functional eyewear can be controlled by changes in eye movements as measured by one or more EOG sensors. In an example, one or more EOG sensors can be integrated into a portion of eyewear which spans the front of a person's face. In an example, the optical attributes of electronically-functional eyewear can be controlled by changes in muscle activity as measured by one or more EMG sensors. In an example, this invention can be embodied in eyewear which comprises one or more electromagnetic energy sensors selected from the group consisting of: EOG sensors which measure electromagnetic activity concerning eye movements; EMG sensors which measure electromagnetic activity concerning muscle activity, and EEG sensors which measure electromagnetic brain activity.

In an example, this invention can be embodied in brainwave-controlled sunglasses. In an example, this invention can comprise sunglasses or other eyewear which partially block light transmission, wherein the amount of light blocked or transmitted can be modified by changes in the person's brain activity. In an example, this invention can comprise sunglasses whose opacity and/or reflectivity is controlled by changes in brain activity by the person wearing them. In an example, this invention enables a person to increase or decrease the transparency or opacity of their eyewear by changing their brainwave activity. In an example, such brainwave-controlled sunglasses can be useful for protecting a person's eyes from intensive light sources. In an example, such brainwave-controlled sunglasses can be useful for maintaining a person's privacy. In an alternative example, the electromagnetic sensors of this invention can measure electromagnetic signals from eye movements instead of brain activity. In an alternative example, this invention can enable a person to increase or decrease the transparency or opacity of their eyewear by moving their eyes in a selected direction or motion pattern.

In an example, a person can change the transparency of lenses or other light-transmitting members by changing the power of their brainwaves in the Delta frequency band. In an example, a person can change the transparency of lenses or other light-transmitting members by changing the power of their brainwaves in the Theta band. In an example, a person can change the transparency of lenses or other light-transmitting members by changing the power of their brainwaves in the Alpha frequency band. In an example, a person can change the transparency of lenses or other light-transmitting members by changing the power of their brainwaves in the Beta frequency band. In an example, a person can change the transparency of lenses or other light-transmitting members by changing the power of their brainwaves in the Gamma band.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein one or more of the light-transmitting optical members has a first configuration which absorbs a first amount of light and a second configuration which absorbs a second amount of light, and wherein one or more light-transmitting optical members are changed from the first configuration to the second configuration, or vice versa, based on data from one or more of the electromagnetic energy sensors; and (c) a data control unit that further comprises a power source and a data processor.

FIGS. 75 and 76 show an example of how this invention can be embodied in eyewear 7501 that modifies visual perception and/or imaging based on electromagnetic energy measured from a person's head, comprising: one or more electromagnetic energy sensors 7502 configured to be within three inches of the surface of a person's head and configured to measure electromagnetic energy from the person's head; one or more light-transmitting optical members 7503 configured to be within three inches of the surface of the person's head and configured to transmit light into one or both of the person's eyes, wherein one or more of the light-transmitting optical members has a first configuration which absorbs a first amount of light and a second configuration which absorbs a second amount of light, and wherein one or more light-transmitting optical members are changed from the first configuration to the second configuration, or vice versa, based on data from one or more of the electromagnetic energy sensors; and a data control unit 7504.

FIG. 75 shows this eyewear in the first configuration. FIG. 76 shows this eyewear having been changed to the second configuration based on electromagnetic brain activity 7601 as measured by electromagnetic energy sensor 7502. The left side of each figure shows a side-view of this eyewear in anatomical context on a person's head. The right side of each figure shows this same eyewear (at the same time) without showing the person's head, in order to show optical changes more clearly. As shown on the right side of FIG. 75, in the first configuration the light-transmitting member 7503 transmits both light rays 7505 and 7506. As shown on the right side of FIG. 76, in the second configuration the light-transmitting member 7503 transmits only light ray 7506. In this example, light ray 7505 is absorbed in response to the measurement and identification of electromagnetic brain activity 7601. In an example, light-transmitting member 7503 can be a lens whose transparency changes due to application of an electrical current.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein the amount of light that is absorbed by one or more light-transmitting optical members is modified based on a change in data from the one or more of the electromagnetic energy sensors; and (c) a data control unit that further comprises a power source and a data processor.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein one or more of the light-transmitting optical members has a first configuration which reflects a first amount of light and a second configuration which reflects a second amount of light, and wherein one or more light-transmitting optical members are changed from the first configuration to the second configuration, or vice versa, based on data from one or more of the electromagnetic energy sensors; and (c) a data control unit that further comprises a power source and a data processor.

FIGS. 77 and 78 show an example of how this invention can be embodied in eyewear 7701 that modifies visual perception and/or imaging based on electromagnetic energy measured from a person's head, comprising: one or more electromagnetic energy sensors 7702 configured to be within three inches of the surface of a person's head and configured to measure electromagnetic energy from the person's head; one or more light-transmitting optical members 7703 configured to be within three inches of the surface of the person's head and configured to transmit light into one or both of the person's eyes, wherein one or more of the light-transmitting optical members has a first configuration which reflects a first amount of light and a second configuration which reflects a second amount of light, and wherein one or more light-transmitting optical members are changed from the first configuration to the second configuration, or vice versa, based on data from one or more of the electromagnetic energy sensors; and a data control unit 7704.

FIG. 77 shows this eyewear in the first configuration. FIG. 78 shows this eyewear having been changed to the second configuration based on electromagnetic brain activity 7601 as measured by electromagnetic energy sensor 7702. The left side of each figure shows a side-view of this eyewear in anatomical context on a person's head. The right side of each figure shows this same eyewear (at the same time) without showing the person's head, in order to show optical changes more clearly. As shown on the right side of FIG. 77, in the first configuration the light-transmitting member 7703 transmits light rays 7705 and 7706. As shown on the right side of FIG. 78, in the second configuration the light-transmitting member 7703 reflects light rays 7705 and 7706. In an example, light-transmitting member can be a lens whose reflectivity is changed by application of an electrical current or a moveable micro-mirror array.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein the amount of light that is reflected by one or more light-transmitting optical members is modified based on a change in data from the one or more of the electromagnetic energy sensors; and (c) a data control unit that further comprises a power source and a data processor.

In an example, this invention can comprise eyewear in which changes in a person's view angle, view direction, or breadth of view are controlled by changes in the person's electromagnetic brain activity. In an example, this invention can enable a person to change the scope or breadth of their field of vision by changing their brainwave pattern. In an example, this invention can enable a person to directly see objects in their peripheral field of vision by changing their brainwave pattern. In an example, this invention can enable a person to selectively adjust the polar coordinate (around the circumference of their head) of their field of vision through the eyewear. In an example, this invention can enable a person to change their perspective to see behind them, wherein this change in perspective is controlled by a change in their brainwave patterns.

In an example, a person can change their view direction and/or the field of vision through lenses or other light-transmitting members by changing the power of their brainwaves in the Delta frequency band. In an example, a person can change their view direction and/or field of vision through lenses or other light-transmitting members by changing the power of their brainwaves in the Theta band. In an example, a person can change their view direction and/or field of vision through lenses or other light-transmitting members by changing the power of their brainwaves in the Alpha frequency band. In an example, a person can change their view direction and/or field of vision through lenses or other light-transmitting members by changing the power of their brainwaves in the Beta frequency band. In an example, a person can change their view direction and/or field of vision through lenses or other light-transmitting members by changing the power of their brainwaves in the Gamma band.

In an example, this invention can be embodied in eyewear which modifies the appearance of a person's eyes as seen by others through a lens or other light-transmitting member. In an example, this change in appearance can be achieved through a selective change in the refraction of light through a central portion of the light-transmitting member. In an example, this change in appearance can be achieved through a selective change in the concavity or convexity of a central portion of a light-transmitting member. In an example, a person can modify and control the appearance of their pupils to other people, in real time, by changing their brain activity. In an example, a person can modify the apparent size or shape of their pupils by changing their brain activity. In an example, a person can increase or decrease the apparent dilation of their pupils by changing their brainwave patterns. In an example, a person can increase the apparent dilation of their pupils to others in order to convey greater excitement or interest.

In an example, a person can change the apparent dilation of their pupils through lenses or other light-transmitting members by changing the power of their brainwaves in the Delta frequency band. In an example, a person can change the apparent dilation of their pupils through lenses or other light-transmitting members by changing the power of their brainwaves in the Theta band. In an example, a person can change the apparent dilation of their pupils through lenses or other light-transmitting members by changing the power of their brainwaves in the Alpha frequency band. In an example, a person can change the apparent dilation of their pupils through lenses or other light-transmitting members by changing the power of their brainwaves in the Beta frequency band. In an example, a person can change the apparent dilation of their pupils through lenses or other light-transmitting members by changing the power of their brainwaves in the Gamma band.

In an example, a person can change the apparent dilation of their pupils through lenses or other light-transmitting members by changing the specific frequency of their brainwaves in the Delta frequency band. In an example, a person can change the apparent dilation of their pupils through lenses or other light-transmitting members by changing the specific frequency of their brainwaves in the Theta band. In an example, a person can change the apparent dilation of their pupils through lenses or other light-transmitting members by changing the specific frequency of their brainwaves in the Alpha frequency band. In an example, a person can change the apparent dilation of their pupils through lenses or other light-transmitting members by changing the specific frequency of their brainwaves in the Beta frequency band. In an example, a person can change the apparent dilation of their pupils through lenses or other light-transmitting members by changing the specific frequency of their brainwaves in the Gamma band.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein one or more of the light-transmitting optical members has a first configuration which refracts light rays to a first exit angle and a second configuration which refracts light rays to a second exit angle, and wherein one or more light-transmitting optical members are changed from the first configuration to the second configuration, or vice versa, based on data from one or more of the electromagnetic energy sensors; and (c) a data control unit that further comprises a power source and a data processor.

FIGS. 79 and 80 show an example of how this invention can be embodied in eyewear 7901 that modifies visual perception and/or imaging based on electromagnetic energy measured from a person's head, comprising: one or more electromagnetic energy sensors 7902 configured to be within three inches of the surface of a person's head and configured to measure electromagnetic energy from the person's head; one or more light-transmitting optical members 7903 configured to be within three inches of the surface of the person's head and configured to transmit light into one or both of the person's eyes, wherein one or more of the light-transmitting optical members has a first configuration which refracts light rays to a first exit angle and a second configuration which refracts light rays to a second exit angle, and wherein one or more light-transmitting optical members are changed from the first configuration to the second configuration, or vice versa, based on data from one or more of the electromagnetic energy sensors; and a data control unit 7904.

FIG. 79 shows this eyewear in the first configuration. FIG. 80 shows this eyewear having been changed to the second configuration based on electromagnetic brain activity 7601 as measured by electromagnetic energy sensor 7902. The left side of each figure shows a side-view of this eyewear on a person's head. The right side of each figure shows this same eyewear without showing the person's head. As shown on the right side of FIG. 79, in the first configuration light-transmitting member 7903 transmits and/or refracts light rays 7905 and 7906 to a first exit angle. As shown on the right side of FIG. 80, in the second configuration light-transmitting member 7903 transmits and/or refracts light rays 7905 and 7906 to a second exit angle. In an example, light-transmitting member 7903 can be a lens, prism, or lens array whose surface angles are changed by application of electrical current.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein the exit angle of light rays refracted by one or more light-transmitting optical members is modified based on a change in data from the one or more of the electromagnetic energy sensors; and (c) a data control unit that further comprises a power source and a data processer.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein one or more of the light-transmitting optical members has a first configuration which refracts light rays from a first entrance angle and a second configuration which refracts light rays from a second entrance angle, and wherein one or more light-transmitting optical members are changed from the first configuration to the second configuration, or vice versa, based on data from one or more of the electromagnetic energy sensors; and (c) a data control unit that further comprises a power source and a data processer.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein the entrance angle of light rays refracted by one or more light-transmitting optical members is modified based on a change in data from the one or more of the electromagnetic energy sensors; and (c) a data control unit that further comprises a power source and a data processer.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein one or more of the light-transmitting optical members has a first configuration through which other people see the person's pupils as having a first size or dilation and a second configuration through which other people see the person's pupils as having a second size or dilation, and wherein one or more light-transmitting optical members are changed from the first configuration to the second configuration, or vice versa, based on data from one or more of the electromagnetic energy sensors; and (c) a data control unit that further comprises a power source and a data processer.

FIGS. 81 and 82 show an example of how this invention can be embodied in eyewear 8101 that modifies visual perception and/or imaging based on electromagnetic energy measured from a person's head, comprising: one or more electromagnetic energy sensors 8102 configured to be within three inches of the surface of a person's head and configured to measure electromagnetic energy from the person's head; one or more light-transmitting optical members 8103 configured to be within three inches of the surface of the person's head and configured to transmit light into one or both of the person's eyes, wherein one or more of the light-transmitting optical members has a first configuration through which other people see the person's pupils as having a first size or dilation and a second configuration through which other people see the person's pupils as having a second size or dilation, and wherein one or more light-transmitting optical members are changed from the first configuration to the second configuration, or vice versa, based on data from one or more of the electromagnetic energy sensors; and a data control unit 8104.

FIG. 81 shows this eyewear in the first configuration. FIG. 82 shows this eyewear having been changed to the second configuration based on electromagnetic brain activity 7601. The left side of each figure shows a side-view of this eyewear on a person's head and the right side of each figure shows this same eyewear without showing the person's head. FIG. 81 shows the first configuration, wherein light-transmitting member 8103 refracts light rays 8105 and 8106 so that the person's pupil appears to have a first size. FIG. 82 shows the second configuration, wherein light-transmitting member 8103 refracts light rays 8105 and 8106 so that the person's pupil appears to have a second size. In an example, light-transmitting member 8103 can be a lens or lens array whose concavity or convexity is changed by the application of electrical current.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein one or more of the light-transmitting optical members has a first configuration which transmits light from a first view direction and a second configuration which transmits light from a second view direction, and wherein one or more light-transmitting optical members are changed from the first configuration to the second configuration, or vice versa, based on data from one or more of the electromagnetic energy sensors; and (c) a data control unit that further comprises a power source and a data processer.

FIGS. 83 and 84 show an example of how this invention can be embodied in eyewear 8301 that modifies visual perception and/or imaging based on electromagnetic energy measured from a person's head, comprising: one or more electromagnetic energy sensors 8302 configured to be within three inches of the surface of a person's head and configured to measure electromagnetic energy from the person's head; one or more light-transmitting optical members 8303 configured to be within three inches of the surface of the person's head and configured to transmit light into one or both of the person's eyes, wherein one or more of the light-transmitting optical members has a first configuration which transmits light from a first view direction and a second configuration which transmits light from a second view direction, and wherein one or more light-transmitting optical members are changed from the first configuration to the second configuration, or vice versa, based on data from one or more of the electromagnetic energy sensors; and a data control unit 8304.

FIG. 83 shows this eyewear in the first configuration. FIG. 84 shows this eyewear having been changed to the second configuration based on electromagnetic brain activity 7601. The left side of each figure shows a side-view of this eyewear on a person's head and the right side of each figure shows this eyewear without showing the person's head. As shown on the right side of FIG. 83, in the first configuration light-transmitting member 8303 transmits and/or refracts light rays 8305 and 8306 so that the person sees in a first view direction. As shown on the right side of FIG. 84, in the second configuration the light-transmitting member 8303 transmits and/or refracts light rays 8305 and 8306 so that the person sees in a second direction. In an example, light-transmitting member 8303 can be a prism, lens, or lens array whose surface angles are changed by the application of electrical current.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein the view direction that is transmitted by one or more light-transmitting optical members is modified based on a change in data from the one or more of the electromagnetic energy sensors; and (c) a data control unit that further comprises a power source and a data processor.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein one or more of the light-transmitting optical members has a first configuration which transmits light from a first view scope and/or breadth and a second configuration which transmits light from a second view scope and/or breadth, and wherein one or more light-transmitting optical members are changed from the first configuration to the second configuration, or vice versa, based on data from one or more of the electromagnetic energy sensors; and (c) a data control unit that further comprises a power source and a data processor.

FIGS. 85 and 86 show an example of how this invention can be embodied in eyewear 8501 that modifies visual perception and/or imaging based on electromagnetic energy measured from a person's head, comprising: one or more electromagnetic energy sensors 8502 configured to be within three inches of the surface of a person's head and configured to measure electromagnetic energy from the person's head; one or more light-transmitting optical members 8503 configured to be within three inches of the surface of the person's head and configured to transmit light into one or both of the person's eyes, wherein one or more of the light-transmitting optical members has a first configuration which transmits light from a first view scope and/or breadth and a second configuration which transmits light from a second view scope and/or breadth, and wherein one or more light-transmitting optical members are changed from the first configuration to the second configuration, or vice versa, based on data from one or more of the electromagnetic energy sensors; and a data control unit 8504.

FIG. 85 shows this eyewear in the first configuration. FIG. 86 shows this eyewear having been changed to the second configuration based on electromagnetic brain activity 7601. The left side of each figure shows this eyewear on a person's head. The right side shows this eyewear without showing the person's head. As shown on the right side of FIG. 85, in the first configuration light-transmitting member 8503 transmits and/or refracts light rays 8505 and 8506 so that the person sees with a first view scope and/or breadth. As shown on the right side of FIG. 86, in the second configuration the light-transmitting member 8503 transmits and/or refracts light rays 8505 and 8506 so that the person sees with a second view scope and/or breadth. In an example, light-transmitting member 8503 can be a lens or lens array whose concavity or convexity is changed by the application of electrical current.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein the view scope and/or breath that is transmitted by one or more light-transmitting optical members is modified based on a change in data from one or more of the electromagnetic energy sensors; and (c) a data control unit that further comprises a power source and a data processor.

In an example, this invention can be embodied in eyewear with a variable focal distance, wherein this focal distance can be modified by a change in a person's electromagnetic brain activity. In an example, this invention can enable a person to focus on environmental objects at difference distances by changing their brainwave patterns. In an example, this invention can comprise thought-controlled bifocal eyewear wherein the same set of lenses can focus on a distant object or on a nearby object, depending on a person's brainwave pattern. In an example, this invention can comprise thought-controlled binoculars, wherein the same set of lenses can focus on a normal-distance object or a far-distance object depending on a person's brainwave pattern.

In an example, a person can change their focal distance through lenses or other light-transmitting members by changing the power of their brainwaves in the Delta frequency band. In an example, a person can change their focal distance through lenses or other light-transmitting members by changing the power of their brainwaves in the Theta band. In an example, a person can change their focal distance through lenses or other light-transmitting members by changing the power of their brainwaves in the Alpha frequency band. In an example, a person can change their focal distance through lenses or other light-transmitting members by changing the power of their brainwaves in the Beta frequency band. In an example, a person can change their focal distance through lenses or other light-transmitting members by changing the power of their brainwaves in the Gamma band.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein one or more of the light-transmitting optical members has a first configuration with a first focal distance and a second configuration with a second focal distance, and wherein one or more light-transmitting optical members are changed from the first configuration to the second configuration, or vice versa, based on data from one or more of the electromagnetic energy sensors; and (c) a data control unit that further comprises a power source and a data processer.

FIGS. 87 and 88 show an example of how this invention can be embodied in eyewear 8701 that modifies visual perception and/or imaging based on electromagnetic energy measured from a person's head, comprising: one or more electromagnetic energy sensors 8702 configured to be within three inches of the surface of a person's head and configured to measure electromagnetic energy from the person's head; one or more light-transmitting optical members 8703 configured to be within three inches of the surface of the person's head and configured to transmit light into one or both of the person's eyes, wherein one or more of the light-transmitting optical members has a first configuration with a first focal distance and a second configuration with a second focal distance, and wherein one or more light-transmitting optical members are changed from the first configuration to the second configuration, or vice versa, based on data from one or more of the electromagnetic energy sensors; and a data control 8704.

FIG. 87 shows this eyewear in the first configuration. FIG. 88 shows this eyewear having been changed to the second configuration based on electromagnetic brain activity 7601. The left side of each figure shows this eyewear on a person's head. The right side shows this eyewear without showing the person's head. The right side of FIG. 87 shows the first configuration wherein light-transmitting member 8703 transmits and/or refracts light rays 8705 and 8706 so that the person sees with a first focal distance. The right side of FIG. 88 shows the second configuration wherein light-transmitting member 8703 transmits and/or refracts light rays 8705 and 8706 so that the person sees with a second focal distance. In an example, light-transmitting member 8703 can be a variable-focal-length lens or lens array whose focal length is changed by the application of electrical current.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein the focal distance of one or more light-transmitting optical members is modified based on a change in data from one or more of the electromagnetic energy sensors; and (c) a data control unit that further comprises a power source and a data processer.

In an example, this invention can be embodied in eyewear which filters, blocks, amplifies, shifts, and/or analyzes light in one or more bands or ranges within the light spectrum, wherein this modification of light spectrum is controlled by changes in a person's electromagnetic brain activity. In an example, a person can automatically change the color and/or tint of lenses in a pair of glasses by changing their brainwave pattern. In an example, a person can literally see the world through rosy-tinted glasses whenever they figuratively see the world through rosy-tinted glasses.

In an example, this invention can be embodied in eyewear which modifies the appearance of a person's eyes to others through a lens or other light-transmitting member. In an example, a person can modify and control the appearance of their pupils to other people, in real time, by changing their electromagnetic brain activity. In an example, a person can change the tint of lenses or other light-transmitting members in real time by changing their electromagnetic brain activity. In an example, a person can change the apparent color of their pupils to red when they are upset. In an example, a person can change the apparent color of their pupils to blue when they are calm.

In an example, a person can automatically filter out light energy in a selected band or range of the spectrum by changing their brainwave pattern. In an example, a person can shift light in a portion of the light spectrum which is transmitted through eyewear based on changes in their brainwave pattern. In an example, a person can extend their vision into the lower or upper non-visible ranges of the light spectrum by shifting light upward or downward. In an example, a person can adjust eyewear by changing their brainwave activity so that infrared light energy becomes visible to them through the eyewear. In an example, a person can adjust eyewear by changing their brainwave activity so that ultraviolet light energy becomes visible to them through the eyewear. In an example, a person can activate spectroscopic analysis of light energy, such as by using Fourier Transform, by changing their electromagnetic brain activity. In an example, a person can use such eyewear to activate spectral analysis of objects within their field of vision to obtain information about the chemical composition of such subjects.

In an example, a person can change the spectral distribution of light seen through lenses or other light-transmitting members by changing the power of their brainwaves in the Delta frequency band. In an example, a person can change the spectral distribution of light seen through lenses or other light-transmitting members by changing the power of their brainwaves in the Theta band. In an example, a person can change the spectral distribution of light seen through lenses or other light-transmitting members by changing the power of their brainwaves in the Alpha frequency band. In an example, a person can change the spectral distribution of light seen through lenses or other light-transmitting members by changing the power of their brainwaves in the Beta frequency band. In an example, a person can change the spectral distribution of light seen through lenses or other light-transmitting members by changing the power of their brainwaves in the Gamma band.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein one or more of the light-transmitting optical members has a first configuration which filters and/or absorbs light in a portion of the light spectrum by a first amount and a second configuration which filters and/or absorbs light in a portion of the light spectrum by a second amount, wherein the first amount can be zero, and wherein one or more light-transmitting optical members are changed from the first configuration to the second configuration, or vice versa, based on data from one or more of the electromagnetic energy sensors; and (c) a data control unit that further comprises a power source and a data processor.

FIGS. 89 and 90 show an example of how this invention can be embodied in eyewear 8901 that modifies visual perception and/or imaging based on electromagnetic energy measured from a person's head, comprising: one or more electromagnetic energy sensors 8902 configured to be within three inches of the surface of a person's head and configured to measure electromagnetic energy from the person's head; one or more light-transmitting optical members 8903 configured to be within three inches of the surface of the person's head and configured to transmit light into one or both of the person's eyes, wherein one or more of the light-transmitting optical members has a first configuration which filters and/or absorbs light in a portion of the light spectrum by a first amount and a second configuration which filters and/or absorbs light in a portion of the light spectrum by a second amount, wherein the first amount can be zero, and wherein one or more light-transmitting optical members are changed from the first configuration to the second configuration, or vice versa, based on data from one or more of the electromagnetic energy sensors; and a data control unit 8904.

FIG. 89 shows this eyewear in the first configuration and FIG. 90 shows this eyewear having been changed to the second configuration based on electromagnetic brain activity 7601. The left sides of the figures show this eyewear on a person's head and the right sides show this eyewear without showing the person's head. FIG. 89 shows the first configuration wherein light-transmitting member 8903 transmits light ray 8905 in a first portion of the light spectrum and light ray 8906 in a second portion of the light spectrum. FIG. 90 shows the second configuration wherein light-transmitting member 8903 transmits only light ray 8906. Light ray 8905 is filtered out. In an example, light-transmitting member 8903 can be a lens or a lens array with a variable spectral filter which is changed by the application of electrical current.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein the amount by which one or more light-transmitting optical members filters and/or absorbs light in a portion of the light spectrum is modified based on a change in data from one or more of the electromagnetic energy sensors; and (c) a data control unit that further comprises a power source and a data processer.

In an example, a person can change the apparent color of their eyes as seen by others through lenses or other light-transmitting members by changing the power of their brainwaves in the Delta frequency band. In an example, a person can change the apparent color of their eyes as seen by others through lenses or other light-transmitting members by changing the power of their brainwaves in the Theta band. In an example, a person can change the apparent color of their eyes as seen by others through lenses or other light-transmitting members by changing the power of their brainwaves in the Alpha frequency band. In an example, a person can change the apparent color of their eyes as seen by others through lenses or other light-transmitting members by changing the power of their brainwaves in the Beta frequency band. In an example, a person can change the apparent color of their eyes as seen by others through lenses or other light-transmitting members by changing the power of their brainwaves in the Gamma band.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein one or more of the light-transmitting optical members has a first configuration through which other people see the person's pupils as having a first color and a second configuration through which other people see the person's pupils as having a second color, and wherein one or more light-transmitting optical members are changed from the first configuration to the second configuration, or vice versa, based on data from one or more of the electromagnetic energy sensors; and (c) a data control unit that further comprises a power source and a data processer.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein one or more of the light-transmitting optical members has a first configuration which shifts the wavelength of light in a portion of the light spectrum by a first amount and a second configuration which shifts the wavelength of light in a portion of the light spectrum by a second amount, wherein the first amount can be zero, and wherein one or more light-transmitting optical members are changed from the first configuration to the second configuration, or vice versa, based on data from one or more of the electromagnetic energy sensors; and (c) a data control unit that further comprises a power source and a data processer.

FIGS. 91 and 92 show an example of how this invention can be embodied in eyewear 9101 that modifies visual perception and/or imaging based on electromagnetic energy measured from a person's head, comprising: one or more electromagnetic energy sensors 9102 configured to be within three inches of the surface of a person's head and configured to measure electromagnetic energy from the person's head; one or more light-transmitting optical members 9103 configured to be within three inches of the surface of the person's head and configured to transmit light into one or both of the person's eyes, wherein one or more of the light-transmitting optical members has a first configuration which shifts the wavelength of light in a portion of the light spectrum by a first amount and a second configuration which shifts the wavelength of light in a portion of the light spectrum by a second amount, wherein the first amount can be zero, and wherein one or more light-transmitting optical members are changed from the first configuration to the second configuration, or vice versa, based on data from one or more of the electromagnetic energy sensors; and a data control unit 9104.

FIG. 91 shows this eyewear in the first configuration and FIG. 92 shows this eyewear having been changed to the second configuration based on electromagnetic brain activity 7601. The left sides of the figures show this eyewear on a person's head and the right sides show this eyewear without showing the person's head. FIG. 91 shows the first configuration wherein light-transmitting member 9103 transmits light rays 9105 and 9106 without changing their wavelengths. FIG. 92 shows the second configuration wherein light-transmitting member 9103 shifts the wavelengths of light rays 9105 and 9106.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein the amount by which one or more light-transmitting optical members shifts the wavelength of light in a portion of the light spectrum is modified based on a change in data from one or more of the electromagnetic energy sensors; and (c) a data control unit that further comprises a power source and a data processor.

In an example, this invention can be embodied in eyewear which polarizes transmitted light in response to a change in a person's electromagnetic brain activity. In an example, being able to selectively activate light polarization can enable a person to selectively view selected 3D images in three dimensions or in two dimensions. In an example, a person can change the polarity of light seen through lenses or other light-transmitting members by changing the power of their brainwaves in the Delta frequency band. In an example, a person can change the polarity of light seen through lenses or other light-transmitting members by changing the power of their brainwaves in the Theta band. In an example, a person can change the polarity of light seen through lenses or other light-transmitting members by changing the power of their brainwaves in the Alpha frequency band. In an example, a person can change the polarity of light seen through lenses or other light-transmitting members by changing the power of their brainwaves in the Beta frequency band. In an example, a person can change the polarity of light seen through lenses or other light-transmitting members by changing the power of their brainwaves in the Gamma band.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein one or more of the light-transmitting optical members has a first configuration which polarizes light by a first amount and a second configuration which polarizes light by a second amount, wherein the first amount can be zero, and wherein one or more light-transmitting optical members are changed from the first configuration to the second configuration, or vice versa, based on data from one or more of the electromagnetic energy sensors; and (c) a data control unit that further comprises a power source and a data processor.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes, wherein the amount by which one or more light-transmitting optical members polarizes light is modified based on a change in data from one or more of the electromagnetic energy sensors; and (c) a data control unit that further comprises a power source and a data processor.

In an example, this invention can be embodied in a system for private viewing of a computer display screen comprising: (a) a computer display screen which displays content in a selected range of the light spectrum which is not normally visible to the human eye; (b) one or more electromagnetic energy sensors which are configured to be within three inches of the surface of a person's head and measure electromagnetic energy from the person's head; and (c) eyewear with one or more light-transmitting members, wherein these one or more light-transmitting members have a first configuration which does not modify transmitted light in the selected spectral range so that it becomes visible to the human eye and a second configuration which does modify transmitted light in the selected spectral range so that it becomes visible to the human eye, and wherein one or more light-transmitting members are changed from the first configuration to the second configuration by changes in the person's electromagnetic brain activity. In an example, a selected range of light which the computer screen displays and the selected range which the eyewear displays can vary in synchronization with each other, so that only a person wearing the eyewear can see the content displayed on the computer screen.

FIGS. 93 and 94 show an example of how this invention can be embodied in a system for private viewing of a computer display screen comprising: a computer display screen 9307 which displays content in a selected range of the light spectrum which is not normally visible to the human eye; one or more electromagnetic energy sensors 9302 which are configured to be within three inches of the surface of a person's head and measure electromagnetic energy from the person's head; and eyewear 9301 with one or more light-transmitting members 9303, wherein these one or more light-transmitting members have a first configuration which does not modify transmitted light in the selected spectral range so that it becomes visible to the human eye and a second configuration which does modify transmitted light in the selected spectral range so that it becomes visible to the human eye, and wherein one or more light-transmitting members are changed from the first configuration to the second configuration by changes in the person's electromagnetic brain activity. These figures also show a data control unit 9304.

FIG. 93 shows this system in the first configuration and FIG. 94 shows this system having been changed to the second configuration based on electromagnetic brain activity 7601. The left sides of the figures show eyewear on a person's head and the right sides show eyewear without showing the person's head. FIG. 93 shows the first configuration wherein light-transmitting member 9303 transmits light rays 9305 and 9306 without changing their wavelengths wherein the content on computer display screen 9307 is not visible. FIG. 94 shows the second configuration wherein light-transmitting member 9303 shifts the wavelengths of light rays 9305 and 9306 so that the content on computer display screen is visible.

In an example, this invention can be embodied in a system for private viewing of a computer display screen comprising: (a) a computer display screen which displays content which requires polarized lenses to be visible to the human eye; (b) one or more electromagnetic energy sensors which are configured to be within three inches of the surface of a person's head and measure electromagnetic energy from the person's head; and (c) eyewear with light-transmitting members, wherein these light-transmitting members have a first configuration with a first amount or direction of polarization and a second configuration with a second amount or direction of polarization, wherein the first amount can be zero, and wherein one or more light-transmitting members are changed from the first configuration to the second configuration by changes in the person's electromagnetic brain activity. In an example, the polarization of content that computer screen displays and a polarization filter of eyewear displays can vary in synchronization with each other, so that only a person wearing the eyewear can see the content displayed on the computer screen.

In an example, this invention can further comprise a specific type and/or shape of wearable eyewear frame. In an example, a wearable frame can hold electromagnetic sensors, light-transmitting members, and a data control unit in a selected configuration. In an example, a wearable frame can position one or more light-transmitting members in front of a person's eyes similar to the way in which a conventional pair of eyeglasses positions one or more lenses in front of a person's eyes. In an example, a wearable frame can be adjustable to enable adjustment of the configuration of electromagnetic sensors, light-transmitting members, and/or a data control unit. In an example, adjustment can be manual. In an example, adjustment can be done by one or more actuators. In an example, adjustment can be automated and iterative based on a specific person's anatomy and physiology.

In an example, a wearable eyewear frame can hold one or more electromagnetic sensors in contact with the surface of a person's head. In an example, one or more electromagnetic sensors can be spring-loaded to maintain compressive contact with the person's head. In an example, the degree of compressive contact can be adjusted. In an example, this adjustment can be manual. In an example, this adjustment can be automated to ensure proper electromagnetic contact and communication. In an example, eyewear can further comprise one or more actuators which maintain proper contact pressure between one or more electromagnetic sensors and the surface of the person's head.

In an example, a wearable eyewear frame can hold one or more electromagnetic sensors in contact with one or both sides of a person's head. In an example, a wearable frame can hold one or more electromagnetic sensors in contact in one or more locations between a person's ear and eye. In an example, a wearable frame can hold one or more electromagnetic sensors in contact with a person's forehead. In an example, a wearable frame can be similar to the frame of conventional eyeglasses, except that it has a central upward bulge, loop, or projection which holds an electrode in contact with a person's forehead. In an example, an upward bulge, loop, or projection can extend upwards from the bridge of a person's nose to cover a portion of the person's forehead. In an example, an upward bulge, loop, or projection can arc over a portion of the person's forehead from a person's left eyebrow to the person's right eyebrow. In an example, an upward bulge, loop, or projection can arc over a portion of the person's forehead from a person's left temple to the person's right temple.

In an example, this invention can be embodied in eyewear that measures electromagnetic energy from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes; (c) a data control unit that further comprises a power source and a data processer; and (d) a wearable frame which holds the one or more electromagnetic energy sensors and the one or more light-transmitting optical members in their respective configurations.

In an example, this invention can be embodied in eyewear that measures electromagnetic energy from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes; (c) a data control unit that further comprises a power source and a data processer; and (d) a wearable frame which holds the one or more electromagnetic energy sensors and the one or more light-transmitting optical members in their respective positions, including one or more positions on the person's forehead. In an example, an electromagnetic energy sensor can be held in contact with a person's forehead by an upward bulge, loop, or projection from the wearable frame.

FIGS. 95 and 96 show side and front views, respectively, of an example of how this invention can be embodied in eyewear that measures electromagnetic energy from a person's head, comprising: one or more electromagnetic energy sensors 9501 configured to be within three inches of the surface of a person's head and configured to measure electromagnetic energy from the person's head; one or more light-transmitting optical members 9502 configured to be within three inches of the surface of the person's head and configured to transmit light into one or both of the person's eyes; a data control unit 9503; and a wearable frame 9504 which holds the one or more electromagnetic energy sensors and the one or more light-transmitting optical members in their respective positions, including one or more positions on the person's forehead.

FIGS. 97 and 98 show side and front views, respectively, of another example of how this invention can be embodied in eyewear that measures electromagnetic energy from a person's head, comprising: one or more electromagnetic energy sensors 9701 configured to be within three inches of the surface of a person's head and configured to measure electromagnetic energy from the person's head; one or more light-transmitting optical members 9702 configured to be within three inches of the surface of the person's head and configured to transmit light into one or both of the person's eyes; a data control unit 9703; and a wearable frame 9704 which holds the one or more electromagnetic energy sensors and the one or more light-transmitting optical members in their respective positions, including one or more positions on the person's forehead. In this example, electromagnetic energy sensor 9701 is held in contact with the person's forehead by an upward bulge, loop, or projection from wearable frame 9704.

In an example, this invention can be embodied in eyewear that measures electromagnetic energy from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes; (c) a data control unit that further comprises a power source and a data processor; and (d) a wearable frame which holds the one or more electromagnetic energy sensors and the one or more light-transmitting optical members in their respective configurations, wherein this wearable frame is configured to span from the person's left ear to the person's face, then span across the front of the person's face including a portion of the person's nose, and then span from the person's face to the person's right ear.

In an example, this invention can be embodied in eyewear that measures electromagnetic energy from a person's head, comprising: (a) one or more electromagnetic energy sensors configured to be within three inches of the surface of a person's head and configured to measure electromagnetic energy from the person's head, wherein at least one of the electromagnetic energy sensors is configured to measure electromagnetic energy from the person's forehead; (b) one or more light-transmitting optical members configured to be within three inches of the surface of the person's head and configured to transmit light into one or both of the person's eyes; (c) a data control unit that further comprises a power source and a data processor; and (d) a wearable frame which holds the one or more electromagnetic energy sensors and the one or more light-transmitting optical members in their respective configurations, wherein this wearable frame is configured to span from the person's left ear to the person's face, then span across the front of the person's face including a portion of the person's forehead, and then span from the person's face to the person's right ear.

In an example, this invention can comprise a wearable eyewear frame that is similar to a conventional eyeglasses frame with the addition of an arcuate member from one ear to the other which spans a portion of the person's forehead. In an example, this invention can comprise a wearable frame with a left side piece between the left ear and left eye, with a right side piece between the right ear and right eye, and an arcuate member spanning from the left side piece to the right side piece which covers a portion of the person's forehead.

In an example, an arcuate member can hold one or more electromagnetic sensors in contact with the person's forehead.

In an example, this invention can be embodied in eyewear that measures electromagnetic energy from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes; (c) a data control unit that further comprises a power source and a data processor; and (d) a wearable frame which holds the one or more electromagnetic energy sensors and the one or more light-transmitting optical members in their respective positions, wherein this wearable frame further comprises a left-side member spanning from the person's left ear to their face, a right-side member spanning from the person's right ear to their face, and an arcuate member which connects the left-side member to the right-side member and spans the person's forehead.

FIGS. 99 and 100 show side and front views, respectively, of an example of how this invention can be embodied in eyewear that measures electromagnetic energy from a person's head, comprising: one or more electromagnetic energy sensors 9901 configured to be within three inches of the surface of a person's head and configured to measure electromagnetic energy from the person's head; one or more light-transmitting optical members 9902 configured to be within three inches of the surface of the person's head and configured to transmit light into one or both of the person's eyes; a data control unit 9903 that further comprises a power source and a data processor; and a wearable frame 9904 which holds the one or more electromagnetic energy sensors and the one or more light-transmitting optical members in their respective positions, wherein this wearable frame further comprises a left-side member spanning from the person's left ear to their face, a right-side member spanning from the person's right ear to their face, and an arcuate member which connects the left-side member to the right-side member and spans the person's forehead.

In an example, this invention can be embodied in eyewear that measures electromagnetic energy from a person's head, comprising: (a) one or more electromagnetic energy sensors configured to be within three inches of the surface of a person's head and configured to measure electromagnetic energy from the person's head, wherein at least one of the electromagnetic energy sensors is configured to measure electromagnetic energy from the person's forehead; (b) one or more light-transmitting optical members configured to be within three inches of the surface of the person's head and configured to transmit light into one or both of the person's eyes; (c) a data control unit that further comprises a power source and a data processor; and (d) a wearable frame which holds the one or more electromagnetic energy sensors and the one or more light-transmitting optical members in their respective configurations, wherein this wearable frame has a first member which is configured to span from one of the person's ears to the person's nose and a second member which is configured to span from one of the person's ears to the person's forehead.

FIGS. 101 and 102 show side and front views, respectively, of an example of how this invention can be embodied in eyewear that measures electromagnetic energy from a person's head, comprising: one or more electromagnetic energy sensors 10101 configured to be within three inches of the surface of a person's head and configured to measure electromagnetic energy from the person's head, wherein at least one of the electromagnetic energy sensors is configured to measure electromagnetic energy from the person's forehead; one or more light-transmitting optical members 10102 configured to be within three inches of the surface of the person's head and configured to transmit light into one or both of the person's eyes; a data control unit 10103; and a wearable frame 10104 which holds the one or more electromagnetic energy sensors and the one or more light-transmitting optical members in their respective configurations, wherein this wearable frame has a first member which is configured to span from one of the person's ears to the person's nose and a second member which is configured to span from one of the person's ears to the person's forehead.

In an example, this invention can be embodied in eyewear with a wearable frame which is similar to the frame of conventional eyeglasses except that it also includes an arcuate member or extension which loops around the rear of the person's head. In an example, this rearward-looping arcuate member or extension can hold additional electromagnetic sensors against the surface of the person's head to improve the scope and accuracy of brain activity measurement. This can be particularly useful for measuring activity from the person's occipital lobe or cerebellum. Further, this rearward-looping arcuate member or extension can also help to hold the device on the person's head if it is heavier than ordinary eyeglasses.

In an example, this invention can be embodied in eyewear that measures electromagnetic energy from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes; (c) a data control unit that further comprises a power source and a data processor; and (d) a wearable frame which holds the one or more electromagnetic energy sensors and the one or more light-transmitting optical members in their respective configurations, wherein this wearable frame is configured to span from the person's left ear to the person's face, then span across the front of the person's face, then span from the person's face to the person's right ear, and then span from the person's right ear to the person's left ear by looping around the rear of the person's head.

FIGS. 103 and 104 show side and front views, respectively, of an example of how this invention can be embodied in eyewear that measures electromagnetic energy from a person's head, comprising: one or more electromagnetic energy sensors 10301 configured to be within three inches of the surface of a person's head and configured to measure electromagnetic energy from the person's head; one or more light-transmitting optical members 10302 configured to be within three inches of the surface of the person's head and configured to transmit light into one or both of the person's eyes; a data control unit 10303 that further comprises a power source and a data processor; and a wearable frame 10304 which holds the one or more electromagnetic energy sensors and the one or more light-transmitting optical members in their respective configurations, wherein this wearable frame is configured to span from the person's left ear to the person's face, then span across the front of the person's face, then span from the person's face to the person's right ear, and then span from the person's right ear to the person's left ear by looping around the rear of the person's head.

FIGS. 105 and 106 show side and front views, respectively, of another example of how this invention can be embodied in eyewear that measures electromagnetic energy from a person's head, comprising: one or more electromagnetic energy sensors 10501 configured to be within three inches of the surface of a person's head and configured to measure electromagnetic energy from the person's head; one or more light-transmitting optical members 10502 configured to be within three inches of the surface of the person's head and configured to transmit light into one or both of the person's eyes; a data control unit 10503 that further comprises a power source and a data processor; and a wearable frame 10504 which holds the one or more electromagnetic energy sensors and the one or more light-transmitting optical members in their respective configurations, wherein this wearable frame is configured to span from the person's left ear to the person's face, then span across the front of the person's face, then span from the person's face to the person's right ear, and then span from the person's right ear to the person's left ear by looping around the rear of the person's head.

FIGS. 107 and 108 show side and front views, respectively, of an example of how this invention can be embodied in eyewear that measures electromagnetic energy from a person's head, comprising: one or more electromagnetic energy sensors 10701 configured to be within three inches of the surface of a person's head and configured to measure electromagnetic energy from the person's head; one or more light-transmitting optical members 10702 configured to be within three inches of the surface of the person's head and configured to transmit light into one or both of the person's eyes; a data control unit 10703 that further comprises a power source and a data processor; and a wearable frame 10704 which holds the one or more electromagnetic energy sensors and the one or more light-transmitting optical members in their respective configurations, wherein this wearable frame is configured to span from the person's left ear to the person's face, then span across the front of the person's face, then span from the person's face to the person's right ear, and then span from the person's right ear to the person's left ear by looping over the top of the person's head.

In an example, this invention can be embodied in eyewear that measures electromagnetic energy from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes; (c) a data control unit that further comprises a power source and a data processor; and (d) a wearable frame which holds the one or more electromagnetic energy sensors and the one or more light-transmitting optical members in their respective configurations, wherein this wearable frame has a first portion which is configured to span from the person's left ear to the person's face, has a second portion which is configured to span across the front of the person's face, has a third portion which is configured to span from the person's face to the person's right ear, has a fourth portion which is configured to span from the person's right ear to the person's left ear by looping around the rear of the person's head, and has a fifth portion which is configured to span from the person's right ear to the person's left ear by looping over the top of the person's head.

FIGS. 109 and 110 show side and front views, respectively, of an example of how this invention can be embodied in eyewear that measures electromagnetic energy from a person's head, comprising: one or more electromagnetic energy sensors 10901 configured to be within three inches of the surface of a person's head and configured to measure electromagnetic energy from the person's head; one or more light-transmitting optical members 10902 configured to be within three inches of the surface of the person's head and configured to transmit light into one or both of the person's eyes; a data control unit 10903; and a wearable frame 10904 which holds the one or more electromagnetic energy sensors and the one or more light-transmitting optical members in their respective configurations, wherein this wearable frame has a first portion which is configured to span from the person's left ear to the person's face, has a second portion which is configured to span across the front of the person's face, has a third portion which is configured to span from the person's face to the person's right ear, has a fourth portion which is configured to span from the person's right ear to the person's left ear by looping around the rear of the person's head, and has a fifth portion which is configured to span from the person's right ear to the person's left ear by looping over the top of the person's head.

In an example, this invention can be embodied in eyewear that measures electromagnetic energy from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes; (c) a data control unit that further comprises a power source and a data processer; and (d) a wearable frame which holds the one or more electromagnetic energy sensors and the one or more light-transmitting optical members in their respective configurations; wherein this wearable frame is configured to curve around the anterior perimeter of the person's left ear, then span from the person's left ear to the person's face, then span across the front of the person's face, then span from the person's face to the person's right ear, and then curve around the anterior perimeter of the person's right ear; and wherein one or more of the electromagnetic energy sensors are located along a portion of the wearable frame which curves around the anterior perimeter of an ear.

FIGS. 111 and 112 show side and front views, respectively, of an example of how this invention can be embodied in eyewear that measures electromagnetic energy from a person's head, comprising: one or more electromagnetic energy sensors 11101 configured to be within three inches of the surface of a person's head and configured to measure electromagnetic energy from the person's head; one or more light-transmitting optical members 11102 configured to be within three inches of the surface of the person's head and configured to transmit light into one or both of the person's eyes; a data control unit 11103; and a wearable frame 11104 which holds the one or more electromagnetic energy sensors and the one or more light-transmitting optical members in their respective configurations; wherein this wearable frame is configured to curve around the anterior perimeter of the person's left ear, then span from the person's left ear to the person's face, then span across the front of the person's face, then span from the person's face to the person's right ear, and then curve around the anterior perimeter of the person's right ear; and wherein one or more of the electromagnetic energy sensors are located along a portion of the wearable frame which curves around the anterior perimeter of an ear.

In an example, this invention can be embodied in eyewear that measures electromagnetic energy from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes; (c) a data control unit that further comprises a power source and a data processer; and (d) a wearable frame which holds the one or more electromagnetic energy sensors and the one or more light-transmitting optical members in their respective configurations; wherein this wearable frame is configured to curve around the posterior perimeter of the person's left ear, then span from the person's left ear to the person's face, then span across the front of the person's face, then span from the person's face to the person's right ear, and then curve around the posterior perimeter of the person's right ear; and wherein one or more of the electromagnetic energy sensors are located along a portion of the wearable frame which curves around the posterior perimeter of an ear.

FIGS. 113 and 114 show side and front views, respectively, of an example of how this invention can be embodied in eyewear that measures electromagnetic energy from a person's head, comprising: one or more electromagnetic energy sensors 11301 configured to be within three inches of the surface of a person's head and configured to measure electromagnetic energy from the person's head; one or more light-transmitting optical members 11302 configured to be within three inches of the surface of the person's head and configured to transmit light into one or both of the person's eyes; a data control unit 11303; and a wearable frame 11304 which holds the one or more electromagnetic energy sensors and the one or more light-transmitting optical members in their respective configurations; wherein this wearable frame is configured to curve around the posterior perimeter of the person's left ear, then span from the person's left ear to the person's face, then span across the front of the person's face, then span from the person's face to the person's right ear, and then curve around the posterior perimeter of the person's right ear; and wherein one or more of the electromagnetic energy sensors are located along a portion of the wearable frame which curves around the posterior perimeter of an ear.

In an example, this invention can be embodied in eyewear that measures electromagnetic energy from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes; (c) a data control unit that further comprises a power source and a data processer; and (d) a wearable frame which holds the one or more electromagnetic energy sensors and the one or more light-transmitting optical members in their respective configurations, wherein this wearable frame is substantially circular or elliptical and wherein this wearable frame spans both the person's forehead and the rear of the person's head.

FIGS. 115 and 116 show side and front views, respectively, of an example of how this invention can be embodied in eyewear that measures electromagnetic energy from a person's head, comprising: one or more electromagnetic energy sensors 11501 configured to be within three inches of the surface of a person's head and configured to measure electromagnetic energy from the person's head; one or more light-transmitting optical members 11502 configured to be within three inches of the surface of the person's head and configured to transmit light into one or both of the person's eyes; a data control unit 11503; and a wearable frame 11504 which holds the one or more electromagnetic energy sensors and the one or more light-transmitting optical members in their respective configurations, wherein this wearable frame is substantially circular or elliptical and wherein this wearable frame spans both the person's forehead and the rear of the person's head.

In an example, this invention can be embodied in eyewear that measures electromagnetic energy from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes; (c) a data control unit that further comprises a power source and a data processer; and (d) a wearable frame which holds the one or more electromagnetic energy sensors and the one or more light-transmitting optical members in their respective configurations, wherein this wearable frame is substantially circular or elliptical and wherein this wearable frame encircles the person's head at an anterior acute angle in the range of 0 to 45 degrees with respect to a horizontal plane when the person's head is upright.

In an example, this invention can be embodied in eyewear that measures electromagnetic energy from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes; (c) a data control unit that further comprises a power source and a data processer; and (d) a wearable frame which holds the one or more electromagnetic energy sensors and the one or more light-transmitting optical members in their respective configurations, wherein this wearable frame is substantially sinusoidal in shape and wherein this wearable frame spans both the person's forehead and the rear of the person's head.

FIGS. 117 and 118 show side and front views, respectively, of an example of how this invention can be embodied in eyewear that measures electromagnetic energy from a person's head, comprising: one or more electromagnetic energy sensors 11701 configured to be within three inches of the surface of a person's head and configured to measure electromagnetic energy from the person's head; one or more light-transmitting optical members 11702 configured to be within three inches of the surface of the person's head and configured to transmit light into one or both of the person's eyes; a data control unit 11703; and a wearable frame 11704 which holds the one or more electromagnetic energy sensors and the one or more light-transmitting optical members in their respective configurations, wherein this wearable frame is substantially sinusoidal in shape and wherein this wearable frame spans both the person's forehead and the rear of the person's head.

In an example, this invention can be embodied in eyewear that measures electromagnetic energy from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes; (c) a data control unit that further comprises a power source and a data processer; and (d) a wearable frame which holds the one or more electromagnetic energy sensors and the one or more light-transmitting optical members in their respective configurations, wherein this wearable frame is substantially sinusoidal in shape and wherein the central axis of sinusoidal undulations encircles the person's head at an anterior acute angle in the range of 0 to 45 degrees with respect to a horizontal plane when the person's head is upright.

In an example, this invention can be embodied in eyewear that measures electromagnetic energy from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head and configured to transmit light into one or both of the person's eyes; (c) a data control unit; and (d) a wearable frame which holds the one or more electromagnetic energy sensors and the one or more light-transmitting optical members in their respective configurations, wherein this wearable frame is substantially the shape of an ellipse projected downward onto the curvature of the person's head and wherein this wearable frame spans both the person's forehead and the rear of the person's head.

In an example, this invention can be embodied in eyewear whose appearance to other people is modified based on electromagnetic energy measured from a person's head, comprising: (a) one or more electromagnetic energy sensors configured to be within three inches of the surface of a person's head and configured to measure electromagnetic energy from the person's head; (b) one or more light-emitting members configured to be within three inches of the surface of the person's head; and (c) a data control unit. In an example, an electromagnetic energy sensor can be an electrode. In an example, a light-emitting member can be selected from the group consisting of: Light Emitting Diode (LED), infrared (IR) light source, laser, ultraviolet (UV) light source, Liquid Crystal Display (LCD), photoluminescent light source, Electro Luminescent (EL) light source. In an example, a data control unit can further comprise a power source and a data processor.

In an example, eyewear can include one or more LEDs or other light-emitting members whose light intensities and/or colors change when a person's electromagnetic brain activity changes. In an example, an eyewear frame can include one or more LEDs wherein different color LEDs light up with increases in the power of different brainwave frequency bands. In an example, different frequency bands selected from the group consisting of Delta, Theta, Alpha, Beta, and Gamma can each be associated with a different color. In an example, the overall color of light emitted from the eyewear can change with changes in the relative power of brainwaves in the Delta, Theta, Alpha, Beta, and/or Gamma frequency bands.

In an example, the spectrum of light emitted from eyewear can change with changes electromagnetic brain activity. In an example, an increase in brainwave activity in the Delta band can cause an increase in light emitted from eyewear in a first frequency range. In an example, an increase in brainwave activity in the Theta band can cause an increase in light emitted from eyewear in a second frequency range. In an example, an increase in brainwave activity in the Alpha band can cause an increase in light emitted from eyewear in a third frequency range. In an example, an increase in brainwave activity in the Beta band can cause an increase in light emitted from eyewear in a third frequency range. In an example, an increase in brainwave activity in the Gamma band can cause an increase in light emitted from eyewear in a third frequency range.

In an example, the device disclosed herein can enable a person to control the intensity, color, spectrum, polarization, and/or collimation of light emitted from eyewear by changing their electromagnetic brain activity. In an example, thought-controlled changes in the intensity, color, and/or spectrum of light emitted from eyewear can be useful for non-verbal communication. In an example, changes in the intensity, color, and/or spectrum of light emitted from eyewear can be useful for maintaining a person's privacy and/or disrupting unwelcome photography. In an example, a person can cause eyewear to emit infrared light energy by changing their brainwaves to a selected pattern. In an example, the emission of infrared light energy can be useful for disrupting unwelcome photography by a proximal imaging device.

In an example, a person can cause eyewear to emit a pulse of high-intensity light energy in the visual spectrum. In an example, a pulse of high-energy light in the visual spectrum can be useful for disrupting unwelcome photography by a nearby imaging device. In an example, a brainwave-controlled pulse of high-energy light in the visual spectrum can serve a safety or emergency purpose. In an example, an unexpected pulse of high-energy light can temporarily blind an attacker.

In an example, this invention can be embodied in eyewear whose appearance is modified based on electromagnetic energy measured from a person's head, comprising: (a) one or more electromagnetic energy sensors configured to be within three inches of the surface of a person's head and configured to measure electromagnetic energy from the person's head; (b) one or more light-emitting members configured to be within three inches of the surface of the person's head, wherein one or more light-emitting members have a first configuration which emits light with a first intensity and a second configuration which emits light with a second intensity, wherein the first intensity can be zero, and wherein the one or more light-emitting members are changed from the first configuration to the second configuration by changes in electromagnetic energy from the person's head; and (c) a data control unit.

FIGS. 119 and 120 show an example of how this invention can be embodied in eyewear whose appearance is modified based on electromagnetic energy measured from a person's head, comprising: one or more electromagnetic energy sensors 11901 configured to be within three inches of the surface of a person's head and configured to measure electromagnetic energy from the person's head; one or more light-emitting members 11902 configured to be within three inches of the surface of the person's head, wherein one or more light-emitting members have a first configuration which emits light with a first intensity and a second configuration which emits light with a second intensity, wherein the first intensity can be zero, and wherein the one or more light-emitting members are changed from the first configuration to the second configuration by changes in electromagnetic energy from the person's head; and a data control unit 11903. FIG. 119 shows this eyewear in the first configuration. FIG. 120 shows this eyewear in the second configuration wherein the light-emitting members are emitting light rays 12001. In an example, the light-emitting members can be LEDs. In an example, the LEDs can be turned on by the identification of a specific pattern of electromagnetic brain activity 7601 which is measured by electromagnetic energy sensor 11901.

In an example, this invention can be embodied in eyewear whose appearance is modified based on electromagnetic energy measured from a person's head, comprising: (a) one or more electromagnetic energy sensors configured to be within three inches of the surface of a person's head and configured to measure electromagnetic energy from the person's head; (b) one or more light-emitting members configured to be within three inches of the surface of the person's head, wherein one or more light-emitting members have a first configuration which emits light with a first spectral distribution and a second configuration which emits light with a second spectral distribution, and wherein the one or more light-emitting members are changed from the first configuration to the second configuration by changes in electromagnetic energy from the person's head; and (c) a data control unit.

FIGS. 121 and 122 show an example of how this invention can be embodied in eyewear whose appearance is modified based on electromagnetic energy measured from a person's head, comprising: one or more electromagnetic energy sensors 12101 configured to be within three inches of the surface of a person's head and configured to measure electromagnetic energy from the person's head; one or more light-emitting members 12102 configured to be within three inches of the surface of the person's head, wherein one or more light-emitting members have a first configuration which emits light with a first spectral distribution and a second configuration which emits light with a second spectral distribution, and wherein the one or more light-emitting members are changed from the first configuration to the second configuration by changes in electromagnetic energy from the person's head; and a data control unit 12103.

FIG. 121 shows this eyewear in the first configuration wherein the light-emitting members are emitting light rays 12101 of a first color. FIG. 122 shows this eyewear in the second configuration wherein the light-emitting members are emitting light rays 12201 of a second color. In an example, the light-emitting members can be LEDs. In an example, the color of the LEDs can be changed based on the pattern of electromagnetic brain activity 7601 which is measured by electromagnetic energy sensor 12101.

In an example, this invention can be embodied in eyewear whose appearance is modified based on electromagnetic energy measured from a person's head, comprising: (a) one or more electromagnetic energy sensors configured to be within three inches of the surface of a person's head and configured to measure electromagnetic energy from the person's head; (b) one or more light-emitting members configured to be within three inches of the surface of the person's head, wherein one or more light-emitting members have a first configuration which emits a first amount of infrared light and a second configuration which emits a second amount of infrared light, and wherein the one or more light-emitting members are changed from the first configuration to the second configuration by changes in electromagnetic energy from the person's head; and (c) a data control unit.

In an example, this invention can be embodied in eyewear which includes one or more near-eye display screens or other image-display members wherein the image displayed can be changed by a change in a person's electromagnetic brain activity. In an example, eyewear can include one or more display screens or other image-display members which can display virtual objects, environmental objects, or a mixture of virtual and environmental objects. In an example, eyewear can include one or more display screens or other image-display members which display environmental objects from different directions or perspectives.

In an example, a display screen or other image-display member can span an upper portion of a person's field of vision. In an example, a display screen or other image-display member can span a side or peripheral portion of a person's field of vision. In an example, an image-display member can be integrated into a lens or other image-transmitting member. In an example, an image-display member can be separate from a lens or other image-transmitting member. In an example, an image-display member can be held in a position near a person's eye by an eyewear frame in a manner similar to the way in which a lens is held near a person's eye by a conventional eyeglasses frame. In an example, eyewear can hold two display screens in positions which are close to a person's eyes. In an example, one or more display screens or other image-display members can be integrated into one or more contact lenses.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the surface of the person's head; and (c) a data control unit. In an example, a data control unit can further comprises a power source, a data processor, and a data transmitter.

In an example, an electromagnetic energy sensor can be an electrode. In an example, an electromagnetic energy sensor can measure electromagnetic brain activity. In an example, an electromagnetic energy sensor can be an electroencephalogram (EEG) electrode. In various examples, one or more electromagnetic energy sensors can be configured at locations selected from the group of electrode sites consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2. In an example, one or more reference sites can be selected from the group of sites consisting of A1 and A2. In an example, brainwave-controlled eyewear can be part of the Internet of Thinks (IOT).

In an example, an image-display member can be a transparent or translucent near-eye display screen. In an example, an image-display member can be a near-eye image projection surface. In an example, an image-display member can be a portion of a generally-transparent member, such as a lens, wherein only this portion displays a virtual image rather than light transmitted directly from the environment. In an example, an image-display member can superimpose an image of a virtual object on a view of an environmental object. In an example, an image-display member can comprise an augmented reality device or system. In an example, an image-display member can be a composite member which partially displays virtual content and partially transmits light from environmental objects. In an example, an image-display member can be co-located with a light-transmitting member. In an example, an image-display member can be adjacent to a light-transmitting member. In an example, an image-display member can be an optical member with variable transparency and/or variable display brightness, wherein the level of transparency or brightness can be controlled by changes in a person's electromagnetic brain activity.

In an example, an image-display member can comprise one or more components selected from the group consisting of: near-eye display screen, compound lens and display screen, lens with nanoscale gratings, Light Emitting Diode (LED), infrared (IR) light source, laser, ultraviolet (UV) light source, Liquid Crystal Display (LCD), photoluminescent light source, Electro Luminescent (EL) light source, incandescent light source, simple lens, concave lens, concentric lenses, convex lens, diverging lens, asymmetric lens, compound lens, fly's eye lens, Fresnel lens, light-transducing element, microlens array, microspheres, optoelectronic lens, parabolic lens, wedge-shaped lens, liquid crystal, liquid lens, Digital Micromirror Device (DMD), Digital Light Processor (DLP), Electromagnetically Induced Transparency (EIT) structure, Liquid Crystal Display (LCD), MEMS-based lens array, MEMS-based mirror array, Holovision™ display, birefringent material, carbon nanotube, light-guiding metamaterial structure, light-guiding metamaterial structure, light-guiding tubes, metamaterial light channel, microscale glass beads, nanorods, nanoscale gratings, nanotubes, etched waveguide, nanoimprint lithography pathways, resonant grating filter, Split Ring Resonators (SRRs), thermoplastic nanoimprint pathways, crystal, crystal array, crystalline structures, photonic metamaterial, photonic crystal, fiber optics, optical fiber, polarizing filter, cylindrical prism, prism, wedge prism, acrylic mirror, concentric reflective surfaces, dielectric mirror, parabolic mirror, reflector array, and retroreflective structure.

In an example, a data control unit can comprise a power source or transducer and a data processor. In an example, a power source can be a battery. In various examples, a data control unit can further comprise one or more components selected from the group consisting of: a wireless data transmitter; a data reception component; a data memory component; a computer-to-human interface; and a human-to-computer interface. In an example, a power source or transducer can further comprise: power from a source that is internal to the device during regular operation (such as an internal battery, capacitor, energy-storing microchip, or wound coil or spring); power that is obtained, harvested, or transduced from a power source other than the person's body that is external to the device (such as a rechargeable battery, electromagnetic inductance from external source, solar energy, indoor lighting energy, wired connection to an external power source, ambient or localized radiofrequency energy, or ambient thermal energy); and power that is obtained, harvested, or transduced from the person's body (such as kinetic or mechanical energy from body motion, electromagnetic energy from the person's body, or thermal energy from the person's body.

In an example, a data control unit can be in direct electrical communication with one or more electromagnetic energy sensors by wires or other electrically-conductive pathways. In an example, a data control unit can be in wireless communication with one or more electromagnetic energy sensors. In an example, a data control unit can be in direct electrical communication with one or more image-display members by wires or other electrically-conductive pathways. In an example, a data control unit can be in wireless communication with one or more image-display members.

In an example, a data control unit can be in wireless communication with a separate wearable device selected from the group consisting of: a wristwatch, smart watch, fitness watch, watch phone, bracelet phone, smart bracelet, fitness bracelet, smart wrist band, electronically-functional wrist band, other wrist-worn electronic device, or smart armband; a smart button, electronically-functional button, pin, brooch, pendant, beads, neck chain, necklace, dog tags, locket, or medallion; a smart finger ring, electronically-functional finger ring, electronically-functional earring, nose ring, or ear bud or clip; a wearable camera; an article of smart clothing, an electronically-functional shirt, electronically-functional pants, or a smart belt.

In an example, a data control unit can be in wireless communication with separate portable device selected from the group consisting of: smart phone, mobile phone, or cellular phone; PDA; electronic tablet; electronic pad; and other electronically-functional handheld device. In an example, a data control unit can be in wireless communication with a relatively fixed-location device selected from the group consisting of: laptop computer, desktop computer, internet terminal, smart appliance, home control system, homebot, and other fixed-location electronic communication device.

In an example, this invention can be embodied in eyewear that modifies visual perception based on electromagnetic energy measured from a person's head, comprising: (a) one or more electrodes configured to be within three inches of the surface of a person's head which measure electromagnetic energy from the person's head; (b) one or more near-eye display screens configured to be within three inches of the surface of the person's head; (c) a power source or transducer; and (d) a data processor or transmitter.

In an example, this invention can be embodied in eyewear that modifies visual perception based on electromagnetic energy measured from a person's head, comprising: (a) one or more electrodes configured to be within three inches of the surface of a person's head which measure electromagnetic energy from the person's head; (b) one or more lenses with virtual display capability which are configured to be within three inches of the surface of the person's head; (c) a power source or transducer; and (d) a data processor or transmitter.

In an example, electromagnetic energy data that is measured by one or more electromagnetic energy sensors can be statistically analyzed in order to identify significant patterns and/or changes in a person's electromagnetic brain activity. Significant changes in brain activity can then be used to control changes in the images which are displayed and/or transmitted by one or more image-display members. In an example, this invention can comprise eyewear whose image display attributes are modified by changes in a person's brainwaves. In an example, one or more image-display members can be turned on or off by changes in a person's electromagnetic brain activity. In an example, the brightness of one or more image-display members can be adjusted by changes in a person's electromagnetic brain activity. In an example, the virtual content displayed by one or more image-display members can be adjusted by changes in a person's electromagnetic brain activity. In an example, the mix of virtual vs. environmental objects displayed by one or more image-display members can be adjusted by changes in a person's electromagnetic brain activity.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the person's head, wherein one or more of the image-display members have a first configuration which shows a first image and a second configuration which shows a second image, and wherein one or more image-display members are changed from the first configuration to the second configuration, or vice versa, based on data from one or more of the electromagnetic energy sensors; and (c) a data control unit that further comprises a power source and a data processor.

In various examples, one or more primary statistical methods can be used to identify specific patterns of electromagnetic brain activity and/or specific changes in electromagnetic brain activity. In an example, data from one or more electromagnetic sensors can be filtered to remove artifacts before the application of a primary statistical method. In an example, a filter can be used to remove electromagnetic signals from eye blinks, eye flutters, or other eye movements before the application of a primary statistical method. In an example, a notch filter can be used as well to remove 60 Hz artifacts caused by AC electrical current. In an example, a pattern or change in electromagnetic brain activity may be a one-time pattern and/or change. In an example, a pattern of electromagnetic brain activity can repeat over time in a rhythmic manner. In an example, a primary statistical method can analyze repeating electromagnetic patterns by analyzing their frequency of repetition, their frequency band or range of repetition, their recurring amplitude, their wave phase, and/or their waveform. In an example, repeating patterns and/or waveforms can be analyzed using Fourier Transform methods.

In an example, this invention can comprise eyewear with an image-display member wherein the brightness or size of the image displayed by the image-display member is modified by changes in the person's electromagnetic brain activity. In an example, an image-display member can be modified from having a very dim or small (perhaps even non-visible) image to have a very bright or large (highly visible) image by changes in a person's electromagnetic brain activity. In an example, this invention can comprise eyewear with an image-display member wherein the brightness or size of the image displayed by the image-display member is controlled by electromagnetic (EMG or EOG) signals from muscles moving the person's eyes. In an example, a person can adjust an image-display member from having a very dim or small (even non-visible) image to have a very bright or large (highly visible) image by moving their eyes.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the person's head, wherein one or more of the image-display members has a first configuration which displays images with a first brightness level and a second configuration which displays images with a second brightness level, and wherein one or more image-display members are changed from the first configuration to the second configuration, or vice versa, based on data from one or more of the electromagnetic energy sensors; and (c) a data control unit that further comprises a power source and a data processor.

FIGS. 123 and 124 show an example of how this invention can be embodied in eyewear that modifies visual perception and/or imaging based on electromagnetic energy measured from a person's head, comprising: one or more electromagnetic energy sensors 12301 configured to be within three inches of the surface of a person's head and configured to measure electromagnetic energy from the person's head; 12302 one or more image-display members configured to be within three inches of the person's head, wherein one or more of the image-display members has a first configuration which displays images with a first brightness level and a second configuration which displays images with a second brightness level, and wherein one or more image-display members are changed from the first configuration to the second configuration, or vice versa, based on data from one or more of the electromagnetic energy sensors; and a data control unit 12303.

FIG. 123 shows this eyewear in the first configuration. FIG. 124 shows this eyewear having been changed to the second configuration based on electromagnetic brain activity 7601. The left side of each figure shows this eyewear on a person's head. The right side shows this eyewear without showing the person's head. As shown on the right side of FIG. 123, in the first configuration image-display member 12302 displays light rays 12304 comprising a virtual object with a first brightness level and displays and/or transmits light rays 12305 of real objects in the person's environment. As shown on the right side of FIG. 124, in the second configuration image-display member 12302 display light rays 12304 comprising a virtual object with a second (higher) brightness level and continues to display and/or transmit light rays 12305 of real objects in the person's environment.

In an example, a person can change the brightness of an image displayed by an image-display member by changing the power of their brainwaves in the Delta frequency band. In an example, a person can change the brightness of an image displayed by an image-display member by changing the power of their brainwaves in the Theta band. In an example, a person can change the brightness of an image displayed by an image-display member by changing the power of their brainwaves in the Alpha frequency band. In an example, a person can change the brightness of an image displayed by an image-display member by changing the power of their brainwaves in the Beta frequency band. In an example, a person can change the brightness of an image displayed by an image-display member by changing the power of their brainwaves in the Gamma band.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the person's head, wherein one or more of the image-display members has a first configuration which displays images in a first display size and a second configuration which displays images in a second display size, and wherein one or more image-display members are changed from the first configuration to the second configuration, or vice versa, based on data from one or more of the electromagnetic energy sensors; and (c) a data control unit that further comprises a power source and a data processor.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the person's head, wherein one or more of the image-display members has a first configuration which displays images in a first display location (relative to an eye) and a second configuration which displays images in a second display location (relative to an eye), and wherein one or more image-display members are changed from the first configuration to the second configuration, or vice versa, based on data from one or more of the electromagnetic energy sensors; and (c) a data control unit that further comprises a power source and a data processor.

In an example, this invention can be embodied in eyewear wherein the person wearing the eyewear sees the environment from different angles or perspectives based on changes in their brain activity. In an example, the eyewear changes a person's view angle, view direction, or breadth of view based on changes in their brain activity. In an example, a person can control the scope or breadth of their field of vision by changing their brainwave pattern. In an example, the person can see objects in the periphery of their field of vision, or even behind them, by changing their brainwave pattern. In an example, eyewear embodied by this invention can enable a person to rotate their angle of vision around the circumference of their head (such as represented by polar coordinates or clockface coordinates) by changing a parameter of their electromagnetic brain activity.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the person's head, wherein one or more of the image-display members has a first configuration which displays a view of the environment from a first direction and a second configuration which displays a view of the environment from a second direction, and wherein one or more image-display members are changed from the first configuration to the second configuration, or vice versa, based on data from one or more of the electromagnetic energy sensors; and (c) a data control unit that further comprises a power source and a data processer.

FIGS. 125 and 126 show an example of how this invention can be embodied in eyewear that modifies visual perception and/or imaging based on electromagnetic energy measured from a person's head, comprising: one or more electromagnetic energy sensors 12501 configured to be within three inches of the surface of a person's head and configured to measure electromagnetic energy from the person's head; one or more image-display members 12502 configured to be within three inches of the person's head, wherein one or more of the image-display members has a first configuration which displays a view of the environment from a first direction and a second configuration which displays a view of the environment from a second direction, and wherein one or more image-display members are changed from the first configuration to the second configuration, or vice versa, based on data from one or more of the electromagnetic energy sensors; and a data control unit 12503. In this example, this eyewear further comprises a forward-facing camera 12504 which receives light rays 12506 from a forward direction and a backward-facing camera 12505 which receives light rays 12507 from a backward direction.

FIG. 125 shows this eyewear in the first configuration. FIG. 126 shows this eyewear having been changed to the second configuration based on electromagnetic brain activity 7601. The left side of each figure shows this eyewear on a person's head. The right side shows this eyewear without showing the person's head. As shown on the right side of FIG. 125, in the first configuration image-display member 12502 displays light rays 12506 from a forward direction received by the forward-facing camera 12504. This enables the person to see ahead. As shown on the right side of FIG. 126, in the second configuration image-display member 12502 displays light rays 12507 from a backward direction received by the backward-facing camera 12505. This enables the person to see behind them. In this example, the person can toggle back and forth from seeing ahead vs. seeing behind by changing their brainwave patterns. In an example, the forward view can be maintained all the time and the rear view (which is toggled on or off) can take up only a small portion of the person's field of view.

In an example, a person can rotate the polar coordinate of the focal direction an image displayed by an image-display member by changing the power of their brainwaves in the Delta frequency band. In an example, a person can rotate the polar coordinate of the focal direction an image displayed by an image-display member by changing the power of their brainwaves in the Theta band. In an example, a person can rotate the polar coordinate of the focal direction an image displayed by an image-display member by changing the power of their brainwaves in the Alpha frequency band. In an example, a person can rotate the polar coordinate of the focal direction an image displayed by an image-display member by changing the power of their brainwaves in the Beta frequency band. In an example, a person can rotate the polar coordinate of the focal direction an image displayed by an image-display member by changing the power of their brainwaves in the Gamma band.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the person's head, wherein one or more of the image-display members has a first configuration which displays images of the environment with a first scope or breadth and a second configuration which displays images of the environment with a first scope or breadth, and wherein one or more image-display members are changed from the first configuration to the second configuration, or vice versa, based on data from one or more of the electromagnetic energy sensors; and (c) a data control unit that further comprises a power source and a data processor.

In an example, this invention can be embodied in eyewear with a variable focal distance, wherein this focal distance can be modified by a change in a person's electromagnetic brain activity. In an example, this invention can enable a person to focus on environmental objects at difference distances by changing their brainwave pattern. In an example, this invention can comprise virtual bifocal eyewear wherein this eyewear displays a distant object or a nearby object, depending on a person's brainwave pattern. In an example, this invention can comprise virtual binoculars which display a normal-distance object or a far-distance object, depending on a person's brainwave pattern.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the person's head, wherein one or more of the image-display members has a first configuration which displays environmental objects at a first focal distance and a second configuration which displays environmental objects at a second focal distance, and wherein one or more image-display members are changed from the first configuration to the second configuration, or vice versa, based on data from one or more of the electromagnetic energy sensors; and (c) a data control unit that further comprises a power source and a data processor.

FIGS. 127 and 128 show an example of how this invention can be embodied in eyewear that modifies visual perception and/or imaging based on electromagnetic energy measured from a person's head, comprising: one or more electromagnetic energy sensors 12701 configured to be within three inches of the surface of a person's head and configured to measure electromagnetic energy from the person's head; one or more image-display members 12702 configured to be within three inches of the person's head, wherein one or more of the image-display members has a first configuration which displays environmental objects at a first focal distance and a second configuration which displays environmental objects at a second focal distance, and wherein one or more image-display members are changed from the first configuration to the second configuration, or vice versa, based on data from one or more of the electromagnetic energy sensors; and a data control unit 12703. In this example, the eyewear further comprises camera 12704. This example also shows near environmental object 12705 and far environmental object 12706.

FIG. 127 shows this eyewear in the first configuration. FIG. 128 shows this eyewear having been changed to the second configuration based on electromagnetic brain activity 7601. The left side of each figure shows this eyewear on a person's head. The right side shows this eyewear without showing the person's head. As shown on the right side of FIG. 127, in the first configuration image-display member 12702 displays a view of the environment which focuses on near object 12705. As shown on the right side of FIG. 128, in the second configuration image-display member 12702 displays a view of the environment which focuses on far object 12706.

In an example, a person can change the focal distance of an image displayed by an image-display member by changing the power of their brainwaves in the Delta frequency band. In an example, a person can change the focal distance of an image displayed by an image-display member by changing the power of their brainwaves in the Theta band. In an example, a person can change the focal distance of an image displayed by an image-display member by changing the power of their brainwaves in the Alpha frequency band. In an example, a person can change the focal distance of an image displayed by an image-display member by changing the power of their brainwaves in the Beta frequency band. In an example, a person can change the focal distance of an image displayed by an image-display member by changing the power of their brainwaves in the Gamma band.

In an example, eyewear embodied by this device can comprise a single near-eye display screen or other image-display member which spans (a portion of) the field of vision of one or a person's eyes. In an example, eyewear embodied by this device can comprise two near-eye display screens or other image-display members which each span (a portion of) the field of vision of one of a person's eyes and which together span (portions of) the fields of vision of both of the person's eyes. In an example, the contents displayed by two display screens or other image-display members to different eyes can differ in perspective so as to create the perception of a 3D image. In an example, eyewear can enable a person to change their image perception from 2D to 3D by changing their electromagnetic brain activity.

In an example, a person can change their perception of images from 2D to 3D, or vice versa, by changing the power of their brainwaves in the Delta frequency band. In an example, a person can change their perception of images from 2D to 3D, or vice versa, by changing the power of their brainwaves in the Theta band. In an example, a person can change their perception of images from 2D to 3D, or vice versa, by changing the power of their brainwaves in the Alpha frequency band. In an example, a person can change their perception of images from 2D to 3D, or vice versa, by changing the power of their brainwaves in the Beta frequency band. In an example, a person can change their perception of images from 2D to 3D, or vice versa, by changing the power of their brainwaves in the Gamma band.

In an example, this invention can be embodied in eyewear which filters, blocks, amplifies, shifts, and/or analyzes light in one or more portions of the light spectrum. This modification of light transmission can be controlled by changes in a person's electromagnetic brain activity. In an example, a person can automatically filter out the display of light energy in a selected portion of the spectrum by changing their brainwave pattern. In an example, a person can shift the display of light in a portion of the light spectrum based on changes in their brainwave pattern. In an example, a person can extend their view into lower or upper non-visible ranges of the light spectrum, by shifting light upward or downward, based on changes in their brainwave activity. In an example, a person can adjust eyewear by changing their brainwave activity so that infrared light energy becomes displayed to them in a visible range. In an example, a person can adjust eyewear by changing their brainwave activity so that ultraviolet light energy becomes displayed to them in a visible range. In an example, a person can activate spectroscopic analysis of light energy, such as by using Fourier Transform, by changing their electromagnetic brain activity. In an example, a person can use eyewear to initiate spectral analysis of material composition, based on a change in their electromagnetic brain activity.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the person's head, wherein one or more of the image-display members has a first configuration which does not display light in a selected range of the light spectrum and a second configuration which does display light in a selected range of the light spectrum, wherein the first portion can be zero, and wherein one or more image-display members are changed from the first configuration to the second configuration, or vice versa, based on data from one or more of the electromagnetic energy sensors; and (c) a data control unit that further comprises a power source and a data processor.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the person's head, wherein one or more of the image-display members has a first configuration which shifts the wavelength of light displayed by a first amount and a second configuration which shifts the wavelength of light displayed by a second amount, wherein the first amount can be zero, and wherein one or more image-display members are changed from the first configuration to the second configuration, or vice versa, based on data from one or more of the electromagnetic energy sensors; and (c) a data control unit that further comprises a power source and a data processor.

In an example, a person can shift the light spectrum of an image displayed by an image-display member in order to perceive normally-invisible light energy by changing the power of their brainwaves in the Delta frequency band. In an example, a person can shift the light spectrum of an image displayed by an image-display member in order to perceive normally-invisible light energy by changing the power of their brainwaves in the Theta band. In an example, a person can shift the light spectrum of an image displayed by an image-display member in order to perceive normally-invisible light energy by changing the power of their brainwaves in the Alpha frequency band. In an example, a person can shift the light spectrum of an image displayed by an image-display member in order to perceive normally-invisible light energy by changing the power of their brainwaves in the Beta frequency band. In an example, a person can shift the light spectrum of an image displayed by an image-display member in order to perceive normally-invisible light energy by changing the power of their brainwaves in the Gamma band.

In an example, an image-display member that is part of the eyewear disclosed herein can: display environmental objects; display virtual objects; or display a mixture of environmental and virtual objects. In an example, a person can modify the mixture of environmental and virtual objects displayed by changing their electromagnetic brain activity pattern. In an example, an image-display member that is part of the eyewear disclosed herein can: display a first view of environmental objects; display a second view of environmental objects; or display a mixture of the first and second views. In an example, a person can modify the mixture of the first and second views by changing their electromagnetic brain activity pattern. In an example, an image-display member that is part of the eyewear disclosed herein can: display a first type of virtual content; display a second type of virtual content; or display a mixture of the first and second types. In an example, a person can modify the mixture of the first and second types by changing their electromagnetic brain activity pattern.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the person's head, wherein one or more of the image-display members has a first configuration which displays objects in the environment and has a second configuration that displays virtual objects, and wherein one or more image-display members are changed from the first configuration to the second configuration, or vice versa, based on data from one or more of the electromagnetic energy sensors; and (c) a data control unit that further comprises a power source and a data processor.

FIGS. 129 and 130 show an example of how this invention can be embodied in eyewear that modifies visual perception and/or imaging based on electromagnetic energy measured from a person's head, comprising: one or more electromagnetic energy sensors 12901 configured to be within three inches of the surface of a person's head and configured to measure electromagnetic energy from the person's head; one or more image-display members 12902 configured to be within three inches of the person's head, wherein one or more of the image-display members has a first configuration which displays objects in the environment and has a second configuration that displays virtual objects, and wherein one or more image-display members are changed from the first configuration to the second configuration, or vice versa, based on data from one or more of the electromagnetic energy sensors; and a data control unit 12903. In this example, the eyewear further comprises camera 12904. This example also shows environmental object 12905 and virtual object or content 13001.

FIG. 129 shows this eyewear in the first configuration. FIG. 130 shows this eyewear having been changed to the second configuration based on electromagnetic brain activity 7601. The left side of each figure shows this eyewear on a person's head. The right side shows this eyewear without showing the person's head. As shown on the right side of FIG. 129, in the first configuration image-display member 12902 displays a view of the environment (including object 12905). As shown on the right side of FIG. 130, in the second configuration image-display member 12902 displays a view of the virtual object or content 13001.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the person's head, wherein one or more of the image-display members has a first configuration which displays objects in the environment and has a second configuration that displays virtual objects superimposed on objects in the environment, and wherein one or more image-display members are changed from the first configuration to the second configuration, or vice versa, based on data from one or more of the electromagnetic energy sensors; and (c) a data control unit that further comprises a power source and a data processor.

FIGS. 131 and 132 show an example of how this invention can be embodied in eyewear that modifies visual perception and/or imaging based on electromagnetic energy measured from a person's head, comprising: one or more electromagnetic energy sensors 13101 configured to be within three inches of the surface of a person's head and configured to measure electromagnetic energy from the person's head; one or more image-display members 13102 configured to be within three inches of the person's head, wherein one or more of the image-display members has a first configuration which displays objects in the environment and has a second configuration that displays virtual objects superimposed on objects in the environment, and wherein one or more image-display members are changed from the first configuration to the second configuration, or vice versa, based on data from one or more of the electromagnetic energy sensors; and a data control unit 13103. In this example, the eyewear further comprises camera 13104. This example also shows environmental object 13105 and virtual object or content 13201.

FIG. 131 shows this eyewear in the first configuration. FIG. 132 shows this eyewear having been changed to the second configuration based on electromagnetic brain activity 7601. The left side of each figure shows this eyewear on a person's head. The right side shows this eyewear without showing the person's head. As shown on the right side of FIG. 131, in the first configuration image-display member 13102 displays a view of the environment (including object 13105). As shown on the right side of FIG. 132, in the second configuration image-display member 13102 displays a view of the virtual object or content 13201 superimposed on a view of the environment (including object 13105).

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the person's head, wherein one or more of the image-display members has a first configuration which displays objects in the environment from a first view direction and has a second configuration that displays objects in the environment from a second view direction, and wherein one or more image-display members are changed from the first configuration to the second configuration, or vice versa, based on data from one or more of the electromagnetic energy sensors; and (c) a data control unit that further comprises a power source and a data processor.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the person's head, wherein one or more of the image-display members has a first configuration which displays a first type of virtual content and has a second configuration that displays a second type of virtual content, and wherein one or more image-display members are changed from the first configuration to the second configuration, or vice versa, based on data from one or more of the electromagnetic energy sensors; and (c) a data control unit that further comprises a power source and a data processor.

In an example, this invention can further comprise an wearable eyewear frame with a specific configuration. In an example, a wearable frame can hold electromagnetic sensors, image-display members, and a data control unit in a selected configuration. In an example, a wearable frame can position image-display members in front of a person's eyes similar to the way in which a conventional pair of eyeglasses positions one or more lenses in front of a person's eyes. In an example, a wearable frame can be adjustable to enable adjustment of the configuration of electromagnetic sensors, image-display members, and/or a data control unit. In an example, adjustment can be manual. In an example, adjustment can be done by one or more actuators. In an example, adjustment can be automated.

In an example, a wearable eyewear frame can hold one or more electromagnetic sensors in contact with the surface of a person's head. In an example, one or more electromagnetic sensors can be spring-loaded to maintain compressive contact with the person's head. In an example, the degree of compressive contact can be adjusted. In an example, adjustment can be manual. In an example, adjustment can be automated to ensure continuous proper contact between the sensors and the surface of the person's head. In an example, a wearable frame can hold one or more electromagnetic sensors in contact with one or both sides of a person's head. In an example, a wearable frame can hold one or more electromagnetic sensors in contact in one or more locations between a person's ear and eye. In an example, a wearable frame can hold one or more electromagnetic sensors in contact with a person's forehead. In an example, a wearable frame can be similar to the frame of conventional eyeglasses, except that it has a central upward bulge, loop, or projection which holds an electrode in contact with a person's forehead.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the surface of the person's head; (c) a data control unit that further comprises a power source and a data processer; and (d) a wearable frame which holds the one or more electromagnetic energy sensors and the one or more image-display members in their respective configurations within three inches of the surface of the person's head.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the surface of the person's head; (c) a data control unit that further comprises a power source and a data processer; and (d) a wearable frame which holds the one or more electromagnetic energy sensors and the one or more image-display members in their respective configurations within three inches of the surface of the person's head, wherein this wearable frame is configured to span from the person's left ear to the person's face, then span across the front of the person's face including a portion of the person's nose, and then span from the person's face to the person's right ear.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head, wherein at least one of the electromagnetic energy sensors is configured to measure electromagnetic energy from the person's forehead; one or more image-display members configured to be within three inches of the surface of the person's head; (c) a data control unit that further comprises a power source and a data processer; and (d) a wearable frame which holds the one or more electromagnetic energy sensors and the one or more image-display members in their respective configurations within three inches of the surface of the person's head, wherein this wearable frame is configured to span from the person's left ear to the person's face, then span across the front of the person's face including a portion of the person's forehead, and then span from the person's face to the person's right ear.

In an example, this invention can include a wearable eyewear frame that is similar to a conventional eyeglasses frame, with the addition of an arcuate member that curves from one ear to the other, spanning the person's forehead. In an example, this invention can comprise a wearable frame with a left-side frame piece between the left ear and left eye, a right-side frame piece between the right ear and right eye, and an arcuate member that curves from the left-side frame piece to the right-side frame piece spanning the person's forehead. In an example, an arcuate member can hold an electromagnetic sensor in contact with the person's forehead.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head, wherein at least one of the electromagnetic energy sensors is configured to measure electromagnetic energy from the person's forehead; one or more image-display members configured to be within three inches of the surface of the person's head; (c) a data control unit that further comprises a power source and a data processer; and (d) a wearable frame which holds the one or more electromagnetic energy sensors and the one or more image-display members in their respective configurations within three inches of the surface of the person's head, wherein this wearable frame has a first member which is configured to span from one of the person's ears to the person's nose and a second member which is configured to span from one of the person's ears to the person's forehead.

In an example, this invention can be embodied in eyewear with a wearable frame which is similar to the frame of conventional eyeglasses, except that it includes an arcuate member or extension which loops completely around the rear of the person's head. In an example, such a rearward-looping arcuate member or extension can hold additional electromagnetic sensors against the surface of the person's head in order to improve the scope and accuracy of brain activity measurement. This can be particularly useful for measuring activity from the person's occipital lobe or cerebellum. Further, this rearward-looping arcuate member or extension can also help to hold the device on the person's head if the device is heavier than conventional eyeglasses.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the surface of the person's head; (c) a data control unit that further comprises a power source and a data processer; and (d) a wearable frame which holds the one or more electromagnetic energy sensors and the one or more image-display members in their respective configurations within three inches of the surface of the person's head, wherein this wearable frame is configured to span from the person's left ear to the person's face, then span across the front of the person's face, then span from the person's face to the person's right ear, and then span from the person's right ear to the person's left ear by looping around the rear of the person's head.

In an example, this invention can be embodied in eyewear with a wearable frame which is similar to the frame of conventional eyeglasses, except that it includes an arcuate member or extension which loops completely over the top of the person's head. In an example, this upward-looping arcuate member or extension can hold additional electromagnetic sensors against the surface of the person's head in order to improve the scope and accuracy of brain activity measurement. This can be particularly useful for measuring activity from a person's parietal lobe and/or occipital lobe. Further, this upward-looping arcuate member or extension can also help to hold the device on a person's head if the device is heavier than conventional eyeglasses.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the surface of the person's head; (c) a data control unit that further comprises a power source and a data processor; and (d) a wearable frame which holds the one or more electromagnetic energy sensors and the one or more image-display members in their respective configurations within three inches of the surface of the person's head, wherein this wearable frame is configured to span from the person's left ear to the person's face, then span across the front of the person's face, then span from the person's face to the person's right ear, and then span from the person's right ear to the person's left ear by looping over the top of the person's head.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the surface of the person's head; (c) a data control unit that further comprises a power source and a data processor; and (d) a wearable frame which holds the one or more electromagnetic energy sensors and the one or more image-display members in their respective configurations within three inches of the surface of the person's head, wherein this wearable frame has a first portion which is configured to span from the person's left ear to the person's face, has a second portion which is configured to span across the front of the person's face, has a third portion which is configured to span from the person's face to the person's right ear, has a fourth portion which is configured to span from the person's right ear to the person's left ear by looping around the rear of the person's head; and has a fifth portion which is configured to span from the person's right ear to the person's left ear by looping over the top of the person's head.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the surface of the person's head; (c) a data control unit that further comprises a power source and a data processor; and (d) a wearable frame which holds the one or more electromagnetic energy sensors and the one or more image-display members in their respective configurations within three inches of the surface of the person's head; wherein this wearable frame is configured to curve around the anterior perimeter of the person's left ear, then span from the person's left ear to the person's face, then span across the front of the person's face, then span from the person's face to the person's right ear, and then curve around the anterior perimeter of the person's right ear; and wherein one or more of the electromagnetic energy sensors is located along a portion of the wearable frame which curves around the anterior perimeter of an ear.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the surface of the person's head; (c) a data control unit that further comprises a power source and a data processor; and (d) a wearable frame which holds the one or more electromagnetic energy sensors and the one or more image-display members in their respective configurations within three inches of the surface of the person's head; wherein this wearable frame is configured to curve around the posterior perimeter of the person's left ear, then span from the person's left ear to the person's face, then span across the front of the person's face, then span from the person's face to the person's right ear, and then curve around the posterior perimeter of the person's right ear; and wherein one or more of the electromagnetic energy sensors is located along a portion of the wearable frame which curves around the posterior perimeter of an ear.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the surface of the person's head; (c) a data control unit that further comprises a power source and a data processor; and (d) a wearable frame which holds the one or more electromagnetic energy sensors and the one or more image-display members in their respective configurations within three inches of the surface of the person's head, wherein this wearable frame is substantially circular or elliptical and wherein this wearable frame spans both the person's forehead and the rear of the person's head.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the surface of the person's head; (c) a data control unit that further comprises a power source and a data processer; and (d) a wearable frame which holds the one or more electromagnetic energy sensors and the one or more image-display members in their respective configurations within three inches of the surface of the person's head, wherein this wearable frame is substantially circular or elliptical and wherein this wearable frame encircles the person's head at an anterior acute angle in the range of 0 to 45 degrees with respect to a horizontal plane when the person's head is upright.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the surface of the person's head; (c) a data control unit that further comprises a power source and a data processer; and (d) a wearable frame which holds the one or more electromagnetic energy sensors and the one or more image-display members in their respective configurations within three inches of the surface of the person's head, wherein this wearable frame is substantially sinusoidal and wherein this wearable frame spans both the person's forehead and the rear of the person's head.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the surface of the person's head; (c) a data control unit that further comprises a power source and a data processer; and (d) a wearable frame which holds the one or more electromagnetic energy sensors and the one or more image-display members in their respective configurations within three inches of the surface of the person's head, wherein this wearable frame is substantially sinusoidal and wherein the central axis of sinusoidal undulations encircles the person's head at an anterior acute angle in the range of 0 to 45 degrees with respect to a horizontal plane when the person's head is upright.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more image-display members configured to be within three inches of the surface of the person's head; (c) a data control unit that further comprises a power source and a data processer; and (d) a wearable frame which holds the one or more electromagnetic energy sensors and the one or more image-display members in their respective configurations within three inches of the surface of the person's head, wherein this wearable frame is substantially the shape of an ellipse projected downward onto the curvature of the person's head and wherein this wearable frame spans both the person's forehead and the rear of the person's head.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head; (c) one or more image-display members configured to be within three inches of the surface of the person's head; and (d) a data control unit that further comprises a power source and a data processer.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more light-transmitting optical members configured to be within three inches of the surface of the person's head; (c) one or more image-display members configured to be within three inches of the surface of the person's head; (d) a data control unit that further comprises a power source and a data processer; and (e) a wearable frame which holds the one or more electromagnetic energy sensors, the one or more light-transmitting optical members, and the one or more image-display members in their respective configurations.

In an example, an electromagnetic energy sensor can be an electrode. In an example, a light-transmitting optical member can be a lens. In an example, an image-display member can be a near-eye display screen. In an example, a data control unit can comprise a power source or transducer and a data processor. In an example, a wearable frame can be similar to the frame of conventional eyeglasses except that it includes a central upward bulge, loop, or projection which holds at least one electromagnetic energy sensor in contact with the person's forehead.

In an example, electromagnetic energy that is measured by one or more electromagnetic energy sensors can be statistically analyzed in order to identify significant changes in a person's electromagnetic brain activity. These significant changes in brain activity can then be used to control changes in the transmission of light through one or more light-transmitting optical members, to control changes in the images displayed by the image-display members, or both. In various examples, one or more primary statistical methods can be used to identify specific patterns of electromagnetic brain activity and/or specific changes in electromagnetic brain activity. In an example, data from one or more electromagnetic sensors can be filtered to remove artifacts before the application of a primary statistical method.

In an example, a pattern or change in electromagnetic brain activity can be a one-time pattern. In an example, a pattern of electromagnetic brain activity can repeat over time in a rhythmic manner. In an example, a primary statistical method can analyze repeating electromagnetic patterns by analyzing the frequency of repetition, the frequency band or range of repetition, their recurring amplitude, their wave phase, and/or their waveform. In an example repeating patterns and/or waveforms can be analyzed using Fourier Transform methods.

In an example, this invention can enable a person to control the absorption, reflection, and/or refraction of light by one or more light-transmitting optical members by changing their electromagnetic brain activity. In an example, this invention can enable a person to control the opacity and/or reflectivity of one or more light-transmitting optical members by changing their electromagnetic brain activity. In an example, this invention can enable a person to control their focal distance, view direction, and/or view scope by changing their electromagnetic brain activity.

In an example, this invention can enable a person to control the polar coordinate (around the circumference of their head) of their field of vision by changing their electromagnetic brain activity. In an example, this invention can enable a person to control the absorption, transmission, or shifting of one or more portions of the light spectrum by changing their electromagnetic brain activity. In an example, this invention can enable a person to control the dimensionality of their view (such as shifting from a two-dimensional view to three-dimensional view) by changing their electromagnetic brain activity.

In an example, this invention can be embodied in a human-to-computer eyewear interface, comprising: (a) a head-worn structure, wherein this structure is configured to: span from a person's left ear to their face; then span across their face within their field of vision, including spanning a portion of their forehead; and then span from their face to their right ear; (b) one or more electromagnetic energy sensors, wherein these sensors are configured to be within three inches of the surface of a person's head, wherein these sensors are configured to measure electromagnetic energy from the person's head, and wherein these sensors are held in place by the head-worn structure; (c) one or more light-transmitting and/or image-displaying members, wherein these members are configured to be within three inches of the surface of the person's head, wherein these members are configured to transmit and/or display light into one or both of the person's eyes, and wherein these members are held in place by the head-worn structure; (d) a power source; and (e) a wireless data transmitter.

In an example, the head-worn structure can be a rigid or semi-rigid eyewear frame. In an example, the head-worn structure can be made of metal or a polymer. In an example, the head-worn structure can be similar to the frame of a conventional pair of eyeglasses with the addition of a bulge, loop, or projection which covers a portion of the person's forehead and holds one or more electromagnetic energy sensors in contact with the person's forehead. In an example, the head-worn structure can be flexible, elastic, compliant, and/or soft. In an example, the head-worn structure can be made of fabric.

In an example, an electromagnetic energy sensor can be an electrode. In an example, an electromagnetic energy sensor can be an electroencephalogram (EEG) electrode. In an example, an electromagnetic energy sensor can be a dry electrode. In an example, an electromagnetic energy sensor can measure electromagnetic brain activity. In an example, an electromagnetic sensor can be within an inch of the surface of a person's head. In an example, an electromagnetic sensor can be in direct contact with the surface of a person's head.

In an example, a light-transmitting and/or image-displaying member can be a lens and/or a near-eye display surface. In an example, light-transmitting and/or image-displaying member can be comprised of one or more optical elements selected from the group consisting of: simple lens, concave lens, concentric lenses, convex lens, diverging lens, asymmetric lens, compound lens, fly's eye lens, Fresnel lens, light-transducing element, microlens array, microspheres, optoelectronic lens, parabolic lens, wedge-shaped lens, liquid crystal, liquid lens, Digital Micromirror Device (DMD), Digital Light Processor (DLP), Electromagnetically Induced Transparency (EIT) structure, Liquid Crystal Display (LCD), MEMS-based lens array, MEMS-based mirror array, birefringent material, carbon nanotube, light-guiding metamaterial structure, light-guiding metamaterial structure, light-guiding tube, metamaterial light channel, microscale glass beads, nanorods, nanoscale gratings, nanotubes, etched waveguide, nanoimprint lithography pathways, resonant grating filter, Split Ring Resonators (SRRs), thermoplastic nanoimprint pathways, crystal, crystal array, crystalline structures, photonic metamaterial, photonic crystal, fiber optics, optical fiber, polarizing filter, cylindrical prism, prism, wedge prism, acrylic mirror, concentric reflective surfaces, dielectric mirror, parabolic mirror, reflector array, and retroreflective structure.

In an example, a person can use this eyewear to wirelessly control the operation of a separate wearable device by changing their electromagnetic brain activity in the Delta, Theta, Alpha, Beta, and/or Gamma frequency bands. In an example, a person can use this eyewear to wirelessly control the operation of a wristwatch, smart watch, fitness watch, watch phone, bracelet phone, smart bracelet, fitness bracelet, smart wrist band, electronically-functional wrist band, other wrist-worn electronic device by changing their electromagnetic brain activity in the Delta, Theta, Alpha, Beta, and/or Gamma frequency bands.

In an example, a person can use this eyewear to wirelessly control the operation of a smart button, electronically-functional button, pin, brooch, pendant, beads, neck chain, necklace, dog tags, locket, or medallion by changing their electromagnetic brain activity in the Delta, Theta, Alpha, Beta, and/or Gamma frequency bands. In an example, a person can use this eyewear to wirelessly control the operation of a smart finger ring, electronically-functional finger ring, electronically-functional earring, nose ring, or ear bud or clip by changing their electromagnetic brain activity in the Delta, Theta, Alpha, Beta, and/or Gamma frequency bands. In an example, a person can use this eyewear to wirelessly control the operation of an article of smart clothing, an electronically-functional shirt, electronically-functional pants, or a smart belt by changing their electromagnetic brain activity in the Delta, Theta, Alpha, Beta, and/or Gamma frequency bands.

In an example, a person can use this eyewear to wirelessly control the operation of a separate mobile or handheld device by changing their electromagnetic brain activity in the Delta, Theta, Alpha, Beta, and/or Gamma frequency bands. In an example, a person can use this eyewear to wirelessly control the operation of a smart phone, mobile phone, holophone, or cellular phone by changing their electromagnetic brain activity in the Delta, Theta, Alpha, Beta, and/or Gamma frequency bands. In an example, a person can use this eyewear to wirelessly control the operation of an electronic tablet, electronic pad, and other electronically-functional handheld device by changing their electromagnetic brain activity in the Delta, Theta, Alpha, Beta, and/or Gamma frequency bands.

In an example, a person can use this eyewear to wirelessly control the operation of a relatively fixed-location electronically-functional device by changing their electromagnetic brain activity in the Delta, Theta, Alpha, Beta, and/or Gamma frequency bands. In an example, a person can use this eyewear to wirelessly control the operation of a laptop computer, desktop computer, or internet terminal by changing their electromagnetic brain activity in the Delta, Theta, Alpha, Beta, and/or Gamma frequency bands. In an example, a person can use this eyewear to wirelessly control the operation of a smart appliance or home control system by changing their electromagnetic brain activity in the Delta, Theta, Alpha, Beta, and/or Gamma frequency bands. In an example, this invention can comprise brainwave-monitoring eyewear which is part of the "Internet of Thinks" (IOT).

In an example, this invention can be embodied in eyewear with one or more electromagnetic energy sensors which enables a person to move a cursor on a computer display screen by changing the power of their brainwaves in the Delta frequency band. In an example, this invention can be embodied in eyewear with one or more electromagnetic energy sensors which enables a person to move a cursor on a computer display screen by changing the power of their brainwaves in the Theta frequency band. In an example, this invention can be embodied in eyewear with one or more electromagnetic energy sensors which enables a person to move a cursor on a computer display screen by changing the power of their brainwaves in the Alpha frequency band. In an example, this invention can be embodied in eyewear with one or more electromagnetic energy sensors which enables a person to move a cursor on a computer display screen by increasing or decreasing the power of their brainwaves in the Beta frequency band.

In an example, this invention can be embodied in eyewear with one or more electromagnetic energy sensors which enables a person to select an option in a computer menu interface by changing the power of their brainwaves in the Delta frequency band. In an example, this invention can be embodied in eyewear with one or more electromagnetic energy sensors which enables a person to select an option in a computer menu interface by changing the power of their brainwaves in the Theta frequency band. In an example, this invention can be embodied in eyewear with one or more electromagnetic energy sensors which enables a person to select an option in a computer menu interface by changing the power of their brainwaves in the Alpha frequency band. In an example, this invention can be embodied in eyewear with one or more electromagnetic energy sensors which enables a person to select an option in a computer menu interface by increasing or decreasing the power of their brainwaves in the Beta frequency band.

In an example, this invention can be embodied in a human-to-computer interface system, comprising: (a) eyewear which monitors a person's electromagnetic brain activity, wherein this eyewear further comprises: a head-worn structure which is configured to span from a person's left ear to their face, across their face within their field of vision including a portion of their forehead, and from their face to their right ear; one or more electromagnetic energy sensors which are configured to be within three inches of the surface of a person's head, which measure electromagnetic energy from the person's head, and which are held in place by the head-worn structure; a power source; and a wireless data transmitter; and (b) a separate wearable, mobile, or fixed-location electronic device with which the eyewear is in wireless communication, wherein the operation of this separate device is controlled changes in the person's electromagnetic brain activity based on data from the eyewear.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more wearable image-recording members; and (c) a data control unit that further comprises a power source and a data processer. In an example, this eyewear can further comprise one or more image-display members.

FIGS. 133 and 134 show side and front views, respectively, of an example of how this invention can be embodied in eyewear that modifies visual perception and/or imaging based on electromagnetic energy measured from a person's head, comprising: one or more electromagnetic energy sensors 13301 configured to be within three inches of the surface of a person's head and configured to measure electromagnetic energy from the person's head; one or more wearable image-recording members 13302; and a data control unit 13303. In an example, an image-recording member can be a camera. In an example, a data control unit can further comprise a power source and a data processer.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more wearable image-recording members; (c) a data control unit that further comprises a power source and a data processer; and (d) a wearable frame which holds the one or more electromagnetic energy sensors, the one or more light-transmitting optical members, and the one or more image-recording members in their respective configurations.

In an example, this eyewear can further comprise one or more image-display members. In an example, an electromagnetic energy sensor can be an electrode. In an example, a wearable frame can be similar to the frame of conventional eyeglasses except that it includes a central upward bulge, loop, or projection which holds at least one electromagnetic energy sensor in contact with a person's forehead.

In an example, a data control unit can comprise a power source or transducer and a data processor. In an example, a data control unit can be in direct electrical communication with one or more electromagnetic energy sensors by wires or other electrically-conductive pathways. In an example, a data control unit can be in wireless communication with one or more electromagnetic energy sensors. In an example, a data control unit can be in direct electrical communication with one or more wearable image-recording members by wires or other electrically-conductive pathways. In an example, a data control unit can be in wireless communication with one or more wearable image-recording members.

In an example, an image-display member can be a near-eye display screen. In an example, an image-recording member can be a wearable camera. In an example, an image-recording member can be selected from the group consisting of: 35 mm camera, analog or film camera, camcorder, CCD camera, CMOS camera, digital camera, motion picture camera, SLR camera, and video camera. In an example, an image-recording member can be integrated into an eyewear frame.

In an example, electromagnetic energy that is measured by one or more electromagnetic energy sensors can be statistically analyzed in order to identify significant changes in a person's electromagnetic brain activity. These significant changes in brain activity can then be used to control changes in the transmission of light through one or more light-transmitting optical members, to control changes in the images recorded by an image-recording member, or both. In various examples, one or more primary statistical methods can be used to identify specific patterns of electromagnetic brain activity and/or specific changes in electromagnetic brain activity. In an example, data from one or more electromagnetic sensors can be filtered to remove artifacts before the application of a primary statistical method.

In an example, this invention can enable a person to control the focal distance, view direction, and/or view scope of an image-recording member by changing their electromagnetic brain activity. In an example, this can be done by changing the configuration of an image-recording optical member. In an example, this can be done by changing a view from that of a first image-recording optical member to that of a second image-recording optical member. In an example, this invention can enable a person to see what is behind them by changing their electromagnetic activity. In an example, first image-recording member can point toward objects in front of a person and a second image-recording member can point toward objects behind the person. In an example, such eyewear can be especially useful for grade school teachers.

In an example, this invention can enable a person to control the absorption, transmission, or shifting of one or more portions of the light spectrum recorded by an image-recording member by changing their electromagnetic brain activity. In an example, this invention can enable a person to control the dimensionality of their view (such as shifting from a two-dimensional view to three-dimensional view) by changing their electromagnetic brain activity.

In an example, this invention can enable a person to change the length of time that a recorded image is kept in memory by changing their electromagnetic brain activity. In an example, an image-recording member can record video images constantly, but the images can be erased after a selected period time unless their erasure is cancelled by a selected pattern of electromagnetic brain activity. In an example, this selected pattern of electromagnetic brain activity can be voluntary and conscious. In an example, this selected pattern of electromagnetic brain activity can be involuntary and/or unconscious.

In an example, this invention can enable a person to start video recording by changing their electromagnetic brain activity. In an example, an image-recording member can start recording video images based on a selected pattern of electromagnetic brain activity. In an example, this selected pattern of electromagnetic brain activity can be voluntary and conscious. In an example, this selected pattern of electromagnetic brain activity can be involuntary and/or unconscious. In an example, involuntary initiation of video recording based on a selected pattern of brain activity can serve a safety or emergency purpose.

In an example, this invention can enable a person to start or stop the wireless transmission of video images by changing their electromagnetic brain activity. In an example, an image-recording member can start or stop recording video images based on a selected pattern of electromagnetic brain activity. In an example, this selected pattern of electromagnetic brain activity can be a voluntary and conscious one. In an example, this selected pattern of electromagnetic brain activity can be an involuntary and/or unconscious one. In an example, involuntary initiation of video recording based on a selected pattern of brain activity can serve a safety or emergency purpose.

In an example, this invention can further comprise a specific shape of wearable frame. In an example, a wearable frame can hold electromagnetic sensors, an image-recording member, and a data control unit in a selected configuration. In an example, a wearable frame can hold one or more electromagnetic sensors in contact with the surface of a person's head. In an example, a wearable frame can hold one or more electromagnetic sensors in contact with one or both sides of a person's head. In an example, a wearable frame can hold one or more electromagnetic sensors in contact in one or more locations between a person's ear and eye. In an example, a wearable frame can hold one or more electromagnetic sensors in contact with a person's forehead. In an example, a wearable frame can be similar to the frame of conventional eyeglasses, except that it has a central upward bulge, loop, or projection which holds an electrode in contact with a person's forehead.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more wearable image-recording members; (c) a data control unit that further comprises a power source and a data processor; and (d) a wearable frame which holds the one or more electromagnetic energy sensors and the one or more image-recording members in their respective configurations. In an example, this eyewear can further comprise one or more image-display members.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more wearable image-recording members; (c) a data control unit that further comprises a power source and a data processor; and (d) a wearable frame which holds the one or more electromagnetic energy sensors and the one or more image-recording members, wherein this wearable frame is configured to span from the person's left ear to the person's face, then span across the front of the person's face including the person's nose, and then span from the person's face to the person's right ear. In an example, this eyewear can further comprise one or more image-display members.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head, wherein at least one of the electromagnetic energy sensors is configured to measure electromagnetic energy from the person's forehead; (b) one or more wearable image-recording members; (c) a data control unit that further comprises a power source and a data processor; and (d) a wearable frame which holds the one or more electromagnetic energy sensors and the one or more image-recording members, wherein this wearable frame is configured to span from the person's left ear to the person's face, then span across the front of the person's face including the person's forehead, and then span from the person's face to the person's right ear. In an example, this eyewear can further comprise one or more image-display members.

In an example, this invention can include a wearable eyewear frame that is similar to a conventional eyeglasses frame, with the addition of an arcuate member that curves from one ear to the other, spanning the person's forehead. In an example, this invention can comprise a wearable frame with a left-side frame piece between the left ear and left eye, a right-side frame piece between the right ear and right eye, and an arcuate member that curves from the left-side frame piece to the right-side frame piece including spanning the person's forehead. In an example, an arcuate member such as one of these above-described can hold an electromagnetic sensor in contact with the person's forehead.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head, wherein at least one of the electromagnetic energy sensors is configured to measure electromagnetic energy from the person's forehead; (b) one or more wearable image-recording members; (c) a data control unit that further comprises a power source and a data processor; and (d) a wearable frame which holds the one or more electromagnetic energy sensors and the one or more image-recording members, wherein this wearable frame has a first member which is configured to span from one of the person's ears to the person's nose and a second member which is configured to span from one of the person's ears to the person's forehead. In an example, this eyewear can further comprise one or more image-display members.

In an example, this invention can be embodied in eyewear with a wearable frame which is similar to the frame of conventional eyeglasses, except that it includes an arcuate member or extension which loops completely around the rear of the person's head. In an example, such a rearward-looping arcuate member or extension can hold additional electromagnetic sensors against the surface of the person's head in order to improve the scope and accuracy of brain activity measurement. This can be particularly useful for measuring activity from the person's occipital lobe or cerebellum. Further, this rearward-looping arcuate member or extension can also help to hold the device on the person's head if the device is heavier than conventional eyeglasses.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more wearable image-recording members; (c) a data control unit that further comprises a power source and a data processor; and (d) a wearable frame which holds the one or more electromagnetic energy sensors and the one or more image-recording members, wherein this wearable frame is configured to span from the person's left ear to the person's face, then span across the front of the person's face, then span from the person's face to the person's right ear, and then span from the person's right ear to the person's left ear by looping around the rear of the person's head. In an example, this eyewear can further comprise one or more image-display members.

In an example, this invention can be embodied in eyewear with a wearable frame which is similar to the frame of conventional eyeglasses, except that it includes an arcuate member which loops completely over the top of the person's head. In an example, this upward-looping arcuate member can hold additional electromagnetic sensors against the surface of the person's head in order to improve the scope and accuracy of brain activity measurement. This can be particularly useful for measuring activity from the person's parietal lobe and/or occipital lobe. Further, this upward-looping arcuate member can also help to hold the device on the person's head if the device is heavier than conventional eyeglasses.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more wearable image-recording members; (c) a data control unit that further comprises a power source and a data processor; and (d) a wearable frame which holds the one or more electromagnetic energy sensors and the one or more image-recording members, wherein this wearable frame is configured to span from the person's left ear to the person's face, then span across the front of the person's face, then span from the person's face to the person's right ear, and then span from the person's right ear to the person's left ear by looping over the top of the person's head. In an example, this eyewear can further comprise one or more image-display members.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more wearable image-recording members; (c) a data control unit that further comprises a power source and a data processor; and (d) a wearable frame which holds the one or more electromagnetic energy sensors and the one or more image-recording members, wherein this wearable frame has a first portion which is configured to span from the person's left ear to the person's face, has a second portion which is configured to span across the front of the person's face, has a third portion which is configured to span from the person's face to the person's right ear, has a fourth portion which is configured to span from the person's right ear to the person's left ear by looping around the rear of the person's head; and has a fifth portion which is configured to span from the person's right ear to the person's left ear by looping over the top of the person's head. In an example, this eyewear can further comprise one or more image-display members.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more wearable image-recording members; (c) a data control unit that further comprises a power source and a data processor; and (d) a wearable frame which holds the one or more electromagnetic energy sensors and the one or more image-recording members; wherein this wearable frame is configured to curve around the anterior perimeter of the person's left ear, then span from the person's left ear to the person's face, then span across the front of the person's face, then span from the person's face to the person's right ear, and then curve around the anterior perimeter of the person's right ear; and wherein one or more of the electromagnetic energy sensors is located along a portion of the wearable frame which curves around the anterior perimeter of an ear. In an example, this eyewear can further comprise one or more image-display members.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more wearable image-recording members; (c) a data control unit that further comprises a power source and a data processor; and (d) a wearable frame which holds the one or more electromagnetic energy sensors and the one or more image-recording members; wherein this wearable frame is configured to curve around the posterior perimeter of the person's left ear, then span from the person's left ear to the person's face, then span across the front of the person's face, then span from the person's face to the person's right ear, and then curve around the posterior perimeter of the person's right ear; and wherein one or more of the electromagnetic energy sensors is located along a portion of the wearable frame which curves around the posterior perimeter of an ear. In an example, this eyewear can further comprise one or more image-display members.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more wearable image-recording members; (c) a data control unit that further comprises a power source and a data processor; and (d) a wearable frame which holds the one or more electromagnetic energy sensors and the one or more image-recording members, wherein this wearable frame is substantially circular or elliptical and wherein this wearable frame spans both the person's forehead and the rear of the person's head. In an example, this eyewear can further comprise one or more image-display members.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more wearable image-recording members; (c) a data control unit that further comprises a power source and a data processor; and (d) a wearable frame which holds the one or more electromagnetic energy sensors and the one or more image-recording members, wherein this wearable frame is substantially circular or elliptical and wherein this wearable frame encircles the person's head at an anterior acute angle in the range of 0 to 45 degrees with respect to a horizontal plane when the person's head is upright. In an example, this eyewear can further comprise one or more image-display members.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more wearable image-recording members; (c) a data control unit that further comprises a power source and a data processor; and (d) a wearable frame which holds the one or more electromagnetic energy sensors and the one or more image-recording members, wherein this wearable frame is substantially sinusoidal and wherein this wearable frame spans both the person's forehead and the rear of the person's head. In an example, this eyewear can further comprise one or more image-display members.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more wearable image-recording members; (c) a data control unit that further comprises a power source and a data processor; and (d) a wearable frame which holds the one or more electromagnetic energy sensors and the one or more image-recording members, wherein this wearable frame is substantially sinusoidal and wherein the central axis of sinusoidal undulations encircles the person's head at an anterior acute angle in the range of 0 to 45 degrees with respect to a horizontal plane when the person's head is upright. In an example, this eyewear can further comprise one or more image-display members.

In an example, this invention can be embodied in eyewear that modifies visual perception and/or imaging based on electromagnetic energy measured from a person's head, comprising: (a) one or more electromagnetic energy sensors configured to be within three inches of the surface of a person's head and configured to measure electromagnetic energy from the person's head; (b) one or more wearable image-recording members; (c) a data control unit that further comprises a power source and a data processor; and (d) a wearable frame which holds the one or more electromagnetic energy sensors and the one or more image-recording members, wherein this wearable frame is substantially the shape of an ellipse projected downward onto the curvature of the person's head and wherein this wearable frame spans both the person's forehead and the rear of the person's head. In an example, this eyewear can further comprise one or more image-display members.

FIGS. 135 through 147 show examples of a shape-transforming eyewear device for collecting data concerning electromagnetic brain activity comprising: (a) a face-spanning support member which is configured to span an upper portion of a person's face; (b) at least one optical member which transmits light from the person's environment and/or light from a virtual image display to at least one of the person's eyes; (c) an electromagnetic energy sensor, wherein this electromagnetic energy sensor has a first sensor configuration wherein it is configured to be at a selected location relative to the surface of the person's head in order to collect data concerning electromagnetic brain activity and wherein this electromagnetic energy sensor has a second sensor configuration wherein it is not at this selected location; and (d) a movable sensor arm which holds the electromagnetic energy sensor and is at least partially connected to the face-spanning support member, wherein this moveable sensor arm has a first arm configuration which holds the electromagnetic energy sensor in the first sensor configuration, wherein this moveable sensor arm has a second arm configuration which holds the electromagnetic energy sensor in the second sensor configuration, and wherein this moveable sensor arm is moved relative to the face-spanning support member in order to change from the first arm configuration to the second arm configuration, or vice versa.

FIGS. 135 through 147 also show examples of a shape-changing eyewear device for measuring electromagnetic brain activity comprising: (a) a face-spanning support member which is configured to span the upper portion of a person's face; (b) at least one optical member which is configured to transmit light from the person's environment, from a virtual image display, or from both sources to at least one of the person's eyes; (c) an electromagnetic energy sensor which has a first sensor configuration wherein it is configured to be in contact with the surface of the person's head at a selected location in order to measure electromagnetic brain activity and which has a second sensor configuration wherein it is not at this selected location; and (d) a movable sensor arm which is at least partially connected to the face-spanning support member, wherein this moveable sensor arm is moved relative to the face-spanning support member from a first arm configuration to a second arm configuration while remaining at least partially connected to the face-spanning support member, wherein this moveable sensor arm holds the electromagnetic energy sensor in the first sensor configuration when the moveable sensor arm is in the first arm configuration, and wherein this moveable sensor arm holds the electromagnetic energy sensor in the second sensor configuration when the moveable sensor arm is in the second arm configuration.

In an example, the face-spanning support member can horizontally span the upper half of a person's face. In an example, a face-spanning support member can span a person's eyes, eyebrows, and/or forehead. In an example, a face-spanning support member can span from one ear to the other ear. In an example, a face-spanning support member can span from one side of a person's head to the other side. In an example, a face-spanning support member can be symmetric with respect to the central longitudinal (right-vs.-left) cross-sectional plane of a person's head. In another example, a face-spanning support member can be asymmetric with respect to this plane.

In an example, a face-spanning support member can have: two side portions, each of which are configured to span from an ear to the front of the face; and a front portion which spans the front of the person's face from one side to the other. In an example, these three portions can be three connected pieces. In an example, these three portions can be connected by hinge mechanisms. In an example, these three portions can be one continuous piece.

In an example, a side portion of a face-spanning support member can be in substantially horizontal alignment with a person's eyes (when the person is standing up). In an example, a side portion can be in substantially horizontal alignment with a person's eyebrows. In an example, a side portion can be in substantially horizontal alignment with a person's forehead. In an example, a rear part of a side portion can be horizontally-aligned with the top of a person's ears and a front part of this side portion can be horizontally-aligned with the person's eyebrows. In an example, a side portion can have a relatively narrow and constant cross-sectional size. In an example, a side portion can flare from a rear part to a front part. In an example, a side portion can be substantially straight. In an example, a side portion can be arcuate.

In an example, a front portion of a face-spanning support member can be in substantially horizontal alignment with a person's eyes (when the person is standing up). In an example, a front portion can be in substantially horizontal alignment with a person's eyebrows. In an example, a front portion can be in substantially horizontal alignment with a person's forehead. In an example, a front portion can be substantially straight. In an example, a front portion can be arcuate. In an example, a front portion can have a central upward curve and/or other protrusion which spans upward onto the middle portion of a person's forehead. In an example, a front portion can have two upward curves and/or other protrusions which span upwards onto the right and left portions of a person's forehead.

In an example, a face-spanning support member can be arcuate. In an example, a face-spanning support member can wrap around a portion of a person's head, from one side to another, and span a portion of the person's upper face in the process. In an example, a face-spanning support member can span a portion of the circumference of a person's head, spanning a portion of the person's face in the process. In an example, a face-spanning support member can span the entire circumference of a person's head, spanning a portion of the person's face in the process. In an example, a face-spanning support member can have a shape which is selected from the group consisting of: spline and/or series of adjacent straight lines; conic section; circle, semicircle, or other section of a circle; ellipse or a section of an ellipse; and sinusoidal shape In an example, a face-spanning support member can comprise multiple connected pieces. In an example, one or more of these individual pieces can be substantially straight. In an example, a face-spanning support member can have a shape comprised of a series of substantially-straight pieces which are connected to each other. In an example, these connections can be hinges. In an example, one or more of these individual pieces can be arcuate. In an example, a face-spanning support member can comprise three connected pieces: two side pieces and one front piece. In an example, the front piece can hold two optical members, such as lenses. In an example, these three pieces can be connected by hinges. In an example, a face-spanning support member can comprise eyeglass frames.

In an example, a face-spanning support member can span a portion of the circumference of a person's head from one ear to the other ear. In an example, a face-spanning support member can span a portion of the circumference of a person's head from one side to the other side. In an example, the rear portions of a face-spanning support member can rest on top of a person's ears. In an example, the read portions of a face-spanning support member can curve around the rear portions of a person's ears.

In an example, a face-spanning support member can span the entire circumference of a person's head from front to back. In an example, a face-spanning support member can span the entire circumference of a person's head in a substantially horizontal manner. In an example, a face-spanning support member can span the entire circumference of a person's head in a plane which forms an angle with the horizontal plane (when the person is standing up) which is less than 50 degrees. In an example, the middle portion of a face-spanning support member which spans the entire circumference of a person's head can rest on top of the person's ears.

In an example, a face-spanning support member can have a longitudinal axis as it spans a portion of a person's head. In an example, this longitudinal axis can be arcuate. In an example, this longitudinal axis can have a spline shape. In an example, a face-spanning support member can have lateral cross-sectional areas which are perpendicular to this longitudinal axis. In an example, the heights of these lateral cross-sectional areas can be less than two inches (with the exception of a section which encompasses the perimeter of a lens). In an example, the heights of these lateral cross-sectional areas can be substantially constant along the side portion of a face-spanning support member which spans from a person's ear to the front of their face. In an example, the heights of lateral cross-sectional areas can vary along the side portion of a face-spanning support member which spans from a person's ear to the front of their face.

In an example, a face-spanning support member can be made of metal, a polymer, a textile, or a combination thereof. In an example, a face-spanning support member can be substantially rigid. In an example, a face-spanning support member can be flexible. In an example, a face-spanning support member can be sufficiently flexible to be placed around (a portion of) a person's head but also sufficiently resilient to be held against a person's head by tension once it is placed around (a portion of) a person's head. In an example, a face-spanning support member can be elastic. In an example, a face-spanning support member can be sufficiently elastic so that it can be placed around (a portion of) a person's head, but also sufficiently resilient to be held against a person's head by tension once it is placed around (a portion) of a person's head.

In an example, a face-spanning support member can be fastened around (a portion) of a person's head by one or more attachment mechanisms selected from the group consisting of: band, elastic, loop, strap, chain, clip, clasp, snap, buckle, clamp, button, hook, pin, plug, hook-and-eye mechanism, adhesive, tape, electronic and/or electromagnetic connector, electronic plug, magnetic connector, threaded member, fiber, thread, and zipper.

In an example, an optical member can transmit, channel, and/or guide light from a person's environment into one or both of the person's eyes. In an example, an optical member can be a lens. In an example, an optical member can be a convex or concave lens. In an example, this device can comprise a single optical member. In an example, this device can comprise a single lens. In an example, this device can comprise two optical members. In an example, this device can comprise two lenses. In an example, two optical members can comprise eyeglass lenses. In an example, a face-spanning support member and two optical members can together comprise a pair of eyeglasses. In an example, a face-spanning support member and two optical members can together comprise a pair of sunglasses. In an example, this device can comprise electronically-functional eyeglasses, electronically-functional goggles, an electronically-functional visor, or other electronically-functional eyewear.

In an example, an optical member can be selected from the group consisting of: simple lens, concave lens, convex lens, bifocal lens, trifocal lens, asymmetric lens, microlens array, MEMS-based lens array, optoelectronic lens, parabolic lens, wedge-shaped lens, liquid lens, Digital Micromirror Device (DMD), Digital Light Processor (DLP), Electromagnetically Induced Transparency (EIT) structure, MEMS-based mirror array, birefringent material, carbon nanotube, light-guiding metamaterial structure, light-guiding tubes, metamaterial light channel, nanorods, nanoscale gratings, nanotubes, etched waveguide, nanoimprint lithography pathways, resonant grating filter, Split Ring Resonator (SRR), thermoplastic nanoimprint pathways, crystalline structures, photonic metamaterial, photonic crystal, optical fiber, polarizing filter, prism, wedge prism, dielectric mirror, parabolic mirror, other mirror, reflector array, and retroreflective structure.

In an example, an optical member comprise a virtual image display, computer display, and/or electronic screen which emits, transmits, channels, and/or guides light into one or both of a person's eyes. In an example, an optical member can display an image in a person's field of vision. In an example, an optical member can display one or more virtual objects in a person's field of vision. In an example, an optical member can display virtual objects in juxtaposition with physical objects in a person's field of vision. In an example, an optical member can display information concerning physical objects in a person's field of vision. In an example, this device can comprise the visual component of a virtual reality and/or augmented reality system.

In an example, an optical member can be selected from the group consisting of: virtual image display, computer screen, heads up display, array or matrix of light-emitting members, infrared display, laser display, light emitting diodes (LED), array or matrix of light emitting diodes (LEDs), waveguide, array or matrix of fiber optic members, optoelectronic lens, computer display, camera or other imaging device, light-emitting member array or matrix, light display array or matrix, liquid crystal display (LCD), and image projector.

In an example, an electromagnetic energy sensor can collect data concerning electromagnetic brain activity from a selected location in a first sensor configuration, but not in a second sensor configuration. In an example, this invention can comprise shape-transforming eyewear which transitions from the first sensor configuration to the second sensor configuration, and vice versa. In an example, an electromagnetic energy sensor can be in direct contact with the surface of a person's head at a selected location in a first sensor configuration and not be in direct contact with the surface of the person's head at this selected location in a second sensor configuration. In an example, an electromagnetic energy sensor can be in direct contact with the surface of a person's head in a first sensor configuration and not in direct contact with the surface of the person's head in a second sensor configuration.

In an example, a selected location from which an electromagnetic energy sensor collects data concerning electromagnetic brain activity can be on (or near) the surface of the person's forehead and/or temple. In an example, the selected location from which an electromagnetic energy sensor collects data concerning electromagnetic brain activity can be on a person's ear and/or within the person's ear canal. In an example, the selected location from which an electromagnetic energy sensor collects data concerning electromagnetic brain activity can be selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2. Also, a reference location can be selected from sites A1 and A2.

In an example, an electromagnetic energy sensor can be sufficiently close to the surface of a person's head so as to be in electromagnetic communication with body tissue. In an example, an electromagnetic energy sensor can be in electromagnetic communication with body tissue at a selected location in a first sensor configuration, but not in a second sensor configuration. In an example, this invention can comprise shape-transforming eyewear which transitions from the first sensor configuration to the second sensor configuration, and vice versa.

In an example, an electromagnetic energy sensor can measure the conductivity, voltage, resistance, and/or impedance of electromagnetic energy transmitted through and/or emitted from a portion of a person's head. In an example, an electromagnetic energy sensor can be an electroencephalographic (EEG) sensor. In an example, an electromagnetic energy sensor can be a dry electrode. In an example, an electromagnetic energy sensor can collect data on electromagnetic energy patterns and/or electromagnetic fields which are naturally generated by electromagnetic brain activity. In an example, an electromagnetic energy sensor can be used in combination with an electromagnetic energy emitter. In an example, an electromagnetic energy emitter can be in contact with the surface of a person's head. In an example, an electromagnetic energy sensor can measure the conductivity, voltage, resistance, and/or impedance of electromagnetic energy emitted from an electromagnetic energy emitter and transmitted through a portion of a person's head.

In an example, this device can comprise a plurality of electromagnetic energy sensors which collect data concerning electromagnetic brain activity from different selected locations. In an example, an electromagnetic energy sensor can measure the conductivity, voltage, resistance, or impedance of electromagnetic energy that is transmitted between two locations. In an example, the locations for a plurality of electromagnetic energy sensors can be selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2. In an example, a plurality of electromagnetic energy sensors can be located in a symmetric manner with respect to the central longitudinal right-vs.-left plane of a person's head. In an example, electromagnetic brain activity data from a selected recording location (relative to a reference location) is a "channel." In an example, electromagnetic brain activity data from multiple recording places is a "montage."

In an example, data from one or more electromagnetic energy sensors can be filtered to remove artifacts before the application of a primary statistical method. In an example, a filter can be used to remove electromagnetic signals from eye blinks, eye flutters, or other eye movements before the application of a primary statistical method. In an example, a notch filter can be used as well to remove 60 Hz artifacts caused by AC electrical current. In various examples, one or more filters can be selected from the group consisting of: a high-pass filter, a band-pass filter, a loss-pass filter, an electromyographic activity filter, a 0.5-1 Hz filter, and a 35-70 Hz filter.

In an example, data from an electromagnetic energy sensor can be analyzed using Fourier transformation methods in order to identify repeating energy patterns in clinical frequency bands. In an example, these clinical frequency bands can be selected from the group consisting of: Delta, Theta, Alpha, Beta, and Gamma. In an example, the relative and combinatorial power levels of energy in two or more different clinical frequency bands can be analyzed. In an example, a person can receive real-time feedback based on analysis of data concerning their electromagnetic brain activity. In an example, a person can control a computer or other device by self-modifying their electromagnetic brain activity.

In an example, a primary statistical method can comprise finding the mean or average value of data from one or more brain activity channels during a period of time. In an example, a statistical method can comprise identifying a significant change in the mean or average value of data from one or more brain activity channels. In an example, a statistical method can comprise finding the median value of data from one or more brain activity channels during a period of time. In an example, a statistical method can comprise identifying a significant change in the median value of data from one or more brain activity channels. In an example, a statistical method can comprise identifying significant changes in the relative mean or median data values among multiple brain activity channels. In an example, a statistical method can comprise identifying significant changes in mean data values from a first set of electrode locations relative to mean data values from a second set of electrode locations. In an example, a statistical method can comprise identifying significant changes in mean data recorded from a first region of the brain relative to mean data recorded from a second region of the brain.

In an example, a primary statistical method can comprise finding the minimum or maximum value of data from one or more brain activity channels during a period of time. In an example, a statistical method can comprise identifying a significant change in the minimum or maximum value of data from one or more brain activity channels. In an example, a statistical method can comprise identifying significant changes in the relative minimum or maximum data values among multiple brain activity channels. In an example, a statistical method can comprise identifying significant changes in minimum or maximum data values from a first set of electrode locations relative to minimum or maximum data values from a second set of electrode locations. In an example, a statistical method can comprise identifying significant changes in minimum or maximum data values recorded from a first region of the brain relative to minimum or maximum data values recorded from a second region of the brain.

In an example, a primary statistical method can comprise finding the variance or the standard deviation of data from one or more brain activity channels during a period of time. In an example, a statistical method can comprise identifying a significant change in the variance or the standard deviation of data from one or more brain activity channels. In an example, a statistical method can comprise identifying significant changes in the covariation and/or correlation among data from multiple brain activity channels. In an example, a statistical method can comprise identifying significant changes in the covariation or correlation between data from a first set of electrode locations relative and data from a second set of electrode locations. In an example, a statistical method can comprise identifying significant changes in the covariation or correlation of data values recorded from a first region of the brain and a second region of the brain.

In an example, a primary statistical method can comprise finding the mean amplitude of waveform data from one or more channels during a period of time. In an example, a statistical method can comprise identifying a significant change in the mean amplitude of waveform data from one or more channels. In an example, a statistical method can comprise identifying significant changes in the relative means of wave amplitudes from one or more channels. In an example, a statistical method can comprise identifying significant changes in the amplitude of electromagnetic signals recorded from a first region of the brain relative to the amplitude of electromagnetic signals recorded from a second region of the brain.

In an example, a primary statistical method can comprise finding the power of waveform brain activity data from one or more channels during a period of time. In an example, a statistical method can comprise identifying a significant change in the power of waveform data from one or more channels. In an example, a statistical method can comprise identifying significant changes in the relative power levels of one or more channels. In an example, a statistical method can comprise identifying significant changes in the power of electromagnetic signals recorded from a first region of the brain relative to the power of electromagnetic signals recorded from a second region of the brain.

In an example, a primary statistical method can comprise finding a frequency or frequency band of waveform and/or rhythmic brain activity data from one or more channels which repeats over time. In an example, Fourier transformation methods can be used to find a frequency or frequency band of waveform and/or rhythmic data which repeats over time. In an example, a statistical method can comprise decomposing a complex waveform into a combination of simpler waveforms which each repeat at a different frequency or within a different frequency band. In an example, Fourier transformation methods can be used to decomposing a complex waveform into a combination of simpler waveforms which each repeat at a different frequency or within a different frequency band.

In an example, a primary statistical method can comprise identifying significant changes in the amplitude, power level, phase, frequency, and/or oscillation of waveform data from one or more channels. In an example, a primary statistical method can comprise identifying significant changes in the amplitude, power level, phase, frequency, and/or oscillation of waveform data within a selected frequency band. In an example, a primary statistical method can comprise identifying significant changes in the relative amplitudes, power levels, phases, frequencies, and/or oscillations of waveform data among different frequency bands. In various examples, these significant changes can be identified using Fourier transformation methods.

In an example, brainwaves (or other rhythmic, cyclical, and/or repeating electromagnetic signals associated with brain activity) can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier transformation methods. In an example, brainwaves can be measured and analyzed using five common clinical frequency bands: Delta, Theta, Alpha, Beta, and Gamma.

In an example, Delta brainwaves can be measured and analyzed within the frequency band of 1 to 4 Hz. In various examples, Delta brainwaves (or other rhythmic, cyclical, and/or repeating electromagnetic signals associated with brain activity) can be measured and analyzed within a frequency band selected from the group consisting of: 0.5-3.5 Hz, 0.5-4 Hz, 1-3 Hz, 1-4 Hz, and 2-4 Hz. In an example, Theta brainwaves can be measured and analyzed within the frequency band of 4 to 8 Hz. In various examples, Theta brainwaves or other rhythmic, cyclical, and/or repeating electromagnetic signals associated with brain activity can be measured and analyzed within a frequency band selected from the group consisting of: 3.5-7 Hz, 3-7 Hz, 4-7 Hz, 4-7.5 Hz, 4-8 Hz, and 5-7 Hz.

In an example, Alpha brainwaves can be measured and analyzed within the frequency band of 7 to 14 Hz. In various examples, Alpha brainwaves or other rhythmic, cyclical, and/or repeating electromagnetic signals associated with brain activity can be measured and analyzed within a frequency band selected from the group consisting of: 7-13 Hz, 7-14 Hz, 8-12 Hz, 8-13 Hz, 7-11 Hz, 8-10 Hz, and 8-10 Hz. In an example, Beta brainwaves can be measured and analyzed within the frequency band of 12 to 30 Hz. In various examples, Beta brainwaves or other rhythmic, cyclical, and/or repeating electromagnetic signals associated with brain activity can be measured and analyzed within a frequency band selected from the group consisting of: 11-30 Hz, 12-30 Hz, 13-18 Hz, 13-22 Hz, 13-26 Hz, 13-26 Hz, 13-30 Hz, 13-32 Hz, 14-24 Hz, 14-30 Hz, and 14-40 Hz. In an example, Gamma brainwaves can be measured and analyzed within the frequency band of 30 to 100 Hz. In various examples, Gamma brainwaves or other rhythmic, cyclical, and/or repeating electromagnetic signals associated with brain activity can be measured and analyzed within a frequency band selected from the group consisting of: 30-100 Hz, 35-100 Hz, 40-100 Hz, and greater than 30 Hz.

In an example, data concerning electromagnetic brain activity which is collected by one or more electromagnetic energy sensors can be analyzed using one or more statistical methods selected from the group consisting of: multivariate linear regression or least squares estimation; factor analysis; Fourier transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; logit model; machine learning; power spectral density; power spectrum analysis; probit model; time-series analysis; inter-band mean; inter-band ratio; inter-channel mean; inter-channel ratio; inter-montage mean; inter-montage ratio; multi-band covariance analysis; multi-channel covariance analysis; and analysis of wave frequency, wave frequency band, wave amplitude, wave phase, and wave form or morphology. In an example, wave form or morphology can be identified from the group consisting of: simple sinusoidal wave, composite sinusoidal wave, simple saw-tooth wave, composite saw-tooth wave, biphasic wave, tri-phasic wave, and spike.

In an example, a moveable sensor arm can be at least partially connected to a face-spanning support member and can hold at least one electromagnetic energy sensor which collects data concerning electromagnetic brain activity. In an example, a moveable sensor arm can be moved relative to a face-spanning support member from a first arm configuration to a second arm configuration, and vice versa. In an example, in the first arm configuration, the moveable sensor arm holds the electromagnetic energy sensor in a selected location from which the electromagnetic energy sensor collects data concerning electromagnetic brain activity. In the second arm configuration the moveable sensor arm holds the electromagnetic energy sensor in a different location.

In an example, a moveable sensor arm can be visually less-obtrusive in a second arm configuration than in a first arm configuration. This allows this eyewear device to collect data concerning electromagnetic brain activity in a more-obtrusive first configuration at times when such data collection is needed, but to transform into a less-obtrusive second configuration at times when such data collection is not needed.

In an example, a moveable sensor arm can be visually less-obtrusive in a second arm configuration because it is substantially hidden behind (from an external perspective) a face-spanning support member when the sensor arm is in the second arm configuration. In an example, a moveable sensor arm can be visually more-obtrusive in a first arm configuration because it moves out from behind (from an external perspective) a face-spanning support member when the sensor arm is in the first arm configuration.

In an example, a moveable sensor arm can be visually less-obtrusive in a second arm configuration because it is substantially aligned with the longitudinal axis of a face-spanning support member when the sensor arm is in the second arm configuration. In an example, a moveable sensor arm can be visually more-intrusive in a first arm configuration because it moves out of alignment with the longitudinal axis of a face-spanning support member when the sensor arm is in the first arm configuration.

In an example, a moveable sensor arm can be visually less-obtrusive in a second arm configuration because it fits within a recess, channel, and/or slot within a face-spanning support member when the sensor arm is in the second arm configuration. In an example, a moveable sensor arm can be visually more-intrusive in a first arm configuration because it moves out of the recess, channel, and/or slot.

In an example, a moveable sensor arm is changed from a first arm configuration to a second arm configuration, or vice versa, by being moved relative to a face-spanning support member. In an example, movement of a moveable sensor arm from a second arm configuration to a first arm configuration causes an electromagnetic energy sensor to be moved to a selected location from which the sensor collects data concerning electromagnetic brain activity. In an example, a moveable sensor arm is at least partially attached to a face-spanning support member in both a first arm configuration and a second arm configuration.

In an example, a moveable sensor arm can be connected to a face-spanning support member at a single point or by a single axle. In an example, a moveable sensor arm can be pivoted and/or rotated around this single point or single axle in order to transition from a first arm configuration to a second arm configuration, or vice versa. In an example, a single point or single axle connection between a moveable sensor arm and a face-spanning support member can be at an end-point of a moveable sensor arm. In an example, a moveable sensor arm can pivot around this single point or single axle. In an example, a single point or single axle connection between a moveable sensor arm and a face-spanning support member can be at a more-central location on a moveable sensor arm. In an example, a moveable sensor arm can rotate around this single point or single axle.

In an example, pivoting or rotating a moveable sensor arm can cause the arm to protrude out from a face-spanning support member in a manner which brings one or more electromagnetic energy sensors into contact with the surface of a person's head at a selected location. In an example, pivoting or rotating a moveable sensor arm can cause the arm to protrude out from a face-spanning support member in a manner which brings one or more electromagnetic energy sensors into electromagnetic communication with a person's head at a selected location. In an example, pivoting or rotating a moveable sensor arm can cause the arm to protrude upwards and bring an electromagnetic energy sensor into electromagnetic communication with a person's forehead and/or temples.

In an example, pivoting or rotating a moveable sensor arm can cause the arm to protrude out from a face-spanning support member in a manner which brings one or more electromagnetic energy sensors into contact with one or more locations selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In an example, a moveable sensor arm can be connected to a face-spanning support member at two or more locations and/or by two or more axles. In an example, a moveable sensor arm can be changed from a first arm configuration to a second arm configuration, or vice versa, by the relative movement of the two or more connection locations or axles. In an example, the distances between two or more connection locations or axles can be changed. In an example, changes in the distances between two or more connection locations or axles can change the shape of a moveable sensor arm. In an example, changes in the distances between two or more connection locations or axles can cause a moveable sensor arm to bend, flex, or fold. In an example, such bending, flexing, or folding can change a moveable sensor arm from a first arm configuration to a second arm configuration, or vice versa.

In an example, bending, flexing, or folding a moveable sensor arm can cause the arm to protrude out from a face-spanning support member in a manner which brings one or more electromagnetic energy sensors into contact with the surface of a person's head at a selected location. In an example, bending, flexing, or folding a moveable sensor arm can cause the arm to protrude out from a face-spanning support member in a manner which brings one or more electromagnetic energy sensors into electromagnetic communication with a person's head at a selected location. In an example, bending, flexing, or folding a moveable sensor arm can cause the arm to protrude upwards and bring an electromagnetic energy sensor into electromagnetic communication with a person's forehead and/or temples.

In an example, bending, flexing, or folding a moveable sensor arm can cause the arm to protrude out from a face-spanning support member in a manner which brings one or more electromagnetic energy sensors into contact with one or more locations selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In an example, a moveable sensor arm can be connected to a face-spanning support member such that the arm can slide along a track or channel. In an example, a moveable sensor arm can be changed from a first arm configuration to a second arm configuration, or vice versa, by sliding along this track or channel. In an example, sliding a moveable sensor arm can bring an electromagnetic energy sensor into electromagnetic communication with a person's forehead and/or temples. In an example, sliding a moveable sensor arm can bring one or more electromagnetic energy sensors into contact with one or more locations selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In an example, a moveable sensor arm can be connected to a face-spanning support member by a hinge mechanism. In an example, a moveable sensor arm can be changed from a first arm configuration to a second arm configuration, or vice versa, by movement of this hinge mechanism. In an example, movement of this hinge can bring an electromagnetic energy sensor into electromagnetic communication with a person's forehead and/or temples. In an example, movement of this hinge can bring one or more electromagnetic energy sensors into contact with one or more locations selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In an example, a moveable sensor arm can be moved from being substantially horizontal in a second arm configuration to being substantially vertical in a first arm configuration. In an example, a portion of a moveable sensor arm can be pivoted or rotated upwards from a face-spanning support in order to span a portion of a person's forehead and/or temples and bring an electromagnetic energy sensor into contact with the person's forehead and/or temples. In an example, a portion of a moveable sensor arm can be bent, flexed, or folded upwards from a face-spanning support in order to span a portion of a person's forehead and/or temples and bring an electromagnetic energy sensor into contact with the person's forehead and/or temples. In an example, a portion of a moveable sensor arm can be slid relative to a face-spanning support in order to span a portion of a person's forehead and/or temples and bring an electromagnetic energy sensor into contact with the person's forehead and/or temples.

In an example, a portion of a moveable sensor arm can be pivoted, rotated, bent, flexed, folded, or slid relative to a face-spanning support in order to span a portion of a person's head and bring an electromagnetic energy sensor into contact with one or more locations selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, 01, Oz, and O2.

In an example, a moveable sensor arm can be substantially straight. In an example, a moveable sensor arm can be arcuate. In an example, a moveable sensor arm can have a shape which is a conic section. In an example, a moveable sensor arm can be an arc of a circle. In an example, a moveable sensor arm can be substantially perpendicular to the longitudinal axis of a face-spanning support member in a first arm configuration and can be substantially parallel to the longitudinal axis of a face-spanning support member in a second arm configuration. In an example, a moveable sensor arm can be an arcuate loop which loops over a person's forehead, over the top of the person's head, and/or around the back of the person's head.

In an example, a moveable sensor arm can change from a more arcuate shape in its first configuration to a less arcuate shape in its second configuration. In an example, a moveable sensor arm can change from a more convex shape in its first configuration to a less convex shape in its second configuration. In an example, moving the two ends of a moveable sensor arm closer together can cause the arm to protrude upwards onto a person's forehead and/or temple. In an example, a moveable sensor arm can be moved from a first arm configuration to a second arm configuration, or vice versa, along a path which is substantially parallel to the surface of a person's head. In an example, a moveable sensor arm can be moved from a first arm configuration to a second arm configuration, or vice versa, along a path which is a substantially constant distance from the arcuate surface of a person's head.

In an example, a moveable sensor arm can be configured to horizontally span a person's forehead and/or temple. In an example, a moveable sensor arm can be configured to loop over the top of a person's head. In an example, a moveable sensor arm can be configured to loop around the back of a person's head. In an example, this device can comprise two symmetric moveable sensor arms, one on the right side of a person's head and one on the left side of a person's head. In an example, this device can comprise a single moveable sensor arm on one side of a person's head.

In an example, a moveable sensor arm can be manually moved from a first arm configuration to a second arm configuration (and vice versa) by a person. In an example, a moveable sensor arm can be automatically moved from a first arm configuration to a second arm configuration (and vice versa) by an actuator which is manually activated by a person. In an example, a moveable sensor arm can be automatically moved from a first arm configuration to a second arm configuration (and vice versa) by an actuator which is automatically activated based on data from one or more wearable sensors. In an example, a moveable sensor arm can be automatically moved from a first arm configuration to a second arm configuration (and vice versa) by an actuator which is automatically activated by a data processing unit.

In an example, a moveable sensor arm can be rigid. In an example, a moveable sensor can be made from metal, a polymer, a textile, or a combination thereof. In an example, a moveable sensor arm can be sufficiently flexible to hold an electromagnetic energy sensor against the surface of a person's head. In an example, a moveable sensor arm can bend. In an example, a moveable sensor arm can be elastic, but sufficiently resistant to hold an electromagnetic energy sensor against the surface of a person's head. In an example, a moveable sensor arm can be kept in close contact with the surface of a person's head by means of a spring or an elastic member. In an example, a moveable sensor arm can keep an electromagnetic energy sensor in close contact with the surface of a person's head by means of a spring or an elastic member.

In an example, a moveable sensor arm can hold a single electromagnetic energy sensor in a selected location in order to collect data concerning electromagnetic brain activity. In an example, a moveable sensor arm can hold a plurality of electromagnetic energy sensors in selected locations in order to collect data concerning electromagnetic brain activity. In an example, the locations of one or more electromagnetic energy sensors relative to a person's head are changed by the movement of a moveable sensor arm relative to a face-spanning support member. In an example, the locations of one or more electromagnetic energy sensors relative to a face-spanning support member can be changed by the movement of a moveable sensor arm relative to a face-spanning support member. In an example, the locations of one or more electromagnetic energy sensors can be changed when a moveable sensor arm is moved from a first arm configuration to a second arm configuration.

In an example, this invention can further comprise one or more components selected from the group consisting of: data processor, power source, data communication component, human-to-computer user interface, computer-to-human interface, digital memory, one or more additional wearable sensors, and an external electromagnetic energy emitter. In an example, one or more of the components selected from this group can be connected to, attached to, and/or integrated into the face-spanning support member.

In an example, a data processor can perform one or more functions selected from the group consisting of: convert analog sensor signals to digital signals, filter sensor signals, amplify sensor signals, analyze sensor data, run software programs, and store data in memory. In an example, a data processor can analyze data using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; logit model; machine learning; power spectral density; power spectrum analysis; probit model; and time-series analysis.

In an example, a power source can be a battery. In an example, a power source can harvest, transduce, or generate electrical energy from kinetic energy, thermal energy, biochemical energy, ambient light energy, and/or ambient electromagnetic energy. In an example, a power source can comprise: power from a source that is internal to the device during regular operation (such as an internal battery, capacitor, energy-storing microchip, wound coil or spring); power that is obtained, harvested, or transduced from a source other than a person's body that is external to the device (such as a rechargeable battery, electromagnetic inductance from external source, solar energy, indoor lighting energy, wired connection to an external power source, ambient or localized radiofrequency energy, or ambient thermal energy); and power that is obtained, harvested, or transduced from a person's body (such as kinetic or mechanical energy from body motion, electromagnetic energy from a person's body, or thermal energy from a person's body).

In an example, a data communication component can perform one or more functions selected from the group consisting of: transmit and receive data via Bluetooth, WiFi, Zigbee, or other wireless communication modality; transmit and receive data to and from a home appliance and/or home control system; transmit and receive data to and from a mobile electronic device such as a cellular phone, mobile phone, smart phone, electronic tablet; transmit and receive data to and from a separate wearable device such as a smart watch or smart clothing; transmit and receive data to and from the internet; send and receive phone calls and electronic messages; and transmit and receive data to and from an implantable medical device.

In an example, a data communication component can be in wireless communication with a separate mobile device selected from the group consisting of: smart phone, mobile phone, holophone, or cellular phone; PDA; electronic tablet; electronic pad; and other electronically-functional handheld device. In an example, a data communication component can be in wireless communication with a relatively fixed-location device selected from the group consisting of: laptop computer, desktop computer, internet terminal, smart appliance, home control system, and other fixed-location electronic communication device. In an example, a data communication component can communicate with one or more other devices selected from the group consisting of: a communication tower or satellite; a CPAP device and/or respiratory mask; an appliance, home environment control system, and/or home security system; a laptop or desktop computer; a smart phone or other mobile communication device; a wearable cardiac monitor; a wearable electromagnetic brain activity monitor; a wearable pulmonary activity monitor; an implantable medical device; an internet server; and another type of wearable device or an array of wearable sensors.

In an example, a human-to-computer interface can further comprise one or more members selected from the group consisting of: buttons, knobs, dials, or keys; display screen; gesture-recognition interface; microphone; physical keypad or keyboard; virtual keypad or keyboard; speech or voice recognition interface; touch screen; EMG-recognition interface; and EEG-recognition interface. In an example, this invention can comprise a device and method that enables a person to control a computer or other electronic device by modifying their electromagnetic brain activity. In an example, this invention can comprise a device and method that enables a health care provider to better diagnose a health condition related to electromagnetic brain activity.

In an example, a computer-to-human interface can further comprise one or more members selected from the group consisting of: a display screen; a speaker or other sound-emitting member; a myostimulating member; a neurostimulating member; a speech or voice recognition interface; a synthesized voice; a vibrating or other tactile sensation creating member; MEMS actuator; an electromagnetic energy emitter; an infrared light projector; an LED or LED array; and an image projector.

In an example, this invention can comprise a device and method for neurofeedback. In an example, the person for whom data concerning their electromagnetic brain activity is collected by one or more electromagnetic energy sensors can receive feedback based on analysis of that data. In an example, this feedback can be in real time. In an example, this device can help a person to self-modify their electromagnetic brain activity in order to improve their mental functioning and/or health status.

In an example, this invention can comprise eyewear that transmits and/or displays a combination of environmental objects and virtual objects. In an example, a person can modify and control the combination of environmental and virtual objects which they see by changing their brainwave patterns. In an example, a person can alter the relative proportion of environmental content vs. virtual content in an augmented reality system based on changes in their electromagnetic brain activity. In an example, a person can alter and control the type of virtual content which is combined with environmental content by changing their brain activity. In various examples, this invention can comprise eyewear selected from the group consisting of: non-prescription eyeglasses, prescription eyeglasses, sunglasses, goggles, contact lenses, visor, monocle, eyewear-based human-to-computer interface, eyeglasses with integrated camera, augmented reality (AR) glasses, and virtual reality (VR) glasses.

In an example, one or more additional wearable sensors can be selected from the group consisting of: motion sensor, inertial sensor, single axis, biaxial, or multi-axial accelerometer, kinematic sensor, gyroscope, tilt sensor, inclinometer, vibration sensor, bend sensor, goniometer, strain gauge, stretch sensor, pressure sensor, force sensor, flow sensor, air pressure sensor, altimeter, barometer, blood flow monitor, blood pressure monitor, microcantilever sensor, microfluidic sensor, peak flow meter, nanotube sensor, gesture recognition sensor, global positioning system (GPS) module, and compass.

In an example, one or more additional sensors can be selected from the group consisting of: light energy sensor, ambient light sensor, electro-optical sensor, infrared sensor, laser sensor, light intensity sensor, optical sensor, optoelectronic sensor, photochemical sensor, photoelectric sensor, photometer, ultraviolet light sensor, chemiluminescence sensor, image recorder, camera, video recorder, spectroscopic sensor, light-spectrum-analyzing sensor, color sensor, spectral analysis sensor, spectrometry sensor, spectrophotometric sensor, spectroscopy sensor, near-infrared, infrared, ultraviolet, or white light spectroscopy sensor, mass spectrometry sensor, Raman spectroscopy sensor, ion mobility spectroscopic sensor, chromatography sensor, optical glucose sensor, gas chromatography sensor, and analytical chromatography sensor. In an example, one or more additional sensors can be selected from the group consisting of: sound sensor, sonic energy sensor, microphone, speech and/or voice recognition interface, breathing sound monitor, chewing and/or swallowing monitor, ambient sound sensor or monitor, and ultrasound sensor.

In an example, one or more additional sensors can be selected from the group consisting of: temperature and/or thermal energy sensor, thermistor, thermometer, thermopile, body temperature sensor, skin temperature sensor, ambient temperature sensor, biochemical sensor, ambient air monitor, amino acid sensor, artificial olfactory sensor, blood glucose monitor, blood oximeter, body fat sensor, capnography sensor, carbon dioxide sensor, carbon monoxide sensor, cerebral oximetry monitor, chemical sensor, chemiresistor sensor, chemoreceptor sensor, cholesterol sensor, cutaneous oxygen monitor, ear oximeter, food identification sensor, food consumption monitor, caloric intake monitor, gas composition sensor, glucometer, glucose monitor, humidity sensor, hydration sensor, microbial sensor, moisture sensor, osmolality sensor, oximeter, oximetry sensor, oxygen consumption monitor, oxygen level monitor or sensor, oxygen saturation monitor, pH level sensor, porosity sensor, pulse oximeter, skin moisture sensor, sodium sensor, tissue oximetry sensor, and tissue saturation oximeter.

In an example, an external electromagnetic energy emitter can transmit electromagnetic energy into the surface of a person's body. In an example, an external electromagnetic energy emitter can be used in combination with an electromagnetic energy sensor in order to measure the electromagnetic conductivity, resistance, and/or impedance of body tissue. In an example, an external electromagnetic energy emitter can transmit electromagnetic energy into body tissue in order to modify, adjust, stimulate, and/or block electromagnetic brain activity. In an example, an external electromagnetic energy emitter can transmit electromagnetic energy into body tissue in order to modify, adjust, stimulate, and/or block peripheral nervous system activity. In an example, an external electromagnetic energy emitter can transmit electromagnetic energy into body tissue in order to modify, adjust, stimulate, and/or block muscular activity. In an example, an external electromagnetic energy emitter can be a neurostimulator or myostimulator.

In an example, electromagnetic energy which is emitted from an external electromagnetic energy emitter can be selectively adjusted. In various examples, adjustable parameters of transmitted electromagnetic energy can be selected from the group consisting of: the particular wave form or wave morphology (e.g. sinusoidal wave, saw tooth wave, square wave, triangle wave, biphasic pattern, tri-phasic pattern, signal spikes, pattern randomization, pattern repetition, Fourier transformation parameter, pattern mimicking a natural neural transmission signal, and pattern inverting a natural neural transmission signal), wave or pulse frequency (e.g. in the range of 0.1 Hz to 2,500 Hz), wave or pulse amplitude (e.g. in the range from 1 µA to 1000 mA), wave or pulse width (e.g. in the range of 5 µSec to 500 mSec), electrical current level (e.g. in the range from 0.01 mA to 1000 mA), electromagnetic field (e.g. in the range of 5 V/m to 500 V/m), electromagnetic field gradient (e.g. over 1 V/m/mm), signal continuity and duty cycle, signal cycling times, signal ramping, and signal dampening.

FIG. 135 shows an example of how this invention can be embodied in a shape-transforming eyewear device for collecting data concerning electromagnetic brain activity comprising: a face-spanning support member which is configured to span an upper portion of a person's face; at least one optical member which transmits light from the person's environment and/or light from a virtual image display to at least one of the person's eyes; an electromagnetic energy sensor, wherein this electromagnetic energy sensor has a first sensor configuration wherein it is configured to be at a selected location relative to the surface of the person's head in order to collect data concerning electromagnetic brain activity and wherein this electromagnetic energy sensor has a second sensor configuration wherein it is not at this selected location; and a movable sensor arm which holds the electromagnetic energy sensor and is at least partially connected to the face-spanning support member, wherein this moveable sensor arm has a first arm configuration which holds the electromagnetic energy sensor in the first sensor configuration, wherein this moveable sensor arm has a second arm configuration which holds the electromagnetic energy sensor in the second sensor configuration, and wherein this moveable sensor arm is moved relative to the face-spanning support member in order to change from the first arm configuration to the second arm configuration, or vice versa.

The lower half of FIG. 135 shows this example at a time when moveable sensor arm 13504 is in the first arm configuration and electromagnetic energy sensor 13503 is in the first sensor configuration. In this first configuration, electromagnetic energy sensor 13503 is at a selected location from which it collects data concerning electromagnetic brain activity 13506. The upper half of FIG. 135 shows this example at different time, when moveable sensor arm 13504 is in the second arm configuration and electromagnetic energy sensor 13503 is in the second sensor configuration. In this second configuration, electromagnetic energy sensor 13503 is not at the selected location. In an example, the selected location from which an electromagnetic energy sensor collects data concerning electromagnetic brain activity can be selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In more detail, the embodiment shown in FIG. 135 comprises: face-spanning support member 13501, two optical members (including optical member 13502), electromagnetic energy sensor 13503, moveable sensor arm 13504, and connecting axle 13505. Connecting axle 13505 connects moveable sensor arm 13504 with face-spanning support member 13501. As discussed earlier, this embodiment can further comprise one or more components selected from the group consisting of: data processor, power source, data communication component, human-to-computer user interface, computer-to-human interface, digital memory, additional sensors, and a non-implantable electromagnetic energy emitter.

In this example, face-spanning support member 13501 is a single-piece member which spans from one ear to the other. In this example, face-spanning support member 13501 has two side portions (which each span from an ear to the front of the face) and a front portion (which spans the face from one side to the other). Although the far side portion is not shown [sorry, Gary] in the angled perspective of FIG. 135, the device in this example is assumed to be symmetric with respect to a central longitudinal (right-vs.-left) plane of the person's head. In this example, side portions are horizontally aligned with the person's eyes and the front portion is horizontally aligned with the person's eyebrows. In this example, the optical members (including 13502) are lenses. In this example, face-spanning support member 13501 and optical members (including 13502) together comprise a pair of electronically-functional eyeglasses. In this example, the selected location from which electromagnetic energy sensor 13503 collects data concerning electromagnetic brain activity 13506 is on a person's forehead and/or temple.

As shown in FIG. 135, moveable sensor arm 13504 is visually less-obtrusive in the second arm configuration (shown in the upper half of the figure) than in the first arm configuration (shown in the lower half of the figure). Thus, this eyewear can collect data concerning electromagnetic brain activity 13506 using a more-obtrusive configuration at times when such data collection is needed, but can transform into a less-obtrusive configuration at times when such data collection is not needed. This enables a person to wear a mobile EEG monitor without looking too dorky—or at least without looking dorky all the time. In FIG. 135, moveable sensor arm 13504 is visually less-obtrusive in the second arm configuration because it is substantially hidden behind (interior to) the side portion of face-spanning support member 13501.

In this example, moveable sensor arm 13504 pivots and/or rotates around axle 13505 in order to change from the first arm configuration to the second arm configuration, or vice versa. In this example, axle 13505 is located near an ear. In this example, in the second arm configuration moveable sensor arm 13504 spans forward from axle 13505 toward the front of the person's face. In this example, moveable sensor arm 13504 is slightly arcuate. In another example, moveable sensor arm 13504 can be straight. In this example, moveable sensor arm 13504 is moved manually. In another example, moveable sensor arm 13504 can be moved automatically by an actuator.

FIG. 136 shows an example of how this invention can be embodied in a shape-transforming eyewear device for collecting data concerning electromagnetic brain activity comprising: a face-spanning support member which is configured to span an upper portion of a person's face; at least one optical member which transmits light from the person's environment and/or light from a virtual image display to at least one of the person's eyes; an electromagnetic energy sensor, wherein this electromagnetic energy sensor has a first sensor configuration wherein it is configured to be at a selected location relative to the surface of the person's head in order to collect data concerning electromagnetic brain activity and wherein this electromagnetic energy sensor has a second sensor configuration wherein it is not at this selected location; and a movable sensor arm which holds the electromagnetic energy sensor and is at least partially connected to the face-spanning support member, wherein this moveable sensor arm has a first arm configuration which holds the electromagnetic energy sensor in the first sensor configuration, wherein this moveable sensor arm has a second arm configuration which holds the electromagnetic energy sensor in the second sensor configuration, and wherein this moveable sensor arm is moved relative to the face-spanning support member in order to change from the first arm configuration to the second arm configuration, or vice versa.

The lower half of FIG. 136 shows this example at a time when moveable sensor arm 13604 is in the first arm configuration and electromagnetic energy sensor 13603 is in the first sensor configuration. In this first configuration, electromagnetic energy sensor 13603 is at a selected location from which it collects data concerning electromagnetic brain activity 13606. The upper half of FIG. 136 shows this example at different time, when moveable sensor arm 13604 is in the second arm configuration and electromagnetic energy sensor 13603 is in the second sensor configuration. In this second configuration, electromagnetic energy sensor 13603 is not at the selected location. In an example, the selected location from which an electromagnetic energy sensor collects data concerning electromagnetic brain activity can be selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In more detail, the embodiment shown in FIG. 136 comprises: face-spanning support member 13601, two optical members (including optical member 13602), electromagnetic energy sensor 13603, moveable sensor arm 13604, and connecting axle 13605. Connecting axle 13605 connects moveable sensor arm 13604 with face-spanning support member 13601. As discussed earlier, this embodiment can further comprise one or more components selected from the group consisting of: data processor, power source, data communication component, human-to-computer user interface, computer-to-human interface, digital memory, additional sensors, and a non-implantable electromagnetic energy emitter.

In this example, face-spanning support member 13601 is a single-piece member which spans from one ear to the other. In this example, face-spanning support member 13601 has two side portions (which each span from an ear to the front of the face) and a front portion (which spans the face from one side to the other). Although the far side portion is not shown [sorry, Gary] in the angled perspective of FIG. 136, the device in this example is assumed to be symmetric with respect to a central longitudinal (right-vs.-left) plane of the person's head. In this example, side portions are horizontally aligned with the person's eyes and the front portion is horizontally aligned with the person's eyebrows. In this example, the optical members (including 13602) are lenses. In this example, face-spanning support member 13601 and optical members (including 13602) together comprise a pair of electronically-functional eyeglasses. In this example, the selected location from which electromagnetic energy sensor 13603 collects data concerning electromagnetic brain activity 13606 is on a person's forehead and/or temple.

As shown in FIG. 136, moveable sensor arm 13604 is visually less-obtrusive in the second arm configuration (shown in the upper half of the figure) than in the first arm configuration (shown in the lower half of the figure). Thus, this eyewear can collect data concerning electromagnetic brain activity 13606 using a more-obtrusive configuration at times when such data collection is needed, but can transform into a less-obtrusive configuration at times when such data collection is not needed. This enables a person to wear a mobile EEG monitor without looking too dorky—or at least without looking dorky all the time. In FIG. 136, moveable sensor arm 13604 is visually less-obtrusive in the second arm configuration because it is substantially hidden behind (interior to) the side portion of face-spanning support member 13601.

In this example, moveable sensor arm 13604 pivots and/or rotates around axle 13605 in order to change from the first arm configuration to the second arm configuration, or vice versa. In this example, axle 13605 is located between the person's ear and the front of the person's face. In this example, in the second arm configuration, moveable sensor arm 13604 spans from axle 13605 backward toward the person's ear. In another example, in the second arm configuration, moveable sensor arm 13604 can span from axle 13605 forward toward the person's face. In this example, moveable sensor arm 13604 is slightly arcuate. In another example, moveable sensor arm 13604 can be straight. In this example, moveable sensor arm 13604 is moved manually. In another example, moveable sensor arm 13604 can be moved automatically by an actuator.

FIG. 137 shows an example of how this invention can be embodied in a shape-transforming eyewear device for collecting data concerning electromagnetic brain activity comprising: a face-spanning support member which is configured to span an upper portion of a person's face; at least one optical member which transmits light from the person's environment and/or light from a virtual image display to at least one of the person's eyes; an electromagnetic energy sensor, wherein this electromagnetic energy sensor has a first sensor configuration wherein it is configured to be at a selected location relative to the surface of the person's head in order to collect data concerning electromagnetic brain activity and wherein this electromagnetic energy sensor has a second sensor configuration wherein it is not at this selected location; and a movable sensor arm which holds the electromagnetic energy sensor and is at least partially connected to the face-spanning support member, wherein this moveable sensor arm has a first arm configuration which holds the electromagnetic energy sensor in the first sensor configuration, wherein this moveable sensor arm has a second arm configuration which holds the electromagnetic energy sensor in the second sensor configuration, and wherein this moveable sensor arm is moved relative to the face-spanning support member in order to change from the first arm configuration to the second arm configuration, or vice versa.

The lower half of FIG. 137 shows this example at a time when moveable sensor arm 13704 is in the first arm configuration and electromagnetic energy sensor 13703 is in the first sensor configuration. In this first configuration, electromagnetic energy sensor 13703 is at a selected location from which it collects data concerning electromagnetic brain activity 13706. The upper half of FIG. 137 shows this example at different time, when moveable sensor arm 13704 is in the second arm configuration and electromagnetic energy sensor 13703 is in the second sensor configuration. In this second configuration, electromagnetic energy sensor 13703 is not at the selected location. In an example, the selected location from which an electromagnetic energy sensor collects data concerning electromagnetic brain activity can be selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In more detail, the embodiment shown in FIG. 137 comprises: face-spanning support member 13701, two optical members (including optical member 13702), electromagnetic energy sensor 13703, moveable sensor arm 13704, and connecting axle 13705. Connecting axle 13705 connects moveable sensor arm 13704 with face-spanning support member 13701. As discussed earlier, this embodiment can further comprise one or more components selected from the group consisting of: data processor, power source, data communication component, human-to-computer user interface, computer-to-human interface, digital memory, additional sensors, and a non-implantable electromagnetic energy emitter.

In this example, face-spanning support member 13701 is a single-piece member which spans from one ear to the other. In this example, face-spanning support member 13701 has two side portions (which each span from an ear to the front of the face) and a front portion (which spans the face from one side to the other). Although the far side portion is not shown [sorry, Gary] in the angled perspective of FIG. 137, the device in this example is assumed to be symmetric with respect to a central longitudinal (right-vs.-left) plane of the person's head. In this example, side portions are horizontally aligned with the person's eyes and the front portion is horizontally aligned with the person's eyebrows. In this example, the optical members (including 13702) are lenses. In this example, face-spanning support member 13701 and optical members (including 13702) together comprise a pair of electronically-functional eyeglasses. In this example, the selected location from which electromagnetic energy sensor 13703 collects data concerning electromagnetic brain activity 13706 is on the forehead.

As shown in FIG. 137, moveable sensor arm 13704 is visually less-obtrusive in the second arm configuration (shown in the upper half of the figure) than in the first arm configuration (shown in the lower half of the figure). Thus, this eyewear can collect data concerning electromagnetic brain activity 13706 using a more-obtrusive configuration at times when such data collection is needed, but can transform into a less-obtrusive configuration at times when such data collection is not needed. This enables a person to wear a mobile EEG monitor without looking too dorky—or at least without looking dorky all the time. In FIG. 137, moveable sensor arm 13704 is visually less-obtrusive in the second arm configuration because it is substantially hidden behind (interior to) the side portion of face-spanning support member 13701.

In this example, moveable sensor arm 13704 pivots and/or rotates around axle 13705 in order to change from the first arm configuration to the second arm configuration, or vice versa. In this example, axle 13705 is located near the front of a side portion of face-spanning support member 13701. In this example, in the second arm configuration, moveable sensor arm 13704 spans backward from axle 13705 toward the person's ear. In this example, moveable sensor arm 13704 is slightly arcuate. In another example, moveable sensor arm 13704 can be straight. In this example, moveable sensor arm 13704 is moved manually. In another example, moveable sensor arm 13704 can be moved automatically by an actuator.

FIG. 138 shows an example of how this invention can be embodied in a shape-transforming eyewear device for collecting data concerning electromagnetic brain activity comprising: a face-spanning support member which is configured to span an upper portion of a person's face; at least one optical member which transmits light from the person's environment and/or light from a virtual image display to at least one of the person's eyes; an electromagnetic energy sensor, wherein this electromagnetic energy sensor has a first sensor configuration wherein it is configured to be at a selected location relative to the surface of the person's head in order to collect data concerning electromagnetic brain activity and wherein this electromagnetic energy sensor has a second sensor configuration wherein it is not at this selected location; and a movable sensor arm which holds the electromagnetic energy sensor and is at least partially connected to the face-spanning support member, wherein this moveable sensor arm has a first arm configuration which holds the electromagnetic energy sensor in the first sensor configuration, wherein this moveable sensor arm has a second arm configuration which holds the electromagnetic energy sensor in the second sensor configuration, and wherein this moveable sensor arm is moved relative to the face-spanning support member in order to change from the first arm configuration to the second arm configuration, or vice versa.

The lower half of FIG. 138 shows this example at a time when moveable sensor arm 13804 is in the first arm configuration and electromagnetic energy sensor 13803 is in the first sensor configuration. In this first configuration, electromagnetic energy sensor 13803 is at a selected location from which it collects data concerning electromagnetic brain activity 13806. The upper half of FIG. 138 shows this example at different time, when moveable sensor arm 13804 is in the second arm configuration and electromagnetic energy sensor 13803 is in the second sensor configuration. In this second configuration, electromagnetic energy sensor 13803 is not at the selected location. In an example, the selected location from which an electromagnetic energy sensor collects data concerning electromagnetic brain activity can be selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In more detail, the embodiment shown in FIG. 138 comprises: face-spanning support member 13801, two optical members (including optical member 13802), electromagnetic energy sensor 13803, moveable sensor arm 13804, and connecting axle 13805. Connecting axle 13805 connects moveable sensor arm 13804 with face-spanning support member 13801. As discussed earlier, this embodiment can further comprise one or more components selected from the group consisting of: data processor, power source, data communication component, human-to-computer user interface, computer-to-human interface, digital memory, additional sensors, and a non-implantable electromagnetic energy emitter.

In this example, face-spanning support member 13801 is a single-piece member which spans from one ear to the other. In this example, face-spanning support member 13801 has two side portions (which each span from an ear to the front of the face) and a front portion (which spans the face from one side to the other). Although the far side portion is not shown [sorry, Gary] in the angled perspective of FIG. 138, the device in this example is assumed to be symmetric with respect to a central longitudinal (right-vs.-left) plane of the person's head. In this example, side portions are horizontally aligned with the person's eyes and the front portion is horizontally aligned with the person's eyebrows. In this example, the optical members (including 13802) are lenses. In this example, face-spanning support member 13801 and optical members (including 13802) together comprise a pair of electronically-functional eyeglasses. In this example, the selected location from which electromagnetic energy sensor 13803 collects data concerning electromagnetic brain activity 13806 is on a person's forehead.

As shown in FIG. 138, moveable sensor arm 13804 is visually less-obtrusive in the second arm configuration (shown in the upper half of the figure) than in the first arm configuration (shown in the lower half of the figure). Thus, this eyewear can collect data concerning electromagnetic brain activity 13806 using a more-obtrusive configuration at times when such data collection is needed, but can transform into a less-obtrusive configuration at times when such data collection is not needed. This enables a person to wear a mobile EEG monitor without looking too dorky—or at least without looking dorky all the time. In FIG. 138, moveable sensor arm 13804 is visually less-obtrusive in the second arm configuration because it is substantially hidden behind (interior to) the front portion of face-spanning support member 13801.

In this example, moveable sensor arm 13804 pivots and/or rotates around axle 13805 in order to change from the first arm configuration to the second arm configuration, or vice versa. In this example, axle 13805 is located near the middle of the front portion of face-spanning support member 13801. In this example, in the second arm configuration, moveable sensor arm 13804 spans sideways from axle 13805. In this example, moveable sensor arm 13804 is straight. In another example, moveable sensor arm 13804 can be arcuate. In this example, moveable sensor arm 13804 is moved manually. In another example, moveable sensor arm 13804 can be moved automatically by an actuator. In this example, there is one central moveable sensor arm and one central electromagnetic energy sensor. In another example, there can be two moveable sensor arms and two electromagnetic energy sensors, one on each side of the forehead and/or one above each of the two optical members.

FIG. 139 shows an example of how this invention can be embodied in a shape-transforming eyewear device for collecting data concerning electromagnetic brain activity comprising: a face-spanning support member which is configured to span an upper portion of a person's face; at least one optical member which transmits light from the person's environment and/or light from a virtual image display to at least one of the person's eyes; one or more electromagnetic energy sensors, wherein these electromagnetic energy sensors have a first sensor configuration wherein they are configured to be at a selected locations relative to the surface of the person's head in order to collect data concerning electromagnetic brain activity and wherein these electromagnetic energy sensors have a second sensor configuration wherein they are not at these selected locations; and a movable sensor arm which holds the electromagnetic energy sensors and is at least partially connected to the face-spanning support member, wherein this moveable sensor arm has a first arm configuration which holds the electromagnetic energy sensors in the first sensor configuration, wherein this moveable sensor arm has a second arm configuration which holds the electromagnetic energy sensors in the second sensor configuration, and wherein this moveable sensor arm is moved relative to the face-spanning support member in order to change from the first arm configuration to the second arm configuration, or vice versa.

The lower half of FIG. 139 shows this example at a time when moveable sensor arm 13905 is in the first arm configuration and electromagnetic energy sensors 13903 and 13904 are in the first sensor configuration. In this first configuration, electromagnetic energy sensors 13903 and 13904 are at selected locations from which they collect data concerning electromagnetic brain activity 13907 and 13908. The upper half of FIG. 139 shows this example at different time, when moveable sensor arm 13905 is in the second arm configuration and electromagnetic energy sensors 13903 and 13904 are in the second sensor configuration. In this second configuration, electromagnetic energy sensors 13903 and 13904 are not at these selected locations. In an example, the selected locations from which electromagnetic energy sensors collect data concerning electromagnetic brain activity can be selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In more detail, the embodiment shown in FIG. 139 comprises: face-spanning support member 13901, two optical members (including optical member 13902), electromagnetic energy sensors 13903 and 13904, moveable sensor arm 13905, and connecting axles (including 13906). Connecting axle 13906 connects moveable sensor arm 13905 with face-spanning support member 13901. As discussed earlier, this embodiment can further comprise one or more components selected from the group consisting of: data processor, power source, data communication component, human-to-computer user interface, computer-to-human interface, digital memory, additional sensors, and a non-implantable electromagnetic energy emitter.

In this example, face-spanning support member 13901 is a single-piece member which spans from one ear to the other. In this example, face-spanning support member 13901 has two side portions (which each span from an ear to the front of the face) and a front portion (which spans the face from one side to the other). Although the far side portion is not shown [sorry, Gary] in the angled perspective of FIG. 139, the device in this example is assumed to be symmetric with respect to a central longitudinal (right-vs.-left) plane of the person's head. In this example, side portions are horizontally aligned with the person's eyes and the front portion is horizontally aligned with the person's eyebrows in the second arm configuration. In this example, the two optical members (including 13902) are lenses. In this example, face-spanning support member 13901 and the two optical members (including 13902) together comprise a pair of electronically-functional eyeglasses. In this example, the selected locations from which electromagnetic energy sensors 13903 and 13904 collect data concerning electromagnetic brain activity 13907 and 13908 are on a person's forehead and/or temple. In an example, there can be a greater number of electromagnetic energy sensors on moveable sensor arm 13905.

As shown in FIG. 139, moveable sensor arm 13905 is visually less-obtrusive in the second arm configuration (shown in the upper half of the figure) than in the first arm configuration (shown in the lower half of the figure). Thus, this eyewear can collect data concerning electromagnetic brain activity 13907 and 13908 using a more-obtrusive configuration at times when such data collection is needed, but can transform into a less-obtrusive configuration at times when such data collection is not needed. This enables a person to wear a mobile EEG monitor without looking too dorky—or at least without looking dorky all the time. In FIG. 139, moveable sensor arm 13905 is visually less-obtrusive in the second arm configuration because it is substantially hidden behind, aligned with, and interior to face-spanning support member 13901.

In this example, in the second arm configuration (shown in the upper half of the figure) moveable sensor arm 13905 is substantially aligned with, hidden behind, and interior to face-spanning support member 13901. In this example, in the first arm configuration (shown in the lower half of the figure) moveable sensor arm 13905 is pivoted and/or rotated upwards to span the person's forehead. In this example, moveable sensor arm 13905 pivots and/or rotates around axle 13906 in order to change from the second arm configuration to the first arm configuration, or vice versa. In this example, axle 13906 is located near the person's ear. Although not shown, in this example a similar axle is assumed to be on the other side of the person's head due to assumed device symmetry. In this example, moveable sensor arm 13905 is moved manually. In another example, moveable sensor arm 13905 can be moved automatically by an actuator.

FIG. 140 shows an example of how this invention can be embodied in a shape-transforming eyewear device for collecting data concerning electromagnetic brain activity comprising: a face-spanning support member which is configured to span an upper portion of a person's face; at least one optical member which transmits light from the person's environment and/or light from a virtual image display to at least one of the person's eyes; one or more electromagnetic energy sensors, wherein these electromagnetic energy sensors have a first sensor configuration wherein they are configured to be at a selected locations relative to the surface of the person's head in order to collect data concerning electromagnetic brain activity and wherein these electromagnetic energy sensors have a second sensor configuration wherein they are not at these selected locations; and a movable sensor arm which holds the electromagnetic energy sensors and is at least partially connected to the face-spanning support member, wherein this moveable sensor arm has a first arm configuration which holds the electromagnetic energy sensors in the first sensor configuration, wherein this moveable sensor arm has a second arm configuration which holds the electromagnetic energy sensors in the second sensor configuration, and wherein this moveable sensor arm is moved relative to the face-spanning support member in order to change from the first arm configuration to the second arm configuration, or vice versa.

The lower half of FIG. 140 shows this example at a time when moveable sensor arm 14005 is in the first arm configuration and electromagnetic energy sensors 14003 and 14004 are in the first sensor configuration. In this first configuration, electromagnetic energy sensors 14003 and 14004 are at selected locations on the upper portion of a person's head from which they collect data concerning electromagnetic brain activity 14007 and 14008. The upper half of FIG. 140 shows this example at different time, when moveable sensor arm 14005 is in the second arm configuration and electromagnetic energy sensors 14003 and 14004 are in the second sensor configuration. In this second configuration, electromagnetic energy sensors 14003 and 14004 are not at these selected locations. In an example, the selected locations from which electromagnetic energy sensors collect data concerning electromagnetic brain activity can be selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In more detail, the embodiment shown in FIG. 140 comprises: face-spanning support member 14001, two optical members (including optical member 14002), electromagnetic energy sensors 14003 and 14004, moveable sensor arm 14005, and connecting axles (including 14006). Connecting axle 14006 connects moveable sensor arm 14005 with face-spanning support member 14001. As discussed earlier, this embodiment can further comprise one or more components selected from the group consisting of: data processor, power source, data communication component, human-to-computer user interface, computer-to-human interface, digital memory, additional sensors, and a non-implantable electromagnetic energy emitter.

In this example, face-spanning support member 14001 is a single-piece member which spans from one ear to the other. In this example, face-spanning support member 14001 has two side portions (which each span from an ear to the front of the face) and a front portion (which spans the face from one side to the other). Although the far side portion is not shown [sorry, Gary] in the angled perspective of FIG. 140, the device in this example is assumed to be symmetric with respect to a central longitudinal (right-vs.-left) plane of the person's head. In this example, side portions are horizontally aligned with the person's eyes and the front portion is horizontally aligned with the person's eyebrows in the second arm configuration. In this example, the two optical members (including 14002) are lenses. In this example, face-spanning support member 14001 and the two optical members (including 14002) together comprise a pair of electronically-functional eyeglasses. In this example, the selected locations from which electromagnetic energy sensors 14003 and 14004 collect data concerning electromagnetic brain activity 14007 and 14008 are on the upper portion of a person's head. In an example, there can be a greater number of electromagnetic energy sensors on moveable sensor arm 14005.

As shown in FIG. 140, moveable sensor arm 14005 is visually less-obtrusive in the second arm configuration (shown in the upper half of the figure) than in the first arm configuration (shown in the lower half of the figure). Thus, this eyewear can collect data concerning electromagnetic brain activity 14007 and 14008 using a more-obtrusive configuration at times when such data collection is needed, but can transform into a less-obtrusive configuration at times when such data collection is not needed. This enables a person to wear a mobile EEG monitor without looking too dorky—or at least without looking dorky all the time. In FIG. 140, moveable sensor arm 14005 is visually less-obtrusive in the second arm configuration because it is substantially hidden behind, aligned with, and interior to face-spanning support member 14001.

In this example, in the second arm configuration (shown in the upper half of the figure) moveable sensor arm 14005 is substantially aligned with, hidden behind, and interior to face-spanning support member 14001. In this example, in the first arm configuration (shown in the lower half of the figure) moveable sensor arm 14005 is pivoted and/or rotated upwards to span an upper portion of a person's head. In this example, moveable sensor arm 14005 pivots and/or rotates around axle 14006 in order to change from the second arm configuration to the first arm configuration, or vice versa. In this example, axle 14006 is located near the person's ear.

Although not shown, in this example a similar axle is assumed to be on the other side of the person's head due to assumed device symmetry. In this example, moveable sensor arm 14005 is moved manually. In another example, moveable sensor arm 14005 can be moved automatically by an actuator.

FIG. 141 shows an example of how this invention can be embodied in a shape-transforming eyewear device for collecting data concerning electromagnetic brain activity comprising: a face-spanning support member which is configured to span an upper portion of a person's face; at least one optical member which transmits light from the person's environment and/or light from a virtual image display to at least one of the person's eyes; one or more electromagnetic energy sensors, wherein these electromagnetic energy sensors have a first sensor configuration wherein they are configured to be at a selected locations relative to the surface of the person's head in order to collect data concerning electromagnetic brain activity and wherein these electromagnetic energy sensors have a second sensor configuration wherein they are not at these selected locations; and a movable sensor arm which holds the electromagnetic energy sensors and is at least partially connected to the face-spanning support member, wherein this moveable sensor arm has a first arm configuration which holds the electromagnetic energy sensors in the first sensor configuration, wherein this moveable sensor arm has a second arm configuration which holds the electromagnetic energy sensors in the second sensor configuration, and wherein this moveable sensor arm is moved relative to the face-spanning support member in order to change from the first arm configuration to the second arm configuration, or vice versa.

The lower half of FIG. 141 shows this example at a time when moveable sensor arm 14104 is in the first arm configuration and electromagnetic energy sensor 14103 is in the first sensor configuration. In this first configuration, electromagnetic energy sensor 14103 is at a selected location on a person's forehead and/or temple from which it collects data concerning electromagnetic brain activity 14107. The upper half of FIG. 141 shows this example at different time, when moveable sensor arm 14104 is in the second arm configuration and electromagnetic energy sensor 14103 is in the second sensor configuration. In this second configuration, electromagnetic energy sensor 14103 is not at this selected location. In an example, the selected location from which an electromagnetic energy sensor collects data concerning electromagnetic brain activity can be selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In more detail, the embodiment shown in FIG. 141 comprises: face-spanning support member 14101, two optical members (including optical member 14102), electromagnetic energy sensor 14103, moveable sensor arm 14104, and connectors 14105 and 14106. Connectors 14105 and 14106 connect moveable sensor arm 14104 with face-spanning support member 14101. As discussed earlier, this embodiment can further comprise one or more components selected from the group consisting of: data processor, power source, data communication component, human-to-computer user interface, computer-to-human interface, digital memory, additional sensors, and a non-implantable electromagnetic energy emitter.

In this example, face-spanning support member 14101 is a single-piece member which spans from one ear to the other. In this example, face-spanning support member 14101 has two side portions (which each span from an ear to the front of the face) and a front portion (which spans the face from one side to the other). Although the far side portion is not shown [sorry, Gary] in the angled perspective of FIG. 141, the device in this example is assumed to be symmetric with respect to a central longitudinal (right-vs.-left) plane of the person's head. In this example, side portions are horizontally aligned with the person's eyes and the front portion is horizontally aligned with the person's eyebrows in the second arm configuration. In this example, the two optical members (including 14102) are lenses. In this example, face-spanning support member 14101 and the two optical members (including 14102) together comprise a pair of electronically-functional eyeglasses. In this example, the selected location from which electromagnetic energy sensor 14103 collects data concerning electromagnetic brain activity 14107 is on a person's forehead and/or temple.

As shown in FIG. 141, moveable sensor arm 14104 is visually less-obtrusive in the second arm configuration (shown in the upper half of the figure) than in the first arm configuration (shown in the lower half of the figure). Thus, this eyewear can collect data concerning electromagnetic brain activity 14107 using a more-obtrusive configuration at times when such data collection is needed, but can transform into a less-obtrusive configuration at times when such data collection is not needed. This enables a person to wear a mobile EEG monitor without looking too dorky—or at least without looking dorky all the time. In FIG. 141, moveable sensor arm 14104 is visually less-obtrusive in the second arm configuration because it is substantially hidden behind, aligned with, and interior to face-spanning support member 14101.

In this example, in the second arm configuration (shown in the upper half of the figure) moveable sensor arm 14104 is substantially aligned with, hidden behind, and interior to face-spanning support member 14101. In this example, moveable sensor arm 14104 is bent, flexed, and/or folded upwards from face-spanning support member 14101 when the distance between connectors 14105 and 14106 is decreased. In this example, the distance between connectors 14105 and 14106 is decreased when connector 14106 is moved toward connector 14105. In an example, this movement can be along a track and/or channel in face-spanning support member 14101. In another example, connector 14105 can be moved toward connector 14106. In another example, both connectors 14105 and 14106 can be moved toward each other. In this example, when moveable sensor arm 14104 is bent, flexed, and/or folded upwards into the first arm configuration, it moves electromagnetic energy sensor 14103 to a selected location on the person's temple and/or forehead from which this sensor collects data concerning electromagnetic brain activity 14107.

In this example, connector 14105 is located near the front end of a side portion of face-spanning support member 14101. In this example, connector 14106 is located near the rear end of a side portion of face-spanning support member 14101 in the second arm configuration and near the middle of the side portion of face-spanning support member 14101 is the first arm configuration. In an example, the device can be symmetric and there can be a similar moveable sensor arm and similar connectors on the other side of the person's head which are not shown from this perspective. In an example, the device can be asymmetric and there can be only one moveable sensor arm on only one side of the person's head. In this example, moveable sensor arm 14104 is moved manually. In another example, moveable sensor arm 14104 can be moved automatically by an actuator.

FIG. 142 shows an example of how this invention can be embodied in a shape-transforming eyewear device for collecting data concerning electromagnetic brain activity comprising: a face-spanning support member which is configured to span an upper portion of a person's face; at least one optical member which transmits light from the person's environment and/or light from a virtual image display to at least one of the person's eyes; one or more electromagnetic energy sensors, wherein these electromagnetic energy sensors have a first sensor configuration wherein they are configured to be at a selected locations relative to the surface of the person's head in order to collect data concerning electromagnetic brain activity and wherein these electromagnetic energy sensors have a second sensor configuration wherein they are not at these selected locations; and a movable sensor arm which holds the electromagnetic energy sensors and is at least partially connected to the face-spanning support member, wherein this moveable sensor arm has a first arm configuration which holds the electromagnetic energy sensors in the first sensor configuration, wherein this moveable sensor arm has a second arm configuration which holds the electromagnetic energy sensors in the second sensor configuration, and wherein this moveable sensor arm is moved relative to the face-spanning support member in order to change from the first arm configuration to the second arm configuration, or vice versa.

The lower half of FIG. 142 shows this example at a time when moveable sensor arm 14204 is in the first arm configuration and electromagnetic energy sensor 14203 is in the first sensor configuration. In this first configuration, electromagnetic energy sensor 14203 is at a selected location on a person's forehead from which it collects data concerning electromagnetic brain activity 14207. In an example, this selected location can be a body surface location which is proximal to the person's pineal gland; in an example, this device can be useful for an astro teller. The upper half of FIG. 142 shows this example at different time, when moveable sensor arm 14204 is in the second arm configuration and electromagnetic energy sensor 14203 is in the second sensor configuration. In this second configuration, electromagnetic energy sensor 14203 is not at the selected location. In an example, the selected location from which an electromagnetic energy sensor collects data concerning electromagnetic brain activity can be selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In more detail, the embodiment shown in FIG. 142 comprises: face-spanning support member 14201, two optical members (including optical member 14202), electromagnetic energy sensor 14203, moveable sensor arm 14204, and connectors 14205 and 14206. Connectors 14205 and 14206 connect moveable sensor arm 14204 to face-spanning support member 14201. As discussed earlier, this embodiment can further comprise one or more components selected from the group consisting of: data processor, power source, data communication component, human-to-computer user interface, computer-to-human interface, digital memory, additional sensors, and a non-implantable electromagnetic energy emitter.

In this example, face-spanning support member 14201 is a single-piece member which spans from one ear to the other. In this example, face-spanning support member 14201 has two side portions (which each span from an ear to the front of the face) and a front portion (which spans the face from one side to the other). Although the far side portion is not shown in the angled perspective of FIG. 142, the device in this example is assumed to be symmetric with respect to a central longitudinal (right-vs.-left) plane of the person's head. In this example, side portions are horizontally aligned with the person's eyes and the front portion is horizontally aligned with the person's eyebrows in the second arm configuration. In this example, the two optical members (including 14202) are lenses. In this example, face-spanning support member 14201 and the two optical members (including 14202) together comprise a pair of electronically-functional eyeglasses. In this example, the selected location from which electromagnetic energy sensor 14203 collects data concerning electromagnetic brain activity 14207 is on a person's forehead.

As shown in FIG. 142, moveable sensor arm 14204 is visually less-obtrusive in the second arm configuration (shown in the upper half of the figure) than in the first arm configuration (shown in the lower half of the figure). Thus, this eyewear can collect data concerning electromagnetic brain activity 14207 using a more-obtrusive configuration at times when such data collection is needed, but can transform into a less-obtrusive configuration at times when such data collection is not needed. This enables a person to wear a mobile EEG monitor without looking too dorky—or at least without looking dorky all the time. In FIG. 142, moveable sensor arm 14204 is visually less-obtrusive in the second arm configuration because it is substantially hidden behind, aligned with, and interior to face-spanning support member 14201.

In this example, in the second arm configuration (shown in the upper half of the figure) moveable sensor arm 14204 is substantially aligned with, hidden behind, and interior to face-spanning support member 14201. In this example, moveable sensor arm 14204 is bent, flexed, and/or folded upwards from face-spanning support member 14201 when the distance between connectors 14205 and 14206 is decreased. In this example, the distance between connectors 14205 and 14206 is decreased when connectors 14205 and 14206 are moved toward each other. In an example, this movement can be along a track and/or channel in face-spanning support member 14201. In other examples, only connector 14205 can be moved toward connector 14206 or only connector 14206 can be moved toward connector 14205. In this example, when moveable sensor arm 14204 is bent, flexed, and/or folded upwards into the first arm configuration, it moves electromagnetic energy sensor 14203 to a selected location on the person's forehead from which this sensor collects data concerning electromagnetic brain activity 14207.

In this example, connectors 14205 and 14206 are located along the front portion of face-spanning support member 14201. In this example, there is one central moveable sensor arm and one central electromagnetic energy sensor. In another example, there can be two moveable sensor arms and two electromagnetic energy sensors, one on each side of the forehead and/or one above each of the two optical members. In this example, moveable sensor arm 14204 is moved manually. In another example, moveable sensor arm 14204 can be moved automatically by an actuator.

FIG. 143 shows an example of how this invention can be embodied in a shape-transforming eyewear device for collecting data concerning electromagnetic brain activity comprising: a face-spanning support member which is configured to span an upper portion of a person's face; at least one optical member which transmits light from the person's environment and/or light from a virtual image display to at least one of the person's eyes; one or more electromagnetic energy sensors, wherein these electromagnetic energy sensors have a first sensor configuration wherein they are configured to be at a selected locations relative to the surface of the person's head in order to collect data concerning electromagnetic brain activity and wherein these electromagnetic energy sensors have a second sensor configuration wherein they are not at these selected locations; and a movable sensor arm which holds the electromagnetic energy sensors and is at least partially connected to the face-spanning support member, wherein this moveable sensor arm has a first arm configuration which holds the electromagnetic energy sensors in the first sensor configuration, wherein this moveable sensor arm has a second arm configuration which holds the electromagnetic energy sensors in the second sensor configuration, and wherein this moveable sensor arm is moved relative to the face-spanning support member in order to change from the first arm configuration to the second arm configuration, or vice versa.

The lower half of FIG. 143 shows this example at a time when moveable sensor arm 14304 is in the first arm configuration and electromagnetic energy sensor 14303 is in the first sensor configuration. In this first configuration, electromagnetic energy sensor 14303 is at a selected location on a person's forehead from which it collects data concerning electromagnetic brain activity 14305. The upper half of FIG. 143 shows this example at different time, when moveable sensor arm 14304 is in the second arm configuration and electromagnetic energy sensor 14303 is in the second sensor configuration. In this second configuration, electromagnetic energy sensor 14303 is not at the selected location. In an example, the selected location from which an electromagnetic energy sensor collects data concerning electromagnetic brain activity can be selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In more detail, the embodiment shown in FIG. 143 comprises: face-spanning support member 14301, two optical members (including optical member 14302), electromagnetic energy sensor 14303, and moveable sensor arm 14304. As discussed earlier, this embodiment can further comprise one or more components selected from the group consisting of: data processor, power source, data communication component, human-to-computer user interface, computer-to-human interface, digital memory, additional sensors, and a non-implantable electromagnetic energy emitter.

In this example, face-spanning support member 14301 is a single-piece member which spans the circumference of a person's head in a substantially-horizontal manner. In an example, face-spanning support member 14301 can have a longitudinal axis which encircles a person's head in a substantially-horizontal manner. In an example, when a person is standing up, a plane formed by this longitudinal axis can intersect a horizontal plane at an angle which is less than 45 degrees. In this example, face-spanning support member 14301 spans a person's face at a horizontal level which is substantially aligned with the person's eyebrows. In another example, face-spanning support member 14301 can span a person's face across the person's forehead. In this example, face-spanning support member 14301 spans the sides of the person's head at levels which are proximal to the upper portions of the person's ears.

In another example, a face-spanning support member can be a single-piece member which spans a portion of the circumference of a person's head. In an example, a face-spanning support member can span from one ear to the other ear in a substantially-horizontal manner. In an example, face-spanning support member can have a longitudinal axis which spans a portion of a person's head in a substantially-horizontal manner. In an example, when a person is standing up, a plane formed by this longitudinal axis can intersect a horizontal plane at an angle which is less than 45 degrees. In this example, face-spanning support member can span a person's face at a horizontal level which is substantially aligned with the person's eyebrows. In another example, a face-spanning support member can span a person's face across the person's forehead. In this example, a face-spanning support member can span the sides of a person's head at levels which are proximal to the upper portions of the person's ears.

In this example, two optical members (including 14302) are lenses. In this example, face-spanning support member 14301 and the two optical members (including 14302) together comprise a pair of electronically-functional eyeglasses. In this example, the selected location from which electromagnetic energy sensor 14303 collects data concerning electromagnetic brain activity 14305 is on a person's forehead.

In this example, moveable sensor arm 14304 can be moved along the longitudinal axis of face-spanning support member 14301 from a first arm configuration to a second arm configuration, and vice versa. In an example, moveable sensor arm 14304 can slide along a track and/or channel on face-spanning support member 14301. In this example, moveable sensor arm 14304 is located on a person's forehead in the first arm configuration (shown in the lower half of the figure) and is located on the side or back of the person's head in the second arm configuration (shown in the upper half of the figure). In this example, there is one moveable sensor arm and one central electromagnetic energy sensor. In another example, there can be a plurality of moveable sensor arms and electromagnetic energy sensors. In this example, moveable sensor arm 14304 is moved manually. In another example, moveable sensor arm 14304 can be moved automatically by an actuator.

As shown in FIG. 143, moveable sensor arm 14304 is visually less-obtrusive (from a frontal perspective) in the second arm configuration (shown in the upper half of the figure) than in the first arm configuration (shown in the lower half of the figure). Thus, this eyewear can collect data concerning electromagnetic brain activity 14305 using a more-obtrusive configuration at times when such data collection is needed, but can transform into a less-obtrusive configuration at times when such data collection is not needed. This enables a person to wear a mobile EEG monitor without looking too dorky—or at least without looking dorky all the time. In FIG. 143, moveable sensor arm 14304 is visually less-obtrusive in the second arm configuration because it is less visible from the perspective of someone facing the person.

FIG. 144 shows an example of how this invention can be embodied in a shape-transforming eyewear device for collecting data concerning electromagnetic brain activity comprising: a face-spanning support member which is configured to span an upper portion of a person's face; at least one optical member which transmits light from the person's environment and/or light from a virtual image display to at least one of the person's eyes; one or more electromagnetic energy sensors, wherein these electromagnetic energy sensors have a first sensor configuration wherein they are configured to be at a selected locations relative to the surface of the person's head in order to collect data concerning electromagnetic brain activity and wherein these electromagnetic energy sensors have a second sensor configuration wherein they are not at these selected locations; and a movable sensor arm which holds the electromagnetic energy sensors and is at least partially connected to the face-spanning support member, wherein this moveable sensor arm has a first arm configuration which holds the electromagnetic energy sensors in the first sensor configuration, wherein this moveable sensor arm has a second arm configuration which holds the electromagnetic energy sensors in the second sensor configuration, and wherein this moveable sensor arm is moved relative to the face-spanning support member in order to change from the first arm configuration to the second arm configuration, or vice versa.

The lower half of FIG. 144 shows this example at a time when moveable sensor arm 14405 is in the first arm configuration and electromagnetic energy sensors 14403 and 14404 are in the first sensor configuration. In this first configuration, electromagnetic energy sensors 14403 and 14404 are at selected locations on a person's head from which they collect data concerning electromagnetic brain activity 14407 and 14408. The upper half of FIG. 144 shows this example at different time, when moveable sensor arm 14405 is in the second arm configuration and electromagnetic energy sensors 14403 and 14404 are in the second sensor configuration. In this second configuration, electromagnetic energy sensors 14403 and 14404 are not at these selected locations.

In more detail, the embodiment shown in FIG. 144 comprises: face-spanning support member 14401, two optical members (including optical member 14402), electromagnetic energy sensors 14403 and 14404, moveable sensor arm 14405, and connecting axles (including 14406). Connecting axle 14406 connects moveable sensor arm 14405 with face-spanning support member 14401. As discussed earlier, this embodiment can further comprise one or more components selected from the group consisting of: data processor, power source, data communication component, human-to-computer user interface, computer-to-human interface, digital memory, additional sensors, and a non-implantable electromagnetic energy emitter.

In this example, face-spanning support member 14401 is a single-piece member which spans the circumference of a person's head in a substantially-horizontal manner. In an example, face-spanning support member 14401 can have a longitudinal axis which encircles a person's head in a substantially-horizontal manner. In an example, when a person is standing up, a plane formed by this longitudinal axis can intersect a horizontal plane at an angle which is less than 45 degrees. In this example, face-spanning support member 14401 spans a person's face at a horizontal level which is substantially aligned with the person's eyebrows. In another example, face-spanning support member 14401 can span a person's face across the person's forehead. In this example, face-spanning support member 14401 spans the sides of the person's head at levels which are proximal to the upper portions of the person's ears.

In another example, a face-spanning support member can be a single-piece member which spans a portion of the circumference of a person's head. In an example, a face-spanning support member can span from one ear to the other ear in a substantially-horizontal manner. In an example, face-spanning support member can have a longitudinal axis which spans a portion of a person's head in a substantially-horizontal manner. In an example, when a person is standing up, a plane formed by this longitudinal axis can intersect a horizontal plane at an angle which is less than 45 degrees. In this example, face-spanning support member can span a person's face at a horizontal level which is substantially aligned with the person's eyebrows. In another example, a face-spanning support member can span a person's face across the person's forehead. In this example, a face-spanning support member can span the sides of a person's head at levels which are proximal to the upper portions of the person's ears.

In this example, two optical members (including 14402) are lenses. In this example, face-spanning support member 14401 and the two optical members (including 14402) together comprise a pair of electronically-functional eyeglasses. In this example, the selected locations from which electromagnetic energy sensors 14403 and 14404 collect data concerning electromagnetic brain activity 14407 and 14408 are on the sides and back of a person's head. In an example, the selected locations from which electromagnetic energy sensors 14403 and 14404 collect data concerning electromagnetic brain activity can be selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In this example, moveable sensor arm 14405 pivots and/or rotates around axle 14406 in order to change from the second arm configuration to the first arm configuration, or vice versa. Although not shown, in this example a similar axle is assumed to be on the other side of the person's head due to assumed device symmetry. In this example, moveable sensor arm 14405 is moved manually. In another example, moveable sensor arm 14405 can be moved automatically by an actuator.

In this example, in the second arm configuration (shown in the upper half of the figure) moveable sensor arm 14405 is substantially aligned with, hidden behind, and interior to face-spanning support member 14401. In this example, moveable sensor arm 14405 is attached the face-spanning support member 14401 via axle 14406 which is located near the side of the person's face. In this example, moveable sensor arm 14405 spans backward from axle 14406 to loop around the back of the person's head. In this example, in the first arm configuration (shown in the lower half of the figure) the rear portion of moveable sensor arm 14405 has been pivoted and/or rotated upwards to loop around the back of the person's head at a higher level. In an example, electromagnetic energy sensors 14403 and 14404 can measure electromagnetic brain activity 14407 and 14408 better from this higher level.

As shown in FIG. 144, moveable sensor arm 14405 is visually less-obtrusive in the second arm configuration (shown in the upper half of the figure) than in the first arm configuration (shown in the lower half of the figure). Thus, this eyewear can collect data concerning electromagnetic brain activity 14407 and 14408 using a more-obtrusive configuration at times when such data collection is needed, but can transform into a less-obtrusive configuration at times when such data collection is not needed. This enables a person to wear a mobile EEG monitor without looking too dorky—or at least without looking dorky all the time.

FIG. 145 shows an example of how this invention can be embodied in a shape-transforming eyewear device for collecting data concerning electromagnetic brain activity comprising: a face-spanning support member which is configured to span an upper portion of a person's face; at least one optical member which transmits light from the person's environment and/or light from a virtual image display to at least one of the person's eyes; one or more electromagnetic energy sensors, wherein these electromagnetic energy sensors have a first sensor configuration wherein they are configured to be at a selected locations relative to the surface of the person's head in order to collect data concerning electromagnetic brain activity and wherein these electromagnetic energy sensors have a second sensor configuration wherein they are not at these selected locations; and a movable sensor arm which holds the electromagnetic energy sensors and is at least partially connected to the face-spanning support member, wherein this moveable sensor arm has a first arm configuration which holds the electromagnetic energy sensors in the first sensor configuration, wherein this moveable sensor arm has a second arm configuration which holds the electromagnetic energy sensors in the second sensor configuration, and wherein this moveable sensor arm is moved relative to the face-spanning support member in order to change from the first arm configuration to the second arm configuration, or vice versa.

The lower half of FIG. 145 shows this example at a time when moveable sensor arm 14504 is in the first arm configuration and electromagnetic energy sensor 14503 is in the first sensor configuration. In this first configuration, electromagnetic energy sensor 14503 is at a selected location on a person's forehead and/or temple from which it collects data concerning electromagnetic brain activity 14507. The upper half of FIG. 145 shows this example at different time, when moveable sensor arm 14504 is in the second arm configuration and electromagnetic energy sensor 14503 is in the second sensor configuration. In this second configuration, electromagnetic energy sensor 14503 is not at the selected location.

In more detail, the embodiment shown in FIG. 145 comprises: face-spanning support member 14501, two optical members (including optical member 14502), electromagnetic energy sensor 14503, an first portion of moveable sensor arm 14504, a second portion of moveable sensor arm 14505, and connecting axle 14506. Connecting axle 14506 connects the moveable sensor arm (14504 and 14505) to face-spanning support member 14501. As discussed earlier, this embodiment can further comprise one or more components selected from the group consisting of: data processor, power source, data communication component, human-to-computer user interface, computer-to-human interface, digital memory, additional sensors, and a non-implantable electromagnetic energy emitter.

In this example, face-spanning support member 14501 is a single-piece member which spans the circumference of a person's head in a substantially-horizontal manner. In an example, face-spanning support member 14501 can have a longitudinal axis which encircles a person's head in a substantially-horizontal manner. In an example, when a person is standing up, a plane formed by this longitudinal axis can intersect a horizontal plane at an angle which is less than 45 degrees. In this example, face-spanning support member 14501 spans a person's face at a horizontal level which is substantially aligned with the person's eyebrows. In another example, face-spanning support member 14501 can span a person's face across the person's forehead. In this example, face-spanning support member 14501 spans the sides of the person's head at levels which are proximal to the upper portions of the person's ears.

In another example, a face-spanning support member can be a single-piece member which spans a portion of the circumference of a person's head. In an example, a face-spanning support member can span from one ear to the other ear in a substantially-horizontal manner. In an example, face-spanning support member can have a longitudinal axis which spans a portion of a person's head in a substantially-horizontal manner. In an example, when a person is standing up, a plane formed by this longitudinal axis can intersect a horizontal plane at an angle which is less than 45 degrees. In an example, a face-spanning support member can span a person's face at a horizontal level which is substantially aligned with the person's eyebrows. In another example, a face-spanning support member can span a person's face across the person's forehead. In this example, a face-spanning support member can span the sides of a person's head at levels which are proximal to the upper portions of the person's ears.

In this example, two optical members (including 14502) are lenses. In this example, face-spanning support member 14501 and the two optical members (including 14502) together comprise a pair of electronically-functional eyeglasses. In this example, the selected location from which electromagnetic energy sensor 14503 collects data concerning electromagnetic brain activity 14507 is on a person's temple and/or forehead. In an example, the selected locations from which electromagnetic energy sensor 14503 collects data concerning electromagnetic brain activity can be selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In this example, the moveable sensor arm (14504 and 14505) rotates around axle 14506 in order to change from the second arm configuration to the first arm configuration, or vice versa. Although not shown from this perspective, in this example there can be a similar moveable arm on the other side of the person's head. In this example, the moveable sensor arm (14504 and 14505) is moved manually. In another example, the moveable sensor arm can be moved automatically by an actuator.

In this example, in the second arm configuration (shown in the upper half of the figure) the moveable sensor arm (14504 and 14505) is substantially aligned with (and partially hidden behind) face-spanning support member 14501. In this example, the moveable sensor arm (14504 and 14505) is attached to face-spanning support member 14501 via axle 14506 which is located on the side of the person's face. In this example, in the second arm configuration, the first part 14504 of the moveable sensor arm spans forward from axle 14506 (on the interior side of face-spanning support member 14501) and the second part 14505 of the moveable sensor arm spans backward from axle 14506 (on the exterior side of face-spanning support member 14501). In this example, in the first arm configuration (shown in the lower half of the figure) the forward spanning portion has been pivoted and/or rotated upwards to bring electromagnetic energy sensor 14503 into contact with the person's temple and/or forehead.

As shown in FIG. 145, the moveable sensor arm (14504 and 14505) is visually less-obtrusive in the second arm configuration (shown in the upper half of the figure) than in the first arm configuration (shown in the lower half of the figure). Thus, this eyewear can collect data concerning electromagnetic brain activity 14507 using a more-obtrusive configuration at times when such data collection is needed, but can transform into a less-obtrusive configuration at times when such data collection is not needed. This enables a person to wear a mobile EEG monitor without looking too dorky—or at least without looking dorky all the time.

FIG. 146 shows an example of how this invention can be embodied in a shape-transforming eyewear device for collecting data concerning electromagnetic brain activity comprising: a face-spanning support member which is configured to span an upper portion of a person's face; at least one optical member which transmits light from the person's environment and/or light from a virtual image display to at least one of the person's eyes; one or more electromagnetic energy sensors, wherein these electromagnetic energy sensors have a first sensor configuration wherein they are configured to be at a selected locations relative to the surface of the person's head in order to collect data concerning electromagnetic brain activity and wherein these electromagnetic energy sensors have a second sensor configuration wherein they are not at these selected locations; and a movable sensor arm which holds the electromagnetic energy sensors and is at least partially connected to the face-spanning support member, wherein this moveable sensor arm has a first arm configuration which holds the electromagnetic energy sensors in the first sensor configuration, wherein this moveable sensor arm has a second arm configuration which holds the electromagnetic energy sensors in the second sensor configuration, and wherein this moveable sensor arm is moved relative to the face-spanning support member in order to change from the first arm configuration to the second arm configuration, or vice versa.

The lower half of FIG. 146 shows this example at a time when moveable sensor arm 14604 is in the first arm configuration and electromagnetic energy sensor 14603 is in the first sensor configuration. In this first configuration, electromagnetic energy sensor 14603 is at a selected location on a person's forehead from which it collects data concerning electromagnetic brain activity 14606. The upper half of FIG. 146 shows this example at different time, when moveable sensor arm 14604 is in the second arm configuration and electromagnetic energy sensor 14603 is in the second sensor configuration. In this second configuration, electromagnetic energy sensor 14603 is not at the selected location.

In more detail, the embodiment shown in FIG. 146 comprises: face-spanning support member 14601, two optical members (including optical member 14602), electromagnetic energy sensor 14603, moveable sensor arm 14604, and connecting axles (including 14605). Connecting axle 14605 connects moveable sensor arm 14604 to face-spanning support member 14601. As discussed earlier, this embodiment can further comprise one or more components selected from the group consisting of: data processor, power source, data communication component, human-to-computer user interface, computer-to-human interface, digital memory, additional sensors, and a non-implantable electromagnetic energy emitter.

In this example, face-spanning support member 14601 is a single-piece member which spans a portion of the circumference of a person's head. In this example, face-spanning support member 14601 spans from one ear to the other ear in a substantially-horizontal manner. In this example, face-spanning support member 14601 has a longitudinal axis which spans a portion of a person's head in a substantially-horizontal manner. In an example, when a person is standing up, a plane formed by this longitudinal axis intersects a horizontal plane at an angle which is less than 45 degrees. In this example, face-spanning support member 14601 spans a person's face at a horizontal level which is substantially aligned with the person's eyebrows. In another example, a face-spanning support member can span a person's face across the person's forehead. In this example, face-spanning support member 14601 spans the sides of a person's head at levels which are proximal to the upper portions of the person's ears.

In this example, two optical members (including 14602) are lenses. In this example, face-spanning support member 14601 and the two optical members (including 14602) together comprise a pair of electronically-functional eyeglasses. In this example, the selected location from which electromagnetic energy sensor 14603 collects data concerning electromagnetic brain activity can be selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In this example, moveable sensor arm 14604 pivots and/or rotates around axle 14605 in order to change from the second arm configuration to the first arm configuration, or vice versa. Although not shown, in this example a similar axle is assumed to be on the other side of the person's head due to assumed device symmetry. In this example, moveable sensor arm 14604 is moved manually. In another example, moveable sensor arm 14604 can be moved automatically by an actuator.

In this example, in the second arm configuration (shown in the upper half of the figure) moveable sensor arm 14604 spans backwards from axle 14605 and loops around the back of the person's head (in a manner which is relatively unobtrusive from the perspective of someone facing the person). In this example, moveable sensor arm 14604 is attached to face-spanning support member 14601 via axle 14605 which is located near the person's ear. In this example, in the first arm configuration (shown in the lower half of the figure) moveable sensor arm 14604 has been pivoted and/or rotated over the top of the person's head in order to bring electromagnetic energy sensor 14603 into contact with the person's forehead. In an example, there can be multiple electromagnetic energy sensors on moveable sensor arm 14604.

As shown in FIG. 146, moveable sensor arm 14604 is visually less-obtrusive (from a frontal perspective) in the second arm configuration (shown in the upper half of the figure) than in the first arm configuration (shown in the lower half of the figure). Thus, this eyewear can collect data concerning electromagnetic brain activity 14606 using a more-obtrusive configuration at times when such data collection is needed, but can transform into a less-obtrusive configuration at times when such data collection is not needed. This enables a person to wear a mobile EEG monitor without looking too dorky—or at least without looking dorky all the time.

FIG. 147 shows an example of how this invention can be embodied in a shape-transforming eyewear device for collecting data concerning electromagnetic brain activity comprising: a face-spanning support member which is configured to span an upper portion of a person's face; at least one optical member which transmits light from the person's environment and/or light from a virtual image display to at least one of the person's eyes; one or more electromagnetic energy sensors, wherein these electromagnetic energy sensors have a first sensor configuration wherein they are configured to be at a selected locations relative to the surface of the person's head in order to collect data concerning electromagnetic brain activity and wherein these electromagnetic energy sensors have a second sensor configuration wherein they are not at these selected locations; and a movable sensor arm which holds the electromagnetic energy sensors and is at least partially connected to the face-spanning support member, wherein this moveable sensor arm has a first arm configuration which holds the electromagnetic energy sensors in the first sensor configuration, wherein this moveable sensor arm has a second arm configuration which holds the electromagnetic energy sensors in the second sensor configuration, and wherein this moveable sensor arm is moved relative to the face-spanning support member in order to change from the first arm configuration to the second arm configuration, or vice versa.

The lower half of FIG. 147 shows this example at a time when moveable sensor arm 14704 is in the first arm configuration and electromagnetic energy sensor 14703 is in the first sensor configuration. In this first configuration, electromagnetic energy sensor 14703 is at a selected location on a person's forehead from which it collects data concerning electromagnetic brain activity 14706. The upper half of FIG. 147 shows this example at different time, when moveable sensor arm 14704 is in the second arm configuration and electromagnetic energy sensor 14703 is in the second sensor configuration. In this second configuration, electromagnetic energy sensor 14703 is not at the selected location.

In more detail, the embodiment shown in FIG. 147 comprises: face-spanning support member 14701, two optical members (including optical member 14702), electromagnetic energy sensor 14703, moveable sensor arm 14704, and connecting axles (including 14705). Connecting axle 14705 connects moveable sensor arm 14704 to face-spanning support member 14701. As discussed earlier, this embodiment can further comprise one or more components selected from the group consisting of: data processor, power source, data communication component, human-to-computer user interface, computer-to-human interface, digital memory, additional sensors, and a non-implantable electromagnetic energy emitter.

In this example, face-spanning support member 14701 is a single-piece member which spans a portion of the circumference of a person's head. In this example, face-spanning support member 14701 spans from one ear to the other ear in a substantially-horizontal manner. In this example, face-spanning support member 14701 has a longitudinal axis which spans a portion of a person's head in a substantially-horizontal manner. In an example, when a person is standing up, a plane formed by this longitudinal axis intersects a horizontal plane at an angle which is less than 45 degrees. In this example, face-spanning support member 14701 spans a person's face at a horizontal level which is substantially aligned with the person's eyebrows. In another example, a face-spanning support member can span a person's face across the person's forehead. In this example, face-spanning support member 14701 spans the sides of a person's head at levels which are proximal to the upper portions of the person's ears.

In this example, two optical members (including 14702) are lenses. In this example, face-spanning support member 14701 and the two optical members (including 14702)

together comprise a pair of electronically-functional eyeglasses. In this example, the selected location from which electromagnetic energy sensor 14703 collects data concerning electromagnetic brain activity can be selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In this example, moveable sensor arm 14704 rotates and/or pivots around axle 14705 in order to change from the second arm configuration to the first arm configuration, or vice versa. Although not shown, in this example a similar axle is assumed to be on the other side of the person's head due to assumed device symmetry. In this example, moveable sensor arm 14704 is moved manually. In another example, moveable sensor arm 14704 can be moved automatically by an actuator.

In this example, in the second arm configuration (shown in the upper half of the figure) moveable sensor arm 14704 spans the circumference of the person's head in a substantially horizontal manner. In this example, as moveable sensor arm 14704 spans the person's face, it is substantially aligned with, hidden by, and interior to the front portion of face-spanning support member 14701. In this example, moveable sensor arm 14704 also loops around the back of the person's head. In this example, moveable sensor arm 14704 is attached to face-spanning support member 14701 via axle 14705 which is located near the person's ear. In this example, in the first arm configuration (shown in the lower half of the figure) moveable sensor arm 14704 has been pivoted and/or rotated in order to bring electromagnetic energy sensor 14703 into contact with the person's forehead. In an example, there can be multiple electromagnetic energy sensors on moveable sensor arm 14704.

As shown in FIG. 147, moveable sensor arm 14704 is visually less-obtrusive in the second arm configuration (shown in the upper half of the figure) than in the first arm configuration (shown in the lower half of the figure). Thus, this eyewear can collect data concerning electromagnetic brain activity 14706 using a more-obtrusive configuration at times when such data collection is needed, but can transform into a less-obtrusive configuration at times when such data collection is not needed. This enables a person to wear a mobile EEG monitor without looking too dorky—or at least without looking dorky all the time.

FIGS. 148 through 155 show examples of an eyewear device which collects data concerning electromagnetic energy from a person's brain. FIG. 148 shows an example of an eyewear device which collects data concerning electromagnetic energy from a person's brain comprising: a frontal support member 14801 which is configured to be worn on a person's head and to span from one eye to the other eye across a portion of the front of the person's face; at least one optical member 14802 which is configured to be worn within 6" of one of the person's eyes and which is attached to or an integrated part of the frontal support member 14801; at least one lateral ear support member 14803 which is attached to or an integrated part of the frontal support member 14801 and which is configured to be worn on or around one of the person's ears; at least one forehead ascending member 14804 which is attached to or an integrated part of the lateral ear support member 14803 which is configured to span at least a portion of the person's temple and/or forehead above the lateral ear support member 14803; at least one electromagnetic energy sensor 14807 and/or 14808 which is attached to or an integrated part of the forehead ascending member 14804 and which is configured to receive electromagnetic energy from the person's brain; and a control unit 14805 with which the at least one electromagnetic energy sensor 14807 and/or 14808 is in electromagnetic communication.

The example in FIG. 148 also shows a reference electrode 14806 which is in electromagnetic communication with the person's head in proximity to the person's ear. In an example, the device shown in FIG. 148 can be symmetric with respect to the sides of the person's head, with similar, symmetric components assumed on both the right and left sides of the person's head, even though only the left side of the person's head is fully shown in FIG. 148. In an example, some of the components may not be symmetric with respect to the right and left sides of the person's head. In an example, there can be a forehead ascending member (and associated electromagnetic sensors) on both sides of the person's head. In an example, there can be a forehead ascending member (and associated electromagnetic sensors) only on one side of the person's head.

In an example, a frontal support member can longitudinally and horizontally span a portion of the person's face within 1" of the person's eyebrows. In an example, a frontal support member can be straight. In an example, a frontal support member can be arcuate. In an example, a frontal support member (or projections from it) can rest on the bridge of the person's nose. In an example, a frontal support member can be the front portion of the frame of a pair of eyeglasses.

In an example, an optical member can be an optical lens which modifies light rays from an object in the environment before these light rays are received by an eye. In an example, an optical member can be a convex or concave lens. In an example, an optical member can be an image-displaying member which creates a virtual image which is seen by an eye. In an example, an optical member can be a display screen. In an example, an optical member can be a composite optical member which allows light rays from an object in the environment to reach an eye and also creates a virtual image which is seen by the eye. In an example, an optical member can be part of a virtual reality or augmented reality system.

In an example, at least one lateral ear support member can be connected to a frontal support member by a hinge and/or spring mechanism. In an example, at least one lateral ear support member can be an integrated part (one continuous piece) of the frontal support member. In an example, a lateral ear support member can be an ear piece or side frame of a pair of eyeglasses. In an example, a lateral ear support member can be straight. In an example, a lateral ear support member can be arcuate. In an example, a distal end of a lateral ear support member can rest on top of a person's ear. In an example, a distal end of lateral ear support member can curve around a person's ear.

In an example, a forehead ascending member can be attached to (and/or branch off from) a lateral ear support member at a location in a middle section of the lateral ear support member. In an example, a forehead ascending member can be attached to (and/or branch off from) a lateral ear support member at a location in the middle section of the lateral ear support member which at least ½ inch from the frontal support member. In an example, a forehead ascending member can be attached to (and/or branch off from) a lateral ear support member at a location in a middle section of the lateral ear support member which at least ½ inch from the distal end of the lateral ear support member. In an example, a forehead ascending member can be attached to (and/or branch off from) a lateral ear support member at a location in a middle section of the lateral ear support member which at least ½ inch from the top of the person's ear.

In an example, a forehead ascending member can span a distance between ¼ inch and 6 inches. In an example, a forehead ascending member can be arcuate. In an example, a forehead ascending member can have an arcuate shape which branches off from the lateral ear support member at an acute angle (X), diverges from the lateral ear support member at a growing angle (Y, which is greater than X), and then further diverges at a shrinking angle (Z, which is less than X). In an example, a forehead ascending member can have an arcuate shape which comprises a portion of a sine curve. In an example, a forehead ascending member can have an arcuate shape which is a conic section. In an example, a forehead ascending member can branch off from a lateral ear support member and ascend to a person's temple. In an example, a forehead ascending member can branch off from a lateral ear support member and ascend to a location on a person's forehead which is directly above the person's eye. In an example, a forehead ascending member can branch off from a lateral ear support member and ascend to the center of the person's forehead. In an example a forehead ascending member can ascend to a location on a person's forehead which is between ¼" and 4" above the person's eyebrows.

In an example, a forehead ascending member can have a lower end which branches off from the lateral ear support member and an upper end which is located over the person's temple or forehead, wherein projecting and plotting the locations of the lower and upper ends onto a vertical plane yields a linear approximation of the slope of the forehead ascending member in the range of 0.5 to 2. In an example, a forehead ascending member can have a lower end which branches off from the lateral ear support member and an upper end which is located over the person's temple or forehead, wherein projecting and plotting the locations of the lower and upper ends onto a vertical plane yields a linear approximation of the upward angle of the forehead ascending member in the range of 30 degrees to 150 degrees.

In an example, a forehead ascending member can travel along an inward (closer to the face) as well as an upward (closer to the top of the head) path after branching off from a lateral ear support member. In an example, a forehead ascending member can have a spring mechanism which keeps it close to (and/or exerts pressure on) the surface of the person's head. In an example, a forehead ascending member can further comprise an inflatable member which keeps it close to (and/or exerts pressure on) the surface of the person's head. In an example, a forehead ascending member can have a motion mechanism which helps to keep it close to (and/or exerts pressure on) the surface of the person's head. In an example this motion mechanism can be selected from the group consisting of: electric motor or actuator; MEMS; pneumatic member; hydraulic member; spring; and other tensile member.

In an example, an electromagnetic energy sensor can be an electroencephalographic (EEG) sensor. In an example, data collected by an electromagnetic energy sensor can be used to measure electromagnetic energy emitted by a person's brain. In an example, data collected by electromagnetic energy sensors can be used to measure a person's brain waves. In an example, data from the sensors can be analyzed using Fourier Transformation to identify wave patterns at different frequencies or within selected frequency ranges. In an example, the relative power of brain waves in different frequency ranges can be tracked and analyzed.

In an example, an electromagnetic energy sensor can be a dry EEG sensor which does not require gel or liquid to make electromagnetic contact with a person's brain. In an example, an electromagnetic energy sensor can be in direct physical contact with the person's skin. In an example, an electromagnetic energy sensor can be in electromagnetic communication with the person's brain without being in direct physical contact with the person's skin. In an example, there can be two electromagnetic energy sensors on one forehead ascending member, one closer to the person's ear and one further up toward the center of the person's forehead. In an example, there can be only one electromagnetic energy sensor on a forehead ascending member. In an example, there can be three or more electromagnetic energy sensors on a forehead ascending member.

In an example, a control unit can further comprise a power source, a data processing unit, a human-to-computer control interface, a computer-to-human interface, and a wireless data transmitter. In an example, one or more electromagnetic energy sensors can be in electromagnetic communication with the control unit. In an example, data from one or more electromagnetic energy sensors can be analyzed within a data processing unit within the control unit. In an example, data from one or more electromagnetic energy sensors can be wirelessly transmitted to a remote data processing unit and analyzed within that remote data processing unit. In an example, a power source can be a battery. In an example, a power source can further comprise an energy harvesting member which transduces kinetic, thermal, and/or ambient electromagnetic energy into power for the device. In an example, a human-to-computer control interface can be selected from the group consisting of: voice or speech recognition; a button or other touch-based control; and gesture recognition. In an example, data from the electromagnetic energy sensors themselves can be analyzed and used as part of the human-to-computer control interface for the device.

FIG. 149 shows another example of an eyewear device to collect data concerning electromagnetic energy from a person's brain. This example is similar to the one shown in FIG. 148 except that the forehead ascending member stops near the person's temple and this member only holds one electromagnetic energy sensor. Apart from component variations which are directly related to these differences, the component variations which were discussed concerning the example shown in FIG. 148 can also apply to the example shown in FIG. 149.

FIG. 149 shows an example of an eyewear device which collects data concerning electromagnetic energy from a person's brain comprising: a frontal support member 14901 which is configured to be worn on a person's head and to span from one eye to the other eye across a portion of the front of the person's face; at least one optical member 14902 which is configured to be worn within 6" of one of the person's eyes and which is attached to or an integrated part of the frontal support member 14901; at least one lateral ear support member 14903 which is attached to or an integrated part of the frontal support member 14901 and which is configured to be worn on or around one of the person's ears; at least one forehead ascending member 14904 which is attached to or an integrated part of the lateral ear support member 14903 which is configured to span at least a portion of the person's temple and/or forehead above the lateral ear support member 14903; an electromagnetic energy sensor 14907 which is attached to or an integrated part of the forehead ascending member 14904 and which is configured to receive electromagnetic energy from the person's brain; and a control unit 14905 with which electromagnetic energy sensor 14907 is in electromagnetic communication. The example in FIG. 149 also shows a reference electrode 14906 which is in electromagnetic communication with the person's head in proximity to the person's ear.

FIG. 150 shows another example of an eyewear device to collect data concerning electromagnetic energy from a person's brain. This example is similar to the one shown in FIG. 148 except that the forehead ascending member stops near the person's temple and this member forms a curve which is connected to the lateral ear support member at two locations. Apart from component variations which are directly related to these differences, the component variations which were discussed concerning the example shown in FIG. 148 can also apply to the example shown in FIG. 150.

FIG. 150 shows an example of an eyewear device which collects data concerning electromagnetic energy from a person's brain comprising: a frontal support member 15001 which is configured to be worn on a person's head and to span from one eye to the other eye across a portion of the front of the person's face; at least one optical member 15002 which is configured to be worn within 6" of one of the person's eyes and which is attached to or an integrated part of the frontal support member 15001; at least one lateral ear support member 15003 which is attached to or an integrated part of the frontal support member 15001 and which is configured to be worn on or around one of the person's ears; at least one arcuate forehead ascending member 15004 which is attached to the lateral ear support member 15003 at two locations and which is configured to span at least a portion of the person's temple and/or forehead above the lateral ear support member 15003; an electromagnetic energy sensor 15007 which is attached to or an integrated part of the forehead ascending member 15004 and which is configured to receive electromagnetic energy from the person's brain; and a control unit 15005 with which the at least one electromagnetic energy sensor 15007 is in electromagnetic communication. The example in FIG. 150 also shows a reference electrode 15006 which is in electromagnetic communication with the person's head in proximity to the person's ear.

FIG. 151 shows another example of an eyewear device to collect data concerning electromagnetic energy from a person's brain. This example is similar to the one shown in FIG. 148 except that there is no separate forehead ascending member. Instead, in this example, a middle section of the lateral ear support member curves upwards near the person's temple and/or forehead to hold an electromagnetic energy sensor there. Apart from component variations which are directly related to this difference, the component variations which were discussed concerning the example shown in FIG. 148 can also apply to the example shown in FIG. 151.

FIG. 151 shows an example of an eyewear device which collects data concerning electromagnetic energy from a person's brain comprising: a frontal support member 15101 which is configured to be worn on a person's head and to span from one eye to the other eye across a portion of the front of the person's face; at least one optical member 15102 which is configured to be worn within 6" of one of the person's eyes and which is attached to or an integrated part of the frontal support member 15101; at least one lateral ear support member 15103 which is attached to or an integrated part of the frontal support member 15101 and which is configured to be worn on or around one of the person's ears, wherein a middle section of this lateral ear support member extends upward to span at least a portion of the person's temple and/or forehead; an electromagnetic energy sensor 15107 which is attached to or an integrated part of the middle section of lateral ear support member 15103 and which is configured to receive electromagnetic energy from the person's brain; and a control unit 15105 with which the at least one electromagnetic energy sensor 15107 is in electromagnetic communication. The example in FIG. 151 also shows a reference electrode 15106 which is in electromagnetic communication with the person's head in proximity to the person's ear.

In an example, a middle section of a lateral ear support can curve upwards in a sinusoidal manner. In an example, a middle section of a lateral ear support which is more than ½ inch from a frontal support member and more than ½ inch from the top of the person's ear can curve upwards in a sinusoidal manner to span a portion of a person's temple and/or forehead. In an example, this middle section can be shaped like a conic section. In an example, a lateral ear support can be generally straight except for a central portion which curves and/or loops upward to hold an electromagnetic energy sensor near a person's temple. In an example, a lateral ear support can be generally straight except for a central portion which curves and/or loops upward to hold one or more electromagnetic energy sensors over one or more locations on the side of a person's forehead. In an example, a lateral ear support can be a longitudinally undulating member with a substantially sinusoidal shape spanning between a person's ear and a frontal support member, wherein one or more electromagnetic energy sensors are located along the upper portions of this sinusoidal shape.

In an example, a middle section of a lateral ear support can hold one or more electromagnetic energy sensors in locations which are at least ¼" higher than a frontal support member. In an example, a middle section of a lateral ear support can hold one or more electromagnetic energy sensors in locations which are at least ½" higher than a frontal support member. In an example, a middle section of a lateral ear support can hold one or more electromagnetic energy sensors in locations which are at least ¼" higher than the top of a person's ear. In an example, a middle section of a lateral ear support can hold one or more electromagnetic energy sensors in locations which are at least ½" higher than the top of a person's ear.

FIG. 152 shows another example of an eyewear device to collect data concerning electromagnetic energy from a person's brain. This example is similar to the one shown in FIG. 151 except that the control unit is located behind the person's ear. The component variations which were discussed concerning the examples shown in FIGS. 148 and 151 can also apply to the example shown in FIG. 152.

FIG. 152 shows an example of an eyewear device which collects data concerning electromagnetic energy from a person's brain comprising: a frontal support member 15201 which is configured to be worn on a person's head and to span from one eye to the other eye across a portion of the front of the person's face; at least one optical member 15202 which is configured to be worn within 6" of one of the person's eyes and which is attached to or an integrated part of the frontal support member 15201; at least one lateral ear support member 15203 which is attached to or an integrated part of the frontal support member 15201 and which is configured to be worn on or around one of the person's ears, wherein a middle section of this lateral ear support member extends upward to span at least a portion of the person's temple and/or forehead; an electromagnetic energy sensor 15207 which is attached to or an integrated part of the middle section of lateral ear support member 15203 and which is configured to receive electromagnetic energy from the person's brain; and a control unit 15205 with which the at least one electromagnetic energy sensor 15207 is in electromagnetic communication. The example in FIG. 152 also shows a reference electrode 15206 which is in electromagnetic communication with the person's head in proximity to the person's ear.

FIG. 153 shows another example of an eyewear device to collect data concerning electromagnetic energy from a person's brain. This example is similar to the one shown in FIG. 152 except that: the lateral ear support member is attached to (or a single piece with) an encircling support member which goes around the back of the person's head (to a lateral ear support on the other side of the person's head). The component variations which were discussed concerning the examples shown in FIGS. 148 and 151 can also apply to the example shown in FIG. 153.

FIG. 153 shows an example of an eyewear device which collects data concerning electromagnetic energy from a person's brain comprising: a frontal support member 15301 which is configured to be worn on a person's head and to span from one eye to the other eye across a portion of the front of the person's face; at least one optical member 15302 which is configured to be worn within 6" of one of the person's eyes and which is attached to or an integrated part of the frontal support member 15301; at least one lateral ear support member 15303 which is attached to or an integrated part of the frontal support member 15301 and which is configured to be worn on or around one of the person's ears, wherein a middle section of this lateral ear support member extends upward to span at least a portion of the person's temple and/or forehead; an electromagnetic energy sensor 15307 which is attached to or an integrated part of the middle section of lateral ear support member 15303 and which is configured to receive electromagnetic energy from the person's brain; an encircling support member 15309 which is attached to or an integrated part of the lateral ear support member 15303 and is configured to partially encircle the back of the person's head; an electromagnetic energy sensor 15310 which is attached to or an integrated part of the encircling support member 15309 and which is configured to receive electromagnetic energy from the person's brain; and a control unit 15305 with which the at least one electromagnetic energy sensor 15307 and/or 15310 is in electromagnetic communication.

The encircling support member 15309 in this example can be useful for holding the device closely to the surface of the person's head in order to maintain good electromagnetic communication between the sensors and the person's brain. The encircling support member 15309 can also be useful for holding one or more additional electromagnetic energy sensors in non-obtrusive locations other than the person's temple and/or forehead. The example in FIG. 153 also shows a reference electrode 15306 which is in electromagnetic communication with the person's head in proximity to the person's ear.

FIG. 154 shows another example of an eyewear device to collect data concerning electromagnetic energy from a person's brain. This example is similar to the one shown in FIG. 148 except that a member branches off from the lateral ear support member in a descending manner (to hold an electromagnetic energy sensor on or in the ear), rather than an ascending manner. Apart from component variations which are directly related to these differences, the component variations which were discussed concerning the example shown in FIG. 148 can also apply to the example shown in FIG. 154.

FIG. 154 shows an example of an eyewear device which collects data concerning electromagnetic energy from a person's brain comprising: a frontal support member 15401 which is configured to be worn on a person's head and to span from one eye to the other eye across a portion of the front of the person's face; at least one optical member 15402 which is configured to be worn within 6" of one of the person's eyes and which is attached to or an integrated part of the frontal support member 15401; at least one lateral ear support member 15403 which is attached to or an integrated part of the frontal support member 15401 and which is configured to be worn on or around one of the person's ears; at least one descending member 15411 which is attached to or an integrated part of the lateral ear support member 15403 which is configured to span at least a portion of the person's ear; an electromagnetic energy sensor 15412 which is attached to or an integrated part of the descending member 15411 and which is configured to receive electromagnetic energy from the person's brain from a location on the person's ear, within the person's ear, and/or within 1" of the person's ear; and a control unit 15405 with which electromagnetic energy sensor 15412 is in electromagnetic communication.

FIG. 155 shows another example of an eyewear device to collect data concerning electromagnetic energy from a person's brain. This example is similar to the one shown in FIG. 148 except that the forehead ascending member spans the entire width of the person's forehead and connects to a symmetric forehead ascending member on the other side of the person's head. Apart from component variations which are directly related to these differences, the component variations which were discussed concerning the example shown in FIG. 148 can also apply to the example shown in FIG. 155.

FIG. 155 shows an example of an eyewear device which collects data concerning electromagnetic energy from a person's brain comprising: a frontal support member 15501 which is configured to be worn on a person's head and to span from one eye to the other eye across a portion of the front of the person's face; at least one optical member 15502 which is configured to be worn within 6" of one of the person's eyes and which is attached to or an integrated part of the frontal support member 15501; at least one lateral ear support member 15503 which is attached to or an integrated part of the frontal support member 15501 and which is configured to be worn on or around one of the person's ears; at least one forehead ascending and spanning member 15504 which is attached to or an integrated part of the lateral ear support member 15503 which is configured to span the entire width of the person's forehead; electromagnetic energy sensors 15507, 15508, and 15513 which are attached to or an integrated part of the forehead ascending and spanning member 15504 and which are configured to receive electromagnetic energy from the person's brain; and a control unit 15505 with which electromagnetic energy sensors 15507, 15508, and 15513 are in electromagnetic communication. The example in FIG. 155 also shows a reference electrode 15506 which is in electromagnetic communication with the person's head in proximity to the person's ear.

In an example, a support member that spans the entire width of a person's forehead (such as 15504) can enable a greater range of options for placement of electromagnetic energy sensors to more fully measure electromagnetic energy from a person's brain. In an example, a support member than spans the entire width of a person's forehead can hold four or more electromagnetic energy sensors. In an example, a support member which spans the entire width of a person's forehead (such as 15504) can be a different (less obvious) color than a frontal support member (such as 15501). In an example, a support member that spans the entire width of a person's forehead can be transparent or translucent.

As shown in preceding FIGS. 1 through 155, this invention can be embodied in a mobile wearable electromagnetic brain activity monitor comprising: a wearable frame which is configured to be worn on a person's head; a plurality of electromagnetic energy sensors which are configured to be held in electromagnetic communication with the person's brain by the wearable frame, wherein these sensors collect data concerning the person's electromagnetic brain activity; and a control unit with one or more components selected from the group consisting of power source and/or power-transducing component, data transmission and data reception component, data memory component, and data processor.

In an example, the wearable frame can be a ring which is configured to encircle the person's head. In an example, the wearable frame can be substantially circular or elliptical and wherein this wearable frame can be configured to encircle the person's head at an anterior acute angle in the range of 0 to 45 degrees with respect to a horizontal plane when the person's head is upright. In an example, the wearable frame can be substantially circular or elliptical and wherein this wearable frame can be configured to span both the person's forehead and the rear of the person's head. In an example, the wearable frame can be a headband. In an example, the wearable frame can be an arcuate element which is configured to loop around the person's head from one ear to the other ear. In an example, the wearable frame can be a set of headphones.

In an example, the wearable frame can be configured to span from the person's left ear to the person's face, then span across the front of the person's face including a portion of the person's forehead, and then span from the person's face to the person's right ear. In an example, the wearable frame can be configured to rest on the bridge of the person's nose and on the person's ears. In an example, the wearable frame can be shaped like an eyeglasses and/or eyewear frame with the addition of extended elements around the ears. In an example, the wearable frame can be an eyeglasses and/or eyewear frame. In an example, the wearable frame can hold one or more light-transmitting optical members. In an example, the wearable frame can hold one or more optical lenses.

In an example, the plurality of electromagnetic energy sensors can be electroencephalogram (EEG) electrodes. In an example, the plurality of electromagnetic energy sensors can be configured to be worn less than one inch from the surface of the person's head. In an example, a power source and/or power-transducing component can be selected from the group consisting of: a power source that is internal to the device during regular operation, an internal battery, capacitor, energy-storing microchip, or wound coil or spring; a component for obtaining, harvesting, or transducing power from a source other than the person's body that is external to the device, a rechargeable battery, electromagnetic inductance from external source, solar energy, indoor lighting energy, wired connection to an external power source, ambient or localized radiofrequency energy, or ambient thermal energy; and a component for obtaining, harvesting, or transducing power from the person's body, as kinetic or mechanical energy from body motion, electromagnetic energy from the person's body, or thermal energy from the person's body.

In an example, this device can further comprise one or more interface components selected from the group consisting of: a computer-to-human interface such as a display screen, one or more lights, one or more speakers, and/or one or more tactile actuators; a human-to-computer interface such as a touch screen, one or more touch-activated buttons, microphone and speech-recognition capability, and/or gesture recognition capability; one or more accelerometers; one or more cameras; and a GPS component.

In an example, this invention can be embodied in a mobile wearable electromagnetic brain activity monitor comprising: an eyeglasses and/or eyewear frame which is configured to be worn on a person's head; a plurality of electromagnetic energy sensors which are configured to be held in electromagnetic communication with the person's brain by the eyeglasses and/or eyewear frame, wherein these sensors collect data concerning the person's electromagnetic brain activity; and a control unit with one or more components selected from the group consisting of power source and/or power-transducing component, data transmission and data reception component, data memory component, and data processor.

In an example, this invention can be embodied in a mobile wearable electromagnetic brain activity monitor comprising: a headband or set of headphones which is configured to be worn on a person's head; a plurality of electromagnetic energy sensors which are configured to be held in electromagnetic communication with the person's brain by the headband or set of headphones, wherein these sensors collect data concerning the person's electromagnetic brain activity; and a control unit with one or more components selected from the group consisting of power source and/or power-transducing component, data transmission and data reception component, data memory component, and data processor.

In an example, this invention can be embodied in a mobile wearable electromagnetic brain activity monitor comprising: a wearable frame which is configured to be worn on a person's head, wherein this wearable frame is configured to completely encircle a portion of the person's head, wherein this wearable frame has a central circular axis which is configured at an anterior acute angle in the range of 0 to 45 degrees with respect to a horizontal plane when the person's head is upright; a plurality of electromagnetic energy sensors which are configured to be held in electromagnetic communication with the person's brain by the wearable frame, wherein these sensors collect data concerning the person's electromagnetic brain activity; and a control unit with one or more components selected from the group consisting of power source and/or power-transducing component, data transmission and data reception component, data memory component, and data processor.

In an example, this invention can be embodied in a mobile wearable electromagnetic brain activity monitor comprising: a wearable frame which is configured to be worn on a person's head, wherein this wearable frame is configured to span from one ear to the other ear across the front of the person's head; a plurality of electromagnetic energy sensors which are configured to be held in electromagnetic communication with the person's brain by the wearable frame, wherein these sensors collect data concerning the person's electromagnetic brain activity; and a control unit with one or more components selected from the group consisting of power source and/or power-transducing component, data transmission and data reception component, data memory component, and data processor.

In an example, this invention can be embodied in a mobile wearable electromagnetic brain activity monitor comprising: a wearable frame which is configured to be worn on a person's head, wherein this wearable frame is configured to span from one ear to the other ear around the rear of the person's head; a plurality of electromagnetic energy sensors which are configured to be held in electromagnetic communication with the person's brain by the wearable frame, wherein these sensors collect data concerning the person's electromagnetic brain activity; and a control unit with one or more components selected from the group consisting of power source and/or power-transducing component, data transmission and data reception component, data memory component, and data processor.

In an example, the shape of the wearable frame can have sinusoidal variation around its central circular axis. In an example, the shape of the wearable frame can be configured to have an arcuate wave above an ear. In an example, the wearable frame can be configured to be supported by the person's ears. In an example, the monitor can further comprise at least one optical lens or other light-transmitting member. In an example, data from the electromagnetic energy sensors can be used to adjust and/or control the light absorption, light reflection, light refraction, light spectrum transformation, focal direction, focal distance, light polarization, and/or parallax view of the at least one optical lens or other light-transmitting member.

In an example, the wearable frame can have a sensor-holding upward arcuate member which is configured to span a portion of the person's temple. In an example, the wearable frame can have a sensor-holding member which can be moved relative to the rest of the frame, wherein this sensor-holding member can be moved from a first configuration in which it does not span a portion of the person's temple to a second configuration in which it does span a portion of the person's temple.

In an example, the wearable frame can have a sensor-holding upward arcuate member which is configured to span a portion of the person's forehead. In an example, the wearable frame can have a sensor-holding member which can be moved relative to the rest of the frame, wherein this sensor-holding member can be moved from a first configuration in which it does not span a portion of the person's forehead to a second configuration in which it does span a portion of the person's forehead.

In an example, this monitor can further comprise one or more other sensors selected from the group consisting of: accelerometer, inclinometer, gyroscope, strain gauge, or other motion or position sensor; microphone or other sound sensor; thermometer or other temperature sensor; camera or other imaging sensor; optical sensor or optoelectronic sensor; blood pressure sensor; ECG/EKG sensor, heart rate monitor, and/or heart rate sensor; EMG sensor or other muscle activity sensor; GPS sensor, other location sensor, magnetometer, or compass; spectroscopy sensor or other spectral analysis sensor; electrochemical sensor; blood oximetry sensor; piezoelectric sensor; chewing sensor or swallowing sensor; respiration sensor; pressure sensor; galvanic skin response sensor; and taste or odor sensor.

In an example, this monitor can further comprise one or more interface components selected from the group consisting of: a computer-to-human interface such as a display screen, one or more lights, one or more speakers, and/or one or more tactile actuators; a human-to-computer interface such as a touch screen, one or more touch-activated buttons, microphone and speech-recognition capability, and/or gesture recognition capability; one or more accelerometers; one or more cameras; and a GPS component.

I claim:

1. A mobile wearable electromagnetic brain activity monitor comprising: a wearable frame which is configured to be worn on a person's head, wherein the wearable frame comprises the frame of a pair of eyeglasses, wherein this wearable frame is configured to completely encircle a portion of the person's head, wherein this wearable frame has a central circular axis which is configured at an anterior acute angle in the range of 0 to 45 degrees with respect to a horizontal plane when the person's head is upright, wherein this wearable frame has two or more full-phase sinusoidal variations around its central circular axis, wherein the wearable frame is configured to have an arcuate wave above an ear which is part of a full-phase sinusoidal variation around the central circular axis of the wearable frame, and wherein the wearable frame is configured to be supported by the person's ears; a plurality of electromagnetic energy sensors which are configured to be held in electromagnetic communication with the person's brain by the wearable frame, wherein these sensors collect data concerning the person's electromagnetic brain activity; and a control unit which is part of the wearable frame with one or more components selected from the group consisting of power source and/or power-transducing component, data transmission and data reception component, data memory component, and data processor.

2. The monitor in claim 1 wherein data from the electromagnetic energy sensors is used to adjust and/or control the light absorption, light reflection, light refraction, light spectrum transformation, focal direction, focal distance, light polarization, and/or parallax view of at least one optical lens or other light-transmitting member.

3. The monitor in claim 1 wherein this monitor further comprises one or more other sensors selected from the group consisting of: accelerometer, inclinometer, gyroscope, strain gauge, or other motion or position sensor; microphone or other sound sensor; thermometer or other temperature sensor; camera or other imaging sensor; optical sensor or optoelectronic sensor; blood pressure sensor; ECG/EKG sensor, heart rate monitor, and/or heart rate sensor; EMG sensor or other muscle activity sensor; GPS sensor, other location sensor, magnetometer, or compass; spectroscopy sensor or other spectral analysis sensor; electrochemical sensor; blood oximetry sensor; piezoelectric sensor; chewing sensor or swallowing sensor; respiration sensor; pressure sensor; galvanic skin response sensor; and taste or odor sensor.

4. The monitor in claim 1 wherein this monitor further comprises one or more interface components selected from the group consisting of: a computer-to-human interface such as a display screen, one or more lights, one or more speakers, and/or one or more tactile actuators; a human-to-computer interface such as a touch screen, one or more touch-activated buttons, microphone and speech-recognition capability, and/or gesture recognition capability; one or more accelerometers; one or more cameras; and a GPS component.

* * * * *